US006492110B1

(12) United States Patent
Hahn et al.

(10) Patent No.: US 6,492,110 B1
(45) Date of Patent: Dec. 10, 2002

(54) REFERENCE CLONES AND SEQUENCES FOR NON-SUBTYPE B ISOLATES OF HUMAN IMMUNODEFICIENCY VIRUS TYPE 1

(75) Inventors: Beatrice H. Hahn, Birmingham, AL (US); George M. Shaw, Birmingham, AL (US); Feng Gao, Hoover, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/184,418

(22) Filed: Nov. 2, 1998

(51) Int. Cl.[7] .................................................. C12Q 1/68

(52) U.S. Cl. .............................. 435/6; 435/5; 435/91.2; 536/23.1; 536/23.72

(58) Field of Search ............................ 536/23.1, 23.72, 536/350, 324; 514/2, 12; 435/6, 91.2

(56) References Cited

U.S. PATENT DOCUMENTS

| | | | |
|---|---|---|---|
| 5,677,147 | A | 10/1997 | Karsten et al. |
| 5,688,637 | A | 11/1997 | Moncany et al. |
| 5,702,918 | A | 12/1997 | Bannworth et al. |
| 5,721,095 | A | 2/1998 | Chan et al. |
| 5,726,017 | A | 3/1998 | Loohrie et al. |
| 5,756,674 | A | 5/1998 | Katinger et al. |
| 5,759,770 | A | 6/1998 | Guertler et al. |
| 5,770,427 | A | 6/1998 | Guertler et al. |
| 5,770,703 | A | 6/1998 | Alizon et al. |
| 5,786,177 | A | 7/1998 | Moncany et al. |

FOREIGN PATENT DOCUMENTS

| | | |
|---|---|---|
| WO | WO 98/34640 | 8/1998 |

OTHER PUBLICATIONS

F. Gao et al., "A comprehensive panel of near–full–length clones and reference sequences for non–subtype B isolates of human immunodeficiency virus type 1" *J. Virol.,* 72:5680–5698 (1998).

F. Gao et al. "Non–recombinant, near–full length reference clones for HIV–1 subtyped A, C, and D" abstract No. 164, *4th Conf. Retrovir. and Opportun. Infect.* (Jan. 22–26, 1997).

F. Gao et al., "Non–recombinant, near–full length reference clones for HIV–1 subtypes A through H" poster No. 83, *Conf. Adv. AIDS Vaccine Dev.* (May 4–, 1997).

Robertson DL; Gao F; Barre–Sinoussi F; Girad M; Srinvasan A; Abimiku AG; Shaw GM; Sharp PM; Hahn BH; "Non–recombinant reference clones and sequences for human immunodeficiency virus type 1 subtypes A, C, D, F, and H"; abstract No. 552, *5th Conf. Retrovir. Oppor. Infect.* (Feb. 1–5, 1998).

*NIH AIDS Research and Reference Reagent Program Courier,* 98–01, pp. 1 and 10–14 (Oct. 1998).

T. Leitner et al., "Updated proposal of reference sequences of HIV–1 genetic subtypes. In: Human Retroviruses and AIDS 1997: a compilation and analysis of nucleic acid and amino acid sequence" *Theoretical Biology and Biophysics Group, Los Alamos National Laboratory,* Los Alamos, N.M., pp. III 19–III 24 (1997).

D.L. Robertson et al,. "Intersubtype recombinant HIV–1 Sequences. In: Human Retroviruses and AIDS 1997: a compilation and analysis of nucleic acid and amino acid sequence" *Theoretical Biology and Biophysics Group, Los Alamos National Laboratory,* Los Alamos, N.M., pp. III 25–III 30 (1997).

See attached chart of Isolates/Clones and GenBank accession numbers printed out from the Los Alamos National Laboratory HIV database and the GenBank database.

*Primary Examiner*—Donna Wortman
*Assistant Examiner*—Robert A. Zeman
(74) *Attorney, Agent, or Firm*—Benjamin Aaron Adler

(57) ABSTRACT

The nucleotide sequences of the genomes of eleven molecular clones for non-subtype B isolates of human immunodeficiency virus type 1 are disclosed. The invention relates to the nucleic acids and peptides encoded by and/or derived from these sequences and their use in diagnostic methods and as immunogens.

6 Claims, 69 Drawing Sheets tat (second exon)

```
                                                         frequency
CONSENSUS_A   P?PQTQG?.?TGPKESKKKVESKTETDRFD*             0/14

CONSENSUS_B   P?SQPRGD.PTGPKESKKKVERETETDP?D*             4/52

CONSENSUS_C   PLPQTRGD.PTGSEESKKKVESKTETDPFD*             0/11

CONSENSUS_D   PSSQPRGD.PTGPKE*                            11/15
ELI           --------.------Q------E--T--*
Z2Z6          --------.------*
NDK           ----S---.-----K*
92UG021.16    --------.------*
92UG024.2     --------.----EKQ----------A----C*
JY1           --------.------*
UG269A        --------.------*
UG274A2       -------N.-----K*
SE365A2       ----H---.------*
93ZR001.3     -L------.------Q------Q--A-R--C*
UG266A2       --------.------Q----------V----*
MAL           ----H---H------*
K124A2        --------.Q-----*
84ZR085.1     --------.---Q--*
94UG114.1     -------N.------*

CONSENSUS_E   PLPIIRGN.PTDPKESKKEVASKAETDPCD*             0/9

CONSENSUS_F   PISQARGN.PTGPKESKKEVESKAKTDPCA*             0/4

CONSENSUS_G   PLPTTRGN.PTGPKESKKEV?SKTETDPFD*             0/8

CONSENSUS_H   PLSRTHGD.PTGPKEQKKEVASKTETDP*               0/1
```

Fig. 7A rev (second exon)

```
                                                                                                                     frequency
CONSENSUS_A   PYP?PKG?.RQARKNRRRRWRARQRQIDSISERILSTCLGRPAEPVPLQLPP?ERLHLDCSEDCGTSGTQQSQG?ETGVGRPQVSVESSVILGSGTKN*     0/14

CONSENSUS_B   PPPSPEGT.RQARRNRRRRWRERQRQIRSIS?WILSTYLGRSAEPVPLQLPPLERLTLDCSEDCGTSGTQ.......GVGSPQILVESPAVLESGTKE*     0/52

CONSENSUS_C   PYPKPEGT.RQAR?NRRRRWRARQRQIHSISERILSTCLGRPAEPVPLQLPPIERLHIDCSES?GTSGTQQSQGTTEGVGSP*                    15/15
93MW959.18    --------.----K--------------------------------------------G----S----------------R-*
93MW960.3     --------.----K------------L----------F------------------T-G----G--P---------------*
93MW965.26    --------.----R----------------G----A---------------------------S-----------A------*
UG268A2       ---N----.----R------------RE-NQ----------S----------L---T------S------------------*
SM145A        --------.----K----------------------------T---S-----------GG---G-------------R----*
ZAM18A        ---E-K--.----K---------------L-G-----F---------F---------------S------------------*
ZAM20A        ---EHQ-GT----K---------------------------------F---------------G-----E------------*
DJ259A        --------.----R-------------D--------A-------------------NL-----G--A--E.......---N-*
DJ373A        ---E-K--.---QR---------------------------------F--------NL-----G-----E.......---N-*
C2220         ---T----.----R--------------TL------NF--------------L---NL----DS----------------N-*
SE364A        -------------K---------------------VH--------------------------S--PD-E----------N-*
92BR025.8     --------.----R------------------------V--------F--------N-N----G-------P--N--R--N-*
94IN476.104   ---R----.---QR---------------------------ST---------------G----G-------P--N--R--N-*
96ZM651.8     ---E-K--.----K-----------E-RA-------------T---------------GD---G------------------*
96ZM751.3     ---N----.----K-------------N--------------P----F----L----------G-A-E--------------*

CONSENSUS_D   PPPSPEGT.RQARRNRRRRWRARQRQIHSIGERILSTYLGRPEEPVPLQLPPLERLNLNC?EDCGTSGTQ.......GVGSPQISVESPAVLDSGTEE*     0/15

CONSENSUS_E   P?PSSEGT.RQTRKNRRRRWRARQRQIRAISERILSTCLGRSTEPVPLQLPPLERLHLDCSEDCGTSGTQQSQGTETGVGRPQISGESSVILGPGTKN*    0/9

CONSENSUS_F   PYPKPEGT.RQARRNRRRRWRARQRQIREISERILSSCLGRPEEPVPLQLPPLERLHINCSEDC?.......QGAEEGVGSPQTSGESHAVLGSGTKE*    0/4

CONSENSUS_G   PYPPPEGT.RQAR?NRRRRWRARQRQIH?ISERILS?CLGRPAEPVPLQLPPLERLHLDCSEDSGTSGTQQSQGTETGVGGPQISVESSVVLGSG?KE*    1/8

CONSENSUS_H   PCPEPTGT.RQARRNRRRRWRARQRQIREISERILTSCLGRPPEPVTLQLPPLERLTLNCSEDCGTSGEK.......GEGSPQISLESSTILGTGTKE*     0/1
```

Fig. 7B

Vpu

```
                                                                   Frequency
CONSENSUS_A    M??L.....EI?AIVGLVVALI?AIVVW.TIVGI                    0/13

CONSENSUS_B    MQSL.....QI?AIVALVVAAIIAIVVW.TIV?I                    0/26

CONSENSUS_C    M?DLLAKVDYRL?VGALIVALIIAIVVW.TIAYI                    10/10
92BR025.8      -LE-IGRI----G----------V-I--.-----
C2220          -V---------IVIV-F-----------.-----
SM145          -LN---G----IAI--FS----------.--V--
UG268          -LN---G----IGI---LI---------.I-V--
DJ259          -I--P-------A---------------.--V--
DJ373          -I----------A-A-F-I-F-------.-----
SE364          -V----------G------------I--.I----
94IN476.104    -VN--ER-----G---------L--I--.----L
96ZM651.8      -L----R-N--VG--------L------.-----
96ZM751.3      -LN-E-R----IG-----A------A--.I-V--

CONSENSUS_D    MQPL.....?ILAIAALVVALIIAIVVW.TIVFI                    0/9

CONSENSUS_F    MSYL.....LAI?I?ALIVALIIAIVVW.TIAYI                    0/4

CONSENSUS_G    MQ?L.....EI?AI?GLVVAFIAAIVVW.SIV?I                    0/3

CONSENSUS_H    MYIL.....G.LGIGALVVTFIIAVIVW.TIVYI                    0/1
```

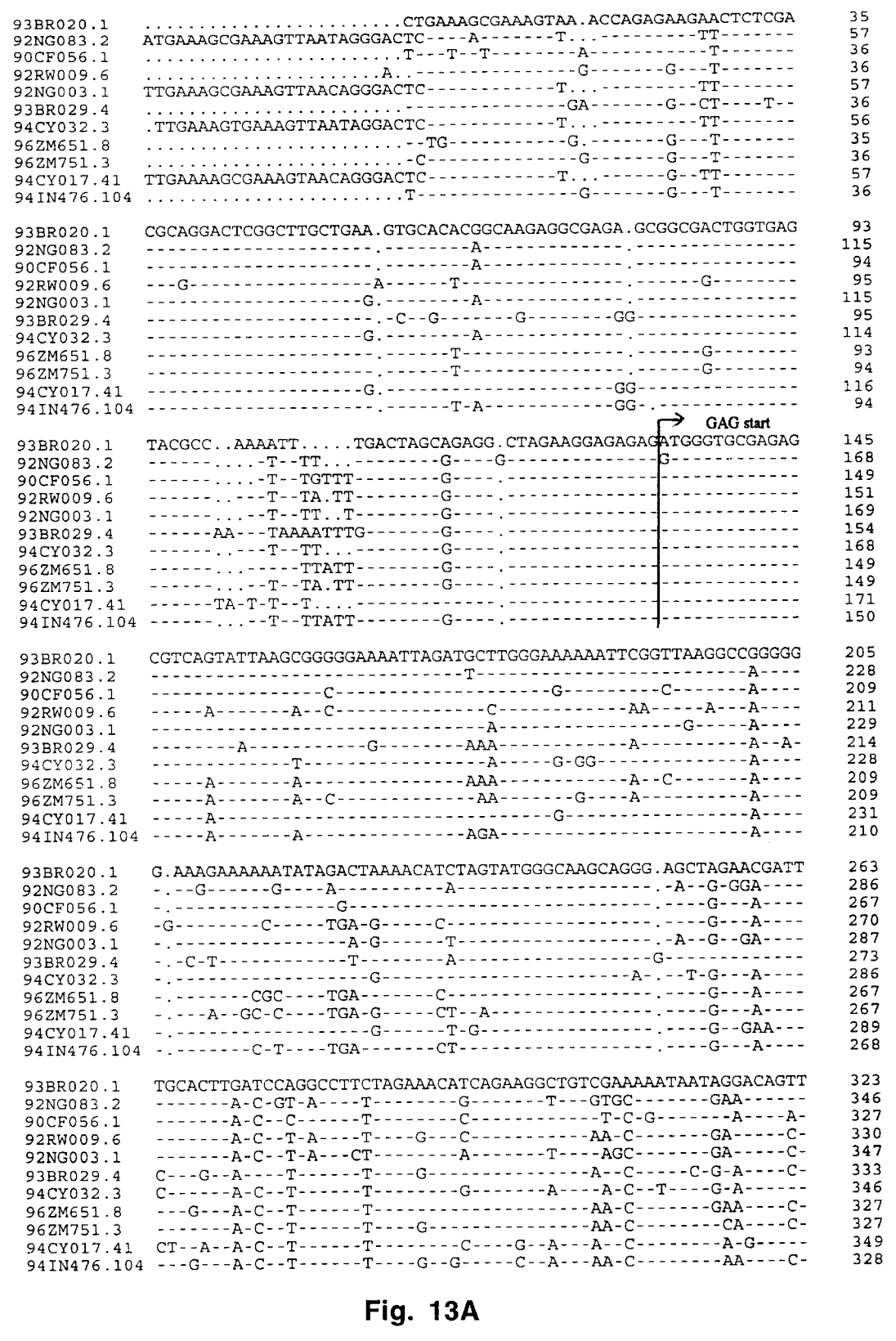

```
93BR020.1    ........................CTGAAAGCGAAAGTAA.ACCAGAGAAGAACTCTCGA    35
92NG083.2    ATGAAAGCGAAAGTTAATAGGGACTC----A-------T..----------TT-------    57
90CF056.1    ........................T---T--T--------A-----------T-------    36
92RW009.6    ......................A..---------------G-------G---T-------    36
92NG003.1    TTGAAAGCGAAAGTTAACAGGGACTC------------T...---------TT-------    57
93BR029.4    ........................---------------GA-------G--CT----T--    36
94CY032.3    .TTGAAAGTGAAAGTTAATAGGACTC------------T...---------TT-------    56
96ZM651.8    ........................--TG-----------G.-------G---T-------    35
96ZM751.3    ........................-C--------------G-------G---T-------    36
94CY017.41   TTGAAAAGCGAAAGTAACAGGGACTC------------T...------G--TT-------    57
94IN476.104  ........................T---------------G-------G---T-------    36

93BR020.1    CGCAGGACTCGGCTTGCTGAA.GTGCACACGGCAAGAGGCGAGA.GCGGCGACTGGTGAG    93
92NG083.2    ---------------------.--------A-------------.---------------   115
90CF056.1    ---------------------.--------A-------------.---------------    94
92RW009.6    ---G-----------------A------T---------------.------G--------    95
92NG003.1    --------------------G.--------A-------------.---------------   115
93BR029.4    ---------------------.-C--G-------G--------GG---------------    95
94CY032.3    --------------------G.--------A-------------.---------------   114
96ZM651.8    ---------------------.------T---------------.------G--------    93
96ZM751.3    ---------------------.------T---------------.------G--------    94
94CY017.41   --------------------G.---------------------GG---------------   116
94IN476.104  ---------------------.------T-A------------GG-.-------------    94
                                                           GAG start
93BR020.1    TACGCC..AAAATT.....TGACTAGCAGAGG.CTAGAAGGAGAGAGATGGGTGCGAGAG   145
92NG083.2    ------....-T--TT...--------G----G--------------G------------   168
90CF056.1    ------....-T--TGTTT--------G----.---------------------------   149
92RW009.6    ------..---T--TA.TT--------G----.---------------------------   151
92NG003.1    ------...--T--TT..T--------G----.---------------------------   169
93BR029.4    ------AA---TAAAATTTG-------G----.---------------------------   154
94CY032.3    ------..---T--TT...--------G----.---------------------------   168
96ZM651.8    ------...-----TTATT--------G----.---------------------------   149
96ZM751.3    ------...--T--TA.TT--------G----.---------------------------   149
94CY017.41   ------TA-T-T--T....-------------.---------------------------   171
94IN476.104  ------...--T--TTATT--------G----.---------------------------   150

93BR020.1    CGTCAGTATTAAGCGGGGGAAAATTAGATGCTTGGGAAAAAATTCGGTTAAGGCCGGGGG   205
92NG083.2    -----------------------------T-------------------------A----   228
90CF056.1    ----------------C--------------------G---------C-------A----   209
92RW009.6    -----A-------A--C--------------C------------AA-----A---A----   211
92NG003.1    -------------------------------A-----------------G-----A----   229
93BR029.4    --------A-----------G--------AAA------------A----------A--A-   214
94CY032.3    -------------T-----------------A-----G-GG--------------A----   228
96ZM651.8    -----A-------A---------------AAA------------A--C-------A----   209
96ZM751.3    -----A-------A--C-------------AA-------G----A----------A----   209
94CY017.41   -----A-------------------------------G-----------------A----   231
94IN476.104  -----A-------A---------------AGA-----------------------A----   210

93BR020.1    G.AAAGAAAAAATATAGACTAAAACATCTAGTATGGGCAAGCAGGG.AGCTAGAACGATT   263
92NG083.2    -.--G------G----A----------A------------------.-A--G-GGA----   286
90CF056.1    -.---------------G----------------------------.----G---A----   267
92RW009.6    -G--------C-----TGA-G-----C-------------------.----G---A----   270
92NG003.1    -.----------------A-G------T------------------.-A--G--GA----   287
93BR029.4    -.-C-T------------T--------A------------------G-------------   273
94CY032.3    -.------------------G-----------------------A-.--T-G---A----   286
96ZM651.8    -.-------CGC----TGA-------C-------------------.----G---A----   267
96ZM751.3    -.---A--GC-C----TGA-G-----CT--A---------------.----G---A----   267
94CY017.41   -.------------------G------T-G----------------.----G--GAA---   289
94IN476.104  -.-------C-T----TGA-------CT------------------.----G---A----   268

93BR020.1    TGCACTTGATCCAGGCCTTCTAGAAACATCAGAAGGCTGTCGAAAAATAATAGGACAGTT   323
92NG083.2    -------A-C-GT-A----T--------G-------T---GTGC-------GAA------   346
90CF056.1    -------A-C--C------T--------C------------T-C-G-------A----A-   327
92RW009.6    -------A-C--T-A----T----G---C-----------AA-C-------GA-----C-   330
92NG003.1    -------A-C--T-A---CT--------A-------T----AGC-------GA-----C-   347
93BR029.4    C---G--A----T------T----G----------------A-C-----C-G-A----C-   333
94CY032.3    C------A-C--T------T--------G-------A----A-C--T----G-A------   346
96ZM651.8    ---G---A-C--T------T--------------------AA-C-------GAA----C-   327
96ZM751.3    -------A-C--T------T----G---------------AA-C--------CA----C-   327
94CY017.41   CT--A--A-C--T------T--------C----G--A---A--C--------A-G-----   349
94IN476.104  ---G---A-C--T------T----G--G-----C--A---AA-C--------AA----C-   328
```

Fig. 13A

```
93BR020.1   ACAACCATCCCTTCAGACAGGATCAGAAGAGCTCAAATCATTATATAATACAATAGCAGT   383
92NG083.2   G------G-T--CT--------A----G-----T-G--------T-------G-----AC   406
90CF056.1   ---G---G-TA--A--------A-------A--T----------T----CT-G-------   387
92RW009.6   G------G-T------------A----T--A--T-GG---------------G-----AC   390
92NG003.1   G--------T--C---------A----G---A-T----------T-------G-----AC   407
93BR029.4   -------G-----A----G-----------A--T-G----------------G-----AC   393
94CY032.3   ----T--A-T--CA-A--------------A--T-G----------------T---A--AC   406
96ZM651.8   -------G-T------------A-G--G--A--T-G---------C--C---G-----AC   387
96ZM751.3   -------G-T--C---------A----G--A--T-GG---------------G-----AC   387
94CY017.41  -------G-T--C--A------A-------A--T-----------------G---T---   409
94IN476.104 ---T---G-T---A--------A----G--A--T-GG-------TC--C---G-----AC   388

93BR020.1   CCTCTATTATGTACATCAAAAGGTAGAGGTAAAAGACACCAAGGAGGCTTTAGAGAAGCT   443
92NG083.2   ------C-G-------------A--------------------A--A---CC----G-AG-   466
90CF056.1   --------GC-------G---AA----T--G-----------------------T---A-   447
92RW009.6   --------G-------------A----T-------------------C-----C---A-   450
92NG003.1   --------G-----------G-A-------------------A--A---C-----G-AG-   467
93BR029.4   --------G-------------A----T-----------------A--------A---A-   453
94CY032.3   -----GG-GC----------GAA----T---C-------------A--------T--AA-   466
96ZM651.8   T-------G-------G--GG----------CG------------A--C-----C-G-A-   447
96ZM751.3   T-------G-------G-----A--A-----CG------------A--CC----C---A-   447
94CY017.41  ------C-GG----------G------T-----------------A---C----T--AA-   469
94IN476.104 T-------G-------GC-GG-A---------CG------------A--C-----C---A-   448

93BR020.1   AGAGGAAGAACAAAACAAAGGTCGGCAAAAGACACAGCAA..............GCGACT   489
92NG083.2   G--AA--AT------G--CA---A----G-A-T------G........GCA...--A-AG   515
90CF056.1   -------AT----------A---A------A--------........GCA...--AG--   496
92RW009.6   -------------------A---A------A--------G........GCAGAA--AG--   502
92NG003.1   G--AA--AT------G--CA---A----G-A------A-G........GCA...--A-TG   516
93BR029.4   ---------G--------.A--AA-A-----G-------........GCA...--AG--   501
94CY032.3   -------AT-----GT--GA-CAA---------------G........GCA...--AG--   515
96ZM651.8   -------------------AT--A------A-T-------AAAACACAGCAA..---G--   505
96ZM751.3   -------------------A---AA-----A-T---AA--........ACAGAA------   499
94CY017.41  -------------------......A---G--A--------T........GCA...--AG--   512
94IN476.104 -------------------A---A------A-T------G........GCAAAA-A-G--   500

93BR020.1   GCTGAAAAAGG.........GGTCAGTCAAAATTACCCTATAGTACAGAATCTTCAGGGA   540
92NG083.2   AA----GG-AACAGTAACCCA-----C---------T---------G------GCA--A--G   575
90CF056.1   -A-A-GG--AAAGACAACAA---------------T----------------GC---A--G   556
92RW009.6   -ACA--GG-A.........AA------------------------G--A---GCA--A--G   553
92NG003.1   -G-A--GG-AACAGCAGCCAA--T--C---------T---------G------GCA--A--G   576
93BR029.4   AACAC-GG-AACAACAGCCA------C--------------------G-----C--------G   561
94CY032.3   --C-C-GG---TAGCAGCAAT-----C--------------------G--A---GCA--A--G   575
96ZM651.8   -AC-G---..........---------------T---------G--------C--A--G   553
96ZM751.3   -GC-G---..........---------------T---------G--------C--A--G   547
94CY017.41  -ACAC-GGGAACAGCAG......-------------T--C-----G--A---GCA--A--G   566
94IN476.104 -AC-G---..........---------------T---------G--A-----C--A--G   548

93BR020.1   CAAATGGTACACCAGTCTTTATCACCTAGAACTTTAAATGCATGGGTAAAGGTGATAGAA   600
92NG083.2   ------A----T---G-CA----------G-----G-----G--------A--AG-----   635
90CF056.1   --G------------G-CA----------G--C--------------------A--AG-----   616
92RW009.6   ---------------G-CA----------------G-----G--------A--A-----G   613
92NG003.1   ---G-----------C-CA----------G-----------------------A--A------   636
93BR029.4   ---------------G-CA----------------------------------A--AG-----   621
94CY032.3   -----------T---AGCA-T----------------G---------------A--A------   635
96ZM651.8   ---------------AAAC------------------G---------------A--A------   613
96ZM751.3   ---------------G--A------------------G---------------A--A-----G   607
94CY017.41  ---------------G--A-----------G--G--G-----C-----C--A--AG-----   626
94IN476.104 ---------------C-CC-----------------G-----G--------A--A-----G   608

93BR020.1   GAGAAGGCTTTTAGTCCAGAAGTAATACCCATGTTTTCAGCATTATCAGAAGGGGCCACT   660
92NG083.2   --A-----C--C-------------------------------------G--A-----C   695
90CF056.1   --A------------C---------------------------------------A-----C   676
92RW009.6   ---------------C-A---G-----------------A----------------A-----C   673
92NG003.1   --A---AAC--C---------------------------A----------------A-----C   696
93BR029.4   ---------------C---------------------------------------A-----C   681
94CY032.3   --A--------C--C-----------------------C--------------G--A-----C   695
96ZM651.8   --A--A---------C-----G-----------------A----------------A-----C   673
96ZM751.3   -------G---C-AC-----G-----------------A----------------A-----C   667
94CY017.41  --A--------C--C-------------T------A----------------A-----C   686
94IN476.104 ---------------C-----G----------------CA----------------A-----C   668
```

Fig. 13B

```
93BR020.1    CCACAAGATTTAAACACCATGTTAAATACAGTGGGGGGACATCAAGCAGCCATGCAAATG    720
92NG083.2    --------------T------C----------------G-----------T---------    755
90CF056.1    --------C-----TG-T---C----------------------------------G---    736
92RW009.6    ---------------------C--------------------------------------    733
92NG003.1    -----------G--T------C----C--C--------G-----------T---------    756
93BR029.4    ---------------------C----C-----------------------T---------    741
94CY032.3    -----------G----TG---C------T------------C--G-----A---------    755
96ZM651.8    ------------------------------------------------------------    733
96ZM751.3    ---------C--------------------------------------------------    727
94CY017.41   --------C-----T--T---C----C-----------------------T---------    746
94IN476.104  --CTCT------------------------------------------------------    728

93BR020.1    TTAAAAGACACCATCAATGAGGAGGCTGCAGAATGGGACAGATTACATCCAACACAGGCA    780
92NG083.2    C----G--T--T--------T--A--------G--------GA--------CAG------    815
90CF056.1    --------T--A-----------A-----------------GG--------GTG--T---    796
92RW009.6    C-------T--A--------------------G-----T--GG--------GTG------    793
92NG003.1    C-------TT-T--T-----A--A--------G-----T--GC--------CA-------    816
93BR029.4    --------A--------------A------------------G--------GTG--T---    801
94CY032.3    --------T--------------A--------C--------GAC-------GT---T---    815
96ZM651.8    --------T--T--------------------------T------------GTG--T---    793
96ZM751.3    --------T--------------A--------------T--G---------GT---T---    787
94CY017.41   --------T--------------A-----------------GG--------GT---T---    806
94IN476.104  --------T--------C-----------G--------T------------GT---T---    788

93BR020.1    GGACCCATCCCCCCAGGTCAGATAAGGGAACCTAGGGGAAGTGATATAGCTGGAACTACT    840
92NG083.2    --G--T--T--A-----C--A-----A--G-----T--------------A---------    875
90CF056.1    --G--T--T--A-----C--A--G--A-----A--------C--------A---------    856
92RW009.6    --G--TG-TG-G-----C--------A-----A-----------C-----A---------    853
92NG003.1    -----T--T--A-----C--------A-----A-----------------A---------    876
93BR029.4    -----T-----A-----C-----G------------------------------------    861
94CY032.3    --G--T--T--A-----C-----G--A-----A-----------------A---------    875
96ZM651.8    --G--T--TG-A-----C--A--G--A-----A-----------------A---------    853
96ZM751.3    --G--T--TG-A-----C--A-----A-----A-----------C-----A---------    847
94CY017.41   --G--T--T--A-----C-----G--A-----A-----------C-----A---------    866
94IN476.104  --G--T-AT--A-----C-----G--A-----A-----------------A---------    848

93BR020.1    AGTACCCTTCAGGAACAAATACAATGGATGACAGGCAACCCACCTGTCCCAGTGGGAGAA    900
92NG083.2    --------G------------AG---------CA-----------A--------------    935
90CF056.1    --------G------------GC---------------T---G--A-------------C    916
92RW009.6    ---------------------GC----------AAT---------A-T------------    913
92NG003.1    --------G------------AC---------CA-----------A--------------    936
93BR029.4    ---------------------------------A--------------------------    921
94CY032.3    -----------A---------GG----------A--------------------------    935
96ZM651.8    --------C--A-----G---GC----------A-T--T--C---A-T-----------C    913
96ZM751.3    G--------------------GC----------AAT---------A-T-----------C    907
94CY017.41   ---------------------GGT--------CA--G-T-----CA--------------    926
94IN476.104  ---------------------GC------------T---------A-T-----------C    908

93BR020.1    ATGTATAAAAGATGGATCATCCTAGGATTAAATAAAATAGTAAGAATGTATAGCCCTGTC    960
92NG083.2    --C--------------A-----G-----------------G------------------    995
90CF056.1    --C--------------A-----G-----------G-----------------T------    976
92RW009.6    --T--------------A--T--G--G---------------------------------    973
92NG003.1    --T--------------A--T--G--G--------------G------------------    996
93BR029.4    --T------------------------------------------------------AC-    981
94CY032.3    --C--------------A---T-G--G-------------------C---------CA-T    995
96ZM651.8    --C--------------A--T--G--G---------------------------------    973
96ZM751.3    --C--------------A--T--G--G-----------------------C---------    967
94CY017.41   --T--------------A-----G------------------------------------    986
94IN476.104  --C--------------A--T--G--G---------------------------------    968

93BR020.1    GGCATTTTGGACATAAGACAAGGGCCAAAAGAACCCTTTAGAGACTATGTAGACAGGTTC    1020
92NG083.2    A-------------------------------------------T--------T------    1055
90CF056.1    A-----C---------A------------------------------------------T    1036
92RW009.6    A----A----------A------------G-----T------------------C-----    1033
92NG003.1    A-T-----A-------A---------------------C-----T-----G--T------    1056
93BR029.4    A-----C---G------------A-----G-----------------------TC-A--T    1041
94CY032.3    A----C-----------------A--------------C-----T--------T------    1055
96ZM651.8    A---------------A------------G------------------------C-----    1033
96ZM751.3    A-----C---------A------A-----G-----------G-----------TC-----    1027
94CY017.41   A-------------------------------------------T-----G--T------    1046
94IN476.104  A----------------------------G------------------------C-----    1028
```

Fig. 13C

```
93BR020.1    TTTAAAACCCTAAGAGCTGAGCAAGCTACACAGGAAGTAAAGGGTTGGATGACAGACACC  1080
92NG083.2    --------TT-G---------------------------A-----------------  1115
90CF056.1    --------TT---------------C--------T--G---AA-----------A---  1096
92RW009.6    --------T-------C--A-----T----A--T-----AAA-----------T---  1093
92NG003.1    --------TT-G-------------C--------G-----AAAC---------------  1116
93BR029.4    -A------T--------A------A--T-------T-----AAA-----------A---  1101
94CY032.3    ------TGT--C-----A--A--------C-----G--G--AAA-----------A---  1115
96ZM651.8    --C-----TT---------A--G--------A--------AAA---------------  1093
96ZM751.3    --------TT---------A----------A--T-----AA.----------------  1086
94CY017.41   --------T----------------C--------G-----AAAC--------G------  1106
94IN476.104  --------TT---------A----------A--------A-----------------  1088

93BR020.1    TTGTTGGTCCAAAATGCGAACCCAGATTGTAAGACCATTTTAAAAGCATTGGGACCAGGG  1140
92NG083.2    --------T----------------------A-----C----G------A--------A  1175
90CF056.1    ----------------A--T--------C-----T--A----G------A----A----  1156
92RW009.6    -----A-----------------------------------G------A--G------  1153
92NG003.1    ------------------------------------CC---G------A---G----A  1176
93BR029.4    -----------------------------C--A------------------------CA  1161
94CY032.3    C--C---------------T-----C------T----C-----------A---A-----  1175
96ZM651.8    ----------------A------------C--------------------A---------  1153
96ZM751.3    --------T--------------------------------GG-----A---------  1146
94CY017.41   ---C--------------------------GAT----C--G-G------A---------  1166
94IN476.104  ----------------A-----------------------G------A---------  1148

93BR020.1    GCTACACTAGAGGAAATGATGACAGCATGTCAGGGAGTGGGAGGACCTAGCCATAAGGCA  1200
92NG083.2    -----------A--------------------------------C--------A---  1235
90CF056.1    ---T--A----A----------------------------------T-----A---  1216
92RW009.6    ---T--T----A-----------------C-----------------CG-------A---  1213
92NG003.1    -----------A------T-------------A-------------C-----C--A---  1236
93BR029.4    -----------A----------------------------G-----CG-------A---  1221
94CY032.3    ------T----A-----------------------------------C--------A---  1235
96ZM651.8    ------T----A--------------------A--------------------C--A---  1213
96ZM751.3    ------T----A----------------------------G------G----C--A---  1206
94CY017.41   --CT--T----A-----------------------------------C--------A---  1226
94IN476.104  ---T--T----A------G-------------A--------------------C--A---  1208

93BR020.1    AGAGTTTTGGCTGAGGCAATGAGCCAAGCAACAAAT......ACAGCT...ATAATGATG  1251
92NG083.2    --------A-----------------G---T--GG-GCAGCAG----AGCC---------  1295
90CF056.1    --------------------------T--------...ACA-ATA-AGCC---------  1273
92RW009.6    --G----------A-------------T-CA-......CAAC--AAC...---------  1264
92NG003.1    --------A----------------GG------GG-...ACAT----AGCC---------  1293
93BR029.4    -----------A--A-------------T--------...TCAGGTA-C...---------  1275
94CY032.3    --------A-----------------G---T------...GCAG----AGCC---------  1292
96ZM651.8    -----G---------------------A---AT-G-.....GTA-A-....---C-----  1264
96ZM751.3    -------------A-------------T--AC---.....ACA-A-....---------  1257
94CY017.41   --G----------A------------T-T-CA--G-...ACA-ATA-AAAC---------  1283
94IN476.104  -----G---------------------T--CAT-G-.........-A-....---------  1256

93BR020.1    CAGAAAAGTAACTTTAAGGGCCAAAGAAGAATTGTTAAATGCTTTAATTGTGGCAAAGAA  1311
92NG083.2    --------C--T----------CG---------A----G--T--C--C--------G---  1355
90CF056.1    ------G-C-------------------A-T-------------C--C-----------G  1333
92RW009.6    ----G-G-C--T----------G---------A----G--T--C--C-----------  1324
92NG003.1    -------AC--T----------CG------GG-A----G--T--C--C--------G---  1353
93BR029.4    ----G-G-C--T----G-AA--------AG-C-A----G--T--C--------------  1335
94CY032.3    --------C--A--------------------C-A----G--T--C--C--------G---  1352
96ZM651.8    --------C--T-----A--AA-T-A------G--------T-----C-----T--G---  1324
96ZM751.3    --------C--T-----A----CT-A---------------T--C--C-------GG---  1317
94CY017.41   ----G-G-C--T----G---T----A-----...A----G--T--C--C--------G---  1340
94IN476.104  ----G-G-C--T-----A----CT-A------------------C--C--------G---  1316

93BR020.1    GGACACATAGCCAAAAATTGCAGGGCCCCTAGAAAAAAGGGCTGTTGGAAGTGTGGAAGA  1371
92NG083.2    -----TC------G-----------------G-----------------A-------AG  1415
90CF056.1    -------------G-----------------G-----------------A---------  1393
92RW009.6    ------C------G-----------------------------------A-------AG  1384
92NG003.1    -----TC------G-----------------G-----A-----------A-------AG  1413
93BR029.4    --G----------------------------G-----------C-----A-------AG  1395
94CY032.3    -----TC------G-----------------G-----------C-------------AG  1412
96ZM651.8    --G----------G-----------------G-----------------A-------AG  1384
96ZM751.3    --G--T-------GG-----------T---G-G-----A-----------A-------AG  1377
94CY017.41   ------C------G-----------------G-----------C-----A-------AG  1400
94IN476.104  --G----------G-----------------------GA-----------A-----GCA-  1376
```

Fig. 13D

```
                                                    POL start
93BR020.1    GAGGGACACCAAATGAAGGACTGCACTGAGAGACAGGCTAATTTTTTAGGGAAAATTTGG  1431
92NG083.2    --------T--------A--A-----G--A--G----------------------------  1475
90CF056.1    --A-----T--G-----A--------A----------------------------------  1453
92RW009.6    -----------------A-------------------------------------------  1444
92NG003.1    --------T--------A--------A----------------------------------  1473
93BR029.4    --A--------G-----A--T--T----------------------------C---  1455
94CY032.3    --------T--------A---------------------------------G---G---  1472
96ZM651.8    -----------------A-----T--------G----------------------------  1444
96ZM751.3    --A--------------A-----T-------------------------------------  1437
94CY017.41   --A-----T--------A--T----------------------------------------  1460
94IN476.104  --A--------------A-----T--------G----------------------------  1436

93BR020.1    CCTTCCAACAAGGGGAGGCCCGGAAACTTCATCCAGAACAGG..................  1473
92NG083.2    -------------------A--------TC----------..................  1517
90CF056.1    -------G---A--------A-----T--TC------G----..................  1495
92RW009.6    -------------------A-----T--TCC-----G---A..................  1486
92NG003.1    -------------------A--G--T--TC-T---------..................  1515
93BR029.4    ------C-------A-----A--G--T---C-T----G---A..................  1497
94CY032.3    -------G---A--------A-----T--TC-T---------..................  1514
96ZM651.8    ------C-------A-----A--G--T---C-T---------..................  1486
96ZM751.3    ------C-G-----------G--G------C-T--------ACCAGAGCCAACAGCCCCA  1497
94CY017.41   -----------A--------A-----T--TCCT----G---A..................  1502
94IN476.104  ------C-------------A--G--T---C-T--A------..................  1478

93BR020.1    CCAGAGCCGTCAGCCCCGCCAGCAGAGAGCTTCAGGTTCGGGGAGGAGACAACCCCATCT  1533
92NG083.2    A-------AA-------A---------------G-A-----A-------T-G----C--C  1577
90CF056.1    -----A--AA-------A---------------G-------A-------TG-----C---  1555
92RW009.6    -TG-----AA-------A----------A---TG-AA-G-----A----T-G--T-TC--  1546
92NG003.1    --------AA-------A--C------------G-------A-------T-G----T--C  1575
93BR029.4    --------AA-------A-------------------T-----A---GT---AA-TC-C  1557
94CY032.3    --------AA----------C--G--AT----AGA-AGGAAA------------T-C---  1574
96ZM651.8    --------AA-------A--------------------A---...---------CG--  1543
96ZM751.3    ----CT--AA-------A--------------------A---...---------TG-C  1554
94CY017.41   A-------AA-------A----------A---G--AA-G-----A----T----T-C--C  1562
94IN476.104  --------AA-------A--------------------AA---...---------CG--  1535

93BR020.1    CC...GAAGCAGGAGCAGAAAGACGAGGGACTGTACCCTCCCTTAGCTTCCCTCAAATCA  1590
92NG083.2    --...----------CA--G--GA---AG--A...TA-------A-------------  1631
90CF056.1    --GAA-C--G--C---T---G---A---A--C.....-----------------G----  1609
92RW009.6    -T...---A---------------AG--A-.........--T---AT------------  1594
92NG003.1    -T...----------C--GG--AA---A-TCA...-----A---A-C-----------  1629
93BR029.4    T-TCA---A-------C--T----A---AGA--...TA---T--G----------G----  1614
94CY032.3    -T...---------A-C--GG---A---A---A...TA---T---A-------------  1628
96ZM651.8    --...----------TC-------AG--A-........G-----A-------------  1591
96ZM751.3    --...--G-----------------A---A-........------A--G----------  1602
94CY017.41   -T...---------A-T-G-GAC-AG--A--CA---AA---TGC-AT------------  1619
94IN476.104  --...----------TC-------AG--A-.......------A-------------  1583
                                   GAG end
93BR020.1    CTCTTTGGCAACGACCCCTAGTCACAATAAGAGTAGGGGGACAGCTAAAGGAAGCTCTAT  1650
92NG083.2    ----------G---------------G---A-A--------------TA-----C----  1691
90CF056.1    ----------G--------T--T---G---A-A---A-------T---G----------  1669
92RW009.6    ------------------T------G---A-A----A--T-------GA----------  1654
92NG003.1    -------------------------G-----A---------------TA----------  1689
93BR029.4    ------------------C------G---AGA-------G--A-----------C----  1674
94CY032.3    ----------G--------T----------A-C-----------A---G---G-----T-  1688
96ZM651.8    ----------G--------T---T------AG--------C--AA-------G-----C-  1651
96ZM751.3    ----------G--------T---T------A---------T---A-------G-----C-  1662
94CY017.41   ------------------T--T---G---AGA---A-------------A----------  1679
94IN476.104  ----------G--------T---T------A---------C---A-------------C-  1643

93BR020.1    TAGATACAGGAGCAGATGATACAGTATTAGAAGACGTAAATTTGCCAGGAAAATGGAAAC  1710
92NG083.2    ----C--------------C------------GAA-------A---------------  1751
90CF056.1    ---------------------------------GA----------G--------------  1729
92RW009.6    ---------------------------------AA------------------------  1714
92NG003.1    ----C---------------------------C-AA-------A----------------  1749
93BR029.4    -------C-------------------------AA-------A-------G--------  1734
94CY032.3    ---------------------------------AA----------------------G-  1748
96ZM651.8    ----C--G-------G-----------------AA--------------C----------  1711
96ZM751.3    -G-------------------------------AA------------------------  1722
94CY017.41   -----------------------G---------AA------------------------  1739
94IN476.104  ----C----------------------------AA--GC-----------G--------  1703
```

Fig. 13E

```
93BR020.1     CAAAAATGATAGGGGGAATTGGAGGTTTTATCAAAGTAAAACAGTATGATAGCATACTCA   1770
92NG083.2     ---------------------------------------G----------CAA-----T-   1811
90CF056.1     ---------------------------------------G---------GCAAG--GC--   1789
92RW009.6     ----------------------------------G---------------CAA-----T-   1774
92NG003.1     -------------------------A------------------------CAA-----T-   1809
93BR029.4     ---------------------------------------G----------CAA----C--   1794
94CY032.3     -------------------C-------------------G---A------CAG----CT-   1808
96ZM651.8     -------------A-----------C------G------G---A------CAA----CT-   1771
96ZM751.3     -------------A-------------------------G----------CAA-----T-   1782
94CY017.41    ---------------------------------------G---A------CAG---GCT-   1799
94IN476.104   -------------A-------------------------G----------CAA-----T-   1763

93BR020.1     TAGAAATTTGTGGACACAGAGCTATAGGTACAGTGTTAGTAGGACCTACGCCTGTCAACA   1830
92NG083.2     --------G-----A-A-AG--------G-----A--------------A---A-T----   1871
90CF056.1     -------C------A-A-AG--------------A--------------A--------T-   1849
92RW009.6     --------------A-A-AG--------------A--------------AT---------   1834
92NG003.1     --------GAA--GA-A-AG--------G-----AC-------------A---A------   1869
93BR029.4     ---------------GT-A-----C---------A--------------A----------   1854
94CY032.3     --------------A-A-AG--C-----C--------------------A----------   1868
96ZM651.8     -G------------A-A-AG--------------A--------------A----------   1831
96ZM751.3     --------------A-A-AG--------------A--------------A----------   1842
94CY017.41    --------------A-A--G--C-----------A--------------C----------   1859
94IN476.104   --------------A-A-AG--------------A--------------A----------   1823

93BR020.1     TAATTGGAAGAAATATGTTGACCCAGATTGGTTGTACTTTACATTTTCCAATTAGTCCTA   1890
92NG083.2     -------G--------------T------------------A-C--------A-------   1931
90CF056.1     ----------G-----A-----T--A--------C--C---A------------------   1909
92RW009.6     -----------------------------------------A-C----------------   1894
92NG003.1     -------G--------------T--A---------------A------------------   1929
93BR029.4     --------------C-------T--------C--C------A-------C----------   1914
94CY032.3     --------C----C--------T---C--------------A------------------   1928
96ZM651.8     ----------------------T---C----A--C--AC--A------------------   1891
96ZM751.3     -------G------------------C----C--C--AC--A------------------   1902
94CY017.41    ----C---------------GTT---C--------------A------------------   1919
94IN476.104   -----------G----------T---C----A--C---C--A-------------C--C-   1883

93BR020.1     TTGAGACTGTACCAGTAAAATTGAAGCCAGGAATGGATGGCCCAAAGGTTAAACAATGGC   1950
92NG083.2     ----A-----------------A----------------------G--------------   1991
90CF056.1     ----A-----------------A-------------------------------------   1969
92RW009.6     -----------------GC---A-------------------------------------   1954
92NG003.1     ----------------------A--A--------A-------------------------   1989
93BR029.4     ----A----------------------------------------G--------------   1974
94CY032.3     ----A-----------------A-------------------------------------   1988
96ZM651.8     ----A-----------------A-------------------------------------   1951
96ZM751.3     ----A-----------------A----------------------G---C----------   1962
94CY017.41    ----A-----------------A-----------------T-------------------   1979
94IN476.104   ----A-----------------A--------------------------------G----   1943

93BR020.1     CATTGACAGAAGAAAAAATAAAAGCATTAACAGAAATATGTATGGAAATGGAAAAGGAAG   2010
92NG083.2     -------------G-----------------------T----AA--C-------------   2051
90CF056.1     -------------------------------G-----T----CA--G--------A----   2029
92RW009.6     ------------------------------G------T----CA-----------A--G-   2014
92NG003.1     -------------G-----------------------T----CA--T-------------   2049
93BR029.4     ------------------------------------------CA-----------A----   2034
94CY032.3     -------------------------C--------G-------CA--C-------------   2048
96ZM651.8     -------------G-----------T-------C---T---GAA--------G-------   2011
96ZM751.3     ---------------------------------C---T---GAA----------------   2022
94CY017.41    -------------------------------------C----AA----------------   2039
94IN476.104   -------------G-----------------------T----AA--------G-------   2003

93BR020.1     GAAAAATTTCAAAAATTGGGCCTGAAAATCCATACAATACTCCAGTATTTGCCATAAAGA   2070
92NG083.2     ----------------------------------T--C------A----C----------   2111
90CF056.1     -------C----G---A--------G----------GC------A-------------A-   2089
92RW009.6     ----------------C-----------------T--C--------------------A-   2074
92NG003.1     ----------------------A--------------C------A---------------   2109
93BR029.4     ----------------------C-------------------------------------   2094
94CY032.3     -C--G---------------------------------------A-------T-------   2108
96ZM651.8     --------A-------------------------T--C--------------------A-   2071
96ZM751.3     --------A----------C-----G--------T--C--------------------A-   2082
94CY017.41    -------------------------------------C--------G-----T-------   2099
94IN476.104   --------A-------------------------T--C--------------------A-   2063
```

Fig. 13F

```
93BR020.1    AAAAAGACAGTACTAAATGGAGGAAATTAGTAGATTTCAGAGAACTTAATAAAAGAACTC  2130
92NG083.2    ----------------------A-----G-------------------------------  2171
90CF056.1    -G--G--T--------------A--------G--------------C-------------  2149
92RW009.6    -G--G-----------G-----A-----------------G-----C--C----------  2134
92NG003.1    ----------------------A--G--G--------------G--C-------------  2169
93BR029.4    -------T--------------A-----------------------------G-------  2154
94CY032.3    ----------C-----------A-----------------------C-------------  2168
96ZM651.8    -G--G-----------G---C-A-----------------G-----C-------------  2131
96ZM751.3    -G--G-----------G-----A-----------------G-----C-------------  2142
94CY017.41   ----------C-----------A--------------T--------C-----G-------  2159
94IN476.104  GG--G-----------G-----A-----------------G--G--C-------------  2123

93BR020.1    AAGATTTTTGGGAGGTTCAATTAGGAATACCGCATCCAGCAGGGTTAAAAAAGAAAAAGT  2190
92NG083.2    ----C--C--------C--------------T--C--C--G----------------GA-  2231
90CF056.1    ----C--C-----A-----G-----------A--C-----------------------A-  2209
92RW009.6    ----C--------A--C--------G-----A--C--------------G--------A-  2194
92NG003.1    ----C--C--------C--------C-----T-----C--G----------------GA-  2229
93BR029.4    ----C--C-----A-----G-----G-----A-----C-----------G--------A-  2214
94CY032.3    -G--C--C-----A-----G--------------C--------------G--------A-  2228
96ZM651.8    ----C--------A-----------------A--C-----------------------A-  2191
96ZM751.3    -G--C--------A-----------------A--C-----G-------------------  2202
94CY017.41   ----C--C-----A-----G-----------A-----------A--------------AG  2219
94IN476.104  ----C--------A-----------------A--C--------T--------------A-  2183

93BR020.1    CAGTAACAGTACTGGATGTGGGGGATGCATATTTTTCAGTTCCCTTAGATAAGGATTTCA  2250
92NG083.2    -------G-----A--------A--------C--------------------A--C--T-  2291
90CF056.1    -----T----------------------------------C--T--------A--A----  2269
92RW009.6    ----G--------------------------C--C--------T------G--AGC----  2254
92NG003.1    -------------A------------------------A-----C-----G-AA-C--T-  2289
93BR029.4    ----------------------T--------------------A--------A--C----  2274
94CY032.3    -----------T--------------------------------------CCA--G----  2288
96ZM651.8    ----G--------------------------------------T------G-AAGC----  2251
96ZM751.3    ----G-----------------------G--------------T------G-A-GC----  2262
94CY017.41   -------------T-----------C-----------C---------C--G-A--C----  2279
94IN476.104  ----G--------------------------------------T------G-A-GC---G  2243

93BR020.1    GGAAGTACACTGCATCCACCATACCTAGTACCAACAATGAGACACCAGGAGTTAGGTACC  2310
92NG083.2    -A-----T-------TT--T----------TA--T--------------GA----A--T-  2351
90CF056.1    -A-----T-------T--------------TA-----------------GA----A--T-  2329
92RW009.6    ----A--T-------T--------------TA--------A---------A-------T-  2314
92NG003.1    -A-----T--A----T---T----------TA--T--------------GA----A--T-  2349
93BR029.4    -------T-------TT--------------A--------A--------GC----A--T-  2334
94CY032.3    ---------------T----------------------------------A----A--T-  2348
96ZM651.8    ----A--T-------T---------------A--------A--------GA----A--T-  2311
96ZM751.3    ----A--T-------T--------------TA--------A-----T--GA----A--T-  2322
94CY017.41   -A--A--T-------T-------------------------------------------T-  2339
94IN476.104  ----A--T-------T--------------TA--------A--------GA----A--T-  2303

93BR020.1    AGTACAATGTGCTTCCACAAGGATGGAAAGGATCACCAGCAATATTCCAATATAGCATGA  2370
92NG083.2    -A-----------------G--------------------------T--GAG--------  2411
90CF056.1    ----T--------------G-----------------------------GAG--------  2389
92RW009.6    -A--T--------------G------------------------------A----T----  2374
92NG003.1    ----------------G-----------------------------T--GAG--------  2409
93BR029.4    -------------------G--G---------------------------AG--------  2394
94CY032.3    -------------------G--C----------------------------G--------  2408
96ZM651.8    -A--T--------------G-----------------------------GAG--------  2371
96ZM751.3    -A--T--------------G------------------T----------GAG--------  2382
94CY017.41   ----------A--------G-----------------------------GAG--------  2399
94IN476.104  -A--T--------------G-----------------------------GAG--------  2363

93BR020.1    CAAAAATCTTAGATCCCTTTAGAGCAAAAAATCCAGACATAGTTATCTACCAATACATGG  2430
92NG083.2    -------T-----G--T--C---A-------------A--G--G----------------  2471
90CF056.1    ------------CG----------A-C-------T--A--G-----T-------------  2449
92RW009.6    -------------G--------G---C----C-A---A-----G-----T-----T----  2434
92NG003.1    -------------A---------A--G----------A-----G-----T--G-------  2469
93BR029.4    -------------G--T------AA-C----------------------T----------  2454
94CY032.3    -------------G---------TTC-----C-----A-----C--A--------T----  2468
96ZM651.8    -------------G-----C--G---C----------------C-----T-----T----  2431
96ZM751.3    T------------G--------GA--C----C-----A-----------T-----T----  2442
94CY017.41   ----G--------G---------T----G---A---AT--A--C----------------  2459
94IN476.104  -------------G--------G---CG-------A-A-----C-----T-----T----  2423
```

Fig. 13G

| | | |
|---|---|---|
| 93BR020.1 | ATGATTTGTATGTAGGGTCTGACTTAGAAATAGGACAGCATAGAACAAAAATAGAAGAGT | 2490 |
| 92NG083.2 | -------A--------A-----------------G---------G----------G---- | 2531 |
| 90CF056.1 | ----------------A-----------------G--A------G----------G---- | 2509 |
| 92RW009.6 | ----C-----C-----A-----------------G--A------G----------G---- | 2494 |
| 92NG003.1 | -------A--------A-------------C---G---------G----------G--A- | 2529 |
| 93BR029.4 | ----------------A-----------------G-----------T--G-----G--A- | 2514 |
| 94CY032.3 | ----------------------------------G--A------G--------------C | 2528 |
| 96ZM651.8 | ----CC----------A-----------------G--A------G--------------- | 2491 |
| 96ZM751.3 | ----C-----------A-----T-----------G--A--C---G----------G---- | 2502 |
| 94CY017.41 | ----C-----------A-----T---------A-C---------GT---------G--A- | 2519 |
| 94IN476.104 | ----C-----------------------------G--T------G----------G---- | 2483 |

| | | |
|---|---|---|
| 93BR020.1 | TAAGAGAACATCTACTGAAATGGGGATTAACTACACCAGACAAAAAACATCAAAAAGAAC | 2550 |
| 92NG083.2 | ----------------------------G--C--------T-----------G------- | 2591 |
| 90CF056.1 | ------CT---T-GT-------------T--C--------------------G------- | 2569 |
| 92RW009.6 | --------------T-A--G--------T--C------------G--------G------- | 2554 |
| 92NG003.1 | -----A-T----------G---------T--C--------T-----------G------- | 2589 |
| 93BR029.4 | -G---C-G---T-GT---GG--------T--C--------------------G------- | 2574 |
| 94CY032.3 | -------G------T---G---------C--C--------------------G------- | 2588 |
| 96ZM651.8 | --------------T-A--G--------T--C------------G--------G------- | 2551 |
| 96ZM751.3 | ----------C---T---G---------T--------------G--G-----G-----G- | 2562 |
| 94CY017.41 | ----G-CT--CT--T-------------TTA---------------------G------- | 2579 |
| 94IN476.104 | ------C-------T-A--G--------C--C--------T--G--------G------- | 2543 |

| | | |
|---|---|---|
| 93BR020.1 | CCCCATTCCTTTGGATGGGGTATGAACTCCATCCTGATAAATGGACAGTGCAGCCTATAC | 2610 |
| 92NG083.2 | -T-----------------A-----G-----------C--------G--A--A------- | 2651 |
| 90CF056.1 | -------T-----------A-----------------C-----------A---A--G--A | 2629 |
| 92RW009.6 | -T-----T--------------------T--------C-----------A--A------- | 2614 |
| 92NG003.1 | -T-----T--C--------A-----G-----------C--------G--A--A------- | 2649 |
| 93BR029.4 | -T-----------------T-----------------------------A---------G | 2634 |
| 94CY032.3 | -------T-----------------------------C---------------------- | 2648 |
| 96ZM651.8 | -------T-----------------------------C-----------A---------- | 2611 |
| 96ZM751.3 | -------T-----------------------------C-----------A---------A | 2622 |
| 94CY017.41 | -T-----T-----------A-----G--T--------C-----------C---------A | 2639 |
| 94IN476.104 | -------T-----------------------------C-----------A---------A | 2603 |

| | | |
|---|---|---|
| 93BR020.1 | AATTGCCAGACAAGGACAGCTGGACTGTCAATGATATACAGAAGTTAGTAGGAAAACTAA | 2670 |
| 92NG083.2 | -GC-------A-----AGAT--------------------A--------G---------- | 2711 |
| 90CF056.1 | --C-------A--A-----------------------------------G---------- | 2689 |
| 92RW009.6 | -GC-------A-----T--------------------------------G------T--- | 2674 |
| 92NG003.1 | -GC-----A----A--A-----------------------A--A-----G---------- | 2709 |
| 93BR029.4 | TGC-------A--A--------------------C--------------G------T-G- | 2694 |
| 94CY032.3 | --CC-G----A-----T--------------C-----C-----------G---------- | 2708 |
| 96ZM651.8 | -GC--G----A--A--T-----------T--------------------G------T--- | 2671 |
| 96ZM751.3 | -GC-------A-----G--------------------------------G------T--- | 2682 |
| 94CY017.41 | -GC-------A--A-----------------------------A--------G---T--- | 2699 |
| 94IN476.104 | -GC-------A-----T--------------------------------G------T--- | 2663 |

| | | |
|---|---|---|
| 93BR020.1 | ATTGGGCAAGTCAGATTTATCCAGGGATTAAAGTAAAACAATTATGTAAACTCCTTAGGG | 2730 |
| 92NG083.2 | -------------------------------------G--CC------G----------- | 2771 |
| 90CF056.1 | -----------------------AAT-----------G---C------------------ | 2749 |
| 92RW009.6 | -C-----------------C------G---------GG-----G---------------- | 2734 |
| 92NG003.1 | -------------------------------------G---C------------------ | 2769 |
| 93BR029.4 | --------------------G---------------GG---------------------- | 2754 |
| 94CY032.3 | -------------------------------------G--------------T------- | 2768 |
| 96ZM651.8 | -C-----------------CG---------------GG---C-T---------------- | 2731 |
| 96ZM751.3 | -C---.-------------CG---------------GG---C-G---------------- | 2741 |
| 94CY017.41 | --------------------G----------------G---C-G--------------A- | 2759 |
| 94IN476.104 | -C-----------------C--------------G-GG---C-T---------------- | 2723 |

| | | |
|---|---|---|
| 93BR020.1 | GAGCCAAGGCACTAACAGACATAGTGCCACTGACTACAGAAGCAGAGTTAGAATTGGCAG | 2790 |
| 92NG083.2 | -G-----A-----------------A--C--A--GG----------AA-G--GC------ | 2831 |
| 90CF056.1 | -G-----A---T-----------A-A--------A-A---G-----A--G---------- | 2809 |
| 92RW009.6 | --A----A---T-------------A-----A---GA---------A------------- | 2794 |
| 92NG003.1 | -G-----A-----------------A---------GA---------A------------- | 2829 |
| 93BR029.4 | --A----A-----------AG----A-----A--AG----G------C-----C------ | 2814 |
| 94CY032.3 | ----T--A--C--------------A-----A--------G--------------A---- | 2828 |
| 96ZM651.8 | -------A-----------------A-----A---GA---------A------------- | 2791 |
| 96ZM751.3 | -------A-----------------A---T-----GA---G-----A------------- | 2801 |
| 94CY017.41 | -------A-----------------AA---------A------------------A-A-- | 2819 |
| 94IN476.104 | -G-----A-----------------A-----A---GA---------A--------A---- | 2783 |

Fig. 13H

93BR020.1 AGAATAGGGAGATTCTAAAAGAACCAGTACATGGGGCATATTATGACCCGTCAAAAGACT 2850
92NG083.2 ----C-----A--------------T--------A-TC---C-------A--------A- 2891
90CF056.1 -A--C-----------G-G-------A-------A-T---------T--A---------- 2869
92RW009.6 -A--C-----A---T-------------------A-T------------A---------- 2854
92NG003.1 ----C-----A--------------T--------A-TC--C--------A--------A- 2889
93BR029.4 -A--C-----------------------------A-TG-----------C---------- 2874
94CY032.3 ----C--------------------------------------------A---------- 2888
96ZM651.8 ----C-A---A---T---------------------T------------A---------- 2851
96ZM751.3 ---GC-----A-----------------------A-T------------A---------- 2861
94CY017.41 ----C-----A---T-----ACC--T----------T---C--------A---------- 2879
94IN476.104 ----C-----A-----------G-----------A-T------------A---------- 2843

93BR020.1 TAATAGCAGAAATACAGAAACAAGGGCAAGGGCAATGGACATATCAAATTTATCAAGAGC 2910
92NG083.2 -----------G-------G-------C--AC---------------------------- 2951
90CF056.1 ---------------G---G-----------C-----------------------G---- 2929
92RW009.6 -------T--------------G-----T-AC--------------------C-----A- 2914
92NG003.1 -----------T--------------TGC-AC---------------------------- 2949
93BR029.4 ----------------------G--------C---------------------------- 2934
94CY032.3 -------------------G-----------T-----------------A---------- 2948
96ZM651.8 -G-----T--------------------T-AC--------------------C--G--A- 2911
96ZM751.3 -------T--------------------T-AC---------------G----C-----A- 2921
94CY017.41 ------------------------------AC-----------------------G--A- 2939
94IN476.104 -------T--------------G-----T-AC--------------------C-----A- 2903

93BR020.1 CATTTAAAAATCTAAAAACAGGAAAGTATGCAAAAATGAGGTCTGCCCACACTAATGATG 2970
92NG083.2 ---AC--------------------A----------G-G--------------------- 3011
90CF056.1 -------------G--G--------A--------------AA-----------------A 2989
92RW009.6 ----C--------G----------------------G----A----------------C- 2974
92NG003.1 ---AC--------G----------------------G-G--------------------- 3009
93BR029.4 ---A-------T-G-------------------GG------GG----------------- 2994
94CY032.3 --CA---------G--------G----------G--CC--A------------------- 3008
96ZM651.8 ----C--------G--------G------------------A-A---------------- 2971
96ZM751.3 ----C--------G---------------------------A------------------ 2981
94CY017.41 -C-----G-----G--------G--A----------G------CA--------------A 2999
94IN476.104 ----C--------G--------G------------------A----T------------- 2963

93BR020.1 TAAAACAGTTAACAGAAGCAGTGCAAAAGATATCTCTAGAAAGCATAGTAATATGGGGCA 3030
92NG083.2 -------A----------T---------A---G-CAC---GG----------C-----A- 3071
90CF056.1 -------A---------------------------AC---------------------A- 3049
92RW009.6 ----------------G---------------G-CA-G--------------------A- 3034
92NG003.1 ----------------------------A---G-CAC---G-----------------A- 3069
93BR029.4 -------AC-------G-----------A---A-CAC---------------------A- 3054
94CY032.3 -T-G---A------------------------G-CA-G---T----------------A- 3068
96ZM651.8 ----------------G-----------A---G-C--G--G-----------------A- 3031
96ZM751.3 ----------------G--G--------A---G-CA-G--------------------A- 3041
94CY017.41 ----------------------A-----A---A-CA-G-----------G--------A- 3059
94IN476.104 ----------------G-----------A---G-CA---------------------.A- 3022

93BR020.1 AGACTCCTAAGTTTAGACTACCCATATTAAAAGAGACATGGGATACATGGTGGACAGAGT 3090
92NG083.2 ---T------A----A------T---CG------A--------AGT-------------- 3131
90CF056.1 -A-T------A-----------T---CA------A--------G--C------------- 3109
92RW009.6 ----------A------T-------CCAG-----A--------A--------------C- 3094
92NG003.1 -AGT------A----A------T---AGG-----A--------AGT------------A- 3129
93BR029.4 ---T------A----A----------CA------A--G-----AG---------T----- 3114
94CY032.3 -----------------T--------CA---G--A--------C--------------A- 3128
96ZM651.8 ---T------A--------------CCA------A--------A--------------C- 3091
96ZM751.3 ---T------A-----G-------TCA------A--------G--------------C- 3101
94CY017.41 ----------A----A-T--------CA---G--A--------G---------G-G---- 3119
94IN476.104 ----C-----A--------------CCA------A--G-----G--------------C- 3082

93BR020.1 ACTGGCAAGCCACCTGGATTCCTGAGTGGGAGTTTGTCAATACCCCCCCTCTAGTAAAAC 3150
92NG083.2 -------G---G----------------------------------T------------- 3191
90CF056.1 -T-----------A-----------A-----------T--C-----T-A---------T 3169
92RW009.6 -T-----------------------------------T--------T--C---------T 3154
92NG003.1 -T-----G-----------------T--------------------T-----------GT 3189
93BR029.4 -T--------------------------------------------T--CT----G---T 3174
94CY032.3 -T-----G-----------C-----A-----A--------------T------------T 3188
96ZM651.8 -T-----------------------------------T--------T-TCT--------T 3151
96ZM751.3 -T-----------------------------------T-----T-----C---------T 3161
94CY017.41 -T-----G--T-----------------------------------T------------- 3179
94IN476.104 -T-----G-----------------T-----------T--------T--C---------T 3142

Fig. 13I

```
93BR020.1    TATGGTATCAGTTAGAAACAGAGCCCATAGTAGGAGCAGAAACCTTCTATGTAGATGGGG  3210
92NG083.2    ----------A-----------A------CC------------T-A--------------  3251
90CF056.1    ------------------------------C------------T-A----A---------  3229
92RW009.6    -------C---C----G-A---A------T----------G--T--------------A-  3214
92NG003.1    ---------GA-----------A------CC------------T-A--------------  3249
93BR029.4    -------C--------G-A---A--------------------T----------------  3234
94CY032.3    -------C--------------C-------C------------T----------------  3248
96ZM651.8    -------C---C-G--G-A---A-----------------------------------A-  3211
96ZM751.3    -------C---C-G--G-A---A-------C------------T-A------------A-  3221
94CY017.41   -G-----C----------A---A-------C------------T----------------  3239
94IN476.104  -------C---C------A---A--------------------T--------------A-  3202

93BR020.1    CATCTAATAGAGAGACCAAAAAAGGAAAAGCAGGATATGTTACTGACAGAGGAAGACAAA  3270
92NG083.2    --G-------G-----A---TT------G------C------------A-----A-----  3311
90CF056.1    --G-------G--A--T---TT------------------C-----T-------AG----  3289
92RW009.6    --G-----C-G--A--T----T------------G--------------------G--G-  3274
92NG003.1    --G------A---A--A---TT------G-------------------------A-----  3309
93BR029.4    --G-------G--A--T---TT------------------G-------------------  3294
94CY032.3    --G----------A--A---C-G-----------------------T-----C-------  3308
96ZM651.8    --G-C-----G--A--T---TT------------G---A----------------G----  3271
96ZM751.3    --G-C-----G--A--T----T------------G--------------------G----  3281
94CY017.41   --G-------------T---CT------G-----G-----C-------------------  3299
94IN476.104  --G-------G--A--T---GT------------G--------------------G--G-  3262

93BR020.1    AAGCGGTCTCCCTAACTGAGACTACAAATCAGAAGGCTGAGTTACAAGCAATTCAGTTAG  3330
92NG083.2    --ATTA-TA----------A--A-----C--A--------A-----T--------AC---  3371
90CF056.1    ---TT-----------G--A--A------------A----A------------T-TC---  3349
92RW009.6    --ATT--T--T--------A--A------------A----A---------------C---  3334
92NG003.1    --ATTA--A--A--CAG--A--A--------A--AA----A-----C---------C---  3369
93BR029.4    ---TT---C-------G--C--A-----------AA-------------------TC---  3354
94CY032.3    ---TT---------T----A--A------------A----A------------T-C----  3368
96ZM651.8    --ATT--TA-T--------A--A------------A----A------------T-CC---  3331
96ZM751.3    --ATT--TA-T--------A--A--------A---A----A-------------------  3341
94CY017.41   --ATT--------G--G-----A--------A---A----A-----T-----CT-T--G-  3359
94IN476.104  --ATT--T--TT-------A--A------------A----A--G------------C---  3322

93BR020.1    CTTTACAGGATTCAGGATCAGAAGTAAACATAGTAACAGACTCACAGTATGCATTAGGAA  3390
92NG083.2    ----G-----C---A--C------------------------------------------  3431
90CF056.1    ----G--A--------G-T------G--------G-----T------------C------  3409
92RW009.6    ------------------------------------------------------------  3394
92NG003.1    ----G-------------------------------------------------------  3429
93BR029.4    ----G--------G----T---------------------------A-------------  3414
94CY032.3    ----G------------------------------------------------A------  3428
96ZM651.8    ----G--A-----------------------------T--------------G-------  3391
96ZM751.3    ----G-------------------------------------------------------  3401
94CY017.41   ------------------T------G--------G-----T-------------------  3419
94IN476.104  ----G--A---------A------------------------------------------  3382

93BR020.1    TCATTCAAGCACAACCAGATAAGAGTGAATCAGAGTTAGTCAATCAAATAATAGAGCAAT  3450
92NG083.2    ---------------------G-----G------A--------------------A--GC  3491
90CF056.1    ----------------C-----------------------T---------------G---  3469
92RW009.6    ---------------------GC--C-----G---GC------------------A--G-  3454
92NG003.1    ---------------------G------------A--------------------A--GC  3489
93BR029.4    ------------------------------T---AA----------------------G-  3474
94CY032.3    ---------------------GA-----------T-----T-----------------G-  3488
96ZM651.8    -------------T-----------------------------C-----------A----  3451
96ZM751.3    ----C-----------------------------A--------------------A--G-  3461
94CY017.41   -------------------A-G-------------A-------------------AA---  3479
94IN476.104  ----------------------A--------------------C-----------A----  3442

93BR020.1    TAATAAAAAAGGAAAAGGTCTACCTGTCATGGGTACCAGCACACAAAGGGATTGGAGGAA  3510
92NG083.2    ------------------------------------------------------------  3551
90CF056.1    -------G-----------------------------------------A----------  3529
92RW009.6    ---------------GA--------------------------T-----A----------  3514
92NG003.1    -----------------------T-AA----------------------A-----G----  3549
93BR029.4    -----------------A--------G----------------------A----------  3534
94CY032.3    -----CGG-----C----------------------------------------------  3548
96ZM651.8    -------G-------G---------------------------T-----A--------T-  3511
96ZM751.3    -G-------------G---T-----------------------------A----------  3521
94CY017.41   -----G---------G---------A----------------------------------  3539
94IN476.104  -------C--A----GA-----T--------------------T-----A--------G-  3502
```

Fig. 13J

```
93BR020.1    ATGAACAAGTAGATAAATTAGTCAGTGCTGGAATCAGGAAAGTACTGTTTCTAGATGGGA  3570
92NG083.2    ----------------GC--------AG----------------T-A---T-G-----C-  3611
90CF056.1    ----------------------T---T-----G----A-----G--A-------------  3589
92RW009.6    ----------------------A---AG-----------G---G--------------A-  3574
92NG003.1    --------------------------AG---------A------------T-------C-  3609
93BR029.4    -------------C------------T-------------------A---T-------A-  3594
94CY032.3    -------------------------CAA---------A--G--G--A---T-------A-  3608
96ZM651.8    -------G--------------A--CAAG--------------G--------------A-  3571
96ZM751.3    -------------------G--A---AG---------------G--------------A-  3581
94CY017.41   -------------C------------T----------------G--A---T---------  3599
94IN476.104  ---------------G------A---AG------T-------------------------  3562

93BR020.1    TAGATAAGGCACAAGAGGAACATGAAAAATATCACAACAATTGGAGAGCAATGGCTAGTG  3630
92NG083.2    -------A--C-----A----------G--------G-----------------------  3671
90CF056.1    -------A--T-----A----------GG-----T---------------G---------  3649
92RW009.6    ----------T-----A----------G--------G-----------------------  3634
92NG003.1    ----C--A--T--------C-------G--------G-----------------------  3669
93BR029.4    ----------C-----A--------G-----------T----------------------  3654
94CY032.3    ----------T-----A--------G-----------T--C-------------------  3668
96ZM651.8    ----C-----T-----A--G----------------------------------------  3631
96ZM751.3    ----------T-----A--G----------------G-----------------------  3641
94CY017.41   ----------T----------------G--------G-------------------CA--  3659
94IN476.104  ----------T-----A--T--------G-------G--------------------A--  3622

93BR020.1    ATTTTAATATACCAGCTGTAGTAGCAAAAGAAATAGTAGCTAGCTGTGATAAATGTCAGC  3690
92NG083.2    --------C-G---C----------------------G--C-----------------A-  3731
90CF056.1    --------C-----C--A------------------------------------------  3709
92RW009.6    --------C-G---C--A----------G-----------C-----------G-------  3694
92NG003.1    --------C-G---C--A-------------------G--C-------------------  3729
93BR029.4    -C-----C------C-------------------------C-------------------  3714
94CY032.3    --------C-G---T-A--G-----------G---------------A------------  3728
96ZM651.8    -A------C-----C-A--------------------------T----------------  3691
96ZM751.3    -G------C-G---C-CA----------------------C-------------------  3701
94CY017.41   -C------C-----C---------------------------------------------  3719
94IN476.104  -G------C-G---C-CA-------------------------------------C----  3682

93BR020.1    TAAAAGGGGAAGCCATGCATGGACAAGTAGATTGTAGCCCAGGGATATGGCAATTAGATT  3750
92NG083.2    -------------------------------C-----T-----A----------------  3791
90CF056.1    -------------------------------C-----------A----------------  3769
92RW009.6    ----------------------G--------C-----T--------------------C-  3754
92NG003.1    -------------------------------C-----T-----A----------------  3789
93BR029.4    -------A-----------------------C-----T-----A--------GC------  3774
94CY032.3    ----------------------------G--C-----T--------------G-------  3788
96ZM651.8    A--------------CA--------------C-----T--------------------C-  3751
96ZM751.3    ----------------A--------------C-----T-----A----------------  3761
94CY017.41   -------------------------------C-----T-----A---------C------  3779
94IN476.104  -------------------------------CC---------------------------  3742

93BR020.1    GCACACATTTAGAAGGAAAAATTATCCTGGTAGCAGTCCATGTAGCTAGTGGGTACCTAG  3810
92NG083.2    -T------------------------A-A--------T--------C-----C--TA---  3851
90CF056.1    ----------G------C--G----T--------------------C-----C--TA---  3829
92RW009.6    -T------C-G-----------A-------------------C---C-----T--TA---  3814
92NG003.1    --------C-----------G-C--TA-A-----------------C-----C--TA---  3849
93BR029.4    -T-----C------------G----------------G--------CG----A--TA---  3834
94CY032.3    -T--------------T---G-----A----------T-----G--------A---A---  3848
96ZM651.8    -T--------------------C-----------------------C-----C---A---  3811
96ZM751.3    -T--C---------------G-C---T-------------------C-----T---A---  3821
94CY017.41   --------C-T---------G----------G-----------G--C-----C--TA---  3839
94IN476.104  -T------C-------------C-----------------------C-----C---A---  3802

93BR020.1    AAGCAGAAGTTATCCCAGCAGAAACAGGACAAGAGACAGCCTACTTCCTACTAAAGTTAG  3870
92NG083.2    ----------------------------G--G--A-----A-----TA--T----A----  3911
90CF056.1    ----------C------------------A-G--A-----A--------GT-G--AC---  3889
92RW009.6    -------G-----T--------------------A-----A-----TA-------A----  3874
92NG003.1    -------------------------------G--------A--------G-----A----  3909
93BR029.4    -------------T--------G-----G-----A-----A-----T--CT----A----  3894
94CY032.3    -------------------------------G--A------------A-------A----  3908
96ZM651.8    -------G--------------------------A-----A----ATA--T----A----  3871
96ZM751.3    -------G--C-C------G--------------A-----ACTT---A-------A----  3881
94CY017.41   ----------C------A-------------G--T-----A-----TA--T----AC---  3899
94IN476.104  -------G--------------------------A-----A----ATA-------A----  3862
```

Fig. 13K

```
93BR020.1    CAGGAAGATGGCCAGTAAAAACAATACATACAGACAATGGCACCAATTTCACCAGTGCCA   3930
92NG083.2    -------G------------GTG-----------------TC---------T------TG   3971
90CF056.1    --A-C---------------GT--------------------G---------G-----TG   3949
92RW009.6    ----------------C---GT--------------------GT------------AAT-   3934
92NG003.1    --------------------GT------C-------------G---------------TG   3969
93BR029.4    ----------------------------C-------------G-------------A-T-   3954
94CY032.3    ----------------G----TG------G-------C---C----------------TG   3968
96ZM651.8    ----------------C---GT------------------T-G------T--------TG   3931
96ZM751.3    ----------------C---GT-G------------------GT--------------TG   3941
94CY017.41   --------------------GT------------------GC---------T------A-   3959
94IN476.104  ----------------C---GT------------------T-GT--------------TG   3922

93BR020.1    CGGTTAAGGCAGCTTGTTGGTGGGCAGGTATCCAGCAGGAATTTGGAATTCCTTACAACC   3990
92NG083.2    -A--A--------A-----------AA----ACA-----------------C-----T-   4031
90CF056.1    -------------C-------------A------A-----------G-----C-----T-   4009
92RW009.6    -A-----A-----C--------------------A-----------------C-----T-   3994
92NG003.1    -AA-G--A-----C------------AA------A-----------------C-----T-   4029
93BR029.4    -A--C-----C--C-----------G--G---A-------------C-----C-----T-   4014
94CY032.3    -------------C-------------A----A-C-----------------C-----T-   4028
96ZM651.8    -A-----------C-------------------A-A--A-------------C-----T-   3991
96ZM751.3    -A--C--------C--------------------C-----------------C-----T-   4001
94CY017.41   -A-----------C--------------------A--A--------G-----C-----T-   4019
94IN476.104  -A-----------C--------------------A-----------------C-----T-   3982

93BR020.1    CCCAAAGTCAAGGAGTAGTAGAATCTATGAATAAAGAGCTAAAGAAAATCATAGGACAGA   4050
92NG083.2    -------C-----------G-------------G--AT-----------C------G   4091
90CF056.1    ----------G-------------------------AT-------G--------G---G   4069
92RW009.6    ----------G------A-------C-----------AT---------------G---G   4054
92NG003.1    -------C-----------G----------------AT----------T-----G---G   4089
93BR029.4    -----------------A------------------AT----------T---------G   4074
94CY032.3    -------C-----------G----------------AT----------------G---G   4088
96ZM651.8    -A--------G--------------C-----------AT---------------G---G   4051
96ZM751.3    -------------------------C-----------AT---------T-----G---G   4061
94CY017.41   -------------------G----------------AT----------------G---G   4079
94IN476.104  -------C--G--------------C-----------AT---------T-----G---G   4042

93BR020.1    TAAGAGATCAAGCTGAACATCTTAAGACAGCAGTCCAAATGGCAGTATTCATTCACAATT   4110
92NG083.2    -TG-----------------------------------A--G---------------------   4151
90CF056.1    -------C-----A-----C--------------A------------------------   4129
92RW009.6    ----------------G--C----G---------A------------------------   4114
92NG003.1    -C--G--------------C--C-----------A--G---------------------   4149
93BR029.4    ----G-----G-----------------------A----C------------C-------   4134
94CY032.3    -C--G--------------C--------------A--G---------------------   4148
96ZM651.8    ----------G-----G--------A--------A------------------------   4111
96ZM751.3    ----------------G--C--------------A------------------------   4121
94CY017.41   -------------------C--------------A------------------------   4139
94IN476.104  -------A---------G--C--------------A------------------------   4102

93BR020.1    TTAAAAGAAAAGGGGGGATTGGGGGATACAGTGCAGGGGAAAGAACAATAGACATAATAG   4170
92NG083.2    ------------------------G-------------------T-------------   4211
90CF056.1    ------------------------G-------------------T-------------   4189
92RW009.6    ------------------------G-------------------T-------------   4174
92NG003.1    ------------------------G-------------------T-------------   4209
93BR029.4    ------------------------G-------------------T-G-----------   4194
94CY032.3    ------------------------G-------------------T-------------   4208
96ZM651.8    -----------A------------G-------------------T-------------   4171
96ZM751.3    ------------------------G-------------------T-------------   4181
94CY017.41   --------------------------------------------T-------------   4199
94IN476.104  ------------------------G-----------------------------------   4162

93BR020.1    CAACAGACATACAAACTAGAGAATTACAAAAACAAATTATAAAAATTCAAAATTTCCGGG   4230
92NG083.2    --T----T----------A----C-----------------------------T----   4271
90CF056.1    -----------------A------------------TC---C--------A--T----   4249
92RW009.6    -----------------AG-------------------C-----------------T----   4234
92NG003.1    --T----T----------A----C----------G----------------------T----   4269
93BR029.4    -------------G----A-------------------C-----------------T----   4254
94CY032.3    --T----T----------A----C---------------C-----------------T----   4268
96ZM651.8    ----------------C-A----C-------------------C--------A--T----   4231
96ZM751.3    ---------------------------------------------------------T----   4241
94CY017.41   -------T----------A----C------G--------C-----------------T----   4259
94IN476.104  -----------------A-------------C-------C-----------------T----   4222
```

Fig. 13L

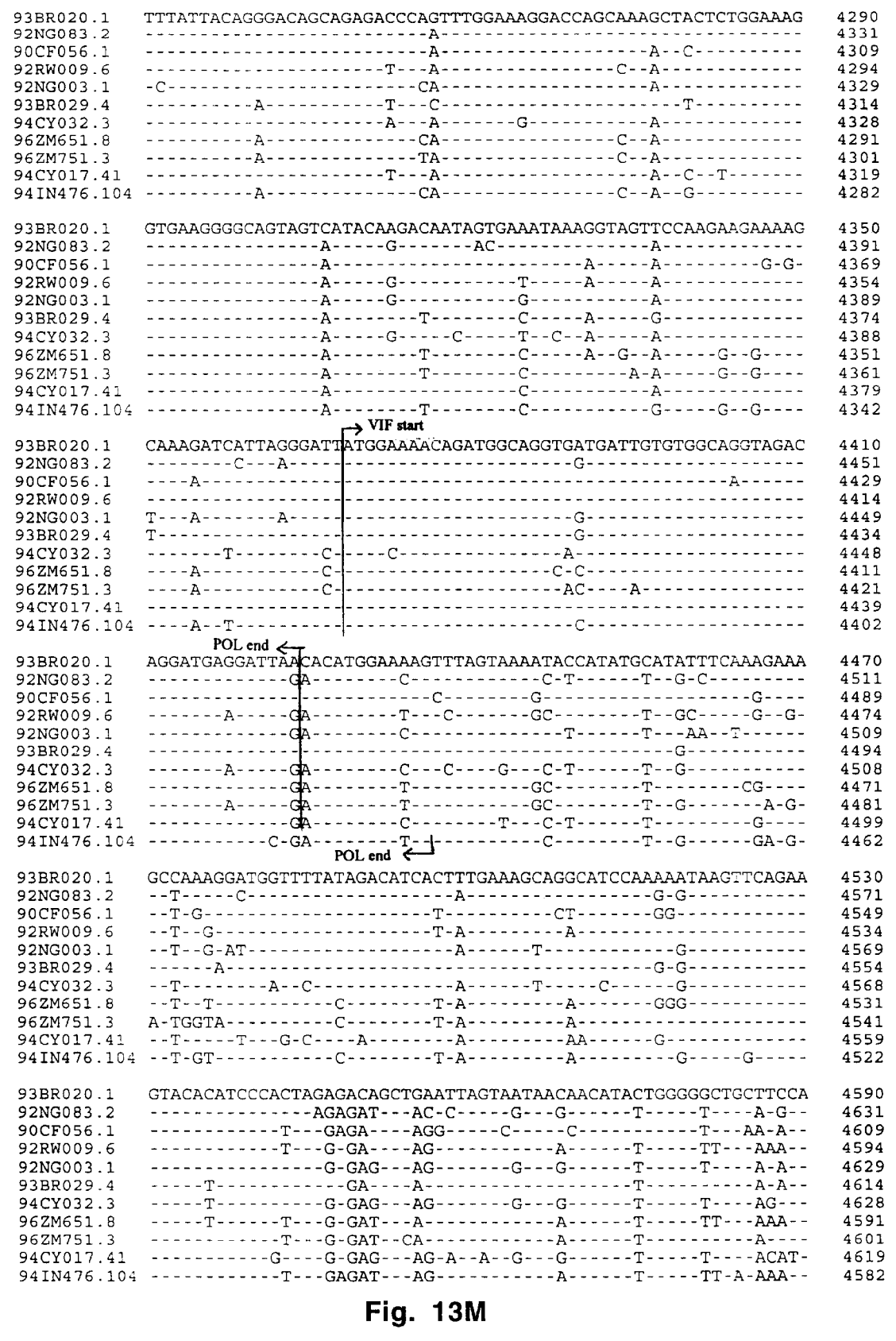

```
93BR020.1    TTTATTACAGGGACAGCAGAGACCCAGTTTGGAAAGGACCAGCAAAGCTACTCTGGAAAG  4290
92NG083.2    --------------------------A---------------------------------  4331
90CF056.1    --------------------------A-------------------A--C----------  4309
92RW009.6    ----------------------T---A----------------C--A-------------  4294
92NG003.1    -C-----------------------CA-------------------A-------------  4329
93BR029.4    ----------A-----------T---C----------------------T----------  4314
94CY032.3    ----------------------A---A-------G-----------A-------------  4328
96ZM651.8    ----------A--------------CA----------------C--A-------------  4291
96ZM751.3    ----------A--------------TA----------------C--A-------------  4301
94CY017.41   ----------------------T---A-------------------A--C--T-------  4319
94IN476.104  ----------A--------------CA----------------C--A--G----------  4282

93BR020.1    GTGAAGGGGCAGTAGTCATACAAGACAATAGTGAAATAAAGGTAGTTCCAAGAAGAAAAG  4350
92NG083.2    ----------------A-----G-------AC--------------A-------------  4391
90CF056.1    ----------------A-----------------------A-----A---------G-G-  4369
92RW009.6    ----------------A-----G-----------T-----A-----A-------------  4354
92NG003.1    ----------------A-----G-----------G-----------A-------------  4389
93BR029.4    ----------------A---------T-------C-----A-----G-------------  4374
94CY032.3    ----------------A-----G-----C-----T--C--A-----A-------------  4388
96ZM651.8    ----------------A---------T-------C-----A--G--A-----G--G----  4351
96ZM751.3    ----------------A---------T-------C---------A-A-----G--G----  4361
94CY017.41   ----------------A-----------------C-----------A-------------  4379
94IN476.104  ----------------A---------T-------C-----------G-----G--G----  4342
                               VIF start
93BR020.1    CAAAGATCATTAGGGATTATGGAAAACAGATGGCAGGTGATGATTGTGTGGCAGGTAGAC  4410
92NG083.2    --------C---A--------------------------G--------------------  4451
90CF056.1    ----A------------------------------------------------A------  4429
92RW009.6    ------------------------------------------------------------  4414
92NG003.1    T---A-------A--------------------------G--------------------  4449
93BR029.4    T--------------------------------------G--------------------  4434
94CY032.3    -------T--------C-----C---------------A---------------------  4448
96ZM651.8    ----A-----------C--------------------C-C--------------------  4411
96ZM751.3    ----A-----------C---------------------AC----A---------------  4421
94CY017.41   ------------------------------------------------------------  4439
94IN476.104  ----A--T-------------------------------C--------------------  4402
                       POL end
93BR020.1    AGGATGAGGATTAACACATGGAAAAGTTTAGTAAAATACCATATGCATATTTCAAAGAAA  4470
92NG083.2    -------------GA--------C------------C-T------T--G-C---------  4511
90CF056.1    --------------------------C--------G-------------------G----  4489
92RW009.6    -------A-----GA--------T---C-------GC--------T--GC-----G--G-  4474
92NG003.1    -------------GA--------C--------------T------T---AA--T------  4509
93BR029.4    ------------------------------------------------G-----------  4494
94CY032.3    -------A-----GA--------C---C----G---C-T------T--G-----------  4508
96ZM651.8    -------------GA--------T-----------GC--------T--------CG----  4471
96ZM751.3    -------A-----GA--------T-----------GC--------T--G-------A-G-  4481
94CY017.41   -------------GA--------C--------T---C-T------T---------G----  4499
94IN476.104  -----------C-GA--------T------------C--------T--G------GA-G-  4462
                              POL end
93BR020.1    GCCAAAGGATGGTTTTATAGACATCACTTTGAAAGCAGGCATCCAAAAATAAGTTCAGAA  4530
92NG083.2    --T-----C-------------------A-----------------G-G-----------  4571
90CF056.1    --T-G---------------------T----------CT-------GG------------  4549
92RW009.6    --T--G--------------------T-A---------A---------------------  4534
92NG003.1    --T--G-AT-------------------A------T------------G-----------  4569
93BR029.4    ------A---------------------------------------G-G-----------  4554
94CY032.3    --T--------A--C-------------A------T-----C------G-----------  4568
96ZM651.8    --T--T-----------C--------T-A---------A-------GGG-----------  4531
96ZM751.3    A-TGGTA----------C--------T-A---------A---------------------  4541
94CY017.41   --T-----T---G-C----A--------A---------AA------G-------------  4559
94IN476.104  --T-GT-----------C--------T-A---------A---------G-----G-----  4522

93BR020.1    GTACACATCCCACTAGAGACAGCTGAATTAGTAATAACAACATACTGGGGGCTGCTTCCA  4590
92NG083.2    ---------------AGAGAT---AC-C-----G---G------T-----T----A-G--  4631
90CF056.1    ------------T---GAGA----AGG-----C-----C-----------T---AA-A--  4609
92RW009.6    ------------T---G-GA----AG-----------A------T-----TT---AAA--  4594
92NG003.1    ----------------G-GAG---AG-------G---G------T-----T----A-A--  4629
93BR029.4    -----T------------GA----A-------------------T----------A-A--  4614
94CY032.3    -----T----------G-GAG---AG-------G---G------T-----T----AG---  4628
96ZM651.8    -----T------T---G-GAT---A------------A------T-----TT---AAA--  4591
96ZM751.3    ------------T---G-GAT--CA------------A------T----------A----  4601
94CY017.41   -----------G----G-GAG---AG-A--A--G---G------T-----T----ACAT-  4619
94IN476.104  ------------T---GAGAT---AG-----------A------T-----TT-A-AAA--  4582
```

Fig. 13M

```
93BR020.1    GGAGAAAGAGAATGGCATCTGGGTCAGGGAGTCTCCATAGAATGGAGGCAGGGGAGGTAT   4650
92NG083.2    -------A---C-----AT----C--T--G--T------------------AAA--A---   4691
90CF056.1    ------------------T-A--C-----------------------A-T-AAA------   4669
92RW009.6    --G--------T------T-------T--------------------ATT-A-A--A---   4654
92NG003.1    -----------C-----CT----------G----------------A----A-A--A---   4689
93BR029.4    -----------T------------------------------------------------   4674
94CY032.3    --G---CA---C-----CT-------T----------------------TCA-A--A---   4688
96ZM651.8    -----------T------T-------T--------------------ATT-A-A--A---   4651
96ZM751.3    --G---------------T-------T--------------------ATT-A-A--A--C   4661
94CY017.41   -------A---C-----CT-------T-----------------------AAAC------   4679
94IN476.104  -----------T------T-------T--C-----------------ATT---A--A---   4642

93BR020.1    AGAACACAAATAGACCCTGGCCTGGCAGACCAACTGATCCATATATATTATTTTGATTGT   4710
92NG083.2    --T---------------AA-ACA--------T-----T---C-G-----------C---   4751
90CF056.1    --C------G----G--------------------A--T-----GC--------------   4729
92RW009.6    -AG------G------------------G------A--------GC--------------   4714
92NG003.1    --C-----------T----A---A--------------T--CC-GC--------A-C---   4749
93BR029.4    --G---------------------------------------------------------   4734
94CY032.3    --C------G-G--T----A---------------A--T-----GC----C---------   4748
96ZM651.8    --C------G----------------------G--A--T-----GC-C------------   4711
96ZM751.3    --C------G----------------------G--A--T-----GC--------A-----   4721
94CY017.41   CAT----------------AT-----------T--A------C-G-----------C---   4739
94IN476.104  --C------G----A-----------------G--A--------GC--------------   4702

93BR020.1    TTTTCAGAATCTGCCATAAGGAAAGCCATATTAGGACATAAAATTAGCCCTAGGTGTAAC   4770
92NG083.2    --------------------A---------------G-G-T-G--------------G-A   4811
90CF056.1    -------------------------------------G-GT-G----A------------   4789
92RW009.6    ---G----C-------------------------------T-G--------------G--   4774
92NG003.1    -----------G---G--------------C-----G-AGT-G----A---------G-A   4809
93BR029.4    ----------------------------------------G----------------G-T   4794
94CY032.3    ----------------------------------------G-G----T---------G-A   4808
96ZM651.8    ---G----C-----------A-----------------C-T-G---TT---------G--   4771
96ZM751.3    ---G----C-----------A------C--C---------T-G---TT---------G-T   4781
94CY017.41   ------------------------------A-----G-A-T-G----T---------G-A   4799
94IN476.104  ---G----C-----------A-----------------C-T-G---TTT--------G-T   4762

93BR020.1    TATCAAGCAGGACATAACAAGGTAGGATCTCTACAATACTTGGCACTAACAGCATTAATA   4830
92NG083.2    --C-C------------T--------------------TC-----TCG-A-------G--   4871
90CF056.1    ----C------------AC--------A-----------------T-----------G-G   4849
92RW009.6    -----------------T-----------------------------G--------G---   4834
92NG003.1    ------A----------TC----------A--------T--A-----C-A-------G--   4869
93BR029.4    -----------------------------------G------------------------   4854
94CY032.3    -----------------T-----------CT--------C--------G-----------   4868
96ZM651.8    -----------------T--------------G--------------G--------G---   4831
96ZM751.3    -----------------T-----------C-----------------G--------G---   4841
94CY017.41   --------------------------G-----G-----T------T-G-A----G--G--   4859
94IN476.104  -----------------T-----------------------------G--------G---   4822
                                                                  -> VPR start
93BR020.1    GCTCCAAAAAAGACAAAGCCGCCTTTGCCTAGTGTCCAGAAACTAGTAGAAGACAGATGG   4890
92NG083.2    A-A----C--G--A--G---A--------A-----TGG----T---C------T------   4931
90CF056.1    --A----------T------A--------------TAGA--G--------G--T------   4909
92RW009.6    AAA----------T------A---C----------TAGT---T-------G--T-A----   4894
92NG003.1    A-A----C-C----------A-----A--------TA----GT--AC------T------   4929
93BR029.4    AAA----------G------A--------C-----TA-------GAC---G--T------   4914
94CY032.3    T-C-----------------A--------------TA----------G--G--T------   4928
96ZM651.8    AAA----------G------A---C----------TAG----T-------G--T------   4891
96ZM751.3    AAA----------T------A-----A--------TAG----T-------G--T------   4901
94CY017.41   ---T---C--G---------A--------------TAG----T-------G--T------   4919
94IN476.104  AAA----------G------A---C----------TA-----T-------G--T------   4882
                                                               VIF end <-
93BR020.1    AACAAGCCCCAGAAGACCAGGGGCCACAGAGAGAGCCATACAATGAATGGACACTAGATC   4950
92NG083.2    ----------------------A-----------A--C---------------T----A-   4991
90CF056.1    -------------------------------G------C-------------------G-   4969
92RW009.6    -------------------------G-----G--A-----------------------G-   4954
92NG003.1    ---G---------------------------G-------T---C--------------A-   4989
93BR029.4    -------------------A--A--------G--------------------------A-   4974
94CY032.3    -------------------------G--------A---A-T-----------------G-   4988
96ZM651.8    -----TT------------A-----G-----G--A-------G---G-----------GA   4951
96ZM751.3    --------------A----A-----G-----G--A-----T---------G-------G-   4961
94CY017.41   -------------------A-----------G-------------------TGT----A-   4979
94IN476.104  -----T----------------A--------G--A-----------------------G-   4942
```

Fig. 13N

```
93BR020.1     TTTTAGAGGAGCTTAAGAATGAAGCTGTTAGACATTTTCCTAGGCCATGGCTCCATAGCT   5010
92NG083.2     -G-----A--------A-----------------------------C---------G---   5051
90CF056.1     -----------A----------G--------G-----------AGT----------CAA-   5029
92RW009.6     ---------CA--C---C-G--------C-----C--------A------------GA--   5014
92NG003.1     -G-----A--A-----AC----------------.............-----T---G-A-   5036
93BR029.4     ----------A-------G-------------------------TT--------------   5034
94CY032.3     ----G-----------A--------------G-----------A--C---------G--C   5048
96ZM651.8     --C-------A--C---C-G--------C-----C--------A----------------   5011
96ZM751.3     -------------C---C-G--------C-----C--------AA------------A--   5021
94CY017.41    -G-----------C---C-G-----------------C-------AC-----A---G--C   5039
94IN476.104   --C-------A--C---C-G--------C-----C--------A--T-A---T-------   5002

93BR020.1     TAGGACAACATATCTATAACACCTATGGGGATACTTGGGAAGGAGTTGAAGCAATCATAA   5070
92NG083.2     -------GT-------------T-----------------------------C--A----   5111
90CF056.1     -------G--------------------A----------T------------TT-A----   5089
92RW009.6     --------T--------G-A------------------AGG-----A-----T--A----   5074
92NG003.1     -------------T----------------------------------T---T--A----   5096
93BR029.4     -----------------G-A--T----------------C------G-----C--A----   5094
94CY032.3     -------G--------------T-----A-----C--------G--------T--A----   5108
96ZM651.8     -----------------G-A--T---------------ACT-----C--G--T--A----   5071
96ZM751.3     ----------------CC-A-----C------------ACG--G--------TC-A----   5081
94CY017.41    --------T-C--------T--------------C----------------TT-------   5099
94IN476.104   --------T--------G-A--A---------G-----AC------C-----TT-A----   5062

93BR020.1     GGATATTGCAACAACTACTGTTTATCCATTTCAGAATTGGGTGCCGTCATAGCAGAATAG   5130
92NG083.2     -A---C-A-----------------------------C-------AA-------------   5171
90CF056.1     -A-CGC-------------------T-------------------AA-------------   5149
92RW009.6     -A--TC----------------------------------------G-------------   5134
92NG003.1     -A-----------------T-----T-----------------T-AA-------------   5156
93BR029.4     -A--TC----------G--------T--------------A--T-AA-------------   5154
94CY032.3     -A--T--------------------T-------------------AA-----T-------   5168
96ZM651.8     -A---C-------------------T-------------------AG--C----------   5131
96ZM751.3     -A---C-------------------T--------------A----AA-------------   5141
94CY017.41    -ATATC-----------------G---------------------AA--------G----   5159
94IN476.104   -A-C-C--------T----------T-------------------AG-------------   5122
                                             ->TAT 1st exon start  VPR end<-
93BR020.1     GCAT...TACTCGACAGAGAAGAG.TAAGAAATGGAACTAGTAGATCCTAACTTAGATCC   5186
92NG083.2     ----...-----C-----------.----GG-----C-CG-----C-----GC----G--   5227
90CF056.1     -A--...-----------------.-----------C-C------------AC----G--   5205
92RW009.6     ----...-TTG-A-----------.C----------G-C------------AC----G--   5190
92NG003.1     ----...--T--C-GG--------.GC--G------G--G----------G-C----G--   5212
93BR029.4     ----...--A---------G----.C---G------G-C-----------GAC----G--   5210
94CY032.3     ----TAC-C---A-AG--------GC-G-GG-----G-C----------G--C----G--   5228
96ZM651.8     ----...GGT--------------.CG---------G-C-----------G-A----G--   5187
96ZM751.3     ----...--TG-------------.C----------G-C-----------GAC----G--   5197
94CY017.41    ----...--T----AGA-------.----GG-----G-C------C-----AC----G--   5215
94IN476.104   ----...-TTA-A--G--------.C----------G-C-------------C----G--   5178

93BR020.1     CTGGAACCATCCAGGAAGCCAGCCTACAACTCCTTGTACCAGATGTTATTGTAAATGGTG   5246
92NG083.2     ------T-----G--G--T--------------C----A--A-------------GT---   5287
90CF056.1     ------------------T------CA----G------A--AT------------AA---   5265
92RW009.6     ------------------T-------A----G-C----AT-AC------------CAC--   5250
92NG003.1     ---------C--------T------------G------A--A------C------ATA--   5272
93BR029.4     ------G-----------T-G----CAG---GG-----AT--T--C---------AA---   5270
94CY032.3     ------------G-----T------------GA-----A--AG----TC------AA---   5288
96ZM651.8     ------------------T-------A----G------AT-AG--------C---C-C--   5247
96ZM751.3     ------T-----------T--A----A-----------AT-AG------------CAC--   5257
94CY017.41    ------------G-----T-------A----G---------A-------------C-C--   5275
94IN476.104   ------------------T-------A----G------AT-C---C---------CAC--   5238
                                                               ->REV 1st exon start
93BR020.1     TTGCTTTCATTGTTACTGGTGCTTTACAACGAAGGGCTTAGGCATCTCCTATGGCAGGAA   5306
92NG083.2     C----GG------C-AGTT------TT--AC--A--------------------------   5347
90CF056.1     C----A-------CC-AAT------TT--A---A--------A--T--------------   5325
92RW009.6     -A---A-------CTAGTT-----CCAGG-A--A-----------T--------------   5310
92NG003.1     C----GG-----CC-A-T-------CTG-AC-----------------------------   5332
93BR029.4     -------------C-AGTT--T--C-----A-----------------------------   5330
94CY032.3     -----GG-----CC-AGTT------CTG-AA--A--------------------------   5348
96ZM651.8     -A---A-------CTAGTT------CAG--A--A-----------T--A-----------   5307
96ZM751.3     -A---A-------CTAGTT------CAG--A--A-----------T--------------   5317
94CY017.41    -----A------CC-G-T--------T--AC--A-----------------C--------   5335
94IN476.104   -A---AC------CTAGTT------CAG--A--A-----------T--------------   5298
```

Fig. 13O

```
93BR020.1     GAAGCGGAGACAGCGACCAAGAACTCCTCAAAGCAGTCAGATACATCAAGATTTTGTACC   5366
92NG083.2     ----------CC----G-G----------GG-----A--GAT------A-CCC------   5407
90CF056.1     ---------C-------AC---------GC---TTTG--AGAT------A---C-A--T-   5385
92RW009.6     ----------------G--ACG------C-------G-AGAT------A--CC-A--T-   5370
92NG003.1     -----------GC----G-G----------G--TCAC---GAT------A--CC------   5392
93BR029.4     ----------------AC-------------------C-----------CC------   5390
94CY032.3     --------A---T----G-G--T---T----G----CA--GGC------A--C--A----   5408
96ZM651.8     ----------------GC--C-------CT-----CG--GAC---------CC-A--T-   5367
96ZM751.3     ------------A----G---CG------C-------G--GAT------A--CC-A--T-   5377
94CY017.41    ------AC---CC----G--AGC--T---C-----A-A--GAC------A--CC-A----   5395
94IN476.104   ----------------GC--CG------C-------G--GAT------A--C--A--T-   5358
 TAT/REV 1st exon end <-|                 |-> VPU start
93BR020.1     AAAGCAGTAAGTATTGTTA...AGCATATGTAATGTCAAATTTG...............T   5408
92NG083.2     -----|-------G-AAC-ATT-AT-------|---CAGGCC--A...............G   5452
90CF056.1     -----|---------A-........C--A.-|----AT-TA--A...............G   5420
92RW009.6     -----|-------G-AA--AAC--T-------|---A-TTC---A...............G   5415
92NG003.1     -----|--G----G-AA--GTT--T------G|---CA-TCC--A...............G   5437
93BR029.4     -----|-------------AGT-AT-------|------T-----...............-   5435
94CY032.3     -----|---------AA......-T-------|----T-TTC-G-...............G   5447
96ZM651.8     -----|--------...................|----T-G----ACTAGCAAGAGTAAAT-   5414
96ZM751.3     -----|-------CAAAG...T-AT-G-----|----T------AGAAGCAAGAGTAGAT-   5434
94CY017.41    -----|-------G-AG--ATT-AT-------|----T-CC---A...............G   5440
94IN476.104   -----|--------...................|---GTG-----ATTAGAAAGAGTAGAT-   5405

93BR020.1     TAGCAATAGGCATAGCAGCATTAATAGTAGCACTAATAATAACAATAGTTGTGTGGACTA   5468
92NG083.2     A-AT..........ATCTG-C-----------T-C---GC-G-C-C-A---------G--   5502
90CF056.1     G...-T----A----G---GC--G-----A--T-T--C---G-CG--A----------C-   5477
92RW009.6     A-ATCTAT-CA----T----C-G-----G--G-----C---GTG---------------T   5475
92NG003.1     A-AT-GCT-CA-------G-C--G--------GCC---GC-G-C--------------....   5493
93BR029.4     ---T------TT---------------C-------------G------------------   5495
94CY032.3     A-ATCTGG-CA----T--G-C-GG-------G-----T---GT------A---------T   5507
96ZM651.8     ATAG-G----AG---G------G------------C-C---G----------------C-   5474
96ZM751.3     ATAG------AG---G-----------C---------C---G------C---------TC-   5494
94CY017.41    --AT-T-G-CA----T--G-C-G--------TT----CT--G----------A-------   5500
94IN476.104   ATAG-T----AG---G----------------T----CT--G-----A----------C-   5465

93BR020.1     TAGCATATATAGAATATAAGAAACTGGTAAGGCAAAGAAAAATAAATAGGTTATATAAAA   5528
92NG083.2     ---T--T----------GA---A-AAG--AA--G-A-------G-A-A----CT-G-T-   5562
90CF056.1     ---T--------------A---T-----------AG------G-C---C--AT-G---   5537
92RW009.6     -----GG---------------T--C---A------G------G--------AT---G-   5535
92NG003.1     ............-CC---GA---A-AAAG-AA--GGAG------G-C------CT-G-T-   5541
93BR029.4     -----------------G-G----A-----------------------------------   5555
94CY032.3     ---T--T----------------T--AG---------G-G----G-C--C--G--C--T-   5567
96ZM651.8     -----------------G---G---T----A------------G-CT-----AT-----   5534
96ZM751.3     ---T-------------GA---T--TC---A------------G-CC-----AT-----   5554
94CY017.41    ---T--TC---------------A-TAAG-A------G------G-CT-----ATC----   5560
94IN476.104   --------C---------G----T--T----A---------------C------AT-G---   5525
                                            |-> ENV start
93BR020.1     GAATAAGCGAAAGAGCAGAAGACAGTGGCAATGAGAGTGAGGGGGATGCAGAGGAATTGG   5588
92NG083.2     -------A-------------------A-|----------A------A-----------   5622
90CF056.1     -----G-A---------------------|-C--------T--A--CA----------AT   5597
92RW009.6     A------A--------------T------|----------T-----CATT--T-----AT   5595
92NG003.1     -------A--------------T------|----------A-----CA-----------   5601
93BR029.4     -------A---------------------|------------------------------   5615
94CY032.3     -------A---------------------|----------T-----------------AT   5627
96ZM651.8     ----T--G---------------------|-------------A---A-T---------   5594
96ZM751.3     ----T--A-----G---------------|----------A------AAT---------   5614
94CY017.41    -------T--G------------------|----------T-----CA--------C-AT   5620
94IN476.104   ----T--G-------T-------------|----------------A-T---------T   5585
                                                          VPU end <-|
93BR020.1     CAGCACTTGGGGAAGTGGGGCCTTTTATTCCTGGGGACATTAATAATCTGTAATGCTGCA   5648
92NG083.2     --A-----AT----A-----GAC---GA----T---TTGG-------T----G---CT--   5682
90CF056.1     -CAAG---AT---GA------ACC---A--T----T-TG--GC-G-------G-------   5657
92RW009.6     --AA-----T--GG------AAC-A-GA--T------TG----C---T----G-------   5655
92NG003.1     --A------T---CA---T-GAC---GA----T---TTGG-G-----T----G---CT--   5661
93BR029.4     --------------A---------------------T---G-----------|-----A-   5675
94CY032.3     -CA------T--G-A-----AAC---GA----T---TTGG-G----------G---CT--   5687
96ZM651.8     --A-GA-G-T---CA------A-C---GG-T-TT---TG-----G--T-----|--TGTGG   5654
96ZM751.3     --A--A-G-T---TA------A-C---GG-T-TT---TGC--T-G--G-----|---AATG   5674
94CY017.41    ---------T---GAG-----A-C--GA-TT------TG--------G-----A---A--   5680
94IN476.104   --A----G-T---TA-----AA-C---GG-T-TT---TGC----G--T-A---|--TA-T-   5645
```

Fig. 13P

```
93BR020.1    GAAAACTTATGGGTTACAGTCTATTATGGGGTACCTGTGTGGAAAGAAGCAACCACTACT  5708
92NG083.2    --T-----G-----C-------------------------G----T---GAT--CC-C  5742
90CF056.1    C-------G-----------A-------------------------G----AA--C---  5717
92RW009.6    A-C-----G--------T-----C---------------------C---GAG--C--C  5715
92NG003.1    A-T-----G-----C------------------A------G----C---GAT--CC--  5721
93BR029.4    A-C...--G-----C------------------------------------------  5732
94CY032.3    A-C-----G-----C-----T--------------------G---C---GAG--C--C  5747
96ZM651.8    -GG-----G-----C-------------------------------------AA------  5714
96ZM751.3    -GG--A--G-----C--------C----------------------------AA------  5734
94CY017.41   --T...--G-----C-----A--C-----A-----------------T---GAT--C-TC  5737
94IN476.104  -GG-----G-----C-------------------------------------AA------  5705

93BR020.1    CTATTCTGTGCATCAGATGCTAAATCATATGAAAAAGAGGCACATAATGTCTGGGCTACA  5768
92NG083.2    -----------C--T---------------AGTTCT--AAA------------------  5802
90CF056.1    -----------------------GG-------G-C---AAAG-----------------  5777
92RW009.6    T----T------------------G-------TCC---AAAG-----------------  5775
92NG003.1    -----T--------T---------G-----AGT-CT--AAG---------------C---  5781
93BR029.4    T-----------------------G------------A--------------------  5792
94CY032.3    -----T-----------A------G-------G-----A-T-------A----------  5807
96ZM651.8    --------------------------------G-----A-TG-----------------  5774
96ZM751.3    T----T------------------G-------G-C---A-TG--------T---------  5794
94CY017.41   -----T------------------G-------T-C---A-TG--------A-----C---  5797
94IN476.104  T-----------------------G-T-----G--G----TG------A-----------  5765

93BR020.1    CATGCTTGTGTACCCACAGATCCCAATCCACAAGAAGTAGTTCTGGAAAATGTAACAGAA  5828
92NG083.2    -----C--------------C--T--C---------A---C-A-A--------------  5862
90CF056.1    -----A--------------C-----C--------GA-G--CA----G-----------G  5837
92RW009.6    -----C----------T---C---G-C---------A--CA-T----------G------  5835
92NG003.1    -----C--------------C-----C--------GA--AC------------------  5841
93BR029.4    -----C------------------------------------------------------  5852
94CY032.3    -----C--------------C-----C-------------C----AT------------G  5867
96ZM651.8    -----C--------------C-----C---------A-----T---G-------------  5834
96ZM751.3    -----C--------------C-----C---------A-G---T-----------------  5854
94CY017.41   -----C--------------C-----C---------A--AAC-----------------  5857
94IN476.104  -----C--------------C-----C--------GA-G-A-T-A-T------------  5825

93BR020.1    AGGTTTAATATGTGGGAAAATAACATGGTAGAACAAATGCATACAGATATAATCAGTTTA  5888
92NG083.2    -AT-----C------A-G----------------G-----GGAG---------------  5922
90CF056.1    --C-----------------------G--G--G-----------C-------------  5897
92RW009.6    GA------C------A---------------G--G-----------------------C--  5895
92NG003.1    -CT-----C------A------------------G------GAG---------------  5901
93BR029.4    -AT---G--------A--------------------------------------------  5912
94CY032.3    -AC-----C------A-----G------------G------GAG---------------  5927
96ZM651.8    -AT-----C------A-----G-------G--T--G------GAG---------------  5894
96ZM751.3    -A------C-----------------G--T--G------GAG-----------------  5914
94CY017.41   -AT------------A---------------G--G-----AGA------------C---  5917
94IN476.104  -AT-----C------A-----G-------G--T--G------GAG---G-----------  5885

93BR020.1    TGGGATCAAAGCCTAAAGCCATGTGTGAAGTTAACCCCACTCTGTGTTACTTTAGATTGT  5948
92NG083.2    -----GG-------------------A---C----T--T------A-C------A-C---  5982
90CF056.1    ------------T-G--A--------A--A---------------------C--A-C---  5957
92RW009.6    -----C--------------------A-----------T-----C-----------G---  5955
92NG003.1    ------G-------------------A---C-------T-----------C---A-C---  5961
93BR029.4    --------------G-------------------------------------CG----  5972
94CY032.3    ---A--G--G-------A-------CA---C-----T-T-------------TACA---  5987
96ZM651.8    --------------------------A-----G--------------C------A-----  5954
96ZM751.3    -----C--------------------A-----G--------------C------A-C---  5974
94CY017.41   --------------------------A--A--------G-----C--C-T----A-----  5977
94IN476.104  --------------------------A-----G--------------C------A-C---  5945

93BR020.1    AGAAACATTGCCACCAATGGCACCAATGACACTATT............GCCATCAATGAC  5996
92NG083.2    -CT--TG-AAA--GTGC-AATCAT-C---G....................GC----A--  6021
90CF056.1    -CT--TG-CAGA-A----AC-T-T--CAG.......................--C-AG-  5993
92RW009.6    -AC-----CA---ATGTCAA--A--C--T.........................---CATT  5991
92NG003.1    -CT--TG-CAATTGT--CA-T-ATGTGAC--GC-C-GGGAACAGTGCT-GG-C---C-CT  6021
93BR029.4    --T--TGCCA-T-----CA-T--TC-AA-.......................-G-CAC-  6008
94CY032.3    -TT--TGCAA-T--T-C-AAT-GT-CCA..............................-T  6017
96ZM651.8    -C-G-GG--AATGTT-CCA-A-ATGT-A-T-A--GCGTGGTTAATAATA---CA----TT  6014
96ZM751.3    -CTGCT-A-ATA-----CAATG-T---ATA--C-AC.........AAT--T-AT-TAAC-  6025
94CY017.41   --C--TGCCAAT----GCAC-CAT-GCA-T-G.................--GT-GCAC-  6019
94IN476.104  --T--GG--A--...---AATG-T-C-.................................  5969
```

Fig. 13Q

```
93BR020.1     ACTCTGAAGGAAGATCCAGAGGCAA...TACAAAACTGTTCTTTCAATACAACCACAGAA   6053
92NG083.2     ---G-AG-AA-CA-AGA---AAT-......A-------C--------G-T----------   6075
90CF056.1     -G-A--G---C--GAGGG--ACT-......AC---T--C---------GT---T----T-   6047
92RW009.6     --GGATG-CATGA-AGG---AAT-......A-------C----------TG---------   6045
92NG003.1     --GTGT--CAT---AGA--CAAAC-ACT--A-------C----------T----------   6081
93BR029.4     CTGAA-G-A--GCCAGGG-CAAT-......-------------------TG---------   6062
94CY032.3     GGCACTGT-ATTA-AGA--GAAT-......A-------C------G---T----------   6071
96ZM651.8     -A-AAT-GCATGA--GG---CATG......A----T--C--------C-T----------   6068
96ZM751.3     -ACTAT--TA-T--AA-T--CATG......AG---T--C----------T----------   6079
94CY017.41    CAGAGCCCCATTA--GA---AAT-......A-------C----A------T------AT-   6073
94IN476.104   ...TAC--TA-TAC-GAT--TAT-......A----T--C-----T---G-----------   6020

93BR020.1     ATAAGAGATAAGCAGCTGAAAGTACATGCACTTTTTTATAAACTTGATATAGTACAAATC   6113
92NG083.2     -GGG---GC---A--AA-G---A-T-C--G-----C-----------G-G----C---T   6135
90CF056.1     C--------------A---------------C-------G-------G------C---T   6107
92RW009.6     T----G------A-A-A--G---GT--T-----------GG----------------T   6105
92NG003.1     ------------A-AAA--C--A-T----G-----C----G-------G-G----C----   6141
93BR029.4     G-------------------------------------GG-------------C----   6122
94CY032.3     -----G------A--AA-----A-T----G-----C----G-A---------G-C---T   6131
96ZM651.8     C---A-------A-AAA---T--GT---------------------------TC-C-T   6128
96ZM751.3     T-----------AG-AG-C-----G-------C---------------------C---T   6139
94CY017.41    C-----------ACA-AA-----TT--T----G-------G-------G--------C-T   6133
94IN476.104   --------C---A-A-GC----AGT-------G-------G---C----------C-C-A   6080

93BR020.1     AA......CAAGGATGAC..............................AATAGAACATA   6136
92NG083.2     -G......T--T-GGA-T..............................--G-CT-GT--   6158
90CF056.1     G-......T--CA--A.................................G--CTCAG--   6127
92RW009.6     --......T-GCA--AGTAATAACAGT..................AGTC---ATCAG--   6140
92NG003.1     G-......TGGTA--A-TAAT........................GTCTCA-AT-AC--   6170
93BR029.4     -G.........---T---A-TAGTAGCAATGATAAT............AGT-GC---GA---   6163
94CY032.3     --......TGCTAG.AGTGCCAATTAATGGTAGTAATAGGAATAATAGT-CAGA-GAG--   6184
96ZM651.8     --......TG--AC----GACTCTGAGACTGGCAACT..........CT-G--A-TAT--   6172
96ZM751.3     --......TG--A-..................................TCC--TGA---   6159
94CY017.41    G-TGAAAGTG-AA--A-GAATA.CATCAGG...............TAGT----CTCTG--   6177
94IN476.104   --......TG--A--A-GAACAGCTCTAGT................AACT----TGAG--   6118

93BR020.1     CAGACTAATAAATTGTGATGCCTCAACCATTACACAGGCTTGTCCAAAGGTATCTTGGGA   6196
92NG083.2     T--G------C-----A---T----------A------------------AA--TT--   6218
90CF056.1     T--G-----------A--A-----GT---------------C--------G--C-TT--   6187
92RW009.6     T--GT----------A--A-----G-------------------------C-TT--   6200
92NG003.1     T--G-----------A---T-----------A---A-------------G----TT--   6230
93BR029.4     ---G-----------A--A--------C------------------------------   6223
94CY032.3     T-TGT----------A-C-------------A---------C--------G----TT--   6244
96ZM651.8     T---T----------A--A-----G--C-A-----A--C-----------C----TT--   6232
96ZM751.3     T---T----------A--A----GG----A-----A--A-----------TA---TT--   6219
94CY017.41    T--------------A--A----------C-----A--G-----------A-C-TT--   6237
94IN476.104   --T-T----------A--A----------A-----A--C-----------C----TT--   6178

93BR020.1     TCCAATTCCCATACATTATTGTGCTCCAGCTGGTTATGCGATTCTAAAGTGTAATGAGAA   6256
92NG083.2     C--------------------------------T-------T---------GG--T--   6278
90CF056.1     A--T---------------------------C-T------------------CA-T--   6247
92RW009.6     G------------A---------C---------TC-----------------A--T--   6260
92NG003.1     C---C--------------------------G-T-------T---------GG-GT--   6290
93BR029.4     -------------------------------G-----------------------T--   6283
94CY032.3     G----------------------C---------T---A---T----------------   6304
96ZM651.8     C--------T-------------------------------------------A-T--   6292
96ZM751.3     C-----C--T------------------------------------------CA-T--   6279
94CY017.41    G--------T-------------C---------T------------------G--TCC   6297
94IN476.104   C--------T-----------------------T------------------A--TG-   6238

93BR020.1     AAATTTCACAGGGACAGGGTCATGCAAGAATGTCAGTACAGTACAATGTACACATGGAAT   6316
92NG083.2     GG-G-A--AT--A-----AC----T--A--------------------------------   6338
90CF056.1     --CA----AT--A-----A-T---T-CA--------------------------------   6307
92RW009.6     ---G----AT--A------C----------------C-----------C-----------   6320
92NG003.1     G--------T--A-----ACA---T--A---------T----------------------   6350
93BR029.4     ---A----AT-----G---C------G---------C-----------------------   6343
94CY032.3     ---------T--ATT----C------CA--------CT-G----G---C--T--------   6364
96ZM651.8     G-CA----AT--------AC-----C-T--------C-----------------------   6352
96ZM751.3     G-CA----AT--A-----AC-------T--------C-----------------------   6339
94CY017.41    G-GA----AT--A-------------------T--CT-----------------------   6357
94IN476.104   G-CA----AT--------AC--------G-G-----------------------------   6298
```

Fig. 13R

```
93BR020.1    TAAACCAGTGGTATCCACTCAATTGTTGTTAAATGGCAGCCTAGCAGAAG...GAGAGAT   6373
92NG083.2    ---G-----------A------C-AC--C-G--------TT---------...A---T--   6395
90CF056.1    --G------------A------C-C--A--------A--------------...A-C----   6364
92RW009.6    C--G-----A-----A-----GC--C-------------T----------...A------   6377
92NG003.1    ---------------A--------AC-AC-------T--T----------...----A--   6407
93BR029.4    ---------------A----------------------------------A...A---T--   6400
94CY032.3    ---G-----------A---------C----------A---T-----ACG-...A----G-   6421
96ZM651.8    ---G-----------A------C-AC-------------T----------...A--G---   6409
96ZM751.3    ---G-----A-----A--------AC----------T--T----------...A------   6396
94CY017.41   ---------A-C---A------C--C----G--------T----------GAG-GA-A--   6417
94IN476.104  ---G-----------A------C-AC----------T---AC-------A...A------   6355

93BR020.1    AGTAATCAGATCTCAAAATATCTCAGATAATGCAAAAACCATAATAGTGCACCTTAATGA   6433
92NG083.2    -AG---T------G-----T--A----C---A-C---GT------------G------A-   6455
90CF056.1    CA----T---A--A-------------C---A-C----A---------A--G-----GAC   6424
92RW009.6    -A----T------G-------TA--A-C-----C--------------A--A-----C--   6437
92NG003.1    ------T------G----CC--A----C-----C---GT---------A--G------A-   6467
93BR029.4    -A----------------------------------------------A--A-------T   6460
94CY032.3    ------T------A--------A----C---A-C----AT--------A--G---GCAA-   6481
96ZM651.8    -A----T------G-----C-GA--A-C----TC-----A--------A--T------AG   6469
96ZM751.3    -A----T------A-------GA----C-----C----TA--------A--T--------   6456
94CY017.41   -A-G--T------G-------TA--A-C-----C----A---------T--GT---C-A-   6477
94IN476.104  -A---CT------G-------AA----C-----------T--------A--T--------   6415

93BR020.1    ATCTGTACAGATTAATTGTACAAGACCCAACAACAATACAAGAAAAAGAATATCTTTAGG   6493
92NG083.2    TAG-A--G-A----------TC--------T-----------------T---C-AA-C--   6515
90CF056.1    -C-A---A-C----CA-----C--G--T-----T-----G----C---T---CA------   6484
92RW009.6    GA-------A---------T-C-----T--------------------TG--CA-A----   6497
92NG003.1    -A--A--GGA-----------C--------------------------T---AGAA-C--   6527
93BR029.4    ------G-C---------------------------------------T---C-AA----   6520
94CY032.3    GG-----A-A-----------C-----TGG------------------TG--CA-A----   6541
96ZM651.8    ----A--G-A---GTG---GT------------T---------C----T---AGAA----   6529
96ZM751.3    -------G-A---GTG-----------------T--------G-----TG-GAGGA----   6516
94CY017.41   GC------TA----C----TC---------------------------T---CGC--T--   6537
94IN476.104  ---CA--A-A---GTA-----------------T--C-----------T---AGGA----   6475

93BR020.1    ACCAGGACGAGTATTTTATACAACAGGAGAAATAATAGGAGACATCAGAAAGGCACATTG   6553
92NG083.2    --------A--CG--C---G-------T--T--------------A---C-A--------   6575
90CF056.1    G----------C---C---G-------T--C--C--------T--A---C-A--------   6544
92RW009.6    --------A--C-------G-------T--CG-------G--T--A---C-A---T----   6557
92NG003.1    ---T----A--CG--C---G-------T------------C-A.................   6570
93BR029.4    -----------C------------------------------------------------   6580
94CY032.3    G-------T-AC--GG---G-------T--------------T--A---C-A--------   6601
96ZM651.8    --------A-AC---C---G----------C--------------A---C-A--------   6589
96ZM751.3    --------A-AC---C---G--------------------A-T--A---C-A---T----   6576
94CY017.41   --------A--CC--C-------AT-A-...--------G-----A---C-A--------   6594
94IN476.104  G-------A--C---C---G-----AAC-GC--------------A---C-A--------   6535

93BR020.1    TAACGTTAGTGGAACACAATGGAGGAACACGTTAGCAAAGGTAAAGGCAAAGTTAGGGTC   6613
92NG083.2    ---T------A---T-A--------G-G-T----AAG--T--C-CA---C--C--A--AA   6635
90CF056.1    ---TA-----A-----G-C----AT--G--T---CACC-----GTTA--C-A-----AAT   6604
92RW009.6    --CT--C-A-------A------AT-GA--T---CA-------GCA-A---A---A-TCA   6617
92NG003.1    ................G-----CA-G-G-T----CAG-------C----C-AC---AACA   6614
93BR029.4    ----------------A------ATG-G-------A--------G----------AA-C-   6640
94CY032.3    ----A---------ATG-T----ATG----C---AA-GT-A---GT-A-G-A--GAAAAG   6661
96ZM651.8    ----A-----A-G--TA-C----CT--G--T---CG-G------G-AAC--A---A-AGA   6649
96ZM751.3    ----A-C----A-GGCA------AT-----TC--CA--G----GGT-A---A---A-AAA   6636
94CY017.41   ---TA-C-ACAA----TT-----ATG----T---CA-------GCT-A-C-A---A-AGA   6654
94IN476.104  ----A------A-T-TA-C----CT--A--T---CA-G-----GGAAA---A----CAAA   6595

93BR020.1    TTATTTCCCTAAT...GCAACAATAAAATTTAACTCATCCTCAGGAGGGGACCTAGAAAT   6670
92NG083.2    AATC-ATAA----...AAG-AC----CC-----------TG-------------------   6692
90CF056.1    AC-C--GAAC---...AG--------GC-----GC--AA-------------A-G---G-   6661
92RW009.6    C--C--TGAG--CATTA---------TT-----GAAC--------G-----TT-------   6677
92NG003.1    GGTC--TAAC--......--GT----CC------------G-------------------   6668
93BR029.4    -C-----------...--------------------------------------------   6697
94CY032.3    ACTC---------...AA-------------GCTC--C--GT------------------   6718
96ZM651.8    AC-C---------...AA--AC----C------AC-------------------------   6706
96ZM751.3    A--C---------...AA--------GC---GCAC-------------------------   6693
94CY017.41   GA-A--------G...AA---C----TC----CTAAC----------------C------   6711
94IN476.104  GC-C---------...AA--------GT--C---CA------------------------   6652
```

Fig. 13S

```
93BR020.1    TACAAGGCATAATTTTAATTGTATGGGAGAATTTTTCTACTGTAATACAGATGAACTGTT   6730
92NG083.2    -----CA----G---C-------GA-----G--------T--C------TCA-G------   6752
90CF056.1    --G--CA----G-----------GA-------------T--C------TCA-GG-----   6721
92RW009.6    -----CA----G----------GGA-------------T---------TCA-GCT----   6737
92NG003.1    -----CA----G-----------GA-------------T---------TCA-G-T----   6728
93BR029.4    -----T-----G-----------GA-----------------C------TCA-G------   6757
94CY032.3    -----CA----GC----------AA-------------T--C------ACACC------   6778
96ZM651.8    -----CA----GC----------GA-------------T--C------TCG-GC-----   6766
96ZM751.3    -----CA----GC----------GA-------------T--C------TCAA-------   6753
94CY017.41   -----CA-T--G----------GCA-------------T--C------ACA-GC-----   6771
94IN476.104 -GT--CA----GC---------GGA-------C--T--T---------TCAAG------   6712

93BR020.1    TAATGACACAAAATTC...AAT...GACACAGGATTCAATGGC.................   6767
92NG083.2    ----A-T-AT-TTAGTAAT-T-...A-T-AT-AG..........................   6783
90CF056.1    ----AGT-GTTGGGAAATGC--...ACT-ATTACACATCAAATGACACAAAGGGAAACGA   6778
92RW009.6    ----AG---CTGGAGTAAA-GA...A-TGGCACC-GGC-GTCAAATGGCACAGAATTA..   6792
92NG003.1    ------AT--GG-GGGAATG--...AC---..............................   6755
93BR029.4    ---------GT-GA-AATGGC.......................................   6779
94CY032.3    ----AGT---C-CA-GCAA---...-GT---AACA-T-CAA-TACAGATTCTACAAATTC   6835
96ZM651.8    --G-ATA-ATT-TACAGAA---...A-T----ATGGT-CAC...................   6804
96ZM751.3    -----GT--GTTTAATGGT-CA...A----TTCTAATG--A-AAGTAATTCG........   6802
94CY017.41   -----GT--GTGG-GGAAC---...-GT--GT-GAA-GGGCC-TACACACCTAATAACAC   6828
94IN476.104 ---C-GT---T-CAATGGT-CAGACATGC-TAC--A------TACAAATTCCAGTTCAGA   6772

93BR020.1    .......ACTATCACTCTCCCATGTCGAATAAAACAAATTGTAAACATGTGGCAGGAAGT   6820
92NG083.2    .......--------A---------AA--------------G-GG---------A----   6836
90CF056.1    A......-AC--T--A--G-----CA----------------------------AG---   6832
92RW009.6    .......-A---A--A--------CA-------G------A----T---------AGGAC   6845
92NG003.1    ........------A---------AAG--------------G-GA---------AG---   6806
93BR029.4    .......-------------------------G-----------T-------------   6832
94CY032.3    A......--C-----A----A---CA--C--------T------GG-------------   6889
96ZM651.8    ........-C-----A--------CA------G-------A----T-------------   6856
96ZM751.3    .......--C--T--G--T-A---CA--------------AC--------------GG--   6855
94CY017.41   CAATGGA-G---A-TC--------CA--------------A--------------AG---   6888
94IN476.104 C......-TC----TG--T-----CA------GG---T--A-------T------A-G--   6826

93BR020.1    GGGACGAGCAATGTATGCCAATCCCATTGCAGGAAACATTACCTGTAACTCAAATATTAC   6880
92NG083.2    -----A-------------CT------C---------C--GTA-----A-----C-----   6896
90CF056.1    A------------------CC------CCA-----------TG---GTA----------   6892
92RW009.6    A----A-------------CC------CCA----GTA--A-G----GTA-----C-----   6905
92NG003.1    -----A-------------CC------C------G-T-----A----GA-----C-----   6866
93BR029.4    ---G---------------GC------------------------G-----------   6892
94CY032.3    ---G-A---------C---TCC----------G-G-----A---C-G----G-------   6949
96ZM651.8    A--------------C---CC--------A---------AG-A-----A---G----C--   6916
96ZM751.3    A----A-------------TCC---A---AA---------A--A-----A--------C--   6915
94CY017.41   A---A--------------CC--------------TA--A-AG----CA-----C-----   6948
94IN476.104 A------------------CC--------A---------A--A---G-A--------C--   6886

93BR020.1    AGGTCTGCTATTGACAAGAGATGGTGGT........CTG.......AATAGTACTAATGA   6925
92NG083.2    ---AT-AA----A--------------G.........AATAACAATG-C-----AG-G--   6947
90CF056.1    ---A--AA---------TT--C-AG---.........AACG...CGTC-GCAGAA---T-   6940
92RW009.6    ---A--A-----A--------------A.........AATA...AT----C---A-C---   6953
92NG003.1    ---G--AT----A--------------G.........GTTA...AT----C-GGA-----   6914
93BR029.4    ------A---------------------.........-A-AA....T---CAG--GG-G--   6940
94CY032.3    ---AA-AA--------------------..................-C--A--A--C---   6991
96ZM651.8    ---G--A------GTTC-G-----A--AAGCACAAATGATAGCACA----A--AC-CA--   6976
96ZM751.3    ---A--A-----A---C-T-----A--G.........ACAAATGAC-CAGAG--ACCA--   6966
94CY017.41   ---AA-AA--------------------...............AAC---G-G--------   6993
94IN476.104 ---A--A-----AGT-C-T-----A--C.........GACA...CA-------GC-CA--   6934

93BR020.1    GACCTTCAGACCTGGGGGAGGAAATATGAAAGACAATTGGAGAAGTGAATTATATAAATA   6985
92NG083.2    ---------------A------G------GG-------------------------G--   7007
90CF056.1    T--------------A------G------GG--------------------G--------   7000
92RW009.6    A--------------A------G------GG--T---------------C----------   7013
92NG003.1    ---------------A------G------GG-------------------------G--   6974
93BR029.4    -----------------------------------C----------------------   7000
94CY032.3    --T------------A------G-C----GG-------------------C---------   7051
96ZM651.8    --TA-----------CA-----G------GG------------G--------G-----G--   7036
96ZM751.3    ---A-----------A------G-C-----G---------------------------   7026
94CY017.41   ---------------A------G------GG---------------------------   7053
94IN476.104 --TA-----------A------G------GG---------------------------   6994
```

Fig. 13T

```
93BR020.1    TAAAGTAGTAGAAATTGAACCACTAGGAGTAGCACCCACCAAGGCAAAAAGACAAGTGGT   7045
92NG083.2    ----AC----A----CA--T---------------------G-----GG---AG------   7067
90CF056.1    ----------A-------------G---A--------------A---GG---AG------   7060
92RW009.6    ----------A------------------------------G------G--GAG------   7073
92NG003.1    ----A-----A-----A-----------A------------------GG---AG------   7034
93BR029.4    ------------------G---T-------------------------------------   7060
94CY032.3    ----------A-G---------A---------------AT-------GG----G------   7111
96ZM651.8    ------G---------A-G---T-G---A----------TG----------GAG------   7096
96ZM751.3    ------G---------A-G---T----------------T------CG---GAG------   7086
94CY017.41   ----------A--C----------------------T----G----------AG------   7113
94IN476.104  ------G---------A-G---T-----A-------T--TG-A--------GAG------   7054

93BR020.1    GAAGAGAGAAAGAAGAGCAGTGGGACTAGGAGCTCTGTTCCTTGGGTTCTTGGGAGCAGC   7105
92NG083.2    -G---------A---------T-----G------G-C--------------A--------   7127
90CF056.1    -G---------A-------------A-G------TCT-----------------------   7120
92RW009.6    -G---------A---------T-----G------G-C---A----------A--------   7133
92NG003.1    -G------G--A---G-----T-----G------G-C--------------A--------   7094
93BR029.4    -----------A-------------A-G------T-------------------------   7120
94CY032.3    -C---------A-T-----------A----G--CA-------------------------   7171
96ZM651.8    -G---------A-------------A--------G-------------------------   7156
96ZM751.3    -G---------A---------A---A--------G-------------------------   7146
94CY017.41   -G---------A---------T-----G------G-C-----------------------   7173
94IN476.104  -G---------A-------------A--------G---------------------T---   7114

93BR020.1    TGGAAGCACTATGGGCGCGGCGTCAATAACGCTGACGGTACAGGCCAGACAATTATTGTC   7165
92NG083.2    A--G----------------------------------C-----T---------------   7187
90CF056.1    A-----------------------------------------------G-----------   7180
92RW009.6    A-----------------------------------------------------------   7193
92NG003.1    A-------------------G-----------------------T---------------   7154
93BR029.4    A-----------------A-------------------C---------------------   7180
94CY032.3    A-----------------A--------G--------------------------------   7231
96ZM651.8    A-----------------A-------------------C-------------G-G-----   7216
96ZM751.3    A-----------------A--A----------------------T---------------   7206
94CY017.41   A------------------------C----------------------------------   7233
94IN476.104  A--------------------------G--------------------------G-----   7174

93BR020.1    TGGAATAGTGCAACAGCAGAGCAATCTGCTGAGGGCTATTGAAGCGCAACAGCATCTGTT   7225
92NG083.2    ---C--------------A------T-------------A--G-----G-----------   7247
90CF056.1    ---T--------G-----A------T-------A-----AC-G----G-------A----   7240
92RW009.6    ---C--------------A------T-------------A--G--T-----------A--   7253
92NG003.1    ---C--------------A------T-------------A--G-----G--A-----A--   7214
93BR029.4    ---C----------------AT---T----------------------------------   7240
94CY032.3    C--C--------G------------T-------------A--G--T-----A--------   7291
96ZM651.8    ---T--------------A------T-------------A--G-----------------   7276
96ZM751.3    ---T--------------A------T-------------A--G-----------CA----   7266
94CY017.41   ---T--------------A------T-----CA------A-----T--------------   7293
94IN476.104  ---T--------------A------T------A------A--G------------A----   7234

93BR020.1    GCAGCTCACAGTCTGGGGCATTAAACAGCTCCAGGCAAGAGTCCTGGCTGTGGAAAGATA   7285
92NG083.2    ---A------------------------------T--------------A-A--------   7307
90CF056.1    ---------G-----------------------------------C--------------   7300
92RW009.6    AA-A---------------------------------------------C----------   7313
92NG003.1    ---A-----------------------------------------------A--------   7274
93BR029.4    ----------------------------------------A-------------------   7300
94CY032.3    -AGA-----G---------------------------------------C-------C--   7351
96ZM651.8    ---A-----G--------------G---------A--------------A-A--------   7336
96ZM751.3    ---A--------------------G------------------T-----A-A--------   7326
94CY017.41   -A-A--------------------------------G--G--------------------   7353
94IN476.104  ---A--------------------G---------A--------T-----A-A--G-----   7294

93BR020.1    CCTAAAGGATCAACAGCTCCTAGGGCTTTGGGGCTGCTCTGGAAAACTCATCTGCACCAC   7345
92NG083.2    -------------------------A----------------------------------   7367
90CF056.1    -----G---------------G---A----------------------------------   7360
92RW009.6    -----G------------------AA----------------------------------   7373
92NG003.1    -------------------------A----------------------------------   7334
93BR029.4    ------------------------------------------------------------   7360
94CY032.3    ------------------------AA----------------------------------   7411
96ZM651.8    ------------------------A-----------------------------------   7396
96ZM751.3    -------------------------A----------------------------------   7386
94CY017.41   ---------------------G--AA-----------------------------G----   7413
94IN476.104  -------------------------A--------------------G--------C----   7354
```

Fig. 13U

```
93BR020.1     TAATGTGCCCTGGAACTCTAGTTGGAGTAATAAATCTCTTGAGGAGATTTGGGGGAACAT   7405
92NG083.2     ----------------A-------------------TA-A-T----------AT-----   7427
90CF056.1     ---------T-------------------------A-AGAGT--A--C----AC-----   7420
92RW009.6     ---------------------------------GA---AGC----A--A----AT-----   7433
92NG003.1     ---------T------A-------------------TA-------------AT-----   7394
93BR029.4     -G-------------------------C-------AG---A----C-----------   7420
94CY032.3     ------A--T--------------------------TA-A-T--T--A----AC--T--   7471
96ZM651.8     -GC------T------ATC-----------------AAAACA--T-------AT-----   7456
96ZM751.3     -GC------T-----------------C--C------GAACG-----------AT-----   7446
94CY017.41    --C-------------A---------------G----AG--T----------AC-----   7473
94IN476.104   -GC------T--------C--C-------------AAAA--T--T------AAT-----   7414

93BR020.1     GACCTGGATGGAGTGGGAAAAAGAGGTTAGCAATTACTCAAAAGAAATATACAGGTTAAT   7465
92NG083.2     ---T---C-A--A-------GG--AA--CA-------A--C--C-C--------CC-G--   7487
90CF056.1     ---T--------A-----T---C-AA-----------A--G-G-------------GC-   7480
92RW009.6     -------CA-C-A-----T-----AA--G--------A--C--AT------T--TC----   7493
92NG003.1     ---------AC-A-------GG--A--C---------A--C--C----------CC----   7454
93BR029.4     ------------------------A----------------C--------T--------   7480
94CY032.3     -------T--C-A-----T-----AA---A-------A--C--AT------TG-----C-   7531
96ZM651.8     ----------C-------T-G---AA----T------A----CAC------------GC-   7516
96ZM751.3     ----------C-------T-G---AA---AT------A--G--AC------T-----GC-   7506
94CY017.41    -------T--C-A-----T-----AA-----------A----CAT------T------C-   7533
94IN476.104   ----------C-------T------A----T------A----CAC-------C----GC-   7474

93BR020.1     TGAAGACTCGCAGAACCAGCAGGAAAAGAATGAACAAGAATTATTAGCATTGGACAAATG   7525
92NG083.2     ------A------------------------------C-----G-----------G--   7547
90CF056.1     -----T------A-C---------------------G--C-------------------   7540
92RW009.6     ------A------------------------------C-----G-----------G--   7553
92NG003.1     ------A------------------------------C-----G-----------G--   7514
93BR029.4     ------G------------------------------------G--------------   7540
94CY032.3     ------A--A---------------------G-----C-----G--C--------G--   7591
96ZM651.8     ---G----------G---------GC-A------A----T----------------GT--   7576
96ZM751.3     -----T------A--------------T------AGG--T---C------------GT--   7566
94CY017.41    ------A-----A-------------------G----C-----G-----A--------   7593
94IN476.104   ------A-----A-T----------C-A----G-A----T----------------GT--   7534

93BR020.1     GGCAAGTCTGTGGAATTGGTTTGACATAACACAGTGGCTGTGGTATATAAAAATATTCAT   7585
92NG083.2     -------T-------------------T--A-T-----A----------G---------   7607
90CF056.1     --------------C-------------T----T------------------------   7600
92RW009.6     -----A----------------------T--A-T------------------------   7613
92NG003.1     -------T-------C--------------A-A-----A-----------------T--   7574
93BR029.4     ----------------------------T--A-A------------------------   7600
94CY032.3     ------C---------------AG-------A-A-----A-----------------T--   7651
96ZM651.8     -AAC-A-------------------------A-A-----------------------T--   7636
96ZM751.3     AAA--A-----------------A-T------A-T-----------------------   7626
94CY017.41    ----GA-T------G------CA----TT----C----------------G------T--   7653
94IN476.104   -CA--A-----------------AG-------A-A-----------------------   7594

93BR020.1     AATGATAGTAGGAGGCTTGATAGGCTTAAGAATAGTTTTTACTGTGCTTTCTATAGTAAA   7645
92NG083.2     ---------------T--A-----T---------------G------------------   7667
90CF056.1     ---------------T--A-----T---------A-----G------------------   7660
92RW009.6     ------------------A-----T---------A-----G-------C--------G--   7673
92NG003.1     ---------------T--A-----T---------------G------------------   7634
93BR029.4     ----------------------------------------G------------------   7660
94CY032.3     ----------------------------------A-----G------------------   7711
96ZM651.8     ------------------A-----T--G------A-----G----A--C--------G--   7696
96ZM751.3     -------A----------------T---------A-----G-------C----------   7686
94CY017.41    ------------------------A---------------G--A-AA--A--G-------   7713
94IN476.104   ---T--------------------T--G------A-----G-------A----------   7654
                                                   |--> TAT/REV 2nd exon start
93BR020.1     TAGAGTTAGGAAGGGATACTCACCTTTGTCATTTCAG|ACCCATATCCCAAGCCCGAGG..   7703
92NG083.2     ----------C------------------G--C---|----T--C--ATCA--A-C--..   7725
90CF056.1     ----------C------------------T------|----T-G----G-A---AC--..   7718
92RW009.6     C---------C------------A--A--G------|----T--------A-------..   7731
92NG003.1     ----------C----------------------C---|----T--C--ACCA--A-----..   7692
93BR029.4     ---------------------------------A---|----GCT----------A---..   7718
94CY032.3     ----------C------------------T--G---|----T---------CAA-CCAACG   7771
96ZM651.8     ----------C------------------G------|----T------G-A---A---..   7754
96ZM751.3     ----------C----G-------------G--G---|----T---------C-------..   7744
94CY017.41    ----------C--------------G----------|-T--C--C---------AGA-..   7771
94IN476.104   ----------C------------------G--G---|----T--C----GA-------..   7712
```

Fig. 13V

```
93BR020.1     .GAACCCGACAGGCCCGAAGGAATCGAAGAAGGAGGTGGAGAGCAAGGCAAAGACAGATC   7762
92NG083.2     .-------------T--G-AA--C--------------C-------A--G---------   7784
90CF056.1     .-G--------------------CA--------------C-------A--G---------   7777
92RW009.6     .-G-----------T--G---------------A-------------A--G--G------   7790
92NG003.1     .------------------A-------------------------A--G---------   7751
93BR029.4     .------------------------------------------C---------------   7777
94CY032.3     G-G--T----------G-----CA-------A------C-------A--G-AG------   7831
96ZM651.8     .--------------A-G-A------------A-------------A------G-----   7813
96ZM751.3     .-----A-------T--G-A------------A-------------A--G---------   7803
94CY017.41    .-GT-----------AG-----C-------------------------G---------   7830
94IN476.104   .-------------T-AG---------------A-------------A-----------   7771
TAT 2nd exon end <-
93BR020.1     CGTGAGATTAGTGACCGGATTCTTAGCTCTTGCCTGGGACGACCTGCGGAACCTGTGCCT   7822
92NG083.2     -ACTC---------G------------G--------------------G---------   7844
90CF056.1     --------------A----------C-AG---T------------C----G-----CA--   7837
92RW009.6     -A-TC---------G------------A----------------A----G---------   7850
92NG003.1     A---C-C-------G------------A------------------------------   7811
93BR029.4     --------------A----------------T-------------A-------------   7837
94CY032.3     -A-TC-C-------A---------GC-A---AT-------------------------   7891
96ZM651.8     ----C---------G------------A----------------A----G---------   7873
96ZM751.3     AA-TC---------A------------A----T------------C----G---------   7863
94CY017.41    GA-TC---------A---G-----C--A----------------A----G---------   7890
94IN476.104   -A-TC---------A------------A-------------T--A----G---------   7831

93BR020.1     CTTCAGCTACCGCCACTTGAGAGACTTCATATTAATTGCAGCGAGGATTGTGGA....CA   7878
92NG083.2     T----------A--G------G-----AG-C--G---------A----CG-----ACTT-T   7904
90CF056.1     --------------T------------AC-C-------T--T-----C------ACTT-T   7897
92RW009.6     T----------A--GA-----------AC----G-------------CG-----ACTT-T   7910
92NG003.1     -----------A--GA-----------AG-C--G-------------CA-CA--ACTC-T   7871
93BR029.4     ----------------------------------------------------.......-   7893
94CY032.3     ---------------------A----AC-C-------T--------C------ACTT-T   7951
96ZM651.8     -----------A--GA-----------------GG-GA-------AGCG-----GCTT-T   7933
96ZM751.3     T----------A--G------------------G------------GGAC-AC-......   7917
94CY017.41    ------T----A--G---------T-G------G-------------C------ACTT-T   7950
94IN476.104   ------T-G--A--GA-----------------GG----------AGCG-----ACTT-T   7891

93BR020.1     GGGG................G.CTGAAGAGGGGGTGGAAGCTCTCAAATATCTGGGGAA   7921
92NG083.2     ---ACGCAGCAGCCTCAAGG-A----GACT-----------GC-----G--CT--T----   7964
90CF056.1     ---.....................-GA------A-------C------------CT----   7936
92RW009.6     ---ACGCAGCAGTCTCAGGG-A--AC-------------A-C--T--G-----A--A--   7970
92NG003.1     -A-ACGCAGCAGTCTCCAGG-A----GACT---------G-GC------------T----   7931
93BR029.4     ---.................A--------------------C-----CT---------   7936
94CY032.3     ---.....................TA---------------C-----G------T----   7990
96ZM651.8     -A-ACGCAGCAGTCTCAAGG-A--AC-----------------C--T--G---------A-G   7993
96ZM751.3     ...................................------A---T--G----------G   7950
94CY017.41    ---ACACTGCAGTCTCAAGG-A----GACT-----------G--------GA-----T----   8010
94IN476.104   ---ACGCAGCAGTCTCAGGG-A--AC-----------------C--T-----------A-G   7951
                                REV 2nd exon end <-      REV 2nd exon end
93BR020.1     TCTCACACAGTATTGGGGTCAGGAACTAAAGAATAGTGCTATTAGCTTGCTTAATGCCAC   7981
92NG083.2     C---CTGTT-----------G--------------------AT------G--A-A-T   8024
90CF056.1     ---TCT---A--C-----A--------------------GAT--------CA----   7996
92RW009.6     ---TGTG-------------T---------A-GG-------ATC-----G--A----   8030
92NG003.1     ----CTGTT-----------G--------------------AT---A--G--A-A-T   7991
93BR029.4     ----G-G-T-------A--------------------------------A----   7996
94CY032.3     CT--CTG-T---------A-----G-------------AT---T-----A----   8050
96ZM651.8     ---TGTG-------------T---G-----A--G-----------TC-A---G--A---T   8053
96ZM751.3     ---TGT--------------TA--G-----A--G-----------T------G--A-T-T   8010
94CY017.41    ---TCTGTTA--C-------G------G---------------AT--G--A-T-T   8070
94IN476.104   ---TGTG-------------T---------A--G-----------TC-----G--A---T   8011

93BR020.1     AGCAATAGCAGTAGCTGAGTGGACAGATAGAGTTATAGAAGCTTTGCAAAGAGCTGGTAG   8041
92NG083.2     ----------AC----A-CG----------G----------TAGCA---------TA---   8084
90CF056.1     -------------------G-A------G-GA------T-ATAG-----------T-G--   8056
92RW009.6     --------T---------AG-A--------GA--------TTAA-A------AT-A-C--   8090
92NG003.1     ----------------A-C-----------G----------TAGCA---G-----T----   8051
93BR029.4     --------T---------G--------------------------------G-----   8056
94CY032.3     -------------------G-A--------GA----------AG-A--G------T----   8110
96ZM651.8     ------------------AG-A--------GA--------TTAA-A---G--AT-T----   8113
96ZM751.3     ------------------AG-A---------A--------TTAACA------AT-T----   8070
94CY017.41    ----G-------------------------G---------ATAGG----------TTC--   8130
94IN476.104   -------A--A--------G-A--------GA--------TT-ACA------AT-T-C--   8071
```

Fig. 13W

```
                                                                          ENV end <--
93BR020.1    AGCTATTCTCAACATACCTAGAAGAATAAGACAGGGCTTGGAAAGGGCTTTGCTATAAA.   8100
92NG083.2    ------------G------C---G--------A-----A-----A-----------|-.    8143
90CF056.1    ---------C----------------------------T-----AAGC--------|TA    8116
92RW009.6    ------CTAT-----------C----------------T---GCA-------A---|-.    8149
92NG003.1    ------------------------G--------A-----------A----------|-.    8110
93BR029.4    ----G----T---G------------------------------------------|-.    8115
94CY032.3    -------TG-----------------C---------C-T-----A--------T--|-.    8169
96ZM651.8    ------C-G----G-------------------------T----CA----------|-.    8172
96ZM751.3    ------C-G----G-------------------------T---GCA-------A--|G.    8129
94CY017.41   --------------------------C-----------A-----------A-----|-.    8189
94IN476.104  ------C-G-------------------------T--T---GCA------------|-.    8130
             --> NEF start
93BR020.1    ATGGGTGGCAAGTGGTCAAAAAGTAGTATAGTTGGATGGCCTGCTATAAGGGAAAGAATG   8160
92NG083.2    -----G--------------------C------------CAG-------------A       8203
90CF056.1    -----A-----A-------------G--G-G---G---T--A--------------       8176
92RW009.6    -----AA--------------T-----CC---A------------G----A------C-A   8209
92NG003.1    --A--A--------------------C-------------C--GG-------G-----A    8170
93BR029.4    ------A-----------------------------G-------------------T-A    8175
94CY032.3    -----A-----A--------------C---------------AG--------------     8229
96ZM651.8    -----G------------------C--------------------G----A--G-----A   8232
96ZM751.3    -----A--------------C-C-----------------AAAG----A--------A     8189
94CY017.41   -----G-------------------G--C---CCA--------------T-----G------ 8249
94IN476.104  -----GA-----AT---------C--A---------------AGG----A---------     8190

93BR020.1    AGGCGAACCCCTCCAA...CCC.......................C..TCCAGCAGCAGAG  8193
92NG083.2    --A-A---T---GT-G...-A.................................-----A   8227
90CF056.1    ------G-TGAA---G...TA.................................-----A   8200
92RW009.6    ----A---TGAG---G...-A.................................------   8233
92NG003.1    --A-A----------G...-A...................................--A   8191
93BR029.4    --A-A----------G...-A.................................-----A   8199
94CY032.3    ------G-T-GAG-TGAGC-AGAAAGAATGAGGCGAGCTCAAGCTGAG----------CA  8289
96ZM651.8    --AA----TGAG---G...-A.................................------   8256
96ZM751.3    GCAA----TGA----G...-A.................................------   8213
94CY017.41   --AA----T-------CAG-A-AAA......GAACAGAAGCAGTGTC----------CCA  8303
94IN476.104  ---A----TGAG---G...-A.................................------   8214

93BR020.1    GGGGTGGGAGCAGTGTCTCAAGACTTAGAAAGACGGGGGGCAATTACAAGCAGCAATACT  8253
92NG083.2    --A--A--------A--------T----CT--G-AT--A-----C-------------A   8287
90CF056.1    -----A-------------G---T--G--T-----C------G-C----TT-AT-----A  8260
92RW009.6    --A--A--------C----------C----C-A-TAT------C-------T-----C--A 8293
92NG003.1    --A--A-------CAC------------CT--G-AT--A-----C--------------A  8251
93BR029.4    ------------------------------------------------------------  8259
94CY032.3    --A--A-------------------G--C-A--AT--------C----TT-A------A   8349
96ZM651.8    --A--A-------C---------------T-A-TAT--A---C------------C--A   8316
96ZM751.3    --A--A-------C---------------T-A-TAT------C----------T--C--A  8273
94CY017.41   --A--A-------------T----CT-CT-AT--A---G-C--------T-----A      8363
94IN476.104  --A--A-------CA------------CT-A--AT--A---C------C------C--A   8274

93BR020.1    AGAGCTAATAATCCTGACTTGGCCTGGCTGGAAGCACAAGAGGAA...GACGAAGTAGGC  8310
92NG083.2    GC-A-C--C--------T-GT----------------------GGACTCA--T------   8347
90CF056.1    GC-T---C-----G---TGCC-----------------------CGGG--G---------  8320
92RW009.6    CCCAGC--C---G----T-GT----------C------------GGAAA-----------  8353
92NG003.1    GC-CAA-C---------T-GT--------A---------C----GAATTCA--G------  8311
93BR029.4    G------------------------------G--------------...--G---------  8316
94CY032.3    GC-----C----------AAAA------------------A--GGAA--A--G-----T   8409
96ZM651.8    --TA-C-C----G---CT-GT----------------------G...--A-----T---   8373
96ZM751.3    --TA-C------G----T-GT--------------G--------GGAG-GA---------  8333
94CY017.41   GC-----C---------T-GC------G---------G-------A--GGAGAGT-------- 8423
94IN476.104  CC-AGC------G---CTGGT---------C----G--------GGAA--A---------  8334

93BR020.1    TTTCCAGTCAGACCTCAGGTACCTTTAAGACCAATGACCTATAAGGGAGCTGTAGATCTC  8370
92NG083.2    -----G--------A-----------G-----------T-------CT---T-T------  8407
90CF056.1    -----------G------------------------------------T-T------    8380
92RW009.6    -------------------G-----------------T-----A-C---A--T------   8413
92NG003.1    -------------AA-----------G-----------T-------CT--CT-T------  8371
93BR029.4    -------------------------------------T------------C-T------   8376
94CY032.3    -----------G--A--------------G----------T---A------T--------  8469
96ZM651.8    -------------------G-----------------T-------C---A--C------   8433
96ZM751.3    -------------------------------------T------TC---AT-T------   8393
94CY017.41   --C--------G--A--------------G----------TC--------GT-T------  8483
94IN476.104  -------------------G-----------------T-----A-----AT-C------   8394
```

Fig. 13X

```
93BR020.1   AGTCACTTTTTAAAAGAAAAGGGGGGACTGGAAGGGTTAATTTACTCCAAGAGAAGACAA  8430
92NG083.2   --CTT---------------------------T---C-----------------------  8467
90CF056.1   --C--T--------------------------T------------------CA------G  8440
92RW009.6   --CTT------------------------------------------T----A---G---  8473
92NG003.1   --CTT---------------------------T---C----------T----A-------  8431
93BR029.4   --------------------------------------------T-------A-------  8436
94CY032.3   --C-----------------------------T---C---------------A-------  8529
96ZM651.8   --CTT------------------------------------------T----A---G---  8493
96ZM751.3   --CTT---------------------------T-------------GT----A-------  8453
94CY017.41  --CTT---------------------------T---------------C---A-------  8543
94IN476.104 GCCTT---------------------------T--------------T----A---G--T  8454

93BR020.1   GAGATCCTTGATCTGTGGGTCTACCACACACAAGGCTACTTCCCTGATTGGCAGAACTAC  8490
92NG083.2   --C-----------A--------TA-T--------A-T------A---------------  8527
90CF056.1   --C---------T-A--------TA----------------------C------------  8500
92RW009.6   --C-----G---T----------TA----------------------------A------  8533
92NG003.1   --C--------C--A--------TA-T--------A--------A---------------  8491
93BR029.4   --------------------T---------------------------------------  8496
94CY032.3   -----------------------T-----------T-T-------------G-T------  8589
96ZM651.8   --A---------T----------T-------------T---------C-----A------  8553
96ZM751.3   --A-----C---T----------T-----------------------------A-----T  8513
94CY017.41  --C---------A-------------------------------------------T---  8603
94IN476.104 --A---------T-A-----T--TA----------------------------A------  8514

93BR020.1   ACACCAGGGCCAGGGATCAGATATCCACTGACCATGGGGTGGTGCTTCAAGCTAGTACCA  8550
92NG083.2   ----------------CT---CTC---------T-T--------------A---------  8587
90CF056.1   ---------------GAG----T---C------T-T------------------------  8560
92RW009.6   --------A------G----------------TT-T--A-----T-A---------G---  8593
92NG003.1   --T-------------CT----TC--------AT-TC-------------A---------  8551
93BR029.4   ----------------C----------------T-A------------------------  8556
94CY032.3   --------A------GAG----TC------TG-T-T--A---------------------  8649
96ZM651.8   -----G--A------G-----------------T-T--A-----------------G---  8613
96ZM751.3   -----G--A------------------------T-T--A-------A---------G---  8573
94CY017.41  -----------------------C---T-A--AT-T--A---------------------  8663
94IN476.104 --------A------G-----------------T-T--A-------A-------------  8574

93BR020.1   GTTGACCCAGAGGAGGTAGAAAAGGCCAATGAAGGAGAGAACAACTGCTTGCTACACCCC  8610
92NG083.2   A-G-------CA---A----GG-A------A-G----------T-A-TC-AT--------  8647
90CF056.1   --AA-T---C-----------C-----------------------A--------------  8620
92RW009.6   ---------AG---A--G---G-A---------------G----------A--------T  8653
92NG003.1   A-G--T----CA---A----GG-A------A--------------A-T--AT-------T  8611
93BR029.4   ------------------------------------------------------------  8616
94CY032.3   --A--T---C-------G---G------C--------------C---T-----G-----T  8709
96ZM651.8   -----T----G---A------G-------C--------A--------TC----------T  8673
96ZM751.3   ---------AG---A------G-A-----C---------G-------T-----------T  8633
94CY017.41  --A--G---TCT---------G-A--T-C-C-G------------A----AT-------T  8723
94IN476.104 ---------AGT-TA------G-------CA-------A--------T-----------T  8634

93BR020.1   ATGAGCCAACATGGAATGGAGGATGAAGA.CAAAGAAGTACTGAAATGGGAGTTTGACAG  8669
92NG083.2   --CT----G--------------------.--G------G---GT----AGA---A----  8706
90CF056.1   -------TG-----------------C-G.G-G------G----TG---A-A--------  8679
92RW009.6   C-------G-----------------G--.--G------CT-A--G---A----------  8712
92NG003.1   --CT----------CC----A----CG--.--G------G---GT----AGA--------  8670
93BR029.4   -----------------------------.--G----A-----C-G---AG---------  8675
94CY032.3   --A-----G--------------------.G-G-------T-A--G---A----------  8768
96ZM651.8   --------G--A--------T-----TC-.--G-------T-A--G---A----------  8732
96ZM751.3   --A-----G--------A--A--------.--G-------T-A-GG---A----------  8692
94CY017.41  --AT-----------G-A--T--CCCT--.A-G------GT-A-G------------T--  8782
94IN476.104 --------------------T--------.TGG-------T-A--G---C----------  8693

93BR020.1   CCGCTTGGCACTGAGACACATAGCCAGAGAGAGACATCCGGAGTACTACCAAGAC...TG  8726
92NG083.2   TA--C-A----G-------C-----C-----CTG---------------A-----TGC--  8766
90CF056.1   T--AC-A---T---C----T-G---C---TA-AG----------...--A-----TGC--  8736
92RW009.6   T-A-C-A----AC--------G---C-C---CT------------T--TA-----TGC--  8772
92NG003.1   TA--C-A----G-------------C----ACA---------------TA-G---TGC--  8730
93BR029.4   ----C-A---T-TCAT-----G---C-----CTG---------------A-G---TGC--  8735
94CY032.3   T---C-----TAC-AG---G-----C-----CTG----------TT---A-----TGC--  8828
96ZM651.8   T-A-C-A----AT-A------G---C-----CT------------T---A-----TGC--  8792
96ZM751.3   TTC-C-A----GC--------G---C-C---CT------------T---A-----TGC--  8752
94CY017.41  AA--C------G--------G----C-----CTG---------------A-----TGC--  8842
94IN476.104 -A--C-A----GC------------C-C---CT------------T---A-----TGC--  8753
```

Fig. 13Y

NEF end

93BR020.1 AGACTGCTGACACAGAGATTGCTGACACAGAAGAATCT.AAA...GGGACTTTCCA.CTG 8781
92NG083.2 -..........................---------TTG--G-C-..A----------GC--- 8800
90CF056.1 -..........................---------T.--G----...-----------G.--- 8767
92RW009.6 -..........................---------GGA--TTCCGCT-----------.--- 8807
92NG003.1 -C--A-AA-T.........-------------T-TTG--G-C-A.G----------GC--- 8780
93BR029.4 -..........................--TT--GTTT---.-C-..A----------G.--- 8767
94CY032.3 -..........................---------TTG--G-C-A.A----------GC-C- 8863
96ZM651.8 -..........................---------GGA--TTCCGCT-----------.--- 8827
96ZM751.3 -..........................---------GGA--TTCCGCT-----------.--- 8787
94CY017.41 -..........................---------TTG--G-CG...----------G.--- 8874
94IN476.104 -..........................--------............-----------.--- 8775

93BR020.1 GGGACTTTCCAGAG..GGTG.GGCCAGAGGGCGGGACTGGGGAGTGGCTCACCCTCAGAT 8838
92NG083.2 --.---------GAGA--C-C----T-G..-A---G-------------A---------A 8857
90CF056.1 --.-------G-G-.A--C-T-AT-T-G..-----GA-----------CA---------- 8823
92RW009.6 ---.-GG-----G..A----T--T-T-G..-------G-A--------CA---------- 8862
92NG003.1 --.-------G-G-.A--C-C---AT-G..-A-----------------A---------A 8836
93BR029.4 ------------G-.A----T----T-G..-----------------GAG--------- 8824
94CY032.3 --.---------G-GA--C-C----T-G..-A---GT------------A---------- 8920
96ZM651.8 ---..-------G..A----T--T-T-G..-----------------TCA---------- 8880
96ZM751.3 ---.-G------G-..----T-AT-T-G..------------------CAG--------A 8842
94CY017.41 ------------G-.A----T--TGT-G..----AGT------------A---------- 8931
94IN476.104 ---.-G------G...--A-T--T-T-G..-------AT--------TCA---------- 8829

93BR020.1 GCTGCATATAAGCAGCCGCTTTTCGCCTGTACTGGGTCTCTCTAGTTAGACCAGATTTGA 8898
92NG083.2 --------------------C--------------------T---G-------------- 8917
90CF056.1 ----------------T---------T--------------T-G------------C--- 8883
92RW009.6 ----------------T------T------------------G-G----------C--- 8922
92NG003.1 --------------------C--------------------T----------------- 8896
93BR029.4 ----------------T-----CT------------------G----------------- 8884
94CY032.3 --------A-----------C---------------------G------------C--- 8980
96ZM651.8 ----------------T---------T--------.---------G----------C--- 8939
96ZM751.3 ----------------T----------------------------G----------C--- 8902
94CY017.41 ----------------T----C----A----------------T---G--------A.-- 8990
94IN476.104 ----------------T---------------------------G-G---------C--- 8889

93BR020.1 GCCCGGGAGCTCTCTGGCTAGCTAGGGAACCCACTGCTTAA.GCCTCAATAAAGCTTGCC 8957
92NG083.2 ---T-------------T-G--AG-----------------.----------------- 8976
90CF056.1 ---T--------------------A----------------.----------------- 8942
92RW009.6 ---T----------------T--------------------.----------------- 8981
92NG003.1 ---T------------------AG-----------------.----------------- 8955
93BR029.4 ---T--------------------------T----------.----------------- 8943
94CY032.3 ---T-------------------------------------.----------------- 9039
96ZM651.8 ---T----------------T--------------------.----------------- 8998
96ZM751.3 --------------------T--------------------.----------------- 8961
94CY017.41 ----------------------AG-----------------.----------------- 9049
94IN476.104 --------------------C----T---------------.----------------- 8948

93BR020.1 TTGAG...TGC.TTT 8968
92NG083.2 -----...----.--C 8987
90CF056.1 -----...----.--- 8953
92RW009.6 -----...----.-C- 8992
92NG003.1 -----...----.--C 8966
93BR029.4 -----...---T-A. 8954
94CY032.3 -----...---T-C. 9050
96ZM651.8 -----...---TC-. 9009
96ZM751.3 -----...---C--. 8972
94CY017.41 -----AGC-T-.... 9060
94IN476.104 -----...----.-C- 8959

Fig. 13Z

```
GAG
93BR20.1      MGARASVLSGGKLDAWEKIRLRPGGKKKYRLKHLVWASRELERFALDPGLLETSEGCRKI   60
92NG083.2     V-------------S----------R---K---I-------G----NRD----A---VQ-   60
90CF056.1     ----------------------------------------------N------P---LQ-   60
92RW009.6     ------I-R----------K-K-----T-MM---------------N-D----P---KQ-   60
92NG003.1     ------------------------------M---------------N-D----T---QQ-   60
93BR029.4     -------I---E--K----------H-------I-----------VN-----------Q-   60
94CY032.3     -----------------R----------------------------N------A---QQL   60
96ZM651.8     ------I-R-----K------------R-MI---------------N----------KQ-   60
96ZM751.3     ------I-R-----E--R---------H-MM---I-----------N----------KQ-   60
94CY017.41    ------I-----------------------------------K-SIN------P----Q-   60
94IN476.104   ------I-R-----R------------H-MI---------------N-------D--KQ-   60

93BR20.1      IGQLQPSLQTGSEELKSLYNTIAVLYYVHQKVEVKDTKEALEKLEEEQNKGRQKTQQATA  120
92NG083.2     MK----A- --T---R--F--V-T--C----I--------P-EV-KI-KNSQ-EI---AK  119
90CF056.1     -E-I--AIK--T------F-LV----C--R-ID--------D-I--I---SQ------A-  120
92RW009.6     MR----A----TD--R-----V-T--C----ID--------D-I------SQ------E-  120
92NG003.1     MR---------T--I---F--V-T--C---RI----------EV-KI-KNSQ-E--K-AM  120
93BR029.4     LE----A-K------R-----V-T--C----ID----------I-----XSKK-A---A-  120
94CY032.3     ME---ST-K------R------TT-WC---RID-Q------D-I--I-S-SK------A-  120
96ZM651.8     MK----A----T---R-----V-T--C--EG---R------DRI------IQ--I--K-.  119
96ZM751.3     -Q----A----T---R-----V-T--C--E-IK-R------D-I------SQ--I-.K-.  118
94CY017.41    -R----A----T---------VV---W---R-D--------D-I------..----H-A-  118
94IN476.104   -K--H-A-K--T---R--F--V-T--C--AGI--R------D-I------SQ--I---KE  120

93BR20.1      EKG....VSQNYPIVQNLQGQMVHQSLSPRTLNAWVKVIEEKAFSPEVIPMFSALSEGAT  176
92NG083.2     NE-NSNP----------A----I--AI-----------V---------------------  179
90CF056.1     D-EKDNK----------A-------AI-----------V---------------------  180
92RW009.6     ADKGK..----------A-------AI------------------Q------T-------  178
92NG003.1     G--NSSQ----------A---V---PI---------------N---------T-------  180
93BR029.4     NT-NNSQ------------------AI-----------V---------------------  180
94CY032.3     AA-GSSN----------A--------I---------------------------------  180
96ZM651.8     QQAADGK------------------K--------------------------T-------  179
96ZM751.3     .EATGGK------------------AI---------------G-N-------T-------  177
94CY017.41    DT-NSS..---------A-------AI-----------V-------------T-------  176
94IN476.104   AD-K...------------------P--------------------------T-------  177

93BR20.1      PQDLNTMLNTVGGHQAAMQMLKDTINEEAAEWDRLHPTQAGPIPPGQIREPRGSDIAGTT  236
92NG083.2     --------------------------D-------I--Q-------------S--------  239
90CF056.1     -----A----------------------------V--VH--------M------------  240
92RW009.6     ----------------------------------V--V----VA----------------  238
92NG003.1     -----------------------S-------------Q----------------------  240
93BR029.4     ----------------------E-----------V--VH--------M------------  240
94CY032.3     -----M---I--------------------D---T--VH--------M------------  240
96ZM651.8     -------------------------------------VH----A---M------------  239
96ZM751.3     -------------------------------------VH----A----------------  237
94CY017.41    ----------------------------------V--VH--------M------------  236
94IN476.104   -S-----------------------------------VH---N----M------------  237

93BR20.1      STLQEQIQWMTGNPPVPVGEMYKRWIILGLNKIVRMYSPVGILDIRQGPKEPFRDYVDRF  296
92NG083.2     -------R---S---I----I-------------------S-------------------  299
90CF056.1     -------A------AI---DI-------------------S----K--------------  300
92RW009.6     -------A---N---I----I-------------------S----K--------------  298
92NG003.1     -------T---S---I----I-------------------S----K--------------  300
93BR029.4     -----------S--------I------------------TS--G----------------  300
94CY032.3     -------G---S--------I--------------T---IS-------------------  300
96ZM651.8     -------A---S---I---DI-------------------S----K--------------  299
96ZM751.3     G------A---N---I---DI-------------------S----K--------------  297
94CY017.41    -------G---SD--I----I-------------------S-------------------  296
94IN476.104   -------A-------I---DI-------------------S-------------------  297

93BR20.1      FKTLRAEQATQEVKGWMTDTLLVQNANPDCKTILKALGPGATLEEMMTACQGVGGPSHKA  356
92NG083.2     ----------------------------------R-------------------------  359
90CF056.1     -----------D--N---E---------------R---Q--SI-----------------  360
92RW009.6     ---------S-D--N-------------------R------S--------------G---  358
92NG003.1     --------------N-------------------R---A-------L-------------  360
93BR029.4     Y-------TS-D--N---E--------------------A----------------G---  360
94CY032.3     --C-----------N---E------------S------T---------------------  360
96ZM651.8     --------------N---------------------------------------------  359
96ZM751.3     -----------D--?-------------------R---------------------G---  356
94CY017.41    --------------N---------------RS--R------S------------------  356
94IN476.104   ----------------------------------R------S----V-------------  357
```

Fig. 14A

| | | |
|---|---|---|
| 93BR20.1 | RVLAEAMSQATNTA...IMMQKSNFKGQRRIVKCFNCGKEGHIAKNCRAPRKKGCWKCGR | 413 |
| 92NG083.2 | ----------SGA-AAA----------P---I----------L-R-------------K | 419 |
| 90CF056.1 | ---------V---N.TA-----G------KF-------------R-------------- | 419 |
| 92RW009.6 | ---------VQQPN...----RG--------I----------L-R-------------K | 415 |
| 92NG003.1 | --------R--G-S.AA-----N----P--GI----------L-R-------------K | 419 |
| 93BR029.4 | ---------V--SG..T----RG--RN--KTI--------------------------K | 418 |
| 94CY032.3 | ----------S-A-.AA------K------TI----------L-R-------------K | 419 |
| 96ZM651.8 | ---------TNSVN...-L--------NK-M-------------R-------------K | 416 |
| 96ZM751.3 | ---------VN--N...----------PK---------R-----R-----G-------K | 413 |
| 94CY017.41 | --------HVQS-N.TN----RG--R--K-.I----------L-R-------------K | 414 |
| 94IN476.104 | ---------SHSN....----RG----PK---------------R------R------Q | 413 |
| | | |
| 93BR20.1 | EGHQMKDCTE.RQANFLGKIWPSNKGRPGNFIQNRP......EPSAPPAESFRFGEE.TT | 465 |
| 92NG083.2 | ------E---.--------------------L---T......--T-------G----.IA | 471 |
| 90CF056.1 | ----------.------------S-------L-S--......--T-------G----.M- | 471 |
| 92RW009.6 | ----------.--------------------P-S-L......--T-----N-GM---.IA | 467 |
| 92NG003.1 | ----------.--------------------L----......--T-------G----.IA | 471 |
| 93BR029.4 | ----------.------------H-------L-S--......--T------------V-- | 471 |
| 94CY032.3 | ----------.-------RM---S-------L----......--T-----CLERK--.-- | 471 |
| 96ZM651.8 | ----------.------------H-------L----......--T---------.--.-- | 467 |
| 96ZM751.3 | ----------.------------Q-------L----EPTAPPA-T---------E-..-- | 470 |
| 94CY017.41 | ----------.--------------------P-S-T......--T-----NL-M---.I- | 466 |
| 94IN476.104 | ----------.------------H-------L----......--T---------K-..-- | 464 |
| | | |
| 93BR20.1 | PSPKQEQKDEGLYPPLASLKSLFGNDP...1 | 492 |
| 92NG083.2 | ------P-EKE--.--T-------S--...1 | 497 |
| 90CF056.1 | -------LKDKEP.-----R----S--LLQ1 | 500 |
| 92RW009.6 | SPL------REP...-I----------LSQ1 | 494 |
| 92NG003.1 | --L---PREKESP.--T----------...1 | 497 |
| 93BR029.4 | --Q---PI-KEM-.-----R-------SSQ1 | 500 |
| 94CY032.3 | S-L---PR-KE--.--T-------S--LSQ1 | 500 |
| 96ZM651.8 | -A----S--RE...A-T-------S--LSQ1 | 494 |
| 96ZM751.3 | -A-R-----KE...--TA------S--LSQ1 | 497 |
| 94CY017.41 | S-L---LETREP-N-AI----------LLQ1 | 496 |
| 94IN476.104 | -A----S--RE...--T-------S--LSQ1 | 491 |

Fig. 14B

```
POL
93BR020.1    FFRENLAFQQGEARKL....HPEQARAVSPASRE......LQVRGGD.NP...IS.EAG     44
92NG083.2    ----------------....S---D--N--T---......-RI-R--.S-...LP.---     44
90CF056.1    ----------R----F....S-----TN--T---......-R--R--.D-...L-.---     44
92RW009.6    ---------------F....S---TG-N--T---......-WNG-R-.SL...S-.-T-     44
92NG003.1    --------------EF....SS-----N--TR--......-R--R--.S-...FP.---     44
93BR029.4    --------P--K--EF....PS--T--N--T---.........---W-RGN-S...L-.-T-  45
94CY032.3    -----V----R----FSSEQA......--N---RGM......-REER--N.....LLS---   44
96ZM651.8    --------P--K--EF....PS-----N--T---......------.--.....R-.---    43
96ZM751.3    --------PE---GE-....PS--T--N--T-SNSPTSRE---.--.......CP---      49
94CY017.41   ----------R----F....SS--N--N--T---......-ENG-R-N.....LLP---     44
94IN476.104  --------P-----EF....PSK---N--T---.........---Q-DN......PRS---   43

93BR020.1    AE.RRGTVPSLSFPQITLWQRPLVTIRVGGQLKEALLDTGADDTVLEDVNLPGKWKPKMI    103
92NG083.2    -K.GE-AI.--N------------VKI----I--------------GI------------    102
90CF056.1    -AEGQ--.----------------VKIE---R--------------EI------------    102
92RW009.6    --.-Q--...FN------------VKI----R--------------EI------------    100
92NG003.1    --.GK-IT.-INL-----------V-I----I--------------QI------------    102
93BR029.4    -D.-Q-D-.-FG------------VKI-------------------EI----R-------    103
94CY032.3    T-.GQ--I.-FN-------------KL---IR--------------EI------------    102
96ZM651.8    V-.-Q-...--N-----------S-K----I---------G-----EI------------     99
96ZM751.3    --.-Q-...T-NC----------S-K----I---------------EI------------    105
94CY017.41   TG.DQ--IQ-CN------------VKIE------------------EI------------    103
94IN476.104  V-.-Q-.T..-N-----------S-K----I---------------EIA---R-------     99

93BR020.1    GGIGGFIKVKQYDSILIEICGHRAIGTVLVGPTPVNIIGRNMLTQIGCTLHFPISPIETV    163
92NG083.2    ---------R---Q-----G-KK-----------I----------------N---------    162
90CF056.1    ---------R--EQVA-----KK------------------I--------N---------    162
92RW009.6    -------------Q-------KK----------S----------------N---------    160
92NG003.1    -------------Q-----E-KK-----------I----------------N---------    162
93BR029.4    ---------R---Q-P-----RK-T----------------L--------N---------    163
94CY032.3    ---------R---Q-P-----KK---------------------L----N---------    162
96ZM651.8    -------E-R---Q-PM----KK---------------------L----N---------    159
96ZM751.3    ---------R---Q-------KK---------------------L----N---------    165
94CY017.41   ---------R---Q-A-----K---------------------V-L----N---------    163
94IN476.104  ---------R---Q-------KK------------------D---L----N---------    159

93BR020.1    PVKLKPGMDGPKVKQWPLTEEKIKALTEICMEMEKEGKISKIGPENPYNTPVFAIKKKDS    223
92NG083.2    -----------R------------------KD-------------------I--------    222
90CF056.1    ------------------------------T---------R-------S--I--------    222
92RW009.6    --A-----------------------R---T-----------------------------    220
92NG003.1    -------I----------------------TD-------------------I--------    222
93BR029.4    -----------R------------------T-----------------------------    223
94CY032.3    ------------------------------TD-------------------I--------    222
96ZM651.8    ---------------------------A--E--------T--------------------    219
96ZM751.3    -----------R---------------A--E--------T--------------------    225
94CY017.41   ------------------------------K-----------------------------    223
94IN476.104  ------------------------------K--------T----------------R---    219

93BR020.1    TKWRKLVDFRELNKRTQDFWEVQLGIPHPAGLKKKKSVTVLDVGDAYFSVPLDKDFRKYT    283
92NG083.2    -----------------------------------R------------------------    282
90CF056.1    --------------------------------------S---------------E-----    282
92RW009.6    -----------------------------------------------------ES-----    280
92NG003.1    -----------------------------------R-------------I---EN-----    282
93BR029.4    ------------------------------------------------------------    283
94CY032.3    -----------------------------------------------------PE-----    282
96ZM651.8    -----------------------------------------------------ES-----    279
96ZM751.3    -----------------------------------------------------EG-----    285
94CY017.41   ------------------------------------A----------------HE------    283
94IN476.104  -----------------------------------------------------EG-G---    279

93BR020.1    ASTIPSTNNETPGVRYQYNVLPQGWKGSPAIFQYSMTKILDPFRAKNPDIVIYQYMDDLY    343
92NG083.2    -F----I------I-------------------S------E-S-T---EM----------    342
90CF056.1    -F----I------I-------------------S------A---EQ--EM----------    342
92RW009.6    -F----I------I-------------------N------E----Q-QE-----------    340
92NG003.1    -F----I------I-------------------S------E---TE--E-----------    342
93BR029.4    -F-----------L-------------------S------E---KQ--------------    343
94CY032.3    -F-----------I-------------------C------E---F---E-----------    342
96ZM651.8    -F-----------I-------------------S------E----Q--------------    339
96ZM751.3    -F----I------I---------------S---S--I---E---TQ--E-----------    345
94CY017.41   -F-------------------------------S------E---S--TELI---------    343
94IN476.104  -F----I------I-------------------S------E----R--K-----------    339
```

Fig. 15A

```
93BR020.1     VGSDLEIGQHRTKIEELREHLLKWGLTTPDKKHQKEPPFLWMGYELHPDKWTVQPIQLPD   403
92NG083.2     -----------A-----------------------------------------------E   402
90CF056.1     -----------A------A------F----------------------------TVK--E   402
92RW009.6     -----------A-------------F---------------------------------E   400
92NG003.1     ------T----A------N---R--F---------------------------------N   402
93BR029.4     ------------------Q---R--F------------------------------V--E   403
94CY032.3     -----------A----------R--F-------------------------------PAE   402
96ZM651.8     -----------A-------------F--------------------------------AE   399
96ZM751.3     -----------A----------R--F------------------------------K--E   405
94CY017.41    -------S---V------A------FY-----------------------------K--E   403
94IN476.104   --------H--A------A------F------------------------------K--E   399

93BR020.1     KDSWTVNDIQKLVGKLNWASQIYPGIKVKQLCKLLRGAKALTDIVPLTTEAELELAENRE   463
92NG083.2     -ED--------------------------H--R---------------A---M-------   462
90CF056.1     ------------------------N-------------------I---K-----------   462
92RW009.6     -------------------------V--R--------T----------E-----------   460
92NG003.1     -E----------------------------------------------E-----------   462
93BR029.4     -----------------------A----R--------T----EV----A-----------   463
94CY032.3     ------------------------------------------------------------   462
96ZM651.8     -----------------------A----R-------------------E---------K-   459
96ZM751.3     -E----------------?----A----R-------------------E--------S--   464
94CY017.41    -----------------------A---------------------T--K------E----   463
94IN476.104   ----------------------------R-------------------E-----------   459

93BR020.1     ILKEPVHGAYYDPSKDLIAEIQKQGQGQWTYQIYQEPFKNLKTGKYAKMRSAHTNDVKQL   523
92NG083.2     --------V-H----E----V----PD----------Y----------RG----------   522
90CF056.1     --R--I--V-----------R-----------------------------T-----I---   522
92RW009.6     --------V----------------HD---------------------R-T---------   520
92NG003.1     --------V------E----L----CD----------Y----------RG----------   522
93BR029.4     --------V----------------------------Y---------R--G---------   523
94CY032.3     -------------------------------------H---------RT--------R--   522
96ZM651.8     --------V----------------HD-----------------------T---------   519
96ZM751.3     --------V----------------HD-----V-----------------T---------   524
94CY017.41    ---T----V-----------------D---------------------R--T----I---   523
94IN476.104   --------V----------------HD-----------------------T---------   519

93BR020.1     TEAVQKISLESIVIWGKT.PKFRLPILKETWDTWWTEYWQATWIPEWEFVNTPPLVKLWY   582
92NG083.2     --V----AT-G------I.---K---R----EV--------A------------------   581
90CF056.1     --------T--------I.-------Q----E---------------------H------   581
92RW009.6     -------AM---------.-------Q----E----D-----------------------   579
92NG003.1     -------AT--------V.---K---R----EV------------D--------------   581
93BR029.4     -------TT--------I.---K---Q----EA--I------------------------   582
94CY032.3     -------AM-C-------.-------Q---------------------------------   581
96ZM651.8     -------A---------I.-------Q----E----D----------------L------   578
96ZM751.3     -------AM--------I.-------Q----E----D-----------------------   583
94CY017.41    -------TM---------.---K---Q----E---A------------------------   582
94IN476.104   -------AI------?--.-------Q----E----D--------D--------------   577

93BR020.1     QLETEPIVGAETFYVDGASNRETKKGKAGYVTDRGRQKAVSLTETTNQKAELQAIQLALQ   642
92NG083.2     -------P----Y-----A-----L----H---K-K--IIT-----------H-------   641
90CF056.1     -------A----Y-I---A-----L----------K--V----------T-----Y----   641
92RW009.6     ---K---L----------A-----I-------------I----------T----------   639
92NG003.1     R------P----Y-----A-K---L----------K--IITIQ------T--H-------   641
93BR029.4     ---K--------------A-----L-------------V-P--D-----T-----H----   642
94CY032.3     ----D--A----------A-----Q-------------V---S------T-----Y----   641
96ZM651.8     ---K--------------A-----L-----I-------I-T--------T-----Y----   638
96ZM751.3     ---K---A----Y-----A-----I-------------I-T--------T----------   643
94CY017.41    ---K---A----------A-----L-------------I----------T--H--Y----   642
94IN476.104   ---K--------------A-----V-------------I----------T----------   637

93BR020.1     DSGSEVNIVTDSQYALGIIQAQPDKSESELVNQIIEQLIKKEKVYLSWVPAHKGIGGNEQ   702
92NG083.2     --RP--------------------R-G---------------------------------   701
90CF056.1     ---L--------------------------------E-----------------------   701
92RW009.6     ------------------------S----A------------R-----------------   699
92NG003.1     ------------------------R---------------------T-------------   701
93BR029.4     ---L-----------------------L-I-------------I--A-------------   702
94CY032.3     ---------------I--------R---D----------R-D------------------   701
96ZM651.8     ---------------------H--------------------R-----------------   698
96ZM751.3     ------------------------------------------R-----------------   703
94CY017.41    ---L-------------------ER----I------K--E--R-----------------   702
94IN476.104   ---T-------------------------------------N--R-----------------   697
```

Fig. 15B

```
93BR020.1    VDKLVSAGIRKVLFLDGIDKAQEEHEKYHNNWRAMASDFNIPAVVAKEIVASCDKCQLKG  762
92NG083.2    ------S-------------------R--S----------L-P-----------------  761
90CF056.1    ------S-V-----------------R-------V-----L-PI----------------  761
92RW009.6    ------S---R---------------R--S----------L-PI----------------  759
92NG003.1    ------S----------------D--R--S----------L-PI----------------  761
93BR029.4    ------S-----------------------------------P-----------------  762
94CY032.3    ------N---------------------------------L-S----------N------  761
96ZM651.8    ------K------------------------------E--L-P--------------Q--  758
96ZM751.3    ------S----------------------S-------E--L-PI----------------  763
94CY017.41   ------S-------------------R--S------H---L-P-----------------  762
94IN476.104  --R---S----------------D-----S------NE--L-PI----------------  757

93BR020.1    EAMHGQVDCSPGIWQLDCTHLEGKIILVAVHVASGYLEAEVIPAETGQETAYFLLKLAGR  822
92NG083.2    --------------------------I---------I----------------I------  821
90CF056.1    -----------------------QV-----------I----------K----------S-  821
92RW009.6    -------------------------------A----I----------------I------  819
92NG003.1    ------------------------V-I---------I-----------------------  821
93BR029.4    ------------------------V--------G--I-----------------------  822
94CY032.3    ------------------------V-M---------I----------------I------  821
96ZM651.8    --T---------------------------------I---------------YI------  818
96ZM751.3    --I---------------------V-----------I----T---------L-I------  823
94CY017.41   ------------------------V-----------I------T----D----I------  822
94IN476.104  --------R---------------------------I---------------YI------  817

93BR020.1    WPVKTIHTDNGTNFTSATVKAACWWAGIQQEFGIPYNPQSQGVVESMNKELKKIIGQIRD  882
92NG083.2    ----V------P--I--A--------N-T----------------------------VG-  881
90CF056.1    ----V------S-----A--------D------------------------------V--  881
92RW009.6    ----V------S----N--------------------------I-------------V--  879
92NG003.1    ----V------S-----AM-------N------------------------------V--  881
93BR029.4    -----------S----T-----------K--------------I-------------V--  882
94CY032.3    ----M--A---P-----A--------D-N----------------------------V--  881
96ZM651.8    ----V------S-----A----------K----------------------------V--  878
96ZM751.3    ----VV-----S-----A----------H----------------------------V--  883
94CY017.41   ----V------P--I------------------------------------------V--  882
94IN476.104  ----V------S-----A---------------------------------------V-E  877

93BR020.1    QAEHLKTAVQMAVFIHNFKRKGGIGGYSAGERTIDIIATDIQTRELQKQIIKIQNFRVYY  942
92NG083.2    --------------------------------I-----S----K----------------  941
90CF056.1    --------------------------------I----------K------SN--K-----  941
92RW009.6    -----R--------------------------I----------K------T---------  939
92NG003.1    --------------------------------I-----S----K----------------  941
93BR029.4    ----------T---------------------IV---------K------T---------  942
94CY032.3    --------------------------------I-----S----K------T---------  941
96ZM651.8    ---------------------R----------I----------K-------N--K-----  938
96ZM751.3    --------------------------------I---------------------------  943
94CY017.41   --------------------------------I----------K---R--T---------  942
94IN476.104  -------------------------------------------K---N--T---------  937

93BR020.1    RDSRDPVWKGPAKLLWKGEGAVVIQDNSEIKVVPRRKAKIIRDYGKQMAGDDCVAGRQDE  1002
92NG083.2    ------I--------------------N------------LK--------G---------  1001
90CF056.1    ------I-----------------------------E------------------S----  1001
92RW009.6    ------I---------------------D-------------------------------   999
92NG003.1    ------I------------------------------V---K--------G---------  1001
93BR029.4    ------L---------------------D--------V------------G---------  1002
94CY032.3    ----E-I---------------------D---------------------N---------  1001
96ZM651.8    ------I---------------------D---------------------A---------   998
96ZM751.3    ------I---------------------D---I-----------------T-S-------  1003
94CY017.41   ------I---------------------D-------------------------------  1002
94IN476.104  ------I---------------------D---------------------A---------   997

93BR020.1    D....1   1003
92NG083.2    -....1   1002
90CF056.1    -....1   1002
92RW009.6    -....1   1000
92NG003.1    -....1   1002
93BR029.4    -....1   1003
94CY032.3    -....1   1002
96ZM651.8    -....1    999
96ZM751.3    -....1   1004
94CY017.41   -....1   1003
94IN476.104  -QNME1   1002
```

Fig. 15C

VIF

```
93BR020.1    MENRWQVMIVWQVDRMRINTWKSLVKYHMHISKKAKGWFYRHHFESRHPKISSEVHIPLE   60
92NG083.2    -------V----------R--N----H--YV------------Y-----RV--------R   60
90CF056.1    --------------------------------R--R----------T--R---------G   60
92RW009.6    ----------------K-R--N----H--YA-RR---------Y---------------G   60
92NG003.1    -------V----------R--N-------YK-----D------Y------V--------G   60
93BR029.4    -------V----------------------V-----R------------RV---------   60
94CY032.3    -A--------------K-R--N----H--YV------ -----Y------V--------G   59
96ZM651.8    ------AL----------R--N----H--Y--R--N-------Y-----RV--------G   60
96ZM751.3    -------L--------K-R--N----H--YV--RTGR------Y---------------G   60
94CY017.41   ------------------R--N----H--Y--R-----V-K--Y---N-R---------G   60
94IN476.104  -------L----------R--N----H--YV-RR-S-------Y------V-A------G   60

93BR020.1    TAELVITTYWGLLPGEREWHLGQGVSIEWRQGRYRTQIDPGLADQLIHIYYFDCFSESAI  120
92NG083.2    D-T--VR-----HA--KD-Q--H--------K--S-----NT--H---L-----------  120
90CF056.1    E-R---------NT-----------------LK--S--VE---------MH----------  120
92RW009.6    E-R---K-----QT---D----H-------LR--K--V-----G----MH-----AD---  120
92NG003.1    E-R--VR-----HT---D-----------K-R--S-----D-------LH--N------V  120
93BR029.4    E-K---------HT---D------------------------------------------  120
94CY032.3    E-R--VR-----Q---QD----H-------LR--S--V--D-------MH----------  119
96ZM651.8    D-K---K-----QT---D----H-------LR--S--V----------MH-----AD---  120
96ZM751.3    D-K---K-----H---------H-------LR--S--V----------MH--N--AD---  120
94CY017.41   E-RIIVR-----HI--KD----H--------N--H-----D---H---L-----------  120
94IN476.104  D-R---K-----QT---D----H-------L---S--VE---------MH-----AD---  120

93BR020.1    RKAILGHKISPRCNYQAGHNKVGSLQYLALTALIAPKKTKPPLPSVQKLVEDRWNKPQKT  180
92NG083.2    ------EIV----E-P-------------SK--VT-TRKR------G--A----------  180
90CF056.1    ------RVVR-----P---KQ--T---------V----I-------R-------------  180
92RW009.6    -------IV----D--------------------K---I-------S-----K-------  180
92NG003.1    ------EVVR---E--T---Q---------K--VT-TQ--------K--T-----E----  180
93BR029.4    -------R-----D--------------------K---R-------K--T----------  180
94CY032.3    -------RV----E----------------A---S-----------K-------------  179
96ZM651.8    -------IVI---D--------------------K---R-------R--------NS---  180
96ZM751.3    ---L---IVI---D--------------------K---I-------R-------------  180
94CY017.41   ----I-EIV----E----------------K-VV-STR--------R-------------  180
94IN476.104  -------IVIS--D--------------------K---R-------K--------N----  180

93BR020.1    RGHRESHTMNGH1   192
92NG083.2    -D---NP-----1   192
90CF056.1    ----G-------1   192
92RW009.6    --R-GN------1   192
92NG003.1    ----G--ST---1   192
93BR029.4    KD--G-------1   192
94CY032.3    --R--NQI----1   191
96ZM651.8    K-R-GN--VS--1   192
96ZM751.3    K-R-GN-I----1   192
94CY017.41   K---G------C1   192
94IN476.104  -D--GN------1   192
```

Fig. 16

VPR

```
93BR020.1    MEQAPEDQGPQREPYNEWTLDLLEELKNEAVRHFPRPWLHSLGQHIYNTYGDTWEGVEAI    60
92NG083.2    --------------------E-------------------G---Y---------------    60
90CF056.1    --------------H-----E----I----------V---Q-------------V----L    60
92RW009.6    --------------------E---A--Q------------D---Y--E------R-----    60
92NG003.1    --R-----------F-----E------H----X....---G----------------V--    56
93BR029.4    --------------------E------S--------L----------E------A-----    60
94CY032.3    --------------N-----E-------------------G-------------------    60
96ZM651.8    ---F-----------S----EI-----Q-------------------E------T-----    60
96ZM751.3    ------N-----------A-E------Q--------T---N------Q------T----L    60
94CY017.41   ------------------M-E------Q--------H---G---Y-------------V-    60
94IN476.104  ---S----------------E------Q--------- ------Y--E----A-T----L    59

93BR020.1    IRILQQLLFIHFRIGCRHSRIGITRQRRVRNGTSRS1    96
92NG083.2    ----------------Q-------P-----D-PG-P1    96
90CF056.1    --T-------------Q---------------P---1    96
92RW009.6    -----------------------LQ---A---A---1    96
92NG003.1    ----------------Q------IPG--G---AG--1    92
93BR029.4    ----------------Q------N----A---A---1    96
94CY032.3    ----------------Q-------P---RGR-W-Q.1    95
96ZM651.8    ----------------Q-----MV----A---A---1    96
96ZM751.3    ----------------Q------M----A---A---1    96
94CY017.41   --Y------V------Q------I-R----D-A--P1    96
94IN476.104  --T-------------Q------LQR--A---A---1    95
```

Fig. 17

TAT

```
93BR020.1    MELVDPNLDPWNHPGSQPTTPCTRCYCKWCCFHCYWCFTTKGLGISYGRKKRRQRPRTPQ    60
92NG083.2    -DP---K-E-------------NK----V--W--QV--LN-------------P-RG---    60
90CF056.1    -DP---K-E---------Q-A-NN----K--Y--QM--LK------------S--H---A    60
92RW009.6    --P---K-E---------K-A-NN----H-SY--LV--QA---------------RNA-P    60
92NG003.1    ------S-E-----------A-NK----I--W--QL--LN-------------R-RG---    60
93BR029.4    --P---R-E--K----R-Q-A-NS----K-----QV-------------------H----    60
94CY032.3    --P---D-E-----------D-NK-F--K--W--QV--LK------------KH-RGSL-    60
96ZM651.8    --P---SIE---------K-A-NK----R-SY--LV--Q----------------RS--P    60
96ZM751.3    --P---R-E---------K---NK----H-SY--LV--Q----------------RSA-P    60
94CY017.41   --P---K-E---------K-A--K----R--Y--QL--IN-------------P-RKPSP    60
94IN476.104  --P-----E---------K-A-NT----H-SY--LV--Q----------------RSA-P    60

93BR020.1    SSQIHQDFVPKQPISQA.RGNPTGPKESKKEVESKAKTDP..1     99
92NG083.2    G-KD--NP-----LPIT.S-----SEKP----A--TE---LD1    101
90CF056.1    -L-D--NSIS---L-RT.H-D------Q----A--TE---..1     99
92RW009.6    --ED--NPIS---L--T.--D---SE----K----TEA--FD1    101
92NG003.1    -H-D--NP-----LPTT.-----------------TE--QCA1    101
93BR029.4    ---L---P-----A---.Q---------------Q-----..1     99
94CY032.3    G-KG--NLI----L--QPN-DS---E-Q--K-A--TEA--FA1    102
96ZM651.8    --ED---PIS---L-RT.Q-----QE----K----T-R--CD1    101
96ZM751.3    --ED--NPIS---L--P.---Q--SE----K----TE--QFD1    101
94CY017.41   -NKD--NPI---SLP--.QRV----E-P--------E--RFD1    101
94IN476.104  --ED--NLIS---LP-T.------SE----K----T----FD1    101
```

Fig. 18

REV

```
93BR020.1  MAGRSGDSDQELLKAVRYIKILYQSNPYPKP.EGTRQARRNRRRRWRARQRQIREISDRI   59
92NG083.2  -------P-E---R---I--T--------S-.A------K-------------HS--E--   59
90CF056.1  ------A--T---QVCKI---------C-E-.T------------------------E--   59
92RW009.6  ---------ET--Q--KI-------------.---------------------HS--E--   59
92NG003.1  -------A-E---RVT-I-----------P-.-------K-------------SAL-E--   59
93BR029.4  ---------T------S----------L---.K------------------------E--   59
94CF032.3  ------NI-ED-F--A-A-----------NNPT-----------------K--HSL-E--   60
96ZM651.8  ---------AA--L-A-T-----------E-.K------K-----------E--A--E--   59
96ZM751.3  -------N-EA--Q---I-----------N-.-------K-------------NS--E--   59
94CY017.41 T----D-P-ES--Q-I-T-------------RGS.---Q--------------DS--E-V   59
94IN476    ---------AA--Q---I-----------R-.------Q--------------HS--E--   59

93BR020.1  LSSCLGRPAEPVPLQLPPLERLHINCSEDCGQGAEE.......GVGSSQISGESHTVLGS  112
92NG083.2  --A----------F------G-SLD--K-G-TSGTQQPQGTET---RP-VLV-PPV----  119
90CF056.1  -T------P---T---------TL-------TSG-K.......-E--P---L--S-I--T  112
92RW009.6  --T-----T----F----I---T-D----G-TSGTQQSQGTTE---NP............  107
92NG003.1  --T---------------I---SLD----SRTPETQQSPGTET---GP---V--PV----  119
93BR029.4  --------E------------------------T--.......----P-T---RA--E-  112
94CF032.3  -ATY----------------K-TL-------TSGDK.......----P-V-V-LPA---T  113
96ZM651.8  --T-----T---------I-----GD--SG-ASETQQSQGTTE----P............  107
96ZM751.3  --T-----P----F----------D---GTT...........E---N-............   96
94CY017.41 -RT-----T---------------D------TSGTLQSQGTET---R--E-V--SVI---  119
94IN476    --T----ST---------I-----G---SG-TSGTQQSQGTTE----P............  107

93BR020.1  GTKE1    116
92NG083.2  ----1    123
90CF056.1  ----1    116
92RW009.6  ....1    107
92NG003.1  ----1    123
93BR029.4  ----1    116
94CF032.3  -A--1    117
96ZM651.8  ....1    107
96ZM751.3  ....1     96
94CY017.41 --E-1    123
94IN476    ....1    107
```

Fig. 19

VPU

```
93BR020.1   MSNL..LAIGIAA...LIVALIITIVVWT.IAYIEYKKLVRQRKINRLYKRISERAEDSG   54
92NG083.2   -QA-..EISX..........----F-AATI--S.-VF---R-IRK-K--EK-LD--R-------   51
90CF056.1   -YI-..G.L--G-...-V-TF--AVI---.-V----------K--D--IE--G-------   53
92RW009.6   -TS-..EIYA-V-...-------V-----.L-G------LK----D--I-K-R-------   54
92NG003.1   -QS-..EIAA--G...-V--A-AA-----.-.....X-IKK-E--D--LD--R-------   49
93BR029.4   --Y-..-V--L--...--A----A-----.------RE--------------R-------   54
94CY032.3   -LFW..EIWA-VG...-V-----V-----.LVF------R---R-DS--N--R-------   54
96ZM651.8   -LD-LARVNYRVGVGA-----L-A-----.------R--L-----DW-I---R-------   59
96ZM751.3   -L--EARVDYRIGVGA--A----A-A--I.-V----R--S-----D--I---R-------   59
94CY017.41  -LP-..VILA-VG...------LA-----.-VF-----IKK----DW-I-----------   54
94IN476.104 -V--LERVDYRLGVGA------LA-.IVWT---L--R--L--------IE--R--V----   59

93BR020.1   NESEGDAEELAALGEVGPFIPGDINNL1   81
92NG083.2   ------T----T-M-M-D-D-WVG---1   78
90CF056.1   ---D--T---SK-M-M-HLNL-YVAD-1   80
92RW009.6   ---D--ID--SK-VG--NYDL--V---1   81
92NG003.1   ------T----T-VDMVD-D-WVGD--1   76
93BR029.4   ---------------M--------D--1   81
94CY032.3   ---D------ST-VGM-N-D-WVGD--1   81
96ZM651.8   ------T----TMVDM-HLRLL-V-D-1   86
96ZM751.3   ------N----TMVDM-HLRLL-AIDV1   86
94CY017.41  ---D--T---S--V-R-HLDF--V--V1   81
94IN476.104 ------T---ST-VDM-NLRLL-A-D-1   86
```

Fig. 20

```
ENV
93BR20.1      MRVRGMQRNWQHLGKWGLLFLGTLIICNAAENLWVTVYYGVPVWKEATTTLFCASDAKSY    60
92NG083.2     ---K-I-------W---T-I--LV---S-SD-------------ED-D-P----------    60
90CF056.1     ...MET---YPS-WR--T-I--M-L--S--Q----------------K----------A-    57
92RW009.6     ---M-TLM-Y-N-WG--TMI--M-T--S--N--------------D-E----------A-    60
92NG003.1     ---K-T-------WT-WT-I--LV---S-SN-------------ED-D-P--------A-    60
93BR029.4     ----------------------I------.----------------------------A-    59
94CY032.3     ---M-----YP--WE--T-I--LV---S-SN-------------RD-E-------E--A-    60
96ZM651.8     ----EIL----RWWT--I-GFWM-M---VWG----------------K------------    60
96ZM751.3     ---K-IM----QWWI--I-GFWM-LM---MGK---------------K----------A-    60
94CY017.41    ---M-T---Y---WRG-I-I--M--M-K-TD.-------------D-D-I--------A-    59
94IN476.104   -----IL--C--WWI--I-GFWM-M-Y-VVG----------------K----------A-    60

93BR20.1      EKEAHNVWATHACVPTDPNPQEVVLENVTERFNMWENNMVEQMHTDIISLWDQSLKPCVK   120
92NG083.2     SS-K------------------IAI-----N----K-------QE------EE-------   120
90CF056.1     -T-K------------------M-M-----S-----------------------------   117
92RW009.6     DP-K-----------I--D---IH------E----K------------------------   120
92NG003.1     ST-R------------------IT------T----K--------E-------E-------   120
93BR029.4     ------------------------------N-D--K------------------------   119
94CY032.3     ---V--I----------------A-I----N----K-D------E------NEG----A-   120
96ZM651.8     ---V------------------I--G----N----K-D--D---E---------------   120
96ZM751.3     -T-V------------------M-------K---------D---E---------------   120
94CY017.41    DT-V------------------IN------N----K-------QE---------------   119
94IN476.104   ---V--I---------------MD-V----N----K-D--D---E-V-------------   120

93BR20.1      LTPLCVTLDCR.........NIATNGTNDTIAIND.TLKEDPEA..IQNCSFNTTTEIRD   168
92NG083.2     -----I--N-T.............-VNSANHTEANN-VENK.-E..-K----KI---RGG   164
90CF056.1     --------N-T.............-VR-N-SNSTS.SMEAG.GE..LT-----V--VL--   160
92RW009.6     --------E-N...............NITNVNNTVNITDDMKGE..-K-----M---L--   163
92NG003.1     --------N-T...NVNCNSNV-STG-SAGTNATCNIE-A.NN..LK-----I------   173
93BR029.4     --------R-S...............NAT-NSTQND----E-G-.--------M---V--   162
94CY032.3     --S----FT-I...............NAT-TNSTNG-VIKEG....-K----DI------   161
96ZM651.8     --------N-TEVNV.......TR-VN-SVVNNTTNVNNSMNGD..MK-----I---LK-   171
96ZM751.3     --------N-TANIT............-NANIT-NANITNYNNETDMR-----I---L--   168
94CY017.41    ------I-N-SNANT.............S-HSNSSS-QSPIN-E..-K---Y----IL--   164
94IN476.104   --------N-SKVTN..................-..ATYNNTDD..-K-----A------   158

93BR20.1      KQLKVHALFYKLDIVQI........NKDDN...RTY....RLINCDASTITQACPKVSWD   213
92NG083.2     -KKEEY-------V-P-........SNGNK...TS-....---H-NV---K------NF-   209
90CF056.1     --Q-------R--V-P-........DNNSTQY........-----NT-V---------FE   204
92RW009.6     -KQR-YS---R------........-SNS-NS.SHNQ..Y-----NT-A---------FE   212
92NG003.1     -KKTEY----R--V-P-........DGNN-VS.NN-....-----NV---K-------F-   220
93BR029.4     ----------R----P-........SN-NSSN.DNSSREY-----NT--L----------   213
94CY032.3     -KK-EY----RI---P-NARVPINGSNRN.....NSTEEYM----N----K-------FE   216
96ZM651.8     -KKN-Y---------SL........-ET-DSETGNSSKYY-----NT-AL--------F-   223
96ZM751.3     -RRQ-D---------P-........-ENS......S..EY-----NT-A--------TF-   212
94CY017.41    -TQ--YS---R--V--LDE......SENK..NTSGSNTLY-----NT----------TFE   216
94IN476.104   -KR-EY----R----PLNE......--NS....SSNYSEYI----NT-----------F-   208

93BR20.1      PIPIHYCAPAGYAILKCNEKNFTGTGSCKNVSTVQCTHGIKPVVSTQLLLNGSLAEGE.I   272
92NG083.2     -----------F-----RD-EYN---P-----------------------------ED.-   268
90CF056.1     -----------F------N-T-N---L-T-----------R---------------EQ.-   263
92RW009.6     ----N------F-----KD-K-N---P-----------------------------E-.-   271
92NG003.1     -L---------F-----RG-------Q-----S-------------------------.-   279
93BR029.4     ------------------D-K-N---P-R---------------------------KD.-   272
94CY032.3     -----------F-----------L-P-T---S-R--------------------TE-.V   275
96ZM651.8     ------------------N-T-N---P-H---------------------------EG.-   282
96ZM751.3     ------------------N-T-N---P-N---------------------------E-.-   271
94CY017.41    -----------F-----KDPR-N---------S----------A-------------GK-   276
94IN476.104   -----------F-----KDET-N---P--E-----------------------T--K-.-   267

93BR20.1      VIRSQNISDNAKTIIVHLNESVQINCTRP.NNNTRKRISLGPGRVFYTTGEIIGDIRKAH   331
92NG083.2     R---E-FT--T-V---Q--N-IE---I--.------S-PI---QA--A--D------Q--   327
90CF056.1     I--TK-----T-N---Q-KTP-N-T----.-----TS-H-----A--A--D------Q--   322
92RW009.6     I---E--TN-------Q---T-----S--.------SVHI---QA--A--DV-----Q-Y   330
92NG003.1     ----E-LT----V---Q--KTIG------.------S-RI---QA--A------......   332
93BR029.4     I---------------Q--V--P------.------S-PI----A---------------   331
94CY032.3     ----K--T--T-N---Q-AKA-K------G--T.--SVHI---LTW-A---------Q--   334
96ZM651.8     I---E-LTN-V--------R-IE-V-V--.-----QS-RI---QT--A--D------Q--   341
96ZM751.3     I---K-MT----I---------E-V----.------SVRI---QT--A------N--Q-Y   330
94CY017.41    M---E--TN---N---QFTKP-L-T-I--.------S-RF---QA---.N-------Q--   334
94IN476.104   IT--E--T-------------IK-V----.------S-RI---QA--A-NG------Q--   326
```

Fig. 21A

```
93BR20.1     CNVSGTQWRNTLAKVKAKLGSYFPNAT.IKFNSSSGGDLEITRHNFNCMGEFFYCNTDEL   390
92NG083.2    ----RIK--EM-KN-T-Q-RKIYN-KN.-T----A-------T-S---R--------SG-   386
90CF056.1    --I-R-D-NK--HQ-VTQ--IHLN-R-.-S-KPN----M-VRT-S---R--------SG-   381
92RW009.6    -T-N--K-NR--Q--AE--SH--E-I-T-I-KN---------T-S---G--------SG-   390
92NG003.1    .....QE-QEM-Q--Q-Q-EQV-NKSI..T----A-------T-S---R--------SG-   385
93BR029.4    ------K-NE--E--R---KPH-----.--------------M-S---R--------SG-   390
94CY032.3    --I--ND-ND--KVISEE-KRL---K-.---APPV-------T-S---K--------TP-   393
96ZM651.8    --I-R-N-TK--RE-RN--REH---KN.-T-KP---------T-S---R--------SG-   400
96ZM751.3    --I-EGK-N---QR-GE--RK----K-.-S-AP---------T-S---R--------SK-   389
94CY017.41   --INK-L-ND--Q--AEQ-REK--KK-.-I-TN-----P---TLS---A--------TG-   393
94IN476.104  --I-ESN-TK--QE-GK--AKH---K-.-S--Q--------VT-S---G--------SR-   385

93BR20.1     FN................DTKFNDTGFNGTITLPCRIKQIVNMWQEVGRAMYANPIAGNI   434
92NG083.2    --..................NNISNIN-E------K-----R---K--Q----L-----L   428
90CF056.1    --SSW.........EMHTNYTS---KG-EN---------------R-------P--Q---   432
92RW009.6    --STW..........SKRNGTWQSN-TELN----------I----RT-Q----P--Q-V-   440
92NG003.1    --.................ESGG...NDT------K-----R---R--Q----P----D-   425
93BR029.4    --..................DTV...D--------------------------A------   429
94CY032.3    --STH.........MQNGTNITSTDST-S----Q--L--F-R------Q----S----S-   444
96ZM651.8    -SINY..TE......NNT........DGTP-------R--I------------P--E---   444
96ZM751.3    --GTF..NGT.....NTS.....NDRS-S----Q------T----G--Q----P--K---   437
94CY017.41   --GTWWNNGTW...NGP....YTPNNT--S-I--------I----R-------P----I-   446
94IN476.104  --GTY..NGTDMPTYNGT......NSSSDI-M-----R-FI-I--K-------P--E---   437

93BR20.1     TCNSNITGLLLTRDGG..LNSTN....ETFRPGGGNMKDNWRSELYKYKVVEIEPLGVAP   488
92NG083.2    V-K------I------..N-NDS..TE--------D-R-----------T-K-KS-----   484
90CF056.1    M-V------I--I-E-..NA-AE...NY-------D-R-------------K-----I--   487
92RW009.6    S-V-------------..N-N-T...T--------D-R-------------K--------   495
92NG003.1    --R-------------..V-N-G...N--------D-R-----------I-K-K---I--   480
93BR029.4    --S-------------..Q-NQT...E---------------------------------   484
94CY032.3    N-S-D---II------.......TNNT-I------D-R-------------K---I----   497
96ZM651.8    A-K-D------V----STND---.NNT-I---A--D-R---------------K---I--   503
96ZM751.3    --K-------------T.NDTET...P--------D-----------------K------   493
94CY017.41   K-T-----II------..N-G-....N--------D-R-------------KL-------   500
94IN476.104  --E--------V----DTNS-.....T-I------D-R---------------K---I--   492

93BR20.1     TKAKRQVVKRERRAVGLGALFLGFLGAAGSTMGAASITLTVQARQLLSGIVQQQSNLLRA   548
92NG083.2    -R-R-R--E--K-------V--------------------A-V-----------------   544
90CF056.1    --TR-R--E--K----M--S----------------------------------------   547
92RW009.6    -R---R--E--K-------V-I--------------------------------------   555
92NG003.1    ---R-R--E-GK-------V--------------G-------V-----------------   540
93BR029.4    -----------K----M-----------------------A-------------N-----   544
94CY032.3    N--R-R--Q--K ---I--M----------------M-----------------------   556
96ZM651.8    -E---R--E--K----I--V--------------------A----V--------------   563
96ZM751.3    ---R-R--E--K----I--V----------------------V-----------------   553
94CY017.41   -R---R--E--K-------V----------------L---------------------Q-   560
94IN476.104  -E---R--E--K----I--V------V---------M---------------------K-   552

93BR20.1     IEAQQHLLQLTVWGIKQLQARVLAVERYLKDQQLLGLWGCSGKLICTTNVPWNSSWSNKS   608
92NG083.2    -------------------S----I-----------I----------------T------   604
90CF056.1    -Q-R--M----------------------R------I-----------------------   607
92RW009.6    --------K---------------L----R------I----------------------T   615
92NG003.1    ------------------------------------I----------------T------   600
93BR029.4    ---------------------I--------------------------D-----------   604
94CY032.3    --------R---------------L-S---------I-----------------------   616
96ZM651.8    -------------------T----I-----------------------A----I------   623
96ZM751.3    ------M-----------------I-----------I-----------A-----------   613
94CY017.41   --------K---------------------------I---------A-T----T------   620
94IN476.104  ------M------------T----I-----------I------V--P-A-----------   612

93BR20.1     LEEIWGNMTWMEWEKEVSNYSKEIYRLIEDSQNQQEKNEQELLALDKWASLWNWFDITQW   668
92NG083.2    YN---D----L---R-IH--TQH--S---E----------D----------------SN-   664
90CF056.1    QS---D-------D-QI---TE-----L-V--T-------D-----------T----SH-   667
92RW009.6    QQ---D----QQ-D--IG--TQI--S---E----------D--------N-------SN-   675
92NG003.1    Y----D----IQ--R-----TQQ--S---E----------D-----------------K-   660
93BR029.4    Q-K-------------I----N-------E---------------------------SK-   664
94CY032.3    YND--D----LQ-D--IN--TQI--G-L-E----------D--------------S--K-   676
96ZM651.8    KTD--D-----Q-DR-I---TNT----L----S---Q--KD-----S-NN--------K-   683
96ZM751.3    ER---D-----Q-DR-IN--TET----L-V------N--RD-----S KN-----N--N-   672
94CY017.41   QD---D----LQ-D--I---TNI----L-E----------D--------D--S--N-SH-   680
94IN476.104  KDD--N-----Q-D--I---TNT----L-E--I---Q-GKD-----S-QN-----S--K-   672
```

Fig. 21B

```
93BR20.1     LWYIKIFIMIVGGLIGLRIVFTVLSIVNRVRKGYSPLSFQTHIPSPRE.PDRPEGIEEGG   727
92NG083.2    ----R----------------A---------Q---------LTHHQ--.---LGKT----   723
90CF056.1    -------------------I-A---------Q---------LV-N--G.------T----   726
92RW009.6    -------------------I-A---------Q---------L--N--G.---LG----E-   734
92NG003.1    ---------------------A---------Q---------LTHHQ--.-----R-----   719
93BR029.4    ---------------------A----------------L--RF-----.-----------   723
94CY032.3    -------------------I-A---------Q------L--L--TTQRGL---G-T--E-   736
96ZM651.8    -------------------I-A---------Q---------L--N---.----GR---E-   742
96ZM751.3    ----------I--------I-A---------Q------L--L--T---.---LGR---E-   731
94CY017.41   ----R----------------AIITV-----Q----V---IPT---EG.----R-T----   739
94IN476.104  --------I----------I-A---------Q------L--LT-D---.---LR----E-   731

93BR20.1     GEQGKDRSVRLVTGFLALAWDDLRNLCLFSYRHLRDFILIAARIVDRGLK.......RGW   780
92NG083.2    ---DR---T---S-----------S------HR---LV-----T-ELLGRSSLKGLRL--   783
90CF056.1    ---DR-------N---PVV-----S-S-----L---LL--VV-T-ELLGR.......--R   779
92RW009.6    ---DRG--I---S-----------S------HR---LL-----T-ELLGRSSLRGLQ---   794
92NG003.1    ---DR-------S------------------HR---LV-----TAELLRRSSLQGLRL--   779
93BR029.4    --P---------N-----V-------------------------------.......---   776
94CY032.3    ---DRS--I---N---P-I----------------NLL--V--T-ELLGIR.......--   789
96ZM651.8    ---D-E------S-----------S------HR------VT--A-ELLRRSSLKGLQ---   802
96ZM751.3    ---DR---I---N-----V-----S------HR----------GLQ...........---   780
94CY017.41   ----R---I---N--F--------S------HR---C------T-ELLGHCSLKGLRL--   799
94IN476.104  ---D----I---N-----------S-----CHR------V---A-ELLGRSSLRGLQ---   791

93BR20.1     EALKYLGNLTQYWGQELKNSAISLLNATAIAVAEWTDRVIEALQRAGRAILNIPRRIRQG   840
92NG083.2    -G----W--LL---R-------N--DTI---T-NG------VA---Y-----V-T-----   843
90CF056.1    ------W--L------------D---T-------G--GI-VIV---W----H--------   839
92RW009.6    -T-------V----L---R---N--DT---V---G---I--LI--IS---Y---S-----   854
92NG003.1    -G----W--LL---R-------N-IDTI-----N-------VA-G-C-------------   839
93BR029.4    ----L----AL--S------------T---V---G--------------V--V-------   836
94CY032.3    ------W-FLL-----------N-F-T-------G---I---V---C---C---------   849
96ZM651.8    -------S-V----L---K------DTI------G---I--LI-GIC---R-V-------   862
96ZM751.3    -T-----S-V----L---K------DTI------G---I--LT--IC---R-V-------   840
94CY017.41   -G--N-W--LL---R---------FDTI-V-----------IG---F-------------   859
94IN476.104  -------S-V----L---K------DTI--TI--G---I--FT--IC---R---------   851

93BR20.1     LERALL1   846
92NG083.2    ------1   849
90CF056.1    F--S--1   845
92RW009.6    F-A--Q1   860
92NG003.1    ------1   845
93BR029.4    ------1   842
94CY032.3    ------1   855
96ZM651.8    F-T---1   868
96ZM751.3    F-A--Q1   846
94CY017.41   ------1   865
94IN476.104  F-A---1   857
```

Fig. 21C

NEF

```
93BR020.1    MGGKWSKSSIVGWPAIRERMRRTPPTPP.AAE............GVGAVSQDLERRGAIT    47
92NG083.2    --------------Q----I-Q--V....---............---------A-H----    44
90CF056.1    --------RMG--ST-------AE-....V--............------R--D----V-    44
92RW009.6    --S----C-P-----V---L-Q-E-....---............----A----DKY--L-    44
92NG003.1    I--------------V---I-Q--.....P--............----AP---A-H----    43
93BR029.4    --S----------------L-Q---....---............----------------    44
94CY032.3    --------------E-------ARA....EP-RMRRAQAEPAAA---------DKH----    56
96ZM651.8    ---------------V---I---E.....P-AE...........----A----DKY--L-    44
96ZM751.3    -------R------KV---IA--D.....P-AE...........----A----DKY--L-    44
94CY017.41   -------R--P---------------AQRTEAV.....S.PAAP---------ATH--V-    54
94IN476.104  --S-M---R-----EV-------E.....P-AE...........----A----AKH--L-    44

93BR020.1    SSNTRANNPDLAWLEAQEED.EVGFPVRPQVPLRPMTYKGAVDLSHFLKEKGGLEGLIYS   106
92NG083.2    ----AT----C---------SD-----------------A-F---F--------D-----   104
90CF056.1    IN--AST-R-A-------DGE--------------------F------------D-----   104
92RW009.6    ----PS--A-C---A----EN------------------A-----F--------------   104
92NG003.1    ----AQT---C------Q-NS-------Q----------A-F---F--------D-----   103
93BR029.4    ----G-------------E.--------------------L------------------   103
94CY032.3    IN--A-T---KT-------EE----------------F---L------------D-----   116
96ZM651.8    ----STT-AAC--------EE.-----------------A-----F--------------   103
96ZM751.3    ----ST--A-C--------EG------------------S-F---F--------D----C   104
94CY017.41   ----A-T---C--V-----ES----------------F---F---F--------D-----   114
94IN476.104  T---PS--AAG---Q----EE--------------------F--AF--------D-----   104

93BR020.1    KRRQEILDLWVYHTQGYFPDWQNYTPGPGIRYPLTMGWCFKLVPVDPEEVEKANEGENNC   166
92NG083.2    ----D-------N---F------------T-L---F--------M--A-I-E--K---IS   164
90CF056.1    -Q--D-------N----------------E-F---F---------N-Q---Q-------S   164
92RW009.6    -K--D-------N----------------V-----F---Y-------R---E-----D--   164
92NG003.1    -K--D-------N----------------T-F---FR-------M--A-I-E--K----S   163
93BR029.4    -K---------------------------T-----L------------------------   163
94CY032.3    -K--------------F----D-------E-F--CF-----------Q---E-T----T-   176
96ZM651.8    -K--------------F------------V-----F-----------G---E--------   163
96ZM751.3    -K---------------------------------F---Y-------R---E-----D--   164
94CY017.41   QK--D---M--------------------------F---------E-S---E-TQ----S   174
94IN476.104  -K-H--------N----------------V-----F---Y-------SV--E--K-----   164

93BR020.1    LLHPMSQHGMEDEDKEVLKWEFDSRLALRHIARERHPEYYQD.1    208
92NG083.2    ----IC--------R---V-R-N-S--R--L---L-----K-C1    207
90CF056.1    ------L-----DGR---M-K-------T-L--VK----.K-C1    206
92RW009.6    ----L---------R-----K---H--H--M---L-----K-C1    207
92NG003.1    ----IC---L--A-R---V-R---S--R------Q-----K-C1    206
93BR029.4    --------------R-I-Q-R------FH-M---L-----K-C1    206
94CY032.3    ----I--------ER-----K------YK-V---L---F-K-C1    219
96ZM651.8    -------Q--D-DHR-----K---H--HK-M---L-----K-C1    206
96ZM751.3    ----I----I----R---R-K---S--R--M---L-----K-C1    207
94CY017.41   ----IC---VD-PER---R----RS--R--R---L-----K-C1    217
94IN476.104  ----------D---G-----Q---S--R------L-----K-C1    207
```

Fig. 22

REFERENCE CLONES AND SEQUENCES FOR NON-SUBTYPE B ISOLATES OF HUMAN IMMUNODEFICIENCY VIRUS TYPE 1

This work was funded by grants RO1 AI25291; and NO1AI35170 from the National Institutes of Health. Therefore, the government may have certain rights in the invention.

FIELD OF THE INVENTION

The present invention is in the field of virology. The invention relates to the nucleotide sequences of the genomes of 11 molecular clones for non-subtype B isolates of human immunodeficiency virus type 1 (HIV-1), and nucleic acids derived therefrom. This invention also relates to peptides encoded by and/or derived from the nucleic acid sequences of these molecular clones, and host cells containing these nucleic acid sequences and peptides. The invention also relates to diagnostic methods, kits and immunogens which employ the nucleic acids, peptides and/or host cells of the invention.

BACKGROUND OF THE INVENTION

A critical question facing current AIDS vaccine development efforts is to what extent HIV-1 genetic variation has to be considered in the design of candidate vaccines (11,21, 42,72). Phylogenetic analyses of globally circulating viral strains have identified two distinct groups of HIV-1, a major M group and an O group (33,45,61,62). Within the M group, ten sequence subtypes (A–J) have been proposed (29,30,45, 72). Sequence variation among viruses belonging to these different lineages is extensive, with envelope amino acid sequence variation ranging from 24% between different subtypes to 47% between the two different groups. Given this extent of diversity, the question has been raised whether immunogens based on a single virus strain can be expected to elicit immune responses effective against a broad spectrum of viruses, or whether vaccine preparations should include mixtures of genetically divergent antigens and/or be tailored toward locally circulating strains (11, 21, 42, 72). This is of particular concern in developing countries where multiple subtypes of HIV-1 are known to co-circulate and where subtype B viruses, which have been the source for most current candidate vaccine preparations (10, 21), are rare or nonexistent (5, 24, 40, 72).

Although the extent of global HIV-1 variation is well defined, little is known about the biological consequences of this genetic diversity and its impact on cellular and humoral immune responses in the infected host. In particular, it remains unknown whether subtype specific differences in virus biology exist that need to be considered for vaccine design. Only a comprehensive analysis of genetically defined representatives of the various groups and subtypes will address the question of whether certain variants differ in fundamental viral properties and whether such differences will need to be incorporated into vaccine strategies. Obviously, such studies require well-characterized reference reagents, in particular full length and replication competent molecular clones that can be used for functional and biological studies.

Full-length reference sequences representing the various subtypes are also urgently needed for phylogenetic comparisons. Until about 1994, it was generally thought that individuals do not become infected with multiple distinct HIV-1 strains, and so the possibility that recombination between divergent viruses could contribute to the evolution of HIV-1 was not widely considered. However, recent analyses of subgenomic (23,52,54,58) as well as full-length HIV-1 sequences (7,18,53,60) identified a surprising number of HIV-1 strains which clustered in different subtypes in different parts of their genome. All of these originated from geographic regions where multiple subtypes co-circulated and are the results of co-infections with highly divergent viruses (52,60,62).

Recombinant viruses can be detected because their phylogenetic affinities vary depending on the region of genome analyzed. A useful initial approach is to examine the extent of sequence divergence/similarity between a new sequence and a bank of reference sequences of different subtypes, for example as a diversity plot (18), or using the RIP program (75); if the extent of relative similarity to different subtypes varies along the sequence, this may indicate that the sequence is a recombinant. However, fuller investigation must involve a phylogenetic approach, comparing trees derived by analyses of different regions of the genome, and assessing the confidence of phylogenetic clustering by a statistical approach such as the bootstrap. A thorough analysis would involve taking a window of sequence of a certain size, and moving this window along the genome in steps of a defined size, generating perhaps hundreds of trees for visual examination in the process. There are at least two short cuts. One is to analyze only a few windows, defining selected regions according to the output of the diversity analysis. Another is to not examine the entire phylogenetic tree of all subtypes, but to focus on one particular phylogenetic question. Thus, if the initial analyses suggest that a sequence may be a recombinant between two particular subtypes, it is possible to ask simply what is the bootstrap value for the clustering of the new sequence with one or another particular subtype, and plot these values as a function of position along the genome; this is the basis of the "bootscanning" approach (57). Once the subtypes putatively involved in the recombination event have been identified, and the crossover points have been approximately localized, more precisely defined breakpoints can be determined, and their statistical significance assessed, using informative site analysis (19, 52, 53).

Detailed phylogenetic characterization revealed that most of the recombinant viruses have a complex genome structure with multiple points of crossover (7,18,53,60). Some recombinants, like the "subtype E" viruses, which are in fact A/E recombinants (7,18), have a wide-spread geographic dissemination and are responsible for much of the Asian HIV-1 epidemic (69,70). In other areas, recombinants appear to be generated with increasing frequencies as many randomly chosen isolates exhibit evidence of mosaicism (4,8, 31,66,71).

Since recombination provides the opportunity for evolutionary leaps with genetic consequences that are far greater than the steady accumulation of individual mutations, the impact of recombination on viral properties must be monitored. Full-length non-recombinant reference sequences for all major HIV-1 groups and subtypes are thus needed to map and characterize the extent of inter-subtype recombination.

Non-subtype B viruses cause the vast majority of new HIV-1 infections worldwide. Although their geographic dissemination is carefully monitored, their immunogenic and biological properties remain largely unknown, in part because well-characterized virological reference reagents are lacking. In particular, full length clones and sequences are rare, since subtype classification is frequently based on small PCR-derived viral fragments. There are currently only five full length, non-recombinant molecular clones available for viruses other than subtype B (45), and these represent only three of the proposed (group M) subtypes (A, C and D). Moreover, only three clones (all derived from subtype D viruses) are replication competent and thus useful for studies requiring functional gene products (45,48,65). Given the unknown impact of genetic variation on correlates of immune protection, subtype specific reagents are critically needed for phylogenetic, immunological and biological studies.

SUMMARY OF INVENTION

The present invention pertains to the isolation and characterization of the genomic sequences of 11 molecular clones for non-subtype B HIV-1 isolates of human immunodeficiency virus type 1 (HIV-1), and nucleic acids derived therefrom. Of these 11 molecular clones, 94IN476.104, 96ZM651.8, and 96ZM751.3 are non-mosaic reference clones of HIV-1 subtype C; 93BR020.1 is a reference clone of HIV-1 subtype F; 90CF056.1 is a reference clone of HIV-1 subtype H; 92RW009.6 is a double recombinant of HIV-1 subtypes A/C; 92NG083.2 and 92NG003.1 are double recombinants of HIV-1 subtypes A/G; 93BR029.4 is a double recombinant of HIV-1 subtypes B/F; 94CY017.41 is a double recombinant of HIV-1 subtype A and a new, as yet undefined, subtype; and 94CY032.3 is a triple recombinant of HIV-1 subtypes A/G/I.

In particular, the present invention relates to nucleic acids comprising the genomic sequences of one or more of these 11 clones for non-subtype B HIV-1 isolates, as well as nucleic acids comprising the complementary (or antisense) sequence of one or more of the genomic sequences of these 11 clones, and nucleic acids derived therefrom.

The invention also relates to vectors comprising the nucleic acid genomic sequence of one or more of these 11 clones, as well as nucleic acids comprising the complementary (or antisense) sequence of one or more of the genomic sequences of these clones, and nucleic acids derived therefrom.

The invention also relates to cultured host cells comprising the nucleic acid genomic sequences of one or more of these 11 clones for non-subtype B HIV-1 isolates, as well as nucleic acids comprising the complementary (or antisense) sequence of one or more of the genomic sequences of these clones, and nucleic acids derived therefrom.

The invention also relates to host cells containing vectors comprising the genomic sequences of one or more of these 11 clones for non-subtype B HIV-1 isolates, as well as nucleic acids comprising the complementary (or antisense) sequence of one or more of the genomic sequences of these clones, and nucleic acids derived therefrom.

The invention also relates to synthetic or recombinant polypeptides encoded by or derived from the nucleic acid sequences of one or more of the genomes of these 11 clones for non-subtype B HIV-1 isolates, and fragments thereof.

The invention also relates to methods for producing the polypeptides of the invention in culture using one or more of these 11 clones for non-subtype B HIV-1 viruses or nucleic acids derived therefrom, including recombinant methods for producing the polypeptides of the invention.

The invention further relates to methods of using the polypeptides of the invention as immunogens to stimulate an immune response in a mammal, such as the production of antibodies, or the generation of cytotoxic or helper T-lymphocytes.

The invention also relates to methods of using the polypeptides of the invention to detect antibodies which immunologically react with non-subtype B HIV-1 viruses in a mammal or in a biological sample.

The invention also relates to kits for the detection of antibodies specific for non-subtype B HIV-1 viruses in a biological sample where said kit contains at least one polypeptide encoded by or derived from the nucleic acid sequences of the invention.

The invention also relates to antibodies, which immunologically react with the virions of one or more of these 11 viruses and/or their encoded polypeptides.

The invention also relates to methods of detecting virions of non-subtype B HIV-1 viruses and/or their encoded polypeptides, or fragments thereof, using antibodies of the invention.

The invention also relates to kits for detecting the virions of non-subtype B HIV-1 viruses and/or their encoded polypeptides, wherein the kit comprises at least one antibody of the invention.

The invention also relates to a method for detecting the presence of non-subtype B HIV-1 viruses in a mammal or a biological sample, said method comprising analyzing the DNA or RNA of a mammal or a sample for the presence of the RNAs, cDNAs or genomic DNAs which will hybridize to a nucleic acid derived from one or more of these 11 non-subtype B HIV-1 molecular clones. Usually, when a completely complementary probe is used, high stringency conditions are desirable in order to prevent false positives. However, conditions of high stringency should only be used if the probes are complementary to target regions which lack heterogeneity. The stringency of hybridization is determined by a number of factors during hybridization and during the washing procedure, including temperature, ionic strength, length of time, and concentration of formamide, if any. The nucleic acid sequences used in probes should be unique to HIV, i.e., the nucleic acid sequences should be absent from individuals not infected with HIV.

The invention also provides diagnostic kits for the detection of non-subtype B HIV-1 viruses in a mammal using the nucleic acids of the invention. In one embodiment, the kit comprises nucleic acids having sequences useful as hybridization probes in determining the presence or absence of the RNAs, cDNAs or genomic DNAs of non-subtype B HIV-1 viruses. In another embodiment, the kit comprises nucleic acids having sequences useful as primers for reverse-transcription polymerase chain reaction (RT-PCR) analysis of RNA for the presence of HIV-1 viruses in a biological sample.

The invention further relates to isolated and substantially purified nucleic acids, polypeptides and/or antibodies of the invention.

The invention further relates to compositions comprising one or more of the nucleic acids, polypeptides and/or antibodies of the invention.

The invention also relates to computer-generated alignments of the nucleic acid sequences of the viral genomes clones of the 11 clones of this invention, as well as alignments of the encoded amino acid sequences. These sequence alignments serve to highlight regions of homology and non-homology between different sequences and hence, can be used in preparing diagnostic reagents as described herein.

BRIEF DESCRIPTION OF THE FIGURES

(FIG. 4A) Bootstrap plots depicting the relationship of 92RW009.6 to representatives of subtype A and C, respectively. Trees were constructed from the multiple genome alignment and the magnitude of the bootstrap value supporting the clustering of 92RW009.6 with U455 and 92UG037.1 (subtype A), or C2220 and 92BR025.8 (subtype C), respectively, was plotted for a window of 500 bp moved in increments of 10 bp along the alignment. Regions of subtype A or C origin are identified by very high bootstrap values (>90%). Points of cross-over of the two curves indicate recombination breakpoints. The beginning of gag, pol, vif, vpr, env and nef open reading frames are shown. The y-axis indicates the percent bootstrap replicates, which support the clustering of 92RW009.6 with representatives of the respective subtypes. (FIG. 4B) Bootstrap plots depicting the relationship of 93BR029.4 to representatives of subtype Band F, respectively. Analyses are as in (FIG. 4A), except that bootstrap values supporting the clustering of 93BR029.4 with SF2, OYI, MN, LAI and RF (subtype B), or 93BR020.1 (subtype F), respectively, were plotted. Subtype D viruses were excluded from this analysis because of their known close relationship with subtype B viruses.

FIGS. 7A–7C. Subtype specific genome features. (FIG. 7A) Alignment of deduced Tat (region encoded by second exon) amino acid sequences. Consensus sequences were generated for available representatives of all major subtypes (question marks indicate sites at which fewer than 50% of the viruses contain the same amino acid residue). Dashes denote sequence identity with the consensus sequence, while dots represent gaps introduced to optimize alignments. A vertical box highlights a premature Tat protein truncation (asterisk) which is present in 11 of 15 subtype D, and 4 of 52 subtype B viruses (frequencies are listed in the column on the right). (FIG. 7B) Alignment of deduced Rev (region encoded by the second exon) protein sequences. (FIG. 7C) Alignment of deduced Vpu protein sequences.

FIGS. 13A–13Z. Nucleotide sequence alignment of the 11 near full-length HIV-1 sequences included in this patent application. Sequences were aligned using CLUSTAL W and adjusted manually using the sequence editor MASE. Dots indicate gaps introduced to optimize the alignment. The beginning and end of all open reading frames are indicated by arrows above or below the alignment. The homologies between the sequences of nucleotides in the eleven independent clones are indicated by dashes. Sequences of nucleotides present uniquely in the various clones (as compared to the corresponding sequences of the other ten clones) are indicated by letters, i.e., the sequences themselves.

FIGS. 14A and 14B. Amino acid sequence alignments of the Gag polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIGS. 15A–15C. Amino acid sequence alignments of the Pol polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIG. 16. Amino acid sequence alignments of the Vif polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIG. 17. Amino acid sequence alignments of the Vpr polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIG. 18. Amino acid sequence alignments of the Tat polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIG. 19. Amino acid sequence alignments of the Rev polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIG. 20. Amino acid sequence alignments of the Vpu polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIGS. 21A–21C. Amino acid sequence alignments of the Env polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

FIG. 22. Amino acid sequence alignments of the Nef polypeptides encoded by the 11 near full-length HIV-1 sequences included in this patent application. The homologies between the sequences of amino acids in the various polypeptides encoded by the eleven independent clones are indicated by dashes. Sequences of amino acids present uniquely in the various polypeptides (as compared to the corresponding polypeptides of the other ten clones) are indicated by letters, i.e., the sequences themselves.

DETAILED DESCRIPTION OF THE INVENTION

Figure 1B:
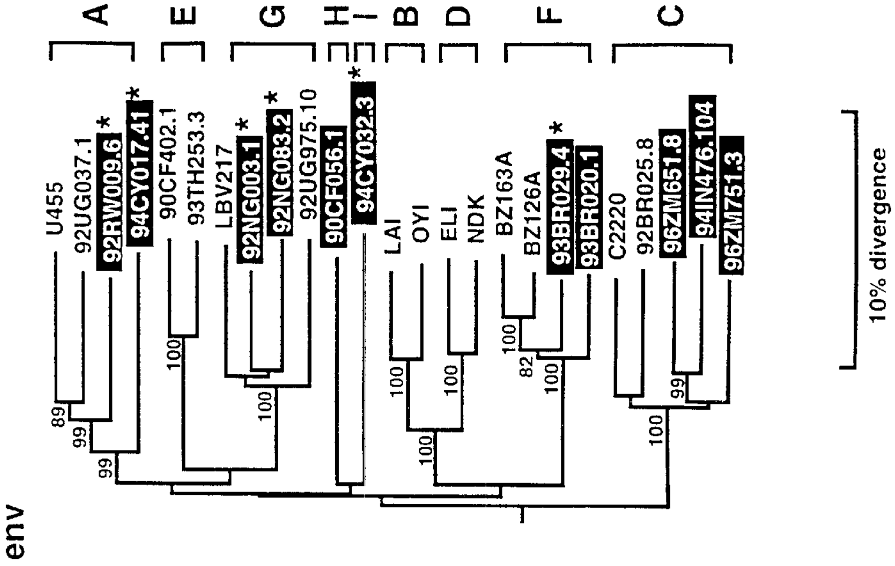
FIGS. 1A and 1B. Phylogenetic relationships of the 11 viral genomes described in this patent application (highlighted) to representatives of all major HIV-1 (group M) subtypes in gag (FIG. 1A) and env (FIG. 1B) regions. Trees were constructed from full-length gag and env nucleotide sequences using the neighbor joining method (see text for details of methodology). Horizontal branch lengths are drawn to scale; vertical separation is for clarity only. Values at the nodes indicate the percent bootstraps in which the cluster to the right was supported (bootstrap values of 75% and higher are shown). Asterisks denote hybrid genomes as determined by additional analyses. Brackets at the right represent the major sequence subtypes of HIV-1 group M. Trees were rooted by using SIVcpzGAB as an outgroup.

The present invention relates to the determination of the nucleic acid sequences of the complete or near complete genomes of 11 non-subtype B HIV-1 viruses isolated from primary isolates collected at major epicenters of the global AIDS pandemic. The nucleotide sequences of these 11 viruses are shown in FIGS. 13A–13Z (SEQ ID NOS: 1 to 11).

The phrase "derived from" is used throughout the specification and claims with respect to nucleic acids to describe nucleic acid sequences which correspond to a region of the designated nucleotide sequence. Preferably, the sequence of the region from which the nucleic acid is derived is, or is complementary to, a sequence which is unique to the genome of any one of the 11 clones of this invention. However, more preferably, the sequence of the region from which the nucleic acid is derived is, or is complementary to, a sequence which is unique to the viruses in the subtype corresponding to the subtype of any one of the 11 clones of this invention, and whose uniqueness was unknown prior to the disclosure of the clones of this invention. For example, sequences in the Cyprus clone 94CY032.3 which map to the I region are unique wherever they are not identical to known prior art sequences. Whether or not a sequence is unique to the genome of one of the molecular clones or a subtype can be determined by techniques known to those of skill in the art. For example, the sequence can be compared to sequences in databanks, e.g., GenBank, to determine whether it is present in the uninfected host or other organisms. The sequence can also be compared to the known sequences of other viral agents, including other retroviruses. The correspondence or non-correspondence of the derived sequence to other sequences can also be determined by hybridization under the appropriate stringency conditions. Hybridization techniques for determining the complementarity of nucleic acid sequences are well known in the art. In addition, mismatches of duplex polynucleotides formed by hybridization can be determined by known techniques, including for example, digestion with a nuclease such as S1 that specifically digests single-stranded areas in duplex polynucleotides.

Regions of the viral genome from which nucleic acid sequences may be derived include, but are not limited to, regions encoding specific epitopes as well as non-transcribed and non-translated sequences. Preferably, the epitope is unique to HIV viruses in the subtype corresponding to the subtype of the corresponding region of a polypeptide encoded by any one of the 11 clones of this invention, and whose uniqueness was unknown prior to the disclosure of the clones of this invention The uniqueness of the epitope may be determined by its immunological reactivity with HIV viruses of the subtype and lack of immunological reactivity with other HIV viruses of the other subtypes. Methods for determining immunological reactivity are known in the art, e.g., radioimmunoassay and ELISA and other assays mentioned herein. The uniqueness of an epitope can also be determined by computer searches of known databases, e.g., for the polynucleotide sequences which encode the eptiope, and by amino acid sequence comparisons with other known proteins.

The derived nucleic acid is not necessarily physically derived from the nucleotide sequence shown, but may be generated in any manner, including for example, chemical synthesis or DNA replication or reverse transcription or transcription, which are based on the information provided by the sequence of bases in the region(s) from which the nucleic acid is derived. The derived nucleic acid is comprised of at least 6–12 bases, more preferably at least 15–19 bases, more preferably at least 30 bases. The derived nucleic acid may also be larger, e.g., at least 100 bases in length, depending on the desired use of the nucleic acid. In addition, regions or combinations of regions corresponding to that of the designated sequence may be modified in ways known in the art to be consistent with an intended use. The derived nucleic acid may be a polynucleotide or polynucleotide analog.

The term "recombinant nucleotide" or "recombinant nucleic acid" as used herein intends a nucleic acid of genomic, cDNA, semisynthetic, or synthetic origin which, by virtue of its origin or manipulation: (1) is not associated with all or a portion of the nucleic acid with which it is associated in nature; and/or (2) is linked to a nucleic acid other than that to which it is linked in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA, as well as double- and single-stranded RNA. It also includes modified, for example, by methylation and/or by capping, and unmodified forms of the polynucleotide.

The present invention relates to nucleic acids having the genomic sequence of any one of the 11 molecular clones for non-subtype HIV-1 isolates of this invention as shown in FIGS. 13A–13Z (SEQ ID NOS: 1 to 11), as well as fragments (or partial sequences) thereof. The invention also relates to nucleic acids having complementary (or antisense) sequences to the sequences shown in FIGS. 13A–13Z (SEQ ID NOS: 1 to 11), as well as fragments (or partial sequences) thereof. Partial sequences may be obtained by various methods, including restriction digestion of nucleic acids with sequences shown in FIGS. 13A–13Z (SEQ ID NOS: 1 to 11), PCR amplification, and direct synthesis. Partial sequences may be all or part of the LTR and/or other untranslated regions of the genomes of one or more of the 11 viral clones of this invention, and/or all or part of the genes encoding the Gag, Pol, Vif, Vpr, Env, Tat, Rev, Nef and Vpu proteins and/or complementary (or antisense) sequences thereof. Nucleic acids of the invention also include cDNA, mRNA, and other nucleic acids derived from the genomic sequences of one or more of these 11 HIV-1 clones. Sequences of the genes encoding Gag, Pol, Vif, Vpr, Env, Tat, Rev, Nef and Vpu are identified in FIGS. 13A–13Z.

Genomic sequences of seven of the 11 clones of the invention have been made publicly available. The GenBank Accession numbers are as follows:

| Clone | Accession No. | Sequence ID No. |
|---|---|---|
| 92RW009.6 | U88823 | |
| 92NG003.1 | U88825 | |
| 92NG083.2 | U88826 | |
| 93BR020.1 | AF005494 | |
| 93BR029.4 | AF005495 | |
| 90CF056.1 | AF005496 | |
| 94CY032.3 | AF049337 | |
| 94CY017.41 | — | |
| 96ZM651.8 | — | |
| 96ZM751.3 | — | |
| 94IN476.104 | — | |

The nucleic acids of the invention may be present in vectors or host cells in tissue culture or other media. The nucleic acids of the invention may also be isolated and substantially purified by methods known in the art.

Nucleic acids of about 17 bases to about 35 bases in length are particularly preferred for use as primers in PCR amplification (see, e.g., the primers UP1A and R/U5 (17 mer and 22 mer, respectively) and UP1AMlu1 and Low1Mlu1 (28 mer and 35 mer respectively)). Nucleic acids of about 14 to about 25 bases in length are particularly preferred for use in nucleotide arrays. (See, eg., ref. 108, which uses 20 to 25 mers).

The present invention also relates to vectors and host cells comprising the nucleic acids of the invention.

The present invention also relates to compositions comprising one or more of the nucleic acids, vectors, and/or host cells of the invention.

The present invention further relates to methods of using the nucleic acids, vectors, and/or host cells of the invention, and/or compositions thereof For example, the invention relates to the use of nucleic acids of the invention as diagnostic agents to detect the presence or absence of non-subtype B HIV-1 viruses in a sample.

The present invention also relates to a method for detecting the presence of HIV-1 viruses which are related to the viruses of this invention in a mammal, using the nucleic acids of this invention.

In one embodiment, the detection method involves analyzing DNA obtained from a mammal suspected of harboring HIV-1 viruses. DNA can be isolated by methods well known in the art.

The methods for analyzing the DNA for the presence of the viruses of this invention include Southern blotting (86), dot and slot hybridization (87), and nucleotide arrays (see, e.g., U.S. Pat. No. 5,445,934 and U.S. Pat. No. 5,733,729).

The nucleic acid probes used in the detection methods set forth above are derived from nucleic acid sequences shown in FIGS. 13A–13Z (SEQ ID NOS: 1 to 11). The size of such probes is at least 10–12 bases long, more usually at least about 19 bases long, more usually from about 200 to about 500 bases, and often exceeding about 1000 bases.

The nucleic acid probes of this invention may be DNA or RNA. Nucleic acids can be synthesized using any of the known methods of nucleotide synthesis (see, e.g., refs. 88, 89, 90), or they can be isolated fragments of naturally occurring or cloned DNA. In addition, those skilled in the art would be aware that nucleotides can be synthesized by automated instruments sold by a variety of manufacturers or can be commercially custom ordered and prepared. The probes of this invention may also be nucleotide analogs, such as nucleotides linked by phosphodiester, phosphorothiodiester, methylphosphonodiester, or methylphosphonothiodiester moieties (91) and peptide nucleic acids (PNAs), in which the sugar-phosphate backbone of the polynucleotide is replaced with a polyamide or "pseudopeptide" backbone (92).

The nucleic acid probes can be labeled using methods known to one skilled in the art. Such labeling techniques can include radioactive labels, biotin, avidin, enzymes and fluorescent molecules (93).

The nucleic acid probes used in the detection methods set forth above are derived from sequences substantially homologous to one or more of the sequences shown in FIGS. 13A–13Z (SEQ ID NOS: 1 to 11), or their complementary sequences. By "substantially homologous", as used throughout the specification and claims to describe the nucleic acid sequence of the present invention, is meant a high level of homology between the nucleic acid sequence and one or more of the sequences of FIGS. 13A–13Z (SEQ ID NOS: 1 to 11), or its complementary sequence. Preferably, the level of homology is in excess of 80%, more preferably in excess of 90%, with a preferred nucleic acid sequence being in excess of 95% homologous with a portion of one or more of the sequences shown in FIGS. 13A–13Z (SEQ ID NOS: 1 to 11), or its complement. The size of such probes is usually at least 20 nucleotides, more usually from about 200 to 500 nucleotides, and often exceeding 1000 nucleotides.

Although complete complementarity is not necessary, it is preferred that the probes are made completely complementary to the corresponding portion of the genome, mRNA or cDNA target of at least one of the 11 viruses of this invention.

The probes can be packaged into diagnostic kits. Diagnostic kits may include ingredients for labeling and other reagents and materials needed for the particular hybridization protocol in addition to the probes.

In another embodiment of the invention, the detection method comprises analyzing the RNA of a mammal for the presence of HIV-1 viruses which are related to one or more of the 11 the viruses of this invention. RNA can be isolated by methods well known in the art.

The methods for analyzing the RNA for the presence of the viruses of this invention include Northern blotting (94), dot and slot hybridization, filter hybridization (95), Rnase protection (93), and reverse-transcription polymerase chain reaction (RT-PCR)(96). A preferred method is RT-PCR. In this method, the RNA can be reverse transcribed to first strand cDNA using a nucleic acid primer or primers derived from one or more of the nucleotide sequences shown in FIGS. 13A–13Z (SEQ ID NOS: 1 to 11). Once the cDNAs are synthesized, PCR amplification is carried out using pairs of primers designed to hybridize with sequences in the genomes of one or more of the non-subtype B HIV-1 viruses of this invention which are an appropriate distance apart (at least about 50 bases) to permit amplification of the cDNA and subsequent detection of the amplification product. Each primer of a pair is a single-stranded nucleic acid of about 20 to about 60 bases in length where one primer (the "upstream" primer) is complementary to the original RNA and the second primer (the "downstream" primer) is complementary to the first strand of cDNA generated by reverse transcriptions of the RNA. The target sequence is generally about 100 to about 300 bases in length but can be as large as 500–1500 bases or more, e.g., 9,000 bases. Optimization of the amplification reaction to obtain sufficiently specific hybridization to the nucleotide sequences of these viruses is well within the skill in the art and is preferably achieved by adjusting the annealing temperature.

The amplification products of PCR can be detected either directly or indirectly. In one embodiment, direct detection of the amplification products is carried out via labeling of primer pairs. Labels suitable for labeling the primers of the present invention are known to one skilled in the art and include radioactive labels, biotin, avidin, enzymes and fluorescent molecules. The desired labels can be incorporated into the primers prior to performing the amplification reaction. Alternatively, the desired labels can be incorporated into the primer extension products during the amplification reaction in the form of one or more labeled dNTPs. In one embodiment of the present invention, the labeled amplified PCR products can be detected by agarose gel electrophoresis followed by ethidium bromide staining and visualization under ultraviolet light or via direct sequencing of the PCR-products. The labeled amplified PCR products can also be detected by binding to immobilized oligonucleotide arrays.

In yet another embodiment, unlabelled amplification products can be detected via hybridization with labeled nucleic acid probes in methods known to one skilled in the art, such as dot or slot blot hybridization or filter hybridization.

The invention also relates to methods of using these nucleic acids to produce polypeptides in vitro or in vivo.

In one embodiment of the invention, a recombinant method of making a polypeptide of the invention comprises:

(a) preparing a nucleic acid capable of directing a host cell to produce a polypeptide encoded by the genome of any one of the non-subtype B HIV-1 viruses of this invention;

(b) cloning the nucleic acid into a vector capable of being transferred into and replicated in a host cell, such vector containing operational elements for expressing the nucleic acid, if necessary;

(c) transferring the vector containing the nucleic acid and operational elements into a host cell capable of expressing the polypeptide;

(d) growing the host under conditions appropriate for expression of the polypeptide; and (e) harvesting the polypeptide.

The present invention also relates to non-recombinant methods of making the polypeptides and nucleic acids of the invention. In addition to synthetic methods, the non-recombinant methods involve culturing the viruses of this invention in cell lines, preferably in uninfected human peripheral blood mononuclear cells, under conditions appropriate for expression of the polypeptides and nucleic acids. This invention thus also relates to the polypeptides and nucleic acids produced by the virus in cell culture. The polypeptides and nucleic acids may be isolated and purified by methods known in the art.

The vectors contemplated for use in the present invention include any vectors into which a nucleic acid sequence as described above can be inserted, along with any preferred or required operational elements, and which vector can then be subsequently transferred into a host cell and, preferably, replicated in such cell. Preferred vectors are those whose restriction sites have been well documented and which contain the operational elements preferred or required for transcription of the nucleic acid sequence. Vectors may also be used to prepare large amounts of nucleic acids of the invention, which may be used, e.g., to prepare probes or other nucleic acid constructs.

When expression of a polypeptide is desired, the "operational elements" as discussed herein include at least one promoter sequence capable of initiating transcription of the nucleic acid sequence, at least one leader sequence, at least one terminator codon and/or termination signal, and any other DNA sequences necessary or preferred for appropriate transcription and subsequent translation of the vector nucleic acid. In particular, it is contemplated that such vectors will preferably contain at least one origin of replication recognized by the host cell along with at least one selectable marker.

Preferred expression vectors of this invention are those which function in bacterial and/or eukaryotic cells. Examples of vectors which function in eukaryotic cells include, but are not limited to Venezuelan equine encephalitis virus vectors, simian virus vectors, vaccinia virus vectors, adenovirus vectors, herpes virus vectors, or vectors based on retroviruses, such as murine leukemia virus, or HIV or other lentivirus (97).

The selected expression vector may be transfected into a suitable bacterial or eukaryotic cell system for purposes of expressing the recombinant polypeptide. Eukaryotic cell systems include but are not limited to cell lines such as HeLa, COS-1, 293T, MRC-5, or CV-1 cells. Primary human cells, such as lymph node cells, macrophages, etc., are also useful in practicing the invention.

The expressed polypeptides may be detected directly by methods known in the art including, but not limited to, Coomassie blue staining and Western blotting or indirectly, such as in detection of the expression product of a reporter gene, such as luciferase.

In another embodiment of the invention, the method comprises administering a composition comprising a vector comprising a nucleic acid of the invention to a mammal to produce a polypeptide in vivo.

The present invention also relates to polypeptides encoded by and/or derived from the nucleotide sequences of this invention. These polypeptides may be natural, synthetic or produced by recombinant methods. Polypeptides can be obtained as a crude lysate or can be purified by standard protein purification procedures known in the art which may include differential precipitation, molecular size exclusion chromatography, ion-exchange chromatography, isolectric focusing, gel electrophoresis and affinity and immunoaffinity chromatography. The polypeptides may be purified by passage through a column containing a resin which has bound thereto antibodies specific for an open reading frame (ORF) polypeptide. The present invention also relates to compositions comprising one or more of the polypeptides of the invention.

A polypeptide or amino acid sequence derived from a designated nucleic acid sequence refers to a polypeptide having an amino acid sequence identical to that of a polypeptide encoded by the sequence, or a portion thereof wherein the portion consists of at least 6–8 amino acids, and more preferably at least 10 amino acids, and more preferably at least 11–15 amino acids, and most preferably at least 30 amino acids or which is immunologically cross-reactive with a polypeptide encoded by the sequence. The polypeptide may also be larger, e.g., at least 100 amino acids in length, depending on the desired use of the polypeptide. Polypeptides from the V3-loop region and the "crown" of gp41 of Env are particularly preferred.

A recombinant or derived polypeptide is not necessarily translated from a designated nucleic acid sequence; it may be generated in any manner, including for example, chemical synthesis, or expression of a recombinant expression system, or isolation from any of the 11 HIV-1 viruses of this invention.

It should be noted that the nucleotide sequences described herein represent one embodiment of the present invention. Due to the degeneracy of the genetic code, it is to be understood that numerous choices of nucleotides may be made that will lead to a sequence capable of directing production of the polypeptides set forth above. As such, nucleic acid sequences which are functionally equivalent to the sequences described herein are intended to be encompassed within the present invention. For example, preferred codons which are appropriate to the host cell may be used (see, e.g., WO 98/34640), or the sequence may be modified to reduce the effect of any inhibitory/instability sequences and to provide for Rev-independent gene expression. (98).

The polypeptides of this invention consist of at least 6–12 amino acids, more preferably at least 3–18 amino acids, even more preferably at least 19–24 amino acids and most preferably at least 25–30 amino acids encoded by, or otherwise derived from, any one of the genomic sequences shown in FIGS. 13A–13Z (SEQ ID NOS: 1 to 11).

The present invention further relates to the use of polypeptides of the invention as diagnostic agents.

In one embodiment, the polypeptides of the invention can be used in immunoassays for detecting the presence of antibodies against non-subtype B HIV-1 viruses in a mammal and for diagnosing the presence of infection of any of these viruses in a mammal.

For the purposes of the present invention, "mammal" as used throughout the specification and claims, includes, but is not limited to humans, chimpanzees, mangabeys, other other primates.

In a preferred embodiment, test serum is reacted with a solid phase reagent having a surface-bound polypeptide of this invention as an antigen. The solid surface reagent can be prepared by known techniques for attaching polypeptides to solid support material. These attachment methods include non-specific adsorption of the polypeptide to the support or covalent attachment of the polypeptide to a reactive group on the support. After reaction of the antigen with an antibody against any one of the viruses of this invention in the serum, unbound serum components are removed by washing and the antigen-antibody complex is reacted with a secondary antibody such as labeled anti-human antibody. The label may be an enzyme which is detected by incubating the solid support in the presence of a suitable fluorimetric or calorimetric reagent. Other detectable labels may also be used, such as radiolabels or colloidal gold, and the like.

Immunoassays of the present invention may be a radioimmunoassay, Western blot assay, immunofluorescent assay, enzyme immunoassay, chemiluminescent assay, immunohistochemical assay and the like. Standard techniques for ELISA are well known in the art. Such assays may be a direct, indirect, competitive, or noncompetitive immunoassay as described in the art (see, e.g. ref. 99). Biological samples appropriate for such detection assays include, but are not limited to serum, liver, saliva, lymphocytes or other mononuclear cells.

Polypeptides of the invention may be prepared in the form of a kit, alone, or in combinations with other reagents such as secondary antibodies, for use in immunoassays.

In yet another embodiment, the polypeptides of the invention can be used as immunogens to raise antibodies and/or stimulate cellular immunity in a mammal.

The immunogen may be a partially or substantially purified peptide. Alternatively, the immunogen may be a cell, cell lysate from cells transfected with a recombinant expression vector, or a culture supernatant containing the expressed polypeptide. The immunogen may comprise one or more structural proteins, and/or one or more non-structural proteins of the HIV-1 clones of this invention, or a mixture thereof.

The effective amount of polypeptide per unit dose sufficient to induce an immune response depends, among other things, on the species of mammal inoculated, the body weight of the mammal and the chosen inoculation regimen, as well as the presence or absence of an adjuvant, as is well known in the art. Inocula typically contain polypeptide concentrations of about 1 microgram to about 50 milligrams per inoculation (dose), preferably about 10 micrograms to about 10 milligrams per dose, most preferably about 100 micrograms to about 5 milligrams per dose.

The term "unit dose" as it pertains to the inocula refers to physically discrete units suitable as unitary dosages for mammals, each unit containing a predetermined quantity of active material (polypeptide) calculated to produce the desired immunogenic effect in association with the required diluent.

Inocula are typically prepared as a solution in a physiologically acceptable carrier such as saline, phosphate-buffered saline and the like to form an aqueous pharmaceutical composition.

The route of inoculation of the polypeptides of the invention is typically parenteral and is preferably intramuscular, sub-cutaneous and the like. The dose is administered at least once. In order to increase the antibody level, at least one booster dose may be administered after the initial injection, preferably at about 4 to 6 weeks after the first dose. Subsequent doses may be administered as indicated.

To monitor the antibody response of individuals administered the compositions of the invention, antibody titers may be determined. In most instances it will be sufficient to assess the antibody titer in serum or plasma obtained from such an individual. Decisions as to whether to administer booster inoculations or to change the amount of the composition administered to the individual may be at least partially based on the titer.

The titer may be based on an immunobinding assay which measures the concentration of antibodies in the serum which bind to a specific antigen. The ability to neutralize in vitro and in vivo biological effects of the viruses of this invention may also be assessed to determine the effectiveness of the immunization.

For all therapeutic, prophylactic and diagnostic uses, the polypeptide of the invention, alone or linked to a carrier, as well as antibodies and other necessary reagents and appropriate devices and accessories may be provided in kit form so as to be readily available and easily used.

Where immunoassays are involved, such kits may contain a solid support, such as a membrane (e.g., nitrocellulose), a bead, sphere, test tube, microtiter well, rod, and so forth, to which a receptor such as an antibody specific for the target molecule will bind. Such kits can also include a second receptor, such as a labeled antibody. Such kits can be used for sandwich assays. Kits for competitive assays are also envisioned.

The immunogens of this invention can also be generated by the direct administration of nucleic acids of this invention to a subject. DNA-based vaccination has been shown to stimulate humoral and cellular responses to HIV-1 antigens in mice (100–103) and macaques (103, 104). More recent studies in infected chimpanzees have shown a possible application of this strategy in HIV-1-infected humans: DNA vaccination of HIV-1-infected chimpanzees with a construct that drives expression of HIV-1 env and rev appeared well-tolerated, and immunized animals demonstrated a boost in antibody response followed by a >1 log decrease in their virus loads (104). A DNA-based vaccine containing HIV-1 env and rev genes was injected into HIV-infected human patients in three doses (30, 100 or 300 micrograms) at 10-week intervals. Increased antibodies against gp120 were observed in the 100 and 300 $\mu$g groups. Increases were also noted in cytotoxic T lymphocyte (CTL) activity against gp160-bearing targets and in lymphocyte proliferative activity (105, 106). DNA-based vaccines containing HIV gag genes, with modification of the viral nucleotide sequence to incorporate host-preferred codons (see, e.g., WO 98/34640), and/or to reduce the effect of inhibitory/instability sequences (see, e.g., ref. 98), have likewise been described.

Therefore, it is anticipated that the direct injection of RNA or DNA vectors of this invention encoding viral antigen can be used for endogenous expression of the antigen to generate the viral antigen for presentation to the immune system without the need for self-replicating agents or adjuvants, resulting in the generation of antigen-specific CTLs and protection from a subsequent challenge with a homologous or heterologous strain of virus.

CTLs in both mice and humans are capable of recognizing epitopes derived from conserved internal viral proteins and are thought to be important in the immune response against viruses. By recognition of epitopes from conserved viral proteins, CTLs may provide cross-strain protection. CTLs specific for conserved viral antigens can respond to different strains of virus, in contrast to antibodies, which are generally strain-specific.

Thus, direct injection of RNA or DNA encoding the viral antigen has the advantage of being without some of the limitations of direct peptide delivery or viral vectors (see, e.g., ref. 107 and the discussions and references therein). Furthermore, the generation of high-titer antibodies to expressed proteins after injection of DNA indicates that this may be a facile and effective means of making antibody-based vaccines targeted towards conserved or non-conserved antigens, either separately or in combination with CTL vaccines targeted towards conserved antigens. These may also be used with traditional peptide vaccines, for the generation of combination vaccines. Furthermore, because protein expression is maintained after DNA injection, the persistence of B and T cell memory may be enhanced, thereby engendering long-lived humoral and cell-mediated immunity.

Nucleic acids encoding a polypeptide of this invention can be introduced into animals or humans in a physiologically or pharmaceutically acceptable carrier using one of several techniques such as injection of DNA directly into human tissues; electroporation or transfection of the DNA into primary human cells in culture (ex vivo), selection of cells for desired properties and reintroduction of such cells into the body, (said selection can be for the successful homologous recombination of the incoming DNA to an appropriate preselected genomic region); generation of infectious particles containing the gag and/or other genes encoded by the viruses of this invention, infection of cells ex vivo and reintroduction of such cells into the body; or direct infection by said particles in vivo. Substantial levels of polypeptide will be produced leading to an efficient stimulation of the immune system.

Also envisioned are therapies based upon vectors, such as viral vectors containing nucleic acid sequences coding for the polypeptides described herein. These molecules, developed so that they do not provoke a pathological effect, will stimulate the immune system to respond to the polypeptides.

The effective amount of nucleic acid immunogen per unit dose to induce an immune response depends, among other things, on the species of mammal inoculated, the body weight of the mammal and the chosen inoculation regimen, as is well known in the art. Inocula typically contain nucleic acid concentrations of about 1 microgram to about 50 milligrams per inoculation (dose), preferably about 10 micrograms to about 10 milligrams per dose, most preferably about 100 micrograms to about 5 milligrams per dose.

Immunization can be conducted by conventional methods. For example, the immunogen can be used in a suitable diluent such as saline or water, or complete or incomplete adjuvants. Further, the immunogen may or may not be bound to a carrier. While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more physiologically or pharmaceutically acceptable carriers and optionally other therapeutic ingredients. The carrier(s) must be "acceptable" in the sense of being compatible with the other ingredients of the formulation and not deleterious to the recipient thereof The formulations may conveniently be presented in unit dosage form and may be prepared by any method well-known in the pharmaceutical art. The immunogen can be administered by any route appropriate for antibody production such as intravenous, intraperitoneal, intramuscular, subcutaneous, and the like. The immunogen may be administered once or at periodic intervals until a significant titer of antibody against any of the 11 viruses of this invention is produced. The antibody may be detected in the serum using an immunoassay. The host serum or plasma may be collected following an appropriate time interval to provide a composition comprising antibodies reactive with the virus particle or encoded polypeptide. The gamma globulin fraction or the IgG antibodies can be obtained, for example, by use of saturated ammonium sulfate or DEAE Sephadex, or other techniques known to those skilled in the art.

In addition to its use to raise antibodies, the administration of the immunogens of the present invention may be for use as a vaccine for either a prophylactic or therapeutic purpose. When provided prophylactically, a vaccine(s) of the invention is provided in advance of any exposure to any one or more of the 11 non-subtype B viruses of this invention or in advance of any symptoms due to infection of these viruses. The prophylactic administration of a vaccine(s) of the invention serves to prevent or attenuate any subsequent infection of these viruses in a mammal. When provided therapeutically, a vaccine(s) of the invention is provided at (or shortly after) the onset of infection or at the onset of any symptom of infection or any disease or deleterious effects caused by these viruses. The therapeutic administration of the vaccine(s) serves to attenuate the infection or disease. The vaccine(s) of the present invention may, thus, be provided either prior to the anticipated exposure to the viruses of this invention or after the initiation of infection.

In another embodiment, the polypeptides of the invention can be used to prepare antibodies against epitopes of the viruses of this invention that are useful in diagnosis.

The term "antibodies" is used herein to refer to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', $F(ab')_2$ and F(v) as well as chimeric antibody molecules.

An antibody of the present invention is typically produced by immunizing a mammal with an immunogen or vaccine of the invention. In one embodiment, the immunogen or vaccine contains one or more polypeptides of the invention, or a structurally and/or antigenically related molecule, to induce, in the mammal, antibody molecules having immunospecificity for the immunizing peptide or peptides. The peptide(s) or related molecule(s) may be monomeric, polymeric, conjugated to a carrier, and/or administered in the presence of an adjuvant. In another embodiment, the immunogen or vaccine contains one or more nucleic acids encoding one or more polypeptides of the invention, or one or more nucleic acids encoding structurally and/or antigenically related molecules, to induce, in the mammal, the production of the immunizing peptide or peptides. The antibody molecules may then be collected from the mammal if they are to be used in immunoassays or for providing passive immunity.

The antibody molecules of the present invention may be polyclonal or monoclonal. Monoclonal antibodies may be produced by methods known in the art. Portions of immunoglobulin molecules may also be produced by methods known in the art.

The antibody of the present invention may be contained in various carriers or media, including blood, plasma, serum (e.g., fractionated or unfractionated serum), hybridoma supernatants and the like. Alternatively, the antibody of the present invention is isolated to the extent desired by well known techniques such as, for example, by using DEAE SEPHADEX, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibody of the IgG class are preferred for purposes of passive protection.

The presence of the antibodies of the present invention, either polyclonal or monoclonal, can be determined by, but are not limited to, the various immunoassays described above.

The antibodies of the present invention have a number of diagnostic and therapeutic uses. The antibodies can be used as an in vitro diagnostic agent to test for the presence of any one or more of the 11 HIV-1 viruses of this invention in biological samples in standard immunoassay protocols.

Preferably, the assays which use the antibodies to detect the presence of these viruses in a sample involve contacting the sample with at least one of the antibodies under conditions which will allow the formation of an immunological complex between the antibody and the viral antigen that may be present in the sample. The formation of an immunological complex if any, indicating the presence of one or more of these viruses in the sample, is then detected and measured by suitable means. Such assays include, but are not limited to, radioimmunoassays, (RIA), ELISA, indirect immunofluorescence assay, Western blot and the like. The antibodies may be labeled or unlabeled depending on the type of assay used. Labels which may be coupled to the antibodies include those known in the art and include, but are not limited to, enzymes, radionucleotides, fluorogenic and chromogenic substrates, cofactors, biotin/avidin, colloidal gold and magnetic particles. Modification of the antibodies allows for coupling by any known means to carrier proteins or peptides or to known supports, for example, polystyrene or polyvinyl microtiter plates, glass tubes or glass beads and chromatographic supports, such as paper, cellulose and cellulose derivatives, and silica.

Such assays may be, for example, of direct format (where the labeled first antibody reacts with the antigen), an indirect format (where a labeled second antibody reacts with the first antibody), a competitive format (such as the addition of a labeled antigen), or a sandwich format (where both labeled and unlabelled antibody are utilized), as well as other formats described in the art. In one such assay, the biological sample is contacted with antibodies of the present invention and a labeled second antibody is used to detect the presence of any one of the HIV-1 viruses of this invention, to which the antibodies are bound.

The antibodies of the present invention are also useful as a means of enhancing the immune response.

The antibodies may be administered with a physiologically or pharmaceutically acceptable carrier or vehicle therefor. A physiologically acceptable carrier is one that does not cause an adverse physical reaction upon administration and one in which the antibodies are sufficiently soluble and retain their activity to deliver a therapeutically effective amount of the compound. The therapeutically effective amount and method of administration of the antibodies may vary based on the individual patient, the indication being treated and other criteria evident to one of ordinary skill in the art. A therapeutically effective amount of the antibodies is one sufficient to reduce the level of infection by one or more of the viruses of this invention or attenuate any dysfunction caused by viral infection without causing significant side effects such as non-specific T cell lysis or organ damage.

The route(s) of administration useful in a particular application are apparent to one or ordinary skill in the art. Routes of administration of the antibodies include, but are not limited to, parenteral, and direct injection into an affected site. Parenteral routes of administration include but are not limited to intravenous, intramuscular, intraperitoneal and subcutaneous.

The present invention includes compositions of the antibodies described above, suitable for parenteral administration including, but not limited to, pharmaceutically acceptable sterile isotonic solutions. Such solutions include, but are not limited to, saline and phosphate buffered saline for intravenous, intramuscular, intraperitoneal, or subcutaneous injection, or direct injection into a joint or other area.

Antibodies for use to elicit passive immunity in humans are preferably obtained from other humans previously inoculated with pharmaceutical compositions comprising one or more of the polypeptides of the invention. Alternatively, antibodies derived from other species may also be used. Such antibodies used in therapeutics suffer from several drawbacks such as a limited half-life and propensity to elicit an immune response. Several methods are available to overcome these drawbacks. Antibodies made by these methods are encompassed by the present invention and are included herein. One such method is the "humanizing" of non-human antibodies by cloning the gene segment encoding the antigen binding region of the antibody to the human gene segments encoding the remainder of the antibody. Only the binding region of the antibody is thus recognized as foreign and is much less likely to cause an immune response.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 5 mg/kg to about 20 mg/kg body weight of the mammal, although a lower or higher dose may be administered. In general, the antibodies will be administered intravenously (IV) or intramuscularly (IM).

The invention also relates to the use of antisense nucleic acids to inhibit translation of peptides encoded by the HIV-1 viruses of this invention. The antisense nucleic acids are complementary to the viral mRNAs encoding peptides of this invention. The antisense nucleic acids may be in the form of synthetic nucleic acids or they may be encoded by a nucleotide construct, or they may be semi-synthetic. The antisense nucleic acids may be delivered to the cells using methods known to those skilled in the art.

Kits designed for diagnosis of the HIV-1 viruses of this invention in a biological sample can be constructed by packaging the appropriate materials, including the nucleic acids and/or polypeptides of this invention and/or antibodies which specifically react with antigens of one or more of these viruses, along with other reagents and materials required for the particular assay.

The present invention further relates to computer-generated alignments of any or more of the nucleotide sequences shown in FIGS. 13A–13Z (SEQ ID NOS: 1 to 11). Computer analysis of the nucleotide sequences, such as the one shown in FIG. 13A–13Z, can be carried out using commercially available computer program known to one skilled in the art.

In one embodiment, the sequences shown in FIGS. 13A–13Z (SEQ ID NOS: 1 to 11) are aligned by the computer program CLUSTAL (67) and adjusted with multiple-aligned sequence editor (12). The computer analysis results in the distribution of 11 sequences into various genotypes. Five of these sequences represent non-recombinant members of HIV-1 subtypes, and the other six sequences represent HIV-1 intersubtype recombinants.

The grouping of the molecular clones into mosaic and non-mosaic genotypes is shown below:

| Name of Clone | Genotypes |
|---|---|
| 94CY017.41 | A/? |
| 94IN476.104 | C |
| 96ZM651.8 | C |

-continued

| Name of Clone | Genotypes |
|---|---|
| 96ZM751.3 | C |
| 93BR020.1 | F |
| 90CF056.1 | H |
| 92RW009.6 | A/C |
| 92NG083.2 | A/G |
| 92NG003.1 | A/G |
| 93BR029.4 | B/F |
| 94CY032.3 | A/G/I |

For those sequences representing recombinant members of HIV-1, a variety of phylogenetic methods were used to further characterize the subtype composition.

The multiple computer-generated alignments of nucleotide sequences are shown in FIGS. 13A–13Z. The multiple computer-generated alignments of encoded amino acid sequences are shown in FIGS. 14–22. These alignments serve to highlight regions of homology and non-homology between different sequences and hence, can be used by one skilled in the art to design oligonucleotides and polypeptides useful as reagents in diagnostic assays for HIV-1.

The following examples illustrate certain embodiments of the present invention, but should not be construed as limiting its scope in any way. Certain modifications and variations will be apparent to those skilled in the art from the teachings of the forgoing disclosure and the following examples, and these are intended to be encompassed by the spirit and scope of the invention.

EXAMPLE 1

Materials and Methods

Virus Isolates

All viruses used were propagated in normal donor peripheral blood mononuclear cells (PBMCs) and thus represent primary isolates. Their biological phenotype (SI/NSI), year of isolation, relevant epidemiological and clinical information, as well as appropriate references are summarized in Table 1. For consistency, isolates are labeled according to WHO nomenclature (28). Preliminary subtype classification was made on the basis of partial env and/or gag gene sequences (1,17,19,43).

Amplification of Near Complete HIV-1 Genomes Using Long PCR Methods (Near) full length HIV-1 genomes were amplified from short-term cultured PMBC DNA essentially as described (18,56) using the GeneAmp XL kit (Perkin Elmer Cetus, Foster City, Calif.) and primers spanning the tRNA primer binding site (upstream primer UP1A: 5'-AGTGGCGCCCGAACAGG-3')(SEQ ID NO: 109) and the R/U5 junction in the 3' long terminal repeat (downstream primer Low2: 5'-TGAGGCTTAAGCAGTGGGTTTC-3') (SEQ ID NO: 110). Some isolates were amplified with primers containing Mlu1 restriction enzyme sites to facilitate subsequent subcloning into plasmid vectors (upstream primer UP1AMlu1: 5'-TCTCTacgcgtGGCGCCCGAACAGGGAC-3' (SEQ ID NO: 111); downstream primer Low1Mlu1: 5'-ACCAGacgcgtACAACAGACGGGCACACACTA-CTT-3' (SEQ ID NO: 112); lower case letters indicate the Mlu1 restriction site). Whenever possible, PBMC DNAs were diluted prior to PCR analysis to attempt amplification from single proviral templates. Cycling conditions included a hot start (94° C., 2 min), followed by 20 cycles of denaturation (94° C.; 30 sec) and extension (68° C.; 10 min), followed by 17 cycles of denaturation (94° C.; 30 sec) and extension (68° C., 10 min) with 15 second increments per cycle. PCT products were visualized by agarose gel electrophoresis and subclone into pCRII by T/A overhang or following cleavage with Mlu1 into a modified pTZ18 vector (pTZ18Mlu1) containing a unique Mlu1 site in its polylinker. Transformations were performed in INVαF' cells, and colonies were screened by restriction enzyme digestion for full length inserts (transformation efficiencies were generally poor, yielding only a few recombinant colonies, however, once sublconed, full length genomes were stable in their respective vectors). One full length clone per isolate was randomly chosen for subsequent sequence analysis.

Construction of a Full Length and Infectious Molecular Clone of 94UG114.1

A 674 bp fragment spanning most of the viral LTR (lacking 1–92 of U3 sequences) as well as the untranslated leader sequence preceding gag, was amplified from 94UG114 PBMC DNA, using primers and conditions described previously (18). After sequence confirmation, this LTR fragment was cloned into the pTZ18Mlu1 vector, which was subsequently cleaved with Nar1 (in the primer binding site) and Mlu1 (in the polylinker) to allow the insertion of the 94UG114.1 long PCR product cleaved with the same restriction enzymes. The resulting plasmid clone comprised a full length 94UG114.1 genome with 3' and 5' LTR fragments containing all regulatory elements necessary for viral replication. A similar strategy could be used to construct replication competent genomes for all 11 clones reported in this application.

Sequence Analysis of HIV-1 Genomes

A number of the clones described herein were sequenced using the shotgun sequencing approach (37). Briefly, viral genomes were released from their respective plasmid vectors by cleavage with the appropriate restriction enzymes, purified by gel electrophoresis, and sonicated (Model XL2020 Sonicator; Heat System Inc., Framingdale, N.Y.) to generate randomly sheared DNA fragments 600–1,000 bp in length. Following purification by gel electrophoresis, fragments were end-repaired using T4 DNA polymerase and Klenow enzyme and ligated into SmaI digested and dephosphorylated M13 or pTZ18 vectors. Approximately 200 shotgun clones were sequenced for each viral genome using cycle sequencing and dye terminator methodologies on an automated DNA sequenator (Model 377A; Applied Biosystems, Inc.). Sequences were determined for both strands of DNA. Other clones were sequenced directly using the primer walking approach (primers were designed approximately every 300 bp along the genome for both strands). Proviral contigs were assembled from individual sequences using the SEQUENCHER program (Gene Codes Corporation, Ann Arbor, Mich.). Sequences were analyzed using EUGENE (Baylor College of Medicine, Houston, Tex.) and MASE (12).

Phylogenetic Tree Analysis

Phylogenetic relationships of the newly derived viruses were estimated from sequence comparisons with previously reported representatives of HIV-1 group M (45). Multiple gag and env sequence alignments were obtained from the Los Alamos sequence database (http://hiv-web.lanl.gov/HTML/alignments.html). Newly derived gag and env sequences were added to these alignments using the CLUSTAL W profile alignment option (67) and adjusted manually using the alignment editor MASE (12). All partial sequences were removed from these alignments. Sites where there was a gap in any of the remaining sequences, as well as areas of uncertain alignment, were excluded from all sequence comparisons. Pairwise evolutionary distances were estimated using Kimura's two parameter method to correct for superimposed substitutions (26). Phylogenetic trees were constructed using the neighbor-joining method (55), and the reliability of topologies was estimated by performing bootstrap analysis using 1,000 replicates (13). NJPLOT was used to draw trees for illustrations (49). Phylogenetic relationships were also determined using maximum-parsimony (with repeated randomized input orders; ten iterations) as well as maximum-likelihood approaches, implemented using the programs DNAPARS and DNAML from the PHYLIP package (14).

Complete Genome Alignment

All newly derived HIV-1 genome sequences were aligned with previously reported (45) full length representatives of HIV-1 subtype A (U445), B (LAI, RF, OYI, MN, SF2), C (C2220), D (ELI, NDK, Z2Z6), and "E" (90CF402.1, 93TH253.3, CM240) as well as SIVcpzGAB as an outgroup using the CLUSTAL W (67) profile alignment option (the alignment includes the untranslated leader sequence, gag, pol, vif, vpr, tat, rev, vpu, env, nef and available 3' LTR sequences). Sequences that needed to be excluded from any particular analysis were removed only after gap-tossing was performed on the complete alignment containing all sequences. This ensured that all positions were comparable in different runs with different sequences.

Diversity Plots

The percent diversity between selected pairs of sequences was determined by moving a window of 500 bp in 10 bp increments along the genome alignment. The divergence values for each pairwise comparison were plotted at the midpoint of the 500 bp segment.

Bootstrap Plots

Bootscanning was performed on neighbor-joining trees using SEQBOOT, DNADIST (using Kimura's correction), NEIGHBOR and CONSENSUS from the PHYLIP package (14) for a window of 500 bp moved along the alignment in increments of 10 bp. 1000 replicates were evaluated for each phylogeny. The program ANALYZE from the bootscanning package (57) was used to examine the clustering of the putative hybrid with representatives of the subtypes presumed to have been involved in the recombination event. The bootstrap values for these sequence were plotted at the midpoint of each window.

Exploratory Tree Analysis

Exploratory tree analysis was performed using the bootstrap plot approach described above, except in this case an increment of 100 bp was used and each neighbor-joining tree was viewed using DRAWTREE from the PHYLIP package (14). In addition, all full length sequences (except known recombinants) were included into the analysis.

Informative Site Analysis

To estimate the location and significance of cross-overs, each putative hybrid sequence was compared with a representative of each of the two subtypes inferred to have been involved in the recombination event, and an appropriate outgroup. Recombination breakpoints were mapped by examining the linear distribution of phylogenetically informative sites supporting the clustering of the hybrid with each of the two "parental" subtypes, essentially as described (52,53). Potential breakpoints were inserted between each pair of adjacent informative sites, and the extent of heterogeneity between the two sides of the breakpoint, with respect to numbers of the two kinds of informative site, was calculated as a 2×2 chi square value; the likely breakpoint was identified as that which gave the maximal chi-square value. Since the alignments contained more than one putative cross-over, this analysis was performed looking for one and two breakpoints at a time, and repeated on subsections of the alignment defined by breakpoints already identified. To assess the probability of obtaining (by chance) chi-square values as high as those observed, 10,000 random permutations of the informative sites were examined Nucleotide Sequence Accession Numbers GenBank accession numbers for several of the (near) full length HIV-1 proviral sequences disclosed in this application are listed in Table 2, and are hereby incorporated by reference.

EXAMPLE 2

Identification of Non-subtype B HIV-1 Viruses

Molecular Cloning of Non-subtype B HIV-1 Isolates

Of the geographically diverse HIV-1 isolates described herein, five had previously been classified as members of (group M) subtypes A (92RW009), F (92BR020, 92BR029), and G (92NG003, 92NG083) on the basis of env (17,19) and/or gag sequences (1). One (90CF056) was chosen because it originated from a major epicenter of the African AIDS epidemic. In addition, 90CF056 was of interest because it did not fall into any known subtype at the time of its first genetic characterization (43). Isolates from Zambia (96ZM651 and 96ZM751) and India (94IN476) were chosen because of the known subtype C prevalence in those countries. The two isolates from Cyprus (94CY017 and 94CY032) were selected because of the extensive diversity of HIV-1 in the drug user population (29). Table 1 summarizes available demographic and clinical information, as well as biological data concerning the isolate phenotype (SI/NSI). Only viruses grown in normal donor PBMCs were selected for analysis.

TABLE 1

Epidemiological and clinical information for study isolates

| Isolate[a] | Sex[b] | Age | City | Country | Risk factor[c] | Disease status[d] | Antiviral therapy | Year of isolation | Source[e] | Biological phenotype[f] | Preliminary subtype assignment | Refs. |
|---|---|---|---|---|---|---|---|---|---|---|---|---|
| 94CY017.41 | F | 35 | Nicosia | Cyprus | Het | SM | n/a | 1994 | ADARC | n/a | A/? | 29 |
| 94CY032.3 | M | 35 | Nicosia | Cyprus | Het | AS | n/a | 1994 | ADARC | n/a | G/A/I | 29 |
| 96ZM651.8 | M | 47 | Lusaka | Zambia | Het | SM | n/a | 1996 | UAB | n/a | n/a | n/a |
| 96ZM751.3 | M | 26 | Lusaka | Zambia | Het | SM | No | 1996 | UAB | n/a | n/a | n/a |
| 94IN476.104 | F | n/a | Pune | India | n/a | n/a | No | 1994 | ADARC | n/a | n/a | n/a |
| 93BR020 | M | 52 | Rio de Janeiro | Brazil | Bi | AS | No | 1993 | WHO | SI | F | 19, 72 |

TABLE 1-continued

Epidemiological and clinical information for study isolates

| Isolate[a] | Sex[b] | Age | City | Country | Risk factor[c] | Disease status[d] | Antiviral therapy | Year of isolation | Source[e] | Biological phenotype[f] | Preliminary subtype assignment | Refs. |
|---|---|---|---|---|---|---|---|---|---|---|---|---|
| 90CF056 (U4056) | M | n/a | Bangui | CAR | Het | AS | No | 1990 | PIB | NSI | U | 43 |
| 92RW009 | F | 24 | Kigali | Rwanda | Het | AS | No | 1992 | WHO | NSI | A[h] | 17, 72 |
| 93BR029 | M | 17 | Sao Paulo | Brazil | n/a | AS | No | 1993 | WHO | NSI | F[h] | 19, 72 |
| 92NG083 (JV1083) | F | 27 | Jos | Nigeria | n/a | AIDS | No | 1992 | IHV | NSI | G[h] | 1 |
| 92NG003 (G3) | F | 24 | Jos | Nigeria | Het | AS | n/a | 1992 | IHV | NSI | G[h] | 1 |

[a]Isolates were named according to WHO nomenclature (previous designations are listed in parentheses).
[b]M, male; F, female.
[c]Het, heterosexual contact; Bi, bisexual contact; Hemo, hemophiliac patient.
[d]AS, asymptomatic; SM, symptomatic.
[e]TJU, Thomas Jefferson University, Philadelphia, PA; PIB, Pasteur Institute, Bangui, CAR; IHV, Institute of Human Virology, Baltimore, MD; WHO, World Health Organization, Geneva, Switzerland; UAB, University of Alabama.
[f]Determined in MT-2 assay as described (72); NSI, non-syncytium inducing; SI, synctium inducing.
[g]n/a, information not available.
[h]Isolates identified to be recombinant in present study.

The viral genomes were cloned by long PCR methods using primers homologous to the tRNA primer binding site (upstream primer) and the polyadenylation signal in the 3' LTR (downstream primer). This amplification strategy generated (near) full length genomes containing all coding and regulatory regions, except for 70 to 80 bps of 5' unique LTR sequences (U5). All isolates, regardless of subtype classification, yielded long PCR products with the same set of primer pairs. In some instances, genomes were amplified with primers containing Mlu1 restriction enzyme sites. This greatly facilitated subsequent subcloning into a plasmid vector (Table 2).

Sequence Analysis of (Near) Full Length HIV-1 Genomes

All eleven HIV-1 genomes were sequenced in their entirety using either shotgun sequencing or primer walking approaches. The long PCR derived clones ranged in size from 8,952 to 8,999 base pairs, and spanned the genome from the primer binding site to the R/U5 junction of the 3' LTR. Inspection of potential coding regions revealed that all clones contained the expected reading frames for gag, pol, vif, vpr, tat, rev, vpu, env and nef. In addition, all major regulatory sequences, including promotor and enhancer elements in the LTR, the packaging signal, splice sites, etc., appeared to be intact. None of the genomes had major deletions or rearrangements, although inspection of the deduced protein sequences identified inactivating mutations in seven of the eleven clones (Table 2). However, most of these were limited to point mutations in single genes and were thus amenable to repair. Only two genomes (92NG003.1 and 92NG083.2) contained stop codons, small deletions and frameshift mutations in several genes, rendering them multiply defective. Importantly, no inactivating mutations were identified in 93BR020.1 (subtype F), 90CF056.1 (subtype H), and 96ZM651.8 (subtype C), suggesting that these clones encoded biologically active genomes (Table 2). Nucleic acids containing repaired coding sequences, as well as the polypeptides encoded by the repaired coding sequences, are also considered to be a part of the invention.

TABLE 2

Inactivating mutations in near-complete HIV-1 genomes

| Clone | Defective gene(s) | Inframe stop codon[a] | Frameshift mutation[a] | Altered initiation codon[a] | Plasmid vector[d] | GenBank accession number |
|---|---|---|---|---|---|---|
| 93BR020.1 | none | — | — | — | pCR2.1 | AF005494 |
| 90CF056.1 | none | — | — | — | pCR2.1 | AF005496 |
| 92RW009.6 | gag | — | 213 | — | pTZ18 (Mlu1) | U88823 |
| 93BR029.4 | gag | — | 260,472 | — | pTZI8 (Mlu1) | AF005495 |
| 92NG083.2 | gag, vpu | 360 | 5462[b] | 157 | pTZ18 (Mlu1) | U88826 |
| 92NG003.1[c] | vpr, vpu, nef | — | 5024[b], 5485[b] | 8113 | pTZ18 (Mlu1) | U88825 |
| 96ZM651.8 | none | — | — | — | pTZ18 (Mlu1) | pending |
| 96ZM751.3 | gag/pol/env | 7567 | 1067/2688 | — | pTZ18 (Mlu1) | pending |
| 94IN476.104 | pol/vpr | 3021 | — | — | pTZI8 (Mlu1) | pending |
| 94CY032.3 | vif/env/vpr | 4518/7125 | 5199 | — | pTZ18 (Mlu1) | pending |
| 94CY017.41 | rev | — | — | 5327 | pCRII | pending |

[a]Numbers indicate the position of the inactivating mutation within the sequence.
[b]Frameshift mutations associated with more extensive nucleotide sequence deletions (10–16 bp).
[c]92NG003.1 also has a 33 bp deletion in the V3 loop region of env.
[d]Genomes were either subcloned by T/A overhang into pCRII, or via Mlu1 sites in the primer sequences into pTZ18 (Mlu1).

EXAMPLE 3

Phylogenetic Analyses in gag and env Regions

Figure 1A:
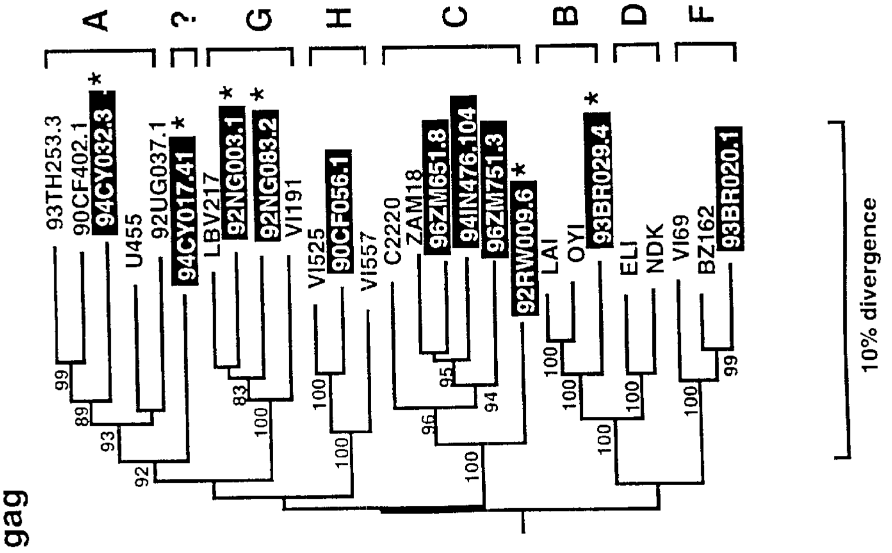

To determine the phylogenetic relationships of the viruses described herein, evolutionary trees from full length gag and env sequences were first constructed. This was done to confirm the authenticity of previously characterized strains, classify the new viruses, and compare viral branching orders in trees from two genomic regions. The results confirmed a broad subtype representation among the selected viruses (FIGS. 1A and 1B). Strains fell into six of the seven major (non-B) clades, including three for which full length sequences are not available (i.e., F, G and H). However, comparison of the gag and env topologies also identified three strains with discordant branching orders. 92RW009.6 grouped with subtype C viruses in gag, but with subtype A viruses in env. Similarly, 93BR029.4 clustered with subtype B viruses in gag, but with subtype F viruses in env. 94CY017.41 appeared to cluster within subtype A viruses in env, but fell into an unknown subtype in gag. However, characterization of the latter strain is still ongoing. These different phylogenetic positions were supported by high bootstrap values and thus indicated that these strains were intersubtype recombinants.

EXAMPLE 4

Diversity Plots

To characterize the putative recombinants as well as the other strains in regions outside gag and env, pairwise sequence comparisons with available fill length sequences from the database were performed. A multiple genome alignment was generated which included the new sequences as well as U455 (subtype A), LAI, RF, OYI, MN and SF2 (subtype B), C2220 (subtype C), ELI, NDK and Z2Z6 (subtype D), and 90CF402.1, 93TH253.3 and CM240 ("subtype E"). The percent nucleotide sequence diversity between sequence pairs was then calculated for a window of 500 bp moved in steps of 10 bp along the alignment. Importantly, distance values were calculated only after all sites with a gap in any of the sequences were removed from the alignment. This ensured that all comparisons were made across the same sites.

FIG. 2 depicts selected distance plots for the newly characterized viruses. For example in FIG. 2A, 93BR020.1 (putative subtype F) is compared to U455 (subtype A), NDK (subtype D), C2220 (subtype C) and 90CF056.1 (putative subtype H). The resulting plots all exhibit very similar diversity profiles characterized by alternating regions of sequence variability and conservation (values range from 7% divergence near the 5' and 3' ends of pol, to 30% in the segment of env encoding the V3 region). Moreover, the four plots are virtually superimposable, indicating that 92BR020.1 is roughly equidistant from U455, NDK, C2220 and 90CF056.1 over the entire length of its genome. A very similar set of distance curves was also obtained from comparisons of 94CY017.41 with 90CF056.1, 92BR025.8, 93BR020.1, U455, and NDK (FIG. 2B), and from comparisons of both 93BR020.1 and 90CF056.1 with representatives of subtype B and "E" (data not shown). These results indicating that 93BR020.1 and 90CF056.1 are equidistant from each other as well as from members of subtypes A, B, C, D and "E", together with the gag and env phylogenetic trees (FIG. 1), suggest that 93BR020.1 and 90CF056.1 represent non-recombinant members of subtypes F and H, respectively.

Figure 2A:
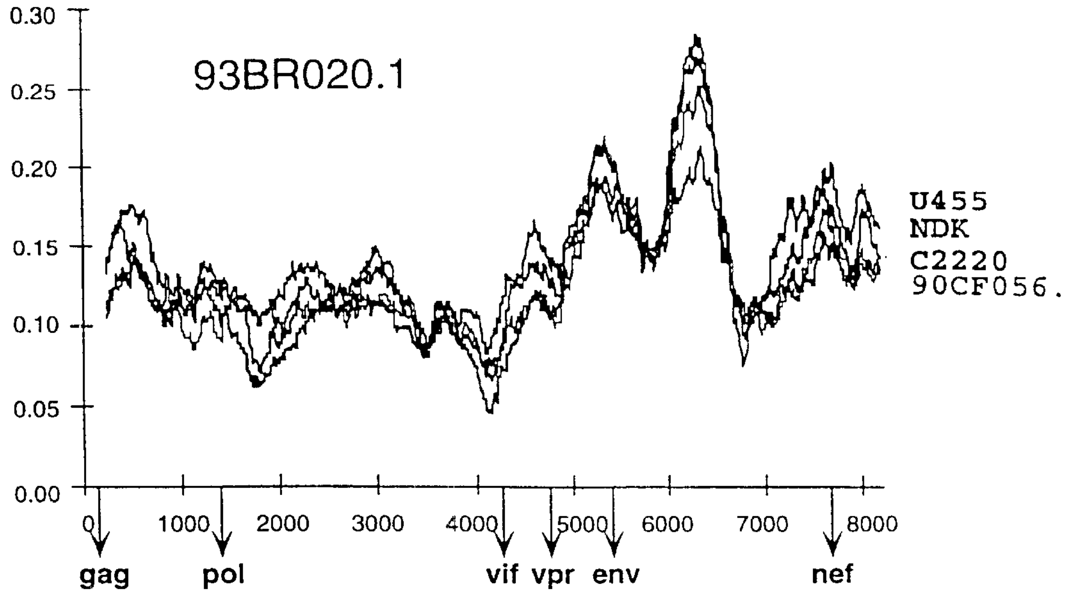
FIGS. 2A–2J. Diversity plots comparing the sequence relationships of the 11 viral genomes described in this patent application to each other and to reference sequences from the database. In each of FIGS. 2A–2J, the sequence named above the plots is compared to the sequences listed at the right. U455, LAI, C2220, and NDK are published reference sequences for subtypes A, B, C and D, respectively. Distance values were calculated for a window of 500 bp moved in steps of 10 nucleotides. The x-axis indicates the nucleotide positions along the alignment (gaps were stripped and removed from the alignment). The positions of the start codons of the gag, pol, vif vpr, env, and nef genes are shown. The y-axis denotes the distance between the viruses compared (0.05=5% divergence).
Figure 2B:
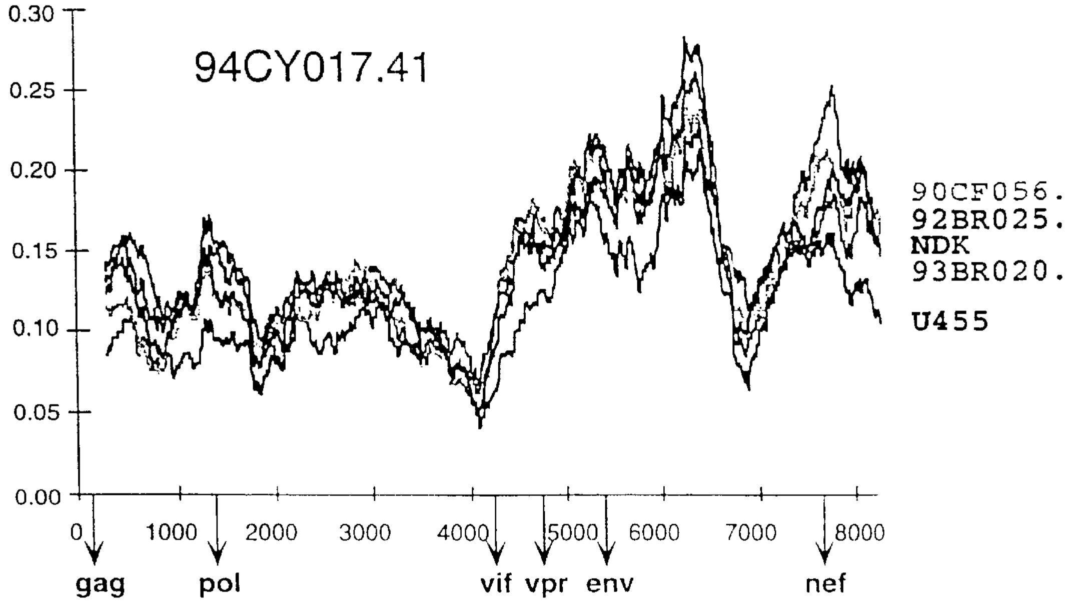
Figure 2C:
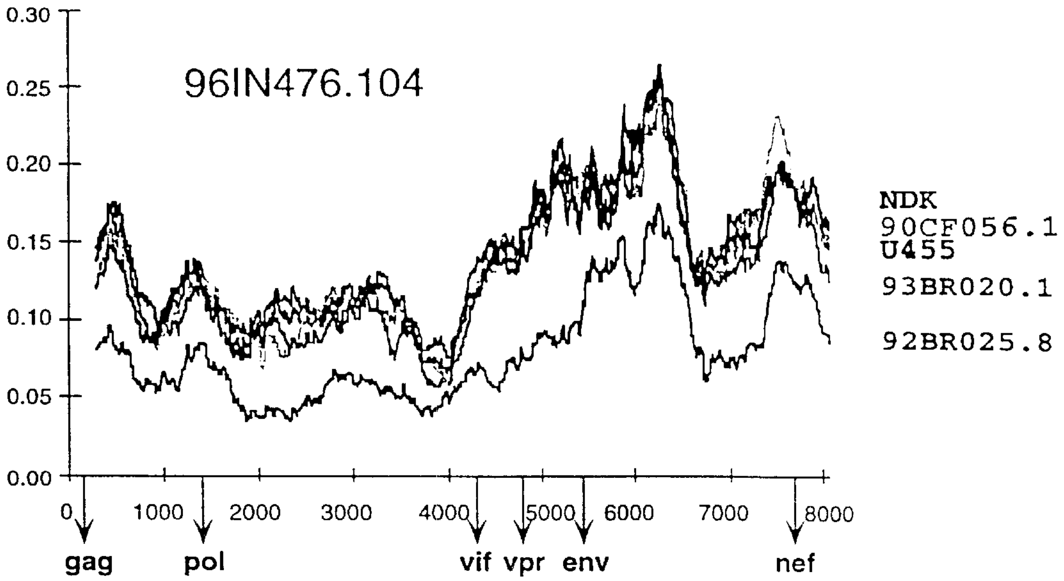
Figure 2D:
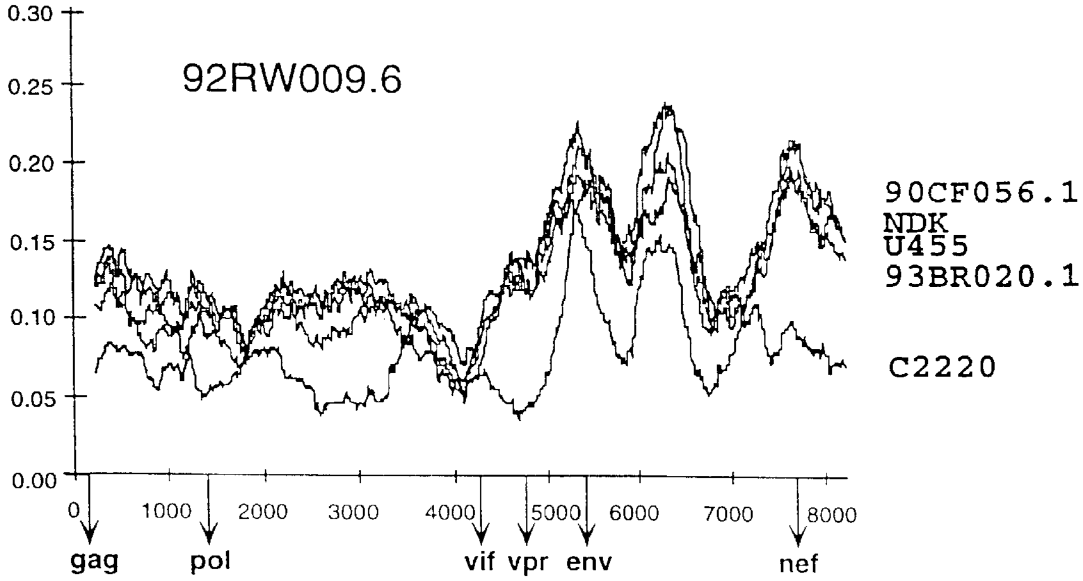
Figure 2E:
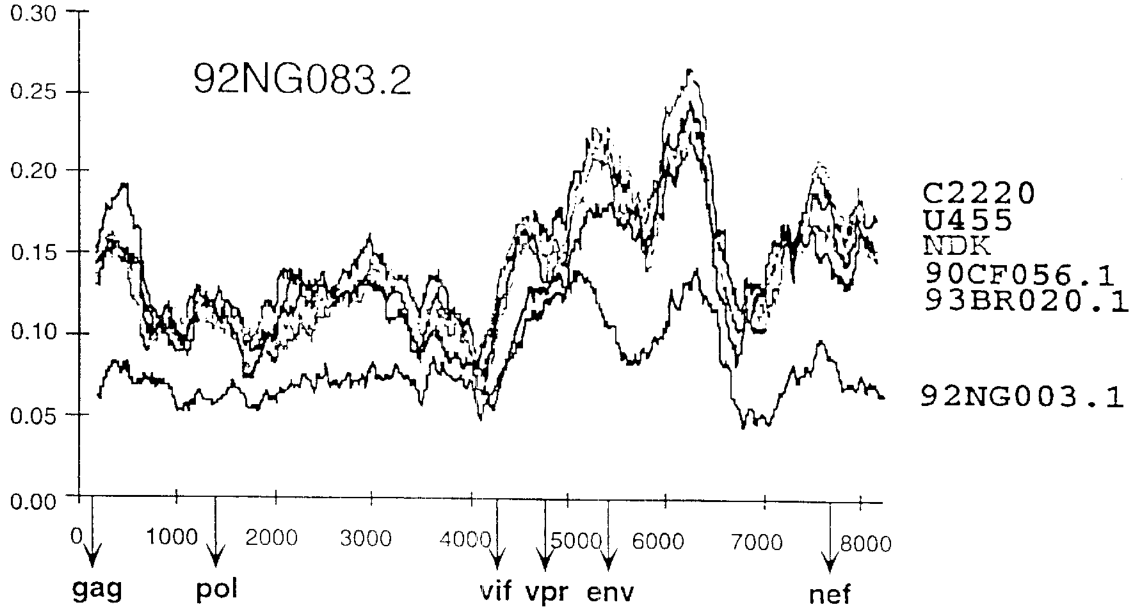
Figure 2F:
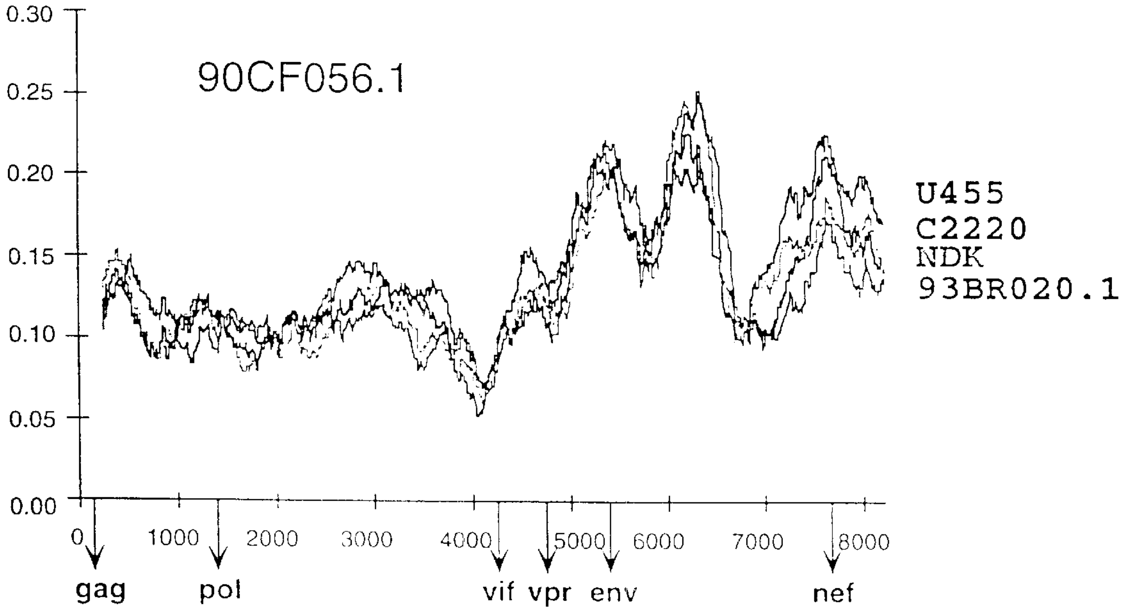
Figure 2G:
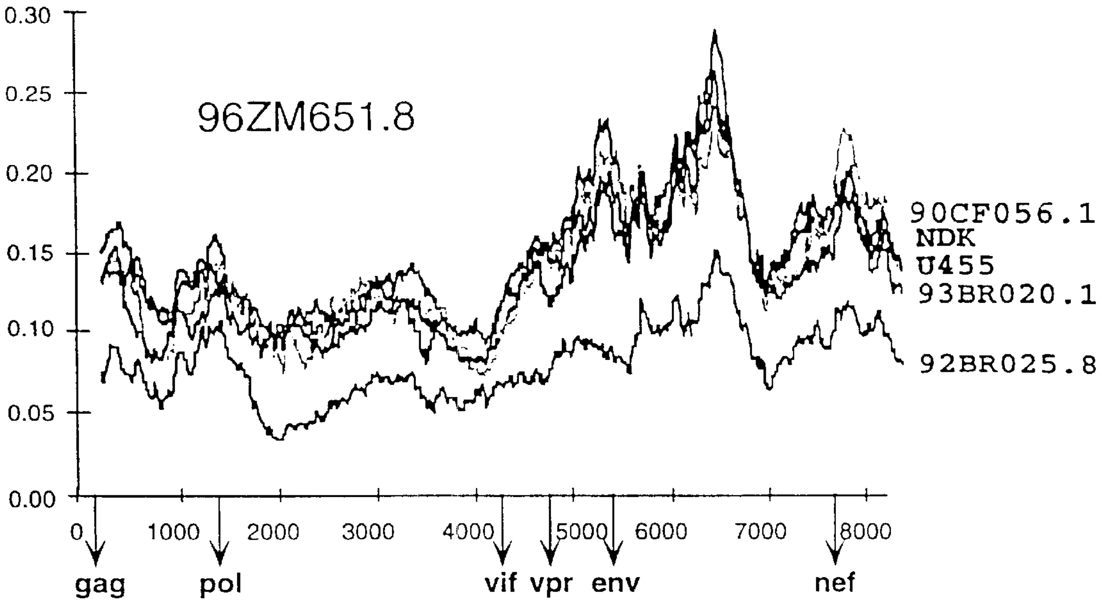
Figure 2H:
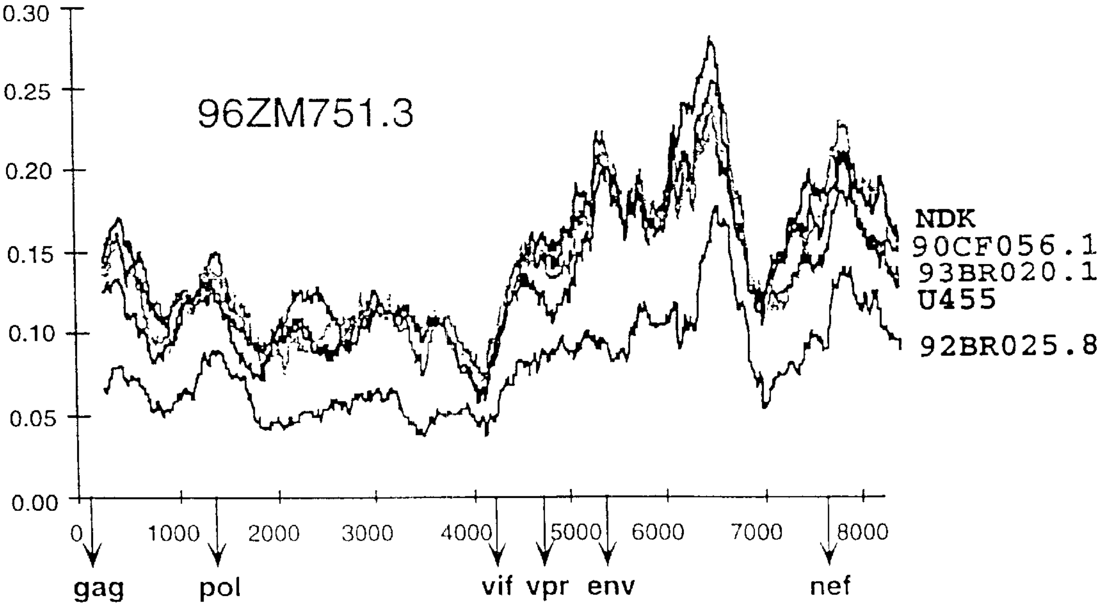
Figure 2I:
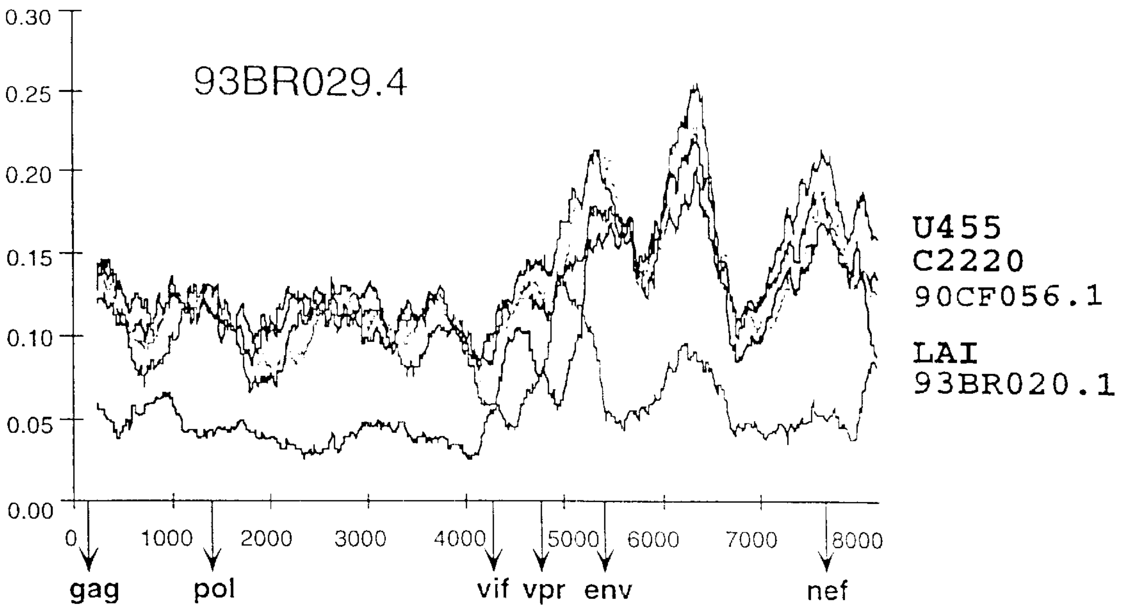
Figure 2J:
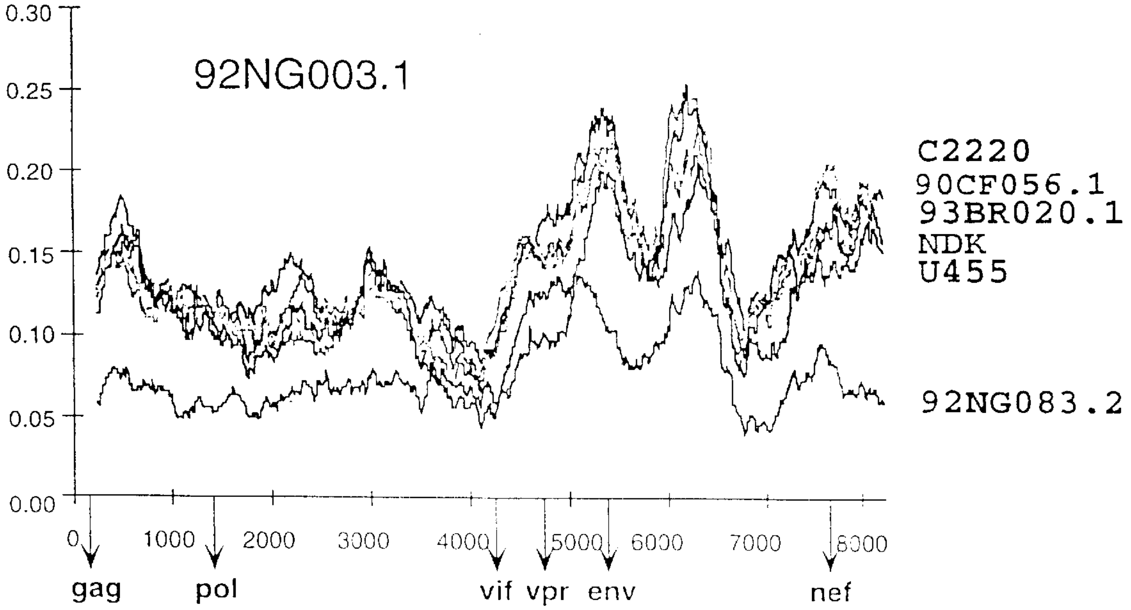
Figure 3A:
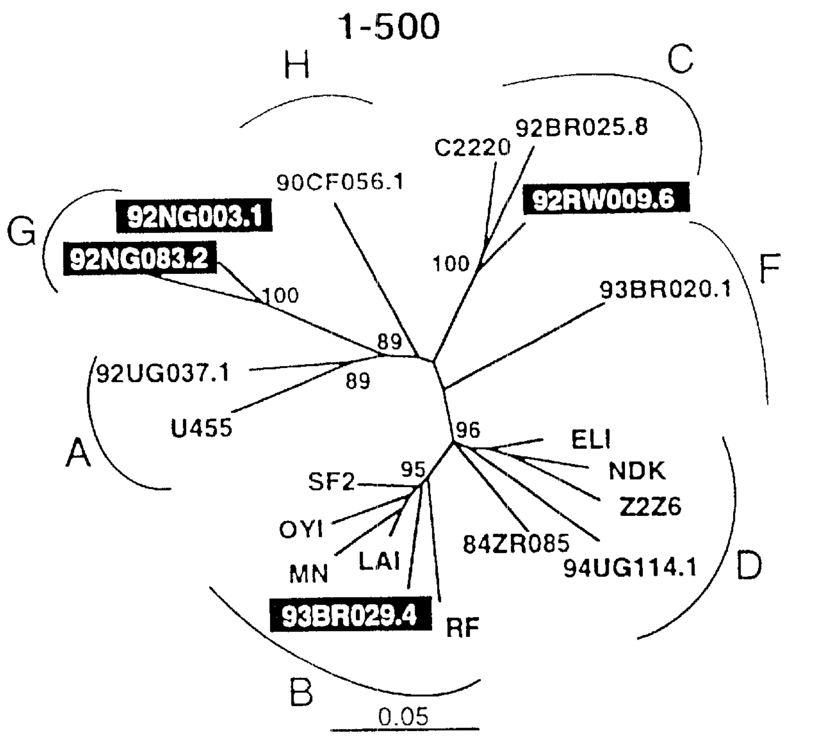
FIGS. 3A–3I. Exploratory tree analysis. Neighbor joining trees were constructed for a 500 bp window moved in increments of 100 bp along the multiple genome alignment. Trees depicting discordant branching orders among four of the 11 sequences included in this patent application are shown in FIGS. 3A–3I (hybrid sequences are boxed). The position of each tree in the alignment is indicated; subtypes are identified by brackets. Numbers at nodes indicate the percentage of bootstrap values with which the adjacent cluster is supported (only values above 80% are shown). Branch lengths are drawn to scale.
Figure 3B:
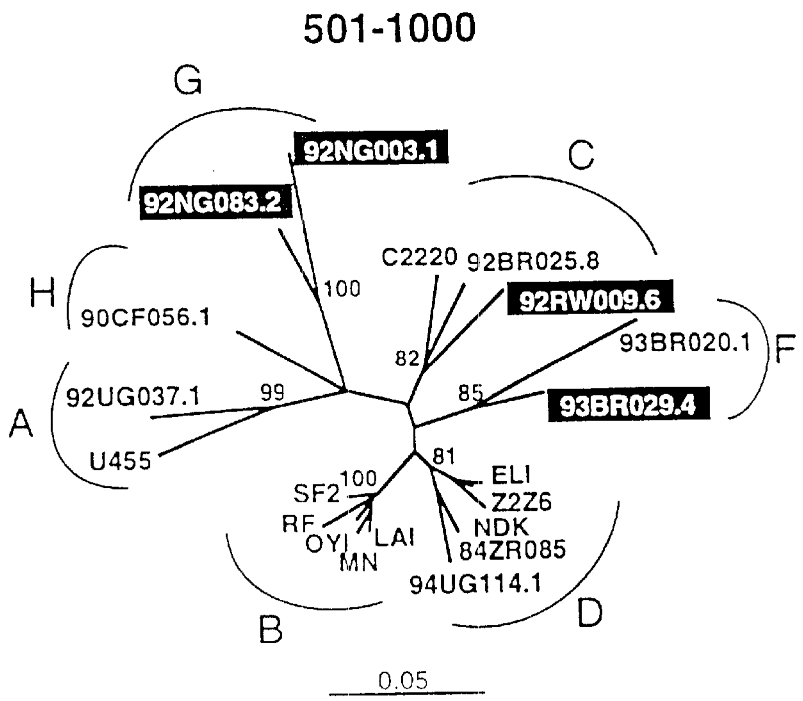
Figure 3C:
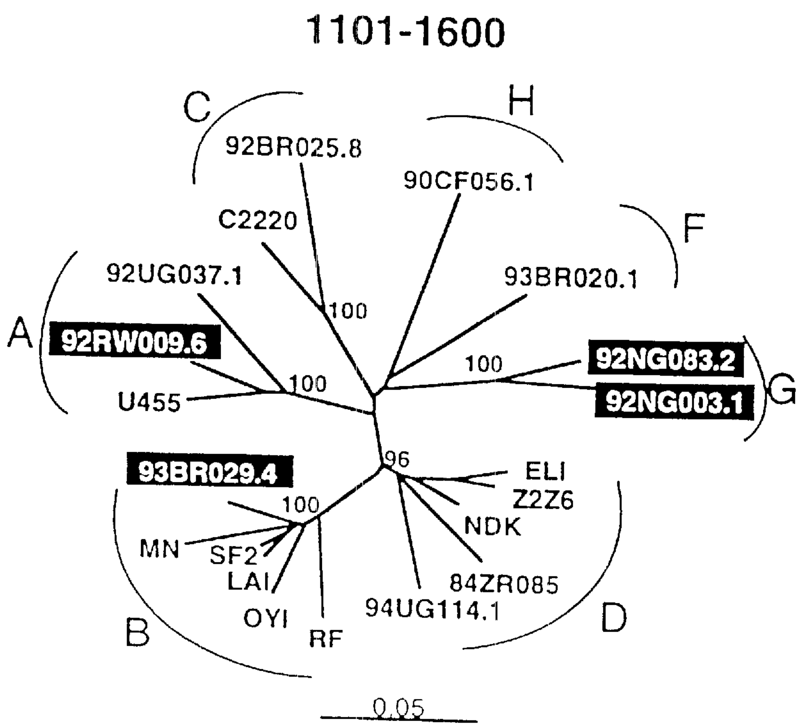
Figure 3D:
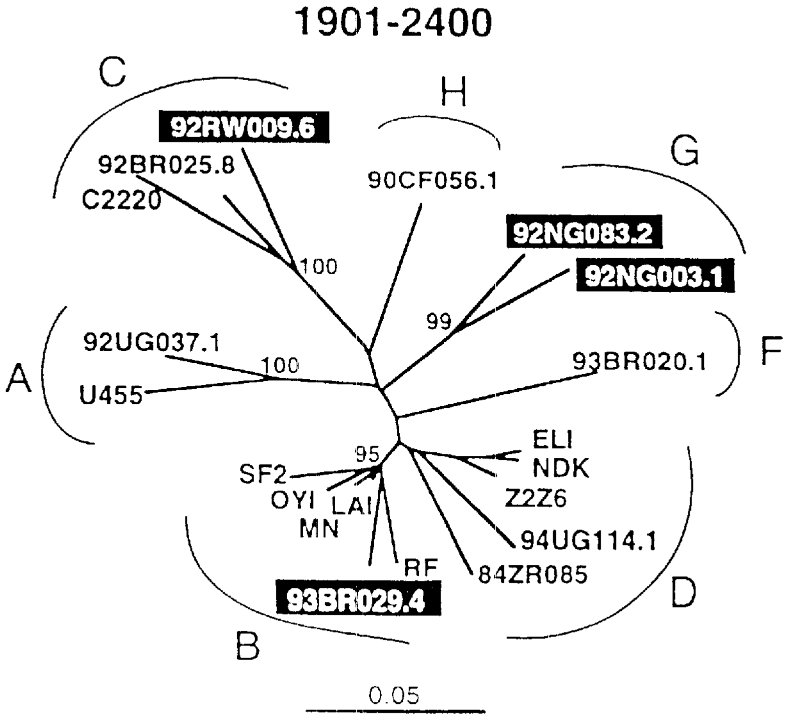
Figure 3E:
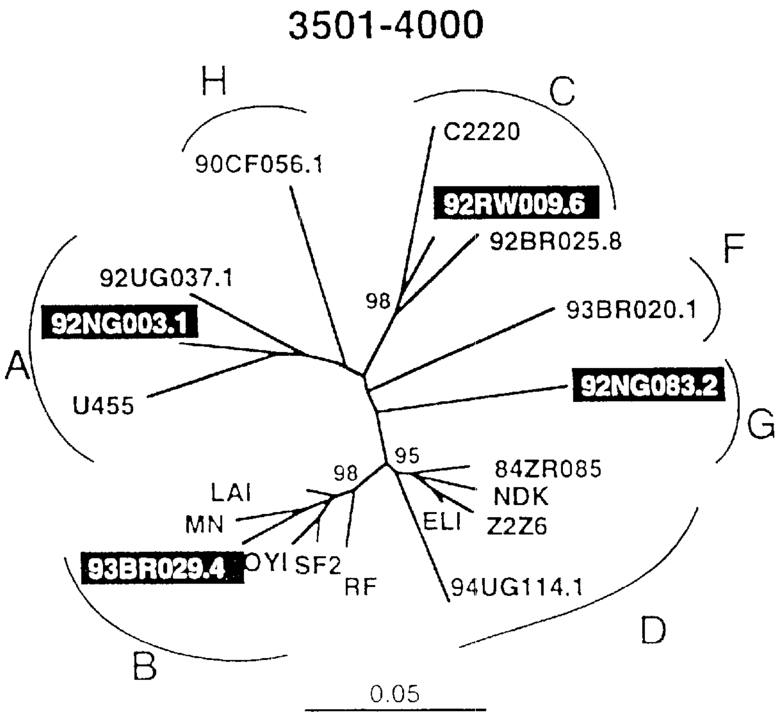
Figure 3F:
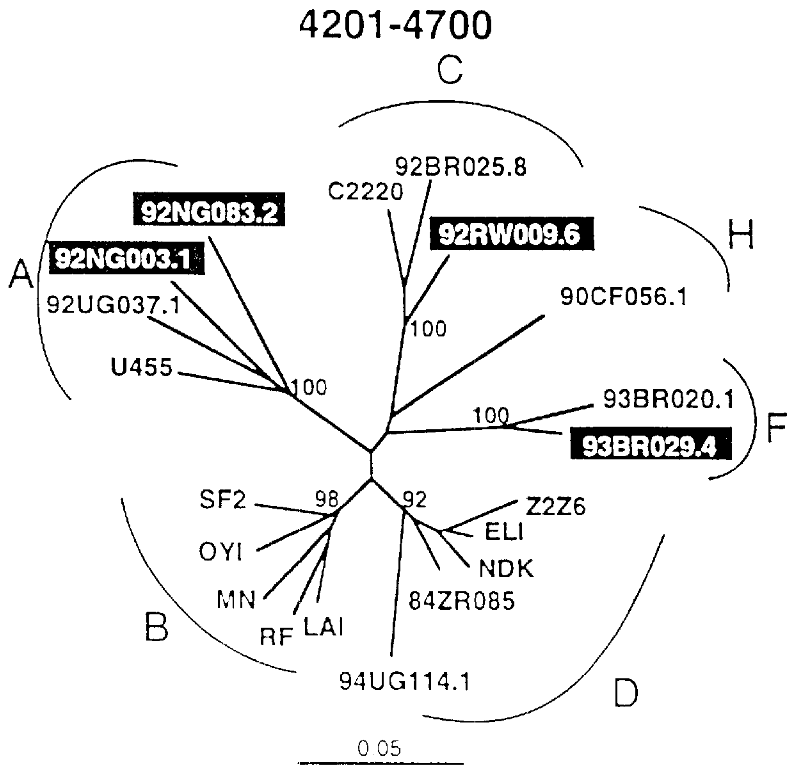
Figure 3G:
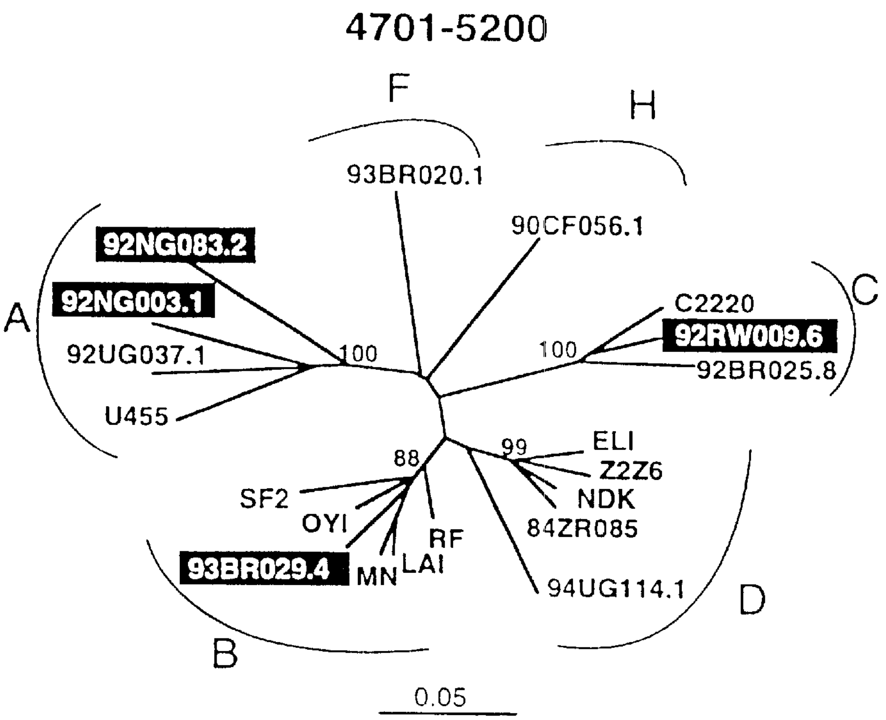
Figure 3H:
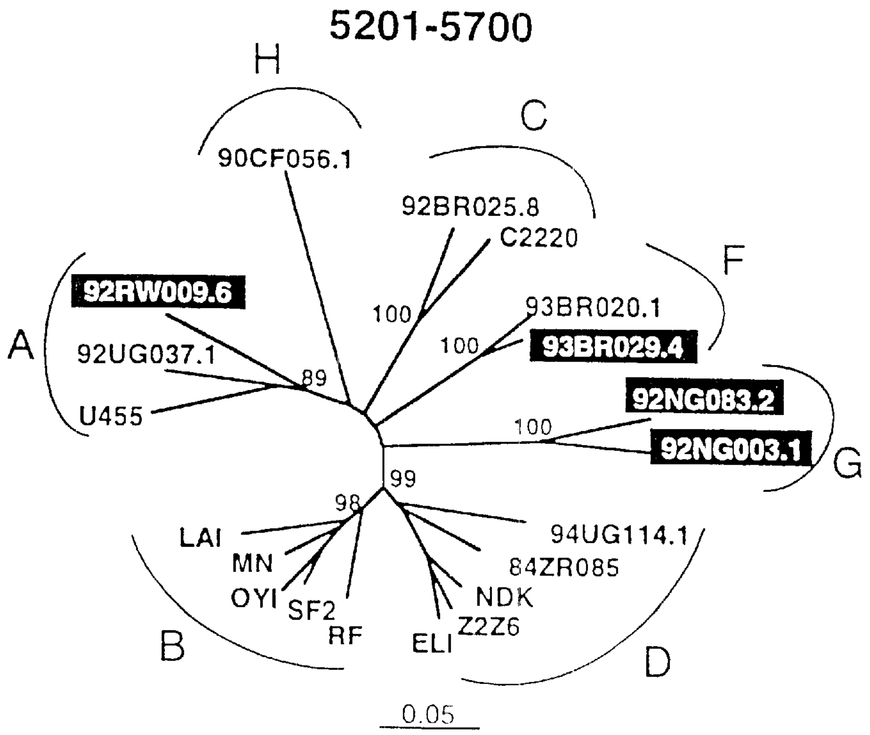
Figure 3I:
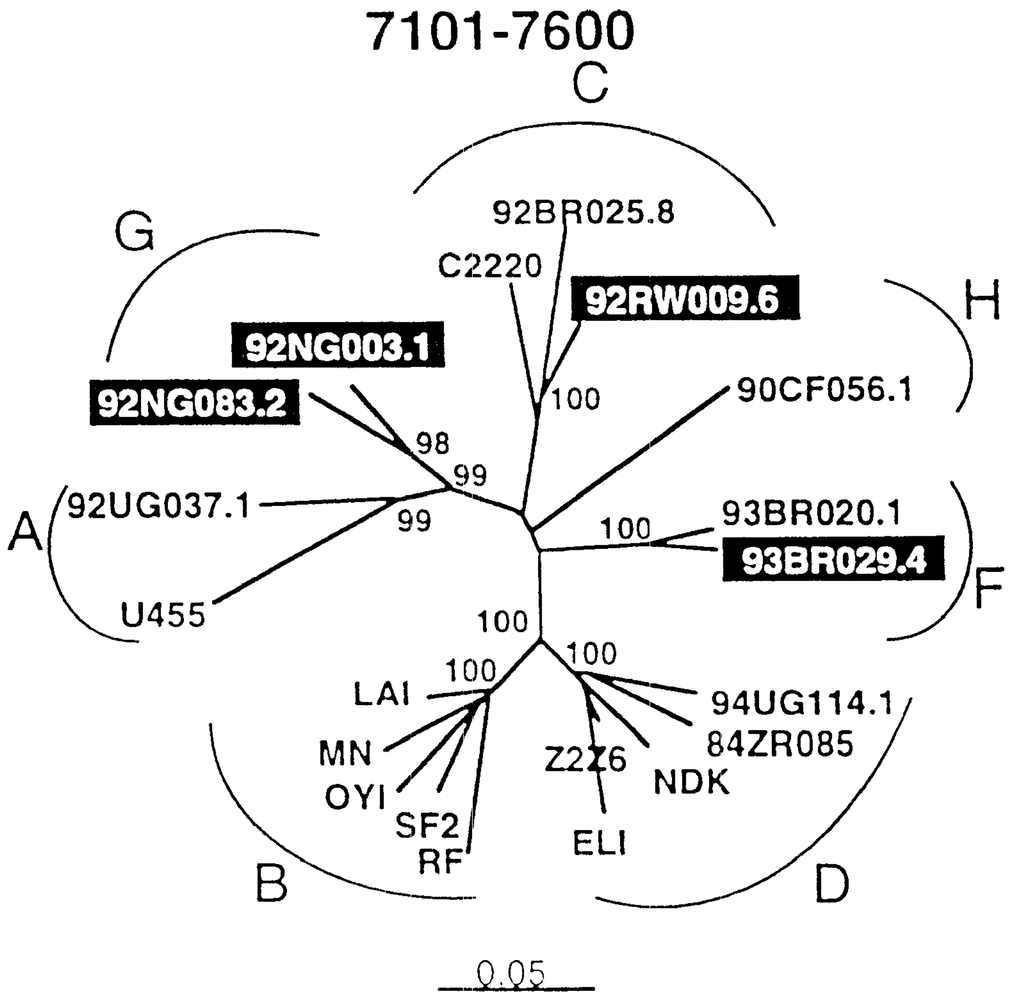

Very similar data were also obtained when 90CF056.1 was subjected to diversity plot analysis using the same set of reference sequences (FIG. 2F). Again, distance curves exhibited very similar profiles indicating approximate equidistance among the strains analyzed, except when viruses from the same subtype were compared. For example, in FIG. 2C distances between 94IN476.104 (putative subtype C) and U455, 93BR020.1, 90CF056.1, NDK and 92BR025.8, respectively, are depicted. As expected, the 92BR025.8 (putative subtype C) plot falls clearly below all others, indicating the lower level of sequence divergence between viruses from the same subtype (ranging from about 4% in pol to about 17% in env). Importantly, however, inter- and intra- diversity plots follow each other very closely, i.e., the same genomic regions exhibit proportionally higher and lower levels of divergence. See also the diversity plot analysis for 92ZM651.8 (FIG. 2G) and 96ZM751.3 (FIG. 2H). Thus, both at the level of inter- and intra-subtype comparisons, there was no evidence of mosaicism in the genomes of these three viruses. Together with the results in FIG. 1, this suggests that strains 94IN476.104, 96ZM651.8 and 96ZM751.3 represent non-mosaic members of subtype C.

By contrast, the diversity plots of the putative recombinants 92RW009.6 (FIG. 2D) and 93BR029.4 (FIG. 2I) exhibited disproportionate levels of sequence divergence from different subtypes along their genome, consistent with their discordant branching orders in gag and env trees. As shown in FIG. 2D, 92RW009.6 is most similar to the subtype C strain C2220 in the 5' half of gag, most of pol, vif, vpr, as well as nef (the C2220 curve falls below all others). However, in the 3' end of gag, the 5' end of pol, and most of env, 92RW009.6 is most similar to the subtype A strain U455 (the U455 curve falls below all others). Similarly in FIG. 2I, 93BR029.4 is most similar to the subtype B strain LAI in gag, pol and vpr, while it is most similar to the putative subtype F strain 93BR020.1 in vif, env and nef regions. In each case, the magnitude of the difference between the new sequence and the most similar subtype was no greater than the diversity seen within subtypes. Thus, these data suggest that 92RW009.6 and 93BR029.1 represent mosaics, comprised of subtypes A/C and B/F, respectively. In each case, the plots suggested several (at least four) cross-overs; these are the minimum number of recombination breakpoints, since the window size used makes it unlikely that recombinant regions shorter than 500 bp would be detected.

Finally, inspection of the diversity plots for 92NG003.1 (FIG. 2J) and 92NG083.2 (FIG. 2E) also revealed disproportionate levels of sequence variation, although not as pronounced as for 92RW009.6 and 93BR029.4. Isolates 92NG003.1 and 92NG083.2 are equidistant from members of subtypes A–F and H for the most part of their genome, suggesting that they represent an independent subtype, i.e., subtype G. However, in the vif/vpr region the U455 distance plot falls below all others, suggesting a disproportionately closer relationship to subtype A. Assuming that U455 is non-mosaic, these results suggest that both 92NG003.1 and 92NG083.2 contain short fragments of subtype A sequence in the central region of their genome.

EXAMPLE 5

Exploratory Tree Analyses

To examine the phylogenetic position of the newly derived strains relative to each other and to the reference sequences over the entire genome, exploratory tree analyses were performed using the same multiple genome alignment generated for the diversity plots (FIGS. 3A–3I). A total of 79 trees were constructed for overlapping fragments of 500 bp, moved in 100 bp increments along the alignment. As expected, four genomes were identified that clustered in different subtypes in different parts of their genome. These included 93BR029.4 which alternated between subtypes F and B, 92RW009.6 which alternated between subtypes A and C, and 92NG083.2 and 92NG003.1 which grouped either independently or within subtype A. Interestingly, the latter two strains exhibited distinct patterns of mosaicism. In trees spanning the region 3501–4000, 92NG003.1 clustered within subtype A, while 92NG083.2 clustered independently, presumably representing subtype G. In contrast to these strains, there was no evidence for a hybrid genome structure in 94IN476.104, 96ZM651.8, 96ZM751.3, 93BR020.1 or 90CF056.1. These viruses branched consistently in all regions analyzed. Based on these findings and the results from the diversity plots, it appeared that five of the eleven selected HIV-1 strains represent non-recombinant reference strains for subtypes C (94IN476.104, 96ZM651.8, 96ZM751.3), F (93BR020.1) and H (90CF056.1), respectively, while at least five are intersubtype recombinants. CY017.41 may be recombinant, but work is in progress in this regard.

EXAMPLE 6

Recombination Breakpoint Analysis

Figure 4A:
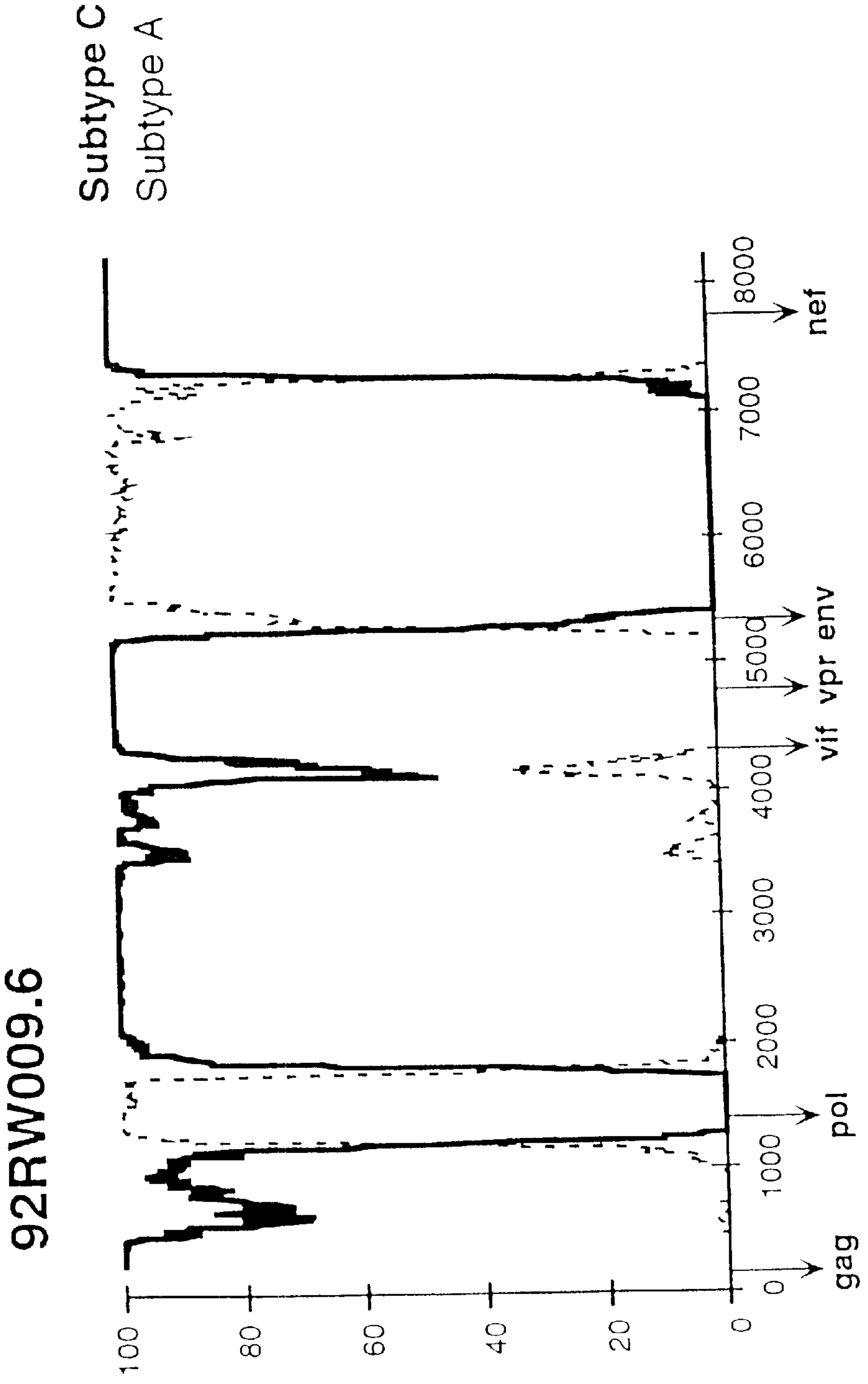
FIGS. 4A and 4B. Recombination breakpoint analysis for 92RW009.6 and 93BR029.4.
Figure 4B:
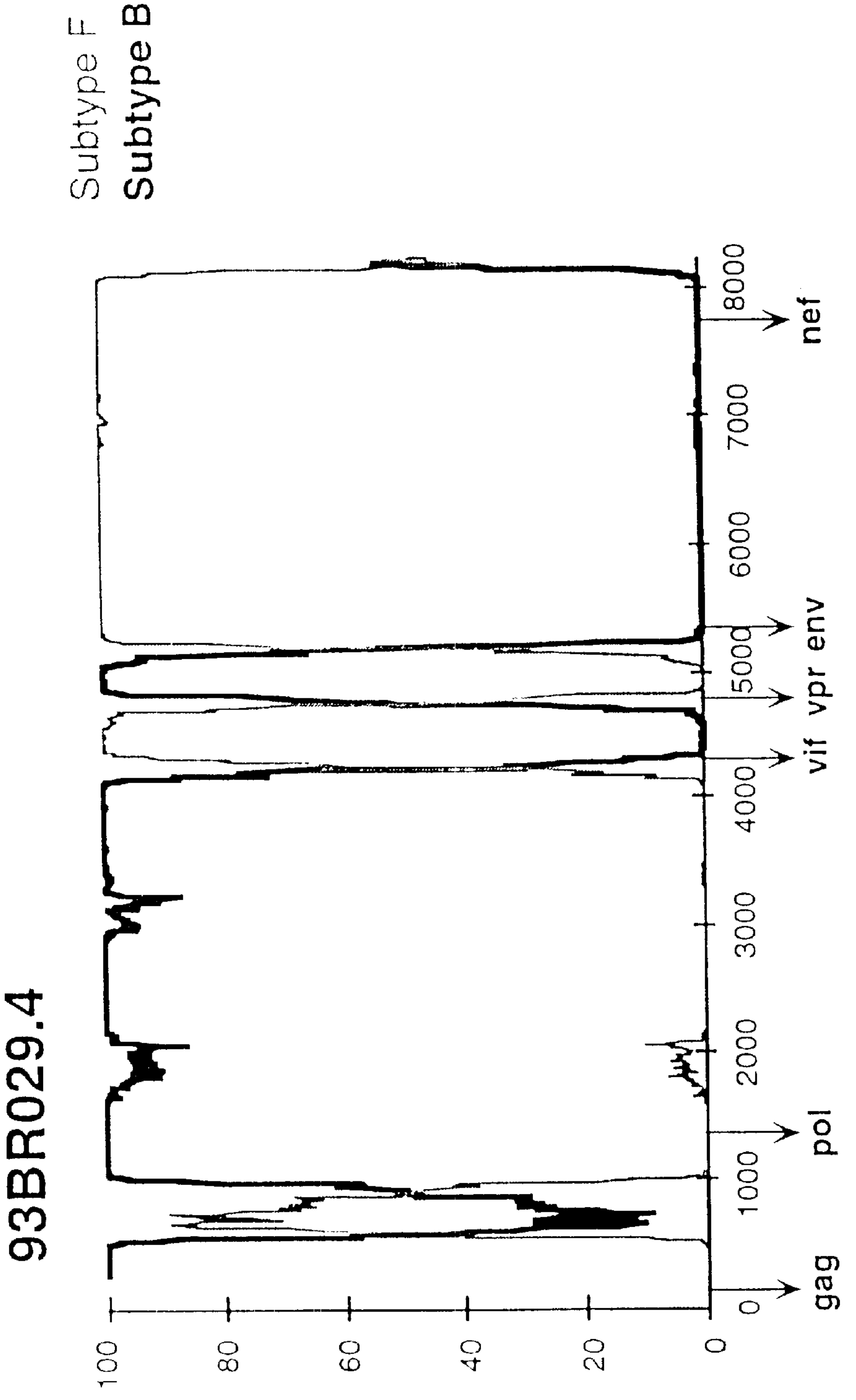
Figure 5B:
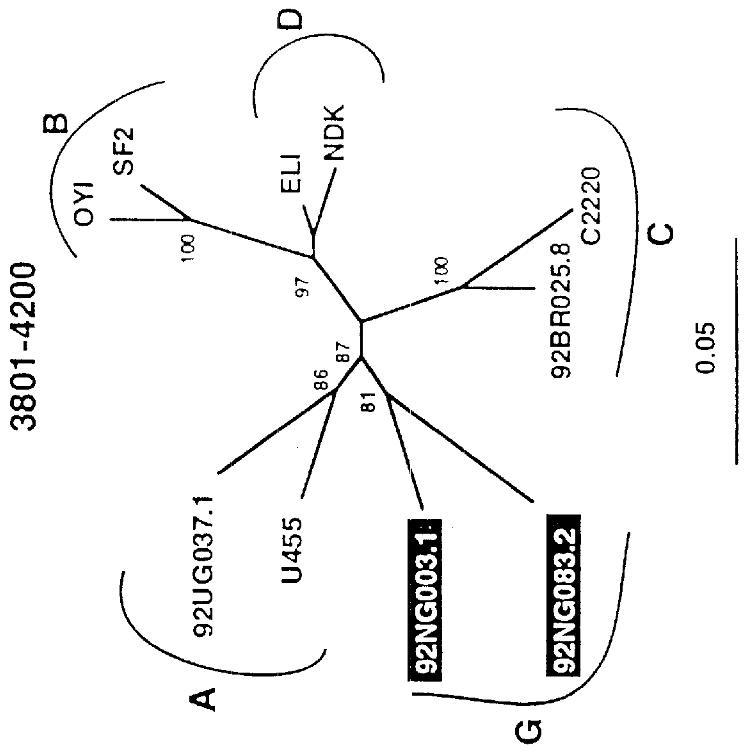
FIGS. 5A–5D. Recombination breakpoint analysis of 92NG083.2 and 92NG003.1. Neighbor joining trees depicting discordant branching orders of 92NG003.1 and 92NG083.2 in regions delineated by breakpoints identified by distance plots (not shown) are shown in FIGS. 5A–5D (hybrid sequences are boxed). The position of each tree in the alignment is indicated; subtypes are identified by brackets. Numbers at nodes indicate the percentage of bootstrap values with which the adjacent cluster is supported (only values above 80% are shown). Branch lengths are drawn to scale.
Figure 5A:
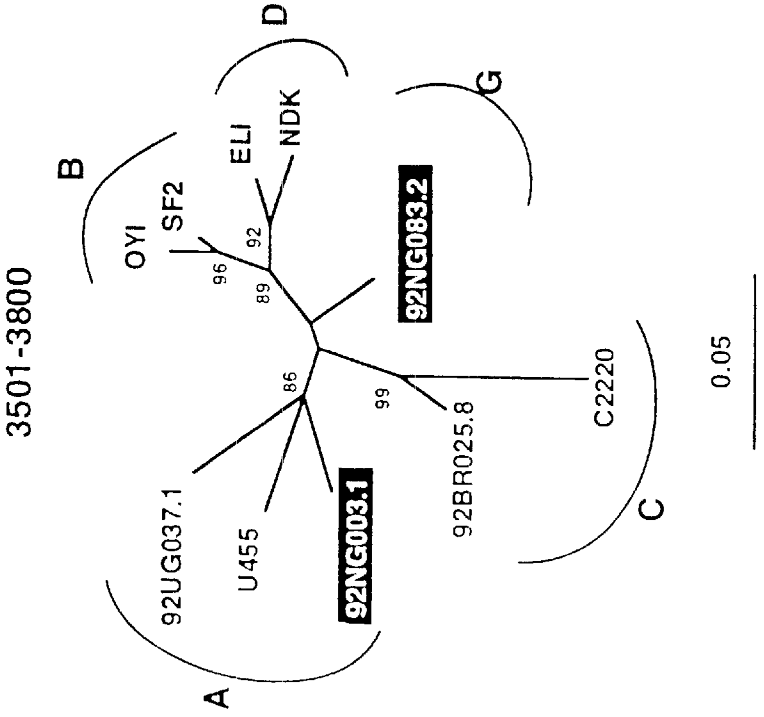
Figure 5D:
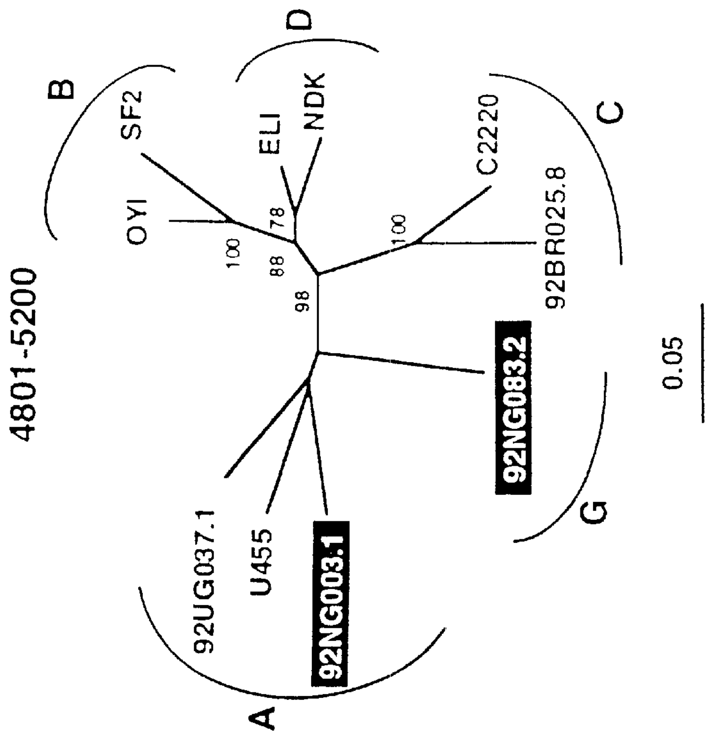
Figure 5C:
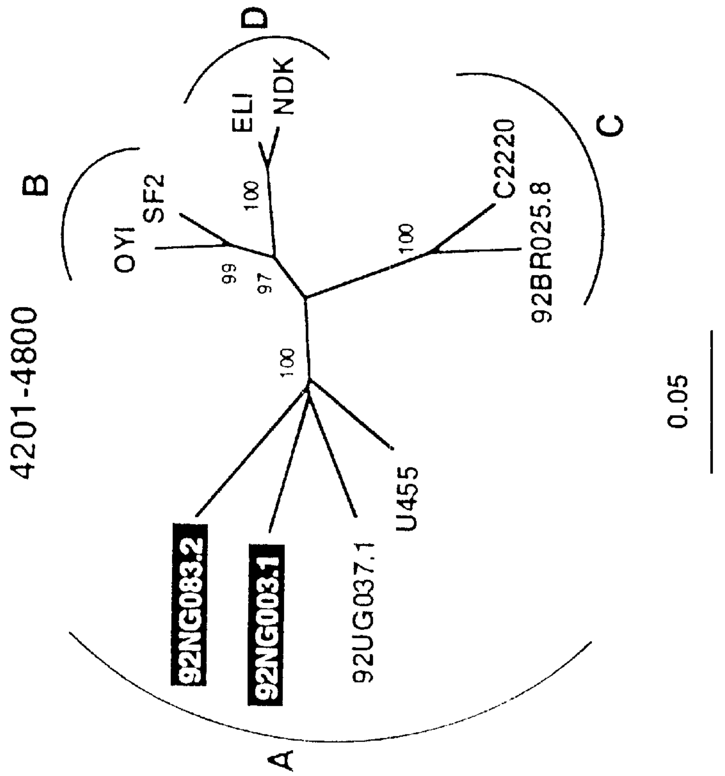

To map the location of the recombination breakpoints in 92RW009.6 and 93BR029.4, bootstrap plots and informative site analyses were used (18,52,53). Unrooted trees were constructed which included U455, 92UG037.1, LAI, MN, OYI, SF2, RF, C2220, 92BR025.1, NDK, ELI, Z2Z6, 93BR020.1 and 90CF056.1; then the magnitude of the bootstrap values supporting (i) the clustering of 92RW009.6 with members of subtype A (U455, 92UG037.1) or C (2220, 92BR025.8), as well as (ii) the clustering of 93BR029.4 with members of subtype B (LAI, MN, OYI, MN, RF) or F (92BR020.1) was determined (in the latter case subtype D viruses were excluded because of their known close relationship to subtype B viruses). FIGS. 4A and 4B depict the results of 797 such phylogenetic analyses generated for each genome, performed on a window of 500 nucleotides moved in steps of 10 nucleotides. Very high bootstrap values (>80%) supporting the clustering of 92RW009.6 with subtype C were apparent in gag, the 3' two-thirds of pol, and nef. By contrast, significant branching of 92RW009.6 with subtype A was apparent in the gag/pol overlap and the env region. In a small region (4,000 to 4,200) in the middle of the genome, 92RW009.6 appeared not to cluster significantly with either subtype, but further inspection revealed that this was due to a small number of informative sites. These data thus indicated four points of recombination crossovers between subtypes A and C (FIG. 4A). A similar analysis identified six recombination breakpoints between subtypes B and F in 93BR029.4 (FIG. 4B). These included two more (in gag) than were apparent from the diversity plot analysis (compare FIGS. 2A–2J), indicating a greater sensitivity of this approach.

Figure 6:
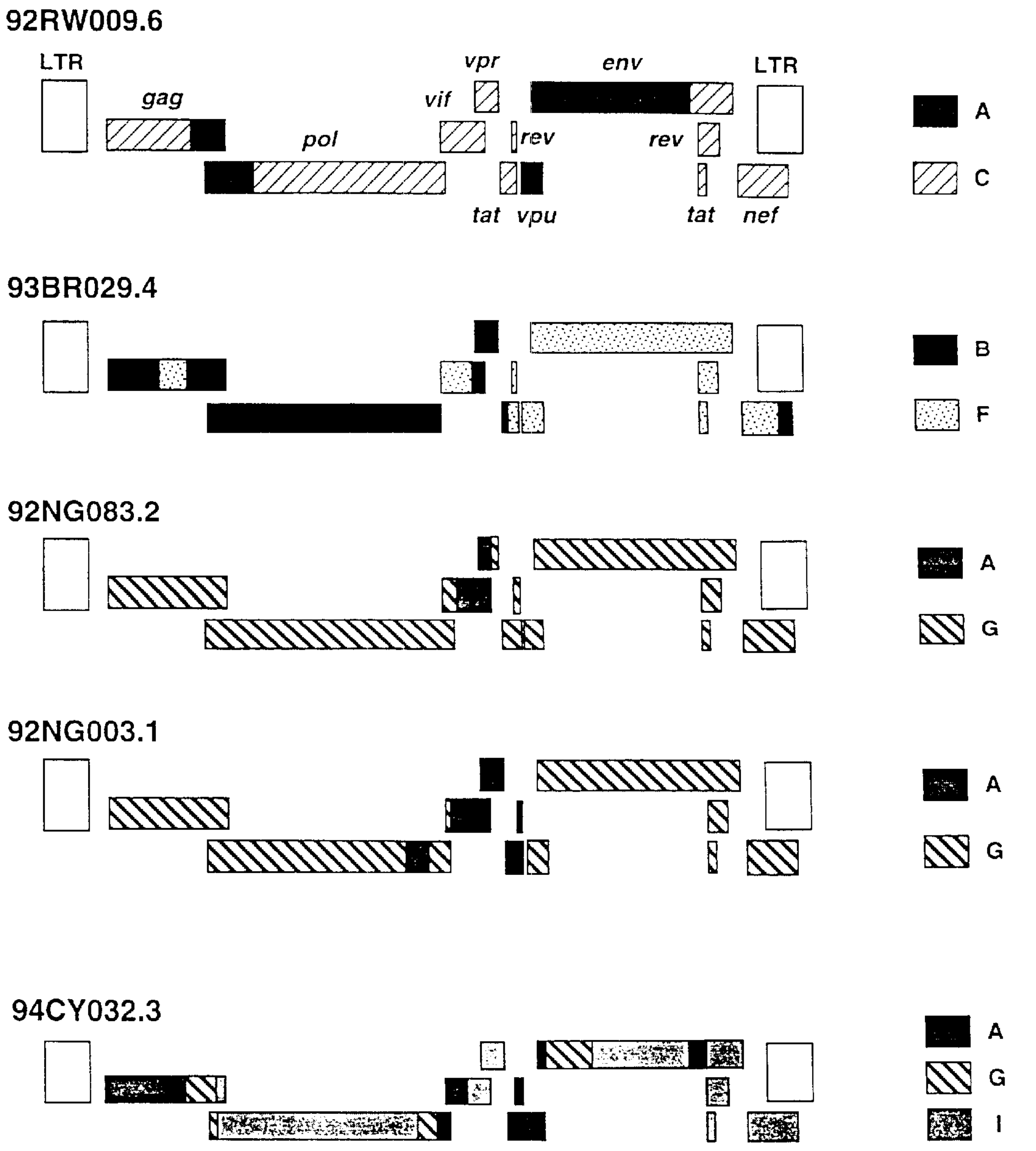
FIG. 6. Inferred structure of the five recombinant genomes included in this patent application. LTR sequences were not analyzed and are thus shown as open boxes.

To map the recombination cross-over points in 92RW009.6 and 93BR029.1 more precisely, the distribution of phylogenetically informative sites supporting alternative tree topologies were examined (52,53). Briefly, this was done in a four sequence alignment which included the query sequence, a representative of each of the two subtypes presumed to have been involved in the recombination event, and an outgroup. Breakpoints were identified by looking for statistically significant differences in the ratios of sites supporting one topology versus another. Consistent with the bootscanning data, this analysis identified four breakpoints in 92RW009.6, and six in 93BR029.4 (Table 3). A schematic representation of the mosaic genomes of 92RW009.6 and 93BR029.4 is depicted in FIG. 6.

TABLE 3

Informative site analysis of 92RW009.6 and 93BR029.4

| Clone | Region# | Sub-type | Informative Sites | | |
|---|---|---|---|---|---|
| | | | subtype A (U455) | subtype C (C2220) | outgroup (NDK) |
| 92RW009.6 | 1–1037 | C | 8 | 32 | 8 |
| | 1085–1940 | A | 17 | 5 | 4 |
| | 1986–5288 | C | 18 | 99 | 27 |
| | 5293–7238 | A | 60 | 9 | 13 |
| | 7254–8431 | C | 12 | 55 | 12 |
| | | | subtype B (LAI) | subtype F (93BR020) | outgroup (C2220) |
| 93BR029.4 | 1–735 | B | 18 | 6 | 3 |
| | 755–896 | F | 1 | 10 | 0 |
| | 930–4247 | B | 99 | 10 | 14 |
| | 4340–4668 | F | 2 | 15 | 1 |
| | 4787–5166 | B | 15 | 0 | 5 |
| | 5244–8242 | F | 15 | 139 | 13 |
| | 8250–8429 | B | 13 | 0 | 0 |

#Numbers mark positions in the four sequence alignment which includes the untranslated leader sequence (1–120), gag (121–1537), pol (1370–4340), vif (4285–4856), vpr (4799–5073), the first tat exon (5054–5271), vpu (5276–5488), env (5406–7726), nef (7727–8313) and the 3' LTR (7991–8468).
Note that position 8468 does not correspond to the end of the LTR but is the last position in the alignment after gaps have been tossed.
The 5' LTR is not included in the alignment.

Because of the lack of a full length subtype G reference sequence, recombination breakpoint analysis of 92NG003.1 and 92NG083.2 required a different approach. The analyses summarized in FIGS. 2A–2J and FIG. 3A–3I suggested that these two viruses contained subtype A sequences in the middle of their genome. To attempt to confirm this, and to define the extent of these putative subtype A fragments, a more detailed diversity plot analysis of the viral middle region (between position 3,000 and 6,000) was performed using different viral strains and varying window sizes (ranging from 200 to 400 bp) to examine the extent of sequence divergence of 92NG083.2 and 92NG003.1 from members of other subtypes, including subtype A. Diversity plots for 92NG003.1 compared to U455, C2220, NDK and 92NG083.2 and for 92NG083.2 compared to U455, C2220, NDK and 92NG003.1 depicted representative results (using a window size of 300 bp moved in steps of 10 bp along the alignment) (data not shown). Similar to the data shown in FIGS. 2A–2J, the two "subtype G" viruses are roughly equidistantly related to members of subtypes A (U455), C (C2220), and D (NDK), except for two regions in 92NG003.1 and one region in 92NG083.2 where both viruses are disproportionately more closely related to U455 than they are to each other. Noting the points at which the "G"-A distance increases or decreases relative to the others allowed the tentative identification of recombination breakpoints. For example, at position 3400, the U455 plot falls whereas the C2220, NDK and 92NG083.2 plots do not, and around site 3600 the U455 plot crosses the 92NG083.2 plot. Bearing in mind the window size of 300 nucleotides, this finding suggested that a recombination cross-over occurred around position 3500. Similar "G"-A plot crossings around positions 3800, 4200 and 5200 (in the diversity plot for 92NG003.1), and around positions 4200 and 4800 (in the diversity plot for 92NG083.2), suggested additional recombination breakpoints.

Phylogenetic trees were then constructed using the regions of sequence defined by these putative breakpoints (FIGS. 5A–5D). This analysis generally supported the conclusions drawn from the diversity plots, i.e., 92NG003.1 clustered with subtype A viruses in the region between 3501 and 3800, whereas 92NG083.2 did not; and both 92NG003.1 and 92NG083.2 clustered with subtype A viruses in the region 4201 and 4800. However, neither the diversity plot nor the tree analysis allowed the definition of the boundaries of the subtype A fragments with certainty. Nevertheless, the data indicated that (i) both 92NG083.2 and 92NG003.1 represent G/A recombinants, (ii) that they are the result of different recombination events because some of their breakpoints are clearly different, and (iii) that 92NG083.2 likely encodes a non-recombinant pol gene. A schematic representation of the mosaic genomes of 92NG083.2 and 92NG003.1 is shown in FIG. 6.

EXAMPLE 7

Subtype Specific Genome Features

Having classified the new viruses with respect to their subtype assignments, their sequences were examined for clade-specific signature sequences. Comparing deduced amino acid sequences gene by gene, several subtype specific features were found (FIGS. 7A–7D). For example, most subtype D viruses contain an in-frame stop codon in the second exon of tat, which removes 13 to 16 amino acids from the carboxy terminus of the Tat protein (FIG. 7A). Similarly, all subtype C viruses (including 94IN476.104, 96ZM651.8 and 96ZM751.3) contain a stop codon in the second exon of rev which would be predicted to shorten this protein by 16 amino acids (FIG. 7B). Subtype C viruses also contain a 15 base pair insertion at the 5' end of the vpu gene (FIG. 7C) which extends the putative membrane spanning domain of the Vpu protein by 5 amino acids (data not shown). Although these changes are unlikely to alter the function of the respective gene products in a major way (e.g., the known functional domains of both Tat and Rev proteins are not affected by these changes), it is possible that they could influence their mechanism of action in a subtle (but nevertheless biologically important) manner.

Figure 8:
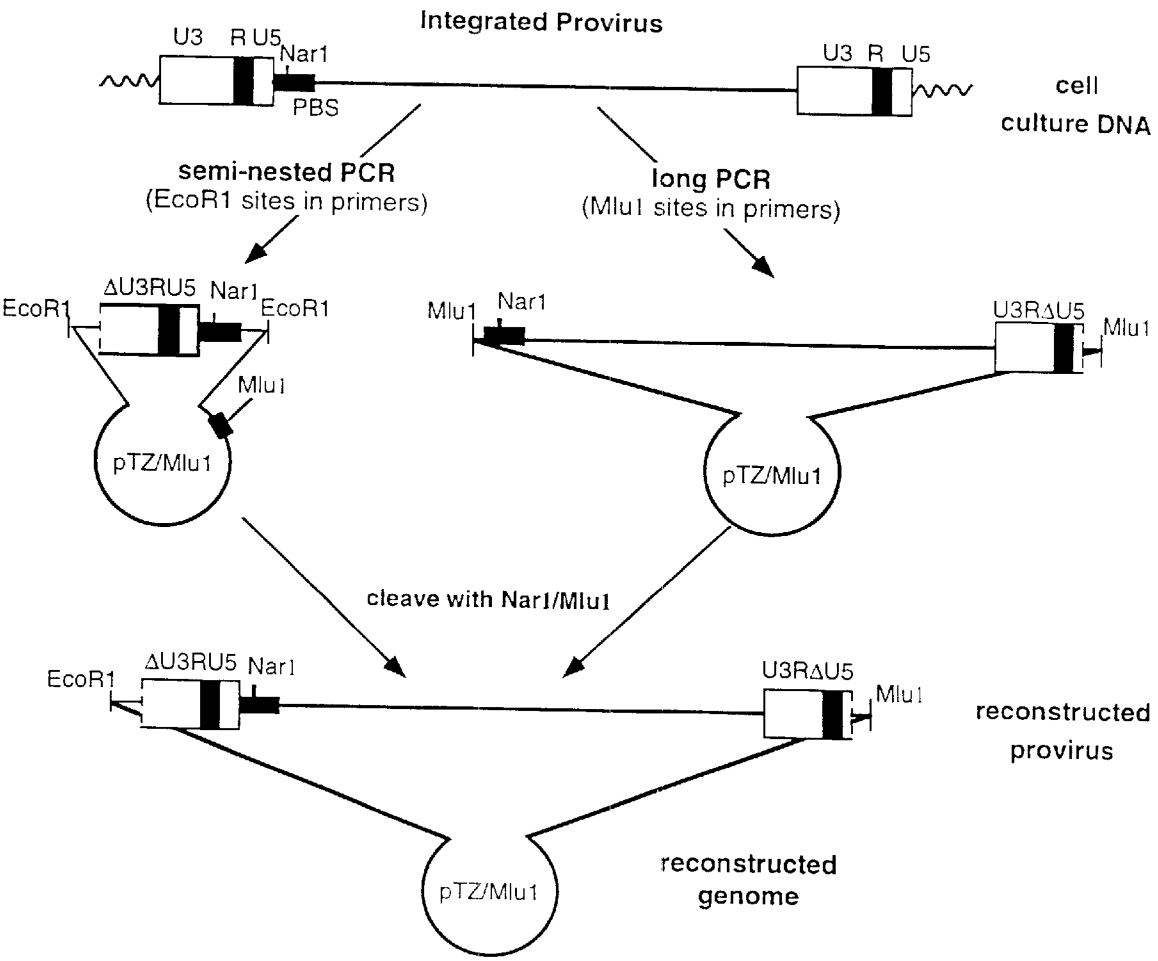
FIG. 8: Generation of replication competent proviral clones from long PCR products. The general construction scheme of a replication competent provirus from two separately amplified genomic regions is depicted.

Of the eleven non-subtype B clones identified herein, phylogenetic analysis identifies five of these viruses as non-recombinant members of subtypes C (three), F and H, which increases the number of non-subtype B reference strains available. Among these, the (near) full length genomes of 93BR020.1 and 90CF056.1 represent the first such strains for subtypes F and H, respectively. Five of the other viruses were found to represent complex mosaics of subtypes A and C, A and G (two), B and F and A, G and I. One, 94CY017.41, is not yet fully characterized. Both A/G recombinants originated from Nigeria, but must have arisen from independent recombination events since they are not closely related and differ in their patterns of mosaicism. One of these (92NG083.2) appears to contain only a single short (perhaps 600 bp) segment of subtype A origin in the vif/vpr region, and in the absence of (as yet) any full length subtype G virus, thus serves as a (non-mosaic) subtype G representative for gag, pot, env, and nef regions. Importantly, the genomes were generated in such a way that they can be tested for biological activity following a simple reconstruction step. An example of such a reconstructed genome giving rise to replication competent virus (94UG114.1) demonstrates that this approach is feasible. See "Materials and Methods," supra, and the schematic diagram in FIG. 8.

Given the apparent prevalence of mosaic viruses, it is clear that subtype specific reference strains can only be defined as such after comprehensive recombination analysis. Small subgenomic fragments or even full length gag and env sequences are not sufficient to identify all hybrid genomes. Although multiple cross-overs are a characteristic feature of retroviral recombination and have been found in many of the mosaic HIV-1 genomes examined (7,19,53,60,62), the examples of 92NG003.1 and 92NG083.2 demonstrate that cross-overs may be confined to regions outside of gag and env. Thus, elimination of the possibility that a virus is recombinant requires the determination of substantial (if not all) portions of its genome. As a consequence, subtype specific reference reagents, such as immunogens for cross-clade CTL and neutralization assays, should be derived from viral isolates for which a complete genome has been characterized.

These considerations emphasize the need for detailed analyses using reliable methods for identification of recombinant viral sequences. The above results indicate that diversity plots, depicting the distance between the query sequence and a set of reference sequences in moving windows along the genome, represent an excellent initial screening tool. The extent of sequence divergence (between any pair of viruses) varies along the genome, but since all plots are shown in the same graph, particular regions where the query sequence is anomalously highly similar to (or divergent from) other sequences can be readily identified. For example, this approach uncovered the subtype A-like regions in the middle of the putative "subtype G" genomes 92NG003.1 and 92NG083.2 (FIGS. 2J and 2E; FIG. 5). However, the results from such analyses relying only on extents of sequence divergence must be treated with some caution, because they are susceptible to variation in evolutionary rate in different lineages. Once suspicious regions have been identified, phylogenetic analyses of windows of sequence around these regions can be used to look for discordant branching orders, and to identify the subtypes likely to have been involved in the recombination event. The bootstrap value supporting the clustering of the query sequence with sequences of the supposed "parental" subtypes can be examined, again in moving windows along the genome. Finally, informative site analysis can be used to map as precisely as possible the breakpoints of the putative recombination events (52,53).

Clearly, recombination analysis relies on the availability of accurately defined non-mosaic reference sequences. Thus, location of the breakpoints in the two G/A recombinant viruses identified here must remain tentative because of the lack of such reference sequences for subtype G. The precise positions of breakpoints in the recently characterized Thai and CAR "subtype E" viruses are similarly uncertain (7,18), in this case for lack of a complete non-mosaic subtype E reference sequence. It should also be emphasized that currently designated reference sequences may require revision in the future. For example, the inadvertent inclusion of recombinant "reference" sequences in previous tree analyses (19,40) led to an incorrect subtype assignment of subtype G and "E" gp41 sequences. As more sequences become available, it is thus possible that one or more of the viral sequences currently designated as non-recombinant may be identified as a hybrid.

EXAMPLE 8

Identification of the HIV-1 Clone 94CY032.3

Full length reference clones and sequences are currently available for eight HIV-1 group M subtypes (A–H), but none have been reported for subtypes I and J, which have only been identified in a handful of individuals. Phylogenetic information for subtype I, in particular, is limited since only a very small env gene fragment (400 bp in the C2–V3 region) obtained from only two individuals (a heterosexual couple of intravenous drug users from Cyprus) has been analyzed. To characterize subtype I in greater detail, long range PCR was employed to clone a full length provirus (94CY032.3) from a short-term cultured isolate (94CY032) established from one of the two individuals originally reported to be infected with this subtype.

Using primers homolgous to the tRNA primer binding site (5'-TCTCT-acgcgtGGCGCCCGAACAGGGAC-3' (SEQ ID NO: 111), lower case letters indicate an Mlu1 site) and the polyadenylation signal in the 3' LTR (5'-ACCAGacgcgtACAACAGACGGGCACACACTACTIT-3')(SEQ ID NO: 112), long range PCR was used to amplify near full length genomic fragments, which contained all coding and regulatory regions except for 102 bp of 5' unique LTR sequences (U5)(for methodological details concerning the long range PCR approach see refs. 18, 56, 79). Amplification products were subcloned into a plasmid vector, mapped by restriction enzyme digestion, and one clone (94CY032.3) was selected for further analysis. A 694 bp fragment spanning the remainder of the LTR was amplified separately using a semi-nested approach (18).

The complete sequence of 94CY032.3 was determined using the primer walking approach [GenBank accession numbers: AF049337 (genome) and AF049338 (LTR)]. Examination of potential coding regions revealed the expected reading frames for gag, pol, vif, vpr, tat, rev, vpu, env and nef (FIG. 13). None of the genes contained major deletions, insertions or rearrangements. However, both env and vif genes contained single in-frame stop codons (FIG. 13). There was also a frameshift at position 5199 (single base pair insertion) which altered the C-terminus (last six amino acid residues) of the Vpr protein. All other protein domains of known function as well as major regulatory sequences, including the primer binding site, the packaging signal and major splice sites, appeared to be intact. Similarly, the number, position and consensus sequences of promoter and enhancer elements in the 94CY032.3 LTR were indistinguishable from those of most other HIV-1 strains, except for the presence of an unusual TATA sequence (TAAAA), thus far only found in "subtype E" (A/E) viruses from Thailand and the Central African Republic (7, 18).

To compare 94CY032.3 to previously reported subtype I sequences, a phylogenetic tree was constructed from C2–V3 sequences, including representatives of all 10 known group M subtypes (data not shown). As expected, 94CY032.3 clustered most closely with CYHO321 and CYHO322, sequences amplified from uncultured PBMC DNA of the same individual (HO32) from whom the 94CY32 isolate was derived. 94CY032.3 also clustered very closely with CYHO311, a sequence derived from the sexual partner of HO32 (29), strongly suggesting that the two infections were epidemiologically linked. Finally, as observed in the past (29), all subtype I sequences clustered independently, forming a distinct lineage roughly equidistant from all other subtypes, including subtype J (30). These findings thus confirmed the authenticity of the 94CY032.3 clone and validated it as a representative of subtype I in the C2–V3 region of the viral envelope.

To characterize the remainder of the 94CY032.3 genome, pairwise sequence comparisons were then performed with recently reported non-mosaic reference sequences for subtypes A–H (32, 79) as well as selected intersubtype recombinants (83). This approach has been useful for identifying regions of unusual sequence similarity (or dissimilarity) as an indicator of recombination (18, 79). Briefly, 94CY032.3 was added (using the profile alignment option of CLUSTAL W; 27) to a multiple genome alignment which included a total of 28 sequences from the database (81) representing subtypes A (U455, 92UG037.1), B (LAI, RF, OYI, MN and SF2), C (C2220, 92BR025.8), D (NDK, Z2Z3, ELI, 84ZR085.1, 94UG114.1), F (93BR020.1), and H (90CF056.1) as well as A/C (ZAMI 84, 92RW009.6), A/G (92NG083.2, 92NG003.1, Z321, IBNG), A/D (MAL), and A/E (93TH253.3, CM240, 90CF402.1) and B/F (93BR029.4) recombinants (SIVcpzGAB was included as an outgroup). All sites with a gap in any of the sequences were removed from the alignment to ensure that all comparisons were made across the same sites. The percent nucleotide sequence diversity between 94CY032.3 and selected other viruses was then calculated for sequence pairs by moving a window of 400 bp in steps of 10 bp along the genome.

Figure 9:
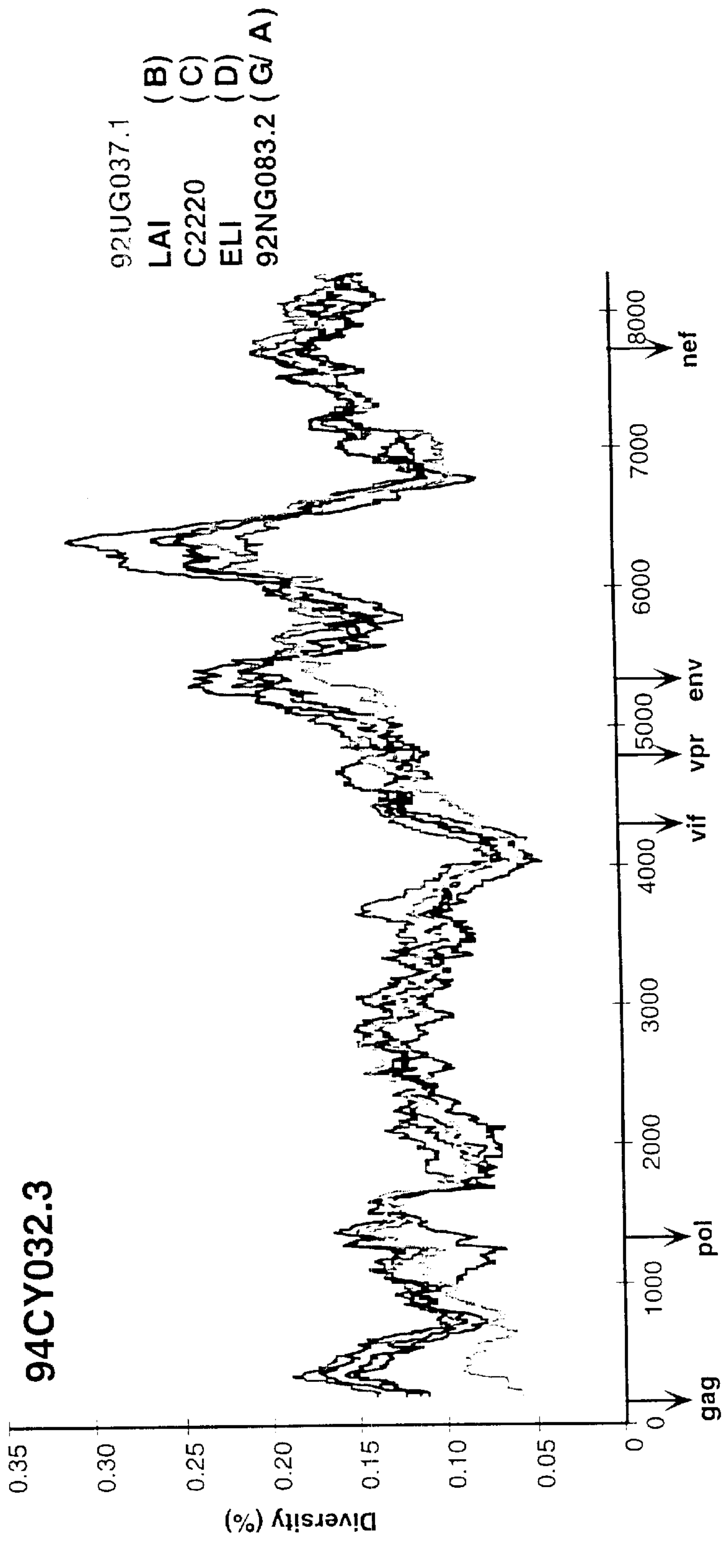
FIG. 9. Diversity plots comparing the sequence relationships of 94CY032.3 to reference sequences from the database. 92UG037.1, LAI, C2220, and ELI are reference sequences for subtypes A, B, C and D, respectively. 92NG083.2 is a known G/A recombinant, but contains only a small subtype A fragment between position 4200 and 4800 (there is presently no full length non-mosaic subtype G reference sequence available). Distance values were calculated for a window of 400 bp moved in steps of 10 nucleotides. The x-axis indicates the nucleotide positions along the alignment (gaps were stripped and removed from the alignment). The positions of the start codons of the gag, pol, vif, vpr, env, and nef genes are shown. The y-axis denotes the distance between the viruses compared (0.05=5% difference).
Figure 10A:
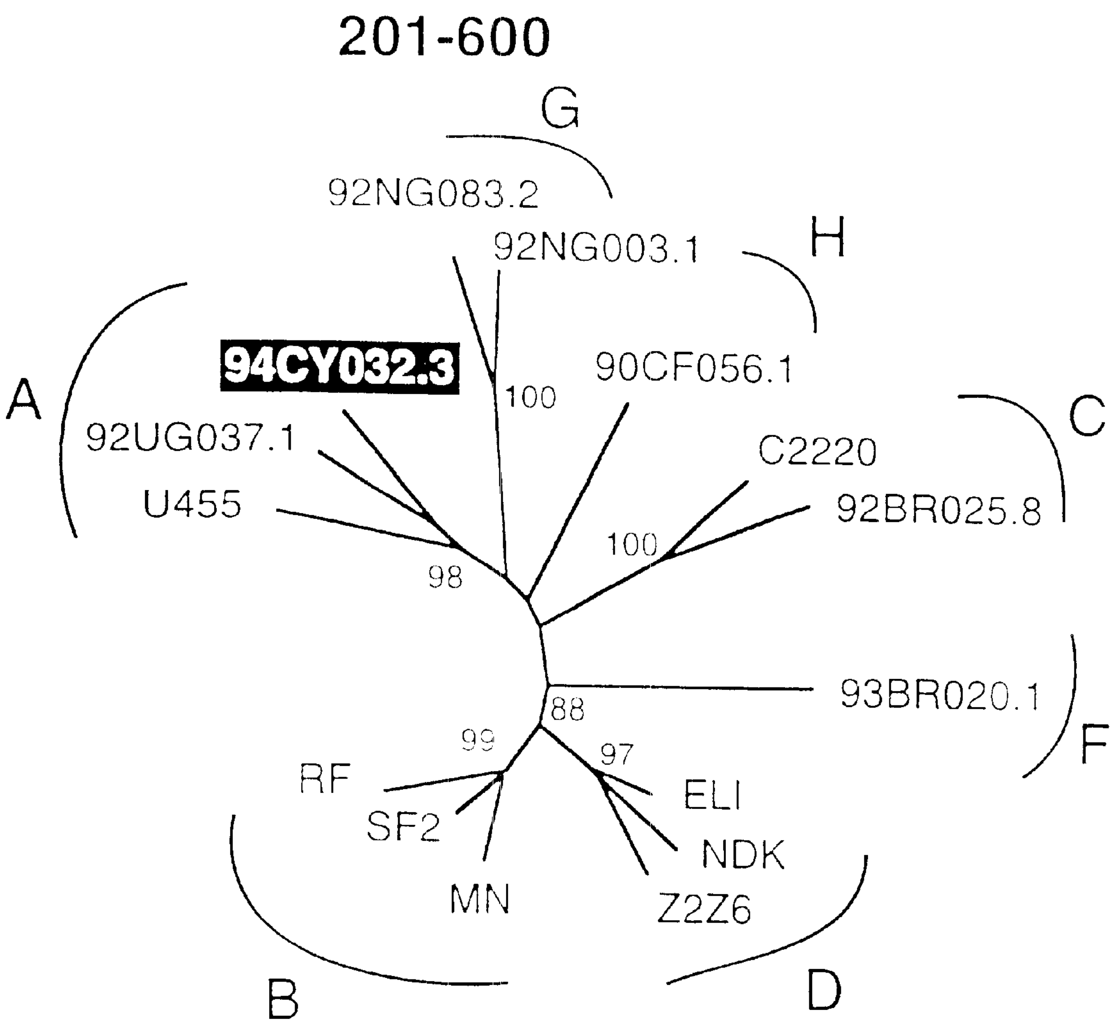
FIGS. 10A–10K. Exploratory tree analysis. Neighbor joining trees were constructed for a 400 bp window moved in increments of 10 bp along the multiple genome alignment. Trees in FIGS. 10A–10K depict the discordant branching orders for 94CY032.3 (highlighted). The position of each tree in the alignment is indicated; subtypes are identified by brackets. Numbers at nodes indicate the percentage of bootstrap values with which the adjacent cluster is supported (only values above 80% are shown). Branch lengths are drawn to scale.
Figure 10B:
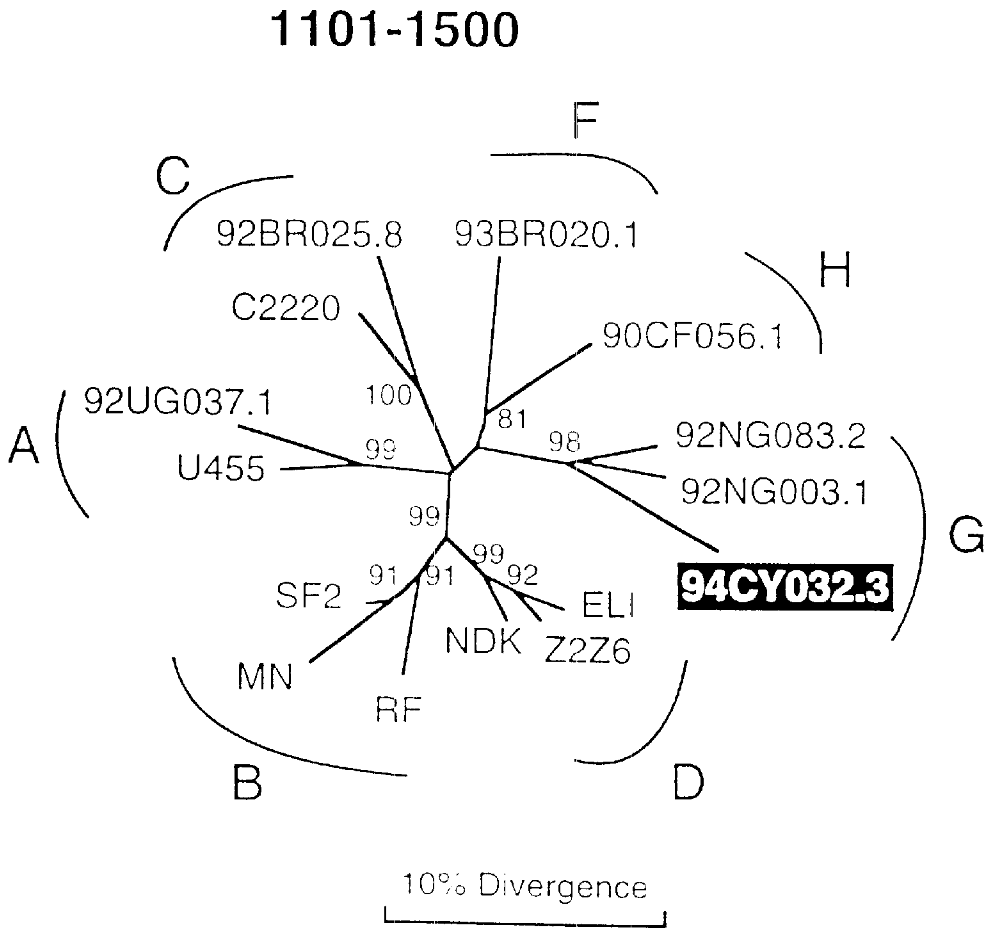
Figure 10C:
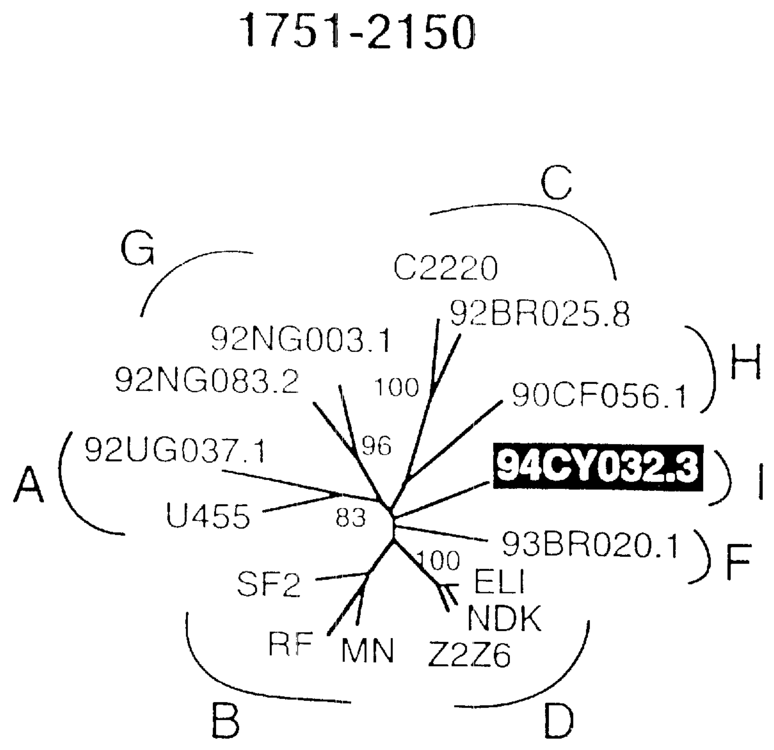
Figure 10D:
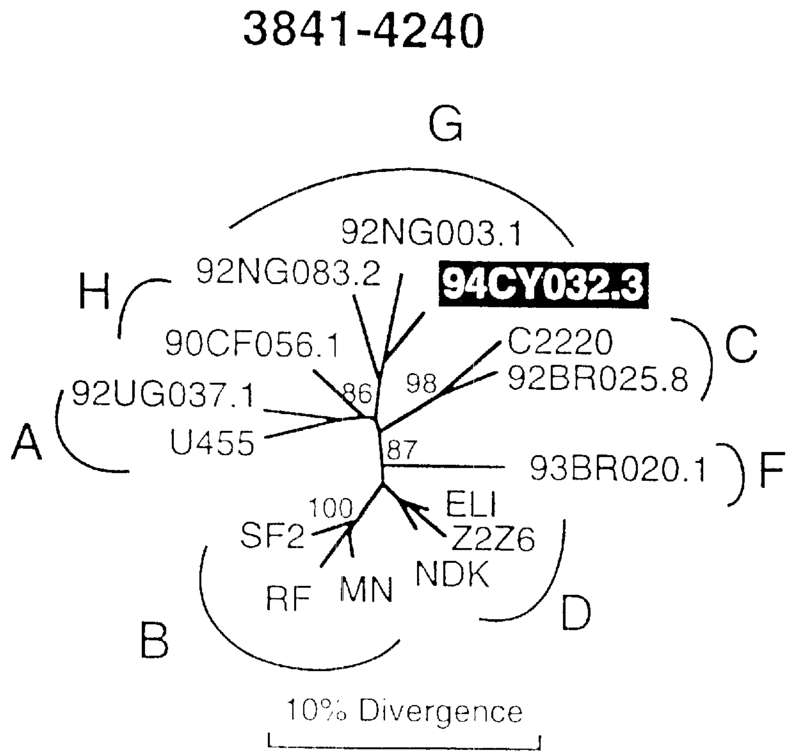
Figure 10E:
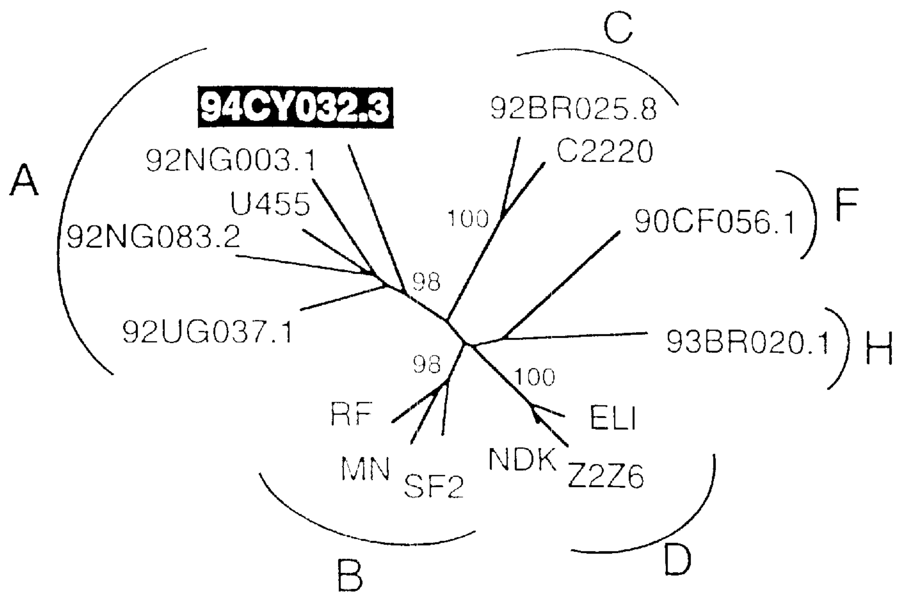
Figure 10F:
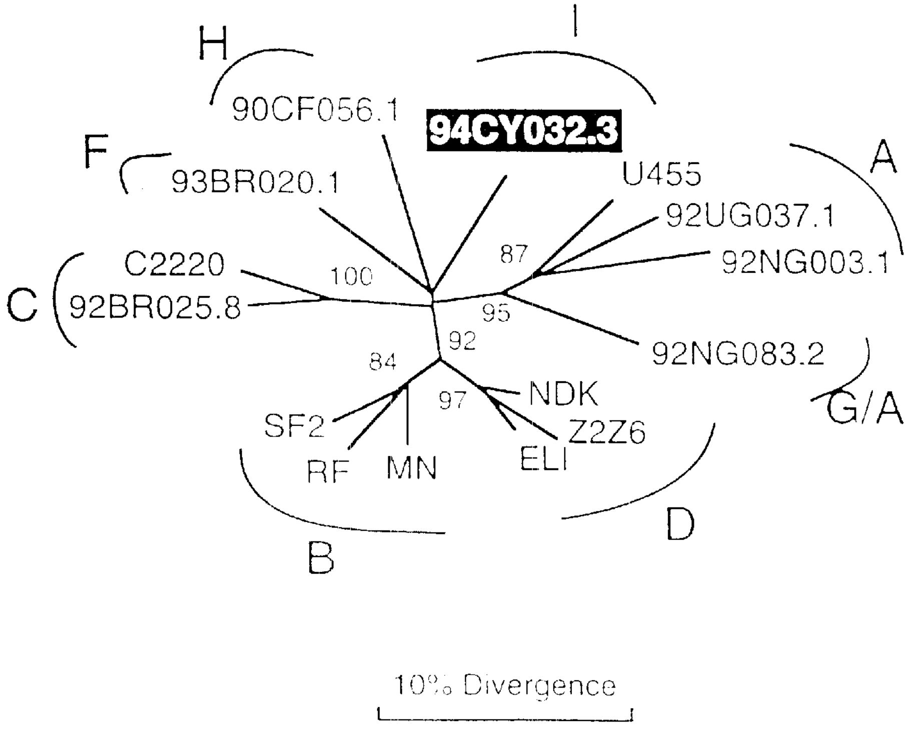
Figure 10G:
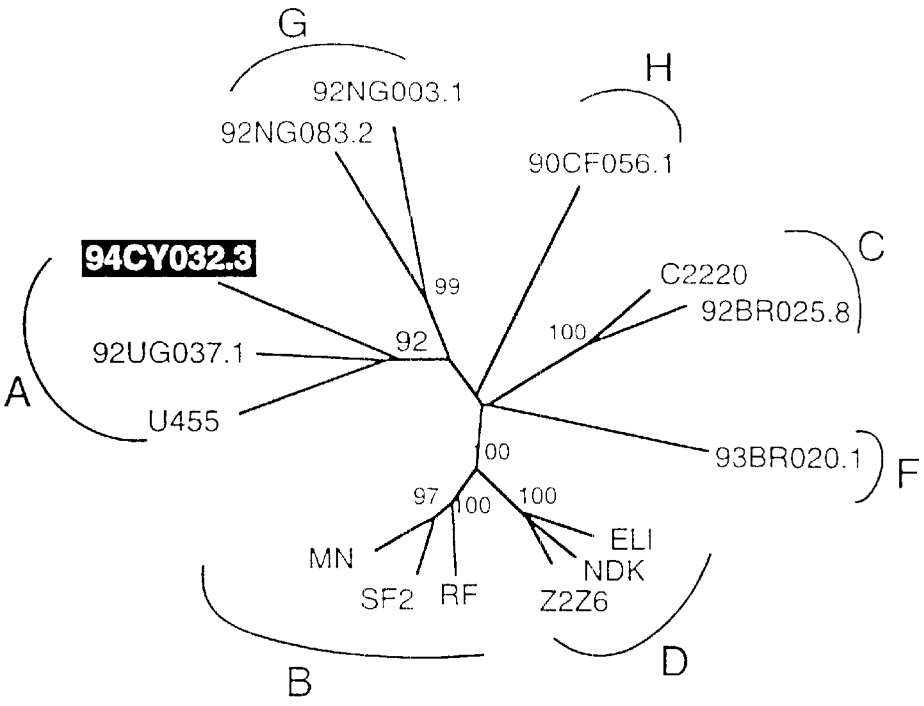
Figure 10H:
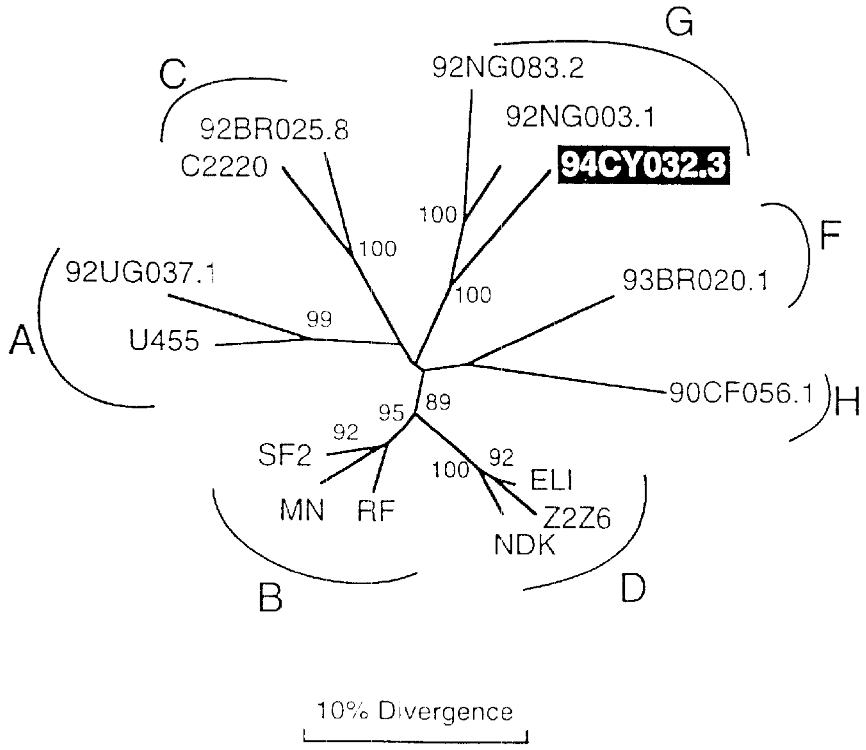
Figure 10I:
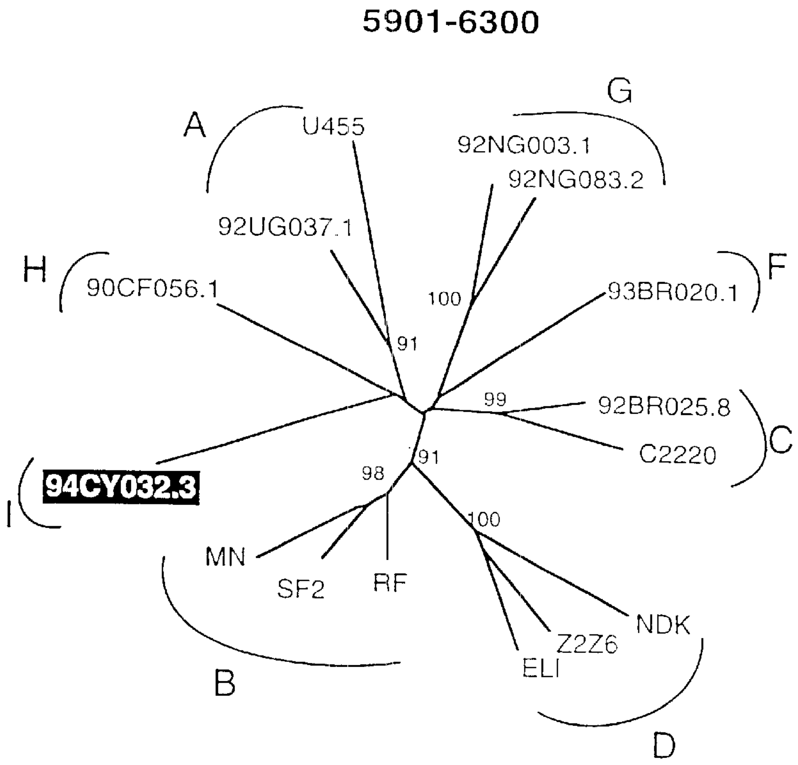
Figure 10J:
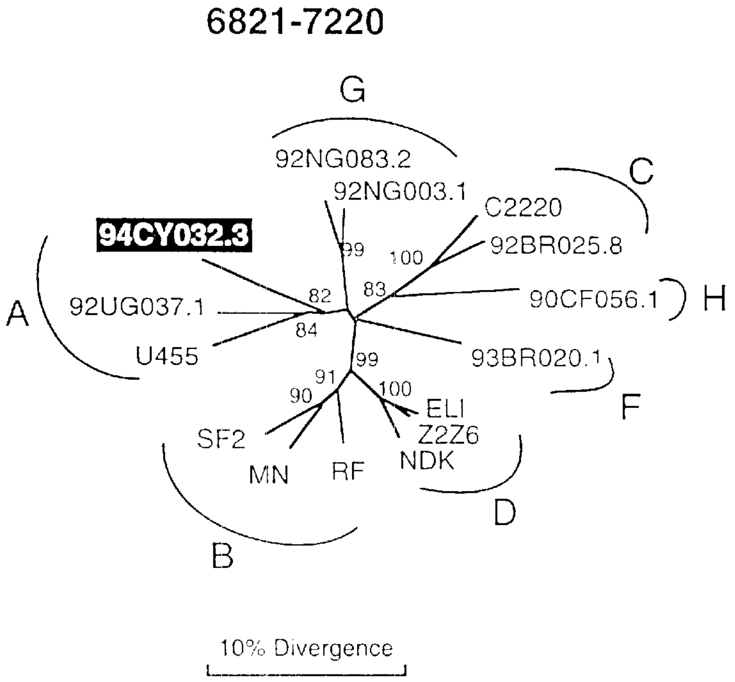
Figure 10K:
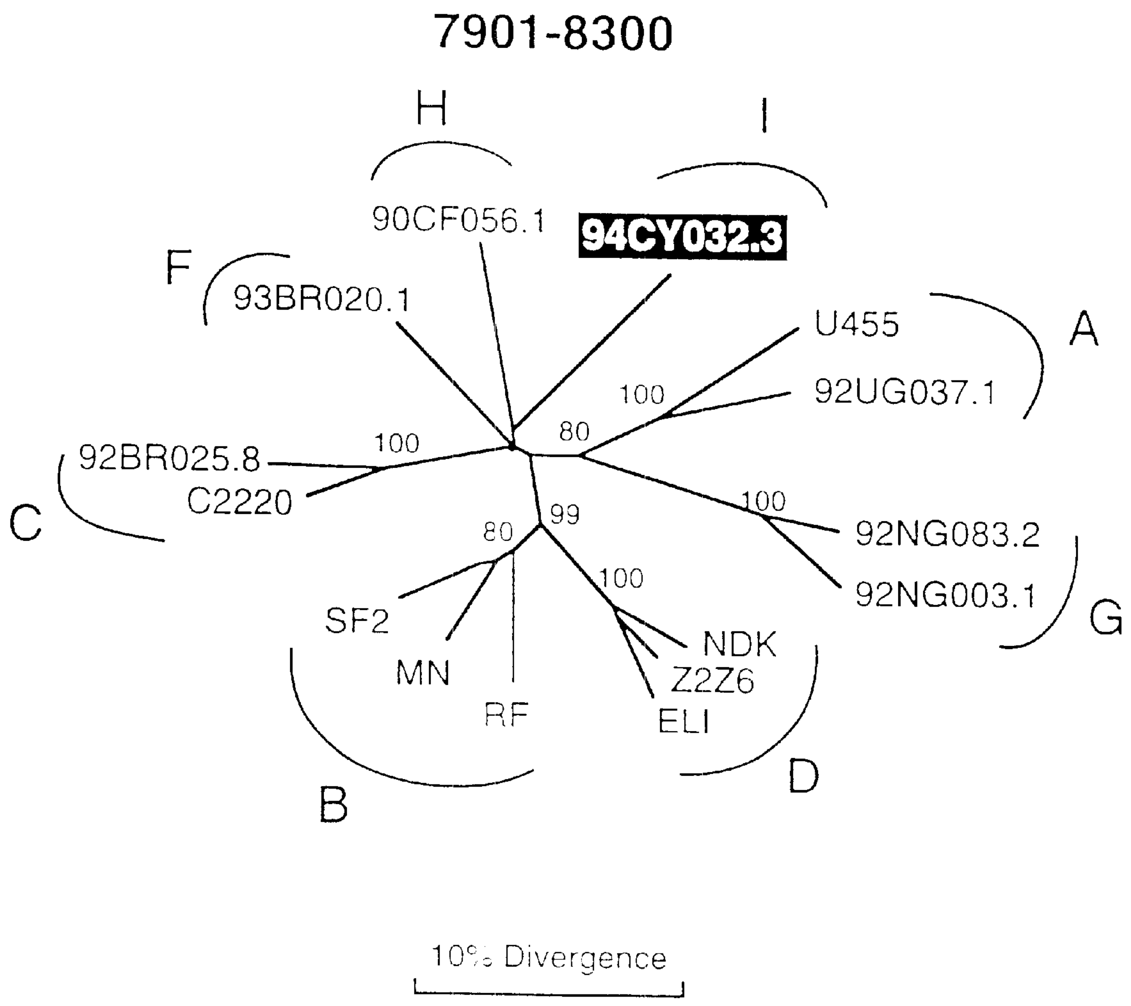

FIG. 9 depicts five such distance plots which illustrate the extent of sequence divergence of 94CY032.3 from representatives of subtypes A (92UG037.1), B (LAI), C (C2220), D (ELI) and G/(A) (92NG083.2). The analysis yielded a set of distance curves with very similar (and for the most part superimposable) diversity profiles, suggesting that 94CY032.3 was roughly equidistant from the other subtypes in most regions of its genome (the same results were also obtained when 94CY032.3 was compared to representatives of subtypes A/E, F, and H; data not shown). However, careful inspection of the graphs revealed several small areas of disproportionate sequence similarity involving two of the five reference sequences. For example, at the 3' end of gag and the 3' end of pol, 92NG083.3 dropped below all others, indicating a relative greater similarity of 94CY032.3 to subtype G. Similarly, in the 5' end of gag, vif, and the 3' and 5' end of env, 92UG037.1 fell below all others, indicating a relative greater similarity of 94CY032.3 to subtype A. Together, these results suggested that 94CY032.3 contained subtype A and G-like segments, in addition to regions that appeared to be equidistant from the other subtypes.

Relative differences in the extent of sequence similarity as determined by diversity plots (18, 79) or other methods of distance measurement (75) are not always an indicator of recombination, but can reflect variations in the evolutionary rates of the lineages compared. To determine whether 94CY032.3 was truly mosaic, an exploratory tree analysis was then performed to look for significantly discordant phylogenetic positions for different parts of its genome (FIG. 10). Using the same multiple genome alignment described above, but excluding all known recombinants (except 92NG083.3 and 92NG003.1), unrooted trees were constructed for overlapping fragments of 400 bp, moved in 10 bp increments along the alignment (for subtypes B and D only three representatives were included). Inspection of the resulting topologies revealed that 94CY032.3 changed its phylogenetic position a total of ten times, alternating between subtype A (FIG. 10A, E, G and J; panels 201–600, 4241–4640, 5071–5470 and 6821–7220), subtype G (FIG. 10B, D and H; panels 1101–1500, 3841–4240 and 5471–5870), and an independent position (FIG. 10C, E, I and K; panels 1751–2150, 4641–5040, 5901–6300 and 7901–8300) that was very similar to the one observed in the C2–V3 region (all discordant positions were supported by significant bootstrap values). Since the latter has served as the basis for subtype I definition, it is most parsimonious to assume that all independently grouping segments in 94CY032.3 are of a common origin and thus represent "subtype I". 94CY032.3 thus appears to be comprised of sequences belonging to at least three different (group M) subtypes.

Figure 11:
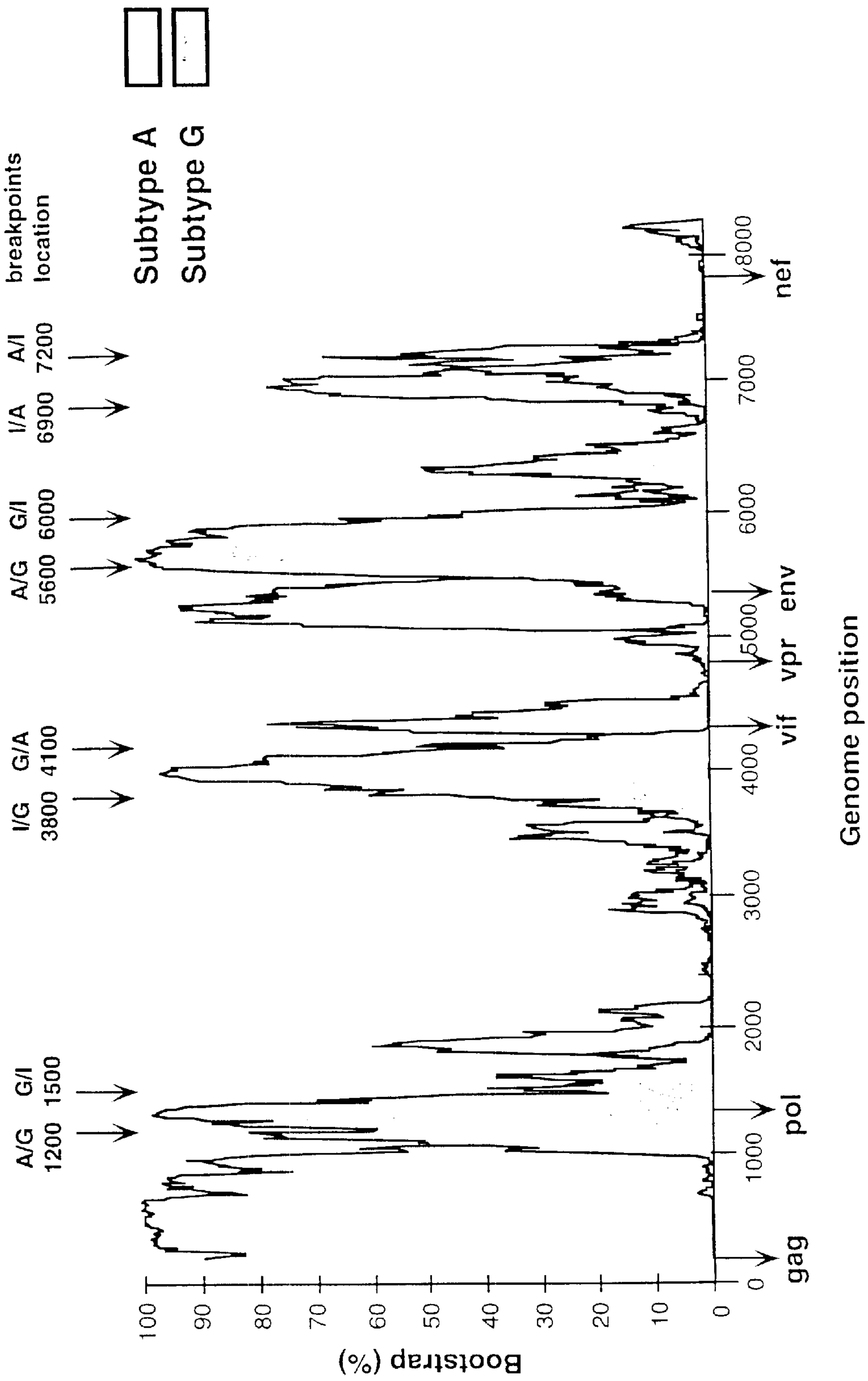
FIG. 11. Bootstrap plot analysis to map recombination breakpoints in 94CY032.3. Bootscanning was performed essentially as described, plotting the magnitude of the bootstrap value supporting the clustering of 94CY032.3 with 92UG037.1 (subtype A) in comparison with that of 94CY032.3 and 92NG083.2 ("subtype G") for a window of 400 bp moved in increments of 10 bp along the alignment. Regions of subtype A or G origin are identified by very high bootstrap values (>80%). The location of eight recombination crossovers is indicated. Breakpoint analysis between position 4200 and 4800 was not possible due to the recombinant nature of 92NG083.2. The beginning of gag, pol, vif vpr, env and nef open reading frames are shown. The y-axis indicates the percent bootstrap replicates, which support the clustering of 94CY032.3 with representatives of the respective subtypes.

To map the boundaries of the putative A, G and I segments, bootstrap plot analyses were performed as previously described (18, 57, 79), plotting the magnitude of the bootstrap values that supported the clustering of 94CY032.3 with 92UG037.1 (subtype A), as well as that of 94CY032.3 with 92NG083.2 ("subtype G"). The results of these analyses allowed us to tentatively map the location and boundaries of the various subtype A an G segments along the 94CY032.3 genome (FIG. 11). Bearing in mind the window size of 400 nucleotides and considering only peaks of significant bootstrap values (>80%), we identified two A/G cross-overs around 1200 and 5600, and one G/A cross-over around 4100. The bootstrap plots also outlined regions with no peaks (or peaks below 80%), which coincided with segments that clustered independently (i.e., in subtype I) in the exploratory tree analysis. Delineating the boundaries of these regions suggested five additional breakpoints: G/I at 1500, I/G at 3800, G/I at 6000, I/A at 6900, and A/I at 7200. Because full length non-mosaic reference sequences for the parental lineages (G and I) were not available, most of the breakpoints could not be mapped with certainty (the A/G breakpoints at 1200 and 5600 were confirmed by informative site analysis; data not shown). Also, the recombinant nature of 92NG083.2 prohibited reliable breakpoint analysis between 4200 and 4800 (32, 79; highlighted in FIG. 11).

Figure 12:
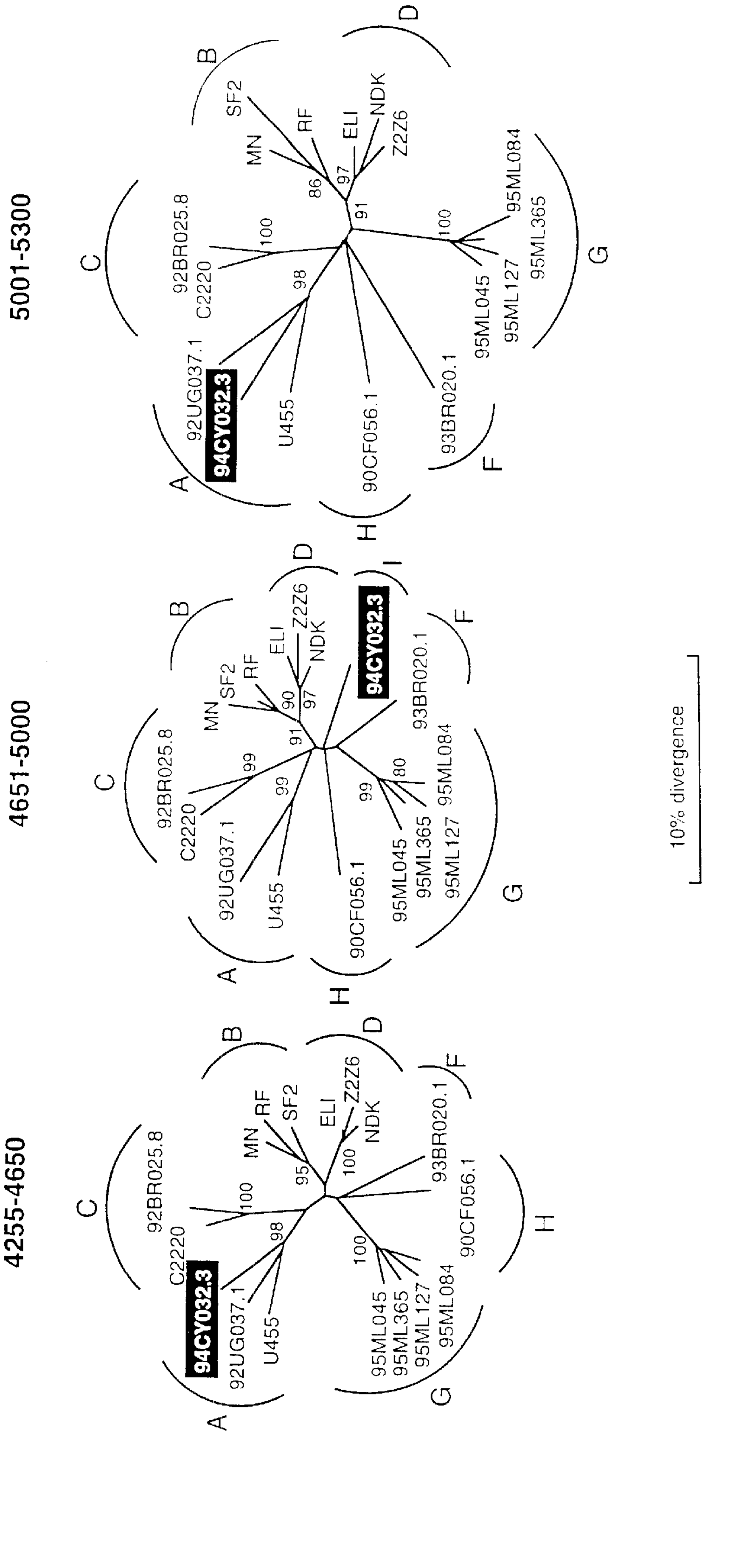
FIG. 12. Recombination breakpoint analysis of 94CY032.3 in the vif/vpr region. Neighbor joining trees depicting the position of 94CY032.3 in regions flanking the breakpoints identified by distance plot analysis (not shown). Trees were constructed from the genomic regions indicated. Subtypes are identified by brackets. Four sequences from Mali represent subtype G (these are the only available subtype G reference sequences in this region, since all other "subtype G" viruses contain A fragments). Numbers at nodes indicate the percentage of bootstrap values with which the adjacent cluster is supported (only values above 80% are shown). Branch lengths are drawn to scale.

To map potential recombination breakpoints in this remaining region, four recently reported, partial but non-mosaic subtype G sequences from Mali which spanned the vif/vpr region and thus bridged the "subtype A gap" of 92NG083.2 were used (77). A set of distance plots that compare 94CY032.3 to one of these newly derived G sequences (95ML045) as well as representatives of subtype A (U455), B (MN), and D (ELI), respectively, were constructed (data not shown). Consistent with the results from the exploratory tree analysis (FIGS. 4A and 4B), 94CY032.3 was disproportionately more closely related to U455 in the 5' and 3' thirds of this fragment, suggesting the presence of subtype A-like segments. However, in the middle of the fragment, 94CY032.3 was clearly equidistant from U455 and the other subtypes, suggesting an independent position (diversity plots were generated for a window of 300 bp moved in increments of 10 bp). Thus, noting the points at which the "A" distance increased and decreased relative to the other distances allowed us to tentatively map the two remaining breakpoints, one at 4650 and the other at 5000. Trees constructed from sequences surrounding these two breakpoints (FIG. 12) confirmed that 94CY032.3 switched position from subtype A (FIG. 12; panel 4255–4650) to subtype I (panel 4651–5000), and back to subtype A (5001–5300; note, that the new subtype G sequences only cover the region between 4255 and 5300).

There are a total of 10 recombination breakpoints between the 5' end of gag and the 3' end of nef in the genome structure of the 94CY032.3. However, the discordant subtype assignments of gag and nef regions necessitate at least one more breakpoint in the viral LTR or the gag leader sequence (LTR sequences were not separately analyzed for mosaicism). Given this extent of mosaic complexity, 94CY032.3 is likely the result multiple sucessive recombination events.

Having identified several fragments of subtype I in 94CY032.3, evidence for its presence in other (full length) recombinants from the database was examined. (Data not shown) Two known mosaics MAL (53, 76) and Z321 (78) were of particular interest, because previous analyses had indicated that these viruses contain regions of uncertain subtype assignment (53, 82, 83). For example, MAL has long been known to represent a mosaic of subtypes A and D, but also contains a sizable pol fragment that has defied previous subtype classification (53, 83). Similarly, Z321 is a known mosaic of subtypes A and G (78), but a recent re-analysis of its recombination breakpoints identified regions that could not be assigned to any known subtype (82, 83). To determine whether any of these regions represented subtype I, distance plot analysis was performed, comparing the diversity profiles of MAL and Z321 with those for representatives of other subtypes. Looking for dips in the curves as an indication of relatively greater sequence similarity, one in the pol region of MAL and another in the vif/vpr region of Z321 were found to coincide with previously unclassified segments of their genomes (indicated as white boxes). Phylogenetic tree analysis confirmed that these regions were indeed of subtype I origin, since MAL and Z321 clustered significantly with the subtype I domains of 94CY032.3. Interestingly, subtype I did not account for all of the unclassifiable regions in MAL and Z321 (82, 83). It thus remains unclear whether these represent still other, as yet unidentified, subtypes or regions of multiple breakpoints that cannot be mapped using current methods.

The above results demonstrate that a strain of HIV-1, proposed in 1995 as a prototypic "subtype I" isolate (29), represents a complex mosaic comprised of subtypes A, G and I, respectively. In addition, two of the oldest known isolates from Africa, MAL (isolated in 1984) (76) and Z321 (isolated in 1976) (80, 84), are shown to contain short segments of sequence closely related to the subtype I domains of 94CY032.3. These findings support the following conclusions: (i) although initially detected in Cyprus, subtype I must have existed in Africa as early as 1976; it is unknown whether full length non-mosaic representatives of subtype I still exist (but have not yet been sampled), or whether this subtype (like subtype E) is represented only by fragments in present day recombinants; (ii) the ancestry of 94CY032.3 must have involved multiple successive recombination events; it remains unclear whether this occurred in Africa and/or in Cyprus, where a number of different subtypes have also been documented (29); (iii) subtype I, along with subtypes A and G, must have diverged substantially earlier than the 1970s in order to be detectable as distinct segments in the Z321 genome; this is consistent with the recent molecular characterization of a virus from 1959 which in phylogenetic analyses appears to have postdated the group M radiation (85); (iv) finally, the finding of subtype I in several different recombinants, including one from an intravenous drug user (29), suggests that this subtype may be more widespread than previously thought, at least in the form of mosaic genome fragments. It will be interesting to screen additional viruses from drug user populations and their contacts in Cyprus and Greece to determine the current prevalence and geographic distribution of subtype I containing viruses.

REFERENCES

1. Abimiku, A. G., et al., 1994. Subgroup G HIV type 1 isolates from Nigeria. *AIDS Res. Hum. Retroviruses* 10:1581–1583.
2. Ausubel, F. M., et al., 1987. Current protocols in molecular biology. John Wiley & Sons, New York.
3. Betts, M. R., et al., 1997. Cross-clade HIV-specific cytotoxic T-lymphocyte responses in HIV-infected Zambians. *J. Virol.*, 71:8908–8911.

4. Bobkov, A., et al., 1996. Complex mosaic structure of the partial envelope sequence from a Gambian HIV Type 1 Isolate. *AIDS Res. Hum. Retroviruses* 12:169–171.

5. Brodine, S. K., J. R. Mascola, and F. E. McCutchan. 1997. Genotypic variation and molecular epidemiology of HIV. *Infect. Med.*, 14:739–748.

6. Cao, H., et al., 1997. Cytotoxic T-lymphocyte cross-reactivity among different human immunodeficiency virus type 1 clades: Implications for vaccine development. *J. Virol.* 71:8615–8623.

7. Carr, J. K., et al., 1996. Full length sequence and mosaic structure of a human immunodeficiency virus type 1 isolate from Thailand. *J. Viro.* 70:5935–5943.

8. Cornelissen, M., et al., 1996. Human immunodeficiency virus type 1 subtypes defined by env show high frequency of recombinant gag genes. *J. Virol.* 70:8209–8212.

9. Dittmar, M. T., et al., 1997. Langerhans cell tropism of human immunodeficiency virus type 1 subtype A through F isolates derived from different transmission groups. *J. Virol.* 71:8008–8013.

10. Dolin, R. 1995. Human studies in the development of human immunodeficiency virus vaccines. *J. Infect. Dis.* 172:1175–1183.

11. Esparaza, J., S. Osmanov, and W. Heyward. 1995. HIV preventive vaccines. *Drugs* 50:792–804.

12. Faulkner, D. M., and J. Jurka. 1988. Multiple aligned sequence editor (MASE). *Trends Biochem. Sci.* 13:321–322.

13. Felsenstein, J. 1985. Confidence limits on phylogenies: an approach using the bootstrap. *Evolution* 39:783–791.

14. Felsenstein, J. 1992. PHYLIP (Phylogeny Inference Package), 3.5c ed. Department of Genetics, University of Washington, Seattle, Wash.

15. Ferrari, G., et al., 1997. Clade B-based HIV-1 vaccines elicit cross-clade cytotoxic T lymphocyte reactivities in uninfected volunteers. *Proc. Natl. Acad. Sci. USA* 94:1396–1401.

16. Gao, F. and B. H. Hahn, unpublished.

17. Gao, F., et al., 1994. Genetic variation of HIV type 1 in four World Health Organization-sponsored vaccine evaluation sites: generation of functional envelope (glycoprotein 160) clones representative of sequence subtypes A, B, C, and E. *AIDS Res. Hum. Retroviruses* 10:1359–1368.

18. Gao, F., et al., 1996. The heterosexual human immunodeficiency virus type 1 epidemic in Thailand is caused by an intersubtype (A/E) recombinant of African origin. *J. Virol.* 70:7013–7029.

19. Gao, F., et al., 1996. Molecular cloning and analysis of functional envelope genes from HIV-1 sequence subtypes A through G. *J. Virol.* 70:1651–1667.

20. Ghosh, S. K., et al., 1993. A molecular clone of HIV-1 tropic and cytopathic for human and chimpanzee lymphocytes. *Virology* 194:858–864.

21. Graham, B. S., and P. F. Wright. 1995. Candidate AIDS Vaccines. N. Engl. J. Med. 333:1331–1339.

22. Hahn, B. H., et al., 1984. Molecular cloning and characterization of the HTLV-III virus associated with AIDS. Nature 312:166–169.

23. Hahn, B. H., D. L. Robertson, and P. M. Sharp. 1995. Intersubtype recombination in HIV-1 and HIV-2, p. III-22–III-29. In G. Myers and B. Korber and S. Wain-Hobson and K.-T. Jeang and L. E. Henderson and G. N. Pavlakis (ed.), Human retroviruses and AIDS 1995: A compilation and analysis of nucleic acid and amino acid sequences. Los Alamos National Laboratory, Los Alamos, N.Mex.

24. Hu, D. J., et al., 1996. The emerging diversity of HIV: the importance of global surveillance for diagnostics, research and prevention. *JAMA* 275:210–216.

25. Kalish, M. L., et al., 1995. The evolving molecular epidemiology of HIV-1 envelope subtypes in injecting drug users in Bangkok, Thailand: implications for HIV vaccine trials. *AIDS* 9:851–857.

26. Kimura, M. 1980. A simple method for estimating evolutionary rates of base substitutions through comparative studies of nucleotide sequences. *J. MoL. Evol.* 16:111–120.

27. Kimura, M. 1983. The neutral theory of molecular evolution. Cambridge University Press, Cambridge, U.K.

28. Korber, B. T. M., et al., . 1994. The World Health Organization Global Programme on AIDS Proposal for Standardization of HIV Sequence Nomenclature. *AIDS Res. Hum. Retroviruses* 10:1355–1358.

29. Kostrikis, L. G., et al., 1995. Genetic analysis of human immunodeficiency virus type 1 strains from patients in Cyprus: Identification of a new subtype designated subtype I. *J. Virol.* 69:6122–6130.

30. Leitner, T., and J. Albert. 1995. A new genetic subtype of HIV-1, p. III-147–III-150. In G. Myers and B. Korber and B. H. Hahn and K.-T. Jeang and J. W. Mellors and F. E. McCutchan and L. E. Henderson and G. N. Pavlakis (ed.), Human Retroviruses and AIDS 1995. Theoretical Biology and Biophysics, Los Alamos.

31. Leitner, T., et al., 1995. Biological and molecular characterization of subtype D, G, and A/D) recombinant HIV-1 transmissions in Sweden. *Virology* 209:136–146.

32. Leitner, T., B. T. M. Korber, D. L. Robertson, F. Gao, and B. H. Hahn. 1997. Updated Proposal of Reference Sequences of HIV-1 Genetic Subtypes. In B. Korber, B. Foley, C. Kuiken, T. Leitner, F. McCutchan, J. W. Mellors and B. H. Hahn (ed), Human Retroviruses and AIDS 1997: a complication and analysis of nucleic acid and amino acid sequence. Theoretical Biology and Biophysics Group, Los Alamos National Laboratory, Los Alamos, N.Mex.

33. Loussert-Ajaka, I., et al., 1995. Variability of human immunodeficiency virus type 1 group O strains isolate from Cameroonian patients living in France. *J. Virol.* 69:5640–5649.

34. Louwagie, J., et al., 1993. Phylogenetic analysis of gag genes from 70 international HIV-1 isolates provides evidence for multiple genotypes. *AIDS* 7:769–780.

35. Louwagie, J., et al., 1995. Genetic diversity of the envelope glycoprotein from human immunodeficiency virus type 1 isolates of African origin. *J. Virol.* 69:263–271.

36. Maniatis, T., E. F. Fritsch, and J. Sambrook. 1982. Molecular cloning: a laboratory manual, p. 269–295. Cold Spring Harbor Laboratory, Cold Spring Harbor, N.Y.

37. Martin-Gallardo, A., J. Lamerdin, and A. Carrano. 1994. Shotgun sequencing, p. 37–41. In M. D. Adams and C. Fields and J. C. Venter (ed.), Automated DNA sequencing and analysis. Academic Press, London.

38. Mascola, J. R., et al., 1996. Human immunodeficiency virus type 1 neutralizing antibody serotyping using serum pools and an infectivity reduction assay. *AIDS Res. Hum. Retroviruses* 12:1319–1328.

39. McCutchan, F. E., et al., 1992. Genetic variants of HIV-1 in Thailand, *AIDS Res. Hum. Retroviruses* 8:1887–1895.

40. McCutchan, F. E., M. O. Salminen, J. K. Carr, and D. S. Burke. 1996. HIV-1 genetic diversity. *AIDS* 10(suppl 3):S13–20.

41. Moore, J. P., et al., 1996. Inter- and intra- subtype neutralization of human immunodeficiency virus type 1: the genetic subtypes do not correspond to neutralization serotypes but partially correspond to gp120 antigenic serotypes. *J. Virol.* 70:427–444.

42. Moore, J., and A. Trkola. 1997. HIV type 1 coreceptors, neutralization serotypes, and vaccine development. *AIDS Res. Hum. Retroviruses* 13:733–736.

43. Murphy, E., et al., 1993. Diversity of V3 region sequences of human immunodeficiency viruses type 1 from the Central African Republic. *AIDS Res. Hum. Retroviruses* 9:997–1007.

44. Myers, G., et al., 1992. Human retroviruses and AIDS: a compilation and analysis of nucleic acid and amino acid sequence. Theoretical Biology and Biophysics Group,Los Alamos National Laboratory, Los Alamos, N.Mex.

45. Myers, G., et al., 1996. Human retroviruses and AIDS: A compilation and analysis of nucleic acid amino acid sequences. Theoretical Biology and Biophysics Group, Los Alamos National Laboratory, Los Alamos, N.Mex.

46. Nyambi, P. N., et al., 1996. Multivariate analysis of human immunodeficiency virus type 1 neutralization data. *J. Virol.* 70:445–458.

47. Ou, C.-Y., et al., 1993. Independent introductions of two major HIV-1 genotypes into distinct high-risk populations in Thailand. *Lancet* 341:1171–1174.

48. Peden, K., M. Emerman, and L. Montagnier. 1997. Changes in growth properties on passage in tissue culture of viruses derived from infectious molecular clones of HIV-1LAI, HIV-1MAL, and HIV-1ELI. *Virology* 185:661–672.

49. Perriere, G. and Gouy, M. 1996. WWW-Query: An on-line retrieval system for biological sequence banks. Biochimie 78:364–369.

50. Pope, M., et al., 1997. HIV-1 strains from subtypes B and E replicate in cutaneous dendritic cell-T cell mixtures without displaying subtype-specific tropism. *J. Virol.* 71:8001–8007.

51. Pope, M., et al., 1997. Different subtypes of HIV-1 and cutaneous dendritic cells. *Science* 278:786–787.

52. Robertson, et al., 1995. Recombination in HIV-1. *Nature* 374:124–126.

53. Robertson, D. L., B. H. Hahn, and P. M. Sharp. 1995. Recombination in AIDS viruses. *J. Mol. Evol.* 40:249–259.

54. Sabino, E. C., et al., 1994. Identification of human immunodeficiency virus type 1 envelope genes recombinant between subtypes B and F in two epidemiologically linked individuals from Brazil. *J. Virol.* 68:6340–6346.

55. Saitou, N., and M. Nei. 1987. The neighbor-joining method: a new method for reconstructing phylogenetic trees. *Mol. Biol. Evol.* 4:406–425.

56. Salminen, M. O., et al., 1995. Recovery of virtually full length HIV-1 provirus of diverse subtypes from primary virus cultures using the polymerase chain reaction. *Virology* 213:80–86.

57. Salminen, M. O., J. K. Carr, D. S. Burke, and F. E. McCutchan. 1995. Identification of breakpoints in intergenotypic recombinants of HIV-1 by bootscanning. *AIDS Res. Hum. Retroviruses* 11:1423–1425.

58. Salminen, M. O., J. K. Carr, D. S. Burke, and F. E. McCutchan. 1995. Genotyping of HIV-1, p. III-30–III-34. In G. Myers and B. Korber and S. Wain-Hobson and K.-T. Jeang and L. E. Henderson and G. N. Pavlakis (ed.), Human retroviruses and AIDS 1995: A compilation and analysis of nucleic acid and amino acid sequences. Los Alamos National Laboratory, Los Alamos.

59. Salminen, M. O., et al., 1996. Full length sequence of an ethiopian human immunodeficiency virus type 1 (HIV-1) isolate of genetic subtype C. *AIDS Res. Hum. Retroviruses* 12:1329–1339.

60. Salminen, M. O., et al., 1997. Evolution and probable transmission of intersubtype recombinant human immunodeficiency virus type 1 in a Zambian couple. *J. Virol.* 71:2647–2655.

61. Sharp, P. M., D. L. Robertson, F. Gao, and B. H. Hahn. 1994. Origins and diversity of human immunodeficiency viruses. *AIDS* 8:S27–S42.

62. Sharp, P. M., D. L. Robertson, and B. H. Hahn. 1995. Cross-species transmission and recombination of AIDS viruses. *Phil. Trans. R. Soc. London* (Ser. B) 349: 41–47.

63. Siepel, A. C., and B. T. Korber. 1995. Scanning the database for recombinant HIV-1 genomes, p. III-35–III-60. In G. Myers and B. Korber and S. Wain-Hobson and K.-T. Jeang and L. E. Henderson and G. N. Pavlakis (ed.), Human retroviruses and AIDS 1995: A compilation and analysis of nucleic acid and amino acid sequences. Los Alamos National Laboratory, Los Alamos, N.Mex.

64. Soto-Ramirez, L. E., et al., 1996. HIV-1 langerhans' cell tropism associated with heterosexual transmission of HIV. *Science* 271:1291–1293.

65. Spire, B., et al., 1989. Nucleotide sequence of HIV1-NDK: a highly cytopathic strain of the human immunodeficiency virus. *Gene* 81:275–284.

66. Takehisa, J., et al., 1997. Phylogenetic analysis of human immunodeficiency virus 1 in Ghana. *Acta. Virologia* 41:51–54.

67. Thompson, J. D., D. G. Higgins, and T. J. Gibson. 1994. CLUSTAL W—improving the sensitivity of progressive multiple sequence alignment through sequence weighting, position-specific gap penalties and weight matrix choice. *Nucleic Acids Res.* 22:4673–4680.

68. Weber, J., et al., 1996. Neutralization serotypes of human immunodeficiency virus type 1 field isolates are not predicted by genetic subtype. *J. Virol.* 70:7827–7832.

69. Weniger, B. G., et al., 1991. The epidemiology of HIV infection in AIDS in Thailand. *AIDS* 5(suppl. 2): S71–S85.

70. Weniger, B. G., et al., 1994. The molecular epidemiology of HIV in Asia. *AIDS* 8(suppl. 2):S13–S28.

71. Wieland, U., et al., 1997. Diversity of the vif gene of human immunodeficiency virus type 1 in Uganda. *J. of Gen. Virol.* 78:393–400.

72. World Health Organization Network for HIV Isolation and Characterization. 1994. HIV-1 variation in WHO-sponsored vaccine-evaluation sites: Genetic screening, sequence analysis and preliminary biological characterization of selected viral strains. *AIDS. Res. Hum. Retroviruses* 10:1327–1344.

73. Zhang, L., et al., 1996. HIV-1 subtype and second-receptor use. *Nature* (*London*) 383:768.

74. Zhang, L., et al., 1997. HIV-1 subtypes, co-receptor usage, and CCR5 polymorphism. *AIDS Res. Hum. Retroviruses* 13: 1357–1366

75. Siepel, A.C., et al., A computer program designed to screen rapidly for HIV type 1 intersubtype recombinant sequences. *AIDS Res. Hum. Retrovirus.* 11: 1413–1416, 1995.

76. Alizon, M., S. et al., 1986. Genetic variability of the AIDS virus: nucleotide sequence analysis of two isolates from African patients. *Cell* 46:63–74.

77. Bibollet-Ruche, F., et al., Genetic characterization of accessory genes from human immunodeficiency virus type 1 subtypes A, C, D, F, G and H from different African countries, in preparation.

78. Choi, D. J., et al., 1997. HIV type 1 isolate Z321, the strain used to make a therapeutic HIV type 1 immunogen, is intersubtype recombinant. *AIDS Res. Hum. Retroviruses* 13:357–361.

79. Gao, F., et al., 1998. A comprehensive panel of near full-length clones and reference sequences for non-subtype B isolates of human immunodeficiency virus type 1. *J. Virol*, in press.

80. Getchell, J. P., et al., 1987. Human immunodeficiency virus isolated from a serum sample collected in 1976 in Central Africa. *J. Infect. Dis.* 156:833–837.

81. B. Korber, et al., 1997. Human retroviruses and AIDS: A compilation and analysis of nucleic acid and amino acid sequences. Theoretical Biology and Biophysics Group, Los Alamos National Laboratory, Los Alamos, N.Mex.

82. Robertson, D. L., F. Gao, and B. H. Hahn. The analysis of complete HIV-1 intersubtype hybrid genomes, in preparation.

83. Robertson, D. L., et al., 1997. Intersubtype Recombinant HIV-1 Sequences. pp. III 25–III 30, In B. Korber, B. Foley, C. Kuiken, T. Leitner, F. McCutchan, J. W. Mellors, and B. H. Hahn (ed.), Human retroviruses and AIDS 1997: A compilation and analysis of nucleic acid and amino acid sequences. Theoretical Biology and Biophysics Group, Los Alamos National Laboratory, Los Alamos, N.Mex.

84. Srinivasan, A., D. et al., 1989. Molecular characterization of HIV-1 isolated from a serum collected in 1976: Nucleotide sequence comparison of recent isolates and generation of hybrid HIV. *AIDS Res. Hum. Retroviruses* 5:121–129.

85. Zhu, T., et al., 1998. An African HIV-1 sequence from 1959 and implications for the origin of the epidemic. *Nature* 391:594–597.

86. Southern, E. M. 1975. *J. Mol. Biol.*, 98:503–517.

87. Kafatos, F. C. et al. 1979. *Nucleic Acids Res.*, 7:1541–1522.

88. Agarwal et al. 1972*, Angew. Chem. Int. Ed. Engl.* 11:451.

89. Baeucage et al. 1981*, Tetrahedron Letters* 22:1859–1862. Automated diethylphosphoramidite method.

90. Hsiung et al. 1979. *Nucleic Acids Res* 6:1371

91. See, e.g., Anderson, et al. 1996. *Antimicrob. Agents Chemother.*, 40:2004–2011; Azad, et al. 1995. *Antiviral Res.*, 28:101–111; Azad, et al. 1993. *Antimicrob. Agents Chemother.*, 37:1945–1954; Leeds, et al. 1997. *Drug. Metab. Dispos.*, 25:921–926; and references therein. See also, Cook, P. D., 1993. Monomers for preparation of oligonucleotides having chiral phosphorus linkages. U.S. Pat. No. 5,212,295 (re: general method of making DNA analogs, including phosphorothioates, thioesters, etc.); and lyer et al. 1990 *J. Org. Chem.* 55:4693–4699 (re: synthetic method for making phosphorothioate oligos).

92. See, e.g., Nielsen, et al., WO 98/03542; Hyrup and Nielsen 1996. *Bioorg. Med. Chem.* 4:5–23; and Nielsen, et al. 1991. *Science* 254:1497–1500; and references therein.

93. Sambrook, J. et al. 1989. In "Molecular Cloning, A Laboratory Manual", Cold Spring Harbor Press, Plainview, N.Y.

94. Alwine, J. C., et al. 1977. *Proc. Natl. Acad. Sci.*, 74:5350–5354.

95. Hollander, M. C. et al. 1990. *Biotechniques*; 9:174–179

96. Watson, J. D., et al. 1992. In "Recombinant DNA" Second Edition, W. H. Freeman and Company, New York.

97. See, e.g., Naldini, N., et al., "In Vivo Gene Delivery and Stable Transduction of Nondividing Cells by a Lentiviral Vector", *Science*, 272:263–267 (1996); Srinivasakumar, N., et al., "The Effect of Viral Regulatory Protein Expression on Gene Delivery by Human Immunodeficiency Virus Type 1 Vectors Produced in Stable Packaging Cell Lines", *J. Virol.*, 71:5841–5848 (August 1997); Zufferey, R., et al., "Multiply Attenuated Lentiviral Vector Achieves Efficient Gene-Delivery In Vivo", *Nature Biotechnology*, 15:871–875 (September 1997); and Kim, V. N., et al., "Minimal Requirement for a Lentivirus Vector Based on Human Immunodeficiency Virus Type 1*", J Virol*, 72:811–816 (January 1998).

98. See, e.g., Schwartz et al.,*J. Virol.*, 66:7176–7182 (1992); International Publication No. WO 93/20212 (1993); Schneider, R., et al., "Inactivation of the human immunodeficiency virus type 1 inhibitory elements allows Rev-independent expression of Gag and Gag/protease and particle formation," *J. Virol.*, 71:4892–4903 (1997) concerning the identification and mutation of inhibitory and instability regions using multiple point mutations within HIV-1 gag, protease and pol coding regions to reduce the effects of these regions and increase expression of the encoded polypeptide.

99. Oellerich, M. 1984. J. Clin. Chem. Clin. BioChem 22:895–904

100. Lu S., et al. Simian immunodeficiency virus DNA vaccine trial in macaques. *J. Virol.* 1996;70:3978–91.

101. Haynes J R, et al., Accell particle-mediated DNA immunization elicits humoral, cytotoxic and protective responses. *AIDS Res. Hum. Retroviruses* 1994; 10 (suppl 2): S43–45

102. Okuda, K, et al. Induction of potent humoral and cell-mediated immune responses following direct injection of DNA encoding the HIV type 1 Env and Rev gene products. *AIDS Res. Hum. Retroviruses* 1995;11:933–43.

103. Wang B., et al. Induction of humoral and cellular immune responses to the human immunodeficiency type 1 virus in non-human primates by in vivo DNA inoculation. *J. Virol.* 1995; 21:102–12

104. Boyer J. D., et al. In vivo protective anti-HIV immune responses in non-human primates through DNA immunization. *J. Med. Primatol.* 1996; 25–242-50.

105. MacGregor et al., *J. Infect Dis.* 178:92–100 (1998)

106. Donnelly et al., *Annu. Rev. Immunol.* 15:617–648 (1997)

107. Ulmer et al., *Science* 259:1745–1749 (1993)

108. Winzeler et al., *Science* 281:1194–1197 (1998)

Modifications of the above described invention that are obvious to those of skill in the fields of genetic engineering, immunology, virology, protein chemistry, medicine, and related fields are intended to be within the scope of the following claims.

All of the references cited herein above are hereby incorporated by reference.

We claim:

1. A nucleic acid comprising the nucleotide sequence of the genome of a non-subtype B HIV-1 virus, wherein said nucleotide sequence is SEQ ID No. 8.

2. A nucleic acid comprising the nucleotide sequence of an LTR of the nucleic acid of claim 1.

3. A nucleic acid encoding a polypeptide selected from the group consisting of Gag, Pol, Vif, Vpr, Env, Tat, Rev, Nef and Vpu, wherein the polypeptide is encoded by the genome of a non-subtype B HIV-1 virus 96ZM651.8, wherein the nucleotide sequence of said genome is SEQ ID No. 8.

4. A nucleic acid comprising a sequence complementary to the sequence of a nucleic acid of any one of claims 1–3.

5. A kit for detecting the presence of a non-subtype B HIV-1 virus in a sample comprising a nucleic acid of any one of claims 1–3.

6. A kit for detecting the presence of a non-subtype B HIV-1 virus in a sample comprising a nucleic acid of claim 4.

* * * * *

SEQUENCE LISTING

<160> NUMBER OF SEQ ID NOS: 108

<210> SEQ ID NO 1
<211> LENGTH: 8968
<212> TYPE: DNA
<213> ORGANISM: Human immunodeficiency virus type 1
<220> FEATURE:
<223> OTHER INFORMATION: isolate=93BR020; 133..1611:gag; 4369.4947:vif;
4887.5177:vpr; 5158.7767:tat; 5297.7957:rev;
5396.5641:vpu; 5559.8099:env; 8101.8727:nef

<400> SEQUENCE: 1
ctgaaagcga aagtaaacca gagaagaact ctcgacgcag gactcggctt gctgaagtgc 60
acacggcaag aggcgagagc ggcgactggt gagtacgcca aaatttgact agcagaggct 120
agaaggagag agatgggtgc gagagcgtca gtattaagcg ggggaaaatt agatgcttgg 180
gaaaaaattc ggttaaggcc gggggaaag aaaaaatata gactaaaaca tctagtatgg 240
gcaagcaggg agctagaacg atttgcactt gatccaggcc ttctagaaac atcagaaggc 300
tgtcgaaaaa taataggaca gttacaacca tcccttcaga caggatcaga agagctcaaa 360
tcattatata atacaatagc agtcctctat tatgtacatc aaaaggtaga ggtaaaagac 420
accaaggagg ctttagagaa gctagaggaa gaacaaaaca aaggtcggca aaagacacag 480
caagcgactg ctgaaaaagg ggtcagtcaa aattacccta tagtacagaa tcttcaggga 540
caaatggtac accagtcttt atcacctaga actttaaatg catgggtaaa ggtgatagaa 600
gagaaggctt ttagtccaga agtaataccc atgttttcag cattatcaga aggggccact 660
ccacaagatt taaacaccat gttaaataca gtgggggac atcaagcagc catgcaaatg 720
ttaaaagaca ccatcaatga ggaggctgca gaatgggaca gattacatcc aacacaggca 780
ggacccatcc ccccaggtca gataagggaa cctaggggaa gtgatatagc tggaactact 840
agtacccttc aggaacaaat acaatggatg acaggcaacc cacctgtccc agtgggagaa 900
atgtataaaa gatggatcat cctaggatta aataaaatag taagaatgta tagccctgtc 960
ggcattttgg acataagaca agggccaaaa gaacccttta gagactatgt agacaggttc 1020
tttaaaaccc taagagctga gcaagctaca caggaagtaa agggttggat gacagacacc 1080
ttgttggtcc aaaatgcgaa cccagattgt aagaccattt taaaagcatt gggaccaggg 1140
gctacactag aggaaatgat gacagcatgt cagggagtgg gaggacctag ccataaggca 1200
agagttttgg ctgaggcaat gagccaagca acaaatacag ctataatgat gcagaaaagt 1260
aactttaagg gccaaagaag aattgttaaa tgctttaatt gtggcaaaga aggacacata 1320
gccaaaaatt gcagggcccc tagaaaaaag ggctgttgga agtgtggaag agagggacac 1380
caaatgaagg actgcactga gagacaggct aattttttag ggaaaatttg gccttccaac 1440
aaggggaggc ccggaaactt catccagaac aggccagagc cgtcagcccc gccagcagag 1500
agcttcaggt tcggggagga gacaacccca tctccgaagc aggagcagaa agacgaggga 1560
ctgtaccctc ccttagcttc cctcaaatca ctctttggca acgaccccta gtcacaataa 1620
gagtaggggg acagctaaag gaagctctat tagatacagg agcagatgat acagtattag 1680
aagacgtaaa tttgccagga aaatggaaac caaaaatgat aggggggaatt ggaggtttta 1740 tcaaagtaaa acagtatgat agcatactca tagaaatttg tggacacaga gctataggta 1800
cagtgttagt aggacctacg cctgtcaaca taattggaag aaatatgttg acccagattg 1860
gttgtacttt acattttcca attagtccta ttgagactgt accagtaaaa ttgaagccag 1920

-continued

```
gaatggatgg cccaaaggtt aaacaatggc cattgacaga agaaaaaata aaagcattaa   1980
cagaaatatg tatggaaatg gaaaaggaag gaaaaatttc aaaaattggg cctgaaaatc   2040
catacaatac tccagtattt gccataaaga aaaaagacag tactaaatgg aggaaattag   2100
tagatttcag agaacttaat aaaagaactc aagatttttg ggaggttcaa ttaggaatac   2160
cgcatccagc agggttaaaa aagaaaaagt cagtaacagt actggatgtg ggggatgcat   2220
atttttcagt tcccttagat aaggatttca ggaagtacac tgcatccacc atacctagta   2280
ccaacaatga gacaccagga gttaggtacc agtacaatgt gcttccacaa ggatggaaag   2340
gatcaccagc aatattccaa tatagcatga caaaaatctt agatcccttt agagcaaaaa   2400
atccagacat agttatctac caatacatgg atgatttgta tgtagggtct gacttagaaa   2460
taggacagca tagaacaaaa atagaagagt taagagaaca tctactgaaa tggggattaa   2520
ctacaccaga caaaaaacat caaaaagaac ccccattcct ttggatgggg tatgaactcc   2580
atcctgataa atggacagtg cagcctatac aattgccaga caaggacagc tggactgtca   2640
atgatataca gaagttagta ggaaaactaa attgggcaag tcagatttat ccagggatta   2700
aagtaaaaca attatgtaaa ctccttaggg gagccaaggc actaacagac atagtgccac   2760
tgactacaga agcagagtta gaattggcag agaataggga gattctaaaa gaaccagtac   2820
atggggcata ttatgacccg tcaaaagact taatagcaga aatacagaaa caagggcaag   2880
ggcaatggac atatcaaatt tatcaagagc catttaaaaa tctaaaaaca ggaaagtatg   2940
caaaaatgag gtctgcccac actaatgatg taaaacagtt aacagaagca gtgcaaaaga   3000
tatctctaga aagcatagta atatggggca agactcctaa gtttagacta cccatattaa   3060
aagagacatg ggatacatgg tggacagagt actggcaagc cacctggatt cctgagtggg   3120
agtttgtcaa tacccccccct ctagtaaaac tatggtatca gttagaaaca gagcccatag   3180
taggagcaga aaccttctat gtagatgggg catctaatag agagaccaaa aaaggaaaag   3240
caggatatgt tactgacaga ggaagacaaa aagcggtctc cctaactgag actacaaatc   3300
agaaggctga gttacaagca attcagttag ctttacagga ttcaggatca gaagtaaaca   3360
tagtaacaga ctcacagtat gcattaggaa tcattcaagc acaaccagat aagagtgaat   3420
cagagttagt caatcaaata atagagcaat taataaaaaa ggaaaaggtc tacctgtcat   3480
gggtaccagc acacaaaggg attggaggaa atgaacaagt agataaatta gtcagtgctg   3540
gaatcaggaa agtactgttt ctagatggga tagataaggc acaagaggaa catgaaaaat   3600
atcacaacaa ttggagagca atggctagtg attttaatat accagctgta gtagcaaaag   3660
aaatagtagc tagctgtgat aaatgtcagc taaaagggga agccatgcat ggacaagtag   3720
attgtagccc agggatatgg caattagatt gcacacattt agaaggaaaa attatcctgg   3780
tagcagtcca tgtagctagt gggtacctag aagcagaagt tatcccagca gaaacaggac   3840
aagagacagc ctacttccta ctaaagttag caggaagatg gccagtaaaa acaatacata   3900
cagacaatgg caccaatttc accagtgcca cggttaaggc agcttgttgg tgggcaggta   3960
tccagcagga atttggaatt ccttacaacc cccaaagtca aggagtagta gaatctatga   4020
ataaagagct aaagaaaatc ataggacaga taagagatca agctgaacat cttaagacag   4080
cagtccaaat ggcagtattc attcacaatt ttaaaagaaa agggggggatt gggggataca   4140
gtgcagggga aagaacaata gacataatag caacagacat acaaactaga gaattacaaa   4200
aacaaattat aaaaattcaa aatttccggg tttattacag ggacagcaga gacccagttt   4260
```

-continued

```
ggaaaggacc agcaaagcta ctctggaaag gtgaaggggc agtagtcata caagacaata   4320
gtgaaataaa ggtagttcca agaagaaaag caaagatcat tagggattat ggaaaacaga   4380
tggcaggtga tgattgtgtg gcaggtagac aggatgagga ttaacacatg gaaaagttta   4440
gtaaaatacc atatgcatat ttcaaagaaa gccaaaggat ggttttatag acatcacttt   4500
gaaagcaggc atccaaaaat aagttcagaa gtacacatcc cactagagac agctgaatta   4560
gtaataacaa catactgggg gctgcttcca ggagaaagag aatggcatct gggtcaggga   4620
gtctccatag aatggaggca ggggaggtat agaacacaaa tagaccctgg cctggcagac   4680
caactgatcc atatatatta ttttgattgt ttttcagaat ctgccataag gaaagccata   4740
ttaggacata aaattagccc taggtgtaac tatcaagcag gacataacaa ggtaggatct   4800
ctacaatact tggcactaac agcattaata gctccaaaaa agacaaagcc gcctttgcct   4860
agtgtccaga aactagtaga agacagatgg aacaagcccc agaagaccag gggccacaga   4920
gagagccata caatgaatgg acactagatc ttttagagga gcttaagaat gaagctgtta   4980
gacattttcc taggccatgg ctccatagct taggacaaca tatctataac acctatgggg   5040
atacttggga aggagttgaa gcaatcataa ggatattgca acaactactg tttatccatt   5100
tcagaattgg gtgccgtcat agcagaatag gcattactcg acagagaaga gtaagaaatg   5160
gaactagtag atcctaactt agatccctgg aaccatccag gaagccagcc tacaactcct   5220
tgtaccagat gttattgtaa atggtgttgc tttcattgtt actggtgctt tacaacgaag   5280
ggcttaggca tctcctatgg caggaagaag cggagacagc gaccaagaac tcctcaaagc   5340
agtcagatac atcaagattt tgtaccaaag cagtaagtat tgttaagcat atgtaatgtc   5400
aaatttgtta gcaataggca tagcagcatt aatagtagca ctaataataa caatagttgt   5460
gtggactata gcatatatag aatataagaa actggtaagg caaagaaaaa taaataggtt   5520
atataaaaga ataagcgaaa gagcagaaga cagtggcaat gagagtgagg gggatgcaga   5580
ggaattggca gcacttgggg aagtggggcc ttttattcct ggggacatta ataatctgta   5640
atgctgcaga aaacttatgg gttacagtct attatggggt acctgtgtgg aaagaagcaa   5700
ccactactct attctgtgca tcagatgcta aatcatatga aaaagaggca cataatgtct   5760
gggctacaca tgcttgtgta cccacagatc ccaatccaca agaagtagtt ctggaaaatg   5820
taacagaaag gtttaatatg tgggaaaata acatggtaga acaaatgcat acagatataa   5880
tcagtttatg ggatcaaagc ctaaagccat gtgtgaagtt aaccccactc tgtgttactt   5940
tagattgtag aaacattgcc accaatggca ccaatgacac tattgccatc aatgacactc   6000
tgaaggaaga tccagaggca atacaaaact gttctttcaa tacaaccaca gaaataagag   6060
ataagcagct gaaagtacat gcactttttt ataaacttga tatagtacaa atcaacaagg   6120
atgacaatag aacatacaga ctaataaatt gtgatgcctc aaccattaca caggcttgtc   6180
caaaggtatc ttgggatcca attcccatac attattgtgc tccagctggt tatgcgattc   6240
taaagtgtaa tgagaaaaat ttcacaggga cagggtcatg caagaatgtc agtacagtac   6300
aatgtacaca tggaattaaa ccagtggtat ccactcaatt gttgttaaat ggcagcctag   6360
cagaaggaga gatagtaatc agatctcaaa atatctcaga taatgcaaaa accataatag   6420
tgcaccttaa tgaatctgta cagattaatt gtacaagacc caacaacaat acaagaaaaa   6480
gaatatcttt aggaccagga cgagtatttt atacaacagg agaaataata ggagacatca   6540
gaaaggcaca ttgtaacgtt agtggaacac aatggaggaa cacgttagca aaggtaaagg   6600
caaagttagg gtcttatttc cctaatgcaa caataaaatt taactcatcc tcaggagggg   6660
```

-continued

```
acctagaaat tacaaggcat aattttaatt gtatgggaga atttttctac tgtaatacag   6720
atgaactgtt taatgacaca aaattcaatg acacaggatt caatggcact atcactctcc   6780
catgtcgaat aaaacaaatt gtaaacatgt ggcaggaagt gggacgagca atgtatgcca   6840
atcccattgc aggaaacatt acctgtaact caaatattac aggtctgcta ttgacaagag   6900
atggtggtct gaatagtact aatgagacct tcagacctgg gggaggaaat atgaaagaca   6960
attggagaag tgaattatat aaatataaag tagtagaaat tgaaccacta ggagtagcac   7020
ccaccaaggc aaaaagacaa gtggtgaaga gagaaagaag agcagtggga ctaggagctc   7080
tgttccttgg gttcttggga gcagctggaa gcactatggg cgcggcgtca ataacgctga   7140
cggtacaggc cagacaatta ttgtctggaa tagtgcaaca gcagagcaat ctgctgaggg   7200
ctattgaagc gcaacagcat ctgttgcagc tcacagtctg gggcattaaa cagctccagg   7260
caagagtcct ggctgtggaa agatacctaa aggatcaaca gctcctaggg ctttggggct   7320
gctctggaaa actcatctgc accactaatg tgccctggaa ctctagttgg agtaataaat   7380
ctcttgagga gatttggggg aacatgacct ggatggagtg ggaaaaagag gttagcaatt   7440
actcaaaaga aatatacagg ttaattgaag actcgcagaa ccagcaggaa aagaatgaac   7500
aagaattatt agcattggac aaatgggcaa gtctgtggaa ttggtttgac ataacacagt   7560
ggctgtggta tataaaaata ttcataatga tagtaggagg cttgataggc ttaagaatag   7620
tttttactgt gctttctata gtaaatagag ttaggaaggg atactcacct ttgtcatttc   7680
agacccatat cccaagcccg agggaacccg acaggcccga aggaatcgaa gaaggaggtg   7740
gagagcaagg caaagacaga tccgtgagat tagtgaccgg attcttagct cttgcctggg   7800
acgacctgcg gaacctgtgc ctcttcagct accgccactt gagagacttc atattaattg   7860
cagcgaggat tgtggacagg gggctgaaga gggggtggga agctctcaaa tatctgggga   7920
atctcacaca gtattggggt caggaactaa agaatagtgc tattagcttg cttaatgcca   7980
cagcaatagc agtagctgag tggacagata gagttataga agctttgcaa agagctggta   8040
gagctattct caacatacct agaagaataa gacagggctt ggaaagggct ttgctataaa   8100
atgggtggca agtggtcaaa aagtagtata gttggatggc ctgctataag ggaaagaatg   8160
aggcgaaccc ctccaacccc tccagcagca gagggggtgg gagcagtgtc tcaagactta   8220
gaaagacggg ggcaattac aagcagcaat actagagcta ataatcctga cttggcctgg    8280
ctggaagcac aagaggaaga cgaagtaggc tttccagtca gacctcaggt acctttaaga   8340
ccaatgacct ataagggagc tgtagatctc agtcactttt taaaagaaaa ggggggactg   8400
gaagggttaa tttactccaa gagaagacaa gagatccttg atctgtgggt ctaccacaca   8460
caaggctact tccctgattg gcagaactac acaccagggc cagggatcag atatccactg   8520
accatggggt ggtgcttcaa gctagtacca gttgacccag aggaggtaga aaaggccaat   8580
gaaggagaga acaactgctt gctacacccc atgagccaac atggaatgga ggatgaagac   8640
aaagaagtac tgaaatggga gtttgacagc cgcttggcac tgagacacat agccagagag   8700
agacatccgg agtactacca agactgagac tgctgacaca gagattgctg acacagaaga   8760
atctaaaggg actttccact ggggactttc cagagggtgg gccagagggc gggactgggg   8820
agtggctcac cctcagatgc tgcatataag cagccgcttt tcgcctgtac tgggtctctc   8880
tagttagacc agatttgagc ccgggagctc tctggctagc tagggaaccc actgcttaag   8940
cctcaataaa gcttgccttg agtgcttt                                      8968
```

-continued

<210> SEQ ID NO 2
<211> LENGTH: 8987
<212> TYPE: DNA
<213> ORGANISM: Human immunodeficiency virus type 1
<220> FEATURE:
<223> OTHER INFORMATION: isolate=92NG083; 156.362:gag; 1727.4465:pol; 4410.4988:vif; 4928.5218:vpr; 5199.7795:tat; 5338.8000:rev; 5440.5466:vpu; 5593.8142:env; 8144.8767:nef

<400> SEQUENCE: 2

```
atgaaagcga aagttaatag ggactcgaaa acgaaagttc cagagaagtt ctctcgacgc     60
aggactcggc ttgctgaagt gcacacagca agaggcgaga gcggcgactg gtgagtacgc    120
cattttttga ctagcggagg gctagaagga gagaggtggg tgcgagagcg tcagtattaa    180
gcgggggaaa attagattct tgggaaaaaa ttcggttaag gccaggggga aggaaaaagt    240
ataaactaaa acatatagta tgggcaagca gggaactggg gagatttgca cttaaccgtg    300
accttttaga aacagcagaa ggttgtgtgc aaataatgaa acagttgcaa ccagctctct    360
agacaggaac agaggagctt agatcattat ttaatacagt agcaaccctc tactgtgtac    420
atcaaaagat agaggtaaaa gacaccaaag aagctccaga ggaagtggaa aaaatacaaa    480
agaacagtca gcaagaaata cagcaggcag caaagaatga aggaaacagt aacccagtca    540
gccaaaatta tcctatagtg cagaatgcac aagggcaaat gatacatcag gccatatcac    600
ctaggacttt gaatgcgtgg gtaaaagtag tagaagaaaa ggccttcagt ccagaagtaa    660
tacccatgtt ttcagcatta tcagagggag ccaccccaca agatttaaat accatgctaa    720
atacagtggg ggggcatcaa gcagctatgc aaatgctaaa ggatactatc aatgatgaag    780
ctgcagagtg ggacaggata catccacagc aggcagggcc tattccacca ggccaaataa    840
gagagcctag tggaagtgat atagcaggaa ctactagtac cctgcaggaa caaataagat    900
ggatgaccag caacccacct atcccagtgg gagaaatcta taaaagatgg ataatcctgg    960
gattaaataa aatagtgaga atgtatagcc ctgtcagcat tttggacata agacaagggc   1020
caaaagaacc ctttagagat tatgtagata ggttctttaa aactttgaga gctgagcaag   1080
ctacacagga agtaaaaggt tggatgacag acaccttgtt ggttcaaaat gcgaacccag   1140
attgtaaaac catcttaaga gcattaggac caggagctac actagaagaa atgatgacag   1200
catgtcaggg agtgggagga cccagccata aagcaagagt tttagctgag gcaatgagcc   1260
aggcatcagg tgcagcagca gcagccataa tgatgcagaa aagcaatttt aagggcccga   1320
gaagaattat taagtgtttc aactgtggca aggaaggaca tctagccaga aattgcaggg   1380
cccctaggaa aaagggctgt tggaaatgtg gaaaggaggg acatcaaatg aaagaatgca   1440
cggaaaggca ggctaatttt ttagggaaaa tttggccttc caacaagggg aggccaggaa   1500
actttctcca gaacaggaca gagccaacag ccccaccagc agagagcttc ggattcggag   1560
aggagatagc cccctccccg aagcaggagc caaaggagaa ggagctatat cccttaactt   1620
ccctcaaatc actctttggc agcgacccct agtcacagta aaaatagggg gacagctaat   1680
agaagcccta ttagacacag gagcagatga cacagtatta gaaggaataa atttaccagg   1740
aaaatggaaa ccaaaaatga tagggggaat tggaggtttt atcaaagtaa gacagtatga   1800
tcaaatactt atagaaattg gtggaaaaaa ggctataggg acagtattag taggacctac   1860
acctattaac ataattggga gaaatatgtt gactcagatt ggttgtactt taaactttcc   1920
aataagtcct attgaaactg taccagtaaa attaaagcca ggaatggatg gcccaagggt   1980
```

-continued

```
taaacaatgg ccattgacag aagagaaaat aaaagcatta acagaaattt gtaaagacat   2040
ggaaaaggaa ggaaaaattt caaaaattgg gcctgaaaat ccatataaca ctccaatatt   2100
cgccataaag aaaaaagaca gtactaaatg gagaaaattg gtagatttca gagaacttaa   2160
taaaagaact caagacttct gggaggtcca attaggaata cctcaccccg cggggttaaa   2220
aaagaaaaga tcagtaacgg tactagatgt gggagatgca tacttttcag ttcccttaga   2280
taaagacttt agaaagtata ctgcatttac tatacctagt ataaataatg agacaccagg   2340
gattagatat caatacaatg tgcttccaca gggatggaaa ggatcaccag caatatttca   2400
gagtagcatg acaaaaattt tagagccttc tagaacaaaa aatccagaaa tggtgatcta   2460
ccaatacatg gatgatttat atgtaggatc tgacttagaa atagggcagc atagagcaaa   2520
aatagaggag ttaagagaac atctactgaa atggggattg accacaccag ataaaaaaca   2580
tcagaaagaa cctccattcc tttggatggg atatgagctc catcctgaca aatggacggt   2640
acaacctata cagctgccag aaaaggaaga ttggactgtc aatgatatac aaaagttagt   2700
gggaaaacta aattgggcaa gtcagattta tccagggatt aaagtaaagc acctatgtag   2760
actccttagg ggggccaaag cactaacaga catagtaccc ctaacggcag aagcagaaat   2820
ggagctggca gagaacaggg aaattctaaa agaacctgta catggagtct atcatgaccc   2880
atcaaaagaa ttaatagcag aagtacagaa gcaagggcca gaccaatgga catatcaaat   2940
ttatcaagag ccatacaaaa atctaaaaac aggaaaatat gcaaaaaggg ggtctgccca   3000
cactaatgat gtaaaacaat taacagaagt agtgcaaaaa atagccacag agggcatagt   3060
aatctgggga aagattccta aatttaaact acctatacga aaagaaacat gggaagtatg   3120
gtggacagag tactggcagg ccgcctggat tcctgagtgg gagtttgtca ataccccctcc  3180
tctagtaaaa ctatggtatc aattagaaac agaacccata ccaggagcag aaacttacta   3240
tgtagatggg gcagctaata gggagacaaa attaggaaag gcaggacatg ttactgacaa   3300
aggaaaacaa aaaattatta ccctaactga aacaacaaac caaaaggctg aattacatgc   3360
aattcaacta gctttgcagg actcaagacc agaagtaaac atagtaacag actcacagta   3420
tgcattagga atcattcaag cacaaccaga taggagtgga tcagaattag tcaatcaaat   3480
aatagaacag ctaataaaaa aggaaaaggt ctacctgtca tgggtaccag cacacaaagg   3540
gattggagga aatgaacaag tagataagct agtcagtagt ggaatcagga aagtattatt   3600
tttggatggc atagataaag cccaagaaga acatgaaaga tatcacagca attggagagc   3660
aatggctagt gattttaatc tgccacctgt agtagcaaaa gaaatagtgg ccagctgtga   3720
taaatgtcaa ctaaaagggg aagccatgca tggacaagta gactgtagtc caggaatatg   3780
gcaattagat tgtacacatt tagaaggaaa aattatcata gtagcagttc atgtagccag   3840
tggctatata gaagcagaag ttatcccagc agaaacaggg caggaaacag catactttat   3900
attaaaatta gcaggaaggt ggccagtaaa agtgatacat acagacaatg gtcccaattt   3960
catcagtgct gcagtaaagg cagcatgttg gtgggcaaat atcacacagg aatttggaat   4020
tccctacaat ccccaaagcc aaggagtagt ggaatctatg aataaggaat taaagaaaat   4080
catcggacag gttggagatc aagctgaaca tcttaagaca gcagtacaga tggcagtatt   4140
cattcacaat tttaaaagaa aaggggggat tgggggggtac agtgcagggg aaagaataat  4200
agacataata gcatcagata tacaaactaa agaactacaa aaacaaatta taaaaattca   4260
aaattttcgg gtttattaca gggacagcag agacccaatt tggaaaggac cagcaaagct   4320
actctggaaa ggtgaagggg cagtagtaat acaggacaat aacgaaataa aggtagtacc   4380
```

-continued

```
aagaagaaaa gcaaagatcc ttaaggatta tggaaaacag atggcaggtg gtgattgtgt   4440
ggcaggtaga caggatgagg attagaacat ggaacagttt agtaaaacat catatgtatg   4500
tctcaaagaa agctaaaggc tggttttata gacatcacta tgaaagcagg catccaagag   4560
taagttcaga agtacacatc ccactaagag atgctacact agtagtaaga acatattggg   4620
gtctgcatgc aggagaaaaa gactggcaat tgggccatgg ggtttccata gaatggaggc   4680
agaaaagata tagtacacaa atagacccta acacagcaga ccatctgatt catctgtatt   4740
attttgactg tttttcagaa tctgccataa gaaaagccat attaggagag atagttagcc   4800
ctaggtgtga atacccagca ggacataata aggtaggatc tctacaatat ctggcatcga   4860
aagcattagt aacaccaaca aggaaaaggc cacctttgcc aagtgttggg aaattagcag   4920
aagatagatg gaacaagccc cagaagacca gggaccacag agagaaccct acaatgaatg   4980
gacattagaa ctgttagaag agcttaaaaa tgaagctgtt agacattttc ctaggccctg   5040
gctccatggc ttaggacagt atatctataa cacttatggg gatacttggg aaggagttga   5100
agccataata agaatactac aacaactact gtttatccat ttcagaatcg ggtgccaaca   5160
tagcagaata ggcattactc cacagagaag agtaagggat ggacccggta gaccctaagc   5220
tagagccctg gaatcatccg gggagtcagc ctacaactcc ctgtaacaaa tgttattgta   5280
aagtgtgctg ctggcattgt caagtttgct ttttaaacaa aggcttaggc atctcctatg   5340
gcaggaagaa gcggagaccc cgacgaggaa ctcctcaggg cagtaaggat catcaaaacc   5400
ctgtaccaaa gcagtaagta gtaacaatta atatatgtaa tgcaggcctt agaaatatct   5460
gactaatagt agcattcata gcagccacaa ttgtgtggag tatagtattt atagaatata   5520
gaaaaataag aaaacagaaa aaaatagaaa agttacttga tagaataaga gaaagagcag   5580
aagacagtgg aaatgagagt gaaggggata cagaggaatt ggcaacactt atggaaatgg   5640
gggactttga tccttgggtt ggtaataatt tgtagtgcct cagataactt gtgggtcaca   5700
gtctattatg gggtacctgt gtgggaagat gcagataccc ccctattctg tgcctctgat   5760
gctaaatcat atagttctga aaaacataat gtctgggcta cacatgcctg tgtacccaca   5820
gaccctaacc cacaagaaat agctatagaa aatgtaacag aaaattttaa catgtggaag   5880
aataacatgg tagaacagat gcaggaggat ataatcagtt tatgggagga aagcctaaag   5940
ccatgtgtaa agctaactcc tctctgtatc actttaaact gtactaatgt aaacagtgct   6000
aatcatactg aggccaataa cactgtagaa aacaaagaag aaataaaaaa ctgctctttc   6060
aagataacca cagaaagggg aggcaagaag aaggaagaat acgcgctttt ctataaactt   6120
gatgtggtac caattagtaa tgggaataag actagttata ggctaataca ttgtaatgtc   6180
tcaaccatta aacaggcttg tccaaaggta aattttgacc caattcccat acattattgt   6240
gctccagctg gttttgcgat tttaaagtgt agggataagg agtacaatgg aacaggacca   6300
tgtaaaaatg tcagtacagt acaatgtaca catggaatta agccagtggt atcaactcaa   6360
ctactgctga atggcagttt agcagaagaa gatataagaa ttagatctga aaatttcaca   6420
gacaatacca aagtcataat agtgcagctt aataatagta tagaaattaa ttgtatcaga   6480
cccaataaca atacaagaaa aagtatacca atcggaccag gacaagcgtt ctatgcaaca   6540
ggtgatataa taggagacat aagacaagca cattgtaatg ttagtagaat aaaatggagg   6600
gagatgttaa agaatgtcac agcacagcta aggaaaatct ataataataa gaacataacc   6660
tttaactcat ctgcaggagg ggacctagaa attacaacac atagtttcaa ttgtagagga   6720
```

-continued

```
gagtttttct attgcaatac atcaggactg tttaataata atattagtaa tattaataat   6780
gagactatca cactcccatg taaaataaaa caaattgtga ggatgtggca gaaagtggga   6840
caagcaatgt atgcccttcc catcgcagga aaccttgtat gtaaatcaaa cattacagga   6900
ttaatattaa caagagatgg tgggaataac aatgacagta cagaggagac cttcagacct   6960
ggaggaggag atatgaggga caattggaga agtgaattat ataagtataa aacagtaaaa   7020
atcaaatcac taggagtagc acccaccagg gcaaggagaa gagtggtgga gagagaaaaa   7080
agagcagttg gactgggagc tgtcttcctt gggttcttag gagcagcagg gagcactatg   7140
ggcgcggcgt caataacgct gacggcacag gtcagacaat tattgtctgg catagtgcaa   7200
cagcaaagca atttgctgag ggctatagag gcgcagcagc atctgttgca actcacagtc   7260
tggggcatta aacagctcca gtcaagagtc ctggctatag aaagatacct aaaggatcaa   7320
cagctcctag ggatttgggg ctgctctgga aaactcatct gcaccactaa tgtgccctgg   7380
aacactagtt ggagtaataa atcttataat gagatttggg ataacatgac ttggctagaa   7440
tgggaaaggg aaattcacaa ttacacacaa cacatataca gcctgattga agaatcgcag   7500
aaccagcagg aaaagaatga acaagactta ttggcattgg acaagtgggc aagtttgtgg   7560
aattggtttg acatatcaaa ttggctatgg tatataagaa tattcataat gatagtagga   7620
ggtttaatag gtttaagaat agtttttgct gtgctttcta tagtaaatag agttaggcag   7680
ggatactcac ctttgtcgtt ccagaccctt acccatcacc agcgggaacc cgacaggctc   7740
ggaaaaaccg aagaaggagg tggcgagcaa gacagagaca gatccactcg attagtgagc   7800
ggattcttag cgcttgcctg ggacgacctg cggagcctgt gccttttcag ctaccaccgc   7860
ttgagggact tagtcttgat tgcagcaagg acggtggaac ttctgggacg cagcagcctc   7920
aagggactga gactggggtg ggaaggcctc aagtacttgt ggaacctcct gttgtattgg   7980
ggtcgggaac taaagaatag tgctattaat ttgcttgata caatagcaat agcaacagct   8040
aacgggacag atagggttat agaagtagca caaagagctt atagagctat tctcaacgta   8100
cctacaagga taagacaagg cttagaaaga gctttgctat aaaatggggg gcaagtggtc   8160
aaaaagtagc atagttggat ggcctcagat aagggaaaga ataagacaaa ctcctgtagc   8220
agcagaagga gtaggagcag tatctcaaga tttagctagg catggagcaa tcacaagcag   8280
caatacagca accaacaatc ctgattgtgc ctggctggaa gcacaagagg aggactcaga   8340
tgtaggcttt ccggtcagac cacaggtacc tttgagacca atgacttata aggctgcttt   8400
tgatctcagc ttctttttaa aagaaaaggg gggactggat gggctaattt actccaagag   8460
aagacaagac atccttgatc tatgggtcta taatacacaa ggattcttcc cagattggca   8520
gaactacaca ccagggccag ggactagact cccactgacc tttgggtggt gcttcaaact   8580
agtaccaatg gacccagcag agatagagga agccaataag ggagagaaca tcagtctatt   8640
acaccccatc tgccagcatg gaatggagga tgaagacaga gaagtgctgg tatggagatt   8700
taacagtagc ctagcacgga gacacctagc ccgagagctg catccggagt actacaaaga   8760
ctgctgacac agaagttgct gacaagggac tttccgcctg ggactttcca ggagaggcgc   8820
ggcctgggag ggctggggga gtggctaacc ctcagaagct gcatataagc agccgcttct   8880
cgcctgtact gggtctctct tgttggacca gatttgagcc tgggagctct ctggttggca   8940
ggggaaccca ctgcttaagc ctcaataaag cttgccttga gtgcttc                 8987
```

<210> SEQ ID NO 3
<211> LENGTH: 8953

-continued

<212> TYPE: DNA
<213> ORGANISM: Human immunodeficiency virus type 1
<220> FEATURE:
<223> OTHER INFORMATION: isolate="90CR056"; 137..1639:gene="gag";
4388..4966:gene"vif";
4906..5196:gene "vpr"; 5177..7782:gene="tat";
5316..7972:gene="rev"; 5408..5650:gene="vpu";
5577..8114:gene="env"; 8117..8737:gene="nef"

<400> SEQUENCE: 3
ttgatagtga aagtaaaacc agagaagatc tctcgacgca ggactcggct tgctgaagtg 60
cacacagcaa gaggcgagag cggcgactgg tgagtacgcc attttgtttt gactagcgga 120
ggctagaagg agagagatgg gtgcgagagc gtcagtatta agcggcggaa aattagatgc 180
ttgggagaaa attcggctaa ggccaggggg aaagaaaaaa tataggctaa aacatctagt 240
atgggcaagc agggagctgg aaagatttgc acttaacccc ggccttttag aaacaccaga 300
aggctgtcta cagataatag aacagataca gccagctatt aagacaggaa cagaagaact 360
taaatcatta tttaatctag tagcagtcct ctattgcgta catcgaaaaa tagatgtgaa 420
agacaccaag gaggctttag ataagataga ggaaatacaa aacaaaagtc agcaaaaaac 480
acagcaagca gcagctgata aggaaaaaga caacaaggtc agtcaaaatt atcctatagt 540
acagaatgct caagggcaga tggtacacca ggccatatca cctaggacct taaatgcatg 600
ggtaaaagta gtagaagaaa aggcttttag cccagaagta atacccatgt tttcagcatt 660
atcagaagga gccaccccac aagacttaaa tgctatgcta aatacagtgg ggggacatca 720
agcagccatg cagatgttaa aagatacaat caatgaggaa gctgcagaat gggacagggt 780
acatccagtg catgcagggc ctattccacc aggccaaatg agagaaccaa ggggaagcga 840
tatagcagga actactagta ccctgcagga acaaatagca tggatgacag gcaatccagc 900
tatcccagtg ggagacatct ataaaagatg gataatcctg ggattaaata agatagtaag 960
aatgtatagt cctgtcagca ttctggacat aaaacaaggg ccaaaagaac cctttagaga 1020
ctatgtagac aggtttttta aaactttaag agctgagcaa gccacacagg atgtgaagaa 1080
ttggatgaca gaaaccttgt tggtccaaaa tgcaaatcca gattgcaaga ctatattaag 1140
agcattagga caaggggctt caatagaaga aatgatgaca gcatgtcagg gagtgggagg 1200
acctagtcat aaagcaagag ttttggctga ggcaatgagc caagtaacaa atacaaatac 1260
agccataatg atgcagaaag gcaactttaa gggccaaaga aaatttgtta aatgcttcaa 1320
ctgtggcaaa gagggacaca tagccagaaa ttgcagggcc cctaggaaaa agggctgttg 1380
gaaatgtgga agagaaggac atcagatgaa agactgcaca gagagacagg ctaatttttt 1440
agggaaaatt tggccttcca gcaaagggag gccaggaaat ttctccaga gcaggccaga 1500 accaacagcc ccaccagcag agagcttcgg gttcggagag gagatgaccc cctctccgaa 1560
gcaggagcag ctgaaggaca aggaacctcc cttagcttcc ctcagatcac tctttggcag 1620
cgaccccttg ttacagtaaa aatagaggga cagttaaggg aagctctatt agatacagga 1680
gcagatgata cagtattaga agagataaat ttgccgggaa aatggaaacc aaaaatgata 1740
gggggaattg gaggttttat caaagtaaga cagtatgagc aagtagccat agaaatctgt 1800
ggaaaaaagg ctataggtac agtattagta ggacctacac ctgtcaatat aattggaagg 1860
aatatattga ctcaaattgg ttgcacctta aattttccaa ttagtcctat tgaaactgta 1920
ccagtaaaat taaagccagg aatggatggc ccaaaggtta aacaatggcc attgacagaa 1980
gaaaaaataa aagcattaac ggaaatttgt acagagatgg aaaaagaagg aaaaatctca 2040

-continued

```
agaatagggc ctgagaatcc atacagcact ccaatatttg ccataaaaaa gaaggatagt   2100
actaaatgga gaaaattagt ggatttcaga gaactcaata aaagaactca agacttctgg   2160
gaagttcagt taggaatacc acacccagca gggttaaaaa agaaaaaatc agtatcagta   2220
ctggatgtgg gggatgcata tttttcagtc cctttagata aagaattcag aaagtatact   2280
gcattcacca tacctagtat aaacaatgag acaccaggga ttagatatca gtataatgtg   2340
cttccacagg gatggaaagg atcaccagca atattccaga gtagcatgac aaaaatctta   2400
gcgcccttta gagaacaaaa tcctgaaatg gttatttacc aatacatgga tgatttgtat   2460
gtaggatctg acttagaaat agggcaacat agagcaaaaa tagaggagtt aagagctcat   2520
ttgttgaaat ggggatttac cacaccagac aaaaaacatc agaaagaacc cccatttctt   2580
tggatgggat atgaactcca tcctgacaaa tggacagtac agactgtaaa actgccagaa   2640
aaagacagct ggactgtcaa tgatatacag aagttagtgg gaaaactaaa ttgggcaagt   2700
cagatttatc caaatattaa agtaaagcaa ctatgtaaac tccttagggg ggccaaagca   2760
ttaacagaca taataccact gacaaaagag gcagaattgg aattggcaga aaacagggag   2820
attctgagag aaccaataca tggagtatat tatgatccat caaaagactt aatagcagaa   2880
atacggaagc aagggcaagg ccaatggaca tatcaaattt atcaggagcc atttaaaaat   2940
ctgaagacag gaaaatatgc aaaaatgaga actgcccaca ctaatgatat aaaacaatta   3000
acagaagcag tgcaaaagat atctacagaa agcatagtaa tatggggaaa aattcctaaa   3060
tttagactac ctatacaaaa agaaacatgg gagacctggt ggacagagta ttggcaagcc   3120
acatggattc ctgaatggga gtttgttaac acccctcatc tagtaaaatt atggtatcag   3180
ttagaaacag agcccatagc aggagcagaa acttactata tagatggggc agctaatagg   3240
gaaactaaat taggaaaagc aggatatgtc actgatagag gaaagcaaaa agttgtctcc   3300
ctaacggaaa caacaaatca gaagactgaa ttacaagcaa tttatctagc tttgcaagat   3360
tcagggttag aagtgaacat agtgacagat tcacagtatg cactaggaat cattcaagca   3420
caacccgata agagtgaatc agagttagtt aatcaaataa tagaggaatt aataaagaag   3480
gaaaaggtct acctgtcatg ggtaccagca cacaaaggaa ttggaggaaa tgaacaagta   3540
gataaattag ttagttctgg agtcagaaaa gtgctatttc tagatgggat agataaagct   3600
caagaagaac atgaaaggta tcataacaat tggagagcag tggctagtga ttttaatcta   3660
ccacctatag tagcaaaaga aatagtagct agctgtgata aatgtcagct aaaaggggaa   3720
gccatgcatg gacaagtaga ctgtagccca ggaatatggc aattagattg cacacatttg   3780
gaaggacaag ttattctggt agcagtccat gtagccagtg gctatataga agcagaagtc   3840
atcccagcag aaacaggaaa ggaaacagca tacttcctgt tgaaactagc aagcagatgg   3900
ccagtaaaag taatacatac agacaatggc agcaatttca cgagtgctgc ggttaaggca   3960
gcctgttggt gggcagatat ccaacaggaa tttgggattc cctacaatcc ccaaagtcag   4020
ggagtagtag aatctatgaa taaagaatta aagaagatca tagggcaggt aagagaccaa   4080
gcagaacacc ttaagacagc agtacaaatg gcagtattca ttcacaattt taaaagaaaa   4140
gggggggattg gggggtacag tgcaggggaa agaataatag acataatagc aacagacata   4200
caaactaaag aattacaaaa acaaatttca aacattcaaa aatttcgggt ttattacagg   4260
gacagcagag acccaatttg gaaaggacca gcaaaactcc tctggaaagg tgaaggggca   4320
gtagtaatac aagacaatag tgaaataaaa gtagtaccaa gaagagaggc aaaaatcatt   4380
agggattatg gaaaacagat ggcaggtgat gattgtgtgg caagtagaca ggatgaggat   4440
```

-continued

```
taacacatgg aaaagcttag taaagtacca tatgcatatt tcaaggaaag ctagaggatg   4500
gttttataga catcattttg aaagcactca tccaaggata agttcagaag tacacatccc   4560
attaggagaa gctaggttag tcataaccac atactggggt ctgaatacag gagaaagaga   4620
atggcattta ggccagggag tctccataga atggagactg aaaaggtata gcacacaagt   4680
agagcctggc ctggcagacc aactaattca tatgcattat tttgattgtt tttcagaatc   4740
tgccataagg aaagccatat taggacgtgt agttagacct aggtgtaact atccagcagg   4800
acataaacag gtaggaactc tacaatactt ggcattaaca gcattagtgg caccaaaaaa   4860
gataaagcca cctttgccta gtgttagaaa gctagtagag gatagatgga acaagcccca   4920
gaagaccagg ggccacagag ggagccacac aatgaatgga cactagagct tttagaggag   4980
attaagaatg aggctgttag gcattttcct agagtatggc tccatcaatt aggacagcat   5040
atctataaca cctatggaga tacttgggta ggagttgaag ctttaataag aacgctgcaa   5100
caactactgt ttattcattt cagaattggg tgccaacata gcagaatagg aattactcga   5160
cagagaagag taagaaatgg acccagtaga tcctaaacta gagccctgga accatccagg   5220
aagtcagcct caaactgctt gtaacaattg ttattgtaaa aagtgctgct atcattgcca   5280
aatgtgcttt ttaaagaaag gcttaggaat ttcctatggc aggaagaagc ggagccagcg   5340
acacagaact cctgcaagtt tgcaagatca tcaaaattct atatcaaagc agtaagtatt   5400
atcataaatg tatatattag gattaggaat aggagcgcta gtagtaacat ttatcatagc   5460
cgtaattgtg tggaccatag tatatataga atataaaaaa ttggtaaggc aaaagaaaat   5520
agacaggcta attgaaagaa taggagaaag agcagaagac agtggcaacg agagtgatgg   5580
agacacagag gaattatcca agcttatgga gatggggcac cttaatcttg ggtatgttgc   5640
tgatctgtag tgctgcacaa aacttgtggg ttacagtata ttatggggta cctgtgtgga   5700
aagaggcaaa aaccactcta ttctgtgcat cagatgctaa ggcatatgag acagaaaagc   5760
ataatgtctg ggctacacat gcatgtgtac ccacagaccc caacccacaa gagatggtca   5820
tggagaatgt aacagagagc tttaatatgt gggaaaataa catggtggag cagatgcata   5880
cagacataat cagtttatgg gatcaaagct tgaaaccatg tgtaaaatta accccactct   5940
gtgttactct aaactgtact aatgtcagaa acaatacctc taacagcact agcagtatgg   6000
aggcaggagg ggaactaaca aattgctctt tcaatgtaac tacagtacta agagataagc   6060
agcagaaagt acatgcactc ttttatagac ttgatgtagt accaattgat aacaatagta   6120
ctcagtatag gctaataaat tgtaatacct cagtcattac acaggcttgc ccaaaggtgt   6180
cctttgaacc tattcccata cattattgtg ctccagctgg ctttgcgatt ctaaagtgta   6240
acaataaaac attcaatgga acaggattat gtacaaatgt cagtacagta caatgtacac   6300
atggaattag accagtggta tcaactcaac tgctattaaa tggaagccta gcagaagaac   6360
agatcataat tagaactaaa aatatctcag acaataccaa aaacataata gtacagctta   6420
agacaccagt aaacattaca tgtaccaggc ctaacaataa tacgagaaca agtatacatt   6480
tagggccagg acgagcattc tatgcaacag gtgacatcat aggagatata agacaagcac   6540
attgtaatat tagtagaaca gactggaata agactttaca ccaggtagtt acacaattag   6600
gaatacactt gaacaataga acaataagct ttaagccaaa ctcaggaggg gacatggaag   6660
ttagaacaca tagttttaat tgtagaggag aatttttcta ttgcaataca tcagggctgt   6720
ttaatagtag ttgggaaatg catactaatt acacatcaaa tgacacaaag ggaaacgaaa   6780
```

-continued

```
acattacact gccatgcaga ataaaacaaa ttgtaaacat gtggcagaga gtaggacgag   6840

caatgtatgc ccctcccatc caaggaaaca ttatgtgtgt atcaaatatt acaggactaa   6900

tattgacaat tgacgagggt aacgcgtctg cagaaaatta taccttcaga cctggaggag   6960

gagatatgag ggacaattgg agaagtgaat tgtataaata taaagtagta aaaattgaac   7020

cactgggaat agcacccacc aagacaagga gaagagtggt ggagagagaa aaaagagcag   7080

tgggaatggg agcttctttc cttgggttct tgggagcagc aggaagcact atgggcgcgg   7140

cgtcaataac gctgacggta caggccaggc aattattgtc tggtatagtg cagcagcaaa   7200

gcaatttgct gagagctata caggcgcgac agcatatgtt gcagctcacg gtctggggca   7260

ttaaacagct ccaggcaaga gtcctcgctg tggaaagata cctaagggat caacagctcc   7320

tggggatttg ggctgctct ggaaaactca tctgcaccac taatgtgcct tggaactcta   7380

gttggagtaa taaatcacag agtgaaatct gggacaacat gacttggatg gaatgggata   7440

aacaaattag caattacaca gaggaaatat acaggttgct tgaagtctcg caaacccagc   7500

aggaaaagaa tgaacaggac ttattagcat tggacaaatg ggcaagtctg tggacttggt   7560

ttgacatatc acattggctg tggtatataa aaatattcat aatgatagta ggaggtttaa   7620

taggtttaag aataattttt gctgtgcttt ctatagtaaa tagagttagg cagggatact   7680

cacctttgtc ttttcagacc cttgtcccga acccacgggg acccgacagg cccgaaggaa   7740

cagaagaagg aggtggcgag caagacagag acagatccgt gagattagtg aacggattct   7800

taccagttgt ctgggacgac ctccggagcc tgtcactctt cagctaccgc ctcttgagag   7860

acttactctt aattgtagtg aggactgtgg aacttctggg gagaaggggg agggaagccc   7920

tcaaatatct ctggaatctt ctacaatact ggggacagga actaaagaat agtgctattg   7980

atttgcttaa caccacagca atagcagtag ctgagggaac agatgggatt atagtaatag   8040

tgcaaagagc ttggagagct attctccaca tacctagaag aataagacag ggctttgaaa   8100

gaagcttgct ataataatgg gaggcaaatg gtcaaaaagt aggatgggtg ggtggtctac   8160

tataagggaa agaatgaggc gagctgaacc agtagcagaa ggggtaggag cagtgtctcg   8220

agatttggat agacgcgggg cagtcacaat taataataca gcatctacta atcgtgatgc   8280

cgcctggctg gaagcacaag aggacgggga ggaagtaggc tttccagtca ggcctcaggt   8340

acctttaaga ccaatgacct ataagggagc ttttgatctc agccattttt taaaagaaaa   8400

ggggggactg gatgggttaa tttactccaa gcaaagacag gacatccttg atttatgggt   8460

ctataacaca caaggctact tccctgactg gcagaactac acaccagggc caggggagag   8520

atttcccctg acctttgggt ggtgcttcaa gctagtacca gtaaatccac aggaggtaga   8580

acaggccaat gaaggagaga acaacagctt gctacacccc atgagcctgc atggaatgga   8640

ggatgacggg agagaagtgc tgatgtggaa atttgacagt cgactagcat tgacacactt   8700

ggcccgagta aagcatccgg agtacaaaga ctgctgacac agaagatctg aaagggactt   8760

tccgctggga ctttccgggg aggcgtgatc tgggcgggga tggggagtgg ccaaccctca   8820

gatgctgcat ataagcagct gcttttcgct tgtactgggt ctctttggtt agaccagatc   8880

tgagcctggg agctctctgg ctagctaagg aacccactgc ttaagcctca ataaagcttg   8940

ccttgagtgc ttt                                                      8953
```

<210> SEQ ID NO 4
<211> LENGTH: 8992
<212> TYPE: DNA
<213> ORGANISM: Human immunodeficiency virus type 1

-continued

```
<220> FEATURE:
<223> OTHER INFORMATION: isolate=92RW009; 139.1624:gag; 1690.4428:
      pol(N-terminus uncertain);
      4373.4951:vif; 4891.5181:vpr; 5162.7801:tat; 5301.7958:rev;
      5403.5648:vpu; 5566.8148:env; 8150.8773:nef

<400> SEQUENCE: 4

atgaaagcga aagtaagacc agaggagatc tctcgacgcg ggactcggct tgctgaaagt     60

gcactcggca agaggcgaga gcggcggctg gtgagtacgc caaattttat ttgactagcg    120

gaggctagaa ggagagagat gggtgcgaga gcgtcaatat taagaggcgg aaaattagat    180

gcctgggaaa aaattaagtt aaagccaggg gggaaagaaa acatatatga tgaaacacct    240

agtatgggca agcagggagc tggaaagatt tgcacttaac cctgaccttt tagagacacc    300

agaaggctgt aaacaaataa tgagacagct gcaaccagct cttcagacag gaacagatga    360

acttaggtca ttatataata cagtagcaac cctctattgt gtacatcaaa agatagatgt    420

aaaagacacc aaggaggcct tagacaagat agaggaagaa caaaacaaaa gtcagcaaaa    480

aacacagcag gcagaagcag ctgacaaagg aaaagtcagt caaaattacc ctatagtgca    540

aaatgcacaa gggcaaatgg tacaccaggc catatcacct agaactttga atgcgtgggt    600

aaaagtaata gaggagaagg cttttagcca agaggtaata cccatgttta cagcattatc    660

agaaggagcc accccacaag atttaaacac catgctaaat acagtggggg gacatcaagc    720

agccatgcaa atgctaaaag atacaatcaa tgaggaggct gcagagtggg atagggtaca    780

tccagtgcag gcagggcctg ttgcgccagg ccagataaga gaaccaaggg gaagtgacat    840

agcaggaact actagtaccc ttcaggaaca aatagcatgg atgacaaata acccacctat    900

tccagtggga gaaatttata aaagatggat aattctgggg ttaaataaaa tagtaagaat    960

gtatagccct gtcagcatat tggacataaa acaagggcca aaggaacctt ttagagacta   1020

tgtagaccgg ttctttaaaa ccttaagagc cgaacaagct tcacaagatg taaaaaattg   1080

gatgacagat accttgttag tccaaaatgc gaacccagat tgtaagacca ttttaagagc   1140

attagggcca ggggcttcat tagaagaaat gatgacagca tgccagggag tgggaggacc   1200

cggccataaa gcaagggttt tggctgaagc aatgagccaa gtacaacaac caaacataat   1260

gatgcagaga ggcaatttta agggccagag aagaattatt aagtgtttca actgtggcaa   1320

agaaggacac ctagccagaa attgcagggc ccctagaaaa aagggctgtt ggaaatgtgg   1380

aaaggaggga caccaaatga aagactgcac tgagagacag gctaattttt tagggaaaat   1440

ttggccttcc aacaagggga ggccaggaaa ttttccccag agcagactgg agccaacagc   1500

cccaccagca gagaactttg gaatggggga agagatagcc tctcctctga aacaggagca   1560

gaaagacagg gaacctttaa tttccctcaa atcactcttt ggcaacgacc ccttgtcaca   1620

gtaaaaatag gaggtcagct aagagaagct ctattagata caggagcaga tgatacagta   1680

ttagaagaaa taaatttgcc aggaaaatgg aaaccaaaaa tgatagggggg aattggaggt   1740

tttatcaagg taaaacagta tgatcaaata cttatagaaa tttgtggaaa aaaggctata   1800

ggtacagtat tagtaggacc tacatctgtc aacataattg gaagaaatat gttgacccag   1860

attggttgta ctttaaactt tccaattagt cctattgaga ctgtaccagt agcattaaag   1920

ccaggaatgg atggcccaaa ggttaaacaa tggccattga cagaagaaaa aataaaagca   1980

ttaagagaaa tttgtacaga aatggaaaaa gagggaaaaa tttcaaaaat cgggcctgaa   2040

aatccatata acactccagt atttgccata aaaaagaagg acagtactaa gtggagaaaa   2100

ttagtagatt tcagggaact caacaaaaga actcaagact tttgggaagt ccaattaggg   2160
```

-continued ataccacacc cagcagggtt aaagaagaaa aaatcagtga cagtactgga tgtgggggat 2220
gcatacttct cagttccttt agatgagagc ttcaggaaat atactgcatt caccatacct 2280
agtataaaca atgaaacacc aggaattagg tatcaatata atgtgcttcc acagggatgg 2340
aaaggatcac cagcaatatt ccaaaatagt atgacaaaaa tcttagagcc ctttagggca 2400
caaaaccaag aaatagtgat ctatcaatat atggatgact tgtacgtagg atctgactta 2460
gaaatagggc aacatagagc aaaaatagag gagttaagag aacatctatt aaagtgggga 2520
tttaccacac cagacaagaa acatcagaaa gaacctccat ttctttggat ggggtatgaa 2580
cttcatcctg acaaatggac agtacaacct atacagctgc cagaaaagga tagctggact 2640
gtcaatgata tacagaagtt agtgggaaaa ttaaactggg caagtcagat ttacccaggg 2700
gttaaagtaa ggcaattgtg taaactcctt aggggaacca aagcattaac agacatagta 2760
ccactaactg aagaagcaga attagaattg gcagaaaaca gggaaatttt aaaagaacca 2820
gtacatggag tatattatga cccatcaaaa gacttaatag ctgaaataca gaaacagggg 2880
catgaccaat ggacatatca aatttaccaa gaaccattca aaaatctgaa aacaggaaag 2940
tatgcaaaaa ggaggactgc ccacactaat gacgtaaaac agttaacaga ggcagtgcaa 3000
aagatagcca tggaaagcat agtaatatgg ggaaagactc ctaaatttag attacccatc 3060
cagaaagaaa catgggaaac atggtggaca gactattggc aagccacctg gattcctgag 3120
tgggagtttg ttaatacccc tcccctagta aaattatggt accagctaga gaaagaaccc 3180
atattaggag cagagacttt ctatgtagat ggagcagcta atcgggaaac taaaatagga 3240
aaagcagggt atgttactga cagaggaagg cagaaaattg tttctctaac tgaaacaaca 3300
aatcagaaga ctgaattaca agcaattcag ctagctttac aggattcagg atcagaagta 3360
aacatagtaa cagactcaca gtatgcatta ggaatcattc aagcacaacc agatagcagc 3420
gaatcggagg cagtcaatca aataatagaa cagttaataa aaaaggaaag agtctacctg 3480
tcatgggtac cagcacataa aggaattgga ggaaatgaac aagtagataa attagtaagt 3540
agtggaatca ggagagtgct gtttctagat ggaatagata aggctcaaga agaacatgaa 3600
agatatcaca gcaattggag agcaatggct agtgatttta atctgccacc tatagtagca 3660
aaggaaatag tagccagctg tgataagtgt cagctaaaag gggaagccat gcatgggcaa 3720
gtagactgta gtccagggat atggcaatta gactgtacac atctggaagg aaaaataatc 3780
ctggtagcag tccatgcagc cagtggttat atagaagcag aggttattcc agcagaaaca 3840
ggacaagaaa cagcatactt tatactaaaa ttagcaggaa gatggccagt caaagtaata 3900
catacagaca atggcagtaa tttcaccagt aatacagtta aagcagcctg ttggtgggca 3960
ggtatccaac aggaatttgg aattccctac aatccccaaa gtcagggagt aatagaatcc 4020
atgaataaag aattaaagaa aatcataggg caggtaagag atcaagctga gcaccttagg 4080
acagcagtac aaatggcagt attcattcac aattttaaaa gaaaaggggg gattgggggg 4140
tacagtgcag gggaaagaat aatagacata atagcaacag acatacaaac taaggaatta 4200
caaaaacaaa ttacaaaaat tcaaaatttt cgggtttatt acagggacag cagagatcca 4260
atttggaaag gaccagccaa actactctgg aaaggtgaag ggcagtagt aatacaggac 4320
aatagtgata taaaagtagt accaagaaga aaagcaaaga tcattaggga ttatggaaaa 4380
cagatggcag gtgatgattg tgtggcaggt agacaggatg aagattagaa catggaatag 4440
tctagtaaag caccatatgt atgcttcaag gagagctaag ggatggtttt atagacatca 4500

-continued

```
ttatgaaagc agacatccaa aaataagttc agaagtacac atcccattag gggaagctag   4560
attagtaata aaaacatatt ggggtttgca aacaggggaa agagattggc atttgggtca   4620
tggagtctcc atagaatgga gattgagaag atataagaca caagtagacc ctggcctggc   4680
aggccaacta atccatatgc attattttga ttgttttgca gactctgcca taaggaaagc   4740
catattagga catatagtta gccctaggtg tgactatcaa gcaggacata ataaggtagg   4800
atctctacaa tacttggcac tgacagcatt gataaaacca aaaaagataa agccacctct   4860
gcctagtgtt agtaaattag tagaggataa atggaacaag ccccagaaga ccaggggccg   4920
cagagggaac catacaatga atggacacta gagcttttag aggcactcaa gcaggaagct   4980
gtcagacact ttcctagacc atggctccat gacttaggac aatatatcta tgaaacctat   5040
ggggatactt ggaggggagt agaagctata ataagaattc tgcaacaact actgtttatc   5100
catttcagaa ttgggtgccg gcatagcaga ataggcattt tgcaacagag aagagcaaga   5160
aatggagcca gtagatccta aactagagcc ctggaaccat ccaggaagtc agcctaaaac   5220
tgcctgtaat aactgttatt gtaaacactg tagctatcat tgtctagttt gcttccaggc   5280
aaaaggctta ggcatttcct atggcaggaa gaagcggaga cagcgacgaa acgctcctcc   5340
aagcagtgaa gatcatcaaa atcctatatc aaagcagtaa gtagtaataa acagtatatg   5400
taatgacttc tttagaaatc tatgcaatag tagcactgat agtggcgcta atcatagtga   5460
tagttgtgtg gactttagca ggtatagaat ataagaaatt gctaaagcaa aggaaaatag   5520
ataggttaat taagaaaata agagaaagag cagaagatag tggcaatgag agtgatgggg   5580
acattgatga attatcaaaa cttgtggggg tggggaacta tgatcttggg gatgttaaca   5640
atttgtagtg ctgcaaacaa cttgtgggtt actgtctact atggggtacc tgtgtggaaa   5700
gacgcagaga ccaccttatt ttgtgcatca gatgctaaag catatgatcc agaaaagcat   5760
aatgtctggg ctacacatgc ctgtgtaccc atagaccccg acccacaaga aatacatttg   5820
gaaaatgtga cagaagagtt taacatgtgg aaaaataaca tggtagagca gatgcataca   5880
gatataatca gtctatggga ccaaagccta aagccatgtg taaagttaac ccctctctgc   5940
gttactttag agtgtaacaa catcaccaat gtcaacaaca ctgtcaacat tacggatgac   6000
atgaaaggag aaataaaaaa ctgctctttc aatatgacca cagaattaag ggataagaaa   6060
cagagagtgt attcactttt ttataggctt gatatagtac aaattaatag caatagtaat   6120
aacagtagtc ataatcagta taggttaata aattgtaata cctcagccat tacacaggct   6180
tgtccaaagg tatcctttga gccaattccc ataaattatt gtgccccagc tggtttcgcg   6240
attctaaagt gtaaagataa aaagttcaat ggaacagggc catgcaagaa tgtcagcaca   6300
gtacaatgca cacatggaat caagccagta gtatcaactc agctgctgtt aaatggcagt   6360
ctagcagaag aagagataat aattagatct gaaaatatta caaacaatgc caaaaccata   6420
atagtacaac ttaacgagac tgtacaaatt aattgttcca gacctaacaa caatacaaga   6480
aaaagtgtac atataggacc aggacaagca ttttatgcaa caggtgacgt aataggggat   6540
ataagacaag catattgtac tgtcaatgga acaaaatgga atagaacttt acaaaaggta   6600
gcagaaaaat taagtcacta ctttgagaac attacaacaa taatttttaa gaactcctca   6660
gggggggatt tagaaattac aacacatagt tttaattgtg gaggagaatt tttctattgt   6720
aatacatcag gcttgtttaa tagcacctgg agtaaaagaa atggcacctg gcagtcaaat   6780
ggcacagaat taaatataac actcccatgc agaataaagc aaattataaa tatgtggcag   6840
aggacaggac aagcaatgta tgcccctccc atccaaggag taataagctg tgtatcaaac   6900
```

-continued

```
attacaggac tactattaac aagagatggt ggaaataata atactacaac tgaaaccttc   6960
agacctggag gaggagatat gagggataat tggagaagtg aactatataa atataaagta   7020
gtaaaaattg aaccactagg agtagcaccc accagggcaa agaggagagt ggtggagaga   7080
gaaaaaagag cagttggact gggagctgtc ttcattgggt tcttaggagc agcaggaagc   7140
actatgggcg cggcgtcaat aacgctgacg gtacaggcca gacaattatt gtctggcata   7200
gtgcaacagc aaagcaattt gctgagggct atagaggctc aacagcatct attaaaactc   7260
acagtctggg gcattaaaca gctccaggca agagtcctgg ctctggaaag atacctaagg   7320
gatcaacagc tcctaggaat ttggggctgc tctggaaaac tcatctgcac cactaatgtg   7380
ccctggaact ctagttggag taataagact cagcaggaaa tatgggataa catgacctgg   7440
cagcaatggg ataaagaaat tggcaattac acacaaataa tatatagtct aattgaagaa   7500
tcgcagaacc agcaggaaaa gaatgaacaa gacttattgg cattggacaa gtgggcaaat   7560
ctgtggaatt ggtttgacat atcaaattgg ctgtggtata taaaaatatt cataatgata   7620
gtaggaggct taataggttt aagaataatt tttgctgtgc tctctatagt gaacagagtt   7680
aggcagggat actcaccatt atcgtttcag acccttatcc caaacccgag gggacccgac   7740
aggctcggag gaatcgaaga agaaggtgga gagcaagaca gaggcagatc cattcgatta   7800
gtgagcggat tcttagcact tgcctgggac gacctacgga gcctgtgcct tttcagctac   7860
caccgattga gagacttact attgattgca gcgaggacgg tggaacttct gggacgcagc   7920
agtctcaggg gactacagag gggtgggaa acccttaagt atctaggaaa tcttgtgcag   7980
tattggggtc tggaactaaa aaggagtgct attaatctgc ttgataccac agcaatagta   8040
gtagctgaag gaacagatag gattatagaa ttaatacaaa gaattagcag agctatctat   8100
aacataccta gcagaataag acagggcttt gaagcagctt tgcaataaaa tgggaagcaa   8160
gtggtcaaaa tgtagtccag taggatggcc tgctgtaaga gaaagactaa ggcaaactga   8220
gccagcagca gagggagtag gagcagcgtc tcaagaccta gacaaatatg gggcacttac   8280
aagtagcaac acacccagca acaatgctga ttgtgcctgg ctggcagcac aagaggagga   8340
aaacgaagta ggctttccag tcagacctca ggtgccttta agaccaatga cttataaagc   8400
agcagttgat ctcagcttct ttttaaaaga aaaggggga ctggaagggt taatttactc    8460
taagaaaagg caagacatcc tggatttgtg ggtctataac acacaaggct acttccctga   8520
ttggcaaaac tacacaccag gaccaggggt cagatatcca ctgacttttg gatggtgtta   8580
caagctagtg ccagttgacc caagggaagt ggaagaagcc aatgaaggag aggacaactg   8640
cttactacac cctctgagcc agcatggaat ggaggatgag gacagagaag tcttaaagtg   8700
gaagtttgac agtcacctag cacacagaca catggcccgc gagctacatc cggagtatta   8760
taaagactgc tgacacagaa gggactttcc gctgggactt tccactgggg cggtccagga   8820
ggtgtggtct gggcgggacg gaggagtggc caaccctcag atgctgcata taagcagctg   8880
ctttttgcct gtactgggtc tctctgggta gaccagatct gagcctggga gctctctggc   8940
tatctaggga acccactgct taagcctcaa taaagcttgc cttgagtgct ct           8992
```

<210> SEQ ID NO 5
<211> LENGTH: 8966
<212> TYPE: DNA
<213> ORGANISM: Human immunodeficiency virus type 1
<220> FEATURE:
<223> OTHER INFORMATION: isolate="92NG003"; 157..1650:gene:"gag";
4408..4986:gene:"vif";

-continued

4926..5039:gene:“vpr”; 5184.7762:tat;
5323..7967:gene:“rev”; 5425..5654:gene:“vpu”;
5572..8109:gene:“env”; 8111..8731:gene:“nef”

<400> SEQUENCE: 5

```
ttgaaagcga aagttaacag ggactcgaaa gcgaaagttc cagagaagtt ctctcgacgc     60
aggactcggc ttgctgaggt gcacacagca agaggcgaga gcggcgactg gtgagtacgc    120
caattttttt gactagcgga ggctagaagg agagagatgg gtgcgagagc gtcagtatta    180
agcgggggaa aattagatgc atgggaaaaa attcggttga ggccaggggg aaagaaaaaa    240
tatagaatga aacatttagt atgggcaagc agggaactgg agagatttgc acttaaccct    300
gacctcttag aaacaacaga aggttgtcag caaataatga gacagctgca accatctctc    360
cagacaggaa cagaggagat taaatcatta tttaatacag tagcaaccct ctattgtgta    420
catcaaagga tagaggtaaa agacaccaaa gaagctctag aggaagtgga aaaaatacaa    480
aagaacagtc agcaagaaac acagaaggca gcaatgggta aaggaaacag cagccaagtt    540
agccaaaatt atcctatagt gcagaatgca caagggcaag tggtacacca gcccatatca    600
cctaggactt taaatgcatg ggtaaaagta atagaagaaa agaacttcag tccagaagta    660
atacccatgt ttacagcatt atcagaagga gccacccccac aagatttgaa taccatgcta    720
aacaccgtgg gggggcatca agcagctatg caaatgctaa aagattctat taatgaagaa    780
gctgcagagt gggataggct acatccacaa caggcaggac ctattccacc aggccagata    840
agagaaccaa ggggaagtga tatagcagga actactagta ccctgcagga acaaataaca    900
tggatgacca gcaacccacc tatcccagtg ggagaaattt ataaaagatg gataattctg    960
gggttaaata aaatagtgag aatgtatagc cctgtcagta ttttagacat aaaacaaggg   1020
ccaaaagaac ccttcagaga ttatgtggat aggttcttta aaactttgag agctgagcaa   1080
gccacacagg aggtaaaaaa ctggatgaca gacaccttgt tggtccaaaa tgcgaaccca   1140
gattgtaaga ccatcctaag agcattagga gcaggagcta cactagaaga aatgttgaca   1200
gcatgtcaag gagtgggagg acccagccac aaagcaagag ttttagctga ggcaatgagc   1260
cgggcaacag gtacatcagc agccataatg atgcagaaaa acaattttaa gggcccgaga   1320
agaggtatta agtgtttcaa ctgtggcaag gaaggacatc tagccagaaa ttgcagggcc   1380
cctaggaaaa aaggctgttg gaaatgtgga aaggagggac atcaaatgaa agactgcaca   1440
gagagacagg ctaatttttt agggaaaatt tggccttcca acaaggggag gccagggaat   1500
tttcttcaga acaggccaga gccaacagcc ccacccgcag agagcttcgg gttcggagag   1560
gagatagccc cttccctgaa gcaggagccg agggaaaagg aatcacctcc attaacctcc   1620
ctcaaatcac tctttggcaa cgacccctag tcacagtaag aataggggga cagctaatag   1680
aagctctatt agacacagga gcagatgata cagtattaga acaaataaat ttaccaggaa   1740
aatggaaacc aaaaatgata gggggaattg gaggatttat caaagtaaaa cagtatgatc   1800
aaatacttat agaaattgaa gggaaaaagg ctatagggac agtactagta ggacctacac   1860
ctatcaacat aattgggaga aatatgttga ctcaaattgg ttgtacttta aattttccaa   1920
ttagtcctat tgagactgta ccagtaaaat taaaaccagg aatagatggc ccaaaggtta   1980
aacaatggcc attgacagaa gagaaaataa aagcattaac agaaatttgt acagatatgg   2040
aaaaggaagg aaaaatttca aaaattgggc cagaaaatcc atacaacact ccaatatttg   2100
ccataaagaa aaaagacagt actaaatgga gaaagttggt agatttcaga gagctcaata   2160
aaagaactca agacttctgg gaggtccaat taggcatacc tcatcccgcg ggttaaaaa   2220
```

-continued

```
agaaaagatc agtaacagta ctagatgtgg gggatgcata tttttcaatt cccctagatg   2280
aaaactttag aaagtataca gcattcacta tacctagtat aaataatgag acaccaggga   2340
ttagatatca gtacaatgtg cttccgcaag gatggaaagg atcaccagca atatttcaga   2400
gtagcatgac aaaaatctta gaacccttta gaacagaaaa tccagaaata gtgatctatc   2460
agtacatgga tgatttatat gtaggatctg acttagaaac agggcagcat agagcaaaaa   2520
tagaggaatt aagaaatcat ctactgagat ggggatttac cacaccagat aaaaaacatc   2580
agaaagaacc tccatttctc tggatgggat atgagctcca tcctgacaaa tggacggtac   2640
aacctataca gctgccaaac aaagaaagct ggactgtcaa tgatatacaa aaattagtgg   2700
gaaaactaaa ttgggcaagt cagatttatc cagggattaa agtaaagcaa ctatgtaaac   2760
tccttagggg ggccaaagca ctaacagaca tagtaccact gactgaagaa gcagaattag   2820
aattggcaga gaacagggaa attctaaaag aacctgtaca tggagtctac tatgacccat   2880
caaaagaatt aatagcagaa ttacagaaac aagggtgcga ccaatggaca tatcaaattt   2940
atcaagagcc atacaaaaat ctgaaaacag gaaagtatgc aaaaaggggg tctgcccaca   3000
ctaatgatgt aaaacagtta acagaagcag tgcaaaaaat agccacagag agcatagtaa   3060
tatggggaaa agttcctaaa tttaaactac ctataaggaa agaaacatgg gaagtatggt   3120
ggacagaata ttggcaggcc acctggattc ctgattggga gtttgtcaat acccctcctc   3180
tagtaaagtt atggtatcga ttagaaacag aacccatacc aggagcagaa acttactatg   3240
tagatggggc agctaataaa gaaacaaaat taggaaaggc aggatatgtt actgacagag   3300
gaaaacaaaa aattatcacc atacaggaaa caacaaatca aaaaactgaa ttacacgcaa   3360
ttcagctagc tttgcaggat tcaggatcag aagtaaacat agtaacagac tcacagtatg   3420
cattaggaat cattcaagca caaccagata ggagtgaatc agaattagtc aatcaaataa   3480
tagaacagct aataaaaaag gaaaaggtct acttaacatg ggtaccagca cacaaaggaa   3540
ttgggggaaa tgaacaagta gataaattag tcagtagtgg aatcagaaaa gtactgtttt   3600
tagatggcat agacaaagct caagaggacc atgaaagata tcacagcaat tggagagcaa   3660
tggctagtga ttttaatctg ccacctatag tagcaaaaga aatagtggcc agctgtgata   3720
aatgtcagct aaaaggggaa gccatgcatg gacaagtaga ctgtagtcca ggaatatggc   3780
aattagattg cacacatcta gaaggaaaag tcattatagt agcagtccat gtagccagtg   3840
gctatataga agcagaagtt atcccagcag aaacaggaca ggagacagca tacttcctgc   3900
taaaattagc aggaagatgg ccagtaaaag taatacacac agacaatggc agcaatttca   3960
ccagtgctgc aatgaaagca gcctgttggt gggcaaatat ccaacaggaa tttggaattc   4020
cctacaatcc ccaaagccaa ggagtagtgg aatctatgaa taaagaatta aagaaaatta   4080
tagggcaggt cagggatcaa gctgaacacc tcaagacagc agtacagatg gcagtattca   4140
ttcacaattt taaaagaaaa ggggggattg gggggtacag tgcaggggaa agaataatag   4200
acataatagc atcagatata caaactaaag aactacaaaa acagattata aaaattcaaa   4260
attttcgggt ctattacagg gacagcagag accccatttg gaaaggacca gcaaaactac   4320
tctggaaagg tgaaggggca gtagtaatac aggacaatag tgagataaag gtagtaccaa   4380
gaagaaaagt aaaaatcatt aaggattatg gaaaacagat ggcaggtggt gattgtgtgg   4440
caggtagaca ggatgaggat tagaacatgg aacagtttag taaaatatca tatgtataaa   4500
tctaagaaag ctaaggattg gttttataga catcactatg aaagtaggca tccaaaagta   4560
```

-continued

```
agttcagaag tacacatccc actaggggag gctagattag tagtaagaac atattggggt   4620
ctgcatacag gagaaagaga ctggcacttg ggtcaggggg tctccataga atggaagcag   4680
agaagatata gcacacaaat agatcctgac ctagcagacc aactgattca cctgcattat   4740
tttaactgtt tttcagaatc ggccgtaagg aaagccatac taggagaagt agttagacct   4800
aggtgtgaat atcaaacagg acataatcag gtaggatcac tacaatattt agcactcaaa   4860
gcattagtaa caccaacaca gacaaagcca cctttaccta gtgttaagaa gttaacagaa   4920
gatagatgga acgagcccca gaagaccagg ggccacagag ggagccattc aacgaatgga   4980
cactagaact gttagaagaa cttaaacatg aagctgttag acatggcttc atggattagg   5040
acaacatatt tataacacct atggggatac ttgggaagga gttgtagcta taataagaat   5100
attgcaacaa ctacttttta ttcatttcag aattgggtgt caacatagca gaataggcat   5160
tattccaggg agaagaggca ggaatggagc tggtagatcc tagcctagag ccctggaacc   5220
acccaggaag tcagcctaca actgcttgta acaaatgtta ctgtaaaata tgctgctggc   5280
attgccaatt gtgctttctg aacaagggct taggcatctc ctatggcagg aagaagcgga   5340
gacgccgacg aggaactcct cagagtcacc aggatcatca aaatcctgta ccaaagcagt   5400
gagtagtaat agttagtata tgtgatgcaa tccttagaaa tagctgcaat agcaggacta   5460
gtagtagcag ccatagcagc catagttgtg tggaccatag aaaaataaag aaacaggaga   5520
aaatagacag gttacttgat agaataagag aaagagcaga agatagtggc aatgagagtg   5580
aaggggacac agaggaattg gcaacacttg tggacatggt ggactttgat ccttgggttg   5640
gtgataattt gtagtgcctc aaataacttg tgggtcacag tctattatgg ggtaccagtg   5700
tgggaagacg cagatacccc tctattttgt gcatctgatg ctaaagcata tagtactgaa   5760
agacataatg tctgggccac acatgcctgt gtacccacag accccaaccc acaagagata   5820
actctggaaa atgtaacaga aacttttaac atgtggaaaa ataacatggt agaacagatg   5880
catgaggata taatcagttt atgggatgaa agcctaaagc catgtgtaaa gctaacccct   5940
ctctgtgtta ccttaaactg tactaatgtc aattgtaaca gtaatgtgac cagcactggg   6000
aacagtgctg ggaccaacgc tacgtgtaac atagaagaag caaacaactt aaaaaactgc   6060
tctttcaata taaccacaga aataagagat aagaaaaaga cagaatatgc gcttttctat   6120
agacttgatg tggtaccaat cgatggtaat aataatgtct caaataacta taggctaata   6180
aattgtaatg tctcaaccat taaacaagct tgtccaaagg tgtcttttga cccacttccc   6240
atacattatt gtgctccagc tgggtttgcg attttaaagt gtaggggtaa gaatttcact   6300
ggaacaggac aatgtaaaaa tgtcagttca gtacaatgta cacatggaat taaaccagtg   6360
gtatcaactc aattactact aaatggtagt ctagcagaag gagaaatagt aattagatct   6420
gaaaacctca cagacaatgc caaagtcata atagtacagc ttaataaaac tataggaatt   6480
aattgtacca gacccaacaa caatacaaga aaaagtataa gaatcggacc tggacaagcg   6540
ttctatgcaa caggtgaaat aataggacaa gaatggcagg agatgttaca gaaggtacag   6600
gcacaactag aacaggtctt taacaaaagt ataacccttta actcatccgc aggaggggac   6660
ctagaaatta caacacatag ttttaattgt agaggagaat tttctattg taatacatca   6720
ggattgttta atgaatcagg agggaatgat accactatca cactcccatg taagataaaa   6780
caaattgtga gaatgtggca gagagtggga caagcaatgt atgcccctcc catcgcagga   6840
gatattacat gtagatcaaa cattacaggg ctattattaa caagagatgg tggggttaat   6900
aatactggaa atgagacctt cagacctgga ggaggagata tgagggacaa ttggagaagt   6960
```

-continued

```
gaattatata agtataaaat agtaaaaatt aaaccactag gaatagcacc caccaaggca   7020
aggagaagag tggtggagag aggaaaaagg gcagttggac tgggagctgt cttccttggg   7080
ttcttaggag cagcaggaag cactatgggc gcggggtcaa taacgctgac ggtacaggtc   7140
agacaattat tgtctggcat agtgcaacag caaagcaatt tgctgagggc tatagaggcg   7200
cagcaacatc tattgcaact cacagtctgg ggcattaaac agctccaggc aagagtcctg   7260
gctgtagaaa gatacctaaa ggatcaacag ctcctaggga tttggggctg ctctggaaaa   7320
ctcatctgca ccactaatgt gccttggaac actagttgga gtaataaatc ttatgaggag   7380
atttgggata acatgacctg gatacaatgg gaaagggaag tcagcaatta cacacaacaa   7440
atatacagcc taattgaaga atcgcagaac cagcaggaaa agaatgaaca agacttattg   7500
gcattggaca agtgggcaag tttgtggaac tggtttgaca taacaaaatg gctatggtat   7560
ataaaaatat ttataatgat agtaggaggt ttaataggtt taagaatagt tttgctgtg    7620
ctttctatag taaatagagt taggcaggga tactcacctt tgtcattcca gacccttacc   7680
caccaccaga gggaacccga caggcccgaa agaatcgaag aaggaggtgg agagcaagac   7740
agagacagat cagtgcgctt agtgagcgga ttcttagcac ttgcctggga cgacctgcgg   7800
aacctgtgcc tcttcagcta ccaccgattg agagacttag tcttgattgc agcgaggaca   7860
gcagaactcc tgagacgcag cagtctccag ggactgagac tggggtggga gggcctcaaa   7920
tatctgtgga atctcctgtt gtattggggt cgggaactaa agaatagtgc tattaatttg   7980
attgatacaa tagcaatagc agtagctaac tggacagata gggttataga agtagcacaa   8040
ggagcttgta gagctattct caacatacct agaaggataa gacaaggctt ggaaagagct   8100
ttgctataaa ataggaggca agtggtcaaa aagtagcata gttggatggc ccgcggtaag   8160
ggagagaata agacaaaccc ctccagcaga aggagtagga gcagcacctc aagacttagc   8220
taggcatgga gcaatcacaa gcagcaatac agcacaaact aatcctgatt gtgcctggct   8280
agaagcacaa caggagaatt cagaggtagg ctttccagtc agacaacagg tacctttgag   8340
accaatgact tataaggctg cctttgatct cagcttcttt ttaaaagaaa aggggggact   8400
ggatgggcta atttactcta agaaaagaca agacatcctt gacctatggg tctataatac   8460
acaaggatac ttcccagatt ggcagaacta cactccaggg ccagggacta gattccccact  8520
gacatttcgg tggtgcttca aactagtacc aatggatcca gcagagatag aggaagccaa   8580
taaaggagag aacaacagtt tattacaccc tatctgccaa catggcctgg aagatgcgga   8640
cagagaagtg ctggtatgga gatttgacag tagcctagca cggagacaca tagcccgaga   8700
acaacatccg gagtactata aggactgctg acacagaagt tgctgacaca gatgttgctg   8760
acaaggggac tttccgcctg ggactttccg gggaggcgcg gcatgggagg gactggggag   8820
tggctaaccc tcagaagctg catataagca gccgcttctc gcctgtactg ggtctctctt   8880
gttagaccag atttgagcct gggagctctc tggctagcag ggaacccac tgcttaagcc    8940
tcaataaagc ttgccttgag tgcttc                                        8966
```

<210> SEQ ID NO 6
<211> LENGTH: 8954
<212> TYPE: DNA
<213> ORGANISM: Human immunodeficiency virus type 1
<220> FEATURE:
<223> OTHER INFORMATION: isolate=93BR029; 142..1579:gene="gag";
1437..4448:gene="pol";
4393..4971:gene="vif"; 4911..5201:gene="vpr";

-continued

5182..7782:gene="tat"; 5321..7972:gene="rev";
5586..8114:gene="env"; 8116..8736:gene="nef"

<400> SEQUENCE: 6
ctgaaagcga aagtagaacc agaggagctc tcttgacgca ggactcggct tgctgaagcg 60
cgcacggcag gaggcgaggg gcggcgactg gtgagtacgc caaaaataaa atttggacta 120
gcggaggcta gaaggagaga gatgggtgcg agagcgtcag taataagcgg gggagaatta 180
gataaatggg aaaaaattag gttaaggcca ggaggacata aaaaatatag attaaaacat 240
atagtatggg caagcagggg agctagaacg attcgcagtt aatcctggcc ttttagagac 300
atcagaaggc tgtagacaaa tactggaaca gctacaacca gcccttaaga cgggatcaga 360
agaacttaga tcattatata atacagtagc aaccctctat tgtgtacatc aaaagataga 420
tgtaaaagac accaaggaag ctttagaaaa gatagaggaa gagcaaaaca aagtaagaaa 480
aaggcacagc aagcagcagc taacacagga aacaacagcc aggtcagcca aaattaccct 540
atagtgcaga accttcaggg gcaaatggta caccaggcca tatcacctag aactttaaat 600
gcatgggtaa aagtagtaga agagaaggct tttagcccag aagtaatacc catgttttca 660
gcattatcag aaggagccac cccacaagat ttaaacacca tgctaaacac agtgggggga 720
catcaagcag ctatgcaaat gttaaaagaa accatcaatg aggaagctgc agaatgggac 780
agagtacatc cagtgcatgc aggacctatc ccaccaggcc agatgaggga acctagggga 840
agtgatatag ctggaactac tagtaccctt caggaacaaa tacaatggat gacaagcaac 900
ccacctgtcc cagtgggaga aatttataaa agatggatca tcctaggatt aaataaaata 960
gtaagaatgt atagccctac cagcattctg ggcataagac aaggaccaaa ggaacccttt 1020
agagactatg tagatcgatt ttataaaact ctaagagcag agcaaacttc acaggatgta 1080
aaaaattgga tgacagaaac cttgttggtc caaaatgcga acccagattg caaaaccatt 1140
ttaaaagcat tgggaccagc agctacacta gaagaaatga tgacagcatg tcagggagtg 1200
gggggacccg gccataaagc aagagttttg gcagaagcaa tgagccaagt aacaaattca 1260
ggtaccataa tgatgcagag aggcaatttt aggaaccaaa gaaagactat taagtgtttc 1320
aattgtggca aagaagggca catagccaaa aattgcaggg cccctaggaa aaagggctgc 1380
tggaaatgtg gaaaggaagg acaccagatg aaagattgta ctgagagaca ggctaatttt 1440
ttagggaaaa tctggccttc ccacaaggga aggccaggga atttccttca gagcagacca 1500
gagccaacag ccccaccagc agagagcttc aggtttgggg aagaggtaac aactccctct 1560
cagaaacagg agccgataga caaggagatg tatcctttgg cttccctcag atcactcttt 1620
ggcaacgacc cctcgtcaca gtaaagatag gggggcaact aaaggaagcc ctattagata 1680
ccggagcaga tgatacagta ttagaagaaa taaatttacc aggaagatgg aaaccaaaaa 1740
tgataggggg aattggaggt tttatcaaag taagacagta tgatcaaata cccatagaaa 1800
tttgtggacg taaagctaca ggtacagtat tagtaggacc tacacctgtc aacataattg 1860
gaagaaatct gttgactcag attggctgca ctttaaattt tcccattagt cctattgaaa 1920
ctgtaccagt aaaattgaag ccaggaatgg atggcccaag ggttaaacaa tggccattga 1980
cagaagaaaa aataaaagca ttaacagaaa tatgtacaga aatggaaaaa gaaggaaaaa 2040
tttcaaaaat tgggcccgaa aatccataca atactccagt atttgccata aagaaaaaag 2100
atagtactaa atggagaaaa ttagtagatt tcagagaact taataagaga actcaagact 2160
tctgggaagt tcagttaggg ataccacatc ccgcagggtt aaagaagaaa aaatcagtaa 2220

-continued

```
cagtactgga tgtgggtgat gcatattttt cagttccatt agataaagac ttcaggaagt   2280
atactgcatt taccatacct agtacaaaca atgaaacacc agggcttaga tatcagtaca   2340
atgtgcttcc acaggggtgg aaaggatcac cagcaatatt ccaaagtagc atgacaaaaa   2400
tcttagagcc ttttagaaaa caaaatccag acatagttat ctatcaatac atggatgatt   2460
tgtatgtagg atctgactta gaaatagggc agcatagaac taagatagag gaattgagac   2520
agcatttgtt gaggtgggga tttaccacac cagacaaaaa acatcagaaa gaacctccat   2580
tcctttggat gggttatgaa ctccatcctg ataaatggac agtacagcct atagtgctgc   2640
cagaaaaaga cagctggact gtcaatgaca tacagaagtt agtgggaaaa ttgaattggg   2700
caagtcagat ttatgcaggg attaaagtaa ggcaattatg taaactcctt aggggaacca   2760
aagcactaac agaagtagta ccactaacag cagaggcaga gctagaactg gcagaaaaca   2820
gggagattct aaaagaacca gtacatggag tgtattatga cccctcaaaa gacttaatag   2880
cagaaataca gaaacagggg caaggccaat ggacatatca aatttatcaa gagccatata   2940
aaaatttgaa aacaggaaag tatgcaagga tgaggggtgc ccacactaat gatgtaaaac   3000
aactaacaga ggcagtgcaa aaaataacca cagaaagcat agtaatatgg ggaaagattc   3060
ctaaatttaa actacccata caaaaagaaa cgtgggaagc atggtggata gagtattggc   3120
aagccacctg gattcctgag tgggagtttg tcaatacccc tcccttagtg aaattatggt   3180
accagttaga gaaagaaccc atagtaggag cagaaacttt ctatgtagat ggggcagcta   3240
atagggaaac taaattagga aaagcaggat atgtgactga cagaggaaga caaaaagttg   3300
tcccccctaac ggacacaaca aatcagaaaa ctgagttaca agcaattcat ctagctttgc   3360
aggattcggg attagaagta aacatagtaa cagactcaca atatgcatta ggaatcattc   3420
aagcacaacc agataagagt gaattagaaa tagtcaatca aataatagag cagttaataa   3480
aaaaggaaaa gatctacctg gcatgggtac cagcacacaa aggaattgga ggaaatgaac   3540
aagtagacaa attagtcagt tctggaatca ggaaagtact atttttagat ggaatagata   3600
aggcccaaga agaacatgag aaatatcaca ataattggag agcaatggct agtgacttta   3660
acataccacc tgtagtagca aaagaaatag tagccagctg tgataaatgt cagctaaaag   3720
gagaagccat gcatggacaa gtagactgta gtccaggaat atggcagcta gattgtacac   3780
acttagaagg aaaagttatc ctggtagcag tgcatgtagc cggtggatat atagaagcag   3840
aagttattcc agcagagaca gggcaagaaa cagcatactt tctcttaaaa ttagcaggaa   3900
gatggccagt aaaaacaata cacacagaca atggcagcaa tttcaccagt actacagtca   3960
aggccgcctg ttggtgggcg gggatcaagc aggaatttgg cattccctac aatccccaaa   4020
gtcaaggagt aatagaatct atgaataaag aattaaagaa aattatagga caggtaaggg   4080
atcaggctga acatcttaag acagcagtac aaacggcagt attcatccac aattttaaaa   4140
gaaaaggggg gattgggggg tacagtgcag gggaaagaat agtagacata atagcaacag   4200
acatacagac taaagaatta caaaaacaaa ttacaaaaat tcaaaatttt cgggtttatt   4260
acagagacag cagagatcca ctttggaaag gaccagcaaa gcttctctgg aaaggtgaag   4320
gggcagtagt aatacaagat aatagtgaca taaaagtagt gccaagaaga aaagtaaaga   4380
tcattaggga ttatggaaaa cagatggcag gtggtgattg tgtggcaggt agacaggatg   4440
aggattaaca catggaaaag tttagtaaaa taccatatgc atgtttcaaa gaaagccaaa   4500
agatggtttt atagacatca ctttgaaagc aggcatccaa gagtaagttc agaagtacat   4560
atcccactag aggaagctaa attagtaata acaacatatt gggggctgca tacaggagaa   4620
```

-continued

```
agagattggc atctgggtca gggagtctcc atagaatgga ggcaggggag gtataggaca   4680
caaatagacc ctggcctggc agaccaactg atccatatat attattttga ttgtttttca   4740
gaatctgcca taaggaaagc catattagga catagaatta gccctaggtg tgattatcaa   4800
gcaggacata acaaggtagg atctctacag tacttggcac taacagcatt aataaaacca   4860
aaaaagagaa agccaccttt gcccagtgtt aagaaactga cagaggatag atggaacaag   4920
ccccagaaga ccaaggacca cagagggagc catacaatga atggacacta gaacttttag   4980
aggaacttaa gagtgaagct gttagacatt ttcctaggtt atggctccat agcttaggac   5040
aacatatcta tgaaacttat ggggatactt gggcaggagt ggaagccata ataagaattc   5100
tgcaacaact gctgtttatt catttcagaa ttggatgtca acatagcaga ataggcatta   5160
atcgacagag gagagcaagg aatggagcca gtagatccta gactagagcc ctggaagcat   5220
ccaggaagtc ggcctcagac ggcttgtaat agttgctatt gtaaaaagtg ttgctttcat   5280
tgtcaagttt gtttcacaac aaagggctta ggcatctcct atggcaggaa gaagcggaga   5340
cagcgacaca gaactcctca aagcagtcag ctacatcaag atcctgtacc aaagcagtaa   5400
gtattgttaa gtaatatatg taatgtcata tttgttagta ataggtttag cagcattaat   5460
agcagcacta ataatagcaa tagttgtgtg gactatagca tatatagaat atagggaact   5520
agtaaggcaa agaaaaataa ataggttata taaaagaata agagaaagag cagaagacag   5580
tggcaatgag agtgaggggg atgcagagga attggcagca cttggggaaa tggggccttt   5640
tattcctggg gatattgata atctgtaatg ctgaaaactt gtgggtcaca gtctattatg   5700
gggtacctgt gtggaaagaa gcaaccacta ctttattctg tgcatcagat gctaaagcat   5760
atgaaaaaga agcacataat gtctgggcta cacatgcctg tgtacccaca gatcccaatc   5820
cacaagaagt agttctggaa aatgtaacag aaaattttga tatgtggaaa aataacatgg   5880
tagaacaaat gcatacagat ataatcagtt tatgggatca aagcctgaag ccatgtgtga   5940
agttaacccc actctgtgtt actttacgtt gtagtaatgc cactaccaac agtactcaaa   6000
acgacaccct gaaggaagag ccaggggcaa tacaaaactg ttctttcaat atgaccacag   6060
aagtaagaga taagcagctg aaagtacatg cactttttta taggcttgat atagtaccaa   6120
tcagcaatga taatagtagc aatgataata gtagcagaga atacaggcta ataaattgta   6180
atacctcaac ccttacacag gcttgtccaa aggtatcttg ggatccaatt cccatacatt   6240
attgtgctcc agctgggtat gcgattctaa agtgtaatga taaaaaattc aatgggacgg   6300
ggccatgcag gaatgtcagc acagtacaat gtacacatgg aattaaacca gtggtatcaa   6360
ctcaattgtt gttaaatggc agcctagcag aaaaagatat aataatcaga tctcaaaata   6420
tctcagataa tgcaaaaacc ataatagtac aacttaatgt atctgtgccg attaattgta   6480
caagacccaa caacaataca agaaaaagta taccaatagg accaggacga gcattttata   6540
caacaggaga aataatagga gacatcagaa aggcacattg taacgttagt ggaacaaaat   6600
ggaatgagac gttagaaaag gtaagggcaa agttaaagcc tcatttccct aatgcaacaa   6660
taaaatttaa ctcatcctca ggaggggacc tagaaattac aatgcatagt tttaattgta   6720
gaggagaatt tttctactgc aatacatcag gactgtttaa tgacacagta gacaatggca   6780
ctatcactct cccatgtcga ataaagcaaa ttgtaaatat gtggcaggaa gtggggcgag   6840
caatgtatgc cgctcccatt gcaggaaaca ttacctgtag ctcaaatatt acaggtctac   6900
tattgacaag agatggtggt cagaataatc agacggagga gaccttcaga cctgggggag   6960
```

-continued

```
gaaatatgaa agacaactgg agaagtgaat tatataaata taaagtagta gaaattgagc   7020

cattaggagt agcacccacc aaggcaaaaa gacaagtggt gaagagagaa aaaagagcag   7080

tgggaatggg agctttgttc cttgggttct tgggagcagc aggaagcact atgggcgcag   7140

cgtcaataac gctgacggca caggccagac aattattgtc tggcatagtg caacagcaga   7200

ataatttgct gagggctatt gaagcgcaac agcatctgtt gcagctcaca gtctggggca   7260

ttaaacagct ccaggcaaga atcctggctg tggaaagata cctaaaggat caacagctcc   7320

tagggctttg gggctgctct ggaaaactca tctgcaccac tgatgtgccc tggaactcta   7380

gttggagtaa caaatctcag gagaagatct gggggaacat gacctggatg gagtgggaaa   7440

aagagattag caattactca aacgaaatat ataggttaat tgaagagtcg cagaaccagc   7500

aggaaaagaa tgaacaagaa ttattggcat tggacaaatg ggcaagtctg tggaattggt   7560

ttgacatatc aaaatggctg tggtatataa aaatattcat aatgatagta ggaggcttga   7620

taggcttaag aatagttttt gctgtgcttt ctatagtaaa tagagttagg aagggatact   7680

cacctttgtc attacagacc cgcttcccaa gcccaaggga acccgacagg cccgaaggaa   7740

tcgaagaagg aggtggagag ccaggcaaag acagatccgt gagattagtg aacggattct   7800

tagctcttgt ctgggacgac ctgaggaacc tgtgcctctt cagctaccgc cacttgagag   7860

acttcatatt aattgcagcg aggattgtgg acaggggact gaagaggggg tgggaagccc   7920

tcaaacttct ggggaatctc gcgctgtatt ggagtcagga actaaagaat agtgctatta   7980

gcttgcttaa taccacagca atagtagtag ctgaggggac agatagagtt atagaagctt   8040

tgcaaagagc gggtagagct gttcttaacg tacctagaag aataagacag ggcttggaaa   8100

gggctttgct ataaaatggg tagcaagtgg tcaaaaagta gtatagttgg gtggcctgct   8160

ataagggaaa gattaagaca aacccctcca gcagcagaag ggtgggagc agtgtctcaa   8220

gacttagaaa gacgggggc aattacaagc agcaatactg gagctaataa tcctgacttg   8280

gcctggctgg aggcacaaga ggaagaggaa gtaggctttc cagtcagacc tcaggtacct   8340

ttaagaccaa tgacttataa gggagctctt gatctcagtc actttttaaa agaaaagggg   8400

ggactggaag ggttaattta ttccaagaaa agacaagaga tccttgatct gtgggtttac   8460

cacacacaag gctacttccc tgattggcag aactacacac cagggccagg gaccagatat   8520

ccactgacct tagggtggtg cttcaagcta gtaccagttg acccagagga ggtagaaaag   8580

gccaatgaag gagagaacaa ctgcttgcta caccccatga gccaacatgg aatggaggat   8640

gaagacagag aaatactgca gtggaggttt gacagccgcc tagcatttca tcacatggcc   8700

cgagagctgc atccggagta ctacaaggac tgctgacatt gagttttcta caaggactt   8760

tccgctgggg actttccagg gaggtgtggc ctgggcggga ctggggagtg gcgagccctc   8820

agatgctgca tataagcagc tgctttctgc ctgtactggg tctctctggt tagaccagat   8880

ttgagcctgg gagctctctg gctagctagg gaacctactg cttaagcctc aataaagctt   8940

gccttgagtg ctta                                                     8954
```

<210> SEQ ID NO 7
<211> LENGTH: 9050
<212> TYPE: DNA
<213> ORGANISM: Human immunodeficiency virus type 1
<220> FEATURE:
<223> OTHER INFORMATION: isolate="94CY032.3"; 156..1658:"gag";
1454..4462:"pol";
4407..4985:"vif"; 4925..5212:"vpr"; 5200..7842:"tat";
5339..8026:"rev"; 5435..5680:"vpu"; 5598..8168:"env";
8170.8829:"nef"

-continued

<400> SEQUENCE: 7

```
ttgaaagtga aagttaatag gactcgaaag cgaaagttcc agagaagttc tctcgacgca     60
ggactcggct tgctgaggtg cacacagcaa gaggcgagag cggcgactgg tgagtacgcc    120
aaattttttg actagcggag gctagaagga gagagatggg tgcgagagcg tcagtattaa    180
gtgggggaaa attagatgca tgggagagga ttcggttaag gccaggggga aagaaaaaat    240
atagactgaa acatctagta tggcaagca gagagttgga aagattcgca cttaaccctg    300
gccttttaga aacagcagaa ggatgtcaac aattaatgga acagttacaa tcaactctca    360
aaacaggatc agaagaactt agatcattat ataatactat aacaaccctc tggtgcgtac    420
atcaaagaat agatgtacaa gacaccaagg aagctttaga taaaatagag gaaatacaaa    480
gtaagagcaa gcaaaagaca cagcaggcag cagctgccgc aggaggtagc agcaatgtca    540
gccaaaatta ccctatagtg caaaatgcac aagggcaaat ggtacatcag agcatttcac    600
ctagaacttt gaatgcatgg gtaaaagtaa tagaagaaaa ggctttcagc ccagaagtaa    660
tacccatgtt ctcagcatta tcagagggag ccaccccaca agatttgaac atgatgctaa    720
atatagtggg gggacaccag gcagcaatgc aaatgttaaa agataccatc aatgaggaag    780
ctgcagactg ggacaggaca catccagtac atgcagggcc tattccacca ggccagatga    840
gagaaccaag gggaagtgat atagcaggaa ctactagtac ccttcaagaa caaataggat    900
ggatgacaag caacccacct gtcccagtgg gagaaatcta taaaagatgg ataatcttgg    960
ggttaaataa aatagtaaga acgtatagcc ccattagcat cttggacata agacaaggac   1020
caaaagaacc cttcagagat tatgtagata ggttctttaa atgtctcaga gcagaacaag   1080
ctacccagga ggtgaaaaat tggatgacag aaaccctgct ggtccaaaat gcgaatccag   1140
actgtaagtc catcttaaaa gcattaggaa caggggctac attagaagaa atgatgacag   1200
catgtcaggg agtgggagga cccagccata aagcaagagt tttagctgag gcaatgagcc   1260
aggcatcaaa tgcagcagca gccataatga tgcagaaaag caaatttaag ggccaaagaa   1320
gaactattaa gtgtttcaac tgtggcaagg aaggacatct agccagaaat tgcagggccc   1380
ctaggaaaaa gggctgctgg aagtgtggaa aggagggaca tcaaatgaaa gactgcactg   1440
agagacaggc taattttta gggagaatgt ggccttccag caaagggagg ccaggaaatt   1500
ttcttcagaa caggccagag ccaacagccc cgcccgcgga atgcttagag aggaaagagg   1560
agacaacctc ctctctgaag caggaaccga gggacaagga actatatcct ttaacttccc   1620
tcaaatcact ctttggcagc gacccttgt cacaataaaa ctagggggac agataaggga   1680
ggctctttta gatacaggag cagatgatac agtattagaa gaaataaatt tgccaggaaa   1740
atggaagcca aaaatgatag ggggaatcgg aggttttatc aaagtaagac aatatgatca   1800
gatacctata gaaatttgtg gaaaaaaggc cataggcaca gtgttagtag gacctacacc   1860
tgtcaacata attggacgaa acatgttgac tcagcttggt tgtactttaa attttccaat   1920
tagtcctatt gaaactgtac cagtaaaatt aaagccagga atggatggcc caaaggttaa   1980
acaatggcca ttgacagaag aaaaaataaa agccttaaca gagatatgta cagacatgga   2040
aaaggaaggc aagatttcaa aaattgggcc tgaaaatcca tacaatactc caatatttgc   2100
tataaagaaa aaagacagca ctaaatggag aaaattagta gatttcagag aactcaataa   2160
aagaactcag gacttctggg aagttcagtt aggaataccg cacccagcag ggttaaagaa   2220
gaaaaaatca gtaacagtat tggatgtggg ggatgcatat ttttcagttc ccttagatcc   2280
```

-continued

```
agagttcagg aagtacactg cattcaccat acctagtacc aacaatgaga caccaggaat   2340
tagatatcag tacaatgtgc ttccacaggg ctggaaagga tcaccagcaa tattccaatg   2400
tagcatgaca aaaatcttag agccctttag attcaaaaac ccagaaatag tcatatacca   2460
atatatggat gatttgtatg tagggtctga cttagaaata gggcaacata gagcaaaaat   2520
agaagagcta agagagcatc tattgagatg gggattcacc acaccagaca aaaaacatca   2580
gaaagaaccc ccatttcttt ggatggggta tgaactccat cctgacaaat ggacagtgca   2640
gcctatacaa ccggcagaaa aggatagctg gactgtcaac gatatccaga agttagtggg   2700
aaaactaaat tgggcaagtc agatttatcc agggattaaa gtaaagcaat tatgtaaact   2760
tcttaggggga gctaaagccc taacagacat agtaccacta actacagagg cagagttaga   2820
attagcagag aacagggaga ttctaaaaga accagtacat ggggcatatt atgacccatc   2880
aaaagactta atagcagaaa tacagaagca agggcaaggt caatggacat atcaaatata   2940
tcaagagcca cataaaaatc tgaaaacagg gaagtatgca agaaccagat ctgcccacac   3000
taatgatgtt agacaattaa cagaagcagt gcaaaagata gccatggaat gcatagtaat   3060
atggggaaag actcctaagt ttagattacc catacaaaag gaaacatggg acacatggtg   3120
gacagaatat tggcaggcca cctggatccc tgaatgggaa tttgtcaata cccctcctct   3180
agtaaaatta tggtaccagt tagaaacaga ccccatagca ggagcagaaa ctttctatgt   3240
agatggggca gctaatagag aaacaaaaca gggaaaagca ggatatgtta ctgatagagg   3300
cagacaaaaa gttgtctccc tatctgaaac aacaaatcag aagactgaat tacaagcaat   3360
ttacttagct ttgcaggatt caggatcaga agtaaacata gtaacagact cacagtatgc   3420
aataggaatc attcaagcac aaccagatag aagtgaatca gatttagtta atcaaataat   3480
agagcagtta atacggaagg acaaggtcta cctgtcatgg gtaccagcac acaaagggat   3540
tggaggaaat gaacaagtag ataaattagt cagcaatgga atcagaaagg tgctattttt   3600
agatggaata gataaggctc aagaagaaca tgagaaatat cacaataact ggagagcaat   3660
ggctagtgat tttaatctgc catcagtggt agcaaaagag atagtagcta gctgtaataa   3720
atgtcagcta aaggggaag ccatgcatgg acaagtggac tgtagtccag ggatatggca   3780
gttagattgt acacatttag aaggtaaagt tatcatggta gcagttcatg tggctagtgg   3840
atacatagaa gcagaagtta tcccagcaga aacaggacag gaaacagcct acttcatact   3900
aaaattagca ggaagatggc cagtgaaaat gatacatgca gacaacggcc ccaatttcac   3960
cagtgctgcg gttaaggcag cctgttggtg ggcagatatc aaccaggaat ttggaattcc   4020
ctacaatccc caaagccaag gagtagtgga atctatgaat aaagaattaa agaaaatcat   4080
agggcaggtc agggatcaag ctgaacacct taagacagca gtacagatgg cagtattcat   4140
tcacaatttt aaaagaaaag gggggattgg ggggtacagt gcaggggaaa gaataataga   4200
cataatagca tcagatatac aaactaaaga actacaaaaa caaattacaa aaattcaaaa   4260
ttttcgggtt tattacaggg acagcagaga accaatttgg aagggaccag caaaactact   4320
ctggaaaggt gaaggggcag tagtaataca ggacaacagt gatatcaaag tagtaccaag   4380
aagaaaagca aagattatta gggactatgg caaacagatg gcaggtaatg attgtgtggc   4440
aggtagacag gatgaagatt agaacatgga acagtctagt gaaacatcat atgtatgttt   4500
caaagaaagc taaaggatga ttctatagac atcactatga aagtaggcac ccaaaagtaa   4560
gttcagaagt acatatccca ctaggggagg ctagattagt agtaagaaca tattggggtc   4620
tgcagccagg ggaacaagac tggcacttgg gtcatggagt ctccatagaa tggaggctca   4680
```

-continued

```
gaagatatag cacacaagtg gatcctgacc tggcagacca actaattcat atgcattact   4740
ttgattgttt ttcagaatct gccataagga aagccatatt aggacataga gttagtccta   4800
ggtgtgaata tcaagcagga cataataagg taggatcctt acaatacctg gcactagcag   4860
cattaatatc cccaaaaaag acaaagccac ctttgcctag tgttaagaaa ctagtggagg   4920
atagatggaa caagccccag aagaccaggg gccgcagaga gaaccaaata atgaatggac   4980
actagagctt ttggaggagc ttaaaaatga agctgttagg cattttccta gaccctggct   5040
ccatggccta ggacagcata tctataacac ttatggagat acctgggaag ggttgaagc    5100
tataataaga attttgcaac aactactgtt tattcatttc agaattgggt gccaacatag   5160
tagaataggc attactcctc aaaggagaag aggcagggga tggagccagt agatcctgac   5220
ctagagccct ggaaccatcc gggaagtcag cctacaactg attgtaacaa gtgtttctgt   5280
aaaaagtgtt gctggcattg ccaagtttgc tttctgaaaa aaggcttagg catctcctat   5340
ggcaggaaga agcggaaaca tcgacgagga tctcttcaag gcagcaaggg ccatcaaaat   5400
cttataccaa agcagtaagt attaagtata tgtaatgtta ttctgggaaa tctgggcaat   5460
agtaggactg gtagtagcgc taattatagt aatagtagtg tggactttag tatttataga   5520
atataagaaa ttgagaaggc aaaggagaat agacagcttg tacaatagaa taagagaaag   5580
agcagaagac agtggcaatg agagtgatgg ggatgcagag gaattatcca cacttgtggg   5640
aatggggaac tttgatcctt gggttggtga taatctgtag tgcctcaaac aacttgtggg   5700
tcacagttta ttatggggta cctgtgtgga gagacgcaga gaccacccta ttttgtgcat   5760
cagaagctaa agcatatgag aaagaagtac ataatatctg ggctacacat gcctgtgtac   5820
ccacagaccc caacccacaa gaagtagctc tgataaatgt aacagagaac tttaacatgt   5880
ggaaaaatga catggtagaa cagatgcatg aggatataat cagtttatgg aatgaaggcc   5940
taaaaccatg tgcaaagcta acctctctct gtgttacttt tacatgtatt aatgcaacta   6000
ctactaatag taccaatggc actgtgatta aagaaggaat aaaaaactgc tctttcgata   6060
taaccacaga aataagggat aagaagaaga aagaatatgc gcttttctat agaattgata   6120
tagtgccaat taatgctaga gtgccaatta atggtagtaa taggaataat agtacagaag   6180
agtatatgtt aataaattgt aacgcctcaa ccattaaaca ggcttgccca aaggtgtctt   6240
ttgagccaat tcccatacat tattgtgccc cagctggttt tgcaatttta aagtgtaatg   6300
agaaaaattt cactggatta gggccatgca caaatgtcag ctcggtacga tgcactcatg   6360
gaattaagcc agtggtatca actcaattgc tgttaaatgg aagcttagca acggaagagg   6420
tagtaattag atctaaaaat atcacagaca ataccaaaaa tataatagta cagcttgcaa   6480
aggctgtaaa aattaattgt accagacctg gcaacaatac aagaaaaagt gtacatatag   6540
ggccaggact aacatggtat gcaacaggtg aaataatagg agatataaga caagcacatt   6600
gtaacattag tggaaatgat tggaatgaca ccttaaaagt gataagtgaa gaattgaaaa   6660
gactcttccc taataaaaca ataaaatttg ctccacccgt aggaggggac ctagaaatta   6720
caacacatag ctttaattgt aaaggagaat ttttctattg caatacaaca ccactgttta   6780
atagtacaca catgcaaaat ggtacaaaca ttacaagtac agattctaca aattcaacca   6840
tcacactcca atgcagacta aaacaatttg taaggatgtg gcaggaagtg ggcaagcaa    6900
tgtacgcctc ccccattgca gggagcatta actgcagctc agatattaca ggaataatat   6960
tgacaagaga tggtggtact aataatactg agatcttcag acctggagga ggagacatga   7020
```

-continued

```
gggacaattg gagaagtgaa ctatataaat ataaagtagt aaagattgaa ccaataggag   7080

tagcacccaa taaggcaagg agacgagtgg tgcagagaga aaaatgagca gtgggaatag   7140

gggccatgtt ccttgggttc ttgggagcag caggaagcac tatgggcgca gcgtcaatga   7200

cgctgacggt acaggccaga caattattgt ccggcatagt gcagcagcag agcaatttgc   7260

tgagggctat agaggctcaa caacatctgt tgagactcac ggtctggggc attaaacagc   7320

tccaggcaag agtcctggct ctggaaagct acctaaagga tcaacagctc ctaggaattt   7380

ggggctgctc tggaaaactc atctgcacca ctaatgtacc ttggaactct agttggagta   7440

ataaatctta taatgatata tgggacaata tgacctggtt gcaatgggat aaagaaatta   7500

acaattacac acaaataata tatgggttac ttgaagaatc acagaaccag caggaaaaga   7560

atgagcaaga cttattggcc ttggacaagt gggcaagcct gtggaattgg tttagcataa   7620

caaaatggct atggtatata aaaatattta taatgatagt aggaggcttg ataggcttaa   7680

gaataatttt tgctgtgctt tctatagtaa atagagttag gcagggatac tcacctttgt   7740

ctttgcagac ccttatccca acaacccaac ggggactcga caggcccgga ggaacagaag   7800

aagaaggtgg cgagcaagac agaagcagat ccattcgctt agtgaacgga ttcttgccac   7860

ttatctggga cgacctgcgg aacctgtgcc tcttcagcta ccgccacttg agaaacttac   7920

tcttaattgt agcgaggact gtggaacttc tggggataag gggtgggaa gccctcaagt    7980

atctgtggaa cttcctgctg tattggggac aggagctaaa gaatagtgct attaatttgt   8040

ttaataccac agcaatagca gtagctgagg gaacagatag gattatagaa gcagtacaga   8100

gagcttgtag agctatttgc aacataccta gaagaatcag acagggcctt gaaagagctt   8160

tgctttaaaa tgggaggcaa atggtcaaaa agtagcatag ttggatggcc tgagataagg   8220

gaaagaatga ggcgagctcg agctgagcca gaaagaatga ggcgagctca agctgagcca   8280

gcagcagcag gagtaggagc agtgtctcaa gacttggaca aacatggggc aatcacaatt   8340

aacaatacag cagctactaa tcctgacaaa acctggctgg aagcacaaga agaggaagaa   8400

gaggtaggtt ttccagtcag gccacaggta cctttaaggc caatgacctt taaaggagct   8460

ttagatctca gccacttttt aaaagaaaag gggggactgg atgggctaat ttactccaag   8520

aaaagacaag agatccttga tctgtgggtc tatcacacac aaggtttctt ccctgattgg   8580

gataactaca caccaggacc aggggagaga ttcccactgt gctttggatg gtgcttcaag   8640

ctagtaccag tagatccaca ggaggtggaa gaggccactg aaggagagaa cacctgtttg   8700

ctgcacccta taagccagca tggaatggag gatgaagaga gagaagtatt aaagtggaag   8760

tttgacagtc gcctggcata caagcacgta gcccgagagc tgcatccgga gttttacaaa   8820

gactgctgac acagaagttg ctgacaaagg gactttccgc ccgggacttt ccaggggagg   8880

cgcggcctgg gaggggttgg ggagtggcta accctcagat gctgcataaa agcagccgct   8940

tctcgcctgt actgggtctc tctggttaga ccagatctga gcctgggagc tctctggcta   9000

gctagggaac ccactgctta agcctcaata aagcttgcct tgagtgcttc              9050
```

<210> SEQ ID NO 8
<211> LENGTH: 9010
<212> TYPE: DNA
<213> ORGANISM: Human immunodeficiency virus type 1
<220> FEATURE:
<223> OTHER INFORMATION: isolate=96ZM651; 137..1621:"gag";
1426..4425:"pol";
4370..4948:"vif"; 4888..5178:"vpr";
5159..5373-7734..7824:"tat"; 5298..5373-7734..7981:"rev";
5387..5647:"vpu"; 5565..8171:"env"; 8173..8793:"nef"

-continued

<400> SEQUENCE: 8

```
cttgaagcga aagtagacca gaggagatct ctcgacgcag gactcggctt gctgaagtgc     60
actcggcaag aggcgagagc ggcggctggt gagtacgcca aattttattt gactagcgga    120
ggctagaagg agagagatgg gtgcgagagc gtcaatatta agaggggggaa aattagataa    180
atgggaaaaa attaggctaa ggccaggggg aaagaaacgc tatatgataa aacacctagt    240
atgggcaagc agggagctgg aaagatttgc gcttaaccct ggcctttttag aaacatcaga    300
aggctgtaaa caaataatga aacagctaca accagctctt cagacaggaa cggaggaact    360
tagatcatta tacaacacag tagcaactct ctattgtgta catgaagggg tagaggtacg    420
agacaccaag gaagccttag acaggataga ggaagaacaa aacaaaattc agcaaaaaat    480
acagcaaaaa acacagcaag cggctgacgg aaaggtcagt caaaattatc ctatagtgca    540
gaatctccaa gggcaaatgg tacaccagaa actatcacct agaactttga atgcatgggt    600
aaaagtaata gaagaaaaag cttttagccc agaggtaata cccatgttta cagcattatc    660
agaaggagcc accccacaag atttaaacac catgttaaat acagtggggg gacatcaagc    720
agccatgcaa atgttaaaag atactatcaa tgaggaggct gcagaatggg atagattaca    780
tccagtgcat gcagggccta ttgcaccagg ccaaatgaga gaaccaaggg gaagtgatat    840
agcaggaact actagtaccc tccaagaaca gatagcatgg atgacaagta atcccccctat    900
tccagtggga gacatctata aaagatggat aattctgggg ttaaataaaa tagtaagaat    960
gtatagccct gtcagcattt tggacataaa acaagggcca aaggaaccct ttagagacta   1020
tgtagaccgg ttcttcaaaa ctttaagagc tgaacaggct acacaagaag taaaaaattg   1080
gatgacagac accttgttgg tccaaaatgc aaacccagat tgcaagacca ttttaaaagc   1140
attaggacca ggggctacat tagaagaaat gatgacagca tgtcaaggag tgggaggacc   1200
tagccacaaa gcaagagtgt tggctgaggc aatgagccaa acaaatagtg taaacatact   1260
gatgcagaaa agcaatttta aaggaaataa aagaatggtt aaatgtttta actgtggtaa   1320
ggaagggcac atagccagaa attgcagggc ccctaggaaa aagggctgtt ggaaatgtgg   1380
aaaggaggga caccaaatga aagactgtac tgagaggcag gctaattttt tagggaaaat   1440
ttggccttcc cacaagggaa ggccagggaa tttccttcag aacaggccag agccaacagc   1500
cccaccagca gagagcttca ggttcgagga gacaaccccc gctccgaagc aggagtcgaa   1560
agacagggaa gccttaactt ccctcaaatc actctttggc agcgacccct tgtctcaata   1620
aaggtagggg gccaaataaa ggaggctctc ttagacacgg gagcaggtga tacagtatta   1680
gaagaaataa atttgccagg caaatggaaa ccaaaaatga taggaggaat tggaggcttt   1740
atcgaagtaa gacaatatga tcaaatacct atggaaattt gtggaaaaaa ggctataggt   1800
acagtattag taggacctac acctgtcaac ataattggaa gaaatatgtt gactcagctt   1860
ggatgcacac taaattttcc aattagtcct attgaaactg taccagtaaa attaaagcca   1920
ggaatggatg gcccaaaggt taaacaatgg ccattgacag aagagaaaat aaaagcttta   1980
acagcaattt gtgaagaaat ggagaaggaa ggaaaaatta caaaaattgg gcctgaaaat   2040
ccatataaca ctccagtatt tgccataaaa aagaaggaca gtactaagtg gcgaaaatta   2100
gtagatttca gggaactcaa taaaagaact caagactttt gggaagttca attaggaata   2160
ccacacccag cagggttaaa aaagaaaaaa tcagtgacag tactggatgt gggggatgca   2220
tatttttcag ttcctttaga tgaaagcttc aggaaatata ctgcattcac catacctagt   2280
```

-continued

```
acaaacaatg aaacaccagg gattagatat caatataatg tgcttccaca gggatggaaa   2340
ggatcaccag caatattcca gagtagcatg acaaaaatct tagagccctt cagggcacaa   2400
aatccagaca tagtcatcta tcaatatatg gatgacctgt atgtaggatc tgacttagaa   2460
atagggcaac atagagcaaa aatagaagag ttaagagaac atctattaaa gtggggattt   2520
accacaccag acaagaaaca tcagaaagaa cccccatttc tttggatggg gtatgaactc   2580
catcctgaca aatggacagt acagcctata cagctggcag aaaaagatag ctggactgtt   2640
aatgatatac agaagttagt gggaaaatta aactgggcaa gtcagattta cgcagggatt   2700
aaagtaaggc aactttgtaa actccttagg ggagccaaag cactaacaga catagtacca   2760
ctaactgaag aagcagaatt agaattggca gagaacaagg aaattttaaa agaaccagta   2820
catggggtat attatgaccc atcaaaagac ttgatagctg aaatacagaa acaagggcat   2880
gaccaatgga catatcaaat ttaccaggaa ccattcaaaa atctgaaaac agggaagtat   2940
gcaaaaatga ggacagccca cactaatgat gtaaaacagt taacagaggc agtgcaaaaa   3000
atagccctgg agagcatagt aatatgggga aagattccta aatttagact acccatccaa   3060
aaagaaacat gggaaacatg gtggacagac tattggcaag ccacctggat tcctgagtgg   3120
gagtttgtta ataccccctct cttagtaaaa ttatggtacc agctggagaa agaacccata   3180
gtaggagcag aaaccttcta tgtagatgga gcagccaata gggaaactaa attaggaaaa   3240
gcagggtata ttactgacag aggaaggcaa aaaattgtta ctctaactga aacaacaaat   3300
cagaagactg aattacaagc aatttaccta gctttgcaag attcaggatc agaagtaaac   3360
atagtaactg actcacagta tgcgttagga atcattcaag cacatccaga taagagtgaa   3420
tcagagttag tcaaccaaat aatagaacaa ttaataaaga aggaaagggt ctacctgtca   3480
tgggtaccag cacataaagg aattggaggt aatgaacagg tagataaatt agtaagcaag   3540
ggaatcagga aagtgctgtt tctagatgga atagacaagg ctcaagaaga gcatgaaaaa   3600
tatcacaaca attggagagc aatggctagt gaatttaatc taccaccagt agtagcaaaa   3660
gaaatagtag ctagttgtga taaatgtcag caaaaagggg aagccacaca tggacaagta   3720
gactgtagtc cagggatatg gcaattagac tgtacacatt tagaaggaaa aatcatcctg   3780
gtagcagtcc atgtagccag tggctacata gaagcagagg ttatcccagc agaaacagga   3840
caagaaacag catactatat attaaaatta gcaggaagat ggccagtcaa agtaatacat   3900
acagacaatg gtagcaattt taccagtgct gcagttaagg cagcctgttg gtgggcaggt   3960
atcaaacaag aatttggaat tccctacaat ccacaaagtc agggagtagt agaatccatg   4020
aataaagaat taaagaaaat catagggcag gtaagagatc aggctgagca tcttaaaaca   4080
gcagtacaaa tggcagtatt cattcacaat tttaaaagaa aaaggggggat tgggggggtac   4140
agtgcagggg aaagaataat agacataata gcaacagaca tacaaaccaa agaactacaa   4200
aaacaaatta taaacattca aaaatttcgg gtttattaca gagacagcag agaccccatt   4260
tggaaaggac cagccaaact actctggaaa ggtgaagggg cagtagtaat acaagataat   4320
agtgacataa aagtggtacc aaggaggaaa gcaaaaatca ttagggacta tggaaaacag   4380
atggcaggcg ctgattgtgt ggcaggtaga caggatgagg attagaacat ggaatagttt   4440
agtaaagcac catatgtata tttcacggaa agctaatgga tggttttaca gacatcatta   4500
tgaaagcaga catccaaggg taagttcaga agtacatatc ccattagggg atgctaaatt   4560
agtaataaaa acatattggg gtttgcaaac aggagaaaga gattggcatt tgggtcatgg   4620
agtctccata gaatggagat tgagaagata tagcacacaa gtagaccctg gcctggcaga   4680
```

-continued

```
ccagctaatt catatgcact attttgattg ttttgcagac tctgccataa gaaaagccat   4740
attaggacac atagttattc ctaggtgtga ctatcaagca ggacataata aggtaggatc   4800
tctgcaatac ttggcactga cagcattgat aaaaccaaaa aagagaaagc cacctctgcc   4860
tagtgttagg aaattagtag aggatagatg gaacaattcc cagaagacca agggccgcag   4920
agggaaccat acagtgagtg gacactagag attctagagg aactcaagca ggaagctgtc   4980
agacactttc ctagaccatg gctccatagc ttaggacaac atatctatga aacttatggg   5040
gatacttgga ctggagtcga ggctataata agaatactgc aacaactact gtttattcat   5100
ttcagaattg ggtgccagca cagcagaata ggcatggttc gacagagaag agcgagaaat   5160
ggagccagta gatcctagca tagagccctg gaaccatcca ggaagtcagc ctaaaactgc   5220
ttgtaataag tgttattgca aacgctgtag ctatcattgt ctagtttgct ttcagacaaa   5280
aggcttaggc atttcatatg gcaggaagaa gcggagacag cgacgcagca ctcctcctag   5340
cagcgaggac catcaagatc ctatatcaaa gcagtaagta tatgtaatgt tagatttact   5400
agcaagagta aattatagag taggagtagg agcattgata gtagcactac tcatagcaat   5460
agttgtgtgg accatagcat atatagaata taggaagctg ttaagacaaa gaaaaataga   5520
ctggttaatt aaaagaatta gggaaagagc agaagacagt ggcaatgaga gtgagggaga   5580
tactgaggaa ttggcaacga tggtggacat ggggcatctt aggcttttgg atgttaatga   5640
tttgtaatgt gtgggggaac ttgtgggtca cagtctatta tggggtacct gtgtggaaag   5700
aagcaaaaac tactctattc tgtgcatcag atgctaaatc atatgagaaa gaagtgcata   5760
atgtctgggc tacacatgcc tgtgtaccca cagaccccaa cccacaagaa atagttttgg   5820
gaaatgtaac agaaaatttt aacatgtgga aaaatgacat ggtggatcag atgcatgagg   5880
atataatcag tttatgggat caaagcctaa agccatgtgt aaagttgacc ccactctgtg   5940
tcactttaaa ttgtacagag gttaatgtta ccagaaatgt taataatagc gtggttaata   6000
ataccacaaa tgttaataat agcatgaatg gagacatgaa aaattgctct ttcaacataa   6060
ccacagaact aaaagataag aaaaagaatg tgtatgcact tttttataaa cttgatatag   6120
tatcacttaa tgagactgac gactctgaga ctggcaactc tagtaaatat tatagattaa   6180
taaattgtaa tacctcagcc ctaacacaag cctgtccaaa ggtctctttt gacccaattc   6240
ctatacatta ttgtgctcca gctggttatg cgattctaaa gtgtaataat aagacattca   6300
atgggacagg accatgccat aatgtcagca cagtacaatg tacacatgga attaagccag   6360
tggtatcaac tcaactactg ttaaatggta gcctagcaga agaagggata ataattagat   6420
ctgaaaatct gacaaacaat gtcaaaacaa taatagtaca tcttaataga tctatagaaa   6480
ttgtgtgtgt aagacccaac aataatacaa gacaaagtat aagaatagga ccaggacaaa   6540
cattctatgc aacaggagac ataataggag acataagaca agcacattgt aacattagta   6600
ggactaactg gactaagact ttacgagagg taaggaacaa attaagagaa cacttcccta   6660
ataaaaacat aacatttaaa ccatcctcag gaggggacct agaaattaca acacatagct   6720
ttaattgtag aggagaattt ttctattgca atacatcggg cctgtttagt ataaattata   6780
cagaaaataa tacagatggt acacccatca cactcccatg cagaataaga caaattataa   6840
atatgtggca ggaagtagga cgagcaatgt acgcccctcc cattgaagga aacatagcat   6900
gtaaatcaga tatcacaggg ctactattgg ttcgggatgg aggaagcaca aatgatagca   6960
caaataataa cacagagata ttcagacctg caggaggaga tatgagggac aattggagga   7020
```

-continued

```
gtgaattgta taagtataaa gtggtagaaa ttaagccatt gggaatagca cccactgagg   7080
caaaaaggag agtggtggag agagaaaaaa gagcagtggg aataggagct gtgttccttg   7140
ggttcttggg agcagcagga agcactatgg gcgcagcgtc aataacgctg acggcacagg   7200
ccagacaagt gttgtctggt atagtgcaac agcaaagcaa tttgctgagg gctatagagg   7260
cgcaacagca tctgttgcaa ctcacggtct ggggcattaa gcagctccag acaagagtcc   7320
tggctataga aagataccta aaggatcaac agctcctagg actttggggc tgctctggaa   7380
aactcatctg caccactgct gtgccttgga acatcagttg gagtaataaa tctaaaacag   7440
atatttggga taacatgacc tggatgcagt gggatagaga aattagtaat tacacaaaca   7500
caatatacag gttgcttgag gactcgcaga gccagcagga gcaaaatgaa aaagatttat   7560
tagcattgga cagttggaac aatctgtgga attggtttga cataacaaaa tggctgtggt   7620
atataaaaat atttataatg atagtaggag gcttaatagg tttgagaata atttttgctg   7680
tactctctat agtgaataga gttaggcagg gatactcacc tttgtcgttt cagaccctta   7740
tcccgaaccc aagggaaccc gacaggccag gaagaatcga agaagaaggt ggagagcaag   7800
acaaagagag atccgtgcga ttagtgagcg gattcttagc acttgcctgg gacgacctac   7860
ggagcctgtg cctcttcagc taccaccgat tgagagactt catattggtg acagcgagag   7920
cggtggagct tctgagacgc agcagtctca agggactaca gaggggggtgg gaagccctta   7980
agtatctggg aagtcttgtg cagtattggg gtctggagct aaaaaagagt gctattagtc   8040
tacttgatac catagcaata gcagtagctg aaggaacaga taggattata gaattaatac   8100
aaggaatttg tagagctatc cgcaacgtac ctagaagaat aagacagggc tttgaaacag   8160
ctttgctata aaatgggggg caagtggtca aaaagcagta tagttggatg gcctgctgta   8220
agagagagaa taagaagaac tgagccagca gcagagggag taggagcagc gtctcaagac   8280
ttagataaat atggagcact tacaagcagc aacacaagta ccactaatgc tgcttgtgcc   8340
tggctggaag cacaagagga ggaagaagtt ggctttccag tcagacctca ggtgccttta   8400
agaccaatga cttataaggc agcagtcgat ctcagcttct ttttaaaaga aaagggggga   8460
ctggaagggt taatttactc taagaaaagg caagaaatcc ttgatttgtg ggtctatcac   8520
acacaaggct tcttccctga ctggcaaaac tacacaccgg gaccaggggt cagatatcca   8580
ctgacctttg gatggtgctt caagctagtg ccagttgatc caggggaagt agaagaggcc   8640
aacgaaggag aaaacaactg tctgctacac cctatgagcc agcaaggaat ggatgatgat   8700
cacagagaag tattaaagtg gaagtttgac agtcacctag cacataaaca catggcccga   8760
gagctacatc cggagtatta caaagactgc tgacacagaa gggactttcc gctgggactt   8820
tccactgggg ttccaggagg tgtggtctgg gcgggactgg ggagtggtca accctcagat   8880
gctgcatata agcagctgct tttcgcttgt actgggtctc tctaggtaga ccagatctga   8940
gcctgggagc tctctggcta tctagggaac ccactgctta agcctcaata aagcttgcct   9000
tgagtgctct                                                          9010
```

<210> SEQ ID NO 9
<211> LENGTH: 8972
<212> TYPE: DNA
<213> ORGANISM: Human immunodeficiency virus type 1
<220> FEATURE:
<223> OTHER INFORMATION: isolate=96ZM751.3; 137.1632:gag; 1419.4435:pol; 4380.4958:vif; 4898.5188:vpr; 5169.7814:tat; 5308.7938:rev; 5407.5667:vpu; 5585.8128:env; 8130.8753:nef -continued

<400> SEQUENCE: 9

```
ccgaaagcga aagtaagacc agaggagatc tctcgacgca ggactcggct tgctgaagtg     60
cactcggcaa gaggcgagag cggcggctgg tgagtacgcc aattttattt gactagcgga    120
ggctagaagg agagagatgg gtgcgagagc gtcaatatta agaggcggaa aattagatga    180
atgggaaaga attaggttaa ggccaggggg aaaaaagcac tatatgatga aacacttaat    240
atgggcaagc agggagctgg aaagatttgc acttaaccct ggccttttag agacatcaga    300
aggctgtaaa caaataatac aacagctaca accagctctc cagacaggaa cagaggaact    360
taggtcatta tataatacag tagcaactct ctattgtgta catgaaaaga taaaggtacg    420
agacaccaag gaagccctag acaagataga ggaagaacaa aacaaaagtc aacaaaaaat    480
acaaaaaaca gaagcgactg gcggaaaggt cagtcaaaat tatcctatag tgcagaatct    540
ccaagggcaa atggtacacc aggctatatc acctagaact ttgaatgcat gggtaaaagt    600
aatagaggag aagggtttca acccagaggt aatacccatg tttacagcat tatcagaagg    660
agccacccca caagatctaa acaccatgtt aaatacagtg gggggacatc aagcagccat    720
gcaaatgtta aaagatacca tcaatgagga agctgcagaa tgggataggt tacatccagt    780
acatgcaggg cctattgcac caggccaaat aagagaacca aggggaagtg acatagcagg    840
aactactggt acccttcagg aacaaatagc atggatgaca aataacccac ctattccagt    900
gggagacatc tataaaagat ggataattct ggggttaaat aaaatagtaa gaatgtacag    960
ccctgtcagc attctggaca taaaacaagg accaaaggaa ccctttaggg actatgtaga   1020
tcggttcttt aaaactttaa gagctgaaca agctacacaa gatgtaaaaa ttggatgaca   1080
gacaccttgt tggttcaaaa tgcgaaccca gattgtaaga ccattttaag ggcattagga   1140
ccaggggcta cattagaaga aatgatgaca gcatgtcagg gagtgggggg acctggccac   1200
aaagcaagag ttttggctga agcaatgagc caagtaaaca atacaaacat aatgatgcag   1260
aaaagcaatt ttaaaggccc taaaagaatt gttaaatgtt tcaactgtgg cagggaaggg   1320
catatagcca ggaattgcag ggctcctggg aaaaaaggct gttggaaatg tggaaaggaa   1380
ggacaccaaa tgaaagactg tactgagaga caggctaatt ttttagggaa aatttggcct   1440
tcccagaagg ggaggccggg gaacttcctt cagaacagac cagagccaac agccccacca   1500
gctccaacag ccccaccagc agagagcttc aggttcgagg agacaacccc tgccccgagg   1560
caggagcaga aagacaagga accettaact gccctcaaat cactctttgg cagcgacccc   1620
ttgtctcaat aaaagtaggg ggtcagataa aggaggctct cttggataca ggagcagatg   1680
atacagtatt agaagaaata aatttgccag gaaaatggaa accaaaaatg ataggaggaa   1740
ttggaggttt tatcaaagta agacagtatg atcaaatact tatagaaatt tgtggaaaaa   1800
aggctatagg tacagtatta gtaggaccta cacctgtcaa cataattggg agaaatatgt   1860
tgacccagct tggctgcaca ctaaattttc caattagtcc tattgaaact gtaccagtaa   1920
aattaaagcc aggaatggat ggcccaaggg tcaaacaatg gccattgaca gaagaaaaaa   1980
taaaagcatt aacagcaatt tgtgaagaaa tggaaaagga aggaaaaatt acaaaaattg   2040
gccctgagaa tccatataac actccagtat ttgccataaa aaagaaggac agtactaagt   2100
ggagaaaatt agtagatttc agggaactca ataaaagaac tcaggacttt tgggaagttc   2160
aattaggaat accacaccca gcggggttaa aaaagaaaaa gtcagtgaca gtactggatg   2220
tgggggatgc gtatttttca gttcctttag atgaaggctt caggaaatat actgcattca   2280
ccatacctag tataaacaat gaaacacctg ggattagata tcaatataat gtgcttccac   2340
```

-continued

```
agggatggaa aggatcacca tcaatattcc agagtagcat gataaaaatc ttagagccct   2400
ttaggacaca aaacccagaa atagttatct atcaatatat ggatgacttg tatgtaggat   2460
ctgatttaga aatagggcaa cacagagcaa aaatagagga gttaagagaa cacctattga   2520
gatggggatt tactacacca gacaagaagc atcagaaaga gcccccattt ctttggatgg   2580
ggtatgaact ccatcctgac aaatggacag tacagcctat aaagctgcca gaaaaggaga   2640
gctggactgt caatgatata cagaagttag tgggaaaatt aaactggcaa gtcagattta   2700
cgcagggatt aaagtaaggc aactgtgtaa actccttagg ggagccaaag cactaacaga   2760
catagtacca ttgactgaag aggcagaatt agaattggca gagagcaggg aaattctaaa   2820
agaaccagta catggagtat attatgaccc atcaaaagac ttaatagctg aaatacagaa   2880
acaagggcat gaccaatgga catatcaagt ttaccaagaa ccattcaaaa atctgaaaac   2940
aggaaagtat gcaaaaatga ggactgccca cactaatgat gtaaaacagt taacagaggc   3000
ggtgcaaaaa atagccatgg aaagcatagt aatatgggga aagattccta aatttaggct   3060
acccattcaa aaagaaacat gggagacatg gtggacagac tattggcaag ccacctggat   3120
tcctgagtgg gagtttgtta atactccccc cctagtaaaa ttatggtacc agctggagaa   3180
agaacccata gcaggagcag aaacttacta tgtagatgga gcagccaata gggaaactaa   3240
aataggaaaa gcagggtatg ttactgacag aggaaggcaa aaaattgtta ctctaactga   3300
aacaacaaat caaaagactg aattacaagc aattcagtta gctttgcagg attcaggatc   3360
agaagtaaac atagtaacag actcacagta tgcattagga atcatccaag cacaaccaga   3420
taagagtgaa tcagaattag tcaatcaaat aatagaacag ttgataaaaa aggaaagggt   3480
ttacctgtca tgggtaccag cacacaaagg aattggagga aatgaacaag tagataaatt   3540
ggtaagtagt ggaatcagga aagtgctgtt tctagatgga atagataagg ctcaagaaga   3600
gcatgaaaaa tatcacagca attggagagc aatggctagt gagtttaatc tgccacccat   3660
agtagcaaaa gaaatagtag ccagctgtga taaatgtcag ctaaaagggg aagccataca   3720
tggacaagta gactgtagtc caggaatatg gcaattagat tgtacccatt tagaaggaaa   3780
agtcatcttg gtagcagtcc atgtagccag tggttacata gaagcagagg tcaccccagc   3840
ggaaacagga caagaaacag cacttttcat actaaaatta gcaggaagat ggccagtcaa   3900
agtagtacat acagacaatg gcagtaattt caccagtgct gcagtcaagg cagcctgttg   3960
gtgggcaggt atccaccagg aatttggaat tccctacaat ccccaaagtc aaggagtagt   4020
agaatccatg aataaagaat taaagaaaat tatagggcag gtaagagatc aagctgagca   4080
ccttaagaca gcagtacaaa tggcagtatt cattcacaat tttaaaagaa aaggggggat   4140
tggggggtac agtgcagggg aaagaataat agacataata gcaacagaca tacaaactag   4200
agaattacaa aaacaaatta taaaaattca aaattttcgg gtttattaca gagacagcag   4260
agaccctatt tggaaaggac cagccaaact actctggaaa ggtgaagggg cagtagtaat   4320
acaagataat agtgacataa aggtaatacc aaggaggaaa gcaaaaatca ttagggacta   4380
tggaaaacag atggcaggta ctgatagtgt ggcaggtaga caggatgaag attagaacat   4440
ggaatagttt agtaaagcac catatgtatg tttcaaaaag aactggtaga tggttttaca   4500
gacatcatta tgaaagcaga catccaaaaa taagttcaga agtacacatc ccattagggg   4560
atgccaaatt agtaataaaa acatattggg ggctgcatcc aggggaaaga gaatggcatt   4620
tgggtcatgg agtctccata gaatggagat tgagaagata cagcacacaa gtagaccctg   4680
```

-continued

```
gcctggcaga ccagctaatt catatgcatt attttaattg ttttgcagac tctgccataa   4740
gaaaagccct actaggacat atagttattc ctaggtgtga ttatcaagca ggacataata   4800
aggtaggatc cctacaatac ttggcactga cagcattgat aaaaccaaaa aagataaagc   4860
cacctttacc tagtgttagg aaattagtag aggatagatg gaacaagccc cagaaaacca   4920
agggccgcag agggaaccat ataatgaatg ggcactagag cttttagagg agctcaagca   4980
ggaagctgtc agacactttc ctagaacatg gctccataac ttaggacaac atatctacca   5040
aacctacggg gatacttgga cgggggttga agctctaata agaatactgc aacaactact   5100
gtttattcat ttcagaattg gatgccaaca tagcagaata ggcattatgc gacagagaag   5160
agcaagaaat ggagccagta gatcctagac tagagccctg gaatcatcca ggaagtcaac   5220
ctaaaactcc ttgtaataag tgttattgta aacactgtag ctatcattgt ctagtttgct   5280
ttcagacaaa aggcttaggc atttcctatg gcaggaagaa gcggagacaa cgacgaagcg   5340
ctcctccaag cagtgaggat catcaaaatc ctatatcaaa gcagtaagta caaagtaata   5400
gatgtaatgt taaatttaga agcaagagta gattatagaa taggagtagg agcattaata   5460
gcagcactaa tcatagcaat agctgtgtgg atcatagtat atatagaata tagaaaattg   5520
tcaagacaaa gaaaaataga ccggttaatt aaaagaatta gagaaagggc agaagacagt   5580
ggcaatgaga gtgaagggga taatgaggaa ttggcaacaa tggtggatat ggggcatctt   5640
aggcttttgg atgctattga tgtgtaatgc aatggggaaa ttgtgggtca cagtctacta   5700
tggggtacct gtgtggaaag aagcaaaaac tactttattt tgtgcatcag atgctaaagc   5760
atatgagaca gaagtgcata atgtttgggc tacacatgcc tgtgtaccca cagaccccaa   5820
cccacaagaa atggttttgg aaaatgtaac agaaaagttt aacatgtggg aaaataacat   5880
ggtggatcag atgcatgagg atataatcag tttatgggac caaagcctaa agccatgtgt   5940
aaagttgacc ccactctgtg tcactttaaa ctgtactgct aatataacca acaatgctaa   6000
tataaccaac aatgctaata taaccaacta taataatgaa actgacatga gaaattgctc   6060
tttcaatata accacagaat taagagataa gaggaggcaa gtagatgcac tcttttataa   6120
acttgatata gtaccaatta atgagaattc cagtgaatat agattaataa attgtaatac   6180
ctcggccata acacaagcat gtccaaaggt tacttttgac ccaatcccta tacattattg   6240
tgctccagct ggttatgcga ttctaaagtg taacaataag acattcaatg gaacaggacc   6300
atgcaataat gtcagcacag tacaatgtac acatggaatt aagccagtag tatcaactca   6360
attactgtta aatggtagtc tagcagaaga agagataata attagatcta aaaatatgac   6420
agacaatgcc aaaataataa tagtacatct taatgaatct gtagaaattg tgtgtacaag   6480
acccaacaat aatacaagga aaagtgtgag gataggacca ggacaaacat tctatgcaac   6540
aggagaaata ataggaaata taagacaagc atattgtaac atcagtgaag gcaaatggaa   6600
taacactcta caaagggtag gtgaaaaatt aagaaaatac ttccctaata aaacaataag   6660
ctttgcacca tcctcaggag gggacctaga aattacaaca catagcttta attgtagagg   6720
agaatttttc tattgcaata catcaaaact gtttaatggt acgtttaatg gtacaaacac   6780
ttctaatgat agaagtaatt cgaccattac gcttcaatgc agaataaaac aaattacaaa   6840
catgtggcag ggggtaggac aagcaatgta tgctcctcca attaaaggaa acataacatg   6900
taaatcaaat atcacaggac tactattaac acgtgatgga gggacaaatg acacagagac   6960
accagagaca ttcagacctg gaggaggaga catgaaggac aattggagaa gtgaattata   7020
taaatataaa gtggtagaaa ttaagccatt aggagtagca cccactaagg cacgaaggag   7080
```

-continued agtggtggag agagaaaaaa gagcagtagg aataggagct gtgttccttg ggttcttggg 7140
agcagcagga agcactatgg gcgcagcatc aataacgctg acggtacagg tcagacaatt 7200
attgtctggt atagtgcaac agcaaagcaa tttgctgagg gctatagagg cgcaacagca 7260
catgttgcaa ctcacagtct ggggcattaa gcagctccag gcaagagtct tggctataga 7320
aagataccta aaggatcaac agctcctagg gatttggggc tgctctggaa aactcatctg 7380
caccactgct gtgccttgga actctagttg gagcaacaaa tctgaacggg agatttggga 7440
taacatgacc tggatgcagt gggatagaga aattaataat tacacagaaa caatatatag 7500
gttgcttgaa gtctcgcaaa accagcagga aaataatgaa agggatttac tagcattgga 7560
cagttgaaaa aatctgtgga attggtttaa tataacaaat tggctgtggt atataaaaat 7620
attcataatg ataataggag gcttgatagg tttaagaata atttttgctg tgctctctat 7680
agtaaataga gttaggcagg ggtactcacc tttgtcgttg cagaccctta tcccaacccc 7740
gagggaacca gacaggctcg gaagaatcga agaagaaggt ggagagcaag acagagacag 7800
atcaattcga ttagtgaacg gattcttagc acttgtctgg gacgacctcc ggagcctgtg 7860
ccttttcagc taccaccgct tgagagactt catattgatt gcagcgaggg gactacagag 7920
ggggtgggaa actcttaagt atctggggag tcttgtacag tattggggtc tagagctaaa 7980
aaagagtgct attagtttgc ttgatactat agcaatagca gtagctgaag gaacagatag 8040
aattatagaa ttaacacaaa gaatttgtag agctatccgc aacgtaccta gaagaataag 8100
acagggcttt gaagcagctt tgcaataaga tgggaggcaa gtggtcaaaa cgcagtatag 8160
ttggatggcc taaagtaaga gaaagaatag caagaactga tccagcagca gagggagtag 8220
gagcagcgtc tcaagactta gataaatatg ggcacttac aagcagtaac acaagtacca 8280
ataatgctga ttgtgcctgg ctggaagcgc aagaggagga gggagaagta ggctttccag 8340
tcagacctca ggtaccttta agaccaatga cttataagtc agcatttgat ctcagcttct 8400
ttttaaaaga aaagggggga ctggatgggt taatttactg taagaaaaga caagaaatcc 8460
tcgatttgtg ggtctatcac acacaaggct acttccctga ttggcaaaac tatacaccgg 8520
gaccagggat cagatatcca ctgacctttg gatggtgcta caagctagtg ccagttgacc 8580
caagggaagt agaagaagcc aacgaaggag aggacaactg tttgctacac cctataagcc 8640
agcatggaat agaagatgaa gacagagaag tattaaggtg gaagtttgac agttccctag 8700
cacgcagaca catggcccgc gagctacatc cggagtatta caaagactgc tgacacagaa 8760
gggactttcc gctgggactt tccactgggg cgttccaggg ggtgtgatct gggcgggact 8820
ggggagtggc cagccctcag aagctgcata taagcagctg cttttcgcct gtactgggtc 8880
tctctaggta gaccagatct gagcccggga gctctctggc tatctaggga acccactgct 8940
taagcctcaa taaagcttgc cttgagtgcc tt 8972

<210> SEQ ID NO 10
<211> LENGTH: 9060
<212> TYPE: DNA
<213> ORGANISM: Human immunodeficiency virus type 1
<220> FEATURE:
<223> OTHER INFORMATION: isolate=94CY017.41; 159.1649:“gag”;
1442.4453:“pol”; 4398.4976:“vif”; 4916.5206:“vpr”;
5187.7841: “tat”; 5326.8046:“rev”;
5428.5673:“vpu”; 5591.8188:“env”; 8190.8843:“nef”

<400> SEQUENCE: 10
ttgaaaagcg aaagtaacag ggactcgaaa gcgaaagttc cagaggagtt ctctcgacgc 60

-continued

```
aggactcggc ttgctgaggt gcacacggca agaggcgagg ggcggcgact ggtgagtacg    120
cctaatattt ttgactagca gaggctagaa ggagagagat gggtgcgaga gcgtcaatat    180
taagcggggg aaaattagat gcttgggaga aaattcggtt aaggccaggg ggaaagaaaa    240
aatatagact gaaacatttg gtatgggcaa gcagggagct ggagaaattc tcaattaacc    300
ctggcctttt agaaacacca gagggatgta gacaaataat aaggcagtta caaccagctc    360
tccaaacagg aacagaagaa cttaaatcat tatataatac agtagtagtc ctctactggg    420
tacatcaaag ggtagatgta aaagacacca aggaagctct agataaaata gaggaagaac    480
aaaacaagca gaaaacacag catgcagcag ctgacacagg gaacagcagc agtcaaaatt    540
atcccatagt gcaaaatgca caagggcaaa tggtacacca ggctatatca cctaggacgt    600
tgaatgcctg ggtcaaagta gtagaagaaa aggctttcag cccagaagta atacctatgt    660
ttacagcatt atcagaagga gccaccccac aagacttaaa tactatgcta aacacagtgg    720
ggggacatca agcagctatg caaatgttaa aagataccat caatgaggaa gctgcagaat    780
gggacagggt acatccagta catgcagggc ctattccacc aggccagatg agagaaccaa    840
ggggaagtga catagcagga actactagta cccttcagga acaaataggt tggatgacca    900
gcgatccacc catcccagtg ggagaaattt ataaaagatg gataatcctg ggattaaata    960
aaatagtaag aatgtatagc cctgtcagca ttttggacat aagacaaggg ccaaaagaac   1020
cctttagaga ttatgtggat aggttcttta aaactctaag agctgagcaa gccacacagg   1080
aggtaaaaaa ctggatgacg gacaccttgc tggtccaaaa tgcgaaccca gattgtagat   1140
ccatcttgag agcattagga ccaggggcct cattagaaga aatgatgaca gcatgtcagg   1200
gagtgggagg acccagccat aaagcaaggg ttttggctga agcaatgagc catgtacaaa   1260
gtacaaatac aaacataatg atgcagagag gcaattttag gggtcaaaaa agaattaagt   1320
gtttcaactg tggcaaggaa ggacacctag ccagaaattg cagggcccct aggaaaaagg   1380
gctgctggaa atgtggaaag gaaggacatc aaatgaaaga ttgcactgag agacaggcta   1440
attttttagg gaaaatttgg ccttccaaca aagggaggcc aggaaatttt cctcagagca   1500
gaacagagcc aacagcccca ccagcagaga acttgagaat gggggaagag ataacctcct   1560
ccctgaagca ggaactggag accagggaac catacaatcc tgcaatttcc ctcaaatcac   1620
tctttggcaa cgaccccttg ttacagtaaa gatagaggga cagctaaaag aagctctatt   1680
agatacagga gcagatgata cagtgttaga agaaataaat ttgccaggaa aatggaaacc   1740
aaaaatgata gggggaattg gaggttttat caaagtaaga caatatgatc agatagctat   1800
agaaatttgt ggaaaaaggg ccataggtac agtattagta ggacctaccc ctgtcaacat   1860
aatcggaaga aatatgttgg ttcagcttgg ttgtacttta aattttccaa ttagtcctat   1920
tgaaactgta ccagtaaaat taaagccagg aatggatggt ccaaaggtta aacaatggcc   1980
attgacagaa gaaaaaataa aagcattaac agaaatctgt aaagaaatgg aaaaggaagg   2040
aaaaatttca aaaattgggc ctgaaaatcc atacaacact ccagtgtttg ctataaagaa   2100
aaaagacagc actaaatgga gaaaattagt agattttaga gaactcaata agagaactca   2160
agacttctgg gaagttcagt taggaatacc acatccagca ggattaaaaa agaaaaaagc   2220
agtaacagta cttgatgtgg gggacgcata tttttccgtt cccttacatg aagacttcag   2280
aaaatatact gcattcacca tacctagtac caacaatgag acaccaggag ttaggtatca   2340
gtacaatgta cttccacagg gatggaaagg atcaccagca atattccaga gtagcatgac   2400
```

-continued

```
aaagatctta gagcccttta gatcaaagaa tacagaatta atcatctacc aatacatgga   2460
tgacttgtat gtaggatctg atttagaaat aagccagcat agagtaaaaa tagaggaatt   2520
aagggctcac ttattgaaat ggggatttta tacaccagac aaaaaacatc agaaagaacc   2580
tccatttctt tggatgggat atgagcttca tcctgacaaa tggacagtcc agcctataaa   2640
gctgccagaa aaagacagct ggactgtcaa tgatatacag aaattagtag ggaaattaaa   2700
ttgggcaagt cagatttatg cagggattaa agtaaagcaa ctgtgtaaac tccttagagg   2760
agccaaagca ctaacagaca tagtaacact gactaaagaa gcagagttag aattagaaga   2820
gaacagggaa attttaaaaa cccctgtaca tggggtatac tatgacccat caaaagactt   2880
aatagcagaa atacagaaac aagggcaaga ccaatggaca tatcaaattt atcaggaacc   2940
ctttaagaat ctgaaaacag ggaaatatgc aaaaaggagg tccacccaca ctaatgatat   3000
aaaacagtta acagaagcag tacaaaaaat aaccatggaa agcatagtga tatggggaaa   3060
gactcctaaa tttaaattac ccatacaaaa ggaaacatgg gagacatggt gggcggagta   3120
ttggcaggct acctggattc ctgagtggga gtttgtcaat acccctcctc tagtaaaact   3180
gtggtaccag ttagaaaaag aacccatagc aggagcagaa actttctatg tagatggggc   3240
agctaataga gagactaaac taggaaaggc agggtatgtc actgacagag gaagacaaaa   3300
aattgtctcc ctgacggaga caacaaatca aaagactgaa ttacatgcaa tctatttggc   3360
tttacaggat tcaggattag aagtgaacat agtgacagat tcacagtatg cattaggaat   3420
cattcaagca caaccagaaa ggagtgaatc agagatagtc aatcaaataa tagaaaaatt   3480
aatagaaaag gaaagggtct acctatcatg ggtaccagca cacaaaggga ttggaggaaa   3540
tgaacaagta gacaaattag tcagttctgg aatcaggaaa gtgctatttt tagatgggat   3600
agataaggct caagaggaac atgaaagata tcacagcaat tggagagcaa tggctcatga   3660
ctttaatcta ccacctgtag tagcaaaaga aatagtagct agctgtgata aatgtcagct   3720
aaaaggggaa gccatgcatg gacaagtaga ctgtagtcca ggaatatggc aactagattg   3780
cacacatctt gaaggaaaag ttatcctggt ggcagtccat gtggccagtg gctatataga   3840
agcagaagtc atcccaacag aaacaggaca ggatacagca tactttatat taaaactagc   3900
aggaagatgg ccagtaaaag taatacatac agacaatggg cccaatttca tcagtgcaac   3960
agttaaggca gcctgttggt gggcaggtat ccaacaagaa tttgggattc cctacaatcc   4020
ccaaagtcaa ggagtagtgg aatctatgaa taaagaatta aagaaaatca tagggcaggt   4080
aagagatcaa gctgaacacc ttaagacagc agtacaaatg gcagtattca ttcacaattt   4140
taaaagaaaa ggggggattg gggggataca gtgcaggggaa agaataatag acataatagc   4200
aacagatata caaactaaag aactacaaag acaaattaca aaaattcaaa attttcgggt   4260
ttattacagg gacagcagag atccaatttg gaaaggacca gcaaaactcc tttggaaagg   4320
tgaaggggca gtagtaatac aagacaatag tgacataaag gtagtaccaa gaagaaaagc   4380
aaagatcatt agggattatg gaaaacagat ggcaggtgat gattgtgtgg caggtagaca   4440
ggatgaggat tagaacatgg aacagtttag ttaaacatca tatgtatatt tcaaggaaag   4500
ctaaaggttg ggtctataaa catcactatg aaagcagaaa tccaagaata agttcagaag   4560
tacacatccc gctaggggag gctagaataa tagtaagaac atattggggt ctgcacatag   4620
gagaaaaaga ctggcacttg ggtcatggag tctccataga atggaggcaa aacaggtatc   4680
atacacaaat agaccctgat ctggcagacc atctaatcca tctgtattat tttgactgtt   4740
tttcagaatc tgccataagg aaagccataa taggagaaat agttagtcct aggtgtgaat   4800
```

-continued

```
atcaagcagg acataacaag gtagggtctc tgcaatattt ggcattgaaa gcagtagtag   4860
cttcaacaag gacaaagcca cctttgccta gtgttaggaa attagtagag gatagatgga   4920
acaagcccca gaagaccaag ggccacagag ggagccatac aatgaatgga tgttagaact   4980
gttagaggag ctcaagcagg aagctgttag acatttccct aggcactggc tacatggcct   5040
aggacaatac atctataata cctatgggga tacctgggaa ggagttgaag ttatcataag   5100
atatctgcaa caactactgt ttgtccattt cagaattggg tgccaacata gcaggatagg   5160
cattattcga agaagaagag taagggatgg agccagtaga ccctaaacta gagccctgga   5220
accatccggg aagtcagcct aaaactgctt gtaccaaatg ttattgtaaa cgctgttgct   5280
atcattgcca gttgtgcttt ataaacaaag gcttaggcat ctcctacggc aggaagaagc   5340
gacgaccccg acgaaagcct tctccaagca ataaggacca tcaaaatcct ataccaaagc   5400
agtaagtagt agtaattaat atatgtaatg ttacctttag taatattggc aatagtagga   5460
ctgatagtag ctttaatctt agcaatagtt gtatggacta tagtattcat agaatataag   5520
aaaattaaga agcaaaggaa aatagactgg ttaatcaaaa gaataagtga gagagcagaa   5580
gacagtggca atgagagtga tggggacaca gaggaactat cagcacttgt ggagaggggg   5640
catcttgatt ttggggatgt taataatgtg taaagctaca gatttgtggg tcacagtata   5700
ctatggagta cctgtgtgga aagatgcaga taccatccta ttttgtgcat cagatgctaa   5760
agcatatgat acagaagtgc ataatgtatg ggccacacat gcctgtgtac ccacagaccc   5820
caacccacaa gaaataaacc tggaaaatgt aacagaaaat tttaatatgt ggaaaaataa   5880
catggtagag cagatgcaag aagatataat cagcttatgg gatcaaagcc taaagccatg   5940
tgtaaaatta accccgctct gcgtcatttt aaattgtagc aatgccaata ccagcaccca   6000
tagcaatagc agtagcaccc agagccccat taatgaagaa ataaaaaact gctcttacaa   6060
tactaccaca atactaagag ataagacaca aaaagtttat tcactgtttt atagacttga   6120
tgtagtacaa cttgatgaaa gtgaaaataa gaatacatca ggtagtaata ctctgtatag   6180
actaataaat tgtaatacct caaccatcac acaagcgtgt ccaaaggtaa cctttgagcc   6240
aattcctata cattattgtg ccccagctgg ttttgcgatt ctaaagtgta aggatccgag   6300
attcaatgga acagggtcat gcaagaatgt tagctcagta caatgtacac atggaattaa   6360
accagtagca tcaactcaac tgctgttgaa tggcagtcta gcagaaggag ggaaaataat   6420
gattagatct gaaaatatta caaacaatgc caaaaacata atagttcagt ttactaagcc   6480
tgtactaatt acttgtatca gacccaacaa caatacaaga aaaagtatac gctttggacc   6540
aggacaagcc ttctatacaa atgaaataat aggggacata agacaagcac attgtaatat   6600
caacaaaaca ttatggaatg acactttaca aaaggtagct gaacaattaa gagagaaatt   6660
ccctaagaaa accataatct ttactaactc ctcaggaggg gacccagaaa ttacaacact   6720
tagttttaat tgtgcaggag aatttttcta ttgcaataca acaggcctgt ttaatggtac   6780
gtggtggaac aatggtacgt ggaacgggcc ctacacacct aataacacca atggaagtat   6840
aatcctccca tgcagaataa aacaaattat aaacatgtgg cagagagtag gaagagcaat   6900
gtatgcccct cccattgcag gaataataaa gtgtacatca aacattacag gaataatatt   6960
gacaagagat ggtggtaaca atgggactaa tgagaccttc agacctggag gaggagatat   7020
gagggacaat tggagaagtg aattatataa atataaagta gtaaaacttg aaccactagg   7080
agtagcacct accagggcaa aaagaagagt ggtggagaga gaaaaaagag cagttggact   7140
```

-continued

```
gggagctgtc ttccttgggt tcttgggagc agcaggaagc actatgggcg cggcgtcact   7200
aacgctgacg gtacaggcca gacaattatt gtctggtata gtgcaacagc aaagcaattt   7260
gctgcaggct atagaagctc aacagcatct gttgaaactc acagtctggg gcattaaaca   7320
gctccaggcg agggtcctgg ctgtggaaag atacctaaag gatcaacagc tcctgggaat   7380
ttggggctgc tctggaaaac tcatctgcgc cactactgtg ccctggaaca ctagttggag   7440
taataagtct caggatgaga tttgggacaa catgacctgg ttgcaatggg ataaagaaat   7500
tagcaattac acaaacataa tatataggtt acttgaagaa tcgcaaaacc agcaggaaaa   7560
gaatgagcaa gacttattgg cattagacaa atgggcagat ttgtggagtt ggttcaacat   7620
ttcacactgg ctgtggtata taagaatatt tataatgata gtaggaggct tgataggatt   7680
aagaatagtt tttgctataa ttactgtagt aaatagagtt aggcagggat actcacctgt   7740
gtcatttcag atccctaccc caagcccaga gggtcccgac aggcccagag gaaccgaaga   7800
aggaggtgga gagcaaggca gagacagatc gattcgatta gtgaacgggt tcttcgcact   7860
tgcctgggac gacctacgga gcctgtgcct cttcagttac caccgcttga gagattgcat   7920
attgattgca gcgaggactg tggaacttct gggacactgc agtctcaagg gactgagact   7980
ggggtgggaa ggtctcaaga atctgtggaa tcttctgtta tactggggtc gggaactgaa   8040
gaatagtgct attagcttat ttgatactat agcagtagca gtagctgagt ggacagatag   8100
ggttatagaa atagggcaaa gagctttcag agctattctc aacataccta gaagaatcag   8160
acagggctta gaaagggctt tactataaaa tgggggggcaa gtggtcaaaa aggagcatac   8220
caggatggcc tgctattagg gagagaatga gaagaactcc tccaacagca caaagaacag   8280
aagcagtgtc tccagcagca ccaggagtag gagcagtgtc tcaagattta gctactcatg   8340
gagcagtcac aagcagtaat acagcagcta ctaatcctga ttgcgcctgg gtggaagcgc   8400
aagaagagga gagtgaagta ggcttcccag tcaggccaca ggtaccttta aggccaatga   8460
ccttcaaggg agcgtttgat ctcagcttct ttttaaaaga aaagggggga ctggatgggt   8520
taatttactc ccagaaaaga caagacatcc ttgatatgtg ggtctaccac acacaaggct   8580
acttccctga ttggcagaat tacacaccag ggccagggat cagataccca ttaacatttg   8640
gatggtgctt caagctagta ccagtagagc catctgaggt agaagaagct actcagggag   8700
agaacaacag cttattacac cctatatgcc aacatggagt agatgaccct gaaagagaag   8760
tgttaagatg ggagtttgat agaagcctgg cacggagaca cagagcccga gagctgcatc   8820
cggagtacta caaagactgc tgacacagaa gttgctgacg ggactttccc gctggggact   8880
ttccagggag gtgtggtgtg ggcggagttg gggagtggct aaccctcaga tgctgcatat   8940
aagcagctgc ttctcgcatg tactgggtct ctcttgttgg accagataga gcccgggagc   9000
tctctggcta gcaggggaac ccactgctta agcctcaata aagcttgcct tgagagcttc   9060
```

<210> SEQ ID NO 11
<211> LENGTH: 8959
<212> TYPE: DNA
<213> ORGANISM: Human immunodeficiency virus type 1
<220> FEATURE:
<223> OTHER INFORMATION: isolate=94IN476.104; 138.1613:"gag"; 1418.4428:"pol"; 4361.4939:"vif"; 4879.5169:"vpr"; 5150.7782:tat"; 5289.7939:"rev"; 5378.5638:"vpu"; 5556.8129:"env"; 8131.8754:nef

<400> SEQUENCE: 11

```
ttgaaagcga aagtaagacc agaggagatc tctcgacgca ggactcggct tgctgaagtg     60
```

-continued

```
cactcagcaa gaggcgaggg gggcgactgg tgagtacgcc aatttttatt tgactagcgg    120
aggctagaag gagagagatg ggtgcgagag cgtcaatatt aagaggggga aaattagata    180
gatgggaaaa aattcggtta aggccagggg gaaagaaaca ttatatgata aaacacttag    240
tatgggcaag cagggagctg gaaagatttg cgcttaaccc tggcctttta gagacgtcag    300
acggatgtaa acaaataata aaacagctac atccagctct taagacagga acagaggaac    360
ttaggtcatt attcaacaca gtagcaactc tctattgtgt acatgcaggg atagaggtac    420
gagacaccaa ggaagcctta gacaagatag aggaagaaca aaacaaaagt cagcaaaaaa    480
tacagcaggc aaaagaggct gacggaaagg tcagtcaaaa ttatcctata gtgcaaaatc    540
tccaagggca aatggtacac cagcccctat cacctagaac tttgaatgcg tgggtaaaag    600
taatagagga gaaggctttt agcccagagg taatacccat gttcacagca ttatcagaag    660
gagccacccc ctctgattta aacaccatgt taaatacagt gggggggacat caagcagcca    720
tgcaaatgtt aaaagatacc atcaacgagg aggctgcgga atgggataga ttacatccag    780
tacatgcagg gcctaatcca ccaggccaga tgagagaacc aaggggaagt gatatagcag    840
gaactactag tacccttcag gaacaaatag catggatgac aggtaaccca cctattccag    900
tgggagacat ctataaaaga tggataattc tggggttaaa taaaatagta agaatgtata    960
gccctgtcag cattttggac ataagacaag ggccaaagga accctttaga gactatgtag   1020
accggttctt taaaacttta agagctgaac aagctacaca agaagtaaaa ggttggatga   1080
cagacacctt gttggtccaa aatgcaaacc cagattgtaa gaccatttta agagcattag   1140
gaccaggggc ttcattagaa gaaatggtga cagcatgtca aggagtggga ggacctagcc   1200
acaaagcaag agtgttggct gaggcaatga gccaatcaca tagtaacata atgatgcaga   1260
gaggcaattt taaaggccct aaaagaattg ttaaatgctt caactgtggc aaggaagggc   1320
acatagccag aaattgcagg gcccctagaa aaagaggctg ttggaaatgt gggcaagaag   1380
gacaccaaat gaaagactgt actgagaggc aggctaattt tttagggaaa atttggcctt   1440
cccacaaggg gaggccaggg aatttccttc aaaacaggcc agagccaaca gccccaccag   1500
cagagagctt caggttcaag gagacaaccc ccgctccgaa gcaggagtcg aaagacaggg   1560
aaccccttaac ttccctcaaa tcactctttg gcagcgaccc cttgtctcaa taaaagtagg   1620
gggccagata aaggaagctc tcttagacac aggagcagat gatacagtat tagaagaaat   1680
agctttgcca ggaagatgga aaccaaaaat gataggagga attggaggtt ttatcaaagt   1740
aagacagtat gatcaaatac ttatagaaat ttgtggaaaa aaggctatag gtacagtatt   1800
agtaggacct acacctgtca acataattgg aagagatatg ttgactcagc ttggatgcac   1860
tctaaatttt ccaattagcc ccattgaaac tgtaccagta aaattaaagc caggaatgga   1920
tggcccaaag gttaaacagt ggccattgac agaagagaaa ataaaagcat taacagaaat   1980
ttgtaaagaa atggagaagg aaggaaaaat tacaaaaatt gggcctgaaa atccatataa   2040
cactccagta tttgccataa aaaggaagga cagtactaag tggagaaaat tagtagattt   2100
cagggagctc aataaaagaa ctcaagactt ttgggaagtt caattaggaa taccacaccc   2160
agcaggttta aaaaagaaaa aatcagtgac agtactggat gtgggggatg catatttttc   2220
agttccttta gatgaaggct tcgggaaata tactgcattc accataccta gtataaacaa   2280
tgaaacacca gggattagat atcaatataa tgtgcttcca cagggatgga aaggatcacc   2340
agcaatattc cagagtagca tgacaaaaat cttagagccc tttagggcac gaaatccaaa   2400
aatagtcatc tatcaatata tggatgactt gtatgtaggg tctgacttag aaatagggca   2460
```

-continued

```
tcatagagca aaaatagagg agttaagagc acatctatta aagtggggat tcaccacacc   2520
agataagaaa catcagaaag aacccccatt tctttggatg gggtatgaac tccatcctga   2580
caaatggaca gtacagccta taaagctgcc agaaaaggat agctggactg tcaatgatat   2640
acagaagtta gtgggaaaat taaactgggc aagtcagatt tacccaggga ttaaagtgag   2700
gcaactttgt aaactcctta ggggggccaa agcactaaca gacatagtac cactaactga   2760
agaagcagaa ttagaattag cagagaacag ggaaattcta aaagagccag tacatggagt   2820
atattatgac ccatcaaaag acttaatagc tgaaatacag aaacaggggc atgaccaatg   2880
gacatatcaa atttaccaag aaccattcaa aaatctgaaa acagggaagt atgcaaaaat   2940
gaggactgct cacactaatg atgtaaaaca gttaacagag gcagtgcaaa aaatagccat   3000
agaaagcata gtaatatggg aaagacccct aaatttagac tacccatcca aaaagaaacg   3060
tgggagacat ggtggacaga ctattggcag gccacctgga ttcctgattg ggagtttgtt   3120
aataccccctc cctagtaaa attatggtac cagctagaaa aagaacccat agtaggagca   3180
gaaactttct atgtagatgg agcagctaat agggaaacta aagtaggaaa agcagggtat   3240
gttactgaca gaggaaggca gaaaattgtt tctttaactg aaacaacaaa tcagaagact   3300
gaattgcaag caattcagct agctttgcaa gattcaggaa cagaagtaaa catagtaaca   3360
gactcacagt atgcattagg aatcattcaa gcacaaccag ataaaagtga atcagagtta   3420
gtcaaccaaa taatagaaca attaataaac aaagaaagag tctatctgtc atgggtacca   3480
gcacataaag gaattggagg gaatgaacaa gtagatagat tagtaagtag tggaattagg   3540
aaagtactgt ttctagatgg gatagataag gctcaagaag atcatgaaaa gtatcacagc   3600
aattggagag caatggctaa tgagtttaat ctgccaccca tagtagcaaa agaaatagta   3660
gctagctgtg ataaatgcca gctaaaaggg gaagccatgc atggacaagt agaccgtagc   3720
ccagggatat ggcaattaga ttgtacacat ctagaaggaa aaatcatcct ggtagcagtc   3780
catgtagcca gtggctacat agaagcagag gttatcccag cagaaacagg acaagaaaca   3840
gcatactata tactaaaatt agcaggaaga tggccagtca aagtaataca tacagacaat   3900
ggtagtaatt tcaccagtgc tgcagttaag gcagcctgtt ggtgggcagg tatccaacag   3960
gaatttggaa ttccctacaa tccccaaagc cagggagtag tagaatccat gaataaagaa   4020
ttaaagaaaa ttatagggca ggtaagagaa caagctgagc accttaagac agcagtacaa   4080
atggcagtat tcattcacaa ttttaaaaga aaagggggga ttggggggta cagtgcaggg   4140
gaaagaacaa tagacataat agcaacagac atacaaacta aagaattaca aaaccaaatt   4200
acaaaaattc aaaattttcg ggtttattac agagacagca gagaccccat ttggaaagga   4260
ccagccaaac tgctctggaa aggtgaaggg gcagtagtaa tacaagataa tagtgacata   4320
aaggtagtgc caaggaggaa agcaaaaatt attagggatt atggaaaaca gatggcaggt   4380
gctgattgtg tggcaggtag acaggatgag gatcagaaca tggaatagtt tagtaaaaca   4440
ccatatgtat gtttcaagaa gagctagtgg atggttttac agacatcatt atgaaagcag   4500
acatccaaaa gtaagtgcag aagtacacat cccattagga gatgctagat tagtaataaa   4560
aacatattgg ggtttacaaa caggagaaag agattggcat ttgggtcatg gcgtctccat   4620
agaatggaga ttgggaagat atagcacaca agtagaacct ggcctggcag accagctaat   4680
ccatatgcat tattttgatt gttttgcaga ctctgccata agaaaagcca tattaggaca   4740
catagttatt tctaggtgtg attatcaagc aggacataat aaggtaggat ctctacaata   4800
```

-continued

```
cttggcactg acagcattga taaaaccaaa aaagagaaag ccacctctgc ctagtgttaa   4860
gaaattagta gaggatagat ggaacaatcc ccagaagacc agggaccaca gagggaacca   4920
tacaatgaat ggacactaga gcttctagag gaactcaagc aggaagctgt cagacacttt   4980
cctagacctt agcttcatag cttaggacaa tatatctatg aaacatatgg ggatgcttgg   5040
acaggagtcg aagctttaat aagaacactg caacaattac tgtttattca tttcagaatt   5100
gggtgccagc atagcagaat aggcatttta caacggagaa gagcaagaaa tggagccagt   5160
agatcctaac ctagagccct ggaaccatcc aggaagtcag cctaaaactg cttgtaatac   5220
atgctattgt aaacactgta gctaccattg tctagtttgc tttcagacaa aaggcttagg   5280
catttcctat ggcaggaaga agcggagaca gcgacgcagc gctcctccaa gcagtgagga   5340
tcatcaaaat cttatatcaa agcagtaagt atatgtaatg gtgaatttat tagaaagagt   5400
agattataga ttaggagtag gagcattaat agtagcatta atcttagcaa taattgtgtg   5460
gaccatagca tatctagaat ataggaaatt gttaagacaa agaaaaataa acaggttaat   5520
tgaaagaatt agggaaagag tagaagacag tggcaatgag agtgaggggg atactgagga   5580
attgtcaaca ctggtggata tggggaatct taggcttttg gatgctaatg atttataatg   5640
tagtagggaa cttgtgggtc acagtctatt atggggtacc tgtgtggaaa gaagcaaaaa   5700
ctactttatt ctgtgcatca gatgctaaag cttatgagaa ggaggtgcat aatatctggg   5760
ctacacatgc ctgtgtaccc acagacccca acccacaaga gatggattta gtaaatgtaa   5820
cagaaaattt taacatgtgg aaaaatgaca tggtggatca gatgcatgag gatgtaatca   5880
gtttatggga tcaaagccta aagccatgtg taaagttgac cccactctgt gtcactttaa   5940
actgtagtaa ggttaccaat aatgctactt acaataatac tgatgatata aaaaattgct   6000
cttttaatgc aaccacagaa ataagagaca agaaacgcaa agagtatgca ctgttttata   6060
gactcgatat agtaccacta aatgagaata agaacagctc tagtaactat agtgagtaca   6120
tattaataaa ttgtaatacc tcaaccataa cacaagcctg tccaaaggtc tcttttgacc   6180
caattcctat acattattgt gctccagctg gttttgcgat tctaaagtgt aaagatgaga   6240
cattcaatgg gacaggacca tgcaaggagg tcagtacagt acaatgtaca catggaatta   6300
agccagtggt atcaactcaa ctactgttaa atggtagcac agcagaaaaa gagataataa   6360
ctagatctga aaatataaca gacaatgcaa aaactataat agtacatctt aatgaatcca   6420
taaaaattgt atgtacaaga cccaacaata acacaagaaa aagtataagg atagggccag   6480
gacaagcatt ctatgcaaca aacggcataa taggagacat aagacaagca cattgtaaca   6540
ttagtgaatc taactggact aaaactttac aagaggtagg aaaaaaatta gcaaagcact   6600
tccctaataa aacaataagt ttcaaccaat cctcaggagg ggacctagaa attgtaacac   6660
atagctttaa ttgtggagga gaattctttt attgtaatac atcaagactg tttaacggta   6720
catacaatgg tacagacatg cctacataca atggtacaaa ttccagttca gacatcatca   6780
tgcttccatg cagaataagg caatttataa acatttggca gaaggtagga cgagcaatgt   6840
atgcccctcc cattgaagga aacataacat gtgaatcaaa tatcacagga ctactattag   6900
tacgtgatgg aggcgacaca aatagtagca cagagatatt cagacctgga ggaggagata   6960
tgagggacaa ttggagaagt gaattatata aatataaagt ggtagaaatt aagccattag   7020
gaatagcacc tactgaagca aaaaggagag tggtggagag agaaaaaaga gcagtgggaa   7080
taggagctgt gttccttggg ttcttgggag tagcaggaag cactatgggc gcggcgtcaa   7140
tgacgctgac ggtacaggcc agacaattgt tgtctggtat agtgcaacag caaagcaatt   7200
```

-continued

```
tgctgaaggc tatagaggcg caacagcata tgttgcaact cacagtctgg ggcattaagc   7260
agctccagac aagagtcttg gctatagaga gatacctaaa ggatcaacag ctcctaggga   7320
tttggggctg ctctggaaaa gtcatctgcc ccactgctgt gccttggaac tccagctgga   7380
gtaataaatc aaaagatgat atttggaata acatgacctg gatgcagtgg gataaagaga   7440
ttagtaatta cacaaacaca atataccggt tgcttgaaga atcgcaaatc cagcaggaac   7500
aaaatggaaa agatttatta gcattggaca gttggcaaaa tctgtggaat tggtttagca   7560
taacaaaatg gctgtggtat ataaaaatat tcataattat agtaggaggc ttgataggtt   7620
tgagaataat ttttgctgtg ctatctatag taaatagagt taggcaggga tactcacctt   7680
tgtcgttgca gacccttacc ccagacccga gggaacccga caggctcaga ggaatcgaag   7740
aagaaggtgg agagcaagac aaagacagat ccattcgatt agtgaacgga ttcttagcac   7800
ttgcctggga cgatctacgg agcctgtgcc tcttcagttg ccaccgattg agagacttca   7860
tattggttgc agcgagagcg gtggaacttc tgggacgcag cagtctcagg ggactacaga   7920
gggggtggga agcccttaaa tatctgggaa gtcttgtgca gtattggggt ctggaactaa   7980
aaaagagtgc tattagtctg cttgatacca tagcaataac aatagctgag ggaacagata   8040
ggattataga atttacacaa agaatttgca gagctatccg caacatacct agaagaataa   8100
gacagggttt tgaagcagct ttgctataaa atggggagca agatgtcaaa aagcagaata   8160
gttggatggc ctgaggtaag agaaagaatg aggagaactg agccagcagc agagggagta   8220
ggagcagcat ctcaagactt agctaaacat ggagcactta caaccagcaa cacaccaagc   8280
aataatgctg ctggtgcctg gctgcaagcg caagaggagg aagaagaagt aggctttcca   8340
gtcagacctc aggtgccttt aagaccaatg acttataaag gagcattcga tctcgccttc   8400
tttttaaaag aaaagggggg actggatggg ttaatttact ctaagaaaag gcatgaaatc   8460
cttgatttat gggtttataa cacacaaggc tacttccctg attggcaaaa ctacacacca   8520
ggaccagggg tcagatatcc actgaccttt ggatggtgct acaagctagt accagttgac   8580
ccaagtgtag tagaagaggc caacaaagga gaaaacaact gtttgctaca ccctatgagc   8640
caacatggaa tggatgatga agatggagaa gtattaaagt ggcagtttga cagcagccta   8700
gcacgcagac acatagcccg cgagctacat ccggagtatt acaaagactg ctgacacaga   8760
agggactttc cactggggcg ttccagggga gtggtctggg cgggacatgg gagtggtcaa   8820
ccctcagatg ctgcatataa gcagctgctt ttcgcctgta ctgggtctct ctaggtggac   8880
cagatctgag cccgggagct ctctggctac ctagtgaacc cactgcttaa gcctcaataa   8940
agcttgcctt gagtgctct                                                8959
```

<210> SEQ ID NO 12
<211> LENGTH: 1479
<212> TYPE: DNA
<213> ORGANISM: Human immunodeficiency virus type 1
<220> FEATURE:
<223> OTHER INFORMATION: isolate=93BR020; gene=gag

<400> SEQUENCE: 12

```
atgggtgcga gagcgtcagt attaagcggg ggaaaattag atgcttggga aaaaattcgg     60
ttaaggccgg ggggaaagaa aaaatataga ctaaaacatc tagtatgggc aagcagggag    120
ctagaacgat ttgcacttga tccaggcctt ctagaaacat cagaaggctg tcgaaaaata    180
ataggacagt tacaaccatc ccttcagaca ggatcagaag agctcaaatc attatataat    240
```

-continued

```
acaatagcag tcctctatta tgtacatcaa aaggtagagg taaaagacac caaggaggct    300

ttagagaagc tagaggaaga acaaaacaaa ggtcggcaaa agacacagca agcgactgct    360

gaaaaagggg tcagtcaaaa ttaccctata gtacagaatc ttcagggaca aatggtacac    420

cagtctttat cacctagaac tttaaatgca tgggtaaagg tgatagaaga gaaggctttt    480

agtccagaag taatacccat gttttcagca ttatcagaag gggccactcc acaagattta    540

aacaccatgt taaatacagt gggggacat caagcagcca tgcaaatgtt aaaagacacc    600

atcaatgagg aggctgcaga atgggacaga ttacatccaa cacaggcagg acccatcccc    660

ccaggtcaga taagggaacc taggggaagt gatatagctg gaactactag tacccttcag    720

gaacaaatac aatggatgac aggcaaccca cctgtcccag tgggagaaat gtataaaaga    780

tggatcatcc taggattaaa taaaatagta agaatgtata gccctgtcgg cattttggac    840

ataagacaag ggccaaaaga accctttaga gactatgtag acaggttctt taaaacccta    900

agagctgagc aagctacaca ggaagtaaag ggttggatga cagacacctt gttggtccaa    960

aatgcgaacc cagattgtaa gaccatttta aaagcattgg gaccaggggc tacactagag   1020

gaaatgatga cagcatgtca gggagtggga ggacctagcc ataaggcaag agttttggct   1080

gaggcaatga gccaagcaac aaatacagct ataatgatgc agaaaagtaa ctttaagggc   1140

caaagaagaa ttgttaaatg ctttaattgt ggcaaagaag gacacatagc caaaaattgc   1200

agggccccta gaaaaaaggg ctgttggaag tgtggaagag agggacacca aatgaaggac   1260

tgcactgaga gacaggctaa tttttaggg aaaatttggc cttccaacaa ggggaggccc   1320

ggaaacttca tccagaacag gccagagccg tcagccccgc cagcagagag cttcaggttc   1380

ggggaggaga caaccccatc tccgaagcag gagcagaaag acgagggact gtaccctccc   1440

ttagcttccc tcaaatcact ctttggcaac gaccccctag                         1479
```

<210> SEQ ID NO 13
<211> LENGTH: 579
<212> TYPE: DNA
<213> ORGANISM: Human immunodeficiency virus type 1
<220> FEATURE:
<223> OTHER INFORMATION: isolate=93BR020; gene=vif

<400> SEQUENCE: 13

```
atggaaaaca gatggcaggt gatgattgtg tggcaggtag acaggatgag gattaacaca     60

tggaaaagtt tagtaaaata ccatatgcat atttcaaaga aagccaaagg atggttttat    120

agacatcact ttgaaagcag gcatccaaaa ataagttcag aagtacacat cccactagag    180

acagctgaat tagtaataac aacatactgg gggctgcttc caggagaaag agaatggcat    240

ctgggtcagg gagtctccat agaatggagg caggggaggt atagaacaca aatagaccct    300

ggcctggcag accaactgat ccatatatat tattttgatt gtttttcaga atctgccata    360

aggaaagcca tattaggaca taaaattagc cctaggtgta actatcaagc aggacataac    420

aaggtaggat ctctacaata cttggcacta acagcattaa tagctccaaa aaagacaaag    480

ccgcctttgc ctagtgtcca gaaactagta gaagacagat ggaacaagcc ccagaagacc    540

aggggccaca gagagagcca tacaatgaat ggacactag                           579
```

<210> SEQ ID NO 14
<211> LENGTH: 291
<212> TYPE: DNA
<213> ORGANISM: Human immunodeficiency virus type 1
<220> FEATURE:
<223> OTHER INFORMATION: isolate=93BR020; gene=vpr

<400> SEQUENCE: 14
atggaacaag ccccagaaga ccaggggcca cagagagagc catacaatga atggacacta 60
gatcttttag aggagcttaa gaatgaagct gttagacatt ttcctaggcc atggctccat 120
agcttaggac aacatatcta taacacctat ggggatactt gggaaggagt tgaagcaatc 180
ataaggatat tgcaacaact actgtttatc catttcagaa ttgggtgccg tcatagcaga 240
ataggcatta ctcgacagag aagagtaaga aatggaacta gtagatccta a 291

<210> SEQ ID NO 15
<211> LENGTH: 2610
<212> TYPE: DNA
<213> ORGANISM: Human immunodeficiency virus type 1
<220> FEATURE:
<223> OTHER INFORMATION: isolate=93BR020; gene=tat

<400> SEQUENCE: 15
atggaactag tagatcctaa cttagatccc tggaaccatc caggaagcca gcctacaact 60
ccttgtacca gatgttattg taaatggtgt tgctttcatt gttactggtg ctttacaacg 120
aagggcttag gcatctccta tggcaggaag aagcggagac agcgaccaag aactcctcaa 180
agcagtcaga tacatcaaga ttttgtacca aagcagtaag tattgttaag catatgtaat 240
gtcaaatttg ttagcaatag gcatagcagc attaatagta gcactaataa taacaatagt 300
tgtgtggact atagcatata tagaatataa gaaactggta aggcaaagaa aaataaatag 360
gttatataaa agaataagcg aaagagcaga agacagtggc aatgagagtg agggggatgc 420
agaggaattg gcagcacttg gggaagtggg gccttttatt cctggggaca ttaataatct 480
gtaatgctgc agaaaactta tgggttacag tctattatgg ggtacctgtg tggaaagaag 540
caaccactac tctattctgt gcatcagatg ctaaatcata tgaaaaagag gcacataatg 600
tctgggctac acatgcttgt gtacccacag atcccaatcc acaagaagta gttctggaaa 660
atgtaacaga aaggtttaat atgtgggaaa ataacatggt agaacaaatg catacagata 720
taatcagttt atgggatcaa agcctaaagc catgtgtgaa gttaacccca ctctgtgtta 780
ctttagattg tagaaacatt gccaccaatg gcaccaatga cactattgcc atcaatgaca 840
ctctgaagga agatccagag gcaatacaaa actgttcttt caatacaacc acagaaataa 900
gagataagca gctgaaagta catgcacttt tttataaact tgatatagta caaatcaaca 960
aggatgacaa tagaacatac agactaataa attgtgatgc ctcaaccatt acacaggctt 1020
gtccaaaggt atcttgggat ccaattccca tacattattg tgctccagct ggttatgcga 1080
ttctaaagtg taatgagaaa aatttcacag ggacagggtc atgcaagaat gtcagtacag 1140
tacaatgtac acatggaatt aaaccagtgg tatccactca attgttgtta aatggcagcc 1200
tagcagaagg agagatagta atcagatctc aaaatatctc agataatgca aaaaccataa 1260
tagtgcacct taatgaatct gtacagatta attgtacaag acccaacaac aatacaagaa 1320
aaagaatatc tttaggacca ggacgagtat tttatacaac aggagaaata ataggagaca 1380
tcagaaaggc acattgtaac gttagtggaa cacaatggag gaacacgtta gcaaaggtaa 1440
aggcaaagtt agggtcttat ttccctaatg caacaataaa atttaactca tcctcaggag 1500
gggacctaga aattacaagg cataatttta attgtatggg agaatttttc tactgtaata 1560
cagatgaact gtttaatgac acaaaattca atgacacagg attcaatggc actatcactc 1620
tcccatgtcg aataaaacaa attgtaaaca tgtggcagga agtgggacga gcaatgtatg 1680

-continued

```
ccaatcccat tgcaggaaac attacctgta actcaaatat tacaggtctg ctattgacaa   1740

gagatggtgg tctgaatagt actaatgaga ccttcagacc tgggggagga aatatgaaag   1800

acaattggag aagtgaatta tataaatata aagtagtaga aattgaacca ctaggagtag   1860

cacccaccaa ggcaaaaaga caagtggtga agagagaaag aagagcagtg ggactaggag   1920

ctctgttcct tgggttcttg ggagcagctg gaagcactat gggcgcggcg tcaataacgc   1980

tgacggtaca ggccagacaa ttattgtctg gaatagtgca acagcagagc aatctgctga   2040

gggctattga agcgcaacag catctgttgc agctcacagt ctggggcatt aaacagctcc   2100

aggcaagagt cctggctgtg gaaagatacc taaaggatca acagctccta gggctttggg   2160

gctgctctgg aaaactcatc tgcaccacta atgtgccctg gaactctagt tggagtaata   2220

aatctcttga ggagatttgg gggaacatga cctggatgga gtgggaaaaa gaggttagca   2280

attactcaaa agaaatatac aggttaattg aagactcgca gaaccagcag gaaaagaatg   2340

aacaagaatt attagcattg gacaaatggg caagtctgtg gaattggttt gacataacac   2400

agtggctgtg gtatataaaa atattcataa tgatagtagg aggcttgata ggcttaagaa   2460

tagtttttac tgtgctttct atagtaaata gagttaggaa gggatactca cctttgtcat   2520

ttcagaccca tatcccaagc ccgagggaac ccgacaggcc cgaaggaatc gaagaaggag   2580

gtggagagca aggcaaagac agatccgtga                                    2610
```

<210> SEQ ID NO 16
<211> LENGTH: 2661
<212> TYPE: DNA
<213> ORGANISM: Human immunodeficiency virus type 1
<220> FEATURE:
<223> OTHER INFORMATION: isolate=93BR020; gene=rev

<400> SEQUENCE: 16

```
atggcaggaa gaagcggaga cagcgaccaa gaactcctca aagcagtcag atacatcaag     60

attttgtacc aaagcagtaa gtattgttaa gcatatgtaa tgtcaaattt gttagcaata    120

ggcatagcag cattaatagt agcactaata ataacaatag ttgtgtggac tatagcatat    180

atagaatata agaaactggt aaggcaaaga aaaataaata ggttatataa aagaataagc    240

gaaagagcag aagacagtgg caatgagagt gaggggggatg cagaggaatt ggcagcactt    300

ggggaagtgg ggccttttat tcctggggac attaataatc tgtaatgctg cagaaaactt    360

atgggttaca gtctattatg gggtacctgt gtggaaagaa gcaaccacta ctctattctg    420

tgcatcagat gctaaatcat atgaaaaaga ggcacataat gtctgggcta cacatgcttg    480

tgtacccaca gatcccaatc cacaagaagt agttctggaa aatgtaacag aaaggtttaa    540

tatgtgggaa aataacatgg tagaacaaat gcatacagat ataatcagtt tatgggatca    600

aagcctaaag ccatgtgtga agttaacccc actctgtgtt actttagatt gtagaaacat    660

tgccaccaat ggcaccaatg acactattgc catcaatgac actctgaagg aagatccaga    720

ggcaatacaa aactgttctt tcaatacaac cacagaaata agagataagc agctgaaagt    780

acatgcactt ttttataaac ttgatatagt acaaatcaac aaggatgaca atagaacata    840

cagactaata aattgtgatg cctcaaccat tacacaggct tgtccaaagg tatcttggga    900

tccaattccc atacattatt gtgctccagc tggttatgcg attctaaagt gtaatgagaa    960

aaatttcaca gggacagggt catgcaagaa tgtcagtaca gtacaatgta cacatggaat   1020

taaaccagtg gtatccactc aattgttgtt aaatggcagc ctagcagaag gagagatagt   1080

aatcagatct caaaatatct cagataatgc aaaaaccata atagtgcacc ttaatgaatc   1140
```

-continued

```
tgtacagatt aattgtacaa gacccaacaa caatacaaga aaaagaatat ctttaggacc   1200
aggacgagta ttttatacaa caggagaaat aataggagac atcagaaagg cacattgtaa   1260
cgttagtgga acacaatgga ggaacacgtt agcaaaggta aaggcaaagt tagggtctta   1320
tttccctaat gcaacaataa aatttaactc atcctcagga ggggacctag aaattacaag   1380
gcataatttt aattgtatgg gagaattttt ctactgtaat acagatgaac tgtttaatga   1440
cacaaaattc aatgacacag gattcaatgg cactatcact ctcccatgtc gaataaaaca   1500
aattgtaaac atgtggcagg aagtgggacg agcaatgtat gccaatccca ttgcaggaaa   1560
cattacctgt aactcaaata ttacaggtct gctattgaca agagatggtg gtctgaatag   1620
tactaatgag accttcagac ctgggggagg aaatatgaaa gacaattgga gaagtgaatt   1680
atataaatat aaagtagtag aaattgaacc actaggagta gcacccacca aggcaaaaag   1740
acaagtggtg aagagagaaa gaagagcagt gggactagga gctctgttcc ttgggttctt   1800
gggagcagct ggaagcacta tgggcgcggc gtcaataacg ctgacggtac aggccagaca   1860
attattgtct ggaatagtgc aacagcagag caatctgctg agggctattg aagcgcaaca   1920
gcatctgttg cagctcacag tctggggcat taaacagctc caggcaagag tcctggctgt   1980
ggaaagatac ctaaaggatc aacagctcct agggctttgg ggctgctctg gaaaactcat   2040
ctgcaccact aatgtgccct ggaactctag ttggagtaat aaatctcttg aggagatttg   2100
gggaacatg acctggatgg agtgggaaaa agaggttagc aattactcaa aagaaatata   2160
caggttaatt gaagactcgc agaaccagca ggaaaagaat gaacaagaat tattagcatt   2220
ggacaaatgg gcaagtctgt ggaattggtt tgacataaca cagtggctgt ggtatataaa   2280
aatattcata atgatagtag gaggcttgat aggcttaaga atagttttta ctgtgctttc   2340
tatagtaaat agagttagga agggatactc acctttgtca tttcagaccc atatcccaag   2400
cccgagggaa cccgacaggc ccgaaggaat cgaagaagga ggtggagagc aaggcaaaga   2460
cagatccgtg agattagtga ccggattctt agctcttgcc tgggacgacc tgcggaacct   2520
gtgcctcttc agctaccgcc acttgagaga cttcatatta attgcagcga ggattgtgga   2580
caggggctg aagagggggt gggaagctct caaatatctg ggaatctca cacagtattg   2640
gggtcaggaa ctaaagaata g                                              2661
```

<210> SEQ ID NO 17
<211> LENGTH: 246
<212> TYPE: DNA
<213> ORGANISM: Human immunodeficiency virus type 1
<220> FEATURE:
<223> OTHER INFORMATION: isolate=93BR020; gene=vpu

<400> SEQUENCE: 17

```
atgtcaaatt tgttagcaat aggcatagca gcattaatag tagcactaat aataacaata     60
gttgtgtgga ctatagcata tatagaatat aagaaactgg taaggcaaag aaaaataaat    120
aggttatata aaagaataag cgaaagagca gaagacagtg gcaatgagag tgagggggat    180
gcagaggaat tggcagcact tggggaagtg gggcctttta ttcctgggga cattaataat    240
ctgtaa                                                               246
```

<210> SEQ ID NO 18
<211> LENGTH: 2541
<212> TYPE: DNA
<213> ORGANISM: Human immunodeficiency virus type 1
<220> FEATURE:

-continued

<223> OTHER INFORMATION: isolate=93BR020; gene=env

<400> SEQUENCE: 18

```
atgagagtga gggggatgca gaggaattgg cagcacttgg ggaagtgggg ccttttattc     60
ctggggacat taataatctg taatgctgca gaaaacttat gggttacagt ctattatggg    120
gtacctgtgt ggaaagaagc aaccactact ctattctgtg catcagatgc taaatcatat    180
gaaaaagagg cacataatgt ctgggctaca catgcttgtg tacccacaga tcccaatcca    240
caagaagtag ttctggaaaa tgtaacagaa aggtttaata tgtgggaaaa taacatggta    300
gaacaaatgc atacagatat aatcagttta tgggatcaaa gcctaaagcc atgtgtgaag    360
ttaaccccac tctgtgttac tttagattgt agaaacattg ccaccaatgg caccaatgac    420
actattgcca tcaatgacac tctgaaggaa gatccagagg caatacaaaa ctgttctttc    480
aatacaacca cagaaataag agataagcag ctgaaagtac atgcactttt ttataaactt    540
gatatagtac aaatcaacaa ggatgacaat agaacataca gactaataaa ttgtgatgcc    600
tcaaccatta cacaggcttg tccaaaggta tcttgggatc caattcccat acattattgt    660
gctccagctg gttatgcgat tctaaagtgt aatgagaaaa atttcacagg gacagggtca    720
tgcaagaatg tcagtacagt acaatgtaca catggaatta aaccagtggt atccactcaa    780
ttgttgttaa atggcagcct agcagaagga gagatagtaa tcagatctca aaatatctca    840
gataatgcaa aaaccataat agtgcacctt aatgaatctg tacagattaa ttgtacaaga    900
cccaacaaca atacaagaaa aagaatatct ttaggaccag gacgagtatt ttatacaaca    960
ggagaaataa taggagacat cagaaaggca cattgtaacg ttagtggaac acaatggagg   1020
aacacgttag caaaggtaaa ggcaaagtta gggtcttatt tccctaatgc aacaataaaa   1080
tttaactcat cctcaggagg ggacctagaa attacaaggc ataattttaa ttgtatggga   1140
gaatttttct actgtaatac agatgaactg tttaatgaca caaaattcaa tgacacagga   1200
ttcaatggca ctatcactct cccatgtcga ataaaacaaa ttgtaaacat gtggcaggaa   1260
gtgggacgag caatgtatgc caatcccatt gcaggaaaca ttacctgtaa ctcaaatatt   1320
acaggtctgc tattgacaag agatggtggt ctgaatagta ctaatgagac cttcagacct   1380
gggggaggaa atatgaaaga caattggaga agtgaattat ataaatataa agtagtagaa   1440
attgaaccac taggagtagc acccaccaag gcaaaaagac aagtggtgaa gagagaaaga   1500
agagcagtgg gactaggagc tctgttcctt gggttcttgg gagcagctgg aagcactatg   1560
ggcgcggcgt caataacgct gacggtacag gccagacaat tattgtctgg aatagtgcaa   1620
cagcagagca atctgctgag ggctattgaa gcgcaacagc atctgttgca gctcacagtc   1680
tggggcatta aacagctcca ggcaagagtc ctggctgtgg aaagatacct aaaggatcaa   1740
cagctcctag ggctttgggg ctgctctgga aaactcatct gcaccactaa tgtgccctgg   1800
aactctagtt ggagtaataa atctcttgag gagatttggg ggaacatgac ctggatggag   1860
tgggaaaaag aggttagcaa ttactcaaaa gaaatataca ggttaattga agactcgcag   1920
aaccagcagg aaaagaatga acaagaatta ttagcattgg acaaatgggc aagtctgtgg   1980
aattggtttg acataacaca gtggctgtgg tatataaaaa tattcataat gatagtagga   2040
ggcttgatag gcttaagaat agtttttact gtgctttcta tagtaaatag agttaggaag   2100
ggatactcac ctttgtcatt tcagacccat atcccaagcc cgagggaacc cgacaggccc   2160
gaaggaatcg aagaaggagg tggagagcaa ggcaaagaca gatccgtgag attagtgacc   2220
ggattcttag ctcttgcctg ggacgacctg cggaacctgt gcctcttcag ctaccgccac   2280
```

-continued ttgagagact tcatattaat tgcagcgagg attgtggaca gggggctgaa gagggggtgg 2340
gaagctctca aatatctggg gaatctcaca cagtattggg gtcaggaact aaagaatagt 2400
gctattagct tgcttaatgc cacagcaata gcagtagctg agtggacaga tagagttata 2460
gaagctttgc aaagagctgg tagagctatt ctcaacatac ctagaagaat aagacagggc 2520
ttggaaaggg ctttgctata a 2541

<210> SEQ ID NO 19
<211> LENGTH: 27
<212> TYPE: DNA
<213> ORGANISM: Human immunodeficiency virus type 1
<220> FEATURE:
<223> OTHER INFORMATION: isolate=93BR020; gene=nef

<400> SEQUENCE: 19
atgggtggca agtggtcaaa aagtagt 27

<210> SEQ ID NO 20
<211> LENGTH: 8
<212> TYPE: DNA
<213> ORGANISM: Human immunodeficiency virus type 1
<220> FEATURE:
<223> OTHER INFORMATION: isolate=93BR020; gene=gag-pol fusion

<400> SEQUENCE: 20 aaaaaaaa 8

<210> SEQ ID NO 21
<211> LENGTH: 207
<212> TYPE: DNA
<213> ORGANISM: Human immunodeficiency virus type 1
<220> FEATURE:
<223> OTHER INFORMATION: isolate=92NG083; gene=gag

<400> SEQUENCE: 21
gtgggtgcga gagcgtcagt attaagcggg ggaaaattag attcttggga aaaaattcgg 60
ttaaggccag ggggaaggaa aaagtataaa ctaaaacata tagtatgggc aagcagggaa 120
ctggggagat ttgcacttaa ccgtgacctt ttagaaacag cagaaggttg tgtgcaaata 180
atgaaacagt tgcaaccagc tctctag 207

<210> SEQ ID NO 22
<211> LENGTH: 2739
<212> TYPE: DNA
<213> ORGANISM: Human immunodeficiency virus type 1
<220> FEATURE:
<223> OTHER INFORMATION: isolate=92NG083; gene=pol; note=NH2-terminus
uncertain

<400> SEQUENCE: 22
ataaatttac caggaaaatg gaaaccaaaa atgatagggg gaattggagg ttttatcaaa 60
gtaagacagt atgatcaaat acttatagaa attggtggaa aaaaggctat agggacagta 120
ttagtaggac ctacacctat taacataatt gggagaaata tgttgactca gattggttgt 180
actttaaact ttccaataag tcctattgaa actgtaccag taaaattaaa gccaggaatg 240
gatggcccaa gggttaaaca atggccattg acagaagaga aaataaaagc attaacagaa 300
atttgtaaag acatggaaaa ggaaggaaaa atttcaaaaa ttgggcctga aaatccatat 360
aacactccaa tattcgccat aaagaaaaaa gacagtacta aatggagaaa attggtagat 420
ttcagagaac ttaataaaag aactcaagac ttctgggagg tccaattagg aatacctcac 480

-continued cccgcggggt taaaaaagaa aagatcagta acggtactag atgtgggaga tgcatacttt 540
tcagttccct tagataaaga ctttagaaag tatactgcat ttactatacc tagtataaat 600
aatgagacac cagggattag atatcaatac aatgtgcttc cacagggatg gaaaggatca 660
ccagcaatat ttcagagtag catgacaaaa attttagagc cttctagaac aaaaaatcca 720
gaaatggtga tctaccaata catggatgat ttatatgtag gatctgactt agaaataggg 780
cagcatagag caaaaataga ggagttaaga gaacatctac tgaaatgggg attgaccaca 840
ccagataaaa aacatcagaa agaacctcca ttcctttgga tgggatatga gctccatcct 900
gacaaatgga cggtacaacc tatacagctg ccagaaaagg aagattggac tgtcaatgat 960
atacaaaagt tagtgggaaa actaaattgg gcaagtcaga tttatccagg gattaaagta 1020
aagcacctat gtagactcct tagggggccc aaagcactaa cagacatagt acccctaacg 1080
gcagaagcag aaatggagct ggcagagaac agggaaattc taaaagaacc tgtacatgga 1140
gtctatcatg acccatcaaa agaattaata gcagaagtac agaagcaagg gccagaccaa 1200
tggacatatc aaatttatca agagccatac aaaaatctaa aaacaggaaa atatgcaaaa 1260
agggggtctg cccacactaa tgatgtaaaa caattaacag aagtagtgca aaaaatagcc 1320
acagagggca tagtaatctg ggggaaagatt cctaaattta aactacctat acgaaaagaa 1380
acatgggaag tatggtggac agagtactgg caggccgcct ggattcctga gtgggagttt 1440
gtcaataccc ctcctctagt aaaactatgg tatcaattag aaacagaacc cataccagga 1500
gcagaaactt actatgtaga tggggcagct aatagggaga caaaattagg aaaggcagga 1560
catgttactg acaaaggaaa acaaaaaatt attaccctaa ctgaaacaac aaaccaaaag 1620
gctgaattac atgcaattca actagctttg caggactcaa gaccagaagt aaacatagta 1680
acagactcac agtatgcatt aggaatcatt caagcacaac cagataggag tggatcagaa 1740
ttagtcaatc aaataataga acagctaata aaaaaggaaa aggtctacct gtcatgggta 1800
ccagcacaca aagggattgg aggaaatgaa caagtagata agctagtcag tagtggaatc 1860
aggaaagtat tatttttgga tggcatagat aaagcccaag aagaacatga aagatatcac 1920
agcaattgga gagcaatggc tagtgatttt aatctgccac ctgtagtagc aaaagaaata 1980
gtggccagct gtgataaatg tcaactaaaa ggggaagcca tgcatggaca agtagactgt 2040
agtccaggaa tatggcaatt agattgtaca catttagaag gaaaaattat catagtagca 2100
gttcatgtag ccagtggcta tatagaagca gaagttatcc cagcagaaac agggcaggaa 2160
acagcatact ttatattaaa attagcagga aggtggccag taaaagtgat acatacagac 2220
aatggtccca atttcatcag tgctgcagta aaggcagcat gttggtgggc aaatatcaca 2280
caggaatttg gaattcccta caatccccaa agccaaggag tagtggaatc tatgaataag 2340
gaattaaaga aaatcatcgg acaggttgga gatcaagctg aacatcttaa gacagcagta 2400
cagatggcag tattcattca caattttaaa agaaaagggg ggattggggg gtacagtgca 2460
ggggaaagaa taatagacat aatagcatca gatatacaaa ctaaagaact acaaaaacaa 2520
attataaaaa ttcaaaattt tcgggtttat tacagggaca gcagagaccc aatttggaaa 2580
ggaccagcaa agctactctg gaaaggtgaa ggggcagtag taatacagga caataacgaa 2640
ataaaggtag taccaagaag aaaagcaaag atccttaagg attatggaaa acagatggca 2700
ggtggtgatt gtgtggcagg tagacaggat gaggattag 2739

<210> SEQ ID NO 23

-continued

<211> LENGTH: 579
<212> TYPE: DNA
<213> ORGANISM: Human immunodeficiency virus type 1
<220> FEATURE:
<223> OTHER INFORMATION: isolate=92NG083; gene=vif

<400> SEQUENCE: 23
atggaaaaca gatggcaggt ggtgattgtg tggcaggtag acaggatgag gattagaaca 60
tggaacagtt tagtaaaaca tcatatgtat gtctcaaaga aagctaaagg ctggttttat 120
agacatcact atgaaagcag gcatccaaga gtaagttcag aagtacacat cccactaaga 180
gatgctacac tagtagtaag aacatattgg ggtctgcatg caggagaaaa agactggcaa 240
ttgggccatg ggtttccat agaatggagg cagaaaagat atagtacaca aatagaccct 300
aacacagcag accatctgat tcatctgtat tattttgact gtttttcaga atctgccata 360
agaaaagcca tattaggaga gatagttagc cctaggtgtg aatacccagc aggacataat 420
aaggtaggat ctctacaata tctggcatcg aaagcattag taacaccaac aaggaaaagg 480
ccacctttgc caagtgttgg gaaattagca gaagatagat ggaacaagcc ccagaagacc 540
agggaccaca gagagaaccc tacaatgaat ggacattag 579

<210> SEQ ID NO 24
<211> LENGTH: 291
<212> TYPE: DNA
<213> ORGANISM: Human immunodeficiency virus type 1
<220> FEATURE:
<223> OTHER INFORMATION: isolate=92NG083; gene=vpr

<400> SEQUENCE: 24
atggaacaag ccccagaaga ccagggacca cagagagaac cctacaatga atggacatta 60
gaactgttag aagagcttaa aaatgaagct gttagacatt ttcctaggcc ctggctccat 120
ggcttaggac agtatatcta taacacttat ggggatactt gggaaggagt tgaagccata 180
ataagaatac tacaacaact actgtttatc catttcagaa tcgggtgcca acatagcaga 240
ataggcatta ctccacagag aagagtaagg gatggacccg gtagacccta a 291

<210> SEQ ID NO 25
<211> LENGTH: 2597
<212> TYPE: DNA
<213> ORGANISM: Human immunodeficiency virus type 1
<220> FEATURE:
<223> OTHER INFORMATION: isolate=92NG083; gene=tat

<400> SEQUENCE: 25
atggacccgg tagaccctaa gctagagccc tggaatcatc cggggagtca gcctacaact 60
ccctgtaaca aatgttattg taaagtgtgc tgctggcatt gtcaagtttg ctttttaaac 120
aaaggcttag gcatctccta tggcaggaag aagcggagac cccgacgagg aactcctcag 180
ggcagtaagg atcatcaaaa ccctgtacca aagcagtaag tagtaacaat taatatatgt 240
aatgcaggcc ttagaaatat ctgactaata gtagcattca tagcagccac aattgtgtgg 300
agtatagtat ttatagaata tagaaaaata agaaaacaga aaaaaataga aaagttactt 360
gatagaataa gagaaagagc agaagacagt ggaaatgaga gtgaagggga tacagaggaa 420
ttggcaacac ttatggaaat gggggacttt gatccttggg ttggtaataa tttgtagtgc 480
ctcagataac ttgtgggtca cagtctatta tggggtacct gtgtgggaag atgcagatac 540
ccccctattc tgtgcctctg atgctaaatc atatagttct gaaaaacata atgtctgggc 600
tacacatgcc tgtgtaccca cagaccctaa cccacaagaa atagctatag aaaatgtaac 660

-continued

```
agaaaatttt aacatgtgga agaataacat ggtagaacag atgcaggagg atataatcag     720
tttatgggag gaaagcctaa agccatgtgt aaagctaact cctctctgta tcactttaaa     780
ctgtactaat gtaaacagtg ctaatcatac tgaggccaat aacactgtag aaaacaaaga     840
agaaataaaa aactgctctt tcaagataac cacagaaagg ggaggcaaga agaaggaaga     900
atacgcgctt ttctataaac ttgatgtggt accaattagt aatgggaata agactagtta     960
taggctaata cattgtaatg tctcaaccat taaacaggct tgtccaaagg taaattttga    1020
cccaattccc atacattatt gtgctccagc tggttttgcg attttaaagt gtagggataa    1080
ggagtacaat ggaacaggac catgtaaaaa tgtcagtaca gtacaatgta cacatggaat    1140
taagccagtg gtatcaactc aactactgct gaatggcagt ttagcagaag aagatataag    1200
aattagatct gaaaatttca cagacaatac caaagtcata atagtgcagc ttaataatag    1260
tatagaaatt aattgtatca gacccaataa caatacaaga aaaagtatac caatcggacc    1320
aggacaagcg ttctatgcaa caggtgatat aataggagac ataagacaag cacattgtaa    1380
tgttagtaga ataaaatgga gggagatgtt aaagaatgtc acagcacagc taaggaaaat    1440
ctataataat aagaacataa cctttaactc atctgcagga ggggacctag aaattacaac    1500
acatagtttc aattgtagag gagagttttt ctattgcaat acatcaggac tgtttaataa    1560
taatattagt aatattaata atgagactat cacactccca tgtaaaataa aacaaattgt    1620
gaggatgtgg cagaaagtgg gacaagcaat gtatgccctt cccatcgcag gaaaccttgt    1680
atgtaaatca aacattacag gattaatatt aacaagagat ggtgggaata acaatgacag    1740
tacagaggag accttcagac ctggaggagg agatatgagg gacaattgga gaagtgaatt    1800
atataagtat aaaacagtaa aaatcaaatc actaggagta gcacccacca gggcaaggag    1860
aagagtggtg gagagagaaa aaagagcagt tggactggga gctgtcttcc ttgggttctt    1920
aggagcagca gggagcacta tgggcgcggc gtcaataacg ctgacggcac aggtcagaca    1980
attattgtct ggcatagtgc aacagcaaag caatttgctg agggctatag aggcgcagca    2040
gcatctgttg caactcacag tctggggcat taaacagctc cagtcaagag tcctggctat    2100
agaaagatac ctaaaggatc aacagctcct agggatttgg ggctgctctg gaaaactcat    2160
ctgcaccact aatgtgccct ggaacactag ttggagtaat aaatcttata atgagatttg    2220
ggataacatg acttggctag aatgggaaag ggaaattcac aattacacac aacacatata    2280
cagcctgatt gaagaatcgc agaaccagca ggaaaagaat gaacaagact tattggcatt    2340
ggacaagtgg gcaagtttgt ggaattggtt tgacatatca aattggctat ggtatataag    2400
aatattcata atgatagtag gaggtttaat aggtttaaga atagtttttg ctgtgctttc    2460
tatagtaaat agagttaggc agggatactc acctttgtcg ttccagaccc ttacccatca    2520
ccagcgggaa cccgacaggc tcggaaaaac cgaagaagga ggtggcgagc aagacagaga    2580
cagatccact cgattag                                                   2597
```

```
<210> SEQ ID NO 26
<211> LENGTH: 2663
<212> TYPE: DNA
<213> ORGANISM: Human immunodeficiency virus type 1
<220> FEATURE:
<223> OTHER INFORMATION: isolate=92NG083; gene=rev

<400> SEQUENCE: 26

atggcaggaa gaagcggaga ccccgacgag gaactcctca gggcagtaag gatcatcaaa      60
```

-continued

```
accctgtacc aaagcagtaa gtagtaacaa ttaatatatg taatgcaggc cttagaaata    120
tctgactaat agtagcattc atagcagcca caattgtgtg gagtatagta tttatagaat    180
atagaaaaat aagaaaacag aaaaaaatag aaaagttact tgatagaata agagaaagag    240
cagaagacag tggaaatgag agtgaagggg atacagagga attggcaaca cttatggaaa    300
tgggggactt tgatccttgg gttggtaata atttgtagtg cctcagataa cttgtgggtc    360
acagtctatt atggggtacc tgtgtgggaa gatgcagata ccccccctatt ctgtgcctct    420
gatgctaaat catatagttc tgaaaaacat aatgtctggg ctacacatgc ctgtgtaccc    480
acagacccta acccacaaga aatagctata gaaaatgtaa cagaaaattt taacatgtgg    540
aagaataaca tggtagaaca gatgcaggag gatataatca gtttatggga ggaaagccta    600
aagccatgtg taaagctaac tcctctctgt atcactttaa actgtactaa tgtaaacagt    660
gctaatcata ctgaggccaa taacactgta gaaaacaaag aagaaataaa aaactgctct    720
ttcaagataa ccacagaaag gggaggcaag aagaaggaag aatacgcgct tttctataaa    780
cttgatgtgg taccaattag taatgggaat aagactagtt ataggctaat acattgtaat    840
gtctcaacca ttaaacaggc ttgtccaaag gtaaattttg acccaattcc catacattat    900
tgtgctccag ctggttttgc gattttaaag tgtagggata aggagtacaa tggaacagga    960
ccatgtaaaa atgtcagtac agtacaatgt acacatggaa ttaagccagt ggtatcaact   1020
caactactgc tgaatggcag tttagcagaa gaagatataa gaattagatc tgaaaatttc   1080
acagacaata ccaaagtcat aatagtgcag cttaataata gtatagaaat taattgtatc   1140
agacccaata acaatacaag aaaaagtata ccaatcggac caggacaagc gttctatgca   1200
acaggtgata taataggaga cataagacaa gcacattgta atgttagtag aataaaatgg   1260
agggagatgt taaagaatgt cacagcacag ctaaggaaaa tctataataa taagaacata   1320
acctttaact catctgcagg aggggaccta gaaattacaa cacatagttt caattgtaga   1380
ggagagtttt tctattgcaa tacatcagga ctgtttaata ataatattag taatattaat   1440
aatgagacta tcacactccc atgtaaaata aaacaaattg tgaggatgtg gcagaaagtg   1500
ggacaagcaa tgtatgccct tcccatcgca ggaaaccttg tatgtaaatc aaacattaca   1560
ggattaatat taacaagaga tggtgggaat aacaatgaca gtacagagga gaccttcaga   1620
cctggaggag gagatatgag ggacaattgg agaagtgaat tatataagta taaaacagta   1680
aaaatcaaat cactaggagt agcacccacc agggcaagga gaagagtggt ggagagagaa   1740
aaaagagcag ttggactggg agctgtcttc cttgggttct taggagcagc agggagcact   1800
atgggcgcgg cgtcaataac gctgacggca caggtcagac aattattgtc tggcatagtg   1860
caacagcaaa gcaatttgct gagggctata gaggcgcagc agcatctgtt gcaactcaca   1920
gtctggggca ttaaacagct ccagtcaaga gtcctggcta tagaaagata cctaaaggat   1980
caacagctcc tagggatttg gggctgctct ggaaaactca tctgcaccac taatgtgccc   2040
tggaacacta gttggagtaa taaatcttat aatgagattt gggataacat gacttggcta   2100
gaatgggaaa gggaaattca caattacaca caacacatat acagcctgat tgaagaatcg   2160
cagaaccagc aggaaaagaa tgaacaagac ttattggcat tggacaagtg ggcaagtttg   2220
tggaattggt ttgacatatc aaattggcta tggtatataa gaatattcat aatgatagta   2280
ggaggtttaa taggtttaag aatagttttt gctgtgcttt ctatagtaaa tagagttagg   2340
cagggatact cacctttgtc gttccagacc cttacccatc accagcggga acccgacagg   2400
ctcggaaaaa ccgaagaagg aggtggcgag caagacagag acagatccac tcgattagtg   2460
```

-continued agcggattct tagcgcttgc ctgggacgac ctgcggagcc tgtgcctttt cagctaccac 2520
cgcttgaggg acttagtctt gattgcagca aggacggtgg aacttctggg acgcagcagc 2580
ctcaagggac tgagactggg gtgggaaggc ctcaagtact tgtggaacct cctgttgtat 2640
tggggtcggg aactaaagaa tag 2663

<210> SEQ ID NO 27
<211> LENGTH: 26
<212> TYPE: DNA
<213> ORGANISM: Human immunodeficiency virus type 1
<220> FEATURE:
<223> OTHER INFORMATION: isolate=92NG083; gene=vpu (defective); note=10 bp deletion early in vpu frameshifts, results in premature termination

<400> SEQUENCE: 27
tgcaggcctt agaaatatct gactaa 26

<210> SEQ ID NO 28
<211> LENGTH: 2550
<212> TYPE: DNA
<213> ORGANISM: Human immunodeficiency virus type 1
<220> FEATURE:
<223> OTHER INFORMATION: isolate=92NG083; gene=env

<400> SEQUENCE: 28
atgagagtga aggggataca gaggaattgg caacacttat ggaaatgggg gactttgatc 60
cttgggttgg taataatttg tagtgcctca gataacttgt gggtcacagt ctattatggg 120
gtacctgtgt gggaagatgc agataccccc ctattctgtg cctctgatgc taaatcatat 180
agttctgaaa aacataatgt ctgggctaca catgcctgtg tacccacaga ccctaaccca 240
caagaaatag ctatagaaaa tgtaacagaa aattttaaca tgtggaagaa taacatggta 300
gaacagatgc aggaggatat aatcagttta tgggaggaaa gcctaaagcc atgtgtaaag 360
ctaactcctc tctgtatcac tttaaactgt actaatgtaa acagtgctaa tcatactgag 420
gccaataaca ctgtagaaaa caaagaagaa ataaaaaact gctctttcaa gataaccaca 480
gaaaggggag gcaagaagaa ggaagaatac gcgcttttct ataaacttga tgtggtacca 540
attagtaatg ggaataagac tagttatagg ctaatacatt gtaatgtctc aaccattaaa 600
caggcttgtc caaaggtaaa ttttgaccca attcccatac attattgtgc tccagctggt 660
tttgcgattt taaagtgtag ggataaggag tacaatggaa caggaccatg taaaaatgtc 720
agtacagtac aatgtacaca tggaattaag ccagtggtat caactcaact actgctgaat 780
ggcagtttag cagaagaaga tataagaatt agatctgaaa atttcacaga caataccaaa 840
gtcataatag tgcagcttaa taatagtata gaaattaatt gtatcagacc caataacaat 900
acaagaaaaa gtataccaat cggaccagga caagcgttct atgcaacagg tgatataata 960
ggagacataa gacaagcaca ttgtaatgtt agtagaataa aatggaggga gatgttaaag 1020
aatgtcacag cacagctaag gaaaatctat aataataaga acataacctt taactcatct 1080
gcaggagggg acctagaaat tacaacacat agtttcaatt gtagaggaga gtttttctat 1140
tgcaatacat caggactgtt taataataat attagtaata ttaataatga gactatcaca 1200
ctcccatgta aaataaaaca aattgtgagg atgtggcaga aagtgggaca agcaatgtat 1260
gcccttccca tcgcaggaaa ccttgtatgt aaatcaaaca ttacaggatt aatattaaca 1320
agagatggtg ggaataacaa tgacagtaca gaggagacct tcagacctgg aggaggagat 1380

-continued

```
atgagggaca attggagaag tgaattatat aagtataaaa cagtaaaaat caaatcacta   1440

ggagtagcac ccaccagggc aaggagaaga gtggtggaga gagaaaaaag agcagttgga   1500

ctgggagctg tcttccttgg gttcttagga gcagcaggga gcactatggg cgcggcgtca   1560

ataacgctga cggcacaggt cagacaatta ttgtctggca tagtgcaaca gcaaagcaat   1620

ttgctgaggg ctatagaggc gcagcagcat ctgttgcaac tcacagtctg gggcattaaa   1680

cagctccagt caagagtcct ggctatagaa agatacctaa aggatcaaca gctcctaggg   1740

atttggggct gctctggaaa actcatctgc accactaatg tgccctggaa cactagttgg   1800

agtaataaat cttataatga gatttgggat aacatgactt ggctagaatg ggaaagggaa   1860

attcacaatt acacacaaca catatacagc ctgattgaag aatcgcagaa ccagcaggaa   1920

aagaatgaac aagacttatt ggcattggac aagtgggcaa gtttgtggaa ttggtttgac   1980

atatcaaatt ggctatggta tataagaata ttcataatga tagtaggagg tttaataggt   2040

ttaagaatag tttttgctgt gctttctata gtaaatagag ttaggcaggg atactcacct   2100

ttgtcgttcc agacccttac ccatcaccag cgggaacccg acaggctcgg aaaaaccgaa   2160

gaaggaggtg gcgagcaaga cagagacaga tccactcgat tagtgagcgg attcttagcg   2220

cttgcctggg acgacctgcg gagcctgtgc cttttcagct accaccgctt gagggactta   2280

gtcttgattg cagcaaggac ggtggaactt ctgggacgca gcagcctcaa gggactgaga   2340

ctggggtggg aaggcctcaa gtacttgtgg aacctcctgt tgtattgggg tcgggaacta   2400

aagaatagtg ctattaattt gcttgataca atagcaatag caacagctaa cgggacagat   2460

agggttatag aagtagcaca aagagcttat agagctattc tcaacgtacc tacaaggata   2520

agacaaggct tagaaagagc tttgctataa                                    2550
```

```
<210> SEQ ID NO 29
<211> LENGTH: 1503
<212> TYPE: DNA
<213> ORGANISM: Human immunodeficiency virus type 1
<220> FEATURE:
<223> OTHER INFORMATION: isolate=90CR056; gene=gag; CDS:
      join(137..1434,1434..4443)

<400> SEQUENCE: 29
```

```
atgggtgcga gagcgtcagt attaagcggc ggaaaattag atgcttggga gaaaattcgg     60

ctaaggccag gggaaagaa aaaatatagg ctaaaacatc tagtatgggc aagcagggag    120

ctggaaagat ttgcacttaa ccccggcctt ttagaaacac cagaaggctg tctacagata    180

atagaacaga tacagccagc tattaagaca ggaacagaag aacttaaatc attatttaat    240

ctagtagcag tcctctattg cgtacatcga aaaatagatg tgaaagacac caaggaggct    300

ttagataaga tagaggaaat acaaaacaaa agtcagcaaa aaacacagca agcagcagct    360

gataaggaaa aagacaacaa ggtcagtcaa aattatccta tagtacagaa tgctcaaggg    420

cagatggtac accaggccat atcacctagg accttaaatg catgggtaaa agtagtagaa    480

gaaaaggctt ttagcccaga agtaataccc atgttttcag cattatcaga aggagccacc    540

ccacaagact taaatgctat gctaaataca gtggggggac atcaagcagc catgcagatg    600

ttaaaagata caatcaatga ggaagctgca gaatgggaca gggtacatcc agtgcatgca    660

gggcctattc caccaggcca aatgagagaa ccaaggggaa gcgatatagc aggaactact    720

agtaccctgc aggaacaaat agcatggatg acaggcaatc cagctatccc agtgggagac    780

atctataaaa gatggataat cctgggatta aataagatag taagaatgta tagtcctgtc    840
```

-continued

```
agcattctgg acataaaaca agggccaaaa gaacccttta gagactatgt agacaggttt     900

tttaaaactt taagagctga gcaagccaca caggatgtga agaattggat gacagaaacc     960

ttgttggtcc aaaatgcaaa tccagattgc aagactatat taagagcatt aggacaaggg    1020

gcttcaatag aagaaatgat gacagcatgt cagggagtgg gaggacctag tcataaagca    1080

agagttttgg ctgaggcaat gagccaagta acaaatacaa atacagccat aatgatgcag    1140

aaaggcaact ttaagggcca aagaaaattt gttaaatgct tcaactgtgg caaagaggga    1200

cacatagcca gaaattgcag ggcccctagg aaaaagggct gttggaaatg tggaagagaa    1260

ggacatcaga tgaaagactg cacagagaga caggctaatt ttttagggaa aatttggcct    1320

tccagcaaag ggaggccagg aaattttctc cagagcaggc cagaaccaac agccccacca    1380

gcagagagct tcgggttcgg agaggagatg accccctctc cgaagcagga gcagctgaag    1440

gacaaggaac ctcccttagc ttccctcaga tcactctttg gcagcgaccc cttgttacag    1500

taa                                                                  1503
```

<210> SEQ ID NO 30
<211> LENGTH: 579
<212> TYPE: DNA
<213> ORGANISM: Human immunodeficiency virus type 1
<220> FEATURE:
<223> OTHER INFORMATION: isolate=90CR056; gene=vif

<400> SEQUENCE: 30

```
atggaaaaca gatggcaggt gatgattgtg tggcaagtag acaggatgag gattaacaca      60

tggaaaagct tagtaaagta ccatatgcat atttcaagga aagctagagg atggttttat     120

agacatcatt ttgaaagcac tcatccaagg ataagttcag aagtacacat cccattagga     180

gaagctaggt tagtcataac cacatactgg ggtctgaata caggagaaag agaatggcat     240

ttaggccagg gagtctccat agaatggaga ctgaaaaggt atagcacaca agtagagcct     300

ggcctggcag accaactaat tcatatgcat tattttgatt gtttttcaga atctgccata     360

aggaaagcca tattaggacg tgtagttaga cctaggtgta actatccagc aggacataaa     420

caggtaggaa ctctacaata cttggcatta acagcattag tggcaccaaa aaagataaag     480

ccacctttgc ctagtgttag aaagctagta gaggatagat ggaacaagcc ccagaagacc     540

aggggccaca gagggagcca cacaatgaat ggacactag                            579
```

<210> SEQ ID NO 31
<211> LENGTH: 291
<212> TYPE: DNA
<213> ORGANISM: Human immunodeficiency virus type 1
<220> FEATURE:
<223> OTHER INFORMATION: isolate=90CR056; gene=vpr

<400> SEQUENCE: 31

```
atggaacaag ccccagaaga ccaggggcca cagagggagc cacacaatga atggacacta      60

gagcttttag aggagattaa gaatgaggct gttaggcatt ttcctagagt atggctccat     120

caattaggac agcatatcta taacacctat ggagatactt gggtaggagt tgaagcttta     180

ataagaacgc tgcaacaact actgtttatt catttcagaa ttgggtgcca acatagcaga     240

ataggaatta ctcgacagag aagagtaaga aatggaccca gtagatccta a              291
```

<210> SEQ ID NO 32
<211> LENGTH: 624
<212> TYPE: DNA
<213> ORGANISM: Human immunodeficiency virus type 1

-continued

<220> FEATURE:
<223> OTHER INFORMATION: isolate=92NG083; gene=nef

<400> SEQUENCE: 32

```
atggggggca agtggtcaaa aagtagcata gttggatggc ctcagataag ggaaagaata     60
agacaaactc ctgtagcagc agaaggagta ggagcagtat ctcaagattt agctaggcat    120
ggagcaatca caagcagcaa tacagcaacc aacaatcctg attgtgcctg gctggaagca    180
caagaggagg actcagatgt aggctttccg gtcagaccac aggtaccttt gagaccaatg    240
acttataagg ctgcttttga tctcagcttc tttttaaaag aaaagggggg actggatggg    300
ctaatttact ccaagagaag acaagacatc cttgatctat gggtctataa tacacaagga    360
ttcttcccag attggcagaa ctacacacca gggccaggga ctagactccc actgaccttt    420
gggtggtgct tcaaactagt accaatggac ccagcagaga tagaggaagc caataaggga    480
gagaacatca gtctattaca ccccatctgc cagcatggaa tggaggatga agacagagaa    540
gtgctggtat ggagatttaa cagtagccta gcacggagac acctagcccg agagctgcat    600
ccggagtact acaaagactg ctga                                           624
```

<210> SEQ ID NO 33
<211> LENGTH: 2606
<212> TYPE: DNA
<213> ORGANISM: Human immunodeficiency virus type 1
<220> FEATURE:
<223> OTHER INFORMATION: isolate=90CR056; gene=tat; CDS: join
      (5177..5391, 7698..7782)

<400> SEQUENCE: 33

```
atggacccag tagatcctaa actagagccc tggaaccatc caggaagtca gcctcaaact     60
gcttgtaaca attgttattg taaaaagtgc tgctatcatt gccaaatgtg ctttttaaag    120
aaaggcttag gaatttccta tggcaggaag aagcggagcc agcgacacag aactcctgca    180
agtttgcaag atcatcaaaa ttctatatca aagcagtaag tattatcata aatgtatata    240
ttaggattag gaataggagc gctagtagta acatttatca tagccgtaat tgtgtggacc    300
atagtatata tagaatataa aaaattggta aggcaaaaga aaatagacag gctaattgaa    360
agaataggag aaagagcaga agacagtggc aacgagagtg atggagacac agaggaatta    420
tccaagctta tggagatggg gcaccttaat cttgggtatg ttgctgatct gtagtgctgc    480
acaaaacttg tgggttacag tatattatgg ggtacctgtg tggaaagagg caaaaaccac    540
tctattctgt gcatcagatg ctaaggcata tgagacagaa aagcataatg tctgggctac    600
acatgcatgt gtacccacag accccaaccc acaagagatg gtcatggaga atgtaacaga    660
gagctttaat atgtgggaaa ataacatggt ggagcagatg catacagaca taatcagttt    720
atgggatcaa agcttgaaac catgtgtaaa attaacccca ctctgtgtta ctctaaactg    780
tactaatgtc agaaacaata cctctaacag cactagcagt atggaggcag gaggggaact    840
aacaaattgc tctttcaatg taactacagt actaagagat aagcagcaga aagtacatgc    900
actcttttat agacttgatg tagtaccaat tgataacaat agtactcagt ataggctaat    960
aaattgtaat acctcagtca ttacacaggc ttgcccaaag gtgtcctttg aacctattcc   1020
catacattat tgtgctccag ctggctttgc gattctaaag tgtaacaata aaacattcaa   1080
tggaacagga ttatgtacaa atgtcagtac agtacaatgt acacatggaa ttagaccagt   1140
ggtatcaact caactgctat taaatggaag cctagcagaa gaacagatca taattagaac   1200
taaaaatatc tcagacaata ccaaaaacat aatagtacag cttaagacac cagtaaacat   1260
```

-continued

```
tacatgtacc aggcctaaca ataatacgag aacaagtata catttagggc caggacgagc   1320
attctatgca acaggtgaca tcataggaga tataagacaa gcacattgta atattagtag   1380
aacagactgg aataagactt tacaccaggt agttacacaa ttaggaatac acttgaacaa   1440
tagaacaata agctttaagc caaactcagg aggggacatg gaagttagaa cacatagttt   1500
taattgtaga ggagaatttt tctattgcaa tacatcaggg ctgtttaata gtagttggga   1560
aatgcatact aattacacat caaatgacac aaagggaaac gaaaacatta cactgccatg   1620
cagaataaaa caaattgtaa acatgtggca gagagtagga cgagcaatgt atgcccctcc   1680
catccaagga aacattatgt gtgtatcaaa tattacagga ctaatattga caattgacga   1740
gggtaacgcg tctgcagaaa attatacctt cagacctgga ggaggagata tgagggacaa   1800
ttggagaagt gaattgtata aatataaagt agtaaaaatt gaaccactgg gaatagcacc   1860
caccaagaca aggagaagag tggtggagag agaaaaaaga gcagtgggaa tgggagcttc   1920
tttccttggg ttcttgggag cagcaggaag cactatgggc gcggcgtcaa taacgctgac   1980
ggtacaggcc aggcaattat tgtctggtat agtgcagcag caaagcaatt tgctgagagc   2040
tatacaggcg cgacagcata tgttgcagct cacggtctgg ggcattaaac agctccaggc   2100
aagagtcctc gctgtggaaa gatacctaag ggatcaacag ctcctgggga tttggggctg   2160
ctctggaaaa ctcatctgca ccactaatgt gccttggaac tctagttgga gtaataaatc   2220
acagagtgaa atctgggaca acatgacttg gatggaatgg gataaacaaa ttagcaatta   2280
cacagaggaa atatacaggt tgcttgaagt ctcgcaaacc cagcaggaaa agaatgaaca   2340
ggacttatta gcattggaca aatgggcaag tctgtggact tggtttgaca tatcacattg   2400
gctgtggtat ataaaaatat tcataatgat agtaggaggt ttaataggtt taagaataat   2460
ttttgctgtg ctttctatag taaatagagt taggcaggga tactcacctt tgtcttttca   2520
gacccttgtc ccgaacccac ggggacccga caggcccgaa ggaacagaag aaggaggtgg   2580
cgagcaagac agagacagat ccgtga                                        2606
```

<210> SEQ ID NO 34
<211> LENGTH: 2657
<212> TYPE: DNA
<213> ORGANISM: Human immunodeficiency virus type 1
<220> FEATURE:
<223> OTHER INFORMATION: isolate=90CR056; gene=rev; CDS: join (5316..5391, 7698..7972)

<400> SEQUENCE: 34

```
atggcaggaa gaagcggagc cagcgacaca gaactcctgc aagtttgcaa gatcatcaaa     60
attctatatc aaagcagtaa gtattatcat aaatgtatat attaggatta ggaataggag    120
cgctagtagt aacatttatc atagccgtaa ttgtgtggac catagtatat atagaatata    180
aaaaattggt aaggcaaaag aaaatagaca ggctaattga aagaatagga gaaagagcag    240
aagacagtgg caacgagagt gatggagaca cagaggaatt atccaagctt atggagatgg    300
ggcaccttaa tcttgggtat gttgctgatc tgtagtgctg cacaaaactt gtgggttaca    360
gtatattatg ggtacctgt gtggaaagag gcaaaaacca ctctattctg tgcatcagat     420
gctaaggcat atgagacaga aaagcataat gtctgggcta cacatgcatg tgtacccaca    480
gaccccaacc cacaagagat ggtcatggag aatgtaacag agagctttaa tatgtgggaa    540
aataacatgg tggagcagat gcatacagac ataatcagtt tatgggatca aagcttgaaa    600
ccatgtgtaa aattaacccc actctgtgtt actctaaact gtactaatgt cagaaacaat    660
```

-continued

```
acctctaaca gcactagcag tatggaggca ggaggggaac taacaaattg ctctttcaat    720
gtaactacag tactaagaga taagcagcag aaagtacatg cactctttta tagacttgat    780
gtagtaccaa ttgataacaa tagtactcag tataggctaa taaattgtaa tacctcagtc    840
attacacagg cttgcccaaa ggtgtccttt gaacctattc ccatacatta ttgtgctcca    900
gctggctttg cgattctaaa gtgtaacaat aaaacattca atggaacagg attatgtaca    960
aatgtcagta cagtacaatg tacacatgga attagaccag tggtatcaac tcaactgcta   1020
ttaaatggaa gcctagcaga agaacagatc ataattagaa ctaaaaatat ctcagacaat   1080
accaaaaaca taatagtaca gcttaagaca ccagtaaaca ttacatgtac caggcctaac   1140
aataatacga gaacaagtat acatttaggg ccaggacgag cattctatgc aacaggtgac   1200
atcataggag atataagaca agcacattgt aatattagta gaacagactg gaataagact   1260
ttacaccagg tagttacaca attaggaata cacttgaaca atagaacaat aagctttaag   1320
ccaaactcag gaggggacat ggaagttaga acacatagtt ttaattgtag aggagaattt   1380
ttctattgca atacatcagg gctgtttaat agtagttggg aaatgcatac taattacaca   1440
tcaaatgaca caaagggaaa cgaaaacatt acactgccat gcagaataaa acaaattgta   1500
aacatgtggc agagagtagg acgagcaatg tatgcccctc ccatccaagg aaacattatg   1560
tgtgtatcaa atattacagg actaatattg acaattgacg agggtaacgc gtctgcagaa   1620
aattatacct tcagacctgg aggaggagat atgagggaca attggagaag tgaattgtat   1680
aaatataaag tagtaaaaat tgaaccactg ggaatagcac ccaccaagac aaggagaaga   1740
gtggtggaga gagaaaaaag agcagtggga atgggagctt ctttccttgg gttcttggga   1800
gcagcaggaa gcactatggg cgcggcgtca ataacgctga cggtacaggc caggcaatta   1860
ttgtctggta tagtgcagca gcaaagcaat ttgctgagag ctatacaggc gcgacagcat   1920
atgttgcagc tcacggtctg ggcattaaa  cagctccagg caagagtcct cgctgtggaa   1980
agatacctaa gggatcaaca gctcctgggg atttggggct gctctggaaa actcatctgc   2040
accactaatg tgccttggaa ctctagttgg agtaataaat cacagagtga aatctgggac   2100
aacatgactt ggatggaatg ggataaacaa attagcaatt acacagagga aatatacagg   2160
ttgcttgaag tctcgcaaac ccagcaggaa aagaatgaac aggacttatt agcattggac   2220
aaatgggcaa gtctgtggac ttggtttgac atatcacatt ggctgtggta tataaaaata   2280
ttcataatga tagtaggagg tttaataggt ttaagaataa tttttgctgt gctttctata   2340
gtaaatagag ttaggcaggg atactcacct ttgtcttttc agacccttgt cccgaaccca   2400
cggggacccg acaggcccga aggaacagaa gaaggaggtg gcgagcaaga cagagacaga   2460
tccgtgagat tagtgaacgg attcttacca gttgtctggg acgacctccg gagcctgtca   2520
ctcttcagct accgcctctt gagagactta ctcttaattg tagtgaggac tgtggaactt   2580
ctggggagaa gggggaggga agccctcaaa tatctctgga atcttctaca atactgggga   2640
caggaactaa agaatag                                                  2657
```

```
<210> SEQ ID NO 35
<211> LENGTH: 243
<212> TYPE: DNA
<213> ORGANISM: Human immunodeficiency virus type 1
<220> FEATURE:
<223> OTHER INFORMATION: isolate=90CR056; gene=vpu

<400> SEQUENCE: 35
```

-continued

```
atgtatatat taggattagg aataggagcg ctagtagtaa catttatcat agccgtaatt      60

gtgtggacca tagtatatat agaatataaa aaattggtaa ggcaaaagaa aatagacagg     120

ctaattgaaa gaataggaga aagagcagaa gacagtggca acgagagtga tggagacaca     180

gaggaattat ccaagcttat ggagatgggg caccttaatc ttgggtatgt tgctgatctg     240

tag                                                                   243
```

<210> SEQ ID NO 36
<211> LENGTH: 2538
<212> TYPE: DNA
<213> ORGANISM: Human immunodeficiency virus type 1
<220> FEATURE:
<223> OTHER INFORMATION: isolate=90CR056; gene=env

<400> SEQUENCE: 36

```
atggagacac agaggaatta tccaagctta tggagatggg gcaccttaat cttgggtatg      60

ttgctgatct gtagtgctgc acaaaacttg tgggttacag tatattatgg ggtacctgtg     120

tggaaagagg caaaaaccac tctattctgt gcatcagatg ctaaggcata tgagacagaa     180

aagcataatg tctgggctac acatgcatgt gtacccacag accccaaccc acaagagatg     240

gtcatggaga atgtaacaga gagctttaat atgtgggaaa ataacatggt ggagcagatg     300

catacagaca taatcagttt atgggatcaa agcttgaaac catgtgtaaa attaacccca     360

ctctgtgtta ctctaaactg tactaatgtc agaaacaata cctctaacag cactagcagt     420

atggaggcag gaggggaact aacaaattgc tctttcaatg taactacagt actaagagat     480

aagcagcaga aagtacatgc actcttttat agacttgatg tagtaccaat tgataacaat     540

agtactcagt ataggctaat aaattgtaat acctcagtca ttacacaggc ttgcccaaag     600

gtgtcctttg aacctattcc catacattat tgtgctccag ctggctttgc gattctaaag     660

tgtaacaata aaacattcaa tggaacagga ttatgtacaa atgtcagtac agtacaatgt     720

acacatggaa ttagaccagt ggtatcaact caactgctat taaatggaag cctagcagaa     780

gaacagatca taattagaac taaaaatatc tcagacaata ccaaaaacat aatagtacag     840

cttaagacac cagtaaacat tacatgtacc aggcctaaca ataatacgag aacaagtata     900

catttagggc caggacgagc attctatgca acaggtgaca tcataggaga tataagacaa     960

gcacattgta atattagtag aacagactgg aataagactt tacaccaggt agttacacaa    1020

ttaggaatac acttgaacaa tagaacaata agctttaagc caaactcagg aggggacatg    1080

gaagttagaa cacatagttt taattgtaga ggagaatttt tctattgcaa tacatcaggg    1140

ctgtttaata gtagttggga aatgcatact aattacacat caaatgacac aaagggaaac    1200

gaaaacatta cactgccatg cagaataaaa caaattgtaa acatgtggca gagagtagga    1260

cgagcaatgt atgcccctcc catccaagga aacattatgt gtgtatcaaa tattacagga    1320

ctaatattga caattgacga gggtaacgcg tctgcagaaa attatacctt cagacctgga    1380

ggaggagata tgagggacaa ttggagaagt gaattgtata aatataaagt agtaaaaatt    1440

gaaccactgg gaatagcacc caccaagaca aggagaagag tggtggagag agaaaaaaga    1500

gcagtgggaa tgggagcttc tttccttggg ttcttgggag cagcaggaag cactatgggc    1560

gcggcgtcaa taacgctgac ggtacaggcc aggcaattat tgtctggtat agtgcagcag    1620

caaagcaatt tgctgagagc tatacaggcg cgacagcata tgttgcagct cacggtctgg    1680

ggcattaaac agctccaggc aagagtcctc gctgtggaaa gatacctaag ggatcaacag    1740

ctcctgggga tttggggctg ctctggaaaa ctcatctgca ccactaatgt gccttggaac    1800
```

-continued

```
tctagttgga gtaataaatc acagagtgaa atctgggaca acatgacttg gatggaatgg   1860

gataaacaaa ttagcaatta cacagaggaa atatacaggt tgcttgaagt ctcgcaaacc   1920

cagcaggaaa agaatgaaca ggacttatta gcattggaca aatgggcaag tctgtggact   1980

tggtttgaca tatcacattg gctgtggtat ataaaaatat tcataatgat agtaggaggt   2040

ttaataggtt taagaataat ttttgctgtg ctttctatag taaatagagt taggcaggga   2100

tactcacctt tgtcttttca gacccttgtc ccgaacccac ggggacccga caggcccgaa   2160

ggaacagaag aaggaggtgg cgagcaagac agagacagat ccgtgagatt agtgaacgga   2220

ttcttaccag ttgtctggga cgacctccgg agcctgtcac tcttcagcta ccgcctcttg   2280

agagacttac tcttaattgt agtgaggact gtggaacttc tggggagaag ggggagggaa   2340

gccctcaaat atctctggaa tcttctacaa tactggggac aggaactaaa gaatagtgct   2400

attgatttgc ttaacaccac agcaatagca gtagctgagg gaacagatgg gattatagta   2460

atagtgcaaa gagcttggag agctattctc cacataccta gaagaataag acagggcttt   2520

gaaagaagct tgctataa                                                 2538
```

<210> SEQ ID NO 37
<211> LENGTH: 621
<212> TYPE: DNA
<213> ORGANISM: Human immunodeficiency virus type 1
<220> FEATURE:
<223> OTHER INFORMATION: isolate=90CR056; gene=nef

<400> SEQUENCE: 37

```
atgggaggca aatggtcaaa aagtaggatg ggtgggtggt ctactataag ggaaagaatg     60

aggcgagctg aaccagtagc agaaggggta ggagcagtgt ctcgagattt ggatagacgc    120

ggggcagtca caattaataa tacagcatct actaatcgtg atgccgcctg gctggaagca    180

caagaggacg gggaggaagt aggctttcca gtcaggcctc aggtaccttt aagaccaatg    240

acctataagg gagcttttga tctcagccat tttttaaaag aaaagggggg actggatggg    300

ttaatttact ccaagcaaag acaggacatc cttgatttat gggtctataa cacacaaggc    360

tacttccctg actggcagaa ctacacacca gggccagggg agagatttcc cctgaccttt    420

gggtggtgct tcaagctagt accagtaaat ccacaggagg tagaacaggc caatgaagga    480

gagaacaaca gcttgctaca ccccatgagc ctgcatggaa tggaggatga cgggagagaa    540

gtgctgatgt ggaaatttga cagtcgacta gcattgacac acttggcccg agtaaagcat    600

ccggagtaca aagactgctg a                                              621
```

<210> SEQ ID NO 38
<211> LENGTH: 1486
<212> TYPE: DNA
<213> ORGANISM: Human immunodeficiency virus type 1
<220> FEATURE:
<223> OTHER INFORMATION: isolate=92RW009; gene=gag

<400> SEQUENCE: 38

```
atgggtgcga gagcgtcaat attaagaggc ggaaaattag atgcctggga aaaaattaag     60

ttaaagccag gggggaaaga aaacatatat gatgaaacac ctagtatggg caagcaggga    120

gctggaaaga tttgcactta accctgacct tttagagaca ccagaaggct gtaaacaaat    180

aatgagacag ctgcaaccag ctcttcagac aggaacagat gaacttaggt cattatataa    240

tacagtagca accctctatt gtgtacatca aaagatagat gtaaaagaca ccaaggaggc    300
```

-continued

```
cttagacaag atagaggaag aacaaaacaa aagtcagcaa aaaacacagc aggcagaagc    360

agctgacaaa ggaaaagtca gtcaaaatta ccctatagtg caaaatgcac aagggcaaat    420

ggtacaccag gccatatcac ctagaacttt gaatgcgtgg gtaaaagtaa tagaggagaa    480

ggcttttagc caagaggtaa tacccatgtt tacagcatta tcagaaggag ccaccccaca    540

agatttaaac accatgctaa atacagtggg gggacatcaa gcagccatgc aaatgctaaa    600

agatacaatc aatgaggagg ctgcagagtg ggatagggta catccagtgc aggcagggcc    660

tgttgcgcca ggccagataa gagaaccaag gggaagtgac atagcaggaa ctactagtac    720

ccttcaggaa caaatagcat ggatgacaaa taacccacct attccagtgg gagaaattta    780

taaaagatgg ataattctgg ggttaaataa aatagtaaga atgtatagcc ctgtcagcat    840

attggacata aaacaagggc caaaggaacc ttttagagac tatgtagacc ggttctttaa    900

aaccttaaga gccgaacaag cttcacaaga tgtaaaaaat tggatgacag ataccttgtt    960

agtccaaaat gcgaacccag attgtaagac cattttaaga gcattagggc caggggcttc   1020

attagaagaa atgatgacag catgccaggg agtgggagga cccggccata aagcaagggt   1080

tttggctgaa gcaatgagcc aagtacaaca accaaacata atgatgcaga gaggcaattt   1140

taagggccag agaagaatta ttaagtgttt caactgtggc aaagaaggac acctagccag   1200

aaattgcagg gcccctagaa aaaagggctg ttggaaatgt ggaaaggagg gacaccaaat   1260

gaaagactgc actgagagac aggctaattt tttagggaaa atttggcctt ccaacaaggg   1320

gaggccagga aattttcccc agagcagact ggagccaaca gccccaccag cagagaactt   1380

tggaatgggg gaagagatag cctctcctct gaaacaggag cagaaagaca gggaaccttt   1440

aatttccctc aaatcactct ttggcaacga ccccttgtca cagtaa                  1486
```

<210> SEQ ID NO 39
<211> LENGTH: 579
<212> TYPE: DNA
<213> ORGANISM: Human immunodeficiency virus type 1
<220> FEATURE:
<223> OTHER INFORMATION: isolate=92RW009; gene=vif

<400> SEQUENCE: 39

```
atggaaaaca gatggcaggt gatgattgtg tggcaggtag acaggatgaa gattagaaca     60

tggaatagtc tagtaaagca ccatatgtat gcttcaagga gagctaaggg atggttttat    120

agacatcatt atgaaagcag acatccaaaa ataagttcag aagtacacat cccattaggg    180

gaagctagat tagtaataaa aacatattgg ggtttgcaaa caggggaaag agattggcat    240

ttgggtcatg gagtctccat agaatggaga ttgagaagat ataagacaca agtagaccct    300

ggcctggcag gccaactaat ccatatgcat tattttgatt gttttgcaga ctctgccata    360

aggaaagcca tattaggaca tatagttagc cctaggtgtg actatcaagc aggacataat    420

aaggtaggat ctctacaata cttggcactg acagcattga taaaaccaaa aaagataaag    480

ccacctctgc ctagtgttag taaattagta gaggataaat ggaacaagcc ccagaagacc    540

aggggccgca gagggaacca tacaatgaat ggacactag                          579
```

<210> SEQ ID NO 40
<211> LENGTH: 291
<212> TYPE: DNA
<213> ORGANISM: Human immunodeficiency virus type 1
<220> FEATURE:
<223> OTHER INFORMATION: isolate=92RW009; gene=vpr

<400> SEQUENCE: 40

-continued

```
atggaacaag ccccagaaga ccaggggccg cagagggaac catacaatga atggacacta     60

gagcttttag aggcactcaa gcaggaagct gtcagacact ttcctagacc atggctccat    120

gacttaggac aatatatcta tgaaacctat ggggatactt ggaggggagt agaagctata    180

ataagaattc tgcaacaact actgtttatc catttcagaa ttgggtgccg gcatagcaga    240

ataggcattt tgcaacagag aagagcaaga aatggagcca gtagatccta a             291
```

<210> SEQ ID NO 41
<211> LENGTH: 2640
<212> TYPE: DNA
<213> ORGANISM: Human immunodeficiency virus type 1
<220> FEATURE:
<223> OTHER INFORMATION: isolate=92RW009; gene=tat

<400> SEQUENCE: 41

```
atggagccag tagatcctaa actagagccc tggaaccatc caggaagtca gcctaaaact     60

gcctgtaata actgttattg taaacactgt agctatcatt gtctagtttg cttccaggca    120

aaaggcttag gcatttccta tggcaggaag aagcggagac agcgacgaaa cgctcctcca    180

agcagtgaag atcatcaaaa tcctatatca aagcagtaag tagtaataaa cagtatatgt    240

aatgacttct ttagaaatct atgcaatagt agcactgata gtggcgctaa tcatagtgat    300

agttgtgtgg actttagcag gtatagaata taagaaattg ctaaagcaaa ggaaaataga    360

taggttaatt aagaaaataa gagaaagagc agaagatagt ggcaatgaga gtgatgggga    420

cattgatgaa ttatcaaaac ttgtggggt ggggaactat gatcttgggg atgttaacaa     480

tttgtagtgc tgcaaacaac ttgtgggtta ctgtctacta tggggtacct gtgtggaaag    540

acgcagagac caccttattt tgtgcatcag atgctaaagc atatgatcca gaaaagcata    600

atgtctgggc tacacatgcc tgtgtaccca tagaccccga cccacaagaa atacatttgg    660

aaaatgtgac agaagagttt aacatgtgga aaaataacat ggtagagcag atgcatacag    720

atataatcag tctatgggac caaagcctaa agccatgtgt aaagttaacc cctctctgcg    780

ttactttaga gtgtaacaac atcaccaatg tcaacaacac tgtcaacatt acggatgaca    840

tgaaaggaga aataaaaaac tgctctttca atatgaccac agaattaagg gataagaaac    900

agagagtgta ttcacttttt tataggcttg atatagtaca aattaatagc aatagtaata    960

acagtagtca taatcagtat aggttaataa attgtaatac ctcagccatt acacaggctt   1020

gtccaaaggt atcctttgag ccaattccca taaattattg tgccccagct ggtttcgcga   1080

ttctaaagtg taaagataaa aagttcaatg gaacagggcc atgcaagaat gtcagcacag   1140

tacaatgcac acatggaatc aagccagtag tatcaactca gctgctgtta aatggcagtc   1200

tagcagaaga agagataata attagatctg aaaatattac aaacaatgcc aaaaccataa   1260

tagtacaact taacgagact gtacaaatta attgttccag acctaacaac aatacaagaa   1320

aaagtgtaca tataggacca ggacaagcat tttatgcaac aggtgacgta ataggggata   1380

taagacaagc atattgtact gtcaatggaa caaaatggaa tagaacttta caaaaggtag   1440

cagaaaaatt aagtcactac tttgagaaca ttacaacaat aatttttaag aactcctcag   1500

ggggggattt agaaattaca acacatagtt ttaattgtgg aggagaattt ttctattgta   1560

atacatcagg cttgtttaat agcacctgga gtaaaagaaa tggcacctgg cagtcaaatg   1620

gcacagaatt aaatataaca ctcccatgca gaataaagca aattataaat atgtggcaga   1680

ggacaggaca agcaatgtat gcccctccca tccaaggagt aataagctgt gtatcaaaca   1740
```

-continued

```
ttacaggact actattaaca agagatggtg gaaataataa tactacaact gaaaccttca   1800

gacctggagg aggagatatg agggataatt ggagaagtga actatataaa tataaagtag   1860

taaaaattga accactagga gtagcaccca ccagggcaaa gaggagagtg gtggagagag   1920

aaaaaagagc agttggactg ggagctgtct tcattgggtt cttaggagca gcaggaagca   1980

ctatgggcgc ggcgtcaata acgctgacgg tacaggccag acaattattg tctggcatag   2040

tgcaacagca aagcaatttg ctgagggcta tagaggctca acagcatcta ttaaaactca   2100

cagtctgggg cattaaacag ctccaggcaa gagtcctggc tctggaaaga tacctaaggg   2160

atcaacagct cctaggaatt tggggctgct ctggaaaact catctgcacc actaatgtgc   2220

cctggaactc tagttggagt aataagactc agcaggaaat atgggataac atgacctggc   2280

agcaatggga taaagaaatt ggcaattaca cacaaataat atatagtcta attgaagaat   2340

cgcagaacca gcaggaaaag aatgaacaag acttattggc attggacaag tgggcaaatc   2400

tgtggaattg gtttgacata tcaaattggc tgtggtatat aaaaatattc ataatgatag   2460

taggaggctt aataggttta agaataattt ttgctgtgct ctctatagtg aacagagtta   2520

ggcagggata ctcaccatta tcgtttcaga cccttatccc aaacccgagg ggacccgaca   2580

ggctcggagg aatcgaagaa gaaggtggag agcaagacag aggcagatcc attcgattag   2640
```

<210> SEQ ID NO 42
<211> LENGTH: 2658
<212> TYPE: DNA
<213> ORGANISM: Human immunodeficiency virus type 1
<220> FEATURE:
<223> OTHER INFORMATION: isolate=92RW009; gene=rev

<400> SEQUENCE: 42

```
atggcaggaa gaagcggaga cagcgacgaa acgctcctcc aagcagtgaa gatcatcaaa     60

atcctatatc aaagcagtaa gtagtaataa acagtatatg taatgacttc tttagaaatc    120

tatgcaatag tagcactgat agtggcgcta atcatagtga tagttgtgtg gactttagca    180

ggtatagaat ataagaaatt gctaaagcaa aggaaaatag ataggttaat taagaaaata    240

agagaaagag cagaagatag tggcaatgag agtgatgggg acattgatga attatcaaaa    300

cttgtggggg tggggaacta tgatcttggg gatgttaaca atttgtagtg ctgcaaacaa    360

cttgtgggtt actgtctact atggggtacc tgtgtggaaa gacgcagaga ccaccttatt    420

ttgtgcatca gatgctaaag catatgatcc agaaaagcat aatgtctggg ctacacatgc    480

ctgtgtaccc atagaccccg acccacaaga aatacatttg gaaaatgtga cagaagagtt    540

taacatgtgg aaaaataaca tggtagagca gatgcataca gatataatca gtctatggga    600

ccaaagccta aagccatgtg taaagttaac ccctctctgc gttactttag agtgtaacaa    660

catcaccaat gtcaacaaca ctgtcaacat tacggatgac atgaaaggag aaataaaaaa    720

ctgctctttc aatatgacca cagaattaag ggataagaaa cagagagtgt attcactttt    780

ttataggctt gatatagtac aaattaatag caatagtaat aacagtagtc ataatcagta    840

taggttaata aattgtaata cctcagccat tacacaggct tgtccaaagg tatcctttga    900

gccaattccc ataaattatt gtgccccagc tggtttcgcg attctaaagt gtaaagataa    960

aaagttcaat ggaacagggc catgcaagaa tgtcagcaca gtacaatgca cacatggaat   1020

caagccagta gtatcaactc agctgctgtt aaatggcagt ctagcagaag aagagataat   1080

aattagatct gaaaatatta caaacaatgc caaaaccata atagtacaac ttaacgagac   1140

tgtacaaatt aattgttcca gacctaacaa caatacaaga aaaagtgtac atataggacc   1200
```

-continued

```
aggacaagca ttttatgcaa caggtgacgt aataggggat ataagacaag catattgtac   1260
tgtcaatgga acaaaatgga atagaacttt acaaaaggta gcagaaaaat taagtcacta   1320
ctttgagaac attacaacaa taatttttaa gaactcctca ggggggatt tagaaattac   1380
aacacatagt tttaattgtg gaggagaatt tttctattgt aatacatcag gcttgtttaa   1440
tagcacctgg agtaaaagaa atggcacctg gcagtcaaat ggcacagaat taaatataac   1500
actcccatgc agaataaagc aaattataaa tatgtggcag aggacaggac aagcaatgta   1560
tgcccctccc atccaaggag taataagctg tgtatcaaac attacaggac tactattaac   1620
aagagatggt ggaaataata atactacaac tgaaaccttc agacctggag gaggagatat   1680
gagggataat tggagaagtg aactatataa atataaagta gtaaaaattg aaccactagg   1740
agtagcaccc accagggcaa agaggagagt ggtggagaga gaaaaaagag cagttggact   1800
gggagctgtc ttcattgggt tcttaggagc agcaggaagc actatgggcg cggcgtcaat   1860
aacgctgacg gtacaggcca gacaattatt gtctggcata gtgcaacagc aaagcaattt   1920
gctgagggct atagaggctc aacagcatct attaaaactc acagtctggg gcattaaaca   1980
gctccaggca agagtcctgg ctctggaaag atacctaagg gatcaacagc tcctaggaat   2040
ttggggctgc tctggaaaac tcatctgcac cactaatgtg ccctggaact ctagttggag   2100
taataagact cagcaggaaa tatgggataa catgacctgg cagcaatggg ataaagaaat   2160
tggcaattac acacaaataa tatatagtct aattgaagaa tcgcagaacc agcaggaaaa   2220
gaatgaacaa gacttattgg cattggacaa gtgggcaaat ctgtggaatt ggtttgacat   2280
atcaaattgg ctgtggtata taaaaatatt cataatgata gtaggaggct taataggttt   2340
aagaataatt tttgctgtgc tctctatagt gaacagagtt aggcagggat actcaccatt   2400
atcgtttcag acccttatcc caaacccgag gggacccgac aggctcggag gaatcgaaga   2460
agaaggtgga gagcaagaca gaggcagatc cattcgatta gtgagcggat tcttagcact   2520
tgcctgggac gacctacgga gcctgtgcct tttcagctac caccgattga gagacttact   2580
attgattgca gcgaggacgg tggaacttct gggacgcagc agtctcaggg gactacagag   2640
ggggtgggaa acccttaa                                                 2658
```

<210> SEQ ID NO 43
<211> LENGTH: 246
<212> TYPE: DNA
<213> ORGANISM: Human immunodeficiency virus type 1
<220> FEATURE:
<223> OTHER INFORMATION: isolate=92RW009; gene=vpu

<400> SEQUENCE: 43

```
atgacttctt tagaaatcta tgcaatagta gcactgatag tggcgctaat catagtgata     60
gttgtgtgga ctttagcagg tatagaatat aagaaattgc taaagcaaag gaaaatagat    120
aggttaatta agaaaataag agaaagagca gaagatagtg gcaatgagag tgatggggac    180
attgatgaat tatcaaaact tgtgggggtg gggaactatg atcttgggga tgttaacaat    240
ttgtag                                                               246
```

<210> SEQ ID NO 44
<211> LENGTH: 2583
<212> TYPE: DNA
<213> ORGANISM: Human immunodeficiency virus type 1
<220> FEATURE:
<223> OTHER INFORMATION: isolate=92RW009; gene=env -continued

<400> SEQUENCE: 44
atgagagtga tggggacatt gatgaattat caaaacttgt gggggtgggg aactatgatc 60
ttggggatgt taacaatttg tagtgctgca aacaacttgt gggttactgt ctactatggg 120
gtacctgtgt ggaaagacgc agagaccacc ttattttgtg catcagatgc taaagcatat 180
gatccagaaa agcataatgt ctgggctaca catgcctgtg tacccataga ccccgaccca 240
caagaaatac atttggaaaa tgtgacagaa gagtttaaca tgtggaaaaa taacatggta 300
gagcagatgc atacagatat aatcagtcta tgggaccaaa gcctaaagcc atgtgtaaag 360
ttaacccctc tctgcgttac tttagagtgt aacaacatca ccaatgtcaa caacactgtc 420
aacattacgg atgacatgaa aggagaaata aaaaactgct ctttcaatat gaccacagaa 480
ttaagggata agaaacagag agtgtattca ctttttata ggcttgatat agtacaaatt 540
aatagcaata gtaataacag tagtcataat cagtataggt taataaattg taatacctca 600
gccattacac aggcttgtcc aaaggtatcc tttgagccaa ttcccataaa ttattgtgcc 660
ccagctggtt tcgcgattct aaagtgtaaa gataaaaagt tcaatggaac agggccatgc 720
aagaatgtca gcacagtaca atgcacacat ggaatcaagc cagtagtatc aactcagctg 780
ctgttaaatg gcagtctagc agaagaagag ataataatta gatctgaaaa tattacaaac 840
aatgccaaaa ccataatagt acaacttaac gagactgtac aaattaattg ttccagacct 900
aacaacaata caagaaaaag tgtacatata ggaccaggac aagcatttta tgcaacaggt 960
gacgtaatag gggatataag acaagcatat tgtactgtca atggaacaaa atggaataga 1020
actttacaaa aggtagcaga aaaattaagt cactactttg agaacattac aacaataatt 1080
tttaagaact cctcaggggg ggatttagaa attacaacac atagttttaa ttgtggagga 1140
gaatttttct attgtaatac atcaggcttg tttaatagca cctggagtaa aagaaatggc 1200
acctggcagt caaatggcac agaattaaat ataacactcc catgcagaat aaagcaaatt 1260
ataaatatgt ggcagaggac aggacaagca atgtatgccc ctcccatcca aggagtaata 1320
agctgtgtat caaacattac aggactacta ttaacaagag atggtggaaa taataatact 1380
acaactgaaa ccttcagacc tggaggagga gatatgaggg ataattggag aagtgaacta 1440
tataaatata aagtagtaaa aattgaacca ctaggagtag cacccaccag ggcaaagagg 1500
agagtggtgg agagagaaaa aagagcagtt ggactgggag ctgtcttcat tgggttctta 1560
ggagcagcag gaagcactat gggcgcggcg tcaataacgc tgacggtaca ggccagacaa 1620
ttattgtctg gcatagtgca acagcaaagc aatttgctga gggctataga ggctcaacag 1680
catctattaa aactcacagt ctggggcatt aaacagctcc aggcaagagt cctggctctg 1740
gaaagatacc taagggatca acagctccta ggaatttggg gctgctctgg aaaactcatc 1800
tgcaccacta atgtgccctg gaactctagt tggagtaata agactcagca ggaaatatgg 1860
gataacatga cctggcagca atgggataaa gaaattggca attacacaca aataatatat 1920
agtctaattg aagaatcgca gaaccagcag gaaaagaatg aacaagactt attggcattg 1980
gacaagtggg caaatctgtg gaattggttt gacatatcaa attggctgtg gtatataaaa 2040
atattcataa tgatagtagg aggcttaata ggtttaagaa taatttttgc tgtgctctct 2100
atagtgaaca gagttaggca gggatactca ccattatcgt ttcagaccct tatcccaaac 2160
ccgaggggac ccgacaggct cggaggaatc gaagaagaag gtggagagca agacagaggc 2220
agatccattc gattagtgag cggattctta gcacttgcct gggacgacct acggagcctg 2280
tgccttttca gctaccaccg attgagagac ttactattga ttgcagcgag gacggtggaa 2340

-continued

```
cttctgggac gcagcagtct caggggacta cagagggggt gggaaaccct taagtatcta   2400

ggaaatcttg tgcagtattg gggtctggaa ctaaaaagga gtgctattaa tctgcttgat   2460

accacagcaa tagtagtagc tgaaggaaca gataggatta tagaattaat acaaagaatt   2520

agcagagcta tctataacat acctagcaga ataagacagg gctttgaagc agctttgcaa   2580

taa                                                                 2583
```

<210> SEQ ID NO 45
<211> LENGTH: 624
<212> TYPE: DNA
<213> ORGANISM: Human immunodeficiency virus type 1
<220> FEATURE:
<223> OTHER INFORMATION: isolate=92RW009; gene=nef

<400> SEQUENCE: 45

```
atgggaagca agtggtcaaa atgtagtcca gtaggatggc ctgctgtaag agaaagacta     60

aggcaaactg agccagcagc agagggagta ggagcagcgt ctcaagacct agacaaatat    120

ggggcactta caagtagcaa cacacccagc aacaatgctg attgtgcctg gctggcagca    180

caagaggagg aaaacgaagt aggctttcca gtcagacctc aggtgccttt aagaccaatg    240

acttataaag cagcagttga tctcagcttc tttttaaaag aaaagggggg actggaaggg    300

ttaatttact ctaagaaaag gcaagacatc ctggatttgt gggtctataa cacacaaggc    360

tacttccctg attggcaaaa ctacacacca ggaccagggg tcagatatcc actgactttt    420

ggatggtgtt acaagctagt gccagttgac ccaagggaag tggaagaagc caatgaagga    480

gaggacaact gcttactaca ccctctgagc cagcatggaa tggaggatga ggacagagaa    540

gtcttaaagt ggaagtttga cagtcaccta gcacacagac acatggcccg cgagctacat    600

ccggagtatt ataaagactg ctga                                           624
```

<210> SEQ ID NO 46
<211> LENGTH: 8
<212> TYPE: DNA
<213> ORGANISM: Human immunodeficiency virus type 1
<220> FEATURE:
<223> OTHER INFORMATION: isolate=92RW009; standard name=3' LTR repeat
region; note=3' R repeat should end one base
beyond end of this

<400> SEQUENCE: 46

```
aaaaaaaa                                                               8
```

<210> SEQ ID NO 47
<211> LENGTH: 1494
<212> TYPE: DNA
<213> ORGANISM: Human immunodeficiency virus type 1
<220> FEATURE:
<223> OTHER INFORMATION: isolate=92NG003; gene=gag

<400> SEQUENCE: 47

```
atgggtgcga gagcgtcagt attaagcggg ggaaaattag atgcatggga aaaaattcgg     60

ttgaggccag gggggaaagaa aaaatataga atgaaacatt tagtatgggc aagcagggaa    120

ctggagagat ttgcacttaa ccctgacctc ttagaaacaa cagaaggttg tcagcaaata    180

atgagacagc tgcaaccatc tctccagaca ggaacagagg agattaaatc attatttaat    240

acagtagcaa ccctctattg tgtacatcaa aggatagagg taaaagacac caaagaagct    300

ctagaggaag tggaaaaaat acaaaagaac agtcagcaag aaacacagaa ggcagcaatg    360
```

-continued

```
ggtaaaggaa acagcagcca agttagccaa aattatccta tagtgcagaa tgcacaaggg    420

caagtggtac accagcccat atcacctagg actttaaatg catgggtaaa agtaatagaa    480

gaaaagaact tcagtccaga agtaataccc atgtttacag cattatcaga aggagccacc    540

ccacaagatt tgaataccat gctaaacacc gtgggggggc atcaagcagc tatgcaaatg    600

ctaaaagatt ctattaatga agaagctgca gagtgggata ggctacatcc acaacaggca    660

ggacctattc caccaggcca gataagagaa ccaaggggaa gtgatatagc aggaactact    720

agtaccctgc aggaacaaat aacatggatg accagcaacc cacctatccc agtgggagaa    780

atttataaaa gatggataat tctggggtta aataaaatag tgagaatgta tagccctgtc    840

agtattttag acataaaaca agggccaaaa gaacccttca gagattatgt ggataggttc    900

tttaaaactt tgagagctga gcaagccaca caggaggtaa aaaactggat gacagacacc    960

ttgttggtcc aaaatgcgaa cccagattgt aagaccatcc taagagcatt aggagcagga   1020

gctacactag aagaaatgtt gacagcatgt caaggagtgg gaggacccag ccacaaagca   1080

agagttttag ctgaggcaat gagccgggca acaggtacat cagcagccat aatgatgcag   1140

aaaaacaatt ttaagggccc gagaagaggt attaagtgtt tcaactgtgg caaggaagga   1200

catctagcca gaaattgcag ggcccctagg aaaaaaggct gttggaaatg tggaaaggag   1260

ggacatcaaa tgaaagactg cacagagaga caggctaatt ttttagggaa aatttggcct   1320

tccaacaagg ggaggccagg gaattttctt cagaacaggc cagagccaac agccccaccc   1380

gcagagagct tcgggttcgg agaggagata gccccttccc tgaagcagga gccgagggaa   1440

aaggaatcac ctccattaac ctccctcaaa tcactctttg gcaacgaccc ctag         1494
```

<210> SEQ ID NO 48
<211> LENGTH: 4307
<212> TYPE: DNA
<213> ORGANISM: Human immunodeficiency virus type 1
<220> FEATURE:
<223> OTHER INFORMATION: isolate=92NG003; gene=gag-pol fusion

<400> SEQUENCE: 48

```
atgggtgcga gagcgtcagt attaagcggg ggaaaattag atgcatggga aaaaattcgg     60

ttgaggccag gggaaagaa aaaatataga atgaaacatt tagtatgggc aagcagggaa    120

ctggagagat ttgcacttaa ccctgacctc ttagaaacaa cagaaggttg tcagcaaata    180

atgagacagc tgcaaccatc tctccagaca ggaacagagg agattaaatc attatttaat    240

acagtagcaa ccctctattg tgtacatcaa aggatagagg taaaagacac caaagaagct    300

ctagaggaag tggaaaaaat acaaaagaac agtcagcaag aaacacagaa ggcagcaatg    360

ggtaaaggaa acagcagcca agttagccaa aattatccta tagtgcagaa tgcacaaggg    420

caagtggtac accagcccat atcacctagg actttaaatg catgggtaaa agtaatagaa    480

gaaaagaact tcagtccaga agtaataccc atgtttacag cattatcaga aggagccacc    540

ccacaagatt tgaataccat gctaaacacc gtgggggggc atcaagcagc tatgcaaatg    600

ctaaaagatt ctattaatga agaagctgca gagtgggata ggctacatcc acaacaggca    660

ggacctattc caccaggcca gataagagaa ccaaggggaa gtgatatagc aggaactact    720

agtaccctgc aggaacaaat aacatggatg accagcaacc cacctatccc agtgggagaa    780

atttataaaa gatggataat tctggggtta aataaaatag tgagaatgta tagccctgtc    840

agtattttag acataaaaca agggccaaaa gaacccttca gagattatgt ggataggttc    900

tttaaaactt tgagagctga gcaagccaca caggaggtaa aaaactggat gacagacacc    960
```

-continued

```
ttgttggtcc aaaatgcgaa cccagattgt aagaccatcc taagagcatt aggagcagga   1020
gctacactag aagaaatgtt gacagcatgt caaggagtgg gaggacccag ccacaaagca   1080
agagttttag ctgaggcaat gagccgggca acaggtacat cagcagccat aatgatgcag   1140
aaaaacaatt ttaagggccc gagaagaggt attaagtgtt tcaactgtgg caaggaagga   1200
catctagcca gaaattgcag ggcccctagg aaaaaaggct gttggaaatg tggaaaggag   1260
ggacatcaaa tgaaagactg cacagagaga caggctaatt ttttagggaa aatttggcct   1320
tccaacaagg ggaggccagg gaattttctt cagaacaggc cagagccaac agccccaccc   1380
gcagagagct tcgggttcgg agaggagata gccccttccc tgaagcagga gccgagggaa   1440
aaggaatcac ctccattaac ctccctcaaa tcactctttg gcaacgaccc ctagtcacag   1500
taagaatagg gggacagcta atagaagctc tattagacac aggagcagat gatacagtat   1560
tagaacaaat aaatttacca ggaaaatgga aaccaaaaat gataggggga attggaggat   1620
ttatcaaagt aaaacagtat gatcaaatac ttatagaaat tgaagggaaa aaggctatag   1680
ggacagtact agtaggacct acacctatca acataattgg gagaaatatg ttgactcaaa   1740
ttggttgtac tttaaatttt ccaattagtc ctattgagac tgtaccagta aaattaaaac   1800
caggaataga tggcccaaag gttaaacaat ggccattgac agaagagaaa ataaaagcat   1860
taacagaaat ttgtacagat atggaaaagg aaggaaaaat ttcaaaaatt gggccagaaa   1920
atccatacaa cactccaata tttgccataa agaaaaaaga cagtactaaa tggagaaagt   1980
tggtagattt cagagagctc aataaaagaa ctcaagactt ctgggaggtc caattaggca   2040
tacctcatcc cgcggggtta aaaaagaaaa gatcagtaac agtactagat gtgggggatg   2100
catatttttc aattccccta gatgaaaact ttagaaagta tacagcattc actataccta   2160
gtataaataa tgagacacca gggattagat atcagtacaa tgtgcttccg caaggatgga   2220
aaggatcacc agcaatattt cagagtagca tgacaaaaat cttagaaccc tttagaacag   2280
aaaatccaga aatagtgatc tatcagtaca tggatgattt atatgtagga tctgacttag   2340
aaacagggca gcatagagca aaaatagagg aattaagaaa tcatctactg agatggggat   2400
ttaccacacc agataaaaaa catcagaaag aacctccatt tctctggatg ggatatgagc   2460
tccatcctga caaatggacg gtacaaccta tacagctgcc aaacaaagaa agctggactg   2520
tcaatgatat acaaaaatta gtgggaaaac taaattgggc aagtcagatt tatccaggga   2580
ttaaagtaaa gcaactatgt aaactcctta ggggggccaa agcactaaca gacatagtac   2640
cactgactga agaagcagaa ttagaattgg cagagaacag ggaaattcta aaagaacctg   2700
tacatggagt ctactatgac ccatcaaaag aattaatagc agaattacag aaacaagggt   2760
gcgaccaatg gacatatcaa atttatcaag agccatacaa aaatctgaaa acaggaaagt   2820
atgcaaaaag ggggtctgcc cacactaatg atgtaaaaca gttaacagaa gcagtgcaaa   2880
aaatagccac agagagcata gtaatatggg gaaaagttcc taaatttaaa ctacctataa   2940
ggaaagaaac atgggaagta tggtggacag aatattggca ggccacctgg attcctgatt   3000
gggagtttgt caatacccct cctctagtaa agttatggta tcgattagaa acagaaccca   3060
taccaggagc agaaacttac tatgtagatg gggcagctaa taaagaaaca aaattaggaa   3120
aggcaggata tgttactgac agaggaaaac aaaaaattat caccatacag gaaacaacaa   3180
atcaaaaaac tgaattacac gcaattcagc tagctttgca ggattcagga tcagaagtaa   3240
acatagtaac agactcacag tatgcattag gaatcattca agcacaacca gataggagtg   3300
```

-continued

```
aatcagaatt agtcaatcaa ataatagaac agctaataaa aaaggaaaag gtctacttaa   3360

catgggtacc agcacacaaa ggaattgggg gaaatgaaca agtagataaa ttagtcagta   3420

gtggaatcag aaaagtactg tttttagatg gcatagacaa agctcaagag gaccatgaaa   3480

gatatcacag caattggaga gcaatggcta gtgattttaa tctgccacct atagtagcaa   3540

aagaaatagt ggccagctgt gataaatgtc agctaaaagg ggaagccatg catggacaag   3600

tagactgtag tccaggaata tggcaattag attgcacaca tctagaagga aaagtcatta   3660

tagtagcagt ccatgtagcc agtggctata tagaagcaga agttatccca gcagaaacag   3720

gacaggagac agcatacttc ctgctaaaat tagcaggaag atggccagta aaagtaatac   3780

acacagacaa tggcagcaat ttcaccagtg ctgcaatgaa agcagcctgt tggtgggcaa   3840

atatccaaca ggaatttgga attccctaca atccccaaag ccaaggagta gtggaatcta   3900

tgaataaaga attaaagaaa attatagggc aggtcaggga tcaagctgaa cacctcaaga   3960

cagcagtaca gatggcagta ttcattcaca attttaaaag aaaagggggg attgggggt   4020

acagtgcagg ggaaagaata atagacataa tagcatcaga tatacaaact aaagaactac   4080

aaaaacagat tataaaaatt caaaatttc gggtctatta cagggacagc agagacccca   4140

tttggaaagg accagcaaaa ctactctgga aaggtgaagg ggcagtagta atacaggaca   4200

atagtgagat aaaggtagta ccaagaagaa aagtaaaaat cattaaggat tatggaaaac   4260

agatggcagg tggtgattgt gtggcaggta gacaggatga ggattag                4307
```

<210> SEQ ID NO 49
<211> LENGTH: 579
<212> TYPE: DNA
<213> ORGANISM: Human immunodeficiency virus type 1
<220> FEATURE:
<223> OTHER INFORMATION: isolate=92NG003; gene=vif

<400> SEQUENCE: 49

```
atggaaaaca gatggcaggt ggtgattgtg tggcaggtag acaggatgag gattagaaca     60

tggaacagtt tagtaaaata tcatatgtat aaatctaaga aagctaagga ttggttttat    120

agacatcact atgaaagtag gcatccaaaa gtaagttcag aagtacacat cccactaggg    180

gaggctagat tagtagtaag aacatattgg ggtctgcata caggagaaag agactggcac    240

ttgggtcagg gggtctccat agaatggaag cagagaagat atagcacaca aatagatcct    300

gacctagcag accaactgat tcacctgcat tattttaact gtttttcaga atcggccgta    360

aggaaagcca tactaggaga agtagttaga cctaggtgtg aatatcaaac aggacataat    420

caggtaggat cactacaata tttagcactc aaagcattag taacaccaac acagacaaag    480

ccacctttac ctagtgttaa gaagttaaca gaagatagat ggaacgagcc ccagaagacc    540

aggggccaca gagggagcca ttcaacgaat ggacactag                           579
```

<210> SEQ ID NO 50
<211> LENGTH: 114
<212> TYPE: DNA
<213> ORGANISM: Human immunodeficiency virus type 1
<220> FEATURE:
<223> OTHER INFORMATION: isolate=92NG003; gene=vpr

<400> SEQUENCE: 50

```
atggaacgag ccccagaaga ccaggggcca cagagggagc cattcaacga atggacacta     60

gaactgttag aagaacttaa acatgaagct gttagacatg gcttcatgga ttag          114
```

-continued

<210> SEQ ID NO 51
<211> LENGTH: 2579
<212> TYPE: DNA
<213> ORGANISM: Human immunodeficiency virus type 1
<220> FEATURE:
<223> OTHER INFORMATION: isolate=92NG003; gene=tat

<400> SEQUENCE: 51
atggagctgg tagatcctag cctagagccc tggaaccacc caggaagtca gcctacaact 60
gcttgtaaca aatgttactg taaaatatgc tgctggcatt gccaattgtg ctttctgaac 120
aagggcttag gcatctccta tggcaggaag aagcggagac gccgacgagg aactcctcag 180
agtcaccagg atcatcaaaa tcctgtacca aagcagtgag tagtaatagt tagtatatgt 240
gatgcaatcc ttagaaatag ctgcaatagc aggactagta gtagcagcca tagcagccat 300
agttgtgtgg accatagaaa aataaagaaa caggagaaaa tagacaggtt acttgataga 360
ataagagaaa gagcagaaga tagtggcaat gagagtgaag gggacacaga ggaattggca 420
acacttgtgg acatggtgga ctttgatcct tgggttggtg ataatttgta gtgcctcaaa 480
taacttgtgg gtcacagtct attatggggt accagtgtgg gaagacgcag atacccctct 540
attttgtgca tctgatgcta aagcatatag tactgaaaga cataatgtct gggccacaca 600
tgcctgtgta cccacagacc ccaacccaca agagataact ctggaaaatg taacagaaac 660
ttttaacatg tggaaaaata acatggtaga acagatgcat gaggatataa tcagtttatg 720
ggatgaaagc ctaaagccat gtgtaaagct aacccctctc tgtgttacct taaactgtac 780
taatgtcaat tgtaacagta atgtgaccag cactgggaac agtgctggga ccaacgctac 840
gtgtaacata gaagaagcaa acaacttaaa aaactgctct ttcaatataa ccacagaaat 900
aagagataag aaaaagacag aatatgcgct tttctataga cttgatgtgg taccaatcga 960
tggtaataat aatgtctcaa ataactatag gctaataaat tgtaatgtct caaccattaa 1020
acaagcttgt ccaaaggtgt cttttgaccc acttcccata cattattgtg ctccagctgg 1080
gtttgcgatt ttaaagtgta ggggtaagaa tttcactgga acaggacaat gtaaaaatgt 1140
cagttcagta caatgtacac atggaattaa accagtggta tcaactcaat tactactaaa 1200
tggtagtcta gcagaaggag aaatagtaat tagatctgaa aacctcacag acaatgccaa 1260
agtcataata gtacagctta ataaaactat aggaattaat tgtaccagac ccaacaacaa 1320
tacaagaaaa agtataagaa tcggacctgg acaagcgttc tatgcaacag gtgaaataat 1380
aggacaagaa tggcaggaga tgttacagaa ggtacaggca caactagaac aggtctttaa 1440
caaaagtata acctttaact catccgcagg aggggaccta gaaattacaa cacatagttt 1500
taattgtaga ggagaatttt tctattgtaa tacatcagga ttgtttaatg aatcaggagg 1560
gaatgatacc actatcacac tcccatgtaa gataaaacaa attgtgagaa tgtggcagag 1620
agtgggacaa gcaatgtatg cccctcccat cgcaggagat attacatgta gatcaaacat 1680
tacagggcta ttattaacaa gagatggtgg ggttaataat actggaaatg agaccttcag 1740
acctggagga ggagatatga gggacaattg gagaagtgaa ttatataagt ataaaatagt 1800
aaaaattaaa ccactaggaa tagcacccac caaggcaagg agaagagtgg tggagagagg 1860
aaaaagggca gttggactgg gagctgtctt ccttgggttc ttaggagcag caggaagcac 1920
tatgggcgcg gggtcaataa cgctgacggt acaggtcaga caattattgt ctggcatagt 1980
gcaacagcaa agcaatttgc tgagggctat agaggcgcag caacatctat tgcaactcac 2040
agtctggggc attaaacagc tccaggcaag agtcctggct gtagaaagat acctaaagga 2100

-continued tcaacagctc ctagggattt ggggctgctc tggaaaactc atctgcacca ctaatgtgcc 2160
ttggaacact agttggagta ataaatctta tgaggagatt tgggataaca tgacctggat 2220
acaatgggaa agggaagtca gcaattacac acaacaaata tacagcctaa ttgaagaatc 2280
gcagaaccag caggaaaaga atgaacaaga cttattggca ttggacaagt gggcaagttt 2340
gtggaactgg tttgacataa caaaatggct atggtatata aaaatattta taatgatagt 2400
aggaggttta ataggtttaa gaatagtttt tgctgtgctt tctatagtaa atagagttag 2460
gcagggatac tcacctttgt cattccagac ccttacccac caccagaggg aacccgacag 2520
gcccgaaaga atcgaagaag gaggtggaga gcaagacaga gacagatcag tgcgcttag 2579

<210> SEQ ID NO 52
<211> LENGTH: 2645
<212> TYPE: DNA
<213> ORGANISM: Human immunodeficiency virus type 1
<220> FEATURE:
<223> OTHER INFORMATION: isolate=92NG003; gene=rev

<400> SEQUENCE: 52
atggcaggaa gaagcggaga cgccgacgag gaactcctca gagtcaccag gatcatcaaa 60
atcctgtacc aaagcagtga gtagtaatag ttagtatatg tgatgcaatc cttagaaata 120
gctgcaatag caggactagt agtagcagcc atagcagcca tagttgtgtg gaccatagaa 180
aaataaagaa acaggagaaa atagacaggt tacttgatag aataagagaa agagcagaag 240
atagtggcaa tgagagtgaa ggggacacag aggaattggc aacacttgtg gacatggtgg 300
actttgatcc ttgggttggt gataatttgt agtgcctcaa ataacttgtg ggtcacagtc 360
tattatgggg taccagtgtg ggaagacgca gataccccctc tattttgtgc atctgatgct 420
aaagcatata gtactgaaag acataatgtc tgggccacac atgcctgtgt acccacagac 480
cccaacccac aagagataac tctggaaaat gtaacagaaa cttttaacat gtggaaaaat 540
aacatggtag aacagatgca tgaggatata atcagtttat gggatgaaag cctaaagcca 600
tgtgtaaagc taacccctct ctgtgttacc ttaaactgta ctaatgtcaa ttgtaacagt 660
aatgtgacca gcactgggaa cagtgctggg accaacgcta cgtgtaacat agaagaagca 720
aacaacttaa aaaactgctc tttcaatata accacagaaa taagagataa gaaaaagaca 780
gaatatgcgc ttttctatag acttgatgtg gtaccaatcg atggtaataa taatgtctca 840
aataactata ggctaataaa ttgtaatgtc tcaaccatta aacaagcttg tccaaaggtg 900
tcttttgacc cacttcccat acattattgt gctccagctg ggtttgcgat tttaaagtgt 960
aggggtaaga atttcactgg aacaggacaa tgtaaaaatg tcagttcagt acaatgtaca 1020
catggaatta aaccagtggt atcaactcaa ttactactaa atggtagtct agcagaagga 1080
gaaatagtaa ttagatctga aaacctcaca gacaatgcca aagtcataat agtacagctt 1140
aataaaacta taggaattaa ttgtaccaga cccaacaaca atacaagaaa aagtataaga 1200
atcggacctg gacaagcgtt ctatgcaaca ggtgaaataa taggacaaga atggcaggag 1260
atgttacaga aggtacaggc acaactagaa caggtcttta acaaaagtat aacctttaac 1320
tcatccgcag gaggggacct agaaattaca acacatagtt ttaattgtag aggagaattt 1380
ttctattgta atacatcagg attgtttaat gaatcaggag ggaatgatac cactatcaca 1440
ctcccatgta agataaaaca aattgtgaga atgtggcaga gagtgggaca agcaatgtat 1500
gcccctccca tcgcaggaga tattacatgt agatcaaaca ttacagggct attattaaca 1560
agagatggtg gggttaataa tactggaaat gagaccttca gacctggagg aggagatatg 1620

-continued

```
agggacaatt ggagaagtga attatataag tataaaatag taaaaattaa accactagga   1680

atagcaccca ccaaggcaag gagaagagtg gtggagagag gaaaaagggc agttggactg   1740

ggagctgtct tccttgggtt cttaggagca gcaggaagca ctatgggcgc ggggtcaata   1800

acgctgacgg tacaggtcag acaattattg tctggcatag tgcaacagca aagcaatttg   1860

ctgagggcta tagaggcgca gcaacatcta ttgcaactca cagtctgggg cattaaacag   1920

ctccaggcaa gagtcctggc tgtagaaaga tacctaaagg atcaacagct cctagggatt   1980

tggggctgct ctggaaaact catctgcacc actaatgtgc cttggaacac tagttggagt   2040

aataaatctt atgaggagat ttgggataac atgacctgga tacaatggga aagggaagtc   2100

agcaattaca cacaacaaat atacagccta attgaagaat cgcagaacca gcaggaaaag   2160

aatgaacaag acttattggc attggacaag tgggcaagtt tgtggaactg gtttgacata   2220

acaaaatggc tatggtatat aaaaatattt ataatgatag taggaggttt aataggttta   2280

agaatagttt ttgctgtgct ttctatagta aatagagtta ggcagggata ctcacctttg   2340

tcattccaga cccttaccca ccaccagagg gaacccgaca ggcccgaaag aatcgaagaa   2400

ggaggtggag agcaagacag agacagatca gtgcgcttag tgagcggatt cttagcactt   2460

gcctgggacg acctgcggaa cctgtgcctc ttcagctacc accgattgag agacttagtc   2520

ttgattgcag cgaggacagc agaactcctg agacgcagca gtctccaggg actgagactg   2580

gggtgggagg gcctcaaata tctgtggaat ctcctgttgt attggggtcg ggaactaaag   2640

aatag                                                               2645
```

<210> SEQ ID NO 53
<211> LENGTH: 230
<212> TYPE: DNA
<213> ORGANISM: Human immunodeficiency virus type 1
<220> FEATURE:
<223> OTHER INFORMATION: isolate=92NG003; gene=vpu

<400> SEQUENCE: 53

```
atgcaatcct tagaaatagc tgcaatagca ggactagtag tagcagccat agcagccata     60

gttgtgtgga ccatagaaaa ataaagaaac aggagaaaat agacaggtta cttgatagaa    120

taagagaaag agcagaagat agtggcaatg agagtgaagg ggacacagag gaattggcaa    180

cacttgtgga catggtggac tttgatcctt gggttggtga taatttgtag               230
```

<210> SEQ ID NO 54
<211> LENGTH: 2538
<212> TYPE: DNA
<213> ORGANISM: Human immunodeficiency virus type 1
<220> FEATURE:
<223> OTHER INFORMATION: isolate=92NG003; gene=env

<400> SEQUENCE: 54

```
atgagagtga aggggacaca gaggaattgg caacacttgt ggacatggtg gactttgatc     60

cttgggttgg tgataatttg tagtgcctca aataacttgt gggtcacagt ctattatggg    120

gtaccagtgt gggaagacgc agatacccct ctattttgtg catctgatgc taaagcatat    180

agtactgaaa gacataatgt ctgggccaca catgcctgtg tacccacaga ccccaaccca    240

caagagataa ctctggaaaa tgtaacagaa acttttaaca tgtggaaaaa taacatggta    300

gaacagatgc atgaggatat aatcagttta tgggatgaaa gcctaaagcc atgtgtaaag    360

ctaacccctc tctgtgttac cttaaactgt actaatgtca attgtaacag taatgtgacc    420
```

-continued

```
agcactggga acagtgctgg gaccaacgct acgtgtaaca tagaagaagc aaacaactta    480
aaaaactgct ctttcaatat aaccacagaa ataagagata agaaaaagac agaatatgcg    540
cttttctata gacttgatgt ggtaccaatc gatggtaata ataatgtctc aaataactat    600
aggctaataa attgtaatgt ctcaaccatt aaacaagctt gtccaaaggt gtcttttgac    660
ccacttccca tacattattg tgctccagct gggtttgcga ttttaaagtg taggggtaag    720
aatttcactg gaacaggaca atgtaaaaat gtcagttcag tacaatgtac acatggaatt    780
aaaccagtgg tatcaactca attactacta aatggtagtc tagcagaagg agaaatagta    840
attagatctg aaaacctcac agacaatgcc aaagtcataa tagtacagct taataaaact    900
ataggaatta attgtaccag acccaacaac aatacaagaa aaagtataag aatcggacct    960
ggacaagcgt tctatgcaac aggtgaaata ataggacaag aatggcagga gatgttacag   1020
aaggtacagg cacaactaga acaggtcttt aacaaaagta taacctttaa ctcatccgca   1080
ggaggggacc tagaaattac aacacatagt tttaattgta gaggagaatt tttctattgt   1140
aatacatcag gattgtttaa tgaatcagga gggaatgata ccactatcac actcccatgt   1200
aagataaaac aaattgtgag aatgtggcag agagtgggac aagcaatgta tgcccctccc   1260
atcgcaggag atattacatg tagatcaaac attacagggc tattattaac aagagatggt   1320
ggggttaata atactggaaa tgagaccttc agacctggag gaggagatat gagggacaat   1380
tggagaagtg aattatataa gtataaaata gtaaaaatta aaccactagg aatagcaccc   1440
accaaggcaa ggagaagagt ggtggagaga ggaaaaaggg cagttggact gggagctgtc   1500
ttccttgggt tcttaggagc agcaggaagc actatgggcg cggggtcaat aacgctgacg   1560
gtacaggtca gacaattatt gtctggcata gtgcaacagc aaagcaattt gctgagggct   1620
atagaggcgc agcaacatct attgcaactc acagtctggg gcattaaaca gctccaggca   1680
agagtcctgg ctgtagaaag atacctaaag gatcaacagc tcctagggat ttggggctgc   1740
tctggaaaac tcatctgcac cactaatgtg ccttggaaca ctagttggag taataaatct   1800
tatgaggaga tttgggataa catgacctgg atacaatggg aaagggaagt cagcaattac   1860
acacaacaaa tatacagcct aattgaagaa tcgcagaacc agcaggaaaa gaatgaacaa   1920
gacttattgg cattggacaa gtgggcaagt ttgtggaact ggtttgacat aacaaaatgg   1980
ctatggtata taaaaatatt tataatgata gtaggaggtt taataggttt aagaatagtt   2040
tttgctgtgc tttctatagt aaatagagtt aggcagggat actcaccttt gtcattccag   2100
acccttaccc accaccagag ggaacccgac aggcccgaaa gaatcgaaga aggaggtgga   2160
gagcaagaca gagacagatc agtgcgctta gtgagcggat tcttagcact tgcctgggac   2220
gacctgcgga acctgtgcct cttcagctac caccgattga gagacttagt cttgattgca   2280
gcgaggacag cagaactcct gagacgcagc agtctccagg gactgagact ggggtgggag   2340
ggcctcaaat atctgtggaa tctcctgttg tattggggtc gggaactaaa gaatagtgct   2400
attaatttga ttgatacaat agcaatagca gtagctaact ggacagatag ggttatagaa   2460
gtagcacaag gagcttgtag agctattctc aacataccta gaaggataag acaaggcttg   2520
gaaagagctt tgctataa                                                 2538
```

<210> SEQ ID NO 55
<211> LENGTH: 621
<212> TYPE: DNA
<213> ORGANISM: Human immunodeficiency virus type 1
<220> FEATURE:
<223> OTHER INFORMATION: isolate=92NG003; gene=nef -continued

<400> SEQUENCE: 55
ataggaggca agtggtcaaa aagtagcata gttggatggc ccgcggtaag ggagagaata 60
agacaaaccc ctccagcaga aggagtagga gcagcacctc aagacttagc taggcatgga 120
gcaatcacaa gcagcaatac agcacaaact aatcctgatt gtgcctggct agaagcacaa 180
caggagaatt cagaggtagg ctttccagtc agacaacagg tacctttgag accaatgact 240
tataaggctg cctttgatct cagcttcttt ttaaaagaaa agggggggact ggatgggcta 300 atttactcta agaaaagaca agacatcctt gacctatggg tctataatac acaaggatac 360
ttcccagatt ggcagaacta cactccaggg ccagggacta gattcccact gacatttcgg 420
tggtgcttca aactagtacc aatggatcca gcagagatag aggaagccaa taaaggagag 480
aacaacagtt tattacaccc tatctgccaa catggcctgg aagatgcgga cagagaagtg 540
ctggtatgga gatttgacag tagcctagca cggagacaca tagcccgaga acaacatccg 600
gagtactata aggactgctg a 621

<210> SEQ ID NO 56
<211> LENGTH: 1438
<212> TYPE: DNA
<213> ORGANISM: Human immunodeficiency virus type 1
<220> FEATURE:
<223> OTHER INFORMATION: isolate=93BR029; gene=gag

<400> SEQUENCE: 56
atgggtgcga gagcgtcagt aataagcggg ggagaattag ataaatggga aaaaattagg 60
ttaaggccag gaggacataa aaaatataga ttaaaacata tagtatgggc aagcagggga 120
gctagaacga ttcgcagtta atcctggcct tttagagaca tcagaaggct gtagacaaat 180
actggaacag ctacaaccag cccttaagac gggatcagaa gaacttagat cattatataa 240
tacagtagca accctctatt gtgtacatca aaagatagat gtaaaagaca ccaaggaagc 300
tttagaaaag atagaggaag agcaaaacaa agtaagaaaa aggcacagca agcagcagct 360
aacacaggaa acaacagcca ggtcagccaa aattacccta tagtgcagaa ccttcagggg 420
caaatggtac accaggccat atcacctaga actttaaatg catgggtaaa agtagtagaa 480
gagaaggctt ttagcccaga agtaataccc atgttttcag cattatcaga aggagccacc 540
ccacaagatt taaacaccat gctaaacaca gtggggggac atcaagcagc tatgcaaatg 600
ttaaaagaaa ccatcaatga ggaagctgca gaatgggaca gagtacatcc agtgcatgca 660
ggacctatcc caccaggcca gatgagggaa cctaggggaa gtgatatagc tggaactact 720
agtacccttc aggaacaaat acaatggatg acaagcaacc cacctgtccc agtgggagaa 780
atttataaaa gatggatcat cctaggatta aataaaatag taagaatgta tagccctacc 840
agcattctgg gcataagaca aggaccaaag gaacccttta gagactatgt agatcgattt 900
tataaaactc taagagcaga gcaaacttca caggatgtaa aaaattggat gacagaaacc 960
ttgttggtcc aaaatgcgaa cccagattgc aaaaccattt taaaagcatt gggaccagca 1020
gctacactag aagaaatgat gacagcatgt cagggagtgg ggggacccgg ccataaagca 1080
agagttttgg cagaagcaat gagccaagta acaaattcag gtaccataat gatgcagaga 1140
ggcaatttta ggaaccaaag aaagactatt aagtgtttca attgtggcaa agaagggcac 1200
atagccaaaa attgcagggc ccctaggaaa aagggctgct ggaaatgtgg aaaggaagga 1260
caccagatga aagattgtac tgagagacag gctaattttt tagggaaaat ctggccttcc 1320

-continued

```
cacaagggaa ggccagggaa tttccttcag agcagaccag agccaacagc cccaccagca   1380

gagagcttca ggtttgggga agaggtaaca actccctctc agaaacagga gccgatag     1438


<210> SEQ ID NO 57
<211> LENGTH: 3012
<212> TYPE: DNA
<213> ORGANISM: Human immunodeficiency virus type 1
<220> FEATURE:
<223> OTHER INFORMATION: isolate=93BR029; gene=pol; note=NH2-terminus
      uncertain

<400> SEQUENCE: 57

tttttaggg aaaatctggc cttcccacaa gggaaggcca gggaatttcc ttcagagcag     60

accagagcca acagccccac cagcagagag cttcaggttt ggggaagagg taacaactcc    120

ctctcagaaa caggagccga tagacaagga gatgtatcct ttggcttccc tcagatcact    180

ctttggcaac gacccctcgt cacagtaaag ataggggggc aactaaagga agccctatta    240

gataccggag cagatgatac agtattagaa gaaataaatt taccaggaag atggaaacca    300

aaaatgatag ggggaattgg aggttttatc aaagtaagac agtatgatca aatacccata    360

gaaatttgtg gacgtaaagc tacaggtaca gtattagtag gacctacacc tgtcaacata    420

attggaagaa atctgttgac tcagattggc tgcactttaa attttcccat tagtcctatt    480

gaaactgtac cagtaaaatt gaagccagga atggatggcc caagggttaa acaatggcca    540

ttgacagaag aaaaaataaa agcattaaca gaaatatgta cagaaatgga aaaagaagga    600

aaaatttcaa aaattgggcc cgaaaatcca tacaatactc cagtatttgc cataaagaaa    660

aaagatagta ctaaatggag aaaattagta gatttcagag aacttaataa gagaactcaa    720

gacttctggg aagttcagtt agggatacca catcccgcag ggttaaagaa gaaaaaatca    780

gtaacagtac tggatgtggg tgatgcatat ttttcagttc cattagataa agacttcagg    840

aagtatactg catttaccat acctagtaca aacaatgaaa caccagggct tagatatcag    900

tacaatgtgc ttccacaggg gtggaaagga tcaccagcaa tattccaaag tagcatgaca    960

aaaatcttag agccttttag aaaacaaaat ccagacatag ttatctatca atacatggat   1020

gatttgtatg taggatctga cttagaaata gggcagcata gaactaagat agaggaattg   1080

agacagcatt tgttgaggtg gggatttacc acaccagaca aaaaacatca gaaagaacct   1140

ccattccttt ggatgggtta tgaactccat cctgataaat ggacagtaca gcctatagtg   1200

ctgccagaaa aagacagctg gactgtcaat gacatacaga agttagtggg aaaattgaat   1260

tgggcaagtc agatttatgc agggattaaa gtaaggcaat tatgtaaact ccttagggga   1320

accaaagcac taacagaagt agtaccacta acagcagagg cagagctaga actggcagaa   1380

aacagggaga ttctaaaaga accagtacat ggagtgtatt atgacccctc aaaagactta   1440

atagcagaaa tacagaaaca ggggcaaggc caatggacat atcaaattta tcaagagcca   1500

tataaaaatt tgaaaacagg aaagtatgca aggatgaggg gtgcccacac taatgatgta   1560

aaacaactaa cagaggcagt gcaaaaaata accacagaaa gcatagtaat atggggaaag   1620

attcctaaat ttaaactacc catacaaaaa gaaacgtggg aagcatggtg gatagagtat   1680

tggcaagcca cctggattcc tgagtgggag tttgtcaata cccctccctt agtgaaatta   1740

tggtaccagt tagagaaaga acccatagta ggagcagaaa ctttctatgt agatggggca   1800

gctaataggg aaactaaatt aggaaaagca ggatatgtga ctgacagagg aagacaaaaa   1860

gttgtccccc taacggacac aacaaatcag aaaactgagt tacaagcaat tcatctagct   1920
```

-continued

```
ttgcaggatt cgggattaga agtaaacata gtaacagact cacaatatgc attaggaatc   1980

attcaagcac aaccagataa gagtgaatta gaaatagtca atcaaataat agagcagtta   2040

ataaaaaagg aaaagatcta cctggcatgg gtaccagcac acaaaggaat tggaggaaat   2100

gaacaagtag acaaattagt cagttctgga atcaggaaag tactattttt agatggaata   2160

gataaggccc aagaagaaca tgagaaatat cacaataatt ggagagcaat ggctagtgac   2220

tttaacatac cacctgtagt agcaaaagaa atagtagcca gctgtgataa atgtcagcta   2280

aaaggagaag ccatgcatgg acaagtagac tgtagtccag gaatatggca gctagattgt   2340

acacacttag aaggaaaagt tatcctggta gcagtgcatg tagccggtgg atatatagaa   2400

gcagaagtta ttccagcaga gacagggcaa gaaacagcat actttctctt aaaattagca   2460

ggaagatggc cagtaaaaac aatacacaca gacaatggca gcaatttcac cagtactaca   2520

gtcaaggccg cctgttggtg ggcggggatc aagcaggaat ttggcattcc ctacaatccc   2580

caaagtcaag gagtaataga atctatgaat aaagaattaa agaaaattat aggacaggta   2640

agggatcagg ctgaacatct taagacagca gtacaaacgg cagtattcat ccacaatttt   2700

aaaagaaaag gggggattgg ggggtacagt gcaggggaaa gaatagtaga cataatagca   2760

acagacatac agactaaaga attacaaaaa caaattacaa aaattcaaaa ttttcgggtt   2820

tattacagag acagcagaga tccactttgg aaaggaccag caaagcttct ctggaaaggt   2880

gaaggggcag tagtaataca agataatagt gacataaaag tagtgccaag aagaaaagta   2940

aagatcatta gggattatgg aaaacagatg gcaggtggtg attgtgtggc aggtagacag   3000

gatgaggatt aa                                                       3012
```

<210> SEQ ID NO 58
<211> LENGTH: 579
<212> TYPE: DNA
<213> ORGANISM: Human immunodeficiency virus type 1
<220> FEATURE:
<223> OTHER INFORMATION: isolate=93BR029; gene=vif

<400> SEQUENCE: 58

```
atggaaaaca gatggcaggt ggtgattgtg tggcaggtag acaggatgag gattaacaca     60

tggaaaagtt tagtaaaata ccatatgcat gtttcaaaga aagccaaaag atggttttat    120

agacatcact ttgaaagcag gcatccaaga gtaagttcag aagtacatat cccactagag    180

gaagctaaat tagtaataac aacatattgg gggctgcata caggagaaag agattggcat    240

ctgggtcagg gagtctccat agaatggagg caggggaggt ataggacaca aatagaccct    300

ggcctggcag accaactgat ccatatatat tattttgatt gtttttcaga atctgccata    360

aggaaagcca tattaggaca tagaattagc cctaggtgtg attatcaagc aggacataac    420

aaggtaggat ctctacagta cttggcacta acagcattaa taaaaccaaa aaagagaaag    480

ccacctttgc ccagtgttaa gaaactgaca gaggatagat ggaacaagcc ccagaagacc    540

aaggaccaca gagggagcca tacaatgaat ggacactag                           579
```

<210> SEQ ID NO 59
<211> LENGTH: 291
<212> TYPE: DNA
<213> ORGANISM: Human immunodeficiency virus type 1
<220> FEATURE:
<223> OTHER INFORMATION: isolate=93BR029; gene=vpr

<400> SEQUENCE: 59

```
atggaacaag ccccagaaga ccaaggacca cagagggagc catacaatga atggacacta     60
```

-continued

```
gaacttttag aggaacttaa gagtgaagct gttagacatt ttcctaggtt atggctccat    120

agcttaggac aacatatcta tgaaacttat ggggatactt gggcaggagt ggaagccata    180

ataagaattc tgcaacaact gctgtttatt catttcagaa ttggatgtca acatagcaga    240

ataggcatta atcgacagag gagagcaagg aatggagcca gtagatccta g             291
```

<210> SEQ ID NO 60
<211> LENGTH: 2601
<212> TYPE: DNA
<213> ORGANISM: Human immunodeficiency virus type 1
<220> FEATURE:
<223> OTHER INFORMATION: isolate=93BR029; gene=tat

<400> SEQUENCE: 60

```
atggagccag tagatcctag actagagccc tggaagcatc caggaagtcg gcctcagacg     60

gcttgtaata gttgctattg taaaaagtgt tgctttcatt gtcaagtttg tttcacaaca    120

aagggcttag gcatctccta tggcaggaag aagcggagac agcgacacag aactcctcaa    180

agcagtcagc tacatcaaga tcctgtacca aagcagtaag tattgttaag taatatatgt    240

aatgtcatat ttgttagtaa taggtttagc agcattaata gcagcactaa taatagcaat    300

agttgtgtgg actatagcat atatagaata tagggaacta gtaaggcaaa gaaaaataaa    360

taggttatat aaaagaataa gagaaagagc agaagacagt ggcaatgaga gtgaggggga    420

tgcagaggaa ttggcagcac ttggggaaat ggggcctttt attcctgggg atattgataa    480

tctgtaatgc tgaaaacttg tgggtcacag tctattatgg ggtacctgtg tggaaagaag    540

caaccactac tttattctgt gcatcagatg ctaaagcata tgaaaaagaa gcacataatg    600

tctgggctac acatgcctgt gtacccacag atcccaatcc acaagaagta gttctggaaa    660

atgtaacaga aaattttgat atgtggaaaa ataacatggt agaacaaatg catacagata    720

taatcagttt atgggatcaa agcctgaagc catgtgtgaa gttaacccca ctctgtgtta    780

ctttacgttg tagtaatgcc actaccaaca gtactcaaaa cgacaccctg aaggaagagc    840

caggggcaat acaaaactgt tctttcaata tgaccacaga agtaagagat aagcagctga    900

aagtacatgc actttttat aggcttgata tagtaccaat cagcaatgat aatagtagca    960

atgataatag tagcagagaa tacaggctaa taaattgtaa tacctcaacc cttacacagg   1020

cttgtccaaa ggtatcttgg gatccaattc ccatacatta ttgtgctcca gctgggtatg   1080

cgattctaaa gtgtaatgat aaaaaattca atgggacggg gccatgcagg aatgtcagca   1140

cagtacaatg tacacatgga attaaaccag tggtatcaac tcaattgttg ttaaatggca   1200

gcctagcaga aaaagatata ataatcagat ctcaaaatat ctcagataat gcaaaaacca   1260

taatagtaca acttaatgta tctgtgccga ttaattgtac aagacccaac aacaatacaa   1320

gaaaaagtat accaatagga ccaggacgag cattttatac aacaggagaa ataataggag   1380

acatcagaaa ggcacattgt aacgttagtg gaacaaaatg gaatgagacg ttagaaaagg   1440

taagggcaaa gttaaagcct catttcccta atgcaacaat aaaatttaac tcatcctcag   1500

gaggggacct agaaattaca atgcatagtt ttaattgtag aggagaattt ttctactgca   1560

atacatcagg actgtttaat gacacagtag acaatggcac tatcactctc ccatgtcgaa   1620

taaagcaaat tgtaaatatg tggcaggaag tggggcgagc aatgtatgcc gctcccattg   1680

caggaaacat tacctgtagc tcaaatatta caggtctact attgacaaga gatggtggtc   1740

agaataatca gacggaggag accttcagac ctgggggagg aaatatgaaa gacaactgga   1800
```

-continued

```
gaagtgaatt atataaatat aaagtagtag aaattgagcc attaggagta gcacccacca   1860

aggcaaaaag acaagtggtg aagagagaaa aaagagcagt gggaatggga gctttgttcc   1920

ttgggttctt gggagcagca ggaagcacta tgggcgcagc gtcaataacg ctgacggcac   1980

aggccagaca attattgtct ggcatagtgc aacagcagaa taatttgctg agggctattg   2040

aagcgcaaca gcatctgttg cagctcacag tctggggcat taaacagctc caggcaagaa   2100

tcctggctgt ggaaagatac ctaaaggatc aacagctcct agggctttgg ggctgctctg   2160

gaaaactcat ctgcaccact gatgtgccct ggaactctag ttggagtaac aaatctcagg   2220

agaagatctg gggaacatg acctggatgg agtgggaaaa agagattagc aattactcaa   2280

acgaaatata taggttaatt gaagagtcgc agaaccagca ggaaaagaat gaacaagaat   2340

tattggcatt ggacaaatgg gcaagtctgt ggaattggtt tgacatatca aaatggctgt   2400

ggtatataaa aatattcata atgatagtag gaggcttgat aggcttaaga atagtttttg   2460

ctgtgctttc tatagtaaat agagttagga agggatactc acctttgtca ttacagaccc   2520

gcttcccaag cccaagggaa cccgacaggc ccgaaggaat cgaagaagga ggtggagagc   2580

caggcaaaga cagatccgtg a                                             2601
```

<210> SEQ ID NO 61
<211> LENGTH: 2652
<212> TYPE: DNA
<213> ORGANISM: Human immunodeficiency virus type 1
<220> FEATURE:
<223> OTHER INFORMATION: isolate=93BR029; gene=rev

<400> SEQUENCE: 61

```
atggcaggaa gaagcggaga cagcgacaca gaactcctca aagcagtcag ctacatcaag     60

atcctgtacc aaagcagtaa gtattgttaa gtaatatatg taatgtcata tttgttagta    120

ataggtttag cagcattaat agcagcacta ataatagcaa tagttgtgtg gactatagca    180

tatatagaat atagggaact agtaaggcaa agaaaaataa ataggttata taaaagaata    240

agagaaagag cagaagacag tggcaatgag agtgaggggg atgcagagga attggcagca    300

cttggggaaa tggggccttt tattcctggg gatattgata atctgtaatg ctgaaaactt    360

gtgggtcaca gtctattatg gggtacctgt gtggaaagaa gcaaccacta ctttattctg    420

tgcatcagat gctaaagcat atgaaaaaga agcacataat gtctgggcta cacatgcctg    480

tgtacccaca gatcccaatc cacaagaagt agttctggaa aatgtaacag aaaattttga    540

tatgtggaaa aataacatgg tagaacaaat gcatacagat ataatcagtt tatgggatca    600

aagcctgaag ccatgtgtga agttaacccc actctgtgtt actttacgtt gtagtaatgc    660

cactaccaac agtactcaaa acgacaccct gaaggaagag ccaggggcaa tacaaaactg    720

ttctttcaat atgaccacag aagtaagaga taagcagctg aaagtacatg cactttttta    780

taggcttgat atagtaccaa tcagcaatga taatagtagc aatgataata gtagcagaga    840

atacaggcta ataaattgta atacctcaac ccttacacag gcttgtccaa aggtatcttg    900

ggatccaatt cccatacatt attgtgctcc agctgggtat gcgattctaa agtgtaatga    960

taaaaaattc aatgggacgg ggccatgcag gaatgtcagc acagtacaat gtacacatgg   1020

aattaaacca gtggtatcaa ctcaattgtt gttaaatggc agcctagcag aaaaagatat   1080

aataatcaga tctcaaaata tctcagataa tgcaaaaacc ataatagtac aacttaatgt   1140

atctgtgccg attaattgta caagacccaa caacaataca agaaaaagta taccaatagg   1200

accaggacga gcattttata caacaggaga aataatagga gacatcagaa aggcacattg   1260
```

-continued

```
taacgttagt ggaacaaaat ggaatgagac gttagaaaag gtaagggcaa agttaaagcc   1320

tcatttccct aatgcaacaa taaaatttaa ctcatcctca ggaggggacc tagaaattac   1380

aatgcatagt tttaattgta gaggagaatt tttctactgc aatacatcag gactgtttaa   1440

tgacacagta gacaatggca ctatcactct cccatgtcga ataaagcaaa ttgtaaatat   1500

gtggcaggaa gtggggcgag caatgtatgc cgctcccatt gcaggaaaca ttacctgtag   1560

ctcaaatatt acaggtctac tattgacaag agatggtggt cagaataatc agacggagga   1620

gaccttcaga cctgggggag gaaatatgaa agacaactgg agaagtgaat tatataaata   1680

taaagtagta gaaattgagc cattaggagt agcacccacc aaggcaaaaa gacaagtggt   1740

gaagagagaa aaaagagcag tgggaatggg agctttgttc cttgggttct tgggagcagc   1800

aggaagcact atgggcgcag cgtcaataac gctgacggca caggccagac aattattgtc   1860

tggcatagtg caacagcaga ataatttgct gagggctatt gaagcgcaac agcatctgtt   1920

gcagctcaca gtctggggca ttaaacagct ccaggcaaga atcctggctg tggaaagata   1980

cctaaaggat caacagctcc tagggctttg gggctgctct ggaaaactca tctgcaccac   2040

tgatgtgccc tggaactcta gttggagtaa caaatctcag gagaagatct gggggaacat   2100

gacctggatg gagtgggaaa aagagattag caattactca aacgaaatat ataggttaat   2160

tgaagagtcg cagaaccagc aggaaaagaa tgaacaagaa ttattggcat tggacaaatg   2220

ggcaagtctg tggaattggt ttgacatatc aaaatggctg tggtatataa aaatattcat   2280

aatgatagta ggaggcttga taggcttaag aatagttttt gctgtgcttt ctatagtaaa   2340

tagagttagg aagggatact cacctttgtc attacagacc cgcttcccaa gcccaaggga   2400

acccgacagg cccgaaggaa tcgaagaagg aggtggagag ccaggcaaag acagatccgt   2460

gagattagtg aacggattct tagctcttgt ctgggacgac ctgaggaacc tgtgcctctt   2520

cagctaccgc cacttgagag acttcatatt aattgcagcg aggattgtgg acaggggact   2580

gaagaggggg tgggaagccc tcaaacttct ggggaatctc gcgctgtatt ggagtcagga   2640

actaaagaat ag                                                       2652
```

<210> SEQ ID NO 62
<211> LENGTH: 2529
<212> TYPE: DNA
<213> ORGANISM: Human immunodeficiency virus type 1
<220> FEATURE:
<223> OTHER INFORMATION: isolate=93BR029; gene=env

<400> SEQUENCE: 62

```
atgagagtga gggggatgca gaggaattgg cagcacttgg ggaaatgggg ccttttattc     60

ctggggatat tgataatctg taatgctgaa aacttgtggg tcacagtcta ttatggggta    120

cctgtgtgga aagaagcaac cactacttta ttctgtgcat cagatgctaa agcatatgaa    180

aaagaagcac ataatgtctg ggctacacat gcctgtgtac ccacagatcc caatccacaa    240

gaagtagttc tggaaaatgt aacagaaaat tttgatatgt ggaaaaataa catggtagaa    300

caaatgcata cagatataat cagtttatgg gatcaaagcc tgaagccatg tgtgaagtta    360

accccactct gtgttacttt acgttgtagt aatgccacta ccaacagtac tcaaaacgac    420

accctgaagg aagagccagg ggcaatacaa aactgttctt tcaatatgac cacagaagta    480

agagataagc agctgaaagt acatgcactt ttttataggc ttgatatagt accaatcagc    540

aatgataata gtagcaatga taatagtagc agagaataca ggctaataaa ttgtaatacc    600
```

-continued

```
tcaaccctta cacaggcttg tccaaaggta tcttgggatc caattcccat acattattgt    660

gctccagctg ggtatgcgat tctaaagtgt aatgataaaa aattcaatgg gacggggcca    720

tgcaggaatg tcagcacagt acaatgtaca catggaatta aaccagtggt atcaactcaa    780

ttgttgttaa atggcagcct agcagaaaaa gatataataa tcagatctca aaatatctca    840

gataatgcaa aaaccataat agtacaactt aatgtatctg tgccgattaa ttgtacaaga    900

cccaacaaca atacaagaaa aagtatacca ataggaccag gacgagcatt ttatacaaca    960

ggagaaataa taggagacat cagaaaggca cattgtaacg ttagtggaac aaaatggaat   1020

gagacgttag aaaaggtaag ggcaaagtta aagcctcatt tccctaatgc aacaataaaa   1080

tttaactcat cctcaggagg ggacctagaa attacaatgc atagttttaa ttgtagagga   1140

gaatttttct actgcaatac atcaggactg tttaatgaca cagtagacaa tggcactatc   1200

actctcccat gtcgaataaa gcaaattgta aatatgtggc aggaagtggg gcgagcaatg   1260

tatgccgctc ccattgcagg aaacattacc tgtagctcaa atattacagg tctactattg   1320

acaagagatg gtggtcagaa taatcagacg gaggagacct tcagacctgg gggaggaaat   1380

atgaaagaca actggagaag tgaattatat aaatataaag tagtagaaat tgagccatta   1440

ggagtagcac ccaccaaggc aaaaagacaa gtggtgaaga gagaaaaaag agcagtggga   1500

atgggagctt tgttccttgg gttcttggga gcagcaggaa gcactatggg cgcagcgtca   1560

ataacgctga cggcacaggc cagacaatta ttgtctggca tagtgcaaca gcagaataat   1620

ttgctgaggg ctattgaagc gcaacagcat ctgttgcagc tcacagtctg ggcattaaa    1680

cagctccagg caagaatcct ggctgtggaa agatacctaa aggatcaaca gctcctaggg   1740

ctttggggct gctctggaaa actcatctgc accactgatg tgccctggaa ctctagttgg   1800

agtaacaaat ctcaggagaa gatctggggg aacatgacct ggatggagtg ggaaaaagag   1860

attagcaatt actcaaacga aatatatagg ttaattgaag agtcgcagaa ccagcaggaa   1920

aagaatgaac aagaattatt ggcattggac aaatgggcaa gtctgtggaa ttggtttgac   1980

atatcaaaat ggctgtggta tataaaaata ttcataatga tagtaggagg cttgataggc   2040

ttaagaatag tttttgctgt gctttctata gtaaatagag ttaggaaggg atactcacct   2100

ttgtcattac agacccgctt cccaagccca agggaacccg acaggcccga aggaatcgaa   2160

gaaggaggtg gagagccagg caaagacaga tccgtgagat tagtgaacgg attcttagct   2220

cttgtctggg acgacctgag gaacctgtgc ctcttcagct accgccactt gagagacttc   2280

atattaattg cagcgaggat tgtggacagg ggactgaaga gggggtggga agccctcaaa   2340

cttctgggga atctcgcgct gtattggagt caggaactaa agaatagtgc tattagcttg   2400

cttaatacca cagcaatagt agtagctgag gggacagata gagttataga agctttgcaa   2460

agagcgggta gagctgttct taacgtacct agaagaataa gacagggctt ggaaagggct   2520

ttgctataa                                                           2529
```

<210> SEQ ID NO 63
<211> LENGTH: 621
<212> TYPE: DNA
<213> ORGANISM: Human immunodeficiency virus type 1
<220> FEATURE:
<223> OTHER INFORMATION: isolate=93BR029; gene=nef

<400> SEQUENCE: 63

```
atgggtagca agtggtcaaa aagtagtata gttgggtggc ctgctataag ggaaagatta     60

agacaaaccc ctccagcagc agaaggggtg ggagcagtgt ctcaagactt agaaagacgg    120
```

-continued

```
ggggcaatta caagcagcaa tactggagct aataatcctg acttggcctg gctggaggca    180

caagaggaag aggaagtagg ctttccagtc agacctcagg tacctttaag accaatgact    240

tataagggag ctcttgatct cagtcacttt ttaaaagaaa aggggggact ggaagggtta    300

atttattcca agaaaagaca agagatcctt gatctgtggg tttaccacac acaaggctac    360

ttccctgatt ggcagaacta cacaccaggg ccagggacca gatatccact gaccttaggg    420

tggtgcttca agctagtacc agttgaccca gaggaggtag aaaaggccaa tgaaggagag    480

aacaactgct tgctacaccc catgagccaa catggaatgg aggatgaaga cagagaaata    540

ctgcagtgga ggtttgacag ccgcctagca tttcatcaca tggcccgaga gctgcatccg    600

gagtactaca aggactgctg a                                              621
```

<210> SEQ ID NO 64
<211> LENGTH: 1503
<212> TYPE: DNA
<213> ORGANISM: Human immunodeficiency virus type 1
<220> FEATURE:
<223> OTHER INFORMATION: isolate=94CY032.3; gene=gag

<400> SEQUENCE: 64

```
atgggtgcga gagcgtcagt attaagtggg ggaaaattag atgcatggga gaggattcgg     60

ttaaggccag ggggaaagaa aaaatataga ctgaaacatc tagtatgggc aagcagagag    120

ttggaaagat tcgcacttaa ccctggcctt ttagaaacag cagaaggatg tcaacaatta    180

atggaacagt tacaatcaac tctcaaaaca ggatcagaag aacttagatc attatataat    240

actataacaa ccctctggtg cgtacatcaa agaatagatg tacaagacac caaggaagct    300

ttagataaaa tagaggaaat acaaagtaag agcaagcaaa agacacagca ggcagcagct    360

gccgcaggag gtagcagcaa tgtcagccaa aattacccta tagtgcaaaa tgcacaaggg    420

caaatggtac atcagagcat ttcacctaga actttgaatg catgggtaaa agtaatagaa    480

gaaaaggctt tcagcccaga agtaataccc atgttctcag cattatcaga gggagccacc    540

ccacaagatt tgaacatgat gctaaatata gtggggggac accaggcagc aatgcaaatg    600

ttaaaagata ccatcaatga ggaagctgca gactgggaca ggacacatcc agtacatgca    660

gggcctattc caccaggcca gatgagagaa ccaaggggaa gtgatatagc aggaactact    720

agtacccttc aagaacaaat aggatggatg acaagcaacc cacctgtccc agtgggagaa    780

atctataaaa gatggataat cttggggtta aataaaatag taagaacgta tagccccatt    840

agcatcttgg acataagaca aggaccaaaa gaacccttca gagattatgt agataggttc    900

tttaaatgtc tcagagcaga acaagctacc caggaggtga aaaattggat gacagaaacc    960

ctgctggtcc aaaatgcgaa tccagactgt aagtccatct taaaagcatt aggaacaggg   1020

gctacattag aagaaatgat gacagcatgt cagggagtgg gaggacccag ccataaagca   1080

agagttttag ctgaggcaat gagccaggca tcaaatgcag cagcagccat aatgatgcag   1140

aaaagcaaat ttaagggcca aagaagaact attaagtgtt tcaactgtgg caaggaagga   1200

catctagcca gaaattgcag ggcccctagg aaaaagggct gctggaagtg tggaaaggag   1260

ggacatcaaa tgaaagactg cactgagaga caggctaatt ttttagggag aatgtggcct   1320

tccagcaaag ggaggccagg aaattttctt cagaacaggc cagagccaac agccccgccc   1380

gcggaatgct tagagaggaa agaggagaca acctcctctc tgaagcagga accgagggac   1440

aaggaactat atcctttaac ttccctcaaa tcactctttg gcagcgaccc cttgtcacaa   1500
```

-continued

```
taa                                                                 1503

<210> SEQ ID NO 65
<211> LENGTH: 3009
<212> TYPE: DNA
<213> ORGANISM: Human immunodeficiency virus type 1
<220> FEATURE:
<223> OTHER INFORMATION: isolate=94CT032.3; gene=pol

<400> SEQUENCE: 65

tttttaggg agaatgtggc cttccagcaa agggaggcca ggaaattttc ttcagaacag      60
gccagagcca acagccccgc ccgcggaatg cttagagagg aaagaggaga caacctcctc     120
tctgaagcag gaaccgaggg acaaggaact atatccttta acttccctca aatcactctt     180
tggcagcgac cccttgtcac aataaaacta gggggacaga taagggaggc tcttttagat     240
acaggagcag atgatacagt attagaagaa ataaatttgc caggaaaatg gaagccaaaa     300
atgatagggg gaatcggagg ttttatcaaa gtaagacaat atgatcagat acctatagaa     360
atttgtggaa aaaaggccat aggcacagtg ttagtaggac ctacacctgt caacataatt     420
ggacgaaaca tgttgactca gcttggttgt actttaaatt ttccaattag tcctattgaa     480
actgtaccag taaaattaaa gccaggaatg gatggcccaa aggttaaaca atggccattg     540
acagaagaaa aaataaaagc cttaacagag atatgtacag acatggaaaa ggaaggcaag     600
atttcaaaaa ttgggcctga aaatccatac aatactccaa tatttgctat aaagaaaaaa     660
gacagcacta aatggagaaa attagtagat ttcagagaac tcaataaaag aactcaggac     720
ttctgggaag ttcagttagg aataccgcac ccagcagggt taaagaagaa aaaatcagta     780
acagtattgg atgtgggggga tgcatatttt tcagttccct tagatccaga gttcaggaag     840
tacactgcat tcaccatacc tagtaccaac aatgagacac caggaattag atatcagtac     900
aatgtgcttc cacagggctg gaaaggatca ccagcaatat tccaatgtag catgacaaaa     960
atcttagagc cctttagatt caaaaaccca gaaatagtca tataccaata tatggatgat    1020
ttgtatgtag ggtctgactt agaaataggg caacatagag caaaaataga agagctaaga    1080
gagcatctat tgagatgggg attcaccaca ccagacaaaa aacatcagaa agaacccccca   1140
tttctttgga tggggtatga actccatcct gacaaatgga cagtgcagcc tatacaaccg    1200
gcagaaaagg atagctggac tgtcaacgat atccagaagt tagtgggaaa actaaattgg    1260
gcaagtcaga tttatccagg gattaaagta aagcaattat gtaaacttct taggggagct    1320
aaagccctaa cagacatagt accactaact acagaggcag agttagaatt agcagagaac    1380
agggagattc taaaagaacc agtacatggg gcatattatg acccatcaaa agacttaata    1440
gcagaaatac agaagcaagg gcaaggtcaa tggacatatc aaatatatca agagccacat    1500
aaaaatctga aaacagggaa gtatgcaaga accagatctg cccacactaa tgatgttaga    1560
caattaacag aagcagtgca aaagatagcc atggaatgca tagtaatatg ggaaagact     1620
cctaagttta gattacccat acaaaaggaa acatgggaca catggtggac agaatattgg    1680
caggccacct ggatccctga atgggaattt gtcaataccc ctcctctagt aaaattatgg    1740
taccagttag aaacagaccc catagcagga gcagaaactt tctatgtaga tggggcagct    1800
aatagagaaa caaaacaggg aaaagcagga tatgttactg atagaggcag acaaaaagtt    1860
gtctccctat ctgaaacaac aaatcagaag actgaattac aagcaattta cttagctttg    1920
caggattcag gatcagaagt aaacatagta acagactcac agtatgcaat aggaatcatt    1980
caagcacaac cagatagaag tgaatcagat ttagttaatc aaataataga gcagttaata    2040
```

-continued cggaaggaca aggtctacct gtcatgggta ccagcacaca aagggattgg aggaaatgaa 2100
caagtagata aattagtcag caatggaatc agaaaggtgc tatttttaga tggaatagat 2160
aaggctcaag aagaacatga gaaatatcac aataactgga gagcaatggc tagtgatttt 2220
aatctgccat cagtggtagc aaaagagata gtagctagct gtaataaatg tcagctaaaa 2280
ggggaagcca tgcatggaca agtggactgt agtccaggga tatggcagtt agattgtaca 2340
catttagaag gtaaagttat catggtagca gttcatgtgg ctagtggata catagaagca 2400
gaagttatcc cagcagaaac aggacaggaa acagcctact tcatactaaa attagcagga 2460
agatggccag tgaaaatgat acatgcagac aacggcccca atttcaccag tgctgcggtt 2520
aaggcagcct gttggtgggc agatatcaac caggaatttg gaattcccta caatccccaa 2580
agccaaggag tagtggaatc tatgaataaa gaattaaaga aaatcatagg gcaggtcagg 2640
gatcaagctg aacaccttaa gacagcagta cagatggcag tattcattca caattttaaa 2700
agaaaagggg ggattggggg gtacagtgca ggggaaagaa taatagacat aatagcatca 2760
gatatacaaa ctaaagaact acaaaaacaa attacaaaaa ttcaaaattt tcgggtttat 2820
tacagggaca gcagagaacc aatttggaag ggaccagcaa aactactctg gaaaggtgaa 2880
ggggcagtag taatacagga caacagtgat atcaaagtag taccaagaag aaaagcaaag 2940
attattaggg actatggcaa acagatggca ggtaatgatt gtgtggcagg tagacaggat 3000
gaagattag 3009

<210> SEQ ID NO 66
<211> LENGTH: 579
<212> TYPE: DNA
<213> ORGANISM: Human immunodeficiency virus type 1
<220> FEATURE:
<223> OTHER INFORMATION: isolate=94CT032.3; gene=vif

<400> SEQUENCE: 66
atggcaaaca gatggcaggt aatgattgtg tggcaggtag acaggatgaa gattagaaca 60
tggaacagtc tagtgaaaca tcatatgtat gtttcaaaga aagctaaagg atgattctat 120
agacatcact atgaaagtag gcacccaaaa gtaagttcag aagtacatat cccactaggg 180
gaggctagat tagtagtaag aacatattgg ggtctgcagc caggggaaca agactggcac 240
ttgggtcatg gagtctccat agaatggagg ctcagaagat atagcacaca agtggatcct 300
gacctggcag accaactaat tcatatgcat tactttgatt gtttttcaga atctgccata 360
aggaaagcca tattaggaca tagagttagt cctaggtgtg aatatcaagc aggacataat 420
aaggtaggat ccttacaata cctggcacta gcagcattaa tatccccaaa aaagacaaag 480
ccacctttgc ctagtgttaa gaaactagtg gaggatagat ggaacaagcc ccagaagacc 540
aggggccgca gagagaacca aataatgaat ggacactag 579

<210> SEQ ID NO 67
<211> LENGTH: 288
<212> TYPE: DNA
<213> ORGANISM: Human immunodeficiency virus type 1
<220> FEATURE:
<223> OTHER INFORMATION: isolate=94CY032.3; gene=vpr

<400> SEQUENCE: 67
atggaacaag ccccagaaga ccaggggccg cagagagaac caaataatga atggacacta 60
gagcttttgg aggagcttaa aaatgaagct gttaggcatt ttcctagacc ctggctccat 120

-continued

```
ggcctaggac agcatatcta taacacttat ggagatacct gggaaggggt tgaagctata    180

ataagaattt tgcaacaact actgtttatt catttcagaa ttgggtgcca acatagtaga    240

ataggcatta ctcctcaaag gagaagaggc aggggatgga gccagtag                 288


<210> SEQ ID NO 68
<211> LENGTH: 2643
<212> TYPE: DNA
<213> ORGANISM: Human immunodeficiency virus type 1
<220> FEATURE:
<223> OTHER INFORMATION: isolate=94CT032.3; gene=tat

<400> SEQUENCE: 68

atggagccag tagatcctga cctagagccc tggaaccatc cgggaagtca gcctacaact     60

gattgtaaca agtgtttctg taaaaagtgt tgctggcatt gccaagtttg ctttctgaaa    120

aaaggcttag gcatctccta tggcaggaag aagcggaaac atcgacgagg atctcttcaa    180

ggcagcaagg gccatcaaaa tcttatacca aagcagtaag tattaagtat atgtaatgtt    240

attctgggaa atctgggcaa tagtaggact ggtagtagcg ctaattatag taatagtagt    300

gtggacttta gtatttatag aatataagaa attgagaagg caaaggagaa tagacagctt    360

gtacaataga ataagagaaa gagcagaaga cagtggcaat gagagtgatg gggatgcaga    420

ggaattatcc acacttgtgg gaatggggaa ctttgatcct tgggttggtg ataatctgta    480

gtgcctcaaa caacttgtgg gtcacagttt attatggggt acctgtgtgg agagacgcag    540

agaccaccct attttgtgca tcagaagcta aagcatatga gaaagaagta cataatatct    600

gggctacaca tgcctgtgta cccacagacc ccaacccaca agaagtagct ctgataaatg    660

taacagagaa ctttaacatg tggaaaaatg acatggtaga acagatgcat gaggatataa    720

tcagtttatg gaatgaaggc ctaaaaccat gtgcaaagct aacctctctc tgtgttactt    780

ttacatgtat taatgcaact actactaata gtaccaatgg cactgtgatt aaagaaggaa    840

taaaaaactg ctctttcgat ataaccacag aaataaggga taagaagaag aaagaatatg    900

cgcttttcta tagaattgat atagtgccaa ttaatgctag agtgccaatt aatggtagta    960

ataggaataa tagtacagaa gagtatatgt taataaattg taacgcctca accattaaac   1020

aggcttgccc aaaggtgtct tttgagccaa ttcccataca ttattgtgcc ccagctggtt   1080

ttgcaatttt aaagtgtaat gagaaaaatt tcactggatt agggccatgc acaaatgtca   1140

gctcggtacg atgcactcat ggaattaagc cagtggtatc aactcaattg ctgttaaatg   1200

gaagcttagc aacggaagag gtagtaatta gatctaaaaa tatcacagac aataccaaaa   1260

atataatagt acagcttgca aaggctgtaa aaattaattg taccagacct ggcaacaata   1320

caagaaaaag tgtacatata gggccaggac taacatggta tgcaacaggt gaaataatag   1380

gagatataag acaagcacat tgtaacatta gtggaaatga ttggaatgac accttaaaag   1440

tgataagtga agaattgaaa agactcttcc ctaataaaac aataaaattt gctccacccg   1500

taggagggga cctagaaatt acaacacata gctttaattg taaaggagaa tttttctatt   1560

gcaatacaac accactgttt aatagtacac acatgcaaaa tggtacaaac attacaagta   1620

cagattctac aaattcaacc atcacactcc aatgcagact aaaacaattt gtaaggatgt   1680

ggcaggaagt ggggcaagca atgtacgcct cccccattgc agggagcatt aactgcagct   1740

cagatattac aggaataata ttgacaagag atggtggtac taataatact gagatcttca   1800

gacctggagg aggagacatg agggacaatt ggagaagtga actatataaa tataaagtag   1860

taaagattga accaatagga gtagcaccca ataaggcaag gagacgagtg gtgcagagag   1920
```

-continued aaaaatgagc agtgggaata ggggccatgt tccttgggtt cttgggagca gcaggaagca 1980
ctatgggcgc agcgtcaatg acgctgacgg tacaggccag acaattattg tccggcatag 2040
tgcagcagca gagcaatttg ctgagggcta tagaggctca acaacatctg ttgagactca 2100
cggtctgggg cattaaacag ctccaggcaa gagtcctggc tctggaaagc tacctaaagg 2160
atcaacagct cctaggaatt tggggctgct ctggaaaact catctgcacc actaatgtac 2220
cttggaactc tagttggagt aataaatctt ataatgatat atgggacaat atgacctggt 2280
tgcaatggga taaagaaatt aacaattaca cacaaataat atatgggtta cttgaagaat 2340
cacagaacca gcaggaaaag aatgagcaag acttattggc cttggacaag tgggcaagcc 2400
tgtggaattg gtttagcata acaaaatggc tatggtatat aaaaatattt ataatgatag 2460
taggaggctt gataggctta agaataattt ttgctgtgct ttctatagta aatagagtta 2520
ggcagggata ctcacctttg tctttgcaga cccttatccc aacaacccaa cggggactcg 2580
acaggcccgg aggaacagaa gaagaaggtg gcgagcaaga cagaagcaga tccattcgct 2640
tag 2643

<210> SEQ ID NO 69
<211> LENGTH: 2688
<212> TYPE: DNA
<213> ORGANISM: Human immunodeficiency virus type 1
<220> FEATURE:
<223> OTHER INFORMATION: isolate=94CT032.3; gene=rev

<400> SEQUENCE: 69
atggcaggaa gaagcggaaa catcgacgag gatctcttca aggcagcaag ggccatcaaa 60
atcttatacc aaagcagtaa gtattaagta tatgtaatgt tattctggga aatctgggca 120
atagtaggac tggtagtagc gctaattata gtaatagtag tgtggacttt agtatttata 180
gaatataaga aattgagaag gcaaaggaga atagacagct tgtacaatag aataagagaa 240
agagcagaag acagtggcaa tgagagtgat ggggatgcag aggaattatc cacacttgtg 300
ggaatgggga actttgatcc ttgggttggt gataatctgt agtgcctcaa acaacttgtg 360
ggtcacagtt tattatgggg tacctgtgtg gagagacgca gagaccaccc tattttgtgc 420
atcagaagct aaagcatatg agaaagaagt acataatatc tgggctacac atgcctgtgt 480
acccacagac cccaacccac aagaagtagc tctgataaat gtaacagaga actttaacat 540
gtggaaaaat gacatggtag aacagatgca tgaggatata atcagtttat ggaatgaagg 600
cctaaaacca tgtgcaaagc taacctctct ctgtgttact tttacatgta ttaatgcaac 660
tactactaat agtaccaatg gcactgtgat taaagaagga ataaaaaact gctctttcga 720
tataaccaca gaaataaggg ataagaagaa gaaagaatat gcgcttttct atagaattga 780
tatagtgcca attaatgcta gagtgccaat taatggtagt aataggaata atagtacaga 840
agagtatatg ttaataaatt gtaacgcctc aaccattaaa caggcttgcc caaaggtgtc 900
ttttgagcca attcccatac attattgtgc cccagctggt tttgcaattt taaagtgtaa 960
tgagaaaaat ttcactggat tagggccatg cacaaatgtc agctcggtac gatgcactca 1020
tggaattaag ccagtggtat caactcaatt gctgttaaat ggaagcttag caacggaaga 1080
ggtagtaatt agatctaaaa atatcacaga caataccaaa aatataatag tacagcttgc 1140
aaaggctgta aaaattaatt gtaccagacc tggcaacaat acaagaaaaa gtgtacatat 1200
agggccagga ctaacatggt atgcaacagg tgaaataata ggagatataa gacaagcaca 1260

-continued ttgtaacatt agtggaaatg attggaatga caccttaaaa gtgataagtg aagaattgaa 1320
aagactcttc cctaataaaa caataaaatt tgctccaccc gtaggagggg acctagaaat 1380
tacaacacat agctttaatt gtaaaggaga atttttctat tgcaatacaa caccactgtt 1440
taatagtaca cacatgcaaa atggtacaaa cattacaagt acagattcta caaattcaac 1500
catcacactc caatgcagac taaaacaatt tgtaaggatg tggcaggaag tggggcaagc 1560
aatgtacgcc tcccccattg cagggagcat taactgcagc tcagatatta caggaataat 1620
attgacaaga gatggtggta ctaataatac tgagatcttc agacctggag gaggagacat 1680
gagggacaat tggagaagtg aactatataa atataaagta gtaaagattg aaccaatagg 1740
agtagcaccc aataaggcaa ggagacgagt ggtgcagaga gaaaaatgag cagtgggaat 1800
aggggccatg ttccttgggt tcttgggagc agcaggaagc actatgggcg cagcgtcaat 1860
gacgctgacg gtacaggcca gacaattatt gtccggcata gtgcagcagc agagcaattt 1920
gctgagggct atagaggctc aacaacatct gttgagactc acggtctggg gcattaaaca 1980
gctccaggca agagtcctgg ctctggaaag ctacctaaag gatcaacagc tcctaggaat 2040
ttggggctgc tctggaaaac tcatctgcac cactaatgta ccttggaact ctagttggag 2100
taataaatct tataatgata tatgggacaa tatgacctgg ttgcaatggg ataaagaaat 2160
taacaattac acacaaataa tatatgggtt acttgaagaa tcacagaacc agcaggaaaa 2220
gaatgagcaa gacttattgg ccttggacaa gtgggcaagc ctgtggaatt ggtttagcat 2280
aacaaaatgg ctatggtata taaaaatatt tataatgata gtaggaggct tgataggctt 2340
aagaataatt tttgctgtgc tttctatagt aaatagagtt aggcagggat actcaccttt 2400
gtctttgcag acccttatcc caacaaccca acggggactc gacaggcccg gaggaacaga 2460
agaagaaggt ggcgagcaag acagaagcag atccattcgc ttagtgaacg gattcttgcc 2520
acttatctgg gacgacctgc ggaacctgtg cctcttcagc taccgccact tgagaaactt 2580
actcttaatt gtagcgagga ctgtggaact tctggggata agggggtggg aagccctcaa 2640
gtatctgtgg aacttcctgc tgtattgggg acaggagcta aagaatag 2688

<210> SEQ ID NO 70
<211> LENGTH: 246
<212> TYPE: DNA
<213> ORGANISM: Human immunodeficiency virus type 1
<220> FEATURE:
<223> OTHER INFORMATION: isolate=94CT032.3; gene=vpu

<400> SEQUENCE: 70
atgttattct gggaaatctg ggcaatagta ggactggtag tagcgctaat tatagtaata 60
gtagtgtgga ctttagtatt tatagaatat aagaaattga gaaggcaaag gagaatagac 120
agcttgtaca atagaataag agaaagagca gaagacagtg gcaatgagag tgatggggat 180
gcagaggaat tatccacact tgtgggaatg gggaactttg atccttgggt tggtgataat 240
ctgtag 246

<210> SEQ ID NO 71
<211> LENGTH: 2571
<212> TYPE: DNA
<213> ORGANISM: Human immunodeficiency virus type 1
<220> FEATURE:
<223> OTHER INFORMATION: isolate=94CY032.3; gene=env

<400> SEQUENCE: 71
atgagagtga tggggatgca gaggaattat ccacacttgt gggaatgggg aactttgatc 60

-continued

```
cttgggttgg tgataatctg tagtgcctca aacaacttgt gggtcacagt ttattatggg    120
gtacctgtgt ggagagacgc agagaccacc ctattttgtg catcagaagc taaagcatat    180
gagaaagaag tacataatat ctgggctaca catgcctgtg tacccacaga ccccaaccca    240
caagaagtag ctctgataaa tgtaacagag aactttaaca tgtggaaaaa tgacatggta    300
gaacagatgc atgaggatat aatcagttta tggaatgaag gcctaaaacc atgtgcaaag    360
ctaacctctc tctgtgttac ttttacatgt attaatgcaa ctactactaa tagtaccaat    420
ggcactgtga ttaaagaagg aataaaaaac tgctctttcg atataaccac agaaataagg    480
gataagaaga agaaagaata tgcgcttttc tatagaattg atatagtgcc aattaatgct    540
agagtgccaa ttaatggtag taataggaat aatagtacag aagagtatat gttaataaat    600
tgtaacgcct caaccattaa acaggcttgc ccaaaggtgt cttttgagcc aattcccata    660
cattattgtg ccccagctgg ttttgcaatt ttaaagtgta atgagaaaaa tttcactgga    720
ttagggccat gcacaaatgt cagctcggta cgatgcactc atggaattaa gccagtggta    780
tcaactcaat tgctgttaaa tggaagctta gcaacggaag aggtagtaat tagatctaaa    840
aatatcacag acaataccaa aaatataata gtacagcttg caaaggctgt aaaaattaat    900
tgtaccagac ctggcaacaa tacaagaaaa agtgtacata tagggccagg actaacatgg    960
tatgcaacag gtgaaataat aggagatata agacaagcac attgtaacat tagtggaaat   1020
gattggaatg acaccttaaa agtgataagt gaagaattga aaagactctt ccctaataaa   1080
acaataaaat ttgctccacc cgtaggaggg gacctagaaa ttacaacaca tagctttaat   1140
tgtaaaggag aatttttcta ttgcaataca acaccactgt ttaatagtac acacatgcaa   1200
aatggtacaa acattacaag tacagattct acaaattcaa ccatcacact ccaatgcaga   1260
ctaaaacaat ttgtaaggat gtggcaggaa gtggggcaag caatgtacgc ctcccccatt   1320
gcagggagca ttaactgcag ctcagatatt acaggaataa tattgacaag agatggtggt   1380
actaataata ctgagatctt cagacctgga ggaggagaca tgagggacaa ttggagaagt   1440
gaactatata aatataaagt agtaaagatt gaaccaatag gagtagcacc caataaggca   1500
aggagacgag tggtgcagag agaaaaatga gcagtgggaa taggggccat gttccttggg   1560
ttcttgggag cagcaggaag cactatgggc gcagcgtcaa tgacgctgac ggtacaggcc   1620
agacaattat tgtccggcat agtgcagcag cagagcaatt tgctgagggc tatagaggct   1680
caacaacatc tgttgagact cacggtctgg ggcattaaac agctccaggc aagagtcctg   1740
gctctggaaa gctacctaaa ggatcaacag ctcctaggaa tttggggctg ctctggaaaa   1800
ctcatctgca ccactaatgt accttggaac tctagttgga gtaataaatc ttataatgat   1860
atatgggaca atatgacctg gttgcaatgg gataaagaaa ttaacaatta cacacaaata   1920
atatatgggt tacttgaaga atcacagaac cagcaggaaa agaatgagca agacttattg   1980
gccttggaca agtgggcaag cctgtggaat tggtttagca taacaaaatg gctatggtat   2040
ataaaaatat ttataatgat agtaggaggc ttgataggct taagaataat ttttgctgtg   2100
ctttctatag taaatagagt taggcaggga tactcacctt tgtctttgca gacccttatc   2160
ccaacaaccc aacggggact cgacaggccc ggaggaacag aagaagaagg tggcgagcaa   2220
gacagaagca gatccattcg cttagtgaac ggattcttgc cacttatctg ggacgacctg   2280
cggaacctgt gcctcttcag ctaccgccac ttgagaaact tactcttaat tgtagcgagg   2340
actgtggaac ttctggggat aagggggtgg gaagccctca agtatctgtg gaacttcctg   2400
```

-continued

```
ctgtattggg gacaggagct aaagaatagt gctattaatt tgtttaatac cacagcaata   2460

gcagtagctg agggaacaga taggattata gaagcagtac agagagcttg tagagctatt   2520

tgcaacatac ctagaagaat cagacagggc cttgaaagag ctttgcttta a            2571
```

<210> SEQ ID NO 72
<211> LENGTH: 660
<212> TYPE: DNA
<213> ORGANISM: Human immunodeficiency virus type 1
<220> FEATURE:
<223> OTHER INFORMATION: nef

<400> SEQUENCE: 72

```
atgggaggca aatggtcaaa aagtagcata gttggatggc ctgagataag ggaaagaatg     60

aggcgagctc gagctgagcc agaaagaatg aggcgagctc aagctgagcc agcagcagca    120

ggagtaggag cagtgtctca agacttggac aaacatgggg caatcacaat taacaataca    180

gcagctacta atcctgacaa aacctggctg gaagcacaag aagaggaaga agaggtaggt    240

tttccagtca ggccacaggt acctttaagg ccaatgacct ttaaaggagc tttagatctc    300

agccactttt taaaagaaaa gggggggactg gatgggctaa tttactccaa gaaaagacaa    360

gagatccttg atctgtgggt ctatcacaca caaggtttct tccctgattg ggataactac    420

acaccaggac caggggagag attcccactg tgctttggat ggtgcttcaa gctagtacca    480

gtagatccac aggaggtgga agaggccact gaaggagaga acacctgttt gctgcaccct    540

ataagccagc atggaatgga ggatgaagag agagaagtat taaagtggaa gtttgacagt    600

cgcctggcat acaagcacgt agcccgagag ctgcatccgg agttttacaa agactgctga    660
```

<210> SEQ ID NO 73
<211> LENGTH: 1485
<212> TYPE: DNA
<213> ORGANISM: Human immunodeficiency virus type 1
<220> FEATURE:
<223> OTHER INFORMATION: isolate=96ZM651.8; gene=gag

<400> SEQUENCE: 73

```
atgggtgcga gagcgtcaat attaagaggg ggaaaattag ataaatggga aaaaattagg     60

ctaaggccag gggaaagaa acgctatatg ataaaacacc tagtatgggc aagcagggag    120

ctggaaagat ttgcgcttaa ccctggcctt ttagaaacat cagaaggctg taaacaaata    180

atgaaacagc tacaaccagc tcttcagaca ggaacggagg aacttagatc attatacaac    240

acagtagcaa ctctctattg tgtacatgaa ggggtagagg tacgagacac caaggaagcc    300

ttagacagga tagaggaaga acaaaacaaa attcagcaaa aaatacagca aaaaacacag    360

caagcggctg acggaaaggt cagtcaaaat tatcctatag tgcagaatct ccaagggcaa    420

atggtacacc agaaactatc acctagaact ttgaatgcat gggtaaaagt aatagaagaa    480

aaagctttta gcccagaggt aatacccatg tttacagcat tatcagaagg agccacccca    540

caagatttaa acaccatgtt aaatacagtg gggggacatc aagcagccat gcaaatgtta    600

aaagatacta tcaatgagga ggctgcagaa tgggatagat tacatccagt gcatgcaggg    660

cctattgcac caggccaaat gagagaacca aggggaagtg atatagcagg aactactagt    720

accctccaag aacagatagc atggatgaca agtaatcccc ctattccagt gggagacatc    780

tataaaagat ggataattct ggggttaaat aaaatagtaa gaatgtatag ccctgtcagc    840

attttggaca taaaacaagg gccaaaggaa ccctttagag actatgtaga ccggttcttc    900

aaaactttaa gagctgaaca ggctacacaa gaagtaaaaa attggatgac agacaccttg    960
```

-continued

```
ttggtccaaa atgcaaaccc agattgcaag accattttaa aagcattagg accaggggct   1020

acattagaag aaatgatgac agcatgtcaa ggagtgggag gacctagcca caaagcaaga   1080

gtgttggctg aggcaatgag ccaaacaaat agtgtaaaca tactgatgca gaaaagcaat   1140

tttaaaggaa ataaaagaat ggttaaatgt tttaactgtg gtaaggaagg gcacatagcc   1200

agaaattgca gggcccctag gaaaaagggc tgttggaaat gtggaaagga gggacaccaa   1260

atgaaagact gtactgagag gcaggctaat tttttaggga aaatttggcc ttcccacaag   1320

ggaaggccag ggaatttcct tcagaacagg ccagagccaa cagccccacc agcagagagc   1380

ttcaggttcg aggagacaac cccgctccg aagcaggagt cgaaagacag ggaagcctta   1440

acttccctca aatcactctt tggcagcgac cccttgtctc aataa                   1485
```

<210> SEQ ID NO 74
<211> LENGTH: 3000
<212> TYPE: DNA
<213> ORGANISM: Human immunodeficiency virus type 1
<220> FEATURE:
<223> OTHER INFORMATION: isolate=96ZM651.8; gene=pol

<400> SEQUENCE: 74

```
ttttttaggg aaaatttggc cttcccacaa gggaaggcca gggaatttcc ttcagaacag     60

gccagagcca acagccccac cagcagagag cttcaggttc gaggagacaa cccccgctcc    120

gaagcaggag tcgaaagaca gggaagcctt aacttccctc aaatcactct ttggcagcga    180

ccccttgtct caataaaggt aggggggccaa ataaaggagg ctctcttaga cacgggagca    240

ggtgatacag tattagaaga aataaatttg ccaggcaaat ggaaaccaaa aatgatagga    300

ggaattggag gctttatcga agtaagacaa tatgatcaaa tacctatgga aatttgtgga    360

aaaaaggcta taggtacagt attagtagga cctacacctg tcaacataat tggaagaaat    420

atgttgactc agcttggatg cacactaaat tttccaatta gtcctattga aactgtacca    480

gtaaaattaa agccaggaat ggatggccca aaggttaaac aatggccatt gacagaagag    540

aaaataaaag ctttaacagc aatttgtgaa gaaatggaga aggaaggaaa aattacaaaa    600

attgggcctg aaaatccata taacactcca gtatttgcca taaaaaagaa ggacagtact    660

aagtggcgaa aattagtaga tttcagggaa ctcaataaaa gaactcaaga cttttgggaa    720

gttcaattag gaataccaca cccagcaggg ttaaaaaaga aaaaatcagt gacagtactg    780

gatgtggggg atgcatattt ttcagttcct ttagatgaaa gcttcaggaa atatactgca    840

ttcaccatac ctagtacaaa caatgaaaca ccagggatta gatatcaata taatgtgctt    900

ccacagggat ggaaaggatc accagcaata ttccagagta gcatgacaaa aatcttagag    960

cccttcaggg cacaaaatcc agacatagtc atctatcaat atatggatga cctgtatgta   1020

ggatctgact tagaaatagg gcaacataga gcaaaaatag aagagttaag agaacatcta   1080

ttaaagtggg gatttaccac accagacaag aaacatcaga aagaaccccc atttctttgg   1140

atggggtatg aactccatcc tgacaaatgg acagtacagc ctatacagct ggcagaaaaa   1200

gatagctgga ctgttaatga tatacagaag ttagtgggaa aattaaactg ggcaagtcag   1260

atttacgcag ggattaaagt aaggcaactt tgtaaactcc ttaggggagc caaagcacta   1320

acagacatag taccactaac tgaagaagca gaattagaat tggcagagaa caaggaaatt   1380

ttaaaagaac cagtacatgg ggtatattat gacccatcaa aagacttgat agctgaaata   1440

cagaaacaag ggcatgacca atggacatat caaatttacc aggaaccatt caaaaatctg   1500
```

-continued

```
aaaacaggga agtatgcaaa aatgaggaca gcccacacta atgatgtaaa acagttaaca   1560
gaggcagtgc aaaaaatagc cctggagagc atagtaatat ggggaaagat tcctaaattt   1620
agactaccca tccaaaaaga aacatgggaa acatggtgga cagactattg gcaagccacc   1680
tggattcctg agtgggagtt tgttaatacc cctctcttag taaaattatg gtaccagctg   1740
gagaaagaac ccatagtagg agcagaaacc ttctatgtag atggagcagc caatagggaa   1800
actaaattag gaaaagcagg gtatattact gacagaggaa ggcaaaaaat tgttactcta   1860
actgaaacaa caaatcagaa gactgaatta caagcaattt acctagcttt gcaagattca   1920
ggatcagaag taaacatagt aactgactca cagtatgcgt taggaatcat tcaagcacat   1980
ccagataaga gtgaatcaga gttagtcaac caaataatag aacaattaat aaagaaggaa   2040
agggtctacc tgtcatgggt accagcacat aaaggaattg gaggtaatga acaggtagat   2100
aaattagtaa gcaagggaat caggaaagtg ctgtttctag atggaataga caaggctcaa   2160
gaagagcatg aaaaatatca caacaattgg agagcaatgg ctagtgaatt taatctacca   2220
ccagtagtag caaaagaaat agtagctagt tgtgataaat gtcagcaaaa aggggaagcc   2280
acacatggac aagtagactg tagtccaggg atatggcaat tagactgtac acatttagaa   2340
ggaaaaatca tcctggtagc agtccatgta gccagtggct acatagaagc agaggttatc   2400
ccagcagaaa caggacaaga aacagcatac tatatattaa aattagcagg aagatggcca   2460
gtcaaagtaa tacatacaga caatggtagc aattttacca gtgctgcagt taaggcagcc   2520
tgttggtggg caggtatcaa acaagaattt ggaattccct acaatccaca aagtcaggga   2580
gtagtagaat ccatgaataa agaattaaag aaaatcatag ggcaggtaag agatcaggct   2640
gagcatctta aaacagcagt acaaatggca gtattcattc acaattttaa aagaaaaagg   2700
gggattgggg ggtacagtgc aggggaaaga ataatagaca taatagcaac agacatacaa   2760
accaaagaac tacaaaaaca aattataaac attcaaaaat ttcgggttta ttacagagac   2820
agcagagacc ccatttggaa aggaccagcc aaactactct ggaaaggtga aggggcagta   2880
gtaatacaag ataatagtga cataaaagtg gtaccaagga ggaaagcaaa aatcattagg   2940
gactatggaa aacagatggc aggcgctgat tgtgtggcag gtagacagga tgaggattag   3000
```

<210> SEQ ID NO 75
<211> LENGTH: 579
<212> TYPE: DNA
<213> ORGANISM: Human immunodeficiency virus type 1
<220> FEATURE:
<223> OTHER INFORMATION: isolate=96ZM651.8; gene=vif

<400> SEQUENCE: 75

```
atggaaaaca gatggcaggc gctgattgtg tggcaggtag acaggatgag gattagaaca     60
tggaatagtt tagtaaagca ccatatgtat atttcacgga aagctaatgg atggttttac    120
agacatcatt atgaaagcag acatccaagg gtaagttcag aagtacatat cccattaggg    180
gatgctaaat tagtaataaa aacatattgg ggtttgcaaa caggagaaag agattggcat    240
ttgggtcatg gagtctccat agaatggaga ttgagaagat atagcacaca agtagaccct    300
ggcctggcag accagctaat tcatatgcac tattttgatt gttttgcaga ctctgccata    360
agaaaagcca tattaggaca catagttatt cctaggtgtg actatcaagc aggacataat    420
aaggtaggat ctctgcaata cttggcactg acagcattga taaaaccaaa aaagagaaag    480
ccacctctgc ctagtgttag gaaattagta gaggatagat ggaacaattc ccagaagacc    540
aagggccgca gagggaacca tacagtgagt ggacactag                           579
```

<210> SEQ ID NO 76
<211> LENGTH: 291
<212> TYPE: DNA
<213> ORGANISM: Human immunodeficiency virus type 1
<220> FEATURE:
<223> OTHER INFORMATION: isolate=96ZM651.8; gene=vpr

<400> SEQUENCE: 76
atggaacaat tcccagaaga ccaagggccg cagagggaac catacagtga gtggacacta 60
gagattctag aggaactcaa gcaggaagct gtcagacact ttcctagacc atggctccat 120
agcttaggac aacatatcta tgaaacttat ggggatactt ggactggagt cgaggctata 180
ataagaatac tgcaacaact actgtttatt catttcagaa ttgggtgcca gcacagcaga 240
ataggcatgg ttcgacagag aagagcgaga aatggagcca gtagatccta g 291

<210> SEQ ID NO 77
<211> LENGTH: 2666
<212> TYPE: DNA
<213> ORGANISM: Human immunodeficiency virus type 1
<220> FEATURE:
<223> OTHER INFORMATION: isolate=96ZM651.8; gene=tat

<400> SEQUENCE: 77
atggagccag tagatcctag catagagccc tggaaccatc caggaagtca gcctaaaact 60
gcttgtaata agtgttattg caaacgctgt agctatcatt gtctagtttg ctttcagaca 120
aaaggcttag gcatttcata tggcaggaag aagcggagac agcgacgcag cactcctcct 180
agcagcgagg accatcaaga tcctatatca aagcagtaag tatatgtaat gttagattta 240
ctagcaagag taaattatag agtaggagta ggagcattga tagtagcact actcatagca 300
atagttgtgt ggaccatagc atatatagaa tataggaagc tgttaagaca aagaaaaata 360
gactggttaa ttaaaagaat tagggaaaga gcagaagaca gtggcaatga gagtgaggga 420
gatactgagg aattggcaac gatggtggac atggggcatc ttaggctttt ggatgttaat 480
gatttgtaat gtgtggggga acttgtgggt cacagtctat tatggggtac ctgtgtggaa 540
agaagcaaaa actactctat tctgtgcatc agatgctaaa tcatatgaga aagaagtgca 600
taatgtctgg gctacacatg cctgtgtacc cacagacccc aacccacaag aaatagtttt 660
gggaaatgta acagaaaatt ttaacatgtg gaaaaatgac atggtggatc agatgcatga 720
ggatataatc agtttatggg atcaaagcct aaagccatgt gtaaagttga ccccactctg 780
tgtcacttta aattgtacag aggttaatgt taccagaaat gttaataata gcgtggttaa 840
taataccaca aatgttaata atagcatgaa tggagacatg aaaaattgct ctttcaacat 900
aaccacagaa ctaaaagata agaaaaagaa tgtgtatgca ctttttttata aacttgatat 960 agtatcactt aatgagactg acgactctga gactggcaac tctagtaaat attatagatt 1020
aataaattgt aatacctcag ccctaacaca agcctgtcca aaggtctctt ttgacccaat 1080
tcctatacat tattgtgctc cagctggtta tgcgattcta aagtgtaata ataagacatt 1140
caatgggaca ggaccatgcc ataatgtcag cacagtacaa tgtacacatg gaattaagcc 1200
agtggtatca actcaactac tgttaaatgg tagcctagca gaagaaggga taataattag 1260
atctgaaaat ctgacaaaca atgtcaaaac aataatagta catcttaata gatctataga 1320
aattgtgtgt gtaagaccca acaataatac aagacaaagt ataagaatag gaccaggaca 1380
aacattctat gcaacaggag acataatagg agacataaga caagcacatt gtaacattag 1440

-continued

```
taggactaac tggactaaga ctttacgaga ggtaaggaac aaattaagag aacacttccc   1500

taataaaaac ataacattta aaccatcctc aggaggggac ctagaaatta caacacatag   1560

ctttaattgt agaggagaat ttttctattg caatacatcg ggcctgttta gtataaatta   1620

tacagaaaat aatacagatg gtacacccat cacactccca tgcagaataa gacaaattat   1680

aaatatgtgg caggaagtag gacgagcaat gtacgcccct cccattgaag gaaacatagc   1740

atgtaaatca gatatcacag ggctactatt ggttcgggat ggaggaagca caaatgatag   1800

cacaaataat aacacagaga tattcagacc tgcaggagga gatatgaggg acaattggag   1860

gagtgaattg tataagtata aagtggtaga aattaagcca ttgggaatag cacccactga   1920

ggcaaaaagg agagtggtgg agagagaaaa aagagcagtg ggaataggag ctgtgttcct   1980

tgggttcttg ggagcagcag gaagcactat gggcgcagcg tcaataacgc tgacggcaca   2040

ggccagacaa gtgttgtctg gtatagtgca acagcaaagc aatttgctga gggctataga   2100

ggcgcaacag catctgttgc aactcacggt ctggggcatt aagcagctcc agacaagagt   2160

cctggctata gaaagatacc taaaggatca acagctccta ggactttggg gctgctctgg   2220

aaaactcatc tgcaccactg ctgtgccttg gaacatcagt tggagtaata aatctaaaac   2280

agatatttgg gataacatga cctggatgca gtgggataga gaaattagta attacacaaa   2340

cacaatatac aggttgcttg aggactcgca gagccagcag gagcaaaatg aaaaagattt   2400

attagcattg gacagttgga acaatctgtg gaattggttt gacataacaa aatggctgtg   2460

gtatataaaa atatttataa tgatagtagg aggcttaata ggtttgagaa taatttttgc   2520

tgtactctct atagtgaata gagttaggca gggatactca cctttgtcgt ttcagaccct   2580

tatcccgaac ccaagggaac ccgacaggcc aggaagaatc gaagaagaag gtggagagca   2640

agacaaagag agatccgtgc gattag                                         2666
```

```
<210> SEQ ID NO 78
<211> LENGTH: 2684
<212> TYPE: DNA
<213> ORGANISM: Human immunodeficiency virus type 1
<220> FEATURE:
<223> OTHER INFORMATION: isolate=96ZM651.8; gene=rev

<400> SEQUENCE: 78
```

```
atggcaggaa gaagcggaga cagcgacgca gcactcctcc tagcagcgag gaccatcaag     60

atcctatatc aaagcagtaa gtatatgtaa tgttagattt actagcaaga gtaaattata    120

gagtaggagt aggagcattg atagtagcac tactcatagc aatagttgtg tggaccatag    180

catatataga atataggaag ctgttaagac aaagaaaaat agactggtta attaaaagaa    240

ttagggaaag agcagaagac agtggcaatg agagtgaggg agatactgag gaattggcaa    300

cgatggtgga catggggcat cttaggcttt tggatgttaa tgatttgtaa tgtgtggggg    360

aacttgtggg tcacagtcta ttatggggta cctgtgtgga aagaagcaaa aactactcta    420

ttctgtgcat cagatgctaa atcatatgag aaagaagtgc ataatgtctg ggctacacat    480

gcctgtgtac ccacagaccc caacccacaa gaaatagttt tgggaaatgt aacagaaaat    540

tttaacatgt ggaaaaatga catggtggat cagatgcatg aggatataat cagtttatgg    600

gatcaaagcc taaagccatg tgtaaagttg accccactct gtgtcacttt aaattgtaca    660

gaggttaatg ttaccagaaa tgttaataat agcgtggtta ataataccac aaatgttaat    720

aatagcatga atggagacat gaaaaattgc tctttcaaca taaccacaga actaaaagat    780

aagaaaaaga atgtgtatgc actttttttat aaacttgata tagtatcact taatgagact    840
```

-continued

```
gacgactctg agactggcaa ctctagtaaa tattatagat taataaattg taatacctca    900
gccctaacac aagcctgtcc aaaggtctct tttgacccaa ttcctataca ttattgtgct    960
ccagctggtt atgcgattct aaagtgtaat aataagacat tcaatgggac aggaccatgc   1020
cataatgtca gcacagtaca atgtacacat ggaattaagc cagtggtatc aactcaacta   1080
ctgttaaatg gtagcctagc agaagaaggg ataataatta gatctgaaaa tctgacaaac   1140
aatgtcaaaa caataatagt acatcttaat agatctatag aaattgtgtg tgtaagaccc   1200
aacaataata caagacaaag tataagaata ggaccaggac aaacattcta tgcaacagga   1260
gacataatag gagacataag acaagcacat tgtaacatta gtaggactaa ctggactaag   1320
actttacgag aggtaaggaa caaattaaga gaacacttcc ctaataaaaa cataacattt   1380
aaaccatcct caggaggggga cctagaaatt acaacacata gctttaattg tagaggagaa   1440
tttttctatt gcaatacatc gggcctgttt agtataaatt atacagaaaa taatacagat   1500
ggtacaccca tcacactccc atgcagaata agacaaatta taaatatgtg gcaggaagta   1560
ggacgagcaa tgtacgcccc tcccattgaa ggaaacatag catgtaaatc agatatcaca   1620
gggctactat tggttcggga tggaggaagc acaaatgata gcacaaataa taacacagag   1680
atattcagac ctgcaggagg agatatgagg gacaattgga ggagtgaatt gtataagtat   1740
aaagtggtag aaattaagcc attgggaata gcacccactg aggcaaaaag gagagtggtg   1800
gagagagaaa aaagagcagt gggaatagga gctgtgttcc ttgggttctt gggagcagca   1860
ggaagcacta tgggcgcagc gtcaataacg ctgacggcac aggccagaca agtgttgtct   1920
ggtatagtgc aacagcaaag caatttgctg agggctatag aggcgcaaca gcatctgttg   1980
caactcacgg tctggggcat taagcagctc cagacaagag tcctggctat agaaagatac   2040
ctaaaggatc aacagctcct aggactttgg ggctgctctg gaaaactcat ctgcaccact   2100
gctgtgcctt ggaacatcag ttggagtaat aaatctaaaa cagatatttg ggataacatg   2160
acctggatgc agtgggatag agaaattagt aattacacaa acacaatata caggttgctt   2220
gaggactcgc agagccagca ggagcaaaat gaaaaagatt tattagcatt ggacagttgg   2280
aacaatctgt ggaattggtt tgacataaca aaatggctgt ggtatataaa aatatttata   2340
atgatagtag gaggcttaat aggtttgaga ataatttttg ctgtactctc tatagtgaat   2400
agagttaggc agggatactc acctttgtcg tttcagaccc ttatcccgaa cccaagggaa   2460
cccgacaggc caggaagaat cgaagaagaa ggtggagagc aagacaaaga gagatccgtg   2520
cgattagtga gcggattctt agcacttgcc tgggacgacc tacggagcct gtgcctcttc   2580
agctaccacc gattgagaga cttcatattg gtgacagcga gagcggtgga gcttctgaga   2640
cgcagcagtc tcaagggact acagaggggg tgggaagccc ttaa                    2684
```

<210> SEQ ID NO 79
<211> LENGTH: 261
<212> TYPE: DNA
<213> ORGANISM: Human immunodeficiency virus type 1
<220> FEATURE:
<223> OTHER INFORMATION: isolate=96ZM651.8; gene=vpu

<400> SEQUENCE: 79

```
atgttagatt tactagcaag agtaaattat agagtaggag taggagcatt gatagtagca     60
ctactcatag caatagttgt gtggaccata gcatatatag aatataggaa gctgttaaga    120
caaagaaaaa tagactggtt aattaaaaga attagggaaa gagcagaaga cagtggcaat    180
```

-continued

```
gagagtgagg gagatactga ggaattggca acgatggtgg acatggggca tcttaggctt    240

ttggatgtta atgatttgta a                                              261


<210> SEQ ID NO 80
<211> LENGTH: 2607
<212> TYPE: DNA
<213> ORGANISM: Human immunodeficiency virus type 1
<220> FEATURE:
<223> OTHER INFORMATION: isolate=96ZM651.8; gene=env

<400> SEQUENCE: 80

atgagagtga gggagatact gaggaattgg caacgatggt ggacatgggg catcttaggc     60

ttttggatgt taatgatttg taatgtgtgg gggaacttgt gggtcacagt ctattatggg    120

gtacctgtgt ggaaagaagc aaaaactact ctattctgtg catcagatgc taaatcatat    180

gagaaagaag tgcataatgt ctgggctaca catgcctgtg tacccacaga ccccaaccca    240

caagaaatag ttttgggaaa tgtaacagaa aattttaaca tgtggaaaaa tgacatggtg    300

gatcagatgc atgaggatat aatcagttta tgggatcaaa gcctaaagcc atgtgtaaag    360

ttgaccccac tctgtgtcac tttaaattgt acagaggtta atgttaccag aaatgttaat    420

aatagcgtgg ttaataatac cacaaatgtt aataatagca tgaatggaga catgaaaaat    480

tgctctttca acataaccac agaactaaaa gataagaaaa agaatgtgta tgcacttttt    540

tataaacttg atatagtatc acttaatgag actgacgact ctgagactgg caactctagt    600

aaatattata gattaataaa ttgtaatacc tcagccctaa cacaagcctg tccaaaggtc    660

tcttttgacc caattcctat acattattgt gctccagctg gttatgcgat tctaaagtgt    720

aataataaga cattcaatgg gacaggacca tgccataatg tcagcacagt acaatgtaca    780

catggaatta agccagtggt atcaactcaa ctactgttaa atggtagcct agcagaagaa    840

gggataataa ttagatctga aaatctgaca aacaatgtca aaacaataat agtacatctt    900

aatagatcta tagaaattgt gtgtgtaaga cccaacaata atacaagaca aagtataaga    960

ataggaccag gacaaacatt ctatgcaaca ggagacataa taggagacat aagacaagca   1020

cattgtaaca ttagtaggac taactggact aagactttac gagaggtaag gaacaaatta   1080

agagaacact tccctaataa aaacataaca tttaaaccat cctcaggagg ggacctagaa   1140

attacaacac atagctttaa ttgtagagga gaatttttct attgcaatac atcgggcctg   1200

tttagtataa attatacaga aaataataca gatggtacac ccatcacact cccatgcaga   1260

ataagacaaa ttataaatat gtggcaggaa gtaggacgag caatgtacgc ccctcccatt   1320

gaaggaaaca tagcatgtaa atcagatatc acagggctac tattggttcg ggatggagga   1380

agcacaaatg atagcacaaa taataacaca gagatattca gacctgcagg aggagatatg   1440

agggacaatt ggaggagtga attgtataag tataaagtgg tagaaattaa gccattggga   1500

atagcaccca ctgaggcaaa aaggagagtg gtggagagag aaaaaagagc agtgggaata   1560

ggagctgtgt tccttgggtt cttgggagca gcaggaagca ctatgggcgc agcgtcaata   1620

acgctgacgg cacaggccag acaagtgttg tctggtatag tgcaacagca aagcaatttg   1680

ctgagggcta tagaggcgca acagcatctg ttgcaactca cggtctgggg cattaagcag   1740

ctccagacaa gagtcctggc tatagaaaga tacctaaagg atcaacagct cctaggactt   1800

tggggctgct ctggaaaact catctgcacc actgctgtgc cttggaacat cagttggagt   1860

aataaatcta aaacagatat ttgggataac atgacctgga tgcagtggga tagagaaatt   1920

agtaattaca caaacacaat atacaggttg cttgaggact cgcagagcca gcaggagcaa   1980
```

-continued aatgaaaaag atttattagc attggacagt tggaacaatc tgtggaattg gtttgacata 2040
acaaaatggc tgtggtatat aaaaatattt ataatgatag taggaggctt aataggtttg 2100
agaataattt ttgctgtact ctctatagtg aatagagtta ggcagggata ctcacctttg 2160
tcgtttcaga cccttatccc gaacccaagg gaacccgaca ggccaggaag aatcgaagaa 2220
gaaggtggag agcaagacaa agagagatcc gtgcgattag tgagcggatt cttagcactt 2280
gcctgggacg acctacggag cctgtgcctc ttcagctacc accgattgag agacttcata 2340
ttggtgacag cgagagcggt ggagcttctg agacgcagca gtctcaaggg actacagagg 2400
gggtgggaag cccttaagta tctgggaagt cttgtgcagt attggggtct ggagctaaaa 2460
aagagtgcta ttagtctact tgataccata gcaatagcag tagctgaagg aacagatagg 2520
attatagaat taatacaagg aatttgtaga gctatccgca acgtacctag aagaataaga 2580
cagggctttg aaacagcttt gctataa 2607

<210> SEQ ID NO 81
<211> LENGTH: 621
<212> TYPE: DNA
<213> ORGANISM: Human immunodeficiency virus type 1
<220> FEATURE:
<223> OTHER INFORMATION: nef

<400> SEQUENCE: 81 atgggggggca agtggtcaaa aagcagtata gttggatggc ctgctgtaag agagagaata 60
agaagaactg agccagcagc agagggagta ggagcagcgt ctcaagactt agataaatat 120
ggagcactta caagcagcaa cacaagtacc actaatgctg cttgtgcctg gctggaagca 180
caagaggagg aagaagttgg ctttccagtc agacctcagg tgcctttaag accaatgact 240
tataaggcag cagtcgatct cagcttcttt ttaaaagaaa agggggggact ggaagggtta 300 atttactcta agaaaaggca agaaatcctt gatttgtggg tctatcacac acaaggcttc 360
ttccctgact ggcaaaacta cacaccggga ccaggggtca gatatccact gacctttgga 420
tggtgcttca agctagtgcc agttgatcca ggggaagtag aagaggccaa cgaaggagaa 480
aacaactgtc tgctacaccc tatgagccag caaggaatgg atgatgatca cagagaagta 540
ttaaagtgga agtttgacag tcacctagca cataaacaca tggcccgaga gctacatccg 600
gagtattaca aagactgctg a 621

<210> SEQ ID NO 82
<211> LENGTH: 1496
<212> TYPE: DNA
<213> ORGANISM: Human immunodeficiency virus type 1
<220> FEATURE:
<223> OTHER INFORMATION: isolate=96ZM751.3; gene=gag

<400> SEQUENCE: 82
atgggtgcga gagcgtcaat attaagaggc ggaaaattag atgaatggga aagaattagg 60
ttaaggccag gggaaaaaaa gcactatatg atgaaacact taatatgggc aagcagggag 120
ctggaaagat ttgcacttaa ccctggcctt ttagagacat cagaaggctg taaacaaata 180
atacaacagc tacaaccagc tctccagaca ggaacagagg aacttaggtc attatataat 240
acagtagcaa ctctctattg tgtacatgaa aagataaagg tacgagacac caaggaagcc 300
ctagacaaga tagaggaaga acaaaacaaa agtcaacaaa aaatacaaaa aacagaagcg 360
actggcggaa aggtcagtca aaattatcct atagtgcaga atctccaagg gcaaatggta 420

-continued

```
caccaggcta tatcacctag aactttgaat gcatgggtaa aagtaataga ggagaagggt    480

ttcaacccag aggtaatacc catgtttaca gcattatcag aaggagccac cccacaagat    540

ctaaacacca tgttaaatac agtgggggga catcaagcag ccatgcaaat gttaaaagat    600

accatcaatg aggaagctgc agaatgggat aggttacatc cagtacatgc agggcctatt    660

gcaccaggcc aaataagaga accaagggga agtgacatag caggaactac tggtaccctt    720

caggaacaaa tagcatggat gacaaataac ccacctattc cagtgggaga catctataaa    780

agatggataa ttctggggtt aaataaaata gtaagaatgt acagccctgt cagcattctg    840

gacataaaac aaggaccaaa ggaacccttt agggactatg tagatcggtt ctttaaaact    900

ttaagagctg aacaagctac acaagatgta aaaattggat gacagacacc ttgttggttc    960

aaaatgcgaa cccagattgt aagaccattt taagggcatt aggaccaggg gctacattag   1020

aagaaatgat gacagcatgt cagggagtgg ggggacctgg ccacaaagca agagttttgg   1080

ctgaagcaat gagccaagta aacaatacaa acataatgat gcagaaaagc aattttaaag   1140

gccctaaaag aattgttaaa tgtttcaact gtggcaggga agggcatata gccaggaatt   1200

gcagggctcc tgggaaaaaa ggctgttgga aatgtggaaa ggaaggacac caaatgaaag   1260

actgtactga gagacaggct aattttttag ggaaaatttg gccttcccag aaggggaggc   1320

cggggaactt ccttcagaac agaccagagc caacagcccc accagctcca acagccccac   1380

cagcagagag cttcaggttc gaggagacaa cccctgcccc gaggcaggag cagaaagaca   1440

aggaaccctt aactgccctc aaatcactct ttggcagcga ccccttgtct caataa       1496
```

<210> SEQ ID NO 83
<211> LENGTH: 3017
<212> TYPE: DNA
<213> ORGANISM: Human immunodeficiency virus type 1
<220> FEATURE:
<223> OTHER INFORMATION: isolate=96AM751.3; gene=pol

<400> SEQUENCE: 83

```
tttttaggg aaaatttggc cttcccagaa ggggaggccg gggaacttcc ttcagaacag      60

accagagcca acagccccac cagctccaac agccccacca gcagagagct tcaggttcga    120

ggagacaacc cctgccccga ggcaggagca gaaagacaag gaacccttaa ctgccctcaa    180

atcactcttt ggcagcgacc ccttgtctca ataaaagtag gggtcagat aaaggaggct    240

ctcttggata caggagcaga tgatacagta ttagaagaaa taaatttgcc aggaaaatgg    300

aaaccaaaaa tgataggagg aattggaggt tttatcaaag taagacagta tgatcaaata    360

cttatagaaa tttgtggaaa aaaggctata ggtacagtat tagtaggacc tacacctgtc    420

aacataattg ggagaaatat gttgacccag cttggctgca cactaaattt tccaattagt    480

cctattgaaa ctgtaccagt aaaattaaag ccaggaatgg atggcccaag ggtcaaacaa    540

tggccattga cagaagaaaa aataaaagca ttaacagcaa tttgtgaaga aatggaaaag    600

gaaggaaaaa ttacaaaaat tggccctgag aatccatata acactccagt atttgccata    660

aaaaagaagg acagtactaa gtggagaaaa ttagtagatt tcagggaact caataaaaga    720

actcaggact tttgggaagt tcaattagga ataccacacc cagcggggtt aaaaaagaaa    780

aagtcagtga cagtactgga tgtgggggat gcgtattttt cagttccttt agatgaaggc    840

ttcaggaaat atactgcatt caccatacct agtataaaca atgaaacacc tgggattaga    900

tatcaatata atgtgcttcc acagggatgg aaaggatcac catcaatatt ccagagtagc    960

atgataaaaa tcttagagcc ctttaggaca caaaacccag aaatagttat ctatcaatat   1020
```

-continued atggatgact tgtatgtagg atctgattta gaaatagggc aacacagagc aaaaatagag 1080
gagttaagag aacacctatt gagatgggga tttactacac cagacaagaa gcatcagaaa 1140
gagcccccat ttctttggat ggggtatgaa ctccatcctg acaaatggac agtacagcct 1200
ataaagctgc cagaaaagga gagctggact gtcaatgata tacagaagtt agtgggaaaa 1260
ttaaactggc aagtcagatt tacgcaggga ttaaagtaag gcaactgtgt aaactcctta 1320
ggggagccaa agcactaaca gacatagtac cattgactga agaggcagaa ttagaattgg 1380
cagagagcag ggaaattcta aaagaaccag tacatggagt atattatgac ccatcaaaag 1440
acttaatagc tgaaatacag aaacaagggc atgaccaatg gacatatcaa gtttaccaag 1500
aaccattcaa aaatctgaaa acaggaaagt atgcaaaaat gaggactgcc cacactaatg 1560
atgtaaaaca gttaacagag gcggtgcaaa aaatagccat ggaaagcata gtaatatggg 1620
gaaagattcc taaatttagg ctacccattc aaaaagaaac atgggagaca tggtggacag 1680
actattggca agccacctgg attcctgagt gggagtttgt taatactccc cccctagtaa 1740
aattatggta ccagctggag aaagaaccca tagcaggagc agaaacttac tatgtagatg 1800
gagcagccaa tagggaaact aaaataggaa aagcagggta tgttactgac agaggaaggc 1860
aaaaaattgt tactctaact gaaacaacaa atcaaaagac tgaattacaa gcaattcagt 1920
tagctttgca ggattcagga tcagaagtaa acatagtaac agactcacag tatgcattag 1980
gaatcatcca agcacaacca gataagagtg aatcagaatt agtcaatcaa ataatagaac 2040
agttgataaa aaaggaaagg gtttacctgt catgggtacc agcacacaaa ggaattggag 2100
gaaatgaaca agtagataaa ttggtaagta gtggaatcag gaaagtgctg tttctagatg 2160
gaatagataa ggctcaagaa gagcatgaaa aatatcacag caattggaga gcaatggcta 2220
gtgagtttaa tctgccaccc atagtagcaa aagaaatagt agccagctgt gataaatgtc 2280
agctaaaagg ggaagccata catggacaag tagactgtag tccaggaata tggcaattag 2340
attgtaccca tttagaagga aaagtcatct tggtagcagt ccatgtagcc agtggttaca 2400
tagaagcaga ggtcacccca gcggaaacag gacaagaaac agcacttttc atactaaaat 2460
tagcaggaag atggccagtc aaagtagtac atacagacaa tggcagtaat ttcaccagtg 2520
ctgcagtcaa ggcagcctgt tggtgggcag gtatccacca ggaatttgga attccctaca 2580
atccccaaag tcaaggagta gtagaatcca tgaataaaga attaaagaaa attatagggc 2640
aggtaagaga tcaagctgag caccttaaga cagcagtaca aatggcagta ttcattcaca 2700
attttaaaag aaaagggggg attgggggt acagtgcagg ggaaagaata atagacataa 2760
tagcaacaga catacaaact agagaattac aaaaacaaat tataaaaatt caaaattttc 2820
gggtttatta cagagacagc agagacccta tttggaaagg accagccaaa ctactctgga 2880
aaggtgaagg ggcagtagta atacaagata atagtgacat aaaggtaata ccaaggagga 2940
aagcaaaaat cattagggac tatggaaaac agatggcagg tactgatagt gtggcaggta 3000
gacaggatga agattag 3017

<210> SEQ ID NO 84
<211> LENGTH: 579
<212> TYPE: DNA
<213> ORGANISM: Human immunodeficiency virus type 1
<220> FEATURE:
<223> OTHER INFORMATION: isolate=96ZM751.3; gene=vif

<400> SEQUENCE: 84

-continued

```
atggaaaaca gatggcaggt actgatagtg tggcaggtag acaggatgaa gattagaaca      60

tggaatagtt tagtaaagca ccatatgtat gtttcaaaaa gaactggtag atggttttac     120

agacatcatt atgaaagcag acatccaaaa ataagttcag aagtacacat cccattaggg     180

gatgccaaat tagtaataaa aacatattgg gggctgcatc caggggaaag agaatggcat     240

ttgggtcatg gagtctccat agaatggaga ttgagaagat acagcacaca agtagaccct     300

ggcctggcag accagctaat tcatatgcat tattttaatt gttttgcaga ctctgccata     360

agaaaagccc tactaggaca tatagttatt cctaggtgtg attatcaagc aggacataat     420

aaggtaggat ccctacaata cttggcactg acagcattga taaaaccaaa aaagataaag     480

ccacctttac ctagtgttag gaaattagta gaggatagat ggaacaagcc ccagaaaacc     540

aagggccgca gagggaacca tataatgaat gggcactag                            579
```

<210> SEQ ID NO 85
<211> LENGTH: 291
<212> TYPE: DNA
<213> ORGANISM: Human immunodeficiency virus type 1
<220> FEATURE:
<223> OTHER INFORMATION: isolate=96ZM751.3; gene=vpr

<400> SEQUENCE: 85

```
atggaacaag ccccagaaaa ccaagggccg cagagggaac catataatga atgggcacta      60

gagcttttag aggagctcaa gcaggaagct gtcagacact ttcctagaac atggctccat     120

aacttaggac aacatatcta ccaaacctac ggggatactt ggacgggggt tgaagctcta     180

ataagaatac tgcaacaact actgtttatt catttcagaa ttggatgcca acatagcaga     240

ataggcatta tgcgacagag aagagcaaga aatggagcca gtagatccta g              291
```

<210> SEQ ID NO 86
<211> LENGTH: 2646
<212> TYPE: DNA
<213> ORGANISM: Human immunodeficiency virus type 1
<220> FEATURE:
<223> OTHER INFORMATION: isolate=96AM751.3; gene=tat

<400> SEQUENCE: 86

```
atggagccag tagatcctag actagagccc tggaatcatc caggaagtca acctaaaact      60

ccttgtaata agtgttattg taaacactgt agctatcatt gtctagtttg ctttcagaca     120

aaaggcttag gcatttccta tggcaggaag aagcggagac aacgacgaag cgctcctcca     180

agcagtgagg atcatcaaaa tcctatatca aagcagtaag tacaaagtaa tagatgtaat     240

gttaaattta gaagcaagag tagattatag aataggagta ggagcattaa tagcagcact     300

aatcatagca atagctgtgt ggatcatagt atatatagaa tatagaaaat tgtcaagaca     360

aagaaaaata gaccggttaa ttaaaagaat tagagaaagg gcagaagaca gtggcaatga     420

gagtgaaggg gataatgagg aattggcaac aatggtggat atggggcatc ttaggctttt     480

ggatgctatt gatgtgtaat gcaatgggga aattgtgggt cacagtctac tatggggtac     540

ctgtgtggaa agaagcaaaa actactttat tttgtgcatc agatgctaaa gcatatgaga     600

cagaagtgca taatgtttgg gctacacatg cctgtgtacc cacagacccc aacccacaag     660

aaatggtttt ggaaaatgta acagaaaagt ttaacatgtg ggaaaataac atggtggatc     720

agatgcatga ggatataatc agtttatggg accaaagcct aaagccatgt gtaaagttga     780

ccccactctg tgtcacttta aactgtactg ctaatataac caacaatgct aatataacca     840

acaatgctaa tataaccaac tataataatg aaactgacat gagaaattgc tctttcaata     900
```

-continued taaccacaga attaagagat aagaggaggc aagtagatgc actcttttat aaacttgata 960
tagtaccaat taatgagaat tccagtgaat atagattaat aaattgtaat acctcggcca 1020
taacacaagc atgtccaaag gttacttttg acccaatccc tatacattat tgtgctccag 1080
ctggttatgc gattctaaag tgtaacaata agacattcaa tggaacagga ccatgcaata 1140
atgtcagcac agtacaatgt acacatggaa ttaagccagt agtatcaact caattactgt 1200
taaatggtag tctagcagaa gaagagataa taattagatc taaaaatatg acagacaatg 1260
ccaaaataat aatagtacat cttaatgaat ctgtagaaat tgtgtgtaca agacccaaca 1320
ataatacaag gaaaagtgtg aggataggac caggacaaac attctatgca acaggagaaa 1380
taataggaaa tataagacaa gcatattgta acatcagtga aggcaaatgg aataacactc 1440
tacaaagggt aggtgaaaaa ttaagaaaat acttccctaa taaaacaata agctttgcac 1500
catcctcagg aggggaccta gaaattacaa cacatagctt taattgtaga ggagaatttt 1560
tctattgcaa tacatcaaaa ctgtttaatg gtacgtttaa tggtacaaac acttctaatg 1620
atagaagtaa ttcgaccatt acgcttcaat gcagaataaa acaaattaca aacatgtggc 1680
agggggtagg acaagcaatg tatgctcctc caattaaagg aaacataaca tgtaaatcaa 1740
atatcacagg actactatta acacgtgatg gagggacaaa tgacacagag acaccagaga 1800
cattcagacc tggaggagga gacatgaagg acaattggag aagtgaatta tataaatata 1860
aagtggtaga aattaagcca ttaggagtag cacccactaa ggcacgaagg agagtggtgg 1920
agagagaaaa aagagcagta ggaataggag ctgtgttcct tgggttcttg ggagcagcag 1980
gaagcactat gggcgcagca tcaataacgc tgacggtaca ggtcagacaa ttattgtctg 2040
gtatagtgca acagcaaagc aatttgctga gggctataga ggcgcaacag cacatgttgc 2100
aactcacagt ctggggcatt aagcagctcc aggcaagagt cttggctata gaaagatacc 2160
taaaggatca acagctccta gggatttggg gctgctctgg aaaactcatc tgcaccactg 2220
ctgtgccttg gaactctagt tggagcaaca aatctgaacg ggagatttgg gataacatga 2280
cctggatgca gtgggataga gaaattaata attacacaga aacaatatat aggttgcttg 2340
aagtctcgca aaaccagcag gaaaataatg aaagggattt actagcattg gacagttgaa 2400
aaaatctgtg gaattggttt aatataacaa attggctgtg gtatataaaa atattcataa 2460
tgataatagg aggcttgata ggtttaagaa taatttttgc tgtgctctct atagtaaata 2520
gagttaggca ggggtactca cctttgtcgt tgcagaccct tatcccaacc ccgagggaac 2580
cagacaggct cggaagaatc gaagaagaag gtggagagca agacagagac agatcaattc 2640
gattag 2646

<210> SEQ ID NO 87
<211> LENGTH: 2631
<212> TYPE: DNA
<213> ORGANISM: Human immunodeficiency virus type 1
<220> FEATURE:
<223> OTHER INFORMATION: isolate=96ZM751.3; gene=rev

<400> SEQUENCE: 87
atggcaggaa gaagcggaga caacgacgaa gcgctcctcc aagcagtgag gatcatcaaa 60
atcctatatc aaagcagtaa gtacaaagta atagatgtaa tgttaaattt agaagcaaga 120
gtagattata gaataggagt aggagcatta atagcagcac taatcatagc aatagctgtg 180
tggatcatag tatatataga atatagaaaa ttgtcaagac aaagaaaaat agaccggtta 240

-continued

```
attaaaagaa ttagagaaag ggcagaagac agtggcaatg agagtgaagg ggataatgag    300
gaattggcaa caatggtgga tatggggcat cttaggcttt tggatgctat tgatgtgtaa    360
tgcaatgggg aaattgtggg tcacagtcta ctatggggta cctgtgtgga aagaagcaaa    420
aactacttta ttttgtgcat cagatgctaa agcatatgag acagaagtgc ataatgtttg    480
ggctacacat gcctgtgtac ccacagaccc caacccacaa gaaatggttt tggaaaatgt    540
aacagaaaag tttaacatgt gggaaaataa catggtggat cagatgcatg aggatataat    600
cagtttatgg gaccaaagcc taaagccatg tgtaaagttg accccactct gtgtcacttt    660
aaactgtact gctaatataa ccaacaatgc taatataacc aacaatgcta atataaccaa    720
ctataataat gaaactgaca tgagaaattg ctctttcaat ataaccacag aattaagaga    780
taagaggagg caagtagatg cactctttta taaacttgat atagtaccaa ttaatgagaa    840
ttccagtgaa tatagattaa taaattgtaa tacctcggcc ataacacaag catgtccaaa    900
ggttactttt gacccaatcc ctatacatta ttgtgctcca gctggttatg cgattctaaa    960
gtgtaacaat aagacattca atggaacagg accatgcaat aatgtcagca cagtacaatg   1020
tacacatgga attaagccag tagtatcaac tcaattactg ttaaatggta gtctagcaga   1080
agaagagata ataattagat ctaaaaatat gacagacaat gccaaaataa taatagtaca   1140
tcttaatgaa tctgtagaaa ttgtgtgtac aagacccaac aataatacaa ggaaaagtgt   1200
gaggatagga ccaggacaaa cattctatgc aacaggagaa ataataggaa atataagaca   1260
agcatattgt aacatcagtg aaggcaaatg gaataacact ctacaaaggg taggtgaaaa   1320
attaagaaaa tacttcccta ataaaacaat aagctttgca ccatcctcag gaggggacct   1380
agaaattaca acacatagct ttaattgtag aggagaattt ttctattgca atacatcaaa   1440
actgtttaat ggtacgttta atggtacaaa cacttctaat gatagaagta attcgaccat   1500
tacgcttcaa tgcagaataa aacaaattac aaacatgtgg caggggggtag gacaagcaat  1560
gtatgctcct ccaattaaag gaaacataac atgtaaatca aatatcacag gactactatt   1620
aacacgtgat ggagggacaa atgacacaga gacaccagag acattcagac ctggaggagg   1680
agacatgaag gacaattgga gaagtgaatt atataaatat aaagtggtag aaattaagcc   1740
attaggagta gcacccacta aggcacgaag gagagtggtg gagagagaaa aaagagcagt   1800
aggaatagga gctgtgttcc ttgggttctt gggagcagca ggaagcacta tgggcgcagc   1860
atcaataacg ctgacggtac aggtcagaca attattgtct ggtatagtgc aacagcaaag   1920
caatttgctg agggctatag aggcgcaaca gcacatgttg caactcacag tctggggcat   1980
taagcagctc caggcaagag tcttggctat agaaagatac ctaaaggatc aacagctcct   2040
agggatttgg ggctgctctg gaaaactcat ctgcaccact gctgtgcctt ggaactctag   2100
ttggagcaac aaatctgaac gggagatttg ggataacatg acctggatgc agtgggatag   2160
agaaattaat aattacacag aaacaatata taggttgctt gaagtctcgc aaaaccagca   2220
ggaaaataat gaaagggatt tactagcatt ggacagttga aaaaatctgt ggaattggtt   2280
taatataaca aattggctgt ggtatataaa aatattcata atgataatag gaggcttgat   2340
aggtttaaga ataatttttg ctgtgctctc tatagtaaat agagttaggc aggggtactc   2400
acctttgtcg ttgcagaccc ttatcccaac cccgagggaa ccagacaggc tcggaagaat   2460
cgaagaagaa ggtggagagc aagacagaga cagatcaatt cgattagtga acggattctt   2520
agcacttgtc tgggacgacc tccggagcct gtgccttttc agctaccacc gcttgagaga   2580
cttcatattg attgcagcga ggggactaca gagggggtgg gaaactctta a              2631
```

<210> SEQ ID NO 88
<211> LENGTH: 261
<212> TYPE: DNA
<213> ORGANISM: Human immunodeficiency virus type 1
<220> FEATURE:
<223> OTHER INFORMATION: isolate=96AM751.3; gene=vpu

<400> SEQUENCE: 88

```
atgttaaatt tagaagcaag agtagattat agaataggag taggagcatt aatagcagca     60
ctaatcatag caatagctgt gtggatcata gtatatatag aatatagaaa attgtcaaga    120
caaagaaaaa tagaccggtt aattaaaaga attagagaaa gggcagaaga cagtggcaat    180
gagagtgaag gggataatga ggaattggca acaatggtgg atatggggca tcttaggctt    240
ttggatgcta ttgatgtgta a                                              261
```

<210> SEQ ID NO 89
<211> LENGTH: 2544
<212> TYPE: DNA
<213> ORGANISM: Human immunodeficiency virus type 1
<220> FEATURE:
<223> OTHER INFORMATION: isolate=96AM751.3; gene=env

<400> SEQUENCE: 89

```
atgagagtga aggggataat gaggaattgg caacaatggt ggatatgggg catcttaggc     60
ttttggatgc tattgatgtg taatgcaatg ggaaattgt gggtcacagt ctactatggg    120
gtacctgtgt ggaaagaagc aaaaactact ttattttgtg catcagatgc taaagcatat    180
gagacagaag tgcataatgt ttgggctaca catgcctgtg tacccacaga ccccaaccca    240
caagaaatgg ttttggaaaa tgtaacagaa aagtttaaca tgtgggaaaa taacatggtg    300
gatcagatgc atgaggatat aatcagttta tgggaccaaa gcctaaagcc atgtgtaaag    360
ttgaccccac tctgtgtcac tttaaactgt actgctaata taaccaacaa tgctaatata    420
accaacaatg ctaatataac caactataat aatgaaactg acatgagaaa ttgctctttc    480
aatataacca cagaattaag agataagagg aggcaagtag atgcactctt ttataaactt    540
gatatagtac caattaatga gaattccagt gaatatagat taataaattg taatacctcg    600
gccataacac aagcatgtcc aaaggttact tttgacccaa tccctataca ttattgtgct    660
ccagctggtt atgcgattct aaagtgtaac aataagacat tcaatggaac aggaccatgc    720
aataatgtca gcacagtaca atgtacacat ggaattaagc cagtagtatc aactcaatta    780
ctgttaaatg gtagtctagc agaagaagag ataataatta gatctaaaaa tatgacagac    840
aatgccaaaa taataatagt acatcttaat gaatctgtag aaattgtgtg tacaagaccc    900
aacaataata caaggaaaag tgtgaggata ggaccaggac aaacattcta tgcaacagga    960
gaaataatag gaaatataag acaagcatat tgtaacatca gtgaaggcaa atggaataac   1020
actctacaaa gggtaggtga aaaattaaga aaatacttcc ctaataaaac aataagcttt   1080
gcaccatcct caggaggga cctagaaatt acaacacata gctttaattg tagaggagaa   1140
tttttctatt gcaatacatc aaaactgttt aatggtacgt ttaatggtac aaacacttct   1200
aatgatagaa gtaattcgac cattacgctt caatgcagaa taaaacaaat tacaaacatg   1260
tggcaggggg taggacaagc aatgtatgct cctccaatta aaggaaacat aacatgtaaa   1320
tcaaatatca caggactact attaacacgt gatggaggga caaatgacac agagacacca   1380
gagacattca gacctggagg aggagacatg aaggacaatt ggagaagtga attatataaa   1440
```

-continued

```
tataaagtgg tagaaattaa gccattagga gtagcaccca ctaaggcacg aaggagagtg   1500

gtggagagag aaaaaagagc agtaggaata ggagctgtgt tccttgggtt cttgggagca   1560

gcaggaagca ctatgggcgc agcatcaata acgctgacgg tacaggtcag acaattattg   1620

tctggtatag tgcaacagca aagcaatttg ctgagggcta tagaggcgca acagcacatg   1680

ttgcaactca cagtctgggg cattaagcag ctccaggcaa gagtcttggc tatagaaaga   1740

tacctaaagg atcaacagct cctagggatt tggggctgct ctggaaaact catctgcacc   1800

actgctgtgc cttggaactc tagttggagc aacaaatctg aacgggagat ttgggataac   1860

atgacctgga tgcagtggga tagagaaatt aataattaca cagaaacaat atataggttg   1920

cttgaagtct cgcaaaacca gcaggaaaat aatgaaaggg atttactagc attggacagt   1980

tgaaaaaatc tgtggaattg gtttaatata acaaattggc tgtggtatat aaaaatattc   2040

ataatgataa taggaggctt gataggttta agaataattt ttgctgtgct ctctatagta   2100

aatagagtta ggcaggggta ctcacctttg tcgttgcaga cccttatccc aaccccgagg   2160

gaaccagaca ggctcggaag aatcgaagaa gaaggtggag agcaagacag agacagatca   2220

attcgattag tgaacggatt cttagcactt gtctgggacg acctccggag cctgtgcctt   2280

ttcagctacc accgcttgag agacttcata ttgattgcag cgaggggact acagaggggg   2340

tgggaaactc ttaagtatct ggggagtctt gtacagtatt ggggtctaga gctaaaaaag   2400

agtgctatta gtttgcttga tactatagca atagcagtag ctgaaggaac agatagaatt   2460

atagaattaa cacaaagaat ttgtagagct atccgcaacg tacctagaag aataagacag   2520

ggctttgaag cagctttgca ataa                                          2544
```

<210> SEQ ID NO 90
<211> LENGTH: 624
<212> TYPE: DNA
<213> ORGANISM: Human immunodeficiency virus type 1
<220> FEATURE:
<223> OTHER INFORMATION: isolate=96AM751.3; gene=nef

<400> SEQUENCE: 90

```
atgggaggca agtggtcaaa acgcagtata gttggatggc ctaaagtaag agaaagaata     60

gcaagaactg atccagcagc agagggagta ggagcagcgt ctcaagactt agataaatat    120

ggggcactta caagcagtaa cacaagtacc aataatgctg attgtgcctg gctggaagcg    180

caagaggagg agggagaagt aggctttcca gtcagacctc aggtaccttt aagaccaatg    240

acttataagt cagcatttga tctcagcttc tttttaaaag aaaagggggg actggatggg    300

ttaatttact gtaagaaaag acaagaaatc ctcgatttgt gggtctatca cacacaaggc    360

tacttccctg attggcaaaa ctatacaccg ggaccaggga tcagatatcc actgaccttt    420

ggatggtgct acaagctagt gccagttgac ccaagggaag tagaagaagc caacgaagga    480

gaggacaact gtttgctaca ccctataagc cagcatggaa tagaagatga agacagagaa    540

gtattaaggt ggaagtttga cagttcccta gcacgcagac acatggcccg cgagctacat    600

ccggagtatt acaaagactg ctga                                           624
```

<210> SEQ ID NO 91
<211> LENGTH: 1491
<212> TYPE: DNA
<213> ORGANISM: Human immunodeficiency virus type 1
<220> FEATURE:
<223> OTHER INFORMATION: isolate=94CY017.41; gene=gag

<400> SEQUENCE: 91

-continued

```
atgggtgcga gagcgtcaat attaagcggg ggaaaattag atgcttggga gaaaattcgg      60
ttaaggccag gggaaagaa aaaatataga ctgaaacatt tggtatgggc aagcagggag      120
ctggagaaat tctcaattaa ccctggcctt ttagaaacac cagagggatg tagacaaata     180
ataaggcagt tacaaccagc tctccaaaca ggaacagaag aacttaaatc attatataat     240
acagtagtag tcctctactg ggtacatcaa agggtagatg taaaagacac caaggaagct     300
ctagataaaa tagaggaaga acaaaacaag cagaaaacac agcatgcagc agctgacaca     360
gggaacagca gcagtcaaaa ttatcccata gtgcaaaatg cacaagggca aatggtacac     420
caggctatat cacctaggac gttgaatgcc tgggtcaaag tagtagaaga aaaggctttc     480
agcccagaag taatacctat gtttacagca ttatcagaag gagccacccc acaagactta     540
aatactatgc taaacacagt gggggacat caagcagcta tgcaaatgtt aaaagatacc      600
atcaatgagg aagctgcaga atgggacagg gtacatccag tacatgcagg gcctattcca     660
ccaggccaga tgagagaacc aaggggaagt gacatagcag gaactactag tacccttcag     720
gaacaaatag gttggatgac cagcgatcca cccatcccag tgggagaaat ttataaaaga     780
tggataatcc tgggattaaa taaaatagta agaatgtata gccctgtcag cattttggac     840
ataagacaag ggccaaaaga accctttaga gattatgtgg ataggttctt taaaactcta     900
agagctgagc aagccacaca ggaggtaaaa aactggatga cggacacctt gctggtccaa     960
aatgcgaacc cagattgtag atccatcttg agagcattag gaccaggggc ctcattagaa    1020
gaaatgatga cagcatgtca gggagtggga ggacccagcc ataaagcaag ggttttggct    1080
gaagcaatga gccatgtaca aagtacaaat acaaacataa tgatgcagag aggcaatttt    1140
aggggtcaaa aaagaattaa gtgtttcaac tgtggcaagg aaggacacct agccagaaat    1200
tgcagggccc ctaggaaaaa gggctgctgg aaatgtggaa aggaaggaca tcaaatgaaa    1260
gattgcactg agagacaggc taattttta gggaaaattt ggccttccaa caaagggagg     1320
ccaggaaatt ttcctcagag cagaacagag ccaacagccc caccagcaga gaacttgaga    1380
atgggggaag agataacctc ctccctgaag caggaactgg agaccaggga accatacaat    1440
cctgcaattt ccctcaaatc actctttggc aacgacccct tgttacagta a             1491
```

<210> SEQ ID NO 92
<211> LENGTH: 3012
<212> TYPE: DNA
<213> ORGANISM: Human immunodeficiency virus type 1
<220> FEATURE:
<223> OTHER INFORMATION: isolate=94CY017.41; gene=pol

<400> SEQUENCE: 92

```
tttttaggg aaaatttggc cttccaacaa agggaggcca ggaaattttc ctcagagcag      60
aacagagcca acagccccac cagcagagaa cttgagaatg ggggaagaga taacctcctc     120
cctgaagcag gaactggaga ccagggaacc atacaatcct gcaatttccc tcaaatcact     180
ctttggcaac gaccccttgt tacagtaaag atagagggac agctaaaaga agctctatta     240
gatacaggag cagatgatac agtgttagaa gaaataaatt tgccaggaaa atggaaacca     300
aaaatgatag gggaattgg aggttttatc aaagtaagac aatatgatca gatagctata      360
gaaatttgtg gaaaaagggc cataggtaca gtattagtag gacctacccc tgtcaacata     420
atcggaagaa atatgttggt tcagcttggt tgtactttaa attttccaat tagtcctatt     480
gaaactgtac cagtaaaatt aaagccagga atggatggtc caaaggttaa acaatggcca     540
```

-continued

```
ttgacagaag aaaaaataaa agcattaaca gaaatctgta aagaaatgga aaaggaagga    600
aaaatttcaa aaattgggcc tgaaaatcca tacaacactc cagtgtttgc tataaagaaa    660
aaagacagca ctaaatggag aaaattagta gattttagag aactcaataa gagaactcaa    720
gacttctggg aagttcagtt aggaatacca catccagcag gattaaaaaa gaaaaaagca    780
gtaacagtac ttgatgtggg ggacgcatat ttttccgttc ccttacatga agacttcaga    840
aaatatactg cattcaccat acctagtacc aacaatgaga caccaggagt taggtatcag    900
tacaatgtac ttccacaggg atggaaagga tcaccagcaa tattccagag tagcatgaca    960
aagatcttag agccctttag atcaaagaat acagaattaa tcatctacca atacatggat   1020
gacttgtatg taggatctga tttagaaata agccagcata gagtaaaaat agaggaatta   1080
agggctcact tattgaaatg ggattttat acaccagaca aaaaacatca gaaagaacct   1140
ccatttcttt ggatgggata tgagcttcat cctgacaaat ggacagtcca gcctataaag   1200
ctgccagaaa aagacagctg gactgtcaat gatatacaga aattagtagg gaaattaaat   1260
tgggcaagtc agatttatgc agggattaaa gtaaagcaac tgtgtaaact ccttagagga   1320
gccaaagcac taacagacat agtaacactg actaaagaag cagagttaga attagaagag   1380
aacagggaaa ttttaaaaac ccctgtacat ggggtatact atgacccatc aaaagactta   1440
atagcagaaa tacagaaaca agggcaagac caatggacat atcaaattta tcaggaaccc   1500
tttaagaatc tgaaaacagg gaaatatgca aaaaggaggt ccacccacac taatgatata   1560
aaacagttaa cagaagcagt acaaaaaata accatggaaa gcatagtgat atggggaaag   1620
actcctaaat ttaaattacc catacaaaag gaaacatggg agacatggtg ggcggagtat   1680
tggcaggcta cctggattcc tgagtgggag tttgtcaata cccctcctct agtaaaactg   1740
tggtaccagt tagaaaaaga acccatagca ggagcagaaa ctttctatgt agatggggca   1800
gctaatagag agactaaact aggaaaggca gggtatgtca ctgacagagg aagacaaaaa   1860
attgtctccc tgacggagac aacaaatcaa aagactgaat tacatgcaat ctatttggct   1920
ttacaggatt caggattaga agtgaacata gtgacagatt cacagtatgc attaggaatc   1980
attcaagcac aaccagaaag gagtgaatca gagatagtca atcaaataat agaaaaatta   2040
atagaaaagg aaagggtcta cctatcatgg gtaccagcac acaaagggat tggaggaaat   2100
gaacaagtag acaaattagt cagttctgga atcaggaaag tgctattttt agatgggata   2160
gataaggctc aagaggaaca tgaaagatat cacagcaatt ggagagcaat ggctcatgac   2220
tttaatctac cacctgtagt agcaaaagaa atagtagcta gctgtgataa atgtcagcta   2280
aaaggggaag ccatgcatgg acaagtagac tgtagtccag gaatatggca actagattgc   2340
acacatcttg aaggaaaagt tatcctggtg gcagtccatg tggccagtgg ctatatagaa   2400
gcagaagtca tcccaacaga aacaggacag gatacagcat actttatatt aaaactagca   2460
ggaagatggc cagtaaaagt aatacataca gacaatgggc ccaatttcat cagtgcaaca   2520
gttaaggcag cctgttggtg ggcaggtatc caacaagaat ttgggattcc ctacaatccc   2580
caaagtcaag gagtagtgga atctatgaat aaagaattaa agaaaatcat agggcaggta   2640
agagatcaag ctgaacacct taagacagca gtacaaatgg cagtattcat tcacaatttt   2700
aaaagaaaag gggggattgg gggatacagt gcaggggaaa gaataataga cataatagca   2760
acagatatac aaactaaaga actacaaaga caaattacaa aaattcaaaa ttttcgggtt   2820
tattacaggg acagcagaga tccaatttgg aaaggaccag caaaactcct ttggaaaggt   2880
gaaggggcag tagtaataca agacaatagt gacataaagg tagtaccaag aagaaaagca   2940
```

-continued aagatcatta gggattatgg aaaacagatg gcaggtgatg attgtgtggc aggtagacag 3000
gatgaggatt ag 3012

<210> SEQ ID NO 93
<211> LENGTH: 579
<212> TYPE: DNA
<213> ORGANISM: Human immunodeficiency virus type 1
<220> FEATURE:
<223> OTHER INFORMATION: isolate=94CY017.41; gene=vif

<400> SEQUENCE: 93
atggaaaaca gatggcaggt gatgattgtg tggcaggtag acaggatgag gattagaaca 60
tggaacagtt tagttaaaca tcatatgtat atttcaagga aagctaaagg ttgggtctat 120
aaacatcact atgaaagcag aaatccaaga ataagttcag aagtacacat cccgctaggg 180
gaggctagaa taatagtaag aacatattgg ggtctgcaca taggagaaaa agactggcac 240
ttgggtcatg gagtctccat agaatggagg caaaacaggt atcatacaca aatagaccct 300
gatctggcag accatctaat ccatctgtat tattttgact gtttttcaga atctgccata 360
aggaaagcca taataggaga aatagttagt cctaggtgtg aatatcaagc aggacataac 420
aaggtagggt ctctgcaata tttggcattg aaagcagtag tagcttcaac aaggacaaag 480
ccacctttgc ctagtgttag gaaattagta gaggatagat ggaacaagcc ccagaagacc 540
aagggccaca gagggagcca tacaatgaat ggatgttag 579

<210> SEQ ID NO 94
<211> LENGTH: 291
<212> TYPE: DNA
<213> ORGANISM: Human immunodeficiency virus type 1
<220> FEATURE:
<223> OTHER INFORMATION: isolate=94CY017.41; gene=vpr

<400> SEQUENCE: 94
atggaacaag ccccagaaga ccaagggcca cagagggagc catacaatga atggatgtta 60
gaactgttag aggagctcaa gcaggaagct gttagacatt tccctaggca ctggctacat 120
ggcctaggac aatacatcta taatacctat ggggatacct gggaaggagt tgaagttatc 180
ataagatatc tgcaacaact actgtttgtc catttcagaa ttgggtgcca acatagcagg 240
ataggcatta ttcgaagaag aagagtaagg gatggagcca gtagacccta a 291

<210> SEQ ID NO 95
<211> LENGTH: 2655
<212> TYPE: DNA
<213> ORGANISM: Human immunodeficiency virus type 1
<220> FEATURE:
<223> OTHER INFORMATION: isolate=94CY017.41; gene=tat

<400> SEQUENCE: 95
atggagccag tagaccctaa actagagccc tggaaccatc cgggaagtca gcctaaaact 60
gcttgtacca aatgttattg taaacgctgt tgctatcatt gccagttgtg ctttataaac 120
aaaggcttag gcatctccta cggcaggaag aagcgacgac cccgacgaaa gccttctcca 180
agcaataagg accatcaaaa tcctatacca aagcagtaag tagtagtaat taatatatgt 240
aatgttacct ttagtaatat tggcaatagt aggactgata gtagctttaa tcttagcaat 300
agttgtatgg actatagtat tcatagaata taagaaaatt aagaagcaaa ggaaaataga 360
ctggttaatc aaaagaataa gtgagagagc agaagacagt ggcaatgaga gtgatgggga 420

-continued

```
cacagaggaa ctatcagcac ttgtggagag ggggcatctt gattttgggg atgttaataa    480

tgtgtaaagc tacagatttg tgggtcacag tatactatgg agtacctgtg tggaaagatg    540

cagataccat cctattttgt gcatcagatg ctaaagcata tgatacagaa gtgcataatg    600

tatgggccac acatgcctgt gtacccacag accccaaccc acaagaaata aacctggaaa    660

atgtaacaga aaattttaat atgtggaaaa ataacatggt agagcagatg caagaagata    720

taatcagctt atgggatcaa agcctaaagc catgtgtaaa attaaccccg ctctgcgtca    780

ttttaaattg tagcaatgcc aataccagca cccatagcaa tagcagtagc acccagagcc    840

ccattaatga agaaataaaa aactgctctt acaatactac cacaatacta agagataaga    900

cacaaaaagt ttattcactg ttttatagac ttgatgtagt acaacttgat gaaagtgaaa    960

ataagaatac atcaggtagt aatactctgt atagactaat aaattgtaat acctcaacca   1020

tcacacaagc gtgtccaaag gtaacctttg agccaattcc tatacattat tgtgccccag   1080

ctggttttgc gattctaaag tgtaaggatc cgagattcaa tggaacaggg tcatgcaaga   1140

atgttagctc agtacaatgt acacatggaa ttaaaccagt agcatcaact caactgctgt   1200

tgaatggcag tctagcagaa ggagggaaaa taatgattag atctgaaaat attacaaaca   1260

atgccaaaaa cataatagtt cagtttacta agcctgtact aattacttgt atcagaccca   1320

acaacaatac aagaaaaagt atacgctttg gaccaggaca agccttctat acaaatgaaa   1380

taatagggga cataagacaa gcacattgta atatcaacaa aacattatgg aatgacactt   1440

tacaaaaggt agctgaacaa ttaagagaga aattccctaa gaaaaccata atctttacta   1500

actcctcagg aggggaccca gaaattacaa cacttagttt taattgtgca ggagaatttt   1560

tctattgcaa tacaacaggc ctgtttaatg gtacgtggtg gaacaatggt acgtggaacg   1620

ggccctacac acctaataac accaatggaa gtataatcct cccatgcaga ataaaacaaa   1680

ttataaacat gtggcagaga gtaggaagag caatgtatgc ccctcccatt gcaggaataa   1740

taaagtgtac atcaaacatt acaggaataa tattgacaag agatggtggt aacaatggga   1800

ctaatgagac cttcagacct ggaggaggag atatgaggga caattggaga agtgaattat   1860

ataaatataa agtagtaaaa cttgaaccac taggagtagc acctaccagg gcaaaaagaa   1920

gagtggtgga gagagaaaaa agagcagttg gactgggagc tgtcttcctt gggttcttgg   1980

gagcagcagg aagcactatg ggcgcggcgt cactaacgct gacggtacag gccagacaat   2040

tattgtctgg tatagtgcaa cagcaaagca atttgctgca ggctatagaa gctcaacagc   2100

atctgttgaa actcacagtc tggggcatta aacagctcca ggcgagggtc ctggctgtgg   2160

aaagatacct aaaggatcaa cagctcctgg gaatttgggg ctgctctgga aaactcatct   2220

gcgccactac tgtgccctgg aacactagtt ggagtaataa gtctcaggat gagatttggg   2280

acaacatgac ctggttgcaa tgggataaag aaattagcaa ttacacaaac ataatatata   2340

ggttacttga agaatcgcaa aaccagcagg aaaagaatga gcaagactta ttggcattag   2400

acaaatgggc agatttgtgg agttggttca acatttcaca ctggctgtgg tatataagaa   2460

tatttataat gatagtagga ggcttgatag gattaagaat agtttttgct ataattactg   2520

tagtaaatag agttaggcag ggatactcac ctgtgtcatt tcagatccct accccaagcc   2580

cagagggtcc cgacaggccc agaggaaccg aagaaggagg tggagagcaa ggcagagaca   2640

gatcgattcg attag                                                    2655
```

<210> SEQ ID NO 96
<211> LENGTH: 2721

-continued

<212> TYPE: DNA
<213> ORGANISM: Human immunodeficiency virus type 1
<220> FEATURE:
<223> OTHER INFORMATION: isolate=94CY017.41; gene=rev

<400> SEQUENCE: 96
acggcaggaa gaagcgacga ccccgacgaa agccttctcc aagcaataag gaccatcaaa 60
atcctatacc aaagcagtaa gtagtagtaa ttaatatatg taatgttacc tttagtaata 120
ttggcaatag taggactgat agtagcttta atcttagcaa tagttgtatg gactatagta 180
ttcatagaat ataagaaaat taagaagcaa aggaaaatag actggttaat caaaagaata 240
agtgagagag cagaagacag tggcaatgag agtgatgggg acacagagga actatcagca 300
cttgtggaga gggggcatct tgattttggg gatgttaata atgtgtaaag ctacagattt 360
gtgggtcaca gtatactatg gagtacctgt gtggaaagat gcagatacca tcctattttg 420
tgcatcagat gctaaagcat atgatacaga agtgcataat gtatgggcca cacatgcctg 480
tgtacccaca gaccccaacc cacaagaaat aaacctggaa aatgtaacag aaaattttaa 540
tatgtggaaa aataacatgg tagagcagat gcaagaagat ataatcagct tatgggatca 600
aagcctaaag ccatgtgtaa aattaacccc gctctgcgtc attttaaatt gtagcaatgc 660
caataccagc acccatagca atagcagtag cacccagagc cccattaatg aagaaataaa 720
aaactgctct tacaatacta ccacaatact aagagataag acacaaaaag tttattcact 780
gttttataga cttgatgtag tacaacttga tgaaagtgaa aataagaata catcaggtag 840
taatactctg tatagactaa taaattgtaa tacctcaacc atcacacaag cgtgtccaaa 900
ggtaaccttt gagccaattc ctatacatta ttgtgcccca gctggttttg cgattctaaa 960
gtgtaaggat ccgagattca atggaacagg gtcatgcaag aatgttagct cagtacaatg 1020
tacacatgga attaaaccag tagcatcaac tcaactgctg ttgaatggca gtctagcaga 1080
aggagggaaa ataatgatta gatctgaaaa tattacaaac aatgccaaaa acataatagt 1140
tcagtttact aagcctgtac taattacttg tatcagaccc aacaacaata caagaaaaag 1200
tatacgcttt ggaccaggac aagccttcta tacaaatgaa ataatagggg acataagaca 1260
agcacattgt aatatcaaca aaacattatg gaatgacact ttacaaaagg tagctgaaca 1320
attaagagag aaattcccta agaaaaccat aatctttact aactcctcag gaggggaccc 1380
agaaattaca acacttagtt ttaattgtgc aggagaattt ttctattgca atacaacagg 1440
cctgtttaat ggtacgtggt ggaacaatgg tacgtggaac gggccctaca cacctaataa 1500
caccaatgga agtataatcc tcccatgcag aataaaacaa attataaaca tgtggcagag 1560
agtaggaaga gcaatgtatg cccctcccat tgcaggaata ataaagtgta catcaaacat 1620
tacaggaata atattgacaa gagatggtgg taacaatggg actaatgaga ccttcagacc 1680
tggaggagga gatatgaggg acaattggag aagtgaatta tataaatata aagtagtaaa 1740
acttgaacca ctaggagtag cacctaccag ggcaaaaaga agagtggtgg agagagaaaa 1800
aagagcagtt ggactgggag ctgtcttcct tgggttcttg ggagcagcag gaagcactat 1860
gggcgcggcg tcactaacgc tgacggtaca ggccagacaa ttattgtctg gtatagtgca 1920
acagcaaagc aatttgctgc aggctataga agctcaacag catctgttga aactcacagt 1980
ctggggcatt aaacagctcc aggcgagggt cctggctgtg gaaagatacc taaaggatca 2040
acagctcctg ggaatttggg gctgctctgg aaaactcatc tgcgccacta ctgtgccctg 2100
gaacactagt tggagtaata agtctcagga tgagatttgg gacaacatga cctggttgca 2160

-continued atgggataaa gaaattagca attacacaaa cataatatat aggttacttg aagaatcgca 2220
aaaccagcag gaaaagaatg agcaagactt attggcatta gacaaatggg cagatttgtg 2280
gagttggttc aacatttcac actggctgtg gtatataaga atatttataa tgatagtagg 2340
aggcttgata ggattaagaa tagtttttgc tataattact gtagtaaata gagttaggca 2400
gggatactca cctgtgtcat ttcagatccc taccccaagc ccagagggtc ccgacaggcc 2460
cagaggaacc gaagaaggag gtggagagca aggcagagac agatcgattc gattagtgaa 2520
cgggttcttc gcacttgcct gggacgacct acggagcctg tgcctcttca gttaccaccg 2580
cttgagagat tgcatattga ttgcagcgag gactgtggaa cttctgggac actgcagtct 2640
caagggactg agactggggt gggaaggtct caagaatctg tggaatcttc tgttatactg 2700
gggtcgggaa ctgaagaata g 2721

<210> SEQ ID NO 97
<211> LENGTH: 246
<212> TYPE: DNA
<213> ORGANISM: Human immunodeficiency virus type 1
<220> FEATURE:
<223> OTHER INFORMATION: isolate=94CY017.41; gene=vpu

<400> SEQUENCE: 97
atgttacctt tagtaatatt ggcaatagta ggactgatag tagctttaat cttagcaata 60
gttgtatgga ctatagtatt catagaatat aagaaaatta agaagcaaag gaaaatagac 120
tggttaatca aaagaataag tgagagagca gaagacagtg gcaatgagag tgatggggac 180
acagaggaac tatcagcact tgtggagagg gggcatcttg attttgggga tgttaataat 240
gtgtaa 246

<210> SEQ ID NO 98
<211> LENGTH: 2598
<212> TYPE: DNA
<213> ORGANISM: Human immunodeficiency virus type 1
<220> FEATURE:
<223> OTHER INFORMATION: isolate=94CY017.41; gene=env

<400> SEQUENCE: 98
atgagagtga tggggacaca gaggaactat cagcacttgt ggagaggggg catcttgatt 60
ttggggatgt taataatgtg taaagctaca gatttgtggg tcacagtata ctatggagta 120
cctgtgtgga aagatgcaga taccatccta ttttgtgcat cagatgctaa agcatatgat 180
acagaagtgc ataatgtatg ggccacacat gcctgtgtac ccacagaccc caacccacaa 240
gaaataaacc tggaaaatgt aacagaaaat tttaatatgt ggaaaaataa catggtagag 300
cagatgcaag aagatataat cagcttatgg gatcaaagcc taaagccatg tgtaaaatta 360
accccgctct gcgtcatttt aaattgtagc aatgccaata ccagcaccca tagcaatagc 420
agtagcaccc agagccccat taatgaagaa ataaaaaact gctcttacaa tactaccaca 480
atactaagag ataagacaca aaaagtttat tcactgtttt atagacttga tgtagtacaa 540
cttgatgaaa gtgaaaataa gaatacatca ggtagtaata ctctgtatag actaataaat 600
tgtaatacct caaccatcac acaagcgtgt ccaaaggtaa cctttgagcc aattcctata 660
cattattgtg ccccagctgg ttttgcgatt ctaaagtgta aggatccgag attcaatgga 720
acagggtcat gcaagaatgt tagctcagta caatgtacac atggaattaa accagtagca 780
tcaactcaac tgctgttgaa tggcagtcta gcagaaggag ggaaaataat gattagatct 840
gaaaatatta caaacaatgc caaaaacata atagttcagt ttactaagcc tgtactaatt 900

-continued

```
acttgtatca gacccaacaa caatacaaga aaaagtatac gctttggacc aggacaagcc     960
ttctatacaa atgaaataat aggggacata agacaagcac attgtaatat caacaaaaca    1020
ttatggaatg acactttaca aaaggtagct gaacaattaa gagagaaatt ccctaagaaa    1080
accataatct ttactaactc ctcaggaggg gacccagaaa ttacaacact tagttttaat    1140
tgtgcaggag aatttttcta ttgcaataca acaggcctgt ttaatggtac gtggtggaac    1200
aatggtacgt ggaacgggcc ctacacacct aataacacca atggaagtat aatcctccca    1260
tgcagaataa aacaaattat aaacatgtgg cagagagtag gaagagcaat gtatgcccct    1320
cccattgcag gaataataaa gtgtacatca aacattacag gaataatatt gacaagagat    1380
ggtggtaaca atgggactaa tgagaccttc agacctggag gaggagatat gagggacaat    1440
tggagaagtg aattatataa atataaagta gtaaaacttg aaccactagg agtagcacct    1500
accagggcaa aaagaagagt ggtggagaga gaaaaaaagag cagttggact gggagctgtc    1560
ttccttgggt tcttgggagc agcaggaagc actatgggcg cggcgtcact aacgctgacg    1620
gtacaggcca gacaattatt gtctggtata gtgcaacagc aaagcaattt gctgcaggct    1680
atagaagctc aacagcatct gttgaaactc acagtctggg gcattaaaca gctccaggcg    1740
agggtcctgg ctgtggaaag atacctaaag gatcaacagc tcctgggaat ttggggctgc    1800
tctggaaaac tcatctgcgc cactactgtg ccctggaaca ctagttggag taataagtct    1860
caggatgaga tttgggacaa catgacctgg ttgcaatggg ataaagaaat tagcaattac    1920
acaaacataa tatataggtt acttgaagaa tcgcaaaacc agcaggaaaa gaatgagcaa    1980
gacttattgg cattagacaa atgggcagat ttgtggagtt ggttcaacat ttcacactgg    2040
ctgtggtata taagaatatt tataatgata gtaggaggct tgataggatt aagaatagtt    2100
tttgctataa ttactgtagt aaatagagtt aggcagggat actcacctgt gtcatttcag    2160
atccctaccc caagcccaga gggtcccgac aggcccagag gaaccgaaga aggaggtgga    2220
gagcaaggca gagacagatc gattcgatta gtgaacgggt tcttcgcact tgcctgggac    2280
gacctacgga gcctgtgcct cttcagttac caccgcttga gagattgcat attgattgca    2340
gcgaggactg tggaacttct gggacactgc agtctcaagg gactgagact ggggtgggaa    2400
ggtctcaaga atctgtggaa tcttctgtta tactggggtc gggaactgaa gaatagtgct    2460
attagcttat ttgatactat agcagtagca gtagctgagt ggacagatag ggttatagaa    2520
atagggcaaa gagctttcag agctattctc aacataccta gaagaatcag acagggctta    2580
gaaagggctt tactataa                                                  2598
```

<210> SEQ ID NO 99
<211> LENGTH: 654
<212> TYPE: DNA
<213> ORGANISM: Human immunodeficiency virus type 1
<220> FEATURE:
<223> OTHER INFORMATION: isolate=94CY017.41; gene=nef

<400> SEQUENCE: 99

```
atggggggca agtggtcaaa aaggagcata ccaggatggc ctgctattag ggagagaatg      60
agaagaactc ctccaacagc acaaagaaca gaagcagtgt ctccagcagc accaggagta     120
ggagcagtgt ctcaagattt agctactcat ggagcagtca caagcagtaa tacagcagct     180
actaatcctg attgcgcctg ggtggaagcg caagaagagg agagtgaagt aggcttccca     240
gtcaggccac aggtaccttt aaggccaatg accttcaagg gagcgtttga tctcagcttc     300
```

-continued

```
tttttaaaag aaaaggggggg actggatggg ttaatttact cccagaaaag acaagacatc    360

cttgatatgt gggtctacca cacacaaggc tacttccctg attggcagaa ttacacacca    420

gggccaggga tcagataccc attaacattt ggatggtgct tcaagctagt accagtagag    480

ccatctgagg tagaagaagc tactcaggga gagaacaaca gcttattaca ccctatatgc    540

caacatggag tagatgaccc tgaaagagaa gtgttaagat gggagtttga tagaagcctg    600

gcacggagac acagagcccg agagctgcat ccggagtact acaaagactg ctga          654
```

<210> SEQ ID NO 100
<211> LENGTH: 1476
<212> TYPE: DNA
<213> ORGANISM: Human immunodeficiency virus type 1
<220> FEATURE:
<223> OTHER INFORMATION: isolate=94IN476.104; gene=gag

<400> SEQUENCE: 100

```
atgggtgcga gagcgtcaat attaagaggg ggaaaattag atagatggga aaaaattcgg     60

ttaaggccag gggaaagaa acattatatg ataaaacact tagtatgggc aagcagggag    120

ctggaaagat ttgcgcttaa ccctggcctt ttagagacgt cagacggatg taaacaaata    180

ataaaacagc tacatccagc tcttaagaca ggaacagagg aacttaggtc attattcaac    240

acagtagcaa ctctctattg tgtacatgca gggatagagg tacgagacac caaggaagcc    300

ttagacaaga tagaggaaga acaaaacaaa agtcagcaaa aaatacagca ggcaaaagag    360

gctgacggaa aggtcagtca aaattatcct atagtgcaaa atctccaagg gcaaatggta    420

caccagcccc tatcacctag aactttgaat gcgtgggtaa aagtaataga ggagaaggct    480

tttagcccag aggtaatacc catgttcaca gcattatcag aaggagccac cccctctgat    540

ttaaacacca tgttaaatac agtgggggga catcaagcag ccatgcaaat gttaaaagat    600

accatcaacg aggaggctgc ggaatgggat agattacatc cagtacatgc agggcctaat    660

ccaccaggcc agatgagaga accaagggga agtgatatag caggaactac tagtaccctt    720

caggaacaaa tagcatggat gacaggtaac ccacctattc cagtgggaga catctataaa    780

agatggataa ttctggggtt aaataaaata gtaagaatgt atagccctgt cagcattttg    840

gacataagac aagggccaaa ggaacccttt agagactatg tagaccggtt ctttaaaact    900

ttaagagctg aacaagctac acaagaagta aaaggttgga tgacagacac cttgttggtc    960

caaaatgcaa acccagattg taagaccatt ttaagagcat taggaccagg ggcttcatta   1020

gaagaaatgg tgacagcatg tcaaggagtg ggaggaccta gccacaaagc aagagtgttg   1080

gctgaggcaa tgagccaatc acatagtaac ataatgatgc agagaggcaa ttttaaaggc   1140

cctaaaagaa ttgttaaatg cttcaactgt ggcaaggaag ggcacatagc cagaaattgc   1200

agggccccta gaaaaagagg ctgttggaaa tgtgggcaag aaggacacca aatgaaagac   1260

tgtactgaga ggcaggctaa ttttttaggg aaaatttggc cttcccacaa ggggaggcca   1320

gggaatttcc ttcaaaacag gccagagcca acagccccac cagcagagag cttcaggttc   1380

aaggagacaa cccccgctcc gaagcaggag tcgaaagaca gggaaccctt aacttccctc   1440

aaatcactct ttggcagcga ccccttgtct caataa                             1476
```

<210> SEQ ID NO 101
<211> LENGTH: 3011
<212> TYPE: DNA
<213> ORGANISM: Human immunodeficiency virus type 1
<220> FEATURE:
<223> OTHER INFORMATION: isolate=94IN476.104; gene=pol -continued

<400> SEQUENCE: 101

```
tttttaggg aaaatttggc cttcccacaa ggggaggcca gggaatttcc ttcaaaacag    60
gccagagcca acagccccac cagcagagag cttcaggttc aaggagacaa cccccgctcc   120
gaagcaggag tcgaaagaca gggaaccctt aacttccctc aaatcactct ttggcagcga   180
ccccttgtct caataaaagt agggggccag ataaaggaag ctctcttaga cacaggagca   240
gatgatacag tattagaaga aatagctttg ccaggaagat ggaaaccaaa aatgatagga   300
ggaattggag gttttatcaa agtaagacag tatgatcaaa tacttataga aatttgtgga   360
aaaaaggcta taggtacagt attagtagga cctacacctg tcaacataat tggaagagat   420
atgttgactc agcttggatg cactctaaat tttccaatta gccccattga aactgtacca   480
gtaaaattaa agccaggaat ggatggccca aaggttaaac agtggccatt gacagaagag   540
aaaataaaag cattaacaga aatttgtaaa gaaatggaga aggaaggaaa aattacaaaa   600
attgggcctg aaaatccata taacactcca gtatttgcca taaaaaggaa ggacagtact   660
aagtggagaa aattagtaga tttcagggag ctcaataaaa gaactcaaga cttttgggaa   720
gttcaattag gaataccaca cccagcaggt ttaaaaaaga aaaaatcagt gacagtactg   780
gatgtggggg atgcatattt ttcagttcct ttagatgaag gcttcgggaa atatactgca   840
ttcaccatac ctagtataaa caatgaaaca ccagggatta gatatcaata taatgtgctt   900
ccacagggat ggaaaggatc accagcaata ttccagagta gcatgacaaa aatcttagag   960
ccctttaggg cacgaaatcc aaaaatagtc atctatcaat atatggatga cttgtatgta  1020
gggtctgact tagaaatagg gcatcataga gcaaaaatag aggagttaag agcacatcta  1080
ttaaagtggg gattcaccac accagataag aaacatcaga aagaaccccc atttctttgg  1140
atggggtatg aactccatcc tgacaaatgg acagtacagc ctataaagct gccagaaaag  1200
gatagctgga ctgtcaatga tatacagaag ttagtgggaa aattaaactg ggcaagtcag  1260
atttacccag ggattaaagt gaggcaactt tgtaaactcc ttagggggc caaagcacta  1320
acagacatag taccactaac tgaagaagca gaattagaat tagcagagaa cagggaaatt  1380
ctaaaagagc cagtacatgg agtatattat gacccatcaa aagacttaat agctgaaata  1440
cagaaacagg ggcatgacca atggacatat caaatttacc aagaaccatt caaaaatctg  1500
aaaacaggga agtatgcaaa aatgaggact gctcacacta atgatgtaaa acagttaaca  1560
gaggcagtgc aaaaaatagc catagaaagc atagtaatat gggaaagacc cctaaattta  1620
gactacccat ccaaaaagaa acgtgggaga catggtggac agactattgg caggccacct  1680
ggattcctga ttgggagttt gttaataccc ctcccctagt aaaattatgg taccagctag  1740
aaaaagaacc catagtagga gcagaaactt tctatgtaga tggagcagct aatagggaaa  1800
ctaaagtagg aaaagcaggg tatgttactg acagaggaag gcagaaaatt gtttctttaa  1860
ctgaaacaac aaatcagaag actgaattgc aagcaattca gctagctttg caagattcag  1920
gaacagaagt aaacatagta acagactcac agtatgcatt aggaatcatt caagcacaac  1980
cagataaaag tgaatcagag ttagtcaacc aaataataga acaattaata aacaaagaaa  2040
gagtctatct gtcatgggta ccagcacata aaggaattgg agggaatgaa caagtagata  2100
gattagtaag tagtggaatt aggaaagtac tgtttctaga tgggatagat aaggctcaag  2160
aagatcatga aaagtatcac agcaattgga gagcaatggc taatgagttt aatctgccac  2220
ccatagtagc aaaagaaata gtagctagct gtgataaatg ccagctaaaa ggggaagcca  2280
```

-continued

```
tgcatggaca agtagaccgt agcccaggga tatggcaatt agattgtaca catctagaag   2340

gaaaaatcat cctggtagca gtccatgtag ccagtggcta catagaagca gaggttatcc   2400

cagcagaaac aggacaagaa acagcatact atatactaaa attagcagga agatggccag   2460

tcaaagtaat acatacagac aatggtagta atttcaccag tgctgcagtt aaggcagcct   2520

gttggtgggc aggtatccaa caggaatttg gaattcccta caatccccaa agccagggag   2580

tagtagaatc catgaataaa gaattaaaga aaattatagg gcaggtaaga gaacaagctg   2640

agcaccttaa gacagcagta caaatggcag tattcattca caattttaaa agaaaagggg   2700

ggattggggg gtacagtgca ggggaaagaa caatagacat aatagcaaca gacatacaaa   2760

ctaaagaatt acaaaaccaa attacaaaaa ttcaaaattt tcgggtttat tacagagaca   2820

gcagagaccc catttggaaa ggaccagcca aactgctctg gaaaggtgaa ggggcagtag   2880

taatacaaga taatagtgac ataaaggtag tgccaaggag gaaagcaaaa attattaggg   2940

attatggaaa acagatggca ggtgctgatt gtgtggcagg tagacaggat gaggatcaga   3000

acatggaata g                                                        3011
```

<210> SEQ ID NO 102
<211> LENGTH: 579
<212> TYPE: DNA
<213> ORGANISM: Human immunodeficiency virus type 1
<220> FEATURE:
<223> OTHER INFORMATION: isolate=94IN476.104; gene=vif

<400> SEQUENCE: 102

```
atggaaaaca gatggcaggt gctgattgtg tggcaggtag acaggatgag gatcagaaca     60

tggaatagtt tagtaaaaca ccatatgtat gtttcaagaa gagctagtgg atggttttac    120

agacatcatt atgaaagcag acatccaaaa gtaagtgcag aagtacacat cccattagga    180

gatgctagat tagtaataaa aacatattgg ggtttacaaa caggagaaag agattggcat    240

ttgggtcatg gcgtctccat agaatggaga ttgggaagat atagcacaca agtagaacct    300

ggcctggcag accagctaat ccatatgcat tattttgatt gttttgcaga ctctgccata    360

agaaaagcca tattaggaca catagttatt tctaggtgtg attatcaagc aggacataat    420

aaggtaggat ctctacaata cttggcactg acagcattga taaaaccaaa aaagagaaag    480

ccacctctgc ctagtgttaa gaaattagta gaggatagat ggaacaatcc ccagaagacc    540

agggaccaca gagggaacca tacaatgaat ggacactag                           579
```

<210> SEQ ID NO 103
<211> LENGTH: 291
<212> TYPE: DNA
<213> ORGANISM: Human immunodeficiency virus type 1
<220> FEATURE:
<223> OTHER INFORMATION: isolate=94IN476.104; gene=vpr

<400> SEQUENCE: 103

```
atggaacaat ccccagaaga ccagggacca cagagggaac catacaatga atggacacta     60

gagcttctag aggaactcaa gcaggaagct gtcagacact ttcctagacc ttagcttcat    120

agcttaggac aatatatcta tgaaacatat ggggatgctt ggacaggagt cgaagcttta    180

ataagaacac tgcaacaatt actgtttatt catttcagaa ttgggtgcca gcatagcaga    240

ataggcattt tacaacggag aagagcaaga aatggagcca gtagatccta a             291
```

<210> SEQ ID NO 104
<211> LENGTH: 2633

-continued

<212> TYPE: DNA
<213> ORGANISM: Human immunodeficiency virus type 1
<220> FEATURE:
<223> OTHER INFORMATION: isolate=94IN476.104; gene=tat

<400> SEQUENCE: 104
atggagccag tagatcctaa cctagagccc tggaaccatc caggaagtca gcctaaaact 60
gcttgtaata catgctattg taaacactgt agctaccatt gtctagtttg ctttcagaca 120
aaaggcttag gcatttccta tggcaggaag aagcggagac agcgacgcag cgctcctcca 180
agcagtgagg atcatcaaaa tcttatatca aagcagtaag tatatgtaat ggtgaattta 240
ttagaaagag tagattatag attaggagta ggagcattaa tagtagcatt aatcttagca 300
ataattgtgt ggaccatagc atatctagaa tataggaaat tgttaagaca aagaaaaata 360
aacaggttaa ttgaaagaat tagggaaaga gtagaagaca gtggcaatga gagtgagggg 420
gatactgagg aattgtcaac actggtggat atggggaatc ttaggctttt ggatgctaat 480
gatttataat gtagtaggga acttgtgggt cacagtctat tatggggtac ctgtgtggaa 540
agaagcaaaa actactttat tctgtgcatc agatgctaaa gcttatgaga aggaggtgca 600
taatatctgg gctacacatg cctgtgtacc cacagacccc aacccacaag agatggattt 660
agtaaatgta acagaaaatt ttaacatgtg gaaaaatgac atggtggatc agatgcatga 720
ggatgtaatc agtttatggg atcaaagcct aaagccatgt gtaaagttga ccccactctg 780
tgtcacttta aactgtagta aggttaccaa taatgctact tacaataata ctgatgatat 840
aaaaaattgc tcttttaatg caaccacaga aataagagac aagaaacgca aagagtatgc 900
actgttttat agactcgata tagtaccact aaatgagaat aagaacagct ctagtaacta 960
tagtgagtac atattaataa attgtaatac ctcaaccata acacaagcct gtccaaaggt 1020
ctcttttgac ccaattccta tacattattg tgctccagct ggttttgcga ttctaaagtg 1080
taaagatgag acattcaatg ggacaggacc atgcaaggag gtcagtacag tacaatgtac 1140
acatggaatt aagccagtgg tatcaactca actactgtta aatggtagca cagcagaaaa 1200
agagataata actagatctg aaaatataac agacaatgca aaaactataa tagtacatct 1260
taatgaatcc ataaaaattg tatgtacaag acccaacaat aacacaagaa aaagtataag 1320
gatagggcca ggacaagcat tctatgcaac aaacggcata ataggagaca taagacaagc 1380
acattgtaac attagtgaat ctaactggac taaaacttta caagaggtag gaaaaaaatt 1440
agcaaagcac ttccctaata aaacaataag tttcaaccaa tcctcaggag gggacctaga 1500
aattgtaaca catagcttta attgtggagg agaattcttt tattgtaata catcaagact 1560
gtttaacggt acatacaatg gtacagacat gcctacatac aatggtacaa attccagttc 1620
agacatcatc atgcttccat gcagaataag gcaatttata aacatttggc agaaggtagg 1680
acgagcaatg tatgcccctc ccattgaagg aaacataaca tgtgaatcaa atatcacagg 1740
actactatta gtacgtgatg gaggcgacac aaatagtagc acagagatat tcagacctgg 1800
aggaggagat atgagggaca attggagaag tgaattatat aaatataaag tggtagaaat 1860
taagccatta ggaatagcac ctactgaagc aaaaaggaga gtggtggaga gagaaaaaag 1920
agcagtggga ataggagctg tgttccttgg gttcttggga gtagcaggaa gcactatggg 1980
cgcggcgtca atgacgctga cggtacaggc cagacaattg ttgtctggta tagtgcaaca 2040
gcaaagcaat ttgctgaagg ctatagaggc gcaacagcat atgttgcaac tcacagtctg 2100
gggcattaag cagctccaga caagagtctt ggctatagag agatacctaa aggatcaaca 2160

-continued

```
gctcctaggg atttggggct gctctggaaa agtcatctgc cccactgctg tgccttggaa   2220

ctccagctgg agtaataaat caaaagatga tatttggaat aacatgacct ggatgcagtg   2280

ggataaagag attagtaatt acacaaacac aatataccgg ttgcttgaag aatcgcaaat   2340

ccagcaggaa caaaatggaa aagatttatt agcattggac agttggcaaa atctgtggaa   2400

ttggtttagc ataacaaaat ggctgtggta tataaaaata ttcataatta tagtaggagg   2460

cttgataggt ttgagaataa tttttgctgt gctatctata gtaaatagag ttaggcaggg   2520

atactcacct ttgtcgttgc agacccttac cccagacccg agggaacccg acaggctcag   2580

aggaatcgaa gaagaaggtg gagagcaaga caaagacaga tccattcgat tag          2633
```

<210> SEQ ID NO 105
<211> LENGTH: 2651
<212> TYPE: DNA
<213> ORGANISM: Human immunodeficiency virus type 1
<220> FEATURE:
<223> OTHER INFORMATION: isolate=94IN476.104; gene=rev

<400> SEQUENCE: 105

```
atggcaggaa gaagcggaga cagcgacgca gcgctcctcc aagcagtgag gatcatcaaa     60

atcttatatc aaagcagtaa gtatatgtaa tggtgaattt attagaaaga gtagattata    120

gattaggagt aggagcatta atagtagcat taatcttagc aataattgtg tggaccatag    180

catatctaga atataggaaa ttgttaagac aaagaaaaat aaacaggtta attgaaagaa    240

ttagggaaag agtagaagac agtggcaatg agagtgaggg ggatactgag gaattgtcaa    300

cactggtgga tatggggaat cttaggcttt tggatgctaa tgatttataa tgtagtaggg    360

aacttgtggg tcacagtcta ttatggggta cctgtgtgga aagaagcaaa aactacttta    420

ttctgtgcat cagatgctaa agcttatgag aaggaggtgc ataatatctg ggctacacat    480

gcctgtgtac ccacagaccc caacccacaa gagatggatt tagtaaatgt aacagaaaat    540

tttaacatgt ggaaaaatga catggtggat cagatgcatg aggatgtaat cagtttatgg    600

gatcaaagcc taaagccatg tgtaaagttg accccactct gtgtcacttt aaactgtagt    660

aaggttacca ataatgctac ttacaataat actgatgata taaaaaattg ctcttttaat    720

gcaaccacag aaataagaga caagaaacgc aaagagtatg cactgtttta tagactcgat    780

atagtaccac taaatgagaa taagaacagc tctagtaact atagtgagta catattaata    840

aattgtaata cctcaaccat aacacaagcc tgtccaaagg tctcttttga cccaattcct    900

atacattatt gtgctccagc tggttttgcg attctaaagt gtaaagatga gacattcaat    960

gggacaggac catgcaagga ggtcagtaca gtacaatgta cacatggaat taagccagtg   1020

gtatcaactc aactactgtt aaatggtagc acagcagaaa aagagataat aactagatct   1080

gaaaatataa cagacaatgc aaaaactata atagtacatc ttaatgaatc cataaaaatt   1140

gtatgtacaa gacccaacaa taacacaaga aaaagtataa ggatagggcc aggacaagca   1200

ttctatgcaa caaacggcat aataggagac ataagacaag cacattgtaa cattagtgaa   1260

tctaactgga ctaaaacttt acaagaggta ggaaaaaaat tagcaaagca cttccctaat   1320

aaaacaataa gtttcaacca atcctcagga ggggacctag aaattgtaac acatagcttt   1380

aattgtggag gagaattctt ttattgtaat acatcaagac tgtttaacgg tacatacaat   1440

ggtacagaca tgcctacata caatggtaca aattccagtt cagacatcat catgcttcca   1500

tgcagaataa ggcaatttat aaacatttgg cagaaggtag gacgagcaat gtatgcccct   1560

cccattgaag gaaacataac atgtgaatca aatatcacag gactactatt agtacgtgat   1620
```

ggaggcgaca caaatagtag cacagagata ttcagacctg gaggaggaga tatgagggac 1680
aattggagaa gtgaattata taaatataaa gtggtagaaa ttaagccatt aggaatagca 1740
cctactgaag caaaaaggag agtggtggag agagaaaaaa gagcagtggg aataggagct 1800
gtgttccttg ggttcttggg agtagcagga agcactatgg gcgcggcgtc aatgacgctg 1860
acggtacagg ccagacaatt gttgtctggt atagtgcaac agcaaagcaa tttgctgaag 1920
gctatagagg cgcaacagca tatgttgcaa ctcacagtct ggggcattaa gcagctccag 1980
acaagagtct tggctataga gagataccta aaggatcaac agctcctagg gatttggggc 2040
tgctctggaa aagtcatctg ccccactgct gtgccttgga actccagctg gagtaataaa 2100
tcaaaagatg atatttggaa taacatgacc tggatgcagt gggataaaga gattagtaat 2160
tacacaaaca caatataccg gttgcttgaa gaatcgcaaa tccagcagga acaaaatgga 2220
aaagatttat tagcattgga cagttggcaa aatctgtgga attggtttag cataacaaaa 2280
tggctgtggt atataaaaat attcataatt atagtaggag gcttgatagg tttgagaata 2340
atttttgctg tgctatctat agtaaataga gttaggcagg gatactcacc tttgtcgttg 2400
cagaccctta ccccagaccc gagggaaccc gacaggctca gaggaatcga agaagaaggt 2460
ggagagcaag acaaagacag atccattcga ttagtgaacg gattcttagc acttgcctgg 2520
gacgatctac ggagcctgtg cctcttcagt tgccaccgat tgagagactt catattggtt 2580
gcagcgagag cggtggaact tctgggacgc agcagtctca ggggactaca gagggggtgg 2640
gaagccctta a 2651

<210> SEQ ID NO 106
<211> LENGTH: 261
<212> TYPE: DNA
<213> ORGANISM: Human immunodeficiency virus type 1
<220> FEATURE:
<223> OTHER INFORMATION: isolate=94IN476.104; gene=vpu

<400> SEQUENCE: 106
atggtgaatt tattagaaag agtagattat agattaggag taggagcatt aatagtagca 60
ttaatcttag caataattgt gtggaccata gcatatctag aatataggaa attgttaaga 120
caaagaaaaa taaacaggtt aattgaaaga attagggaaa gagtagaaga cagtggcaat 180
gagagtgagg gggatactga ggaattgtca acactggtgg atatggggaa tcttaggctt 240
ttggatgcta atgatttata a 261

<210> SEQ ID NO 107
<211> LENGTH: 2574
<212> TYPE: DNA
<213> ORGANISM: Human immunodeficiency virus type 1
<220> FEATURE:
<223> OTHER INFORMATION: isolate=94IN476.104; gene=env

<400> SEQUENCE: 107
atgagagtga gggggatact gaggaattgt caacactggt ggatatgggg aatcttaggc 60
ttttggatgc taatgattta taatgtagta gggaacttgt gggtcacagt ctattatggg 120
gtacctgtgt ggaaagaagc aaaaactact ttattctgtg catcagatgc taaagcttat 180
gagaaggagg tgcataatat ctgggctaca catgcctgtg tacccacaga ccccaaccca 240
caagagatgg atttagtaaa tgtaacagaa aattttaaca tgtggaaaaa tgacatggtg 300
gatcagatgc atgaggatgt aatcagttta tgggatcaaa gcctaaagcc atgtgtaaag 360

-continued

```
ttgaccccac tctgtgtcac tttaaactgt agtaaggtta ccaataatgc tacttacaat    420
aatactgatg atataaaaaa ttgctctttt aatgcaacca cagaaataag agacaagaaa    480
cgcaaagagt atgcactgtt ttatagactc gatatagtac cactaaatga gaataagaac    540
agctctagta actatagtga gtacatatta ataaattgta atacctcaac cataacacaa    600
gcctgtccaa aggtctcttt tgacccaatt cctatacatt attgtgctcc agctggtttt    660
gcgattctaa agtgtaaaga tgagacattc aatgggacag gaccatgcaa ggaggtcagt    720
acagtacaat gtacacatgg aattaagcca gtggtatcaa ctcaactact gttaaatggt    780
agcacagcag aaaaagagat aataactaga tctgaaaata taacagacaa tgcaaaaact    840
ataatagtac atcttaatga atccataaaa attgtatgta caagacccaa caataacaca    900
agaaaaagta taaggatagg gccaggacaa gcattctatg caacaaacgg cataatagga    960
gacataagac aagcacattg taacattagt gaatctaact ggactaaaac tttacaagag   1020
gtaggaaaaa aattagcaaa gcacttccct aataaaacaa taagtttcaa ccaatcctca   1080
ggaggggacc tagaaattgt aacacatagc tttaattgtg gaggagaatt cttttattgt   1140
aatacatcaa gactgtttaa cggtacatac aatggtacag acatgcctac atacaatggt   1200
acaaattcca gttcagacat catcatgctt ccatgcagaa taaggcaatt tataaacatt   1260
tggcagaagg taggacgagc aatgtatgcc cctcccattg aaggaaacat aacatgtgaa   1320
tcaaatatca caggactact attagtacgt gatggaggcg acacaaatag tagcacagag   1380
atattcagac ctggaggagg agatatgagg gacaattgga gaagtgaatt atataaatat   1440
aaagtggtag aaattaagcc attaggaata gcacctactg aagcaaaaag gagagtggtg   1500
gagagagaaa aaagagcagt gggaatagga gctgtgttcc ttgggttctt gggagtagca   1560
ggaagcacta tgggcgcggc gtcaatgacg ctgacggtac aggccagaca attgttgtct   1620
ggtatagtgc aacagcaaag caatttgctg aaggctatag aggcgcaaca gcatatgttg   1680
caactcacag tctggggcat taagcagctc cagacaagag tcttggctat agagagatac   1740
ctaaaggatc aacagctcct agggatttgg ggctgctctg gaaaagtcat ctgccccact   1800
gctgtgcctt ggaactccag ctggagtaat aaatcaaaag atgatatttg gaataacatg   1860
acctggatgc agtgggataa agagattagt aattacacaa acacaatata ccggttgctt   1920
gaagaatcgc aaatccagca ggaacaaaat ggaaaagatt tattagcatt ggacagttgg   1980
caaaatctgt ggaattggtt tagcataaca aaatggctgt ggtatataaa aatattcata   2040
attatagtag gaggcttgat aggtttgaga ataatttttg ctgtgctatc tatagtaaat   2100
agagttaggc agggatactc acctttgtcg ttgcagaccc ttaccccaga cccgagggaa   2160
cccgacaggc tcagaggaat cgaagaagaa ggtggagagc aagacaaaga cagatccatt   2220
cgattagtga acggattctt agcacttgcc tgggacgatc tacggagcct gtgcctcttc   2280
agttgccacc gattgagaga cttcatattg gttgcagcga gagcggtgga acttctggga   2340
cgcagcagtc tcaggggact acagaggggg tgggaagccc ttaaatatct gggaagtctt   2400
gtgcagtatt ggggtctgga actaaaaaag agtgctatta gtctgcttga taccatagca   2460
ataacaatag ctgagggaac agataggatt atagaattta cacaaagaat ttgcagagct   2520
atccgcaaca tacctagaag aataagacag ggttttgaag cagctttgct ataa         2574
```

<210> SEQ ID NO 108
<211> LENGTH: 624
<212> TYPE: DNA
<213> ORGANISM: Human immunodeficiency virus type 1

-continued

```
<220> FEATURE:
<223> OTHER INFORMATION: isolate=94IN476.104; gene=nef

<400> SEQUENCE: 108

atggggagca agatgtcaaa aagcagaata gttggatggc ctgaggtaag agaaagaatg     60

aggagaactg agccagcagc agagggagta ggagcagcat ctcaagactt agctaaacat    120

ggagcactta caaccagcaa cacaccaagc aataatgctg ctggtgcctg gctgcaagcg    180

caagaggagg aagaagaagt aggctttcca gtcagacctc aggtgccttt aagaccaatg    240

acttataaag gagcattcga tctcgccttc tttttaaaag aaaagggggg actggatggg    300

ttaatttact ctaagaaaag gcatgaaatc cttgatttat gggtttataa cacacaaggc    360

tacttccctg attggcaaaa ctacacacca ggaccagggg tcagatatcc actgaccttt    420

ggatggtgct acaagctagt accagttgac ccaagtgtag tagaagaggc caacaaagga    480

gaaaacaact gtttgctaca ccctatgagc caacatggaa tggatgatga agatggagaa    540

gtattaaagt ggcagtttga cagcagccta gcacgcagac acatagcccg cgagctacat    600

ccggagtatt acaaagactg ctga                                           624
```